United States Patent
Amin et al.

(10) Patent No.: US 7,772,181 B2
(45) Date of Patent: *Aug. 10, 2010

(54) PERSONAL CARE COMPOSITIONS COMPRISING MODIFIED VARIANT BOWMAN BIRK PROTEASE INHIBITORS

(75) Inventors: Neelam S. Amin, Palo Alto, CA (US); Katherine D. Collier, Los Altos, CA (US); Melodie Estabrook, Mountain View, CA (US); David A. Estell, San Francisco, CA (US); Bryan P. Fox, Pacifica, CA (US); Scott D. Power, San Bruno, CA (US); Brian F. Schmidt, Half Moon Bay, CA (US); Gudrun Vogtentanz, Santa Clara, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/252,032

(22) Filed: Oct. 15, 2008

(65) Prior Publication Data

US 2010/0092409 A1 Apr. 15, 2010

(51) Int. Cl.
*A61K 38/00* (2006.01)
*A61K 8/00* (2006.01)
(52) U.S. Cl. .............. 514/2; 424/70.1; 424/59; 424/63; 424/69
(58) Field of Classification Search ............. None
See application file for complete search history.

(56) References Cited

U.S. PATENT DOCUMENTS

| | | | |
|---|---|---|---|
| 2,531,427 A | 11/1950 | Hauser | |
| 3,755,560 A | 8/1973 | Dickert et al. | |
| 3,929,678 A | 12/1975 | Laughlin et al. | |
| 4,076,663 A | 2/1978 | Masuda et al. | |
| 4,152,416 A | 5/1979 | Spitzer et al. | |
| 4,421,769 A | 12/1983 | Dixon et al. | |
| 4,937,370 A | 6/1990 | Sabatelli | |
| 4,999,186 A | 3/1991 | Sabatelli et al. | |
| 5,011,681 A | 4/1991 | Ciotti et al. | |
| 5,073,371 A | 12/1991 | Turner et al. | |
| 5,073,372 A | 12/1991 | Turner et al. | |
| 5,087,372 A | 2/1992 | Toyomoto et al. | |
| 5,411,873 A | 5/1995 | Adams et al. | |
| 5,429,950 A | 7/1995 | Power et al. | |
| 5,679,543 A | 10/1997 | Lawlis | |
| 5,827,508 A | 10/1998 | Tanner et al. | |
| 5,935,556 A | 8/1999 | Tanner et al. | |
| 5,968,485 A | 10/1999 | Robinson | |
| 5,972,316 A | 10/1999 | Robinson | |
| 6,063,611 A | 5/2000 | Van Solingen | |
| 6,093,748 A | 7/2000 | Ahluwalia et al. | |
| 6,537,968 B1 | 3/2003 | Lezdey et al. | |
| 6,872,563 B1 | 3/2005 | Beckwith et al. | |
| 7,485,618 B2 | 2/2009 | Day et al. | |
| 7,524,816 B2 | 4/2009 | Day et al. | |
| 2002/0098524 A1 | 7/2002 | Murray et al. | |
| 2005/0112692 A1 | 5/2005 | Murray et al. | |
| 2008/0113917 A1 | 5/2008 | Day et al. | |
| 2008/0269139 A1 | 10/2008 | Day et al. | |

FOREIGN PATENT DOCUMENTS

| | | |
|---|---|---|
| DE | 29 17 504 A1 | 11/1979 |
| DE | 36 27 970 A1 | 2/1988 |
| DE | 37 40 186 A1 | 1/1989 |
| DE | 39 38 140 A1 | 8/1991 |
| DE | 40 09 347 A1 | 9/1991 |
| DE | 42 04 321 A1 | 8/1993 |
| DE | 42 24 761 A1 | 2/1994 |
| DE | 42 25 045 A1 | 2/1994 |
| DE | 42 29 707 A1 | 3/1994 |
| DE | 42 29 737 A1 | 3/1994 |
| DE | 42 37 081 A1 | 5/1994 |
| DE | 42 41 118 A1 | 6/1994 |
| DE | 43 09 372 A1 | 9/1994 |
| DE | 43 14 305 A1 | 11/1994 |
| DE | 43 24 219 A1 | 1/1995 |
| DE | 44 11 664 A1 | 10/1995 |
| DE | 44 23 410 A1 | 1/1996 |
| DE | 44 29 467 A1 | 2/1996 |
| DE | 195 16 705 A1 | 11/1996 |
| DE | 195 41 967 A1 | 5/1997 |
| DE | 195 43 695 A1 | 5/1997 |
| DE | 195 43 696 A1 | 5/1997 |
| DE | 195 47 160 A1 | 6/1997 |

(Continued)

OTHER PUBLICATIONS

U.S. Appl. No. 11/919,717, filed Apr. 25, 2006, Kolkman et al.
Altschul, S.F. et al. "Local alignment statistics." *Methods Enzymol* 266: 460-80, 1996.
Altschul, S.F. et al. "Basic local alignment search tool." *J. Mol. Biol* 215(3): 403-410, 1990.
Amin, N. S. et al. "Direct transformation of site-saturation libraries in *Bacillus subtilis.*" *BioTechniques* 35(6): 1134-1140, Dec. 2003.
Asadullah, K. et al. "The pathophysiological role of cytokines in psoriasis." *Drugs of Today* (Barcelona, Spain) 35(12): 913-924, Dec. 1999.

(Continued)

*Primary Examiner*—Christina Bradley

(57) ABSTRACT

The present invention relates to compositions that comprise modified variant Bowman Birk Protease Inhibitor proteins (BBPIs). The modified variant BBPIs comprise peptides that bind target proteins, and that are further modified to have greater protease inhibitory activity and/or be produced at greater yields than the unmodified BBPIs. The invention encompasses the compositions comprising the modified variant BBPIs, and the methods for making and using the compositions in personal care.

93 Claims, 22 Drawing Sheets

FOREIGN PATENT DOCUMENTS

| | | |
|---|---|---|
| DE | 196 02 108 A1 | 7/1997 |
| DE | 196 02 110 A1 | 7/1997 |
| DE | 196 02 111 A1 | 7/1997 |
| DE | 196 31 004 A1 | 2/1998 |
| DE | 196 34 019 A1 | 2/1998 |
| DE | 196 310 03 A1 | 2/1998 |
| EP | 0 065 193 A2 | 11/1982 |
| EP | A 0 619 111 | 10/1994 |
| EP | 0 776 657 A2 | 6/1997 |
| WO | WO 88/02025 A1 | 3/1988 |
| WO | WO 96/03964 A1 | 2/1996 |
| WO | WO 98/22085 A1 | 5/1998 |
| WO | WO 99/53038 A2 | 10/1999 |
| WO | WO 00/05406 A1 | 2/2000 |
| WO | WO 00/06110 A1 | 2/2000 |
| WO | WO 00/24372 A1 | 5/2000 |
| WO | WO 2005/046709 A2 | 5/2005 |
| WO | WO 2005/046710 A2 | 5/2005 |
| WO | WO 2005/047302 A1 | 5/2005 |
| WO | WO 2005/047314 A2 | 5/2005 |
| WO | WO 2005/047511 A2 | 5/2005 |
| WO | WO 2006/121610 A2 | 11/2006 |
| WO | WO 2007/085846 A1 | 8/2007 |

OTHER PUBLICATIONS

Asano, M. et al. "An Anti-Human VEGF Monoclonal Antibody, MV833, That Exhibits Potent Anti-Tumor Activity In Vivo." *Hybridoma* 17(2): 185, 1998. dan.

Bakhiet, N et al. "Studies on transfection and transformation of protoplasts of *Bacillus* larvae, *Bacillus subtilis*, and *Bacillus popilliae*." *Appl. Environ. Microbiol*. 49(3): 577-581, Mar. 1, 1985.

Barnett, G. "Emollient Creams and Lotions." In *Cosmetics: Science and Technology*, pp. 32-43. New York: Wiley-Interscience, 1972.

Billings, P.C. et al. "A growth-regulated protease activity that is inhibited by the anticarcinogenic Bowman-Birk protease inhibitor." *Proc. Natl. Acad. Sci. U.S.A* 89(7): 3120-4, Apr. 1, 1992.

Birk, Y. "The Bowman-Birk inhibitor. Trypsin- and chymotrypsin-inhibitor from soybeans." *Int. J. Pept. Protein Res* 25(2): 113-31, Feb. 1985.

Blaudschun, R. et al. "The first peak of the UVB irradiation-dependent biphasic induction of vascular endothelial growth factor (VEGF) is due to phosphorylation of the epidermal growth factor receptor and independent of autocrine transforming growth factor [alpha]." *FEBS Letters* 474(2-3): 195-200, Jun. 2, 2000.

Blobe, G.C. et al. "Role of Transforming Growth Factor {beta} in Human Disease." *N Engl J Med* 342(18): 1350-1358, May 4, 2000.

Bode, W. et al. "Natural protein proteinase inhibitors and their interaction with proteinases." *Eur. Jur. Biochem*. 204(2): 433-451, 1992.

Borgström, P et al. "Neutralizing anti-vascular endothelial growth factor antibody completely inhibits angiogenesis and growth of human prostate carcinoma micro tumors in vivo." *The Prostate* 35(1): 1-10, Apr. 1, 1998.

Borgström, P et al. "Complete inhibition of angiogenesis and growth of microtumors by anti-vascular endothelial growth factor neutralizing antibody: novel concepts of angiostatic therapy from intravital videomicroscopy." *Cancer Research* 56(17): 4032-4039, Sep. 1, 1996.

Boyman, O. et al. "Spontaneous Development of Psoriasis in a New Animal Model Shows an Essential Role for Resident T Cells and Tumor Necrosis Factor-α." *The Journal of Experimental Medicine* 199(5): 731-736, Mar. 1, 2004.

Brown, J. Martin et al. "The Unique Physiology of Solid Tumors: Opportunities (and Problems) for Cancer Therapy." *Cancer Res* 58(7): 1408-1416, Apr. 1, 1998.

Chang, S. et al. "High frequency transformation of *Bacillus subtilis* protoplasts by plasmid DNA." *Mol. Gen. Genet* 168: 111-115, 1979.

Chaudhari, U. et al. "Efficacy and safety of infliximab monotherapy for plaque-type psoriasis: a randomised trial." *The Lancet* 357(9271): 1842-1847, Jun. 9, 2001.

Chen, P. et al. "Reactive sites of an anticarcinogenic Bowman-Birk proteinase inhibitor are similar to other trypsin inhibitors." *J. Biol. Chem*. 267(3): 1990-1994, Jan. 25, 1992.

Christmann, A. et al. "The cystine knot of a squash-type protease inhibitor as a structural scaffold for *Eschericia coli* cell surface display of conformationally constrained peptides." *Protein Engineering* 12(9): 797-806, 1999.

Contente, S. et al. "Marker rescue transformation by linear plasmid DNA in *Bacillus subtilis*." *Plasmid* 2(4): 555-71, Oct. 1979.

Cosmetic, Toiletry, and Fragrance Association. "Titanium Dioxide." In *International Cosmetic Ingredient Dictionary*, pp. 1026-1028. Washington, D.C.: Cosmetic, Toiletry, and Fragrance Association, 1995.

Cosmetic, Toiletry, and Fragrance Association. "Zinc Oxide." In *International Cosmetic Ingredient Dictionary*, pp. 1103. Washington, D.C.: Cosmetic, Toiletry, and Fragrance Association, 1995.

Database UniProt. "Bowman-Birk type proteinase inhibitor." Accession No. P01055, Jul. 21, 1986.

Database UniProt. "Bowman-Birk type proteinase inhibitor." Accession No. P01056, Jul. 21, 1986.

Detmar, M et al. "Keratinocyte-derived vascular permeability factor (vascular endothelial growth factor) is a potent mitogen for dermal microvascular endothelial cells." *The Journal of Investigative Dermatology* 105(1): 44-50, Jul. 1995.

Devereux, P. et al. "A comprehensive set of sequence analysis programs for the VAX." *Nucl. Acids Res* 12: 387-395, 1984.

Ehrlich, S.D. "DNA cloning in *Bacillus subtilis*." *Proceedings of the National Academy of Sciences of the United States of America* 75(3): 1433-1436, Mar. 1978.

Feng, D.F. et al. "Progressive sequence alignment as a prerequisite to correct phylogenetic trees." *J. Mol. Evol* 25(4): 351-360, 1987.

Ferrari, E. et al. "Transcription of *Bacillus subtilis* subtilisin and expression of subtilisin in sporulation mutants.." *J. Bacteriol*. 170(1): 289-295, Jan. 1, 1988.

Ferrari, E. et al. "Genetics." in *Bacillus*, edited by C.R. Harwood, pp. 57-72. Biotechnology Handbooks 2. New York: Plenum Press, 1989.

Fiedler, H.P., ed. "Chitosan." In *Lexikon der Hilfsstoffe für Pharmazie, Kosmetik und angrenzende Gebiete*, 3rd ed., pp. 293-294. Aulendorf, Germany: Editio Cantor, 1989.

Fischer, H.-M. et al. "Introduction of plasmid pC194 into *Bacillus thuringiensis* by protoplast transformation and plasmid transfer." *Archives of Microbiology* 139(2): 213-217, Oct. 1, 1984.

Flecker, P. "A new and general procedure for refolding mutant Bowman-Birk-type proteinase inhibitors on trypsin-Sepharose as a matrix with complementary structure." *FEBS Letters* 252(1-2): 153-157, Jul. 1989.

Flecker, P. "Chemical Synthesis, Molecular cloning and expression of gene coding for a Bowman-Birk-type proteinase inhibitor." *Eur. J. Biochem* 166: 151-156, 1987.

Foitzik, K. et al. "Control of murine hair follicle regression (catagen) by TGF-β1 in vivo." *FASEB J*. 14(5): 752-760, Apr. 1, 2000.

Foitzik, K. et al. "The TGF-β2 Isoform Is Both a Required and Sufficient Inducer of Murine Hair Follicle Morphogenesis." *Developmental Biology* 212(2): 278-289, Aug. 15, 1999.

Gottlieb, A.B. et al. "Infliximab monotherapy provides rapid and sustained benefit for plaque-type psoriasis." *Journal of the American Academy of Dermatology* 48(6): 829-835, Jun. 2003.

Hahn, J. et al. "Regulatory inputs for the synthesis of ComK, the competence transcription factor of *Bacillus subtilis*." *Molecular Microbiology* 21(4): 763-775, 1996.

Haima, P. et al. "Novel plasmid marker rescue transformation system for molecular cloning in *Bacillus subtilis* enabling direct selection of recombinants." *Molecular and General Genetics* 223(2): 185-191, 1990.

He, M.M. et al. "Small-Molecule Inhibition of TNF-{alpha}." *Science* 310(5750): 1022-1025, Nov. 11, 2005.

Hébert, J.M. et al. "FGF5 as a regulator of the hair growth cycle: Evidence from targeted and spontaneous mutations." *Cell* 78(6): 1017-1025, Sep. 23, 1994.

Helmann, J.D. et al. "RNA Polymerase and Sigma Factors." In *Bacillus subtilis and Its Closest Relatives: From Genes to Cells*, edited by A.L. Sonenshein, pp. 289-312. Washington, D.C.: ASM Press, 2002.

Hengen, P.N. "Purification of His-Tag fusion proteins from *Escherichia coli.*" *Trends in Biochemical Sciences* 20(7): 285-286, Jul. 1995.

Henner, D.J. et al. "Location of the targets of the hpr-97, sacU32(Hy), and sacQ36(Hy) mutations in upstream regions of the subtilisin promoter." *J. Bacteriol.* 170(1): 296-300, Jan. 1, 1988.

Higgins, D.G. et al. "Fast and sensitive multiple alignment sequence on a microcomputer." *CABIOS* 5: 151-153, 1989.

Hoch, J.A. et al. "Transformation and Transduction in Recombination-defective Mutants of *Bacillus subtilis.*" *J. Bacteriol.* 93(6): 1925-1937, Jun. 1, 1967.

Holubová, I. et al. "Transfer of liposome-encapsulated plasmid DNA to *Bacillus subtilis* protoplasts and calcium-treated *Escherichia coli* cells." *Folia Microbiologica* 30(2): 97-100, Apr. 1, 1985.

Hwang, D.L. et al. "A soybean trypsin inhibitor. Crystallization and x-ray crystallographic study." *J. Biol. Chem.* 252(3): 1099-1101, Feb. 10, 1977.

Inui, S. et al. "Androgen-inducible TGF-β1 from balding dermal papilla cells inhibits epithelial cell growth: a clue to understand paradoxical effects of androgen on human hair growth." *FASEB J.* 16(14): 1967-9, Dec. 2002.

Ito, C. et al. "Decapeptide with fibroblast growth factor (FGF)-5 partial sequence inhibits hair growth suppressing activity of FGF-5." *Journal of Cellular Physiology* 197(2): 272-283, 2003.

Kajino, T. et al. "A Protein Disulfide Isomerase Gene Fusion Expression System That Increases the Extracellular Productivity of *Bacillus brevis.*" *Appl. Environ. Microbiol.* 66(2): 638-642, Feb. 1, 2000.

Karlin, S. et al. "Applications and statistics for multiple high-scoring segments in molecular sequences." *Proc. Natl. Acad. Sci. USA* 90(12): 5873-7, Jun. 15, 1993.

Kemperman, R. et al. "Identificaiton and Characterization of Two Novel Clostridial Bacteriocins, Circularin A and Closticin 574." *Applied and Environmental Microbiology* 69(3): 1589-1597, 2003.

Kennedy, A.R. "The Bowman-Birk inhibitor from soybeans as an anticarcinogenic agent." *Am J Clin Nutr* 68: 1406S-12S, 1998.

Kim, K.J. et al. "Inhibition of vascular endothelial growth factor-induced angiogenesis suppresses tumour growth in vivo." *Nature* 362(6423): 841-844, Apr. 29, 1993.

Kim, M.-S. et al. "All-Trans Retinoic Acid Antagonizes UV-Induced VEGF Production and Angiogenesis via the Inhibition of ERK Activation in Human Skin Keratinocytes." *J Invest Dermatol* 126(12): 2697-2706, Jun. 29, 2006.

Kincaid, L. "Psoriasis: TNF-[alpha] inhibitors and beyond." *Drug Discovery Today* 10(13): 884-886, Jul. 1, 2005.

Kissin, E.Y. et al. "Fibrosis in scleroderma." *Rheumatic Disease Clinics of North America* 29(2): 351-369, May 2003.

Kosmadaki, M.G. et al. "UV induces VEGF through a TNF-alpha independent pathway." *FASEB J.* 17(3): 446-448, Mar. 1, 2003.

Kroll, D.J. et al. "A multifunctional prokaryotic protein expression system: overproduction, affinity purification, and selective detection." *DNA Cell Biol* 12(5): 441-53, 1993.

Landon, M. "Cleavage at Aspartyl-Prolyl Bonds." In *Enzyme Structure Part E*, edited by C.H.W. Hirs et al., pp. 145-149. Methods in Enzymology 47. New York: Academic Press, 1977.

Leonardi, C.L. et al. "Etanercept as Monotherapy in Patients with Psoriasis." *N Engl J Med* 349(21): 2014-2022, Nov. 20, 2003.

Li, A.G. et al. "Role of TGFbeta in skin inflammation and carcinogenesis." *Molecular Carcinogenesis* 45(6): 389-396, 2006.

Lidell, M.E. et al., "An Autocatalytic Cleavage in the Terminus of the Human MUC$^2$ Mucin Occurs at the Low pH of the Late Secretory Pathway." *The Journal of Biological Chemistry* 278(16): 13944-13951, 2003.

Lin, G. et al. "The 0.25-nm X-ray structure of the Bowman-Birk-type inhibitor from mung bean in ternary complex with porcine trypsin." *Eur. Jur. Biochem.* 212(2): 549-555, 1993.

Linden, K.G. et al. "Psoriasis: current perspectives with an emphasis on treatment." *The American Journal of Medicine* 107(6): 595-605, Dec. 1999.

Liu, K. "Soybeans: Chemistry, Technology, and Utilization." *A Chapman & Hall Food Science Book*; pp. 32-35, 1999.

Liu, X. et al. "Conditional epidermal expression of TGF-β1 blocks neonatal lethality but causes a reversible hyperplasia and alopecia." *Proc. Natl. Acad. Sci. U.S.A* 98(16): 9139-44, Jul. 31, 2001.

Luo, Jin Cai et al. "Differential Inhibition of Fluid Accumulation and Tumor Growth in Two Mouse Ascites Tumors by an Antivascular Endothelial Growth Factor/Permeability Factor Neutralizing Antibody." *Cancer Res* 58(12): 2594-2600, Jun. 15, 1998.

Luo, Jin Cai et al. "Significant Expression of Vascular Endothelial Growth Factor/Vascular Permeability Factor in Mouse Ascites Tumors." *Cancer Res* 58(12): 2652-2660, Jun. 15, 1998.

Mann, S.P. et al. "Transformation of *Bacillus* spp.: An examination of the transformation of *Bacillus* protoplasts by plasmids pUB110 and pHV33." *Current Microbiology* 13(4): 191-195, Jul. 29, 1986.

McDonald, K.O. et al. "Plasmid transformation of *Bacillus sphaericus* 1593." *Journal of General Microbiology* 130(1): 203-8, Jan. 1984.

Meima, R. et al. "The bdbDC Operon of *Bacillus subtilis* Encodes Thiol-disulfide Oxidoreductases Required for Competence Development." *J. Biol. Chem.* 277(9): 6994-7001, Feb. 22, 2002.

Mesiano, Sam et al. "Role of Vascular Endothelial Growth Factor in Ovarian Cancer : Inhibition of Ascites Formation by Immunoneutralization." *Am J Pathol* 153(4): 1249-1256, Oct. 1, 1998.

Mussi, A. et al. "Serum TNF-alpha levels correlate with disease severity and are reduced by effective therapy in plaque-type psoriasis." *Journal of Biological Regulators and Homeostatic Agents* 11(3): 115-118, Sep. 1997.

Nakamura, Y. et al. "Codon usage tabulated from international DNA sequence databases: status for the year 2000." *Nucl. Acids Res.* 28(1): 292, Jan. 1, 2000.

Needleman, S.B. et al. "A general method applicable to the search for similarities in the amino acid sequence of two proteins." *J. Mol. Biol* 48(3): 443-53, Mar. 1970.

Neidhardt, F.C. et al. "Culture Medium for Enterobacteria." *J. Bacteriol.* 119(3): 736-747, Sep. 1, 1974.

Neumüller, O.-A. "Montmorillonite." In *Römpps Chemi-Lexikon*, 8$^{th}$ ed., pp. 2668-2669 Stuttgart, Germany: Franckh, 1985.

NIH-National Institute Of Dental And Craniofacial Research. "Topical Application of a Protein Heals Wounds." *ScienceDaily*. http://www.sciencedaily.com/releases/2000/10/001002071718.htm, Oct. 2, 2000.

Odani, S. et al. "Studies on Soybean Trypsin Inhibitors: IV. Complete Amino Acid Sequence and the Anti-proteinase proteinase Sites of Bowman-Birk Soybean Proteinase Inhibitor." *J Biochem* 71(5): 839-848, May 1, 1972.

Paine, C. et al. "An Alternative Approach to Depigmentation by Soybean Extracts via Inhibition of the PAR-2 Pathway" 116(4): 587-595, Apr. 2001.

Palmeros, B. et al. "A family of removable cassettes designed to obtain antibiotic-resistance-free genomic modifications of *Escherichia coli* and other bacteria." *Gene* 247(1-2): 255-264, Apr. 18, 2000.

Pearson, W.R. et al. "Improved Tools for Biological Sequence Comparison." *Proc. Natl. Acad. Sci. USA* 85(8): 2444-2448, Apr. 15, 1988.

Perego, M. "Integrational vectors for genetic manipulation in *Bacillus subtilis.*" In *Bacillus subtilis and other Gram-positive bacteria: biochemistry physiology and molecular genetics*, edited by A.L. Sonenshein et al., pp. 615-624. Washington, D.C.: American Society for Microbiology, 1993.

Porath, J. "Immobilized metal ion affinity chromatography." *Protein Expr Purif* 3(4): 263-81, 1992.

Power, S.D. et al. "Secretion and autoproteolytic maturation of subtilisin." *Proc. Natl. Acad. Sci. U.S.A* 83(10): 3096-100, May 1986.

Prakash, B. et al. "Analysis of the amino acid sequences of plant Bowman-Birk inhibitors." *Journal of Molecular Evolution* 42(5): 560-569, May 10, 1996.

Sahu, A. et al. "Inhibition of human complement by a C3-binding peptide isolated from a phage-displayed random peptide library." *J Immunol* 157(2): 884-891, Jul. 15, 1996.

Saunders, C W et al. "Use of chromosomal integration in the establishment and expression of blaZ, a *Staphylococcus aureus* beta-lactamase gene, in *Bacillus subtilis.*." *J. Bacteriol.* 157(3): 718-726, Mar. 1, 1984.

Sayre, R.M. et al. "Physical suncreens." *J. Soc. Cosmet. Chem.* 41: 103-109, 1990.

Seeboth, P.G. et al. "In-vitro cleavage of a fusion protein bound to cellulose using the soluble yscF$_s$ (Kex2) variant." *Applied Microbiology Biotechnology*. 37:621-625, 1992.

Ségalas, I. et al. "A particularly labile Asp-Pro bond in the green mamba muscarinic toxin MTX2. Effect of protein conformation on the rate of cleavage." *FEBS Letters*. 371:171-175, 1995.

Shaw, A. et al. "A Novel Combination of Two Classic Catalytic Schemes." *Journal of Molecular Biology* 320(2): 303-309, Jul. 5, 2002.

Siemeister, Gerhard et al. "The pivotal role of VEGF in tumor angiogenesis: Molecular facts and therapeutic opportunities." *Cancer and Metastasis Reviews* 17(2): 241-248, Jun. 1, 1998.

Smith, M.D. et al. "Protoplast transformation in coryneform bacteria and introduction of an α-amylase gene from *Bacillus amyloliquefaciens* into *Brevibacterium lactofermentum*." *Appl. Enviro. Microbiol*. 51(3): 634-639, 1986.

Smith, T.F. et al. "Comparison of biosequences." *Adv. Appl. Math* 2: 482-489, 1981.

Soma, T. et al. "Involvement of Transforming Growth Factor-bgr2 in Catagen Induction During the Human Hair Cycle." *J. Invest. Dermatol*. 118(6): 993-997, Jun. 2002.

Song, H.K. et al. "Kunitz-type Soybean Trypsin Inhibitor Revisted: Refined Structure of its Complex With Procine Trypsin Reveals an Insight into the Interaction Between a Homologous Inhibitor from *Erythrina caffra* and Tissue-type Plasminogen Activator." *J. Mol. Biol*. 275:347-363, 1998.

Stahl, M.L. et al. "Replacement of the *Bacillus subtilis* subtilisin structural gene with an In vitro-derived deletion mutation.." *J. Bacteriol*. 158(2): 411-418, May 1, 1984.

Stenn, K.S. et al. "What controls hair follicle cycling?." *Experimental Dermatology* 8(4): 229-236, 1999.

Stickler, M.M. et al. "CD4+ T-Cell Epitope Determination Using Unexposed Human Donor Peripheral Blood Mononuclear Cells." *Journal of Immunotherapy* 23(6). http://journals.lww.com/immunotherapy-journal/Fulltext/2000/11000/CD4_T_Cell_Epitope_Determination_Using_Unexposed.6.aspx 2000.

van Tilbeurgh, H. "Fluorogenic and chromogenic glycosides as substrates and ligands of carbohydrases." In *Biomass Part A: Cellulose and Hemicellulose*, edited by W.A. Wood et al., pp. 45-59. Methods in Enzymology 160. New York: Academic Press, 1988.

Vogtentanz, G. et al. "A *Bacillus subtilis* fusion protein system to produce soybean Bowman-Birk protease inhibitor." *Protein Expression and Purification* 55(1): 40-52, Sep. 2007.

Vorobjeva, I.P. et al. "Transformation of *Bacillus magaterium* protoplasts by plasmid DNA." *FEMS Microbiology Ecology* 7(3): 261-3, 1980.

Voss, R.-H. et al. "Crystal Structure of the Bifunctional Soybean Bowman-Birk Inhibitor at 0.28-nm Resolution." *European Journal of Biochemistry* 242(1): 122-131, 1996.

Wang, L. et al. "Engineering the Independent Folding of the Subtilisin BPN' Pro-Domain: Correlation of Pro-Domain Stability with the Rate of Subtilisin Folding." *Biochemistry* 37(9): 3165-3171, Mar. 3, 1998.

Wei, C.H. et al. "Preliminary crystallographic data for Bowman-Birk inhibitor from soybean seeds." *J. Biol. Chem*. 254(11): 4892-4894, Jun. 10, 1979.

Weinrauch, Y. et al. "Plasmid marker rescue transformation in *Bacillus subtilis*." *J. Bacteriol*. 154(3): 1077-1087, Jun. 1, 1983.

Weinrauch, Y. et al. "Plasmid marker rescue transformation proceeds by breakage-reunion in *Bacillus subtilis*." *J. Bacteriol*. 169(3): 1205-1211, Mar. 1, 1987.

Werner, M.H. et al. "Three-dimensional structure of soybean trypsin/chymotrypsin Bowman-Birk inhibitor in solution." *Biochemistry* 31(4): 999-1010, Feb. 4, 1992.

Wolfson, A.J. et al. "Modularity of Protein Function: Chimeric Interleukin 1βs Containing Specific Protease Inhibitor Loops Retain Functon of Both Molecules." *Biochemistry*. 32: 5327-5331, 1993.

Wong, M. et al. "TNF[alpha] blockade in human diseases: Mechanisms and future directions." *Clinical Immunology* 126(2): 121-136, Feb. 2008.

Xia, Yu-Ping et al. "Transgenic delivery of VEGF to mouse skin leads to an inflammatory condition resembling human psoriasis." *Blood* 102(1): 161-168, Jul. 1, 2003.

Yano, K. et al. "Control of hair growth and follicle size by VEGF-mediated angiogenesis." *The Journal of Clinical Investigation* 107(4): 409-417, Feb. 2001.

Zachary, I. et al. "Signaling transduction mechanisms mediating biological actions of the vascular endothelial growth factor family." *Cardiovasc Res* 49(3): 568-581, Feb. 16, 2001.

FIG. 1

```
                    aprE promoter region
         ~~~~~~~~~~~~~~~~~~~~~~~~~~~~~~~~~~~~~~~~~~~~~~~~~~~~
         EcoRI
         ~~~~~
     1   AATTCTCCAT TTTCTTCTGC TATCAAAATA ACAGACTCGT GATTTTCCAA aprE promoter region
         ~~~~~~~~~~~~~~~~~~~~~~~~~~~~~~~~~~~~~~~~~~~~~~~~~~~~
    51   ACGAGCTTTC AAAAAAGCCT CTGCCCCTTG CAAATCGGAT GCCTGTCTAT aprE promoter region
         ~~~~~~~~~~~~~~~~~~~~~~~~~~~~~~~~~~~~~~~~~~~~~~~~~~~~
                                            EagI
                                            ~~~~~~~
                                              NotI
                                              ~~~~~~~~~
   101   AAAATTCCCG ATATTGGTTA AACAGCGGCG CAATGGCGGC CGCATCTGAT aprE promoter region
         ~~~~~~~~~~~~~~~~~~~~~~~~~~~~~~~~~~~~~~~~~~~~~~~~~~~~
   151   GTCTTTGCTT GGCGAATGTT CATCTTATTT CTTCCTCCCT CTCAATAATT aprE promoter region
         ~~~~~~~~~~~~~~~~~~~~~~~~~~~~~~~~~~~~~~~~~~~~~~~~~~~~
   201   TTTTCATTCT ATCCCTTTTC TGTAAAGTTT ATTTTTCAGA ATACTTTTAT aprE promoter region
         ~~~~~~~~~~~~~~~~~~~~~~~~~~~~~~~~~~~~~~~~~~~~~~~~~~~~
   251   CATCATGCTT TGAAAAAATA TCACGATAAT ATCCATTGTT CTCACGGAAG aprE promoter region
         ~~~~~~~~~~~~~~~~~~~~~~~~~~~~~~~~~~~~~~~~~~~~~~~~~~~~
   301   CACACGCAGG TCATTTGAAC GAATTTTTTC GACAGGAATT TGCCGGGACT aprE promoter region
         ~~~~~~~~~~~~~~~~~~~~~~~~~~~~~~~~~~~~~~~~~~~~~~~~~~~~
   351   CAGGAGCATT TAACCTAAAA AAGCATGACA TTTCAGCATA ATGAACATTT aprE promoter region
         ~~~~~~~~~~~~~~~~~~~~~~~~~~~~~~~~~~~~~~~~~~~~~~~~~~~~
   401   ACTCATGTCT ATTTTCGTTC TTTTCTGTAT GAAAATAGTT ATTTCGAGTC aprE promoter region
         ~~~~~~~~~~~~~~~~~~~~~~~~~~~~~~~~~~~~~~~~~~~~~~~~~~~~
   451   TCTACGGAAA TAGCGAGAGA TGATATACCT AAATAGAGAT AAAATCATCT
```

*FIG. 1A*

```
                          aprE promoter region
                ~~~~~~~~~~~~~~~~~~~~~~~~~~~~~~~~~~~~~~~~~~~~~~~~~~~
         501    CAAAAAAATG GGTCTACTAA AATATTATTC CATCTATTAC AATAAATTCA aprE promoter region
                ~~~~~~~~~~~~~~~~~~~~~~~~~~~~~~~~~~~~~~~~~~~~~~~~~~~
         551    CAGAATAGTC TTTTAAGTAA GTCTACTCTG AATTTTTTTA AAAGGAGAGG AprE signal peptide
                          ~~~~~~~~~~~~~~~~~~~~~~~~~~~~~~~~~~~~~~~~~~
                aprE promoter region
                ~~~~~~~
                           M   R   S   K   K   L   W   I   S   L   L   F   A   L   T  •
         601    GTAAAGAGTG AGAAGCAAAA AATTGTGGAT CAGCTTGTTG TTTGCGTTAA AprE signal peptide
                ~~~~~~~~~~~~~~~~~~~~~~~~~~~~~~~~~~~~~~~~~~~~~~~~~~
                                                                    BCE103
                                                                    ~~~~~~
                •  L   I   F   T   M   A   F   S   N   M   S   A   Q   A   D   D
         651    CGTTAATCTT TACGATGGCG TTCAGCAACA TGTCTGCGCA GGCTGATGAT BCE103
                ~~~~~~~~~~~~~~~~~~~~~~~~~~~~~~~~~~~~~~~~~~~~~~~~~~
                   Y   S   V   V   E   E   H   G   Q   L   S   I   S   N   G   E   L  •
         701    TATTCAGTTG TAGAGGAACA TGGGCAACTA AGTATTAGTA ACGGTGAATT BCE103
                ~~~~~~~~~~~~~~~~~~~~~~~~~~~~~~~~~~~~~~~~~~~~~~~~~~
                                                                     NcoI
                                                                    ~~~~~
                •  V   N   E   R   G   E   Q   V   Q   L   K   G   M   S   S   H   G  •
         751    AGTCAATGAA CGAGGCGAAC AAGTTCAGTT AAAAGGGATG AGTTCCCATG BCE103
                ~~~~~~~~~~~~~~~~~~~~~~~~~~~~~~~~~~~~~~~~~~~~~~~~~~
                NcoI
                ~
                •  L   Q   W   Y   G   Q   F   V   N   Y   E   S   M   K   W   L
         801    GTTTGCAATG GTACGGTCAA TTTGTAAACT ATGAAAGCAT GAAATGGCTA BCE103
                ~~~~~~~~~~~~~~~~~~~~~~~~~~~~~~~~~~~~~~~~~~~~~~~~~~
                   R   D   D   W   G   I   T   V   F   R   A   A   M   Y   T   S   S  •
         851    AGAGATGATT GGGGAATAAC TGTATTCCGA GCAGCAATGT ATACCTCTTC BCE103
                ~~~~~~~~~~~~~~~~~~~~~~~~~~~~~~~~~~~~~~~~~~~~~~~~~~
                •  G   G   Y   I   D   D   P   S   V   K   E   K   V   K   E   T   V  •
         901    AGGAGGATAT ATTGACGATC CATCAGTAAA GGAAAAAGTA AAAGAGACTG BCE103
                ~~~~~~~~~~~~~~~~~~~~~~~~~~~~~~~~~~~~~~~~~~~~~~~~~~
                •  E   A   A   I   D   L   G   I   Y   V   I   I   D   W   H   I
         951    TTGAGGCTGC GATAGACCTT GGCATATATG TGATCATTGA TTGGCATATC
```

FIG. 1B

```
                            BCE103
          ~~~~~~~~~~~~~~~~~~~~~~~~~~~~~~~~~~~~~~~~~~~~~~~~~~~
           L   S   D   N   D   P   N   I   Y   K   E   E   A   K   D   F   F  •
     1001 CTTTCAGACA ATGACCCGAA TATATATAAA GAAGAAGCGA AGGATTTCTT

BCE103
          ~~~~~~~~~~~~~~~~~~~~~~~~~~~~~~~~~~~~~~~~~~~~~~~~~~~
          •  D   E   M   S   E   L   Y   G   D   Y   P   N   V   I   Y   E   I  •
     1051 TGATGAAATG TCAGAGTTGT ATGGAGACTA TCCGAATGTG ATATACGAAA

BCE103
          ~~~~~~~~~~~~~~~~~~~~~~~~~~~~~~~~~~~~~~~~~~~~~~~~~~~
          •  A   N   E   P   N   G   S   D   V   T   W   D   N   Q   I   K
     1101 TTGCAAATGA ACCGAATGGT AGTGATGTTA CGTGGGACAA TCAAATAAAA

BCE103
          ~~~~~~~~~~~~~~~~~~~~~~~~~~~~~~~~~~~~~~~~~~~~~~~~~~~
           P   Y   A   E   E   V   I   P   V   I   R   D   N   D   P   N   N  •
     1151 CCGTATGCAG AAGAAGTGAT TCCGGTTATT CGTGACAATG ACCCTAATAA

BCE103
          ~~~~~~~~~~~~~~~~~~~~~~~~~~~~~~~~~~~~~~~~~~~~~~~~~~~
          •  I   V   I   V   G   T   G   T   W   S   Q   D   V   H   H   A   A  •
     1201 CATTGTTATT GTAGGTACAG GTACATGGAG TCAGGATGTC CATCATGCAG

BCE103
          ~~~~~~~~~~~~~~~~~~~~~~~~~~~~~~~~~~~~~~~~~~~~~~~~~~~
          •  D   N   Q   L   A   D   P   N   V   M   Y   A   F   H   F   Y
     1251 CCGATAATCA GCTTGCAGAT CCTAACGTCA TGTATGCATT TCATTTTTAT

BCE103
          ~~~~~~~~~~~~~~~~~~~~~~~~~~~~~~~~~~~~~~~~~~~~~~~~~~~
           A   G   T   H   G   Q   N   L   R   D   Q   V   D   Y   A   L   D  •
     1301 GCAGGAACAC ATGGACAAAA TTTACGAGAC CAAGTAGATT ATGCATTAGA

BCE103
          ~~~~~~~~~~~~~~~~~~~~~~~~~~~~~~~~~~~~~~~~~~~~~~~~~~~
          •  Q   G   A   A   I   F   V   S   E   W   G   T   S   A   A   T   G  •
     1351 TCAAGGAGCA GCGATATTTG TTAGTGAATG GGGGACAAGT GCAGCTACAG

BCE103
          ~~~~~~~~~~~~~~~~~~~~~~~~~~~~~~~~~~~~~~~~~~~~~~~~~~~
          •  D   G   G   V   F   L   D   E   A   Q   V   W   I   D   F   M
     1401 GTGATGGTGG TGTGTTTTTA GATGAAGCAC AAGTGTGGAT TGACTTTATG

BCE103
          ~~~~~~~~~~~~~~~~~~~~~~~~~~~~~~~~~~~~~~~~~~~~~~~~~~~
           D   E   R   N   L   S   W   A   N   W   S   L   T   H   K   D   E  •
     1451 GATGAAAGAA ATTTAAGCTG GGCCAACTGG TCTCTAACGC ATAAGGATGA

BCE103
          ~~~~~~~~~~~~~~~~~~~~~~~~~~~~~~~~~~~~~~~~~~~~~~~~~~~
              PstI
           ~~~~~~~
          •  S   S   A   A   L   M   P   G   A   N   P   T   G   W   T   E  •
     1501 GTCATCTGCA GCGTTAATGC CAGGTGCAAA TCCAACTGGT GGTTGGACAG
```

*FIG. 1C*

```
                                    BCE103
            ·  A   E   L   S   P   S   G   T   F   V   R   E   K   I   R   E
      1551  AGGCTGAACT ATCTCCATCT GGTACATTTG TGAGGGAAAA AATAAGAGAA

BCE103
                                          1st CBD Linker
              S   A   S   I   P   P   S   D   P   T   P   P   S   D   P   G   E ·
      1601  TCAGCATCTA TTCCGCCAAG CGATCCAACA CCGCCATCTG ATCCAGGAGA BBI
                fusion site 1st CBD Linker BamHI            SacI ·  P   D   P   D   D   E   S   S   K   P   C   C   D   Q   C   A   C ·
      1651  ACCGGATCCA GACGATGAGA GCTCTAAACC CTGTTGCGAT CAATGCGCAT

BBI

·  T   K   S   N   P   P   Q   C   R   C   S   D   M   R   L   N
      1701  GTACGAAATC AAATCCTCCA CAGTGTCGGT GTTCCGATAT GCGTCTGAAT

BBI

SphI

S   C   H   S   A   C   K   S   C   I   C   A   L   S   Y   P   A ·
      1751  AGCTGTCATA GTGCATGCAA AAGCTGTATC TGCGCCCTGA GTTATCCAGC

BBI

SalI

·  Q   C   F   C   V   D   I   T   D   F   C   Y   E   P   C   K   P ·
      1801  TCAATGTTTT TGCGTCGACA TCACGGACTT CTGCTATGAG CCATGTAAAC

6xHIS

BBI
            ·  S   E   D   D   K   E   N   H   H   H   H   H   H   Stop    (SEQ ID NO:2)
      1851  CAAGCGAGGA CGATAAAGAG AACCATCATC ACCATCACCA TTAAAAGTTA LAT terminator HindIII 1901  ACAGAGGACG GATTTCCTGA AGGAAATCCG TTTTTTTATT TTTAAGCTTG    (SEQ ID NO:1)
```

FIG. 1D

```
              12BBIck81
       ~~~~~~~~~~~~~~~~~~~~~~~~~~~~~~~~~~~~~~~~~
    BamHI         SacI
    ~~~~~~        ~~~~~~
      D   P   D   D   E   S   S   K   P   C   C   D   Q   C   A   C   Y •
1   GGATCCAGAC GATGAGAGCT CTAAACCCTG TTGCGATCAA TGCGCATGTT
    CCTAGGTCTG CTACTCTCGA GATTTGGGAC AACGCTAGTT ACGCGTACAA

12BBIck81
      ~~~~~~~~~~~~~~~~~~~~~~~~~~~~~~~~~~~~~~~~~~~~~~~
                                 PstI              EcoRI
                                 ~~~~~~~           ~~~~~~
    •  N   L   Y   G   W   T   C   R   C   S   D   M   R   L   N   S
51  ATAATTTGTA TGGGTGGACT TGTCGCTGCA GCGATATGCG TCTGAATTCC
    TATTAAACAT ACCCACCTGA ACAGCGACGT CGCTATACGC AGACTTAAGG

12BBIck81
      ~~~~~~~~~~~~~~~~~~~~~~~~~~~~~~~~~~~~~~~~~~~~
      C   H   S   A   C   K   S   C   A   C   Y   N   L   Y   G   W   T •
101 TGTCATAGTG CCTGCAAAAG CTGCGCATGT TATAACCTGT ACGGGTGGAC
    ACAGTATCAC GGACGTTTTC GACGCGTACA ATATTGGACA TGCCCACCTG

12BBIck81
      ~~~~~~~~~~~~~~~~~~~~~~~~~~~~~~~~~~~~~~~~
           SalI
           ~~~~~~
    •  C   F   C   V   D   I   T   D   F   C   Y   E   P   C   K   P   S •
151 CTGTTTTTGC GTCGACATCA CGGACTTCTG CTATGAGCCA TGTAAACCAA
    GACAAAAACG CAGCTGTAGT GCCTGAAGAC GATACTCGGT ACATTTGGTT

12BBIck81
      ~~~~~~~~~~~~~~~~~~~~~~~~~~
    •  E   D   D   K   E   N   *   (SEQ ID NO:4)
201 GCGAGGACGA TAAAGAGAAC TAA      (SEQ ID NO:3)
    CGCTCCTGCT ATTTCTCTTG ATT
```

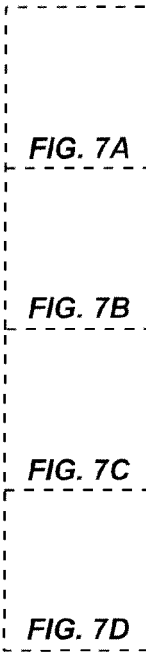
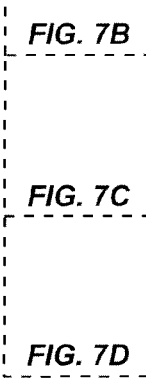
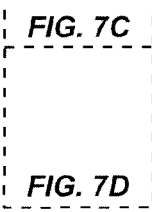
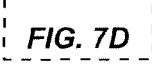

```
                          hiPDI
         ~~~~~~~~~~~~~~~~~~~~~~~~~~~~~~~~~~~~~~~~~~~~~~~
     AprE signal cleavage site
     ~~~~~~~~~~~~~~
       BssHII    NheI         BsrGI
       ~~~~~~    ~~~~~~~      ~~~~~~
       S  A  Q  A  S  D  V    V  Y  N  L  K  K  D    F  D  D •
  1    AGCGCGCAGG CTAGCGATGT TGTACAACTG AAAAAAGACA CTTTCGACGA
       TCGCGCGTCC GATCGCTACA ACATGTTGAC TTTTTTCTGT GAAAGCTGCT hiPDI
         ~~~~~~~~~~~~~~~~~~~~~~~~~~~~~~~~~~~~~~~~~~~~~~~~~~~~~
       • F  I  K  T  N  D  L  V  L  A  E  F  F  A  P  W  C •
 51    CTTCATCAAA ACAAATGACC TTGTTCTTGC TGAATTTTTC GCGCCGTGGT
       GAAGTAGTTT TGTTTACTGG AACAAGAACG ACTTAAAAAG CGCGGCACCA hiPDI
         ~~~~~~~~~~~~~~~~~~~~~~~~~~~~~~~~~~~~~~~~~~~~~~~~~~~~~
       • G  H  C  K  A  L  A  P  E  Y  E  E  A  A  T  T
101    GCGGTCACTG CAAAGCTCTT GCTCCTGAGT ACGAGGAAGC TGCAACTACA
       CGCCAGTGAC GTTTCGAGAA CGAGGACTCA TGCTCCTTCG ACGTTGATGT hiPDI
         ~~~~~~~~~~~~~~~~~~~~~~~~~~~~~~~~~~~~~~~~~~~~~~~~~~~~~
       L  K  E  K  N  I  K  L  A  K  V  D  C  T  E  E  T •
151    CTGAAAGAAA AGAACATCAA ACTTGCTAAA GTAGACTGCA CAGAAGAGAC
       GACTTTCTTT TCTTGTAGTT TGAACGATTT CATCTGACGT GTCTTCTCTG hiPDI
         ~~~~~~~~~~~~~~~~~~~~~~~~~~~~~~~~~~~~~~~~~~~~~~~~~~~~~
       • D  L  C  Q  Q  H  G  V  E  G  Y  P  T  L  K  V  F •
201    TGATCTTTGC CAACAACATG GTGTTGAGGG CTACCCAACT CTTAAAGTTT
       ACTAGAAACG GTTGTTGTAC CACAACTCCC GATGGGTTGA GAATTTCAAA
```

FIG. 7A

```
                              hiPDI
     ·  R    G    L    D    N    V    S    P    Y    K    G    Q    R    K    A    A
251  TCCGTGGCCT TGACAACGTA TCTCCTTACA AAGGTCAACG TAAAGCTGCT
     AGGCACCGGA ACTGTTGCAT AGAGGAATGT TTCCAGTTGC ATTTCGACGA hiPDI
        A    I    T    S    Y    M    I    K    Q    S    L    P    A    V    S    E    V ·
301  GCAATCACTT CATACATGAT CAAACAATCT CTGCCTGCTG TATCTGAAGT
     CGTTAGTGAA GTATGTACTA GTTTGTTAGA GACGGACGAC ATAGACTTCA hiPDI
     ·  T    K    D    N    L    E    E    F    K    K    A    D    K    A    V    L    V ·
351  TACAAAAGAC AACCTTGAAG AATTTAAAAA AGCTGACAAA GCTGTTCTTG
     ATGTTTTCTG TTGGAACTTC TTAAATTTTT TCGACTGTTT CGACAAGAAC hiPDI
     ·  A    Y    V    D    A    S    D    K    A    S    S    E    V    F    T    Q
401  TTGCTTATGT AGATGCTTCT GACAAAGCAT CTAGCGAAGT TTTCACTCAA
     AACGAATACA TCTACGAAGA CTGTTTCGTA GATCGCTTCA AAAGTGAGTT hiPDI
        V    A    E    K    L    R    D    N    Y    P    F    G    S    S    S    D    A ·
451  GTTGCTGAAA AACTGCGCGA TAACTACCCA TTCGGCTCTA GCTCTGATGC
     CAACGACTTT TTGACGCGCT ATTGATGGGT AAGCCGAGAT CGAGACTACG hiPDI
     ·  A    L    A    E    A    E    G    V    K    P    A    I    V    L    Y    K ·
501  TGCACTGGCT GAAGCTGAGG GCGTTAAAGC ACCTGCTATT GTTCTTTACA
     ACGTGACCGA CTTCGACTCC CGCAATTTCG TGGACGATAA CAAGAAATGT hiPDI
     ·    D    F    D    E    G    K    A    V    F    S    E    K    F    E    V    E
551  AAGACTTTGA TGAAGGTAAA GCGGTTTTCT CTGAAAAATT CGAAGTAGAG
     TTCTGAAACT ACTTCCATTT CGCCAAAAGA GACTTTTTAA GCTTCATCTC hiPDI
        A    I    E    K    F    A    K    T    G    A    T    P    L    I    G    E    I ·
601  GCAATCGAAA AATTCGCTAA AACAGGTGCT ACTCCACTTA TTGGCGAAAT
     CGTTAGCTTT TTAAGCGATT TTGTCCACGA TGAGGTGAAT AACCGCTTTA hiPDI
     ·   G    P    E    T    Y    S    D    Y    M    S    A    G    I    P    L    A    Y ·
651  CGGACCTGAA ACTTACTCTG ATTACATGTC AGCTGGCATC CCTCTGGCAT
     GCCTGGACTT TGAATGAGAC TAATGTACAG TCGACCGTAG GGAGACCGTA
```

*FIG. 7B*

```
                                  hiPDI
              ~~~~~~~~~~~~~~~~~~~~~~~~~~~~~~~~~~~~~~~~~~~~~~~~
                            SapI
                          ~~~~~~~
            • I  F  A   E  T  A   E  E  R   K  E  L   S  D  K  L
       701  ACATTTTCGC TGAAACAGCT GAAGAGCGTA AAGAACTCAG CGACAAACTT
            TGTAAAAGCG ACTTTGTCGA CTTCTCGCAT TTCTTGAGTC GCTGTTTGAA hiPDI
              ~~~~~~~~~~~~~~~~~~~~~~~~~~~~~~~~~~~~~~~~~~~~~~~~
               K  P  I   A  E  A  Q   R  G  V   I  N  F   G  T  I  D •
       751  AAACCAATCG CTGAAGCTCA ACGTGGCGTT ATTAACTTTG GTACTATTGA
            TTTGGTTAGC GACTTCGAGT TGCACCGCAA TAATTGAAAC CATGATAACT hiPDI
              ~~~~~~~~~~~~~~~~~~~~~~~~~~~~~~~~~~~~~~~~~~~~~~~~
            • A  K  A   F  G  A  H   A  G  N   L  N  L   K  T  D  K •
       801  CGCTAAAGCA TTTGGTGCTC ACGCTGGAAA CCTGAATCTG AAAACTGACA
            GCGATTTCGT AAACCACGAG TGCGACCTTT GGACTTAGAC TTTTGACTGT hiPDI
              ~~~~~~~~~~~~~~~~~~~~~~~~~~~~~~~~~~~~~~~~~~~~~~~~
            • F  P  A   F  A  I   Q  E  V   A  K  N   Q  K  F  P
       851  AATTCCCTGC TTTCGCAATC CAAGAAGTTG CTAAAAACCA AAAATTCCCT
            TTAAGGGACG AAAGCGTTAG GTTCTTCAAC GATTTTTGGT TTTTAAGGGA hiPDI
              ~~~~~~~~~~~~~~~~~~~~~~~~~~~~~~~~~~~~~~~~~~~~~~~~
               F  D  Q   E  K  E  I   T  F  E   A  I  K   A  F  V  D •
       901  TTTGATCAAG AAAAAGAAAT TACTTTTGAA GCGATCAAAG CATTCGTTGA
            AAACTAGTTC TTTTTCTTTA ATGAAAACTT CGCTAGTTTC GTAAGCAACT hiPDI
              ~~~~~~~~~~~~~~~~~~~~~~~~~~~~~~~~~~~~~~~~~~~~~~~~
            • D  F  V   A  G  K  I   E  P  S   I  K  S   E  P  I  P •
       951  CGATTTTGTT GCTGGTAAAA TCGAACCAAG CATCAAATCA GAACCAATCC
            GCTAAAACAA CGACCATTTT AGCTTGGTTC GTAGTTTAGT CTTGGTTAGG hiPDI
              ~~~~~~~~~~~~~~~~~~~~~~~~~~~~~~~~~~~~~~~~~~~~~~~~
            • E  K  Q   E  G  P   V  T  V   V  V  A  K   N  Y  N
      1001  CTGAAAAACA AGAAGGTCCT GTTACTGTAG TTGTAGCTAA AAACTACAAT
            GACTTTTTGT TCTTCCAGGA CAATGACATC AACATCGATT TTTGATGTTA hiPDI
              ~~~~~~~~~~~~~~~~~~~~~~~~~~~~~~~~~~~~~~~~~~~~~~~~
               E  I  V   L  D  D  T   K  D  V   L  I  E  F   Y  A  P •
      1051  GAAATCGTTC TGGACGATAC TAAAGATGTA TTAATTGAAT TTTACGCTCC
            CTTTAGCAAG ACCTGCTATG ATTTCTACAT AATTAACTTA AAATGCGAGG hiPDI
              ~~~~~~~~~~~~~~~~~~~~~~~~~~~~~~~~~~~~~~~~~~~~~~~~
            • W  C  G   H  C  K   A  L  A  P   K  Y  E   E  L  G  A •
      1101  TTGGTGCGGT CACTGCAAAG CTCTTGCTCC TAAATACGAA GAACTTGGTG
            AACCACGCCA GTGACGTTTC GAGAACGAGG ATTTATGCTT CTTGAACCAC
```

*FIG. 7C*

```
                               hiPDI
      ~~~~~~~~~~~~~~~~~~~~~~~~~~~~~~~~~~~~~~~~~~~~~~~~~~~
         . L   Y   A   K   S   E   F   K   D   R   V   V   I   A   K   V
1151  CTCTGTATGC AAAAAGCGAG TTCAAAGACC GTGTTGTAAT TGCTAAAGTT
      GAGACATACG TTTTTCGCTC AAGTTTCTGG CACAACATTA ACGATTTCAA hiPDI
      ~~~~~~~~~~~~~~~~~~~~~~~~~~~~~~~~~~~~~~~~~~~~~~~~~~~
         D   A   T   A   N   D   V   P   D   E   I   Q   G   F   P   T   I   .
1201  GATGCAACAG CTAACGATGT TCCAGATGAA ATTCAAGGAT TCCCTACTAT
      CTACGTTGTC GATTGCTACA AGGTCTACTT TAAGTTCCTA AGGGATGATA hiPDI
      ~~~~~~~~~~~~~~~~~~~~~~~~~~~~~~~~~~~~~~~~~~~~~~~~~~~
       . K   L   Y   P   A   G   A   K   G   Q   P   V   T   Y   S   G   S   .
1251  CAAACTATAC CCAGCTGGTG CAAAAGGTCA ACCTGTTACT TACTCTGGTT
      GTTTGATATG GGTCGACCAC GTTTTCCAGT TGGACAATGA ATGAGACCAA hiPDI
      ~~~~~~~~~~~~~~~~~~~~~~~~~~~~~~~~~~~~~~~~~~~~~~~~~~~
       . R   T   V   E   D   L   I   K   F   I   A   E   N   G   K   Y
1301  CACGCACTGT TGAAGACCTT ATCAAATTCA TTGCTGAAAA CGGTAAATAC
      GTGCGTGACA ACTTCTGGAA TAGTTTAAGT AACGACTTTT GCCATTTATG hiPDI
      ~~~~~~~~~~~~~~~~~~~~~~~~~~~~~~~~~~~~~~~~~~~~~~~~~~~
                                              SpeI
                                           ~~~~~~
         K   A   A   I   S   E   D   A   E   E   T   S   S   A   T   E   T   .
1351  AAAGCTGCAA TCTCAGAAGA TGCTGAAGAG ACTAGTTCAG CAACTGAAAC
      TTTCGACGTT AGAGTCTTCT ACGACTTCTC TGATCAAGTC GTTGACTTTG hiPDI
      ~~~~~~~~~~~~~~~~~~~~~~~~~~~~~~~~~~~~~~~~~~~~~~~~~~~
       . T   T   E   T   A   T   K   S   E   E   A   A   K   E   T   A   T   .
1401  AACTACAGAA ACTGCTACAA AGTCAGAAGA AGCTGCAAAA GAAACTGCAA
      TTGATGTCTT TGACGATGTT TCAGTCTTCT TCGACGTTTT CTTTGACGTT

Enteropeptidase cleavage linker
                                       ~~~~~~~~~~~~~~~~~~~~~~~~~~~~~~
             hiPDI                                               N-term BBI
      ~~~~~~~~~~~~~~~~~~~                                        ~~~
       . E   H   D   E   L   G   S   G   S   G   D   D   D   K   D
1451  CAGAACACGA CGAACTTGGA TCTGGTTCCG GAGATGACGA TGACAAAGAC
      GTCTTGTGCT GCTTGAACCT AGACCAAGGC CTCTACTGCT ACTGTTTCTG N-term BBI
      ~~~~~~~~~~~~~~
            SacI
           ~~~~~~
         D   E   S   S
1501  GATGAGAGCT CT   (SEQ ID NO:5)
      CTACTCTCGA GA   (SEQ ID NO:6)
```

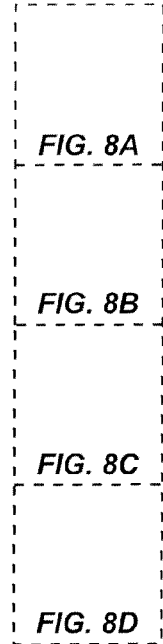
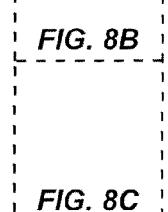
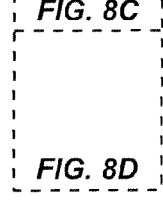
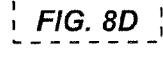

```
            aprE promoter
    ~~~~~~~~~~~~~~~~~~~~~~~~~~~~~~~~~~~~~~~~~~~~~~~~~~~
    EcoRI
    ~~~~~~
1   GAATTCTCCA TTTTCTTCTG CTATCAAAAT AACAGACTCG TGATTTTCCA
    CTTAAGAGGT AAAAGAAGAC GATAGTTTTA TTGTCTGAGC ACTAAAAGGT aprE promoter
    ~~~~~~~~~~~~~~~~~~~~~~~~~~~~~~~~~~~~~~~~~~~~~~~~~~~
51  AACGAGCTTT CAAAAAAGCC TCTGCCCCTT GCAAATCGGA TGCCTGTCTA
    TTGCTCGAAA GTTTTTTCGG AGACGGGGAA CGTTTAGCCT ACGGACAGAT aprE promoter
    ~~~~~~~~~~~~~~~~~~~~~~~~~~~~~~~~~~~~~~~~~~~~~~~~~~~
                                            NotI
                                            ~~~~~~~~~
101 TAAAATTCCC GATATTGGTT AAACAGCGGC GCAATGGCGG CCGCATCTGA
    ATTTTAAGGG CTATAACCAA TTTGTCGCCG CGTTACCGCC GGCGTAGACT
```

FIG. 8A

```
                              aprE promoter
         ~~~~~~~~~~~~~~~~~~~~~~~~~~~~~~~~~~~~~~~~~~~~~~~~~~~~~~
   151   TGTCTTTGCT TGGCGAATGT TCATCTTATT TCTTCCTCCC TCTCAATAAT
         ACAGAAACGA ACCGCTTACA AGTAGAATAA AGAAGGAGGG AGAGTTATTA aprE promoter
         ~~~~~~~~~~~~~~~~~~~~~~~~~~~~~~~~~~~~~~~~~~~~~~~~~~~~~~
   201   TTTTTCATTC TATCCCTTTT CTGTAAAGTT TATTTTTCAG AATACTTTTA
         AAAAAGTAAG ATAGGGAAAA GACATTTCAA ATAAAAAGTC TTATGAAAAT aprE promoter
         ~~~~~~~~~~~~~~~~~~~~~~~~~~~~~~~~~~~~~~~~~~~~~~~~~~~~~~
   251   TCATCATGCT TTGAAAAAAT ATCACGATAA TATCCATTGT TCTCACGGAA
         AGTAGTACGA AACTTTTTTA TAGTGCTATT ATAGGTAACA AGAGTGCCTT aprE promoter
         ~~~~~~~~~~~~~~~~~~~~~~~~~~~~~~~~~~~~~~~~~~~~~~~~~~~~~~
   301   GCACACGCAG GTCATTTGAA CGAATTTTTT CGACAGGAAT TTGCCGGGAC
         CGTGTGCGTC CAGTAAACTT GCTTAAAAAA GCTGTCCTTA AACGGCCCTG aprE promoter
         ~~~~~~~~~~~~~~~~~~~~~~~~~~~~~~~~~~~~~~~~~~~~~~~~~~~~~~
   351   TCAGGAGCAT TTAACCTAAA AAAGCATGAC ATTTCAGCAT AATGAACATT
         AGTCCTCGTA AATTGGATTT TTTCGTACTG TAAAGTCGTA TTACTTGTAA aprE promoter
         ~~~~~~~~~~~~~~~~~~~~~~~~~~~~~~~~~~~~~~~~~~~~~~~~~~~~~~
   401   TACTCATGTC TATTTTCGTT CTTTTCTGTA TGAAAATAGT TATTTCGAGT
         ATGAGTACAG ATAAAAGCAA GAAAAGACAT ACTTTTATCA ATAAAGCTCA aprE promoter
         ~~~~~~~~~~~~~~~~~~~~~~~~~~~~~~~~~~~~~~~~~~~~~~~~~~~~~~
   451   CTCTACGGAA ATAGCGAGAG ATGATATACC TAAATAGAGA TAAAATCATC
         GAGATGCCTT TATCGCTCTC TACTATATGG ATTTATCTCT ATTTTAGTAG aprE promoter
         ~~~~~~~~~~~~~~~~~~~~~~~~~~~~~~~~~~~~~~~~~~~~~~~~~~~~~~
   501   TCAAAAAAAT GGGTCTACTA AAATATTATT CCATCTATTA CAATAAATTC
         AGTTTTTTTA CCCAGATGAT TTTATAATAA GGTAGATAAT GTTATTTAAG aprE promoter
         ~~~~~~~~~~~~~~~~~~~~~~~~~~~~~~~~~~~~~~~~~~~~~~~~~~~~~~
   551   ACAGAATAGT CTTTTAAGTA AGTCTACTCT GAATTTTTTT AAAAGGAGAG
         TGTCTTATCA GAAAATTCAT TCAGATGAGA CTTAAAAAAA TTTTCCTCTC aprE promoter
         ~~~~~~~~~
                              AprE signal peptide
                    ~~~~~~~~~~~~~~~~~~~~~~~~~~~~~~~~~~~~~~~~~~~~
                    V  R  S  K  K  L  W  I  S  L  L  F  A  L
   601   GGTAAAGAGT GAGAAGCAAA AAATTGTGGA TCAGCTTGTT GTTTGCGTTA
         CCATTTCTCA CTCTTCGTTT TTTAACACCT AGTCGAACAA CAAACGCAAT
```

FIG. 8B

```
                                                                Cutinase
                                                                ~~~~~
                    Cutinase signal peptide
         ~~~~~~~~~~~~~~~~~~~~~~~~~~~~~~~~~~~~~~~~~~~~~~~~~~~~~
          T   L   A   A   S   C   L   S   V   C   A   T   V   A   A   A   P •
   651   ACGCTGGCGG CCTCTTGCCT GTCCGTCTGT GCCACTGTCG CGGCGGCTCC
         TGCGACCGCC GGAGAACGGA CAGGCAGACA CGGTGACAGC GCCGCCGAGG Cutinase
         ~~~~~~~~~~~~~~~~~~~~~~~~~~~~~~~~~~~~~~~~~~~~~~~~~~~~~
         • L   P   D   T   P   G   A   P   F   P   A   V   A   N   F   D   R •
   701   CCTGCCGGAT ACACCGGGAG CGCCATTTCC GGCTGTCGCC AATTTCGACC
         GGACGGCCTA TGTGGCCCTC GCGGTAAAGG CCGACAGCGG TTAAAGCTGG Cutinase
         ~~~~~~~~~~~~~~~~~~~~~~~~~~~~~~~~~~~~~~~~~~~~~~~~~~~~~
         •   S   G   P   Y   T   T   S   S   Q   S   E   G   P   S   C   R
   751   GCAGTGGCCC CTACACCACC AGCAGCCAGA GCGAGGGGCC GAGCTGTCGC
         CGTCACCGGG GATGTGGTGG TCGTCGGTCT CGCTCCCCGG CTCGACAGCG Cutinase
         ~~~~~~~~~~~~~~~~~~~~~~~~~~~~~~~~~~~~~~~~~~~~~~~~~~~~~
          I   Y   R   P   R   D   L   G   Q   G   G   V   R   H   P   V   I •
   801   ATCTATCGGC CCCGCGACCT GGGTCAGGGG GGCGTGCGTC ATCCGGTGAT
         TAGATAGCCG GGGCGCTGGA CCCAGTCCCC CCGCACGCAG TAGGCCACTA Cutinase
         ~~~~~~~~~~~~~~~~~~~~~~~~~~~~~~~~~~~~~~~~~~~~~~~~~~~~~
         • L   W   G   N   G   T   G   A   G   P   S   T   Y   A   G   L   L •
   851   TCTCTGGGGC AATGGCACCG GTGCCGGGCC GTCCACCTAT GCCGGCTTGC
         AGAGACCCCG TTACCGTGGC CACGGCCCGG CAGGTGGATA CGGCCGAACG Cutinase
         ~~~~~~~~~~~~~~~~~~~~~~~~~~~~~~~~~~~~~~~~~~~~~~~~~~~~~
         •   S   H   W   A   S   H   G   F   V   V   A   A   A   E   T   S
   901   TATCGCACTG GGCAAGCCAC GGTTTCGTGG TGGCGGCGGC GGAAACCTCC
         ATAGCGTGAC CCGTTCGGTG CCAAAGCACC ACCGCCGCCG CCTTTGGAGG Cutinase
         ~~~~~~~~~~~~~~~~~~~~~~~~~~~~~~~~~~~~~~~~~~~~~~~~~~~~~
          N   A   G   T   G   R   E   M   L   A   C   L   D   Y   L   V   R •
   951   AATGCCGGTA CCGGGCGGGA AATGCTCGCC TGCCTGGACT ATCTGGTACG
         TTACGGCCAT GGCCCGCCCT TTACGAGCGG ACGGACCTGA TAGACCATGC Cutinase
         ~~~~~~~~~~~~~~~~~~~~~~~~~~~~~~~~~~~~~~~~~~~~~~~~~~~~~
         • E   N   D   T   P   Y   G   T   Y   S   G   K   L   N   T   G   R •
  1001   TGAGAACGAC ACCCCCTACG GCACCTATTC CGGCAAGCTC AATACCGGGC
         ACTCTTGCTG TGGGGGATGC CGTGGATAAG GCCGTTCGAG TTATGGCCCG Cutinase
         ~~~~~~~~~~~~~~~~~~~~~~~~~~~~~~~~~~~~~~~~~~~~~~~~~~~~~
         • V   G   T   S   G   H   S   Q   G   G   G   G   S   I   M   A
  1051   GAGTCGGCAC TTCTGGGCAT TCCCAGGGTG GTGGCGGCTC GATCATGGCC
         CTCAGCCGTG AAGACCCGTA AGGGTCCCAC CACCGCCGAG CTAGTACCGG
```

FIG. 8C

```
                              Cutinase
       ~~~~~~~~~~~~~~~~~~~~~~~~~~~~~~~~~~~~~~~~~~~~~~~~~~~~~~~~
        G    Q    D    T    R    V    R    T    T    A    P    I    Q    P    Y    T    L  •
1101   GGGCAGGATA CGAGGGTGCG TACCACGGCG CCGATCCAGC CCTACACCCT
       CCCGTCCTAT GCTCCCACGC ATGGTGCCGC GGCTAGGTCG GGATGTGGGA Cutinase
       ~~~~~~~~~~~~~~~~~~~~~~~~~~~~~~~~~~~~~~~~~~~~~~~~~~~~~~~~
        •   G    L    G    H    D    S    A    S    Q    R    R    Q    Q    G    P    M    F  •
1151   CGGCCTGGGG CACGACAGCG CCTCGCAGCG GCGGCAGCAG GGGCCGATGT
       GCCGGACCCC GTGCTGTCGC GGAGCGTCGC CGCCGTCGTC CCCGGCTACA Cutinase
       ~~~~~~~~~~~~~~~~~~~~~~~~~~~~~~~~~~~~~~~~~~~~~~~~~~~~~~~~
        •    L    M    S    G    G    G    D    T    I    A    F    P    Y    L    N    A
1201   TCCTGATGTC CGGTGGCGGT GACACCATCG CCTTTCCCTA CCTCAACGCT
       AGGACTACAG GCCACCGCCA CTGTGGTAGC GGAAAGGGAT GGAGTTGCGA Cutinase
       ~~~~~~~~~~~~~~~~~~~~~~~~~~~~~~~~~~~~~~~~~~~~~~~~~~~~~~~~
        Q    P    V    Y    R    R    A    N    V    P    V    F    W    G    E    R    R  •
1251   CAGCCGGTCT ACCGGCGTGC CAATGTGCCG GTGTTCTGGG GCGAACGGCG
       GTCGGCCAGA TGGCCGCACG GTTACACGGC CACAAGACCC CGCTTGCCGC°

Cutinase
       ~~~~~~~~~~~~~~~~~~~~~~~~~~~~~~~~~~~~~~~~~~~~~~~~~~~~~~~~
        •  Y    V    S    H    F    E    P    V    G    S    G    G    A    Y    R    G    P  •
1301   TTACGTCAGC CACTTCGAGC CGGTCGGTAG CGGTGGGGCC TATCGCGGCC
       AATGCAGTCG GTGAAGCTCG GCCAGCCATC GCCACCCCGG ATAGCGCCGG Cutinase
       ~~~~~~~~~~~~~~~~~~~~~~~~~~~~~~~~~~~~~~~~~~~~~~~~~~~~~~~~
        •  S    T    A    W    F    R    F    Q    L    M    D    D    Q    D    A    R
1351   CGAGCACGGC ATGGTTCCGC TTCCAGCTGA TGGATGACCA AGACGCCCGC
       GCTCGTGCCG TACCAAGGCG AAGGTCGACT ACCTACTGGT TCTGCGGGCG Cutinase
       ~~~~~~~~~~~~~~~~~~~~~~~~~~~~~~~~~~~~~~~~~~~~~~~~~~~~~~~~
                                              Alw44I
                                             ~~~~~~~
        A    T    F    Y    G    A    Q    C    S    L    C    T    S    L    L    W    S  •
1401   GCTACCTTCT ACGGCGCGCA GTGCAGTCTG TGCACTTCTC TGCTTTGGTC
       CGATGGAAGA TGCCGCGCGT CACGTCAGAC ACGTGAAGAG ACGAAACCAG Linker 2
                              ~~~~~~~~~~~~~~~~~~~~~~~~~~~~~~
                Cutinase
       ~~~~~~~~~~~~~~~~~~~~
                                                        BamHI
                                                       ~~~~~~~
        •  V    E    R    R    G    L    D    N    N    D    P    I    P    D
1451   TGTTGAACGC AGAGGTCTTG ACAACAATGA TCCTATTCCG GATCC   (SEQ ID NO:7)
       ACAACTTGCG TCTCCAGAAC TGTTGTTACT AGGATAAGGC CTAGG   (SEQ ID NO:8)
```

FIG. 8D

Trypsin Loop — VEGF Loop

```
BBIt-AV  = DDESSKPCCDQCACTKSNPPQCRCSDMRLNSCHSACKSCACYNLYGWTCF
BBdb-AV  = PSESSKPCCDQCACTKSIPPQCRCTDVRLNSCHSACSSCACYNLYGWTCV
BBsb3-AV = DDEYSKPCCDLCMCTRSMPPQCSCEDIRLNSCHSDCKSCACYNLYGWTCR
BBtc-AV  = -SSKWEACCDRCACTKSIPPQCHCADIRLNSCHSACESCACYNLYGWTCR

BBIt-AV  = CVDITDFCYEPCKPSE     (SEQ ID NO:187)
BBdb-AV  = CVDMKDFCYEPCK        (SEQ ID NO:452)
BBsb3-AV = CLDTNDFCYKPCKSRDD    (SEQ ID NO:453)
BBtc-AV  = CFDITDFCYKPCSG       (SEQ ID NO:454)
```

FIG. 15

```
              1      4 5       *     *  11 13 *      18       *  *25 27 29 31 *       *   38*40*          *50
BBIt-AV   =   DDESSKPCCDQCACTKSNPPQCRCSDMRLNSCHSACKSCACYNLYGWTCF
BBdb-AV   =   PSESSKPCCDQCACTKSIPPQCRCTDVRLNSCHSACSSCACYNLYGWTCV
BBsb3-AV  =   DDEYSKPCCDLCMCTRSMPPQCSCEDIRLNSCHSDCKSCACYNLYGWTCR
BBtc-AV   =   -SSKWEACCDRCACTKSIPPQCHCADIRLNSCHSACESCACYNLYGWTCR
BBI       =   DDESSKPCCDQCACTKSNPPQCRCSDMRLNSCHSACKSCICALSYPAQCF
BBIt      =   DDESSKPCCDQCACTKSNPPQCRCSDMRLNSCHSACKSCICALSYPAQCF
BBdb      =   PSESSKPCCDQCACTKSIPPQCRCTDVRLNSCHSACSSCVCTFSIPAQCV
BBsb3     =   DDEYSKPCCDLCMCTRSMPPQCSCEDIRLNSCHSDCKSCMCTRSQPGQCR
BBtc      =   -SSKWEACCDRCACTKSIPPQCHCADIRLNSCHSACESCACTHSIPAQCR

*52  55      *         65
BBIt-AV   =   CVDITDFCYEPCKPSE                    (SEQ ID NO:187)
BBdb-AV   =   CVDMKDFCYEPCK                       (SEQ ID NO:452)
BBsb3-AV  =   CLDTNDFCYKPCKSRDD                   (SEQ ID NO:453)
BBtc-AV   =   CFDITDFCYKPCSG                      (SEQ ID NO:454)
BBI       =   CVDITDFCYEPCKPSEDDKEN               (SEQ ID NO:13)
BBIt      =   CVDITDFCYEPCKPSE                    (SEQ ID NO:185)
BBdb      =   CVDMKDFCYEPCK                       (SEQ ID NO:449)
BBsb3     =   CLDTNDFCYKPCKSRDD                   (SEQ ID NO:450)
BBtc      =   CFDITDFCYKPCSG                      (SEQ ID NO:451)
```

FIG. 17

SEQUENCE LISTING

```
<160> NUMBER OF SEQ ID NOS: 685

<210> SEQ ID NO 1
<211> LENGTH: 1900
<212> TYPE: DNA
<213> ORGANISM: Artificial
<220> FEATURE:
<223> OTHER INFORMATION: synthetic sequence encoding fusion peptide of
      SEQ ID NO:2

<400> SEQUENCE: 1
aattctccat tttcttctgc tatcaaaata acagactcgt gattttccaa acgagctttc      60
aaaaaagcct ctgccccttg caaatcggat gcctgtctat aaaattcccg atattggtta    120
aacagcggcg caatggcggc cgcatctgat gtctttgctt ggcgaatgtt catcttattt    180
cttcctccct ctcaataatt ttttcattct atcccttttc tgtaaagttt attttcaga    240 atactttat catcatgctt tgaaaaata tcacgataat atccattgtt ctcacggaag     300
cacacgcagg tcatttgaac gaatttttc gacaggaatt tgccgggact caggagcatt    360
taacctaaaa aagcatgaca tttcagcata atgaacattt actcatgtct attttcgttc   420
ttttctgtat gaaaatagtt atttcgagtc tctacgaaa tagcgagaga tgatatacct    480
aaatagagat aaaatcatct caaaaaatg ggtctactaa aatattattc catctattac    540
aataaattca gtaaagagtg agaagcaaaa aattgtggat cagcttgttg tttgcgttaa    600
cgttaatctt tacgatggcg ttcagcaaca tgtctgcgca ggctgatgat tattcagttg    660
tagaggaaca tgggcaacta agtattagta acggtgaatt agtcaatgaa cgaggcgaac    720
aagttcagtt aaaagggatg agttcccatg gtttgcaatg gtacggtcaa tttgtaaact    780
atgaaagcat gaaatggcta agagatgatt ggggaataac tgtattccga gcagcaatgt    840
atacctcttc aggaggatat attgacgatc catcagtaaa ggaaaaagta aaagagactg    900
ttgaggctgc gatagacctt ggcatatatg tgatcattga ttggcatatc ctttcagaca    960
atgacccgaa tatatataaa gaagaagcga aggatttctt tgatgaaatg tcagagttgt   1020
atggagacta tccgaatgtg atatacgaaa ttgcaaatga accgaatggt agtgatgtta   1080
cgtgggacaa tcaaataaaa ccgtatgcag aagaagtgat tccggttatt cgtgacaatg   1140
accctaataa cattgttatt gtaggtacag gtacatggag tcaggatgtc catcatgcag   1200
ccgataatca gcttgcagat cctaacgtca tgtatgcatt tcattttat gcaggaacac   1260 atggacaaaa tttacgagac caagtagatt atgcattaga tcaaggagca gcgatatttg   1320
```

-continued

```
ttagtgaatg ggggacaagt gcagctacag gtgatggtgg tgtgttttta gatgaagcac    1380
aagtgtggat tgactttatg gatgaaagaa atttaagctg ggccaactgg tctctaacgc    1440
ataaggatga gtcatctgca gcgttaatgc caggtgcaaa tccaactggt ggttggacag    1500
aggctgaact atctccatct ggtacatttg tgagggaaaa aataagagaa tcagcatcta    1560
ttccgccaag cgatccaaca ccgccatctg atccaggaga accggatcca gacgatgaga    1620
gctctaaacc ctgttgcgat caatgcgcat gtacgaaatc aaatcctcca cagtgtcggt    1680
gttccgatat gcgtctgaat agctgtcata gtgcatgcaa aagctgtatc tgcgccctga    1740
gttatccagc tcaatgtttt tgcgtcgaca tcacggactt ctgctatgag ccatgtaaac    1800
caagcgagga cgataaagag aaccatcatc accatcacca ttaaaagtta acagaggacg    1860
gatttcctga aggaaatccg tttttttatt tttaagcttg                          1900
```

<210> SEQ ID NO 2
<211> LENGTH: 428
<212> TYPE: PRT
<213> ORGANISM: Artificial
<220> FEATURE:
<223> OTHER INFORMATION: synthetic fusion peptide

<400> SEQUENCE: 2

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Asp Asp Tyr
            20                  25                  30

Ser Val Val Glu Glu His Gly Gln Leu Ser Ile Ser Asn Gly Glu Leu
        35                  40                  45

Val Asn Glu Arg Gly Gln Val Gln Leu Lys Gly Met Ser Ser His
    50                  55                  60

Gly Leu Gln Trp Tyr Gly Gln Phe Val Asn Tyr Glu Ser Met Lys Trp
65                  70                  75                  80

Leu Arg Asp Asp Trp Gly Ile Thr Val Phe Arg Ala Ala Met Tyr Thr
                85                  90                  95

Ser Ser Gly Gly Tyr Ile Asp Asp Pro Ser Val Lys Glu Lys Val Lys
            100                 105                 110

Glu Thr Val Glu Ala Ala Ile Asp Leu Gly Ile Tyr Val Ile Ile Asp
        115                 120                 125

Trp His Ile Leu Ser Asp Asn Asp Pro Asn Ile Tyr Lys Glu Glu Ala
    130                 135                 140

Lys Asp Phe Phe Asp Glu Met Ser Glu Leu Tyr Gly Asp Tyr Pro Asn
145                 150                 155                 160

Val Ile Tyr Glu Ile Ala Asn Glu Pro Asn Gly Ser Asp Val Thr Trp
                165                 170                 175

Asp Asn Gln Ile Lys Pro Tyr Ala Glu Glu Val Ile Pro Val Ile Arg
            180                 185                 190

Asp Asn Asp Pro Asn Asn Ile Val Ile Val Gly Thr Gly Thr Trp Ser
        195                 200                 205

Gln Asp Val His His Ala Ala Asp Asn Gln Leu Ala Asp Pro Asn Val
    210                 215                 220

Met Tyr Ala Phe His Phe Tyr Ala Gly Thr His Gly Gln Asn Leu Arg
225                 230                 235                 240

Asp Gln Val Asp Tyr Ala Leu Asp Gln Gly Ala Ala Ile Phe Val Ser
                245                 250                 255

Glu Trp Gly Thr Ser Ala Ala Thr Gly Asp Gly Gly Val Phe Leu Asp
```

```
                260                 265                 270
Glu Ala Gln Val Trp Ile Asp Phe Met Asp Glu Arg Asn Leu Ser Trp
            275                 280                 285

Ala Asn Trp Ser Leu Thr His Lys Asp Glu Ser Ser Ala Ala Leu Met
        290                 295                 300

Pro Gly Ala Asn Pro Thr Gly Trp Thr Glu Ala Glu Leu Ser Pro
305                 310                 315                 320

Ser Gly Thr Phe Val Arg Glu Lys Ile Arg Glu Ser Ala Ser Ile Pro
                325                 330                 335

Pro Ser Asp Pro Thr Pro Pro Ser Asp Pro Gly Glu Pro Asp Pro Asp
            340                 345                 350

Asp Glu Ser Ser Lys Pro Cys Cys Asp Gln Cys Ala Cys Thr Lys Ser
        355                 360                 365

Asn Pro Pro Gln Cys Arg Cys Ser Asp Met Arg Leu Asn Ser Cys His
    370                 375                 380

Ser Ala Cys Lys Ser Cys Ile Cys Ala Leu Ser Tyr Pro Ala Gln Cys
385                 390                 395                 400

Phe Cys Val Asp Ile Thr Asp Phe Cys Tyr Glu Pro Cys Lys Pro Ser
                405                 410                 415

Glu Asp Asp Lys Glu Asn His His His His His His
            420                 425

<210> SEQ ID NO 3
<211> LENGTH: 223
<212> TYPE: DNA
<213> ORGANISM: Artificial
<220> FEATURE:
<223> OTHER INFORMATION: synthetic sequence encoding fusion peptide of
      SEQ ID NO:4

<400> SEQUENCE: 3
ggatccagac gatgagagct ctaaaccctg ttgcgatcaa tgcgcatgtt ataatttgta      60
tgggtggact tgtcgctgca gcgatatgcg tctgaattcc tgtcatagtg cctgcaaaag    120
ctgcgcatgt tataacctgt acgggtggac tgttttttgc gtcgacatca cggacttctg    180
ctatgagcca tgtaaaccaa gcgaggacga taaagagaac taa                      223

<210> SEQ ID NO 4
<211> LENGTH: 73
<212> TYPE: PRT
<213> ORGANISM: Artificial
<220> FEATURE:
<223> OTHER INFORMATION: synthetic fusion peptide

<400> SEQUENCE: 4

Asp Pro Asp Asp Glu Ser Ser Lys Pro Cys Cys Asp Gln Cys Ala Cys
1               5                   10                  15

Tyr Asn Leu Tyr Gly Trp Thr Cys Arg Cys Ser Asp Met Arg Leu Asn
                20                  25                  30

Ser Cys His Ser Ala Cys Lys Ser Cys Ala Cys Tyr Asn Leu Tyr Gly
            35                  40                  45

Trp Thr Cys Phe Cys Val Asp Ile Thr Asp Phe Cys Tyr Glu Pro Cys
        50                  55                  60

Lys Pro Ser Glu Asp Asp Lys Glu Asn
65                  70

<210> SEQ ID NO 5
<211> LENGTH: 1512
```

<212> TYPE: DNA
<213> ORGANISM: Artificial
<220> FEATURE:
<223> OTHER INFORMATION: synthetic sequence encoding fusion peptide of
    SEQ ID NO:6

<400> SEQUENCE: 5

```
agcgcgcagg ctagcgatgt tgtacaactg aaaaaagaca ctttcgacga cttcatcaaa    60
acaaatgacc ttgttcttgc tgaattttc gcgccgtggt gcggtcactg caaagctctt    120
gctcctgagt acgaggaagc tgcaactaca ctgaaagaaa agaacatcaa acttgctaaa    180
gtagactgca cagaagagac tgatctttgc caacaacatg gtgttgaggg ctacccaact    240
cttaaagttt tccgtggcct tgacaacgta tctccttaca aggtcaacg taaagctgct     300
gcaatcactt catacatgat caaacaatct ctgcctgctg tatctgaagt acaaaaagac    360
aaccttgaag aatttaaaaa agctgacaaa gctgttcttg ttgcttatgt agatgcttct    420
gacaaagcat ctagcgaagt tttcactcaa gttgctgaaa actgcgcga taactaccca     480
ttcggctcta gctctgatgc tgcactggct gaagctgagg gcgttaaagc acctgctatt    540
gttctttaca agactttga tgaaggtaaa gcggttttct ctgaaaaatt cgaagtagag    600
gcaatcgaaa aattcgctaa acaggtgct actccactta ttggcgaaat cggacctgaa     660
acttactctg attacatgtc agctggcatc cctctggcat acattttcgc tgaaacagct    720
gaagagcgta agaactcag cgacaaactt aaaccaatcg ctgaagctca acgtggcgtt    780
attaactttg gtactattga cgctaaagca tttggtgctc acgctggaaa cctgaatctg    840
aaaactgaca aattccctgc tttcgcaatc caagaagttg ctaaaaacca aaaattccct    900
tttgatcaag aaaagaaat tactttgaa gcgatcaaag cattcgttga cgattttgtt    960
gctggtaaaa tcgaaccaag catcaaatca gaaccaatcc ctgaaaaaca agaaggtcct   1020
gttactgtag ttgtagctaa aaactacaat gaaatcgttc tggacgatac taaagatgta   1080
ttaattgaat tttacgctcc ttggtgcggt cactgcaaag ctcttgctcc taaatacgaa   1140
gaacttggtg tctctgtatg caaaaagcgag ttcaaagacc gtgttgtaat tgctaaagtt   1200
gatgcaacag ctaacgatgt tccagatgaa attcaaggat tccctactat caaactatac   1260
ccagctggtg caaaaggtca acctgttact tactctggtt cacgcactgt tgaagacctt   1320
atcaaattca ttgctgaaaa acggtaaatac aaagctgcaa tctcagaaga tgctgaagag   1380
actagttcag caactgaaac aactacagaa actgctacaa agtcagaaga agctgcaaaa   1440
gaaactgcaa cagaacacga cgaacttgga tctggttccg agatgacga tgacaaagac   1500
gatgagagct ct                                                       1512
```

<210> SEQ ID NO 6
<211> LENGTH: 504
<212> TYPE: PRT
<213> ORGANISM: Artificial
<220> FEATURE:
<223> OTHER INFORMATION: synthetic fusion peptide

<400> SEQUENCE: 6

```
Ser Ala Gln Ala Ser Asp Val Val Gln Leu Lys Lys Asp Thr Phe Asp
1               5                   10                  15

Asp Phe Ile Lys Thr Asn Asp Leu Val Leu Ala Glu Phe Phe Ala Pro
            20                  25                  30

Trp Cys Gly His Cys Lys Ala Leu Ala Pro Glu Tyr Glu Glu Ala Ala
        35                  40                  45
```

```
Thr Thr Leu Lys Glu Lys Asn Ile Lys Leu Ala Lys Val Asp Cys Thr
 50                  55                  60

Glu Glu Thr Asp Leu Cys Gln Gln His Gly Val Glu Gly Tyr Pro Thr
 65                  70                  75                  80

Leu Lys Val Phe Arg Gly Leu Asp Asn Val Ser Pro Tyr Lys Gly Gln
                 85                  90                  95

Arg Lys Ala Ala Ala Ile Thr Ser Tyr Met Ile Lys Gln Ser Leu Pro
                100                 105                 110

Ala Val Ser Glu Val Thr Lys Asp Asn Leu Glu Glu Phe Lys Lys Ala
            115                 120                 125

Asp Lys Ala Val Leu Val Ala Tyr Val Asp Ala Ser Asp Lys Ala Ser
    130                 135                 140

Ser Glu Val Phe Thr Gln Val Ala Glu Lys Leu Arg Asp Asn Tyr Pro
145                 150                 155                 160

Phe Gly Ser Ser Asp Ala Ala Leu Ala Glu Ala Glu Gly Val Lys
                165                 170                 175

Ala Pro Ala Ile Val Leu Tyr Lys Asp Phe Asp Glu Gly Lys Ala Val
                180                 185                 190

Phe Ser Glu Lys Phe Glu Val Glu Ala Ile Glu Lys Phe Ala Lys Thr
            195                 200                 205

Gly Ala Thr Pro Leu Ile Gly Glu Ile Gly Pro Glu Thr Tyr Ser Asp
    210                 215                 220

Tyr Met Ser Ala Gly Ile Pro Leu Ala Tyr Ile Phe Ala Glu Thr Ala
225                 230                 235                 240

Glu Glu Arg Lys Glu Leu Ser Asp Lys Leu Lys Pro Ile Ala Glu Ala
                245                 250                 255

Gln Arg Gly Val Ile Asn Phe Gly Thr Ile Asp Ala Lys Ala Phe Gly
            260                 265                 270

Ala His Ala Gly Asn Leu Asn Leu Lys Thr Asp Lys Phe Pro Ala Phe
    275                 280                 285

Ala Ile Gln Glu Val Ala Lys Asn Gln Lys Phe Pro Phe Asp Gln Glu
290                 295                 300

Lys Glu Ile Thr Phe Glu Ala Ile Lys Ala Phe Val Asp Asp Phe Val
305                 310                 315                 320

Ala Gly Lys Ile Glu Pro Ser Ile Lys Ser Glu Pro Ile Pro Glu Lys
                325                 330                 335

Gln Glu Gly Pro Val Thr Val Val Ala Lys Asn Tyr Asn Glu Ile
            340                 345                 350

Val Leu Asp Asp Thr Lys Asp Val Leu Ile Glu Phe Tyr Ala Pro Trp
    355                 360                 365

Cys Gly His Cys Lys Ala Leu Ala Pro Lys Tyr Glu Glu Leu Gly Ala
370                 375                 380

Leu Tyr Ala Lys Ser Glu Phe Lys Asp Arg Val Val Ile Ala Lys Val
385                 390                 395                 400

Asp Ala Thr Ala Asn Asp Val Pro Asp Glu Ile Gln Gly Phe Pro Thr
                405                 410                 415

Ile Lys Leu Tyr Pro Ala Gly Ala Lys Gly Gln Pro Val Thr Tyr Ser
            420                 425                 430

Gly Ser Arg Thr Val Glu Asp Leu Ile Lys Phe Ile Ala Glu Asn Gly
    435                 440                 445

Lys Tyr Lys Ala Ala Ile Ser Glu Asp Ala Glu Glu Thr Ser Ser Ala
450                 455                 460

Thr Glu Thr Thr Thr Glu Thr Ala Thr Lys Ser Glu Glu Ala Ala Lys
```

```
                    465                 470                 475                 480
Glu Thr Ala Thr Glu His Asp Glu Leu Gly Ser Gly Ser Gly Asp Asp
                            485                 490                 495

Asp Asp Lys Asp Asp Glu Ser Ser
            500

<210> SEQ ID NO 7
<211> LENGTH: 295
<212> TYPE: PRT
<213> ORGANISM: Artificial
<220> FEATURE:
<223> OTHER INFORMATION: synthetic fusion peptide

<400> SEQUENCE: 7

Val Arg Ser Lys Lys Leu Trp Ile Ser Leu Leu Phe Ala Leu Thr Leu
1               5                   10                  15

Ala Ala Ser Cys Leu Ser Val Cys Ala Thr Val Ala Ala Pro Leu
                20                  25                  30

Pro Asp Thr Pro Gly Ala Pro Phe Pro Ala Val Ala Asn Phe Asp Arg
                35                  40                  45

Ser Gly Pro Tyr Thr Thr Ser Ser Gln Ser Glu Gly Pro Ser Cys Arg
            50                  55                  60

Ile Tyr Arg Pro Arg Asp Leu Gly Gln Gly Gly Val Arg His Pro Val
65                  70                  75                  80

Ile Leu Trp Gly Asn Gly Thr Gly Ala Gly Pro Ser Thr Tyr Ala Gly
                85                  90                  95

Leu Leu Ser His Trp Ala Ser His Gly Phe Val Val Ala Ala Ala Glu
                100                 105                 110

Thr Ser Asn Ala Gly Thr Gly Arg Glu Met Leu Ala Cys Leu Asp Tyr
            115                 120                 125

Leu Val Arg Glu Asn Asp Thr Pro Tyr Gly Thr Tyr Ser Gly Lys Leu
130                 135                 140

Asn Thr Gly Arg Val Gly Thr Ser Gly His Ser Gln Gly Gly Gly Gly
145                 150                 155                 160

Ser Ile Met Ala Gly Gln Asp Thr Arg Val Arg Thr Thr Ala Pro Ile
                165                 170                 175

Gln Pro Tyr Thr Leu Gly Leu Gly His Asp Ser Ala Ser Gln Arg Arg
                180                 185                 190

Gln Gln Gly Pro Met Phe Leu Met Ser Gly Gly Gly Asp Thr Ile Ala
            195                 200                 205

Phe Pro Tyr Leu Asn Ala Gln Pro Val Tyr Arg Arg Ala Asn Val Pro
210                 215                 220

Val Phe Trp Gly Glu Arg Arg Tyr Val Ser His Phe Glu Pro Val Gly
225                 230                 235                 240

Ser Gly Gly Ala Tyr Arg Gly Pro Ser Thr Ala Trp Phe Arg Phe Gln
                245                 250                 255

Leu Met Asp Asp Gln Asp Ala Arg Ala Thr Phe Tyr Gly Ala Gln Cys
            260                 265                 270

Ser Leu Cys Thr Ser Leu Leu Trp Ser Val Glu Arg Gly Leu Asp
            275                 280                 285

Asn Asn Asp Pro Ile Pro Asp
    290                 295

<210> SEQ ID NO 8
<211> LENGTH: 1495
<212> TYPE: DNA
```

-continued

<213> ORGANISM: Artificial
<220> FEATURE:
<223> OTHER INFORMATION: synthetic sequence encoding fusion peptide of
SEQ ID NO:7

<400> SEQUENCE: 8

```
gaattctcca ttttcttctg ctatcaaaat aacagactcg tgattttcca aacgagcttt     60
caaaaaagcc tctgcccctt gcaaatcgga tgcctgtcta taaaattccc gatattggtt    120
aaacagcggc gcaatggcgg ccgcatctga tgtctttgct tggcgaatgt tcatcttatt    180
tcttcctccc tctcaataat ttttcattc tatccctttt ctgtaaagtt tatttttcag     240
aatactttta tcatcatgct ttgaaaaaat atcacgataa tatccattgt tctcacggaa    300
gcacacgcag gtcatttgaa cgaatttttt cgacaggaat ttgccgggac tcaggagcat    360
ttaacctaaa aaagcatgac atttcagcat aatgaacatt tactcatgtc tattttcgtt    420
cttttctgta tgaaaatagt tatttcgagt ctctacggaa atagcgagag atgatatacc    480
taaatagaga taaaatcatc tcaaaaaaat gggtctacta aaatattatt ccatctatta    540
caataaattc acagaatagt cttttaagta agtctactct gaattttttt aaaaggagag    600
ggtaaagagt gagaagcaaa aaattgtgga tcagcttgtt gtttgcgtta acgctggcgg    660
cctcttgcct gtccgtctgt gccactgtcg cggcggctcc cctgccggat acaccgggag    720
cgccatttcc ggctgtcgcc aatttcgacc gcagtggccc ctacaccacc agcagccaga    780
gcgaggggcc gagctgtcgc atctatcggc cccgcgacct gggtcagggg ggcgtgcgtc    840
atccggtgat tctctggggc aatggcaccg gtgccgggcc gtccacctat gccggcttgc    900
tatcgcactg ggcaagccac ggtttcgtgg tggcggcggc ggaaacctcc aatgccggta    960
ccgggcggga aatgctcgcc tgcctggact atctggtacg tgagaacgac acccccctacg  1020 gcacctattc cggcaagctc aataccgggc gagtcggcac ttctgggcat tcccagggtg   1080
gtggcggctc gatcatggcc gggcaggata cgagggtgcg taccacggcg ccgatccagc   1140
cctacaccct cggcctgggg cacgacagcg cctcgcagcg gcggcagcag ggccgatgt    1200 tcctgatgtc cggtggcggt gacaccatcg cctttcccta cctcaacgct cagccggtct   1260
accggcgtgc caatgtgccg gtgttctggg gcgaacggcg ttacgtcagc cacttcgagc   1320
cggtcggtag cggtggggcc tatcgcggcc cgagcacggc atggttccgc ttccagctga   1380
tggatgacca agacgcccgc gctaccttct acggcgcgca gtgcagtctg tgcacttctc   1440
tgctttggtc tgttgaacgc agaggtcttg acaacaatga tcctattccg gatcc        1495
```

<210> SEQ ID NO 9
<211> LENGTH: 10
<212> TYPE: PRT
<213> ORGANISM: Artificial
<220> FEATURE:
<223> OTHER INFORMATION: synthetic VEGF binding protein

<400> SEQUENCE: 9

```
Ala Cys Tyr Asn Leu Tyr Gly Trp Thr Cys
1               5                   10
```

<210> SEQ ID NO 10
<211> LENGTH: 288
<212> TYPE: DNA
<213> ORGANISM: Artificial
<220> FEATURE:
<223> OTHER INFORMATION: synthetic pro-BBI coding sequence

<400> SEQUENCE: 10

```
aacctgcgtc tgtctaagct tggcctgctt atgaaatcag accatcagca cagcaatgac    60
gatgagagct ctaaaccctg ttgcgatcaa tgcgcatgta cgaaatcaaa tcctccacag   120
tgtcggtgtt ccgatatgcg tctgaatagc tgtcatagtg catgcaaaag ctgtatctgc   180
gccctgagtt atccagctca atgttttgc gtcgacatca cggacttctg ctatgagcca   240
tgtaaaccaa gcgaggacga taaagagaac catcatcacc atcaccat                288
```

```
<210> SEQ ID NO 11
<211> LENGTH: 96
<212> TYPE: PRT
<213> ORGANISM: Artificial
<220> FEATURE:
<223> OTHER INFORMATION: synthetic pro-BBI coding protein

<400> SEQUENCE: 11

Asn Leu Arg Leu Ser Lys Leu Gly Leu Leu Met Lys Ser Asp His Gln
1               5                   10                  15

His Ser Asn Asp Asp Glu Ser Ser Lys Pro Cys Cys Asp Gln Cys Ala
            20                  25                  30

Cys Thr Lys Ser Asn Pro Pro Gln Cys Arg Cys Ser Asp Met Arg Leu
        35                  40                  45

Asn Ser Cys His Ser Ala Cys Lys Ser Cys Ile Cys Ala Leu Ser Tyr
    50                  55                  60

Pro Ala Gln Cys Phe Cys Val Asp Ile Thr Asp Phe Cys Tyr Glu Pro
65                  70                  75                  80

Cys Lys Pro Ser Glu Asp Asp Lys Glu Asn His His His His His His
                85                  90                  95
```

```
<210> SEQ ID NO 12
<211> LENGTH: 213
<212> TYPE: DNA
<213> ORGANISM: Artificial
<220> FEATURE:
<223> OTHER INFORMATION: synthetic BBI coding sequence

<400> SEQUENCE: 12
gacgatgaga gctctaaacc ctgttgcgat caatgcgcat gtacgaaatc aaatcctcca    60
cagtgtcggt gttccgatat gcgtctgaat agctgtcata gtgcatgcaa agctgtatc   120 tgcgccctga gttatccagc tcaatgtttt tgcgtcgaca tcacggactt ctgctatgag   180
ccatgtaaac caagcgagga cgataaagag aac                                213
```

```
<210> SEQ ID NO 13
<211> LENGTH: 71
<212> TYPE: PRT
<213> ORGANISM: Glycine max

<400> SEQUENCE: 13

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70
```

```
<210> SEQ ID NO 14
<211> LENGTH: 34
<212> TYPE: DNA
<213> ORGANISM: Artificial
<220> FEATURE:
<223> OTHER INFORMATION: synthetic primer

<400> SEQUENCE: 14
cagcacggat ccagacgatg agagctctaa accc                              34

<210> SEQ ID NO 15
<211> LENGTH: 84
<212> TYPE: DNA
<213> ORGANISM: Artificial
<220> FEATURE:
<223> OTHER INFORMATION: synthetic primer

<400> SEQUENCE: 15
ctgcagaagc ttaaaaataa aaaaacggat ttccttcagg aaatccgtcc tctgttaact   60
tttagttctc tttatcgtcc tcgc                                         84

<210> SEQ ID NO 16
<211> LENGTH: 88
<212> TYPE: DNA
<213> ORGANISM: Artificial
<220> FEATURE:
<223> OTHER INFORMATION: synthetic primer

<400> SEQUENCE: 16
ctgcagaagc ttaaaaataa aaaaacggat ttccttcagg aaatccgtcc tctgttaact   60
tttaatggtg atggtgatga tggttctc                                     88

<210> SEQ ID NO 17
<211> LENGTH: 31
<212> TYPE: DNA
<213> ORGANISM: Artificial
<220> FEATURE:
<223> OTHER INFORMATION: synthetic primer

<400> SEQUENCE: 17
gatatgcgtc tgaattcctg tcatagtgca t                                 31

<210> SEQ ID NO 18
<211> LENGTH: 31
<212> TYPE: DNA
<213> ORGANISM: Artificial
<220> FEATURE:
<223> OTHER INFORMATION: synthetic primer

<400> SEQUENCE: 18
atgcactatg acaggaattc agacgcatat c                                 31

<210> SEQ ID NO 19
<211> LENGTH: 74
<212> TYPE: DNA
<213> ORGANISM: Artificial
<220> FEATURE:
<223> OTHER INFORMATION: synthetic oligonucleotide

<400> SEQUENCE: 19
ctaaaccctg ttgcgatcaa tgcgcatgtt ataatttgta tgggtggact tgtcgctgca   60
gcgatatgcg tctg                                                    74
```

<210> SEQ ID NO 20
<211> LENGTH: 82
<212> TYPE: DNA
<213> ORGANISM: Artificial
<220> FEATURE:
<223> OTHER INFORMATION: synthetic oligonucleotide

<400> SEQUENCE: 20
aattcagacg catatcgctg cagcgacaag tccacccata caaattataa catgcgcatt    60
gatcgcaaca gggtttagag ct                                            82

<210> SEQ ID NO 21
<211> LENGTH: 67
<212> TYPE: DNA
<213> ORGANISM: Artificial
<220> FEATURE:
<223> OTHER INFORMATION: synthetic oligonucleotide

<400> SEQUENCE: 21
aattcctgtc atagtgcctg caaaagctgc gcatgttata acctgtacgg gtggacctgt    60
ttttgcg                                                             67

<210> SEQ ID NO 22
<211> LENGTH: 67
<212> TYPE: DNA
<213> ORGANISM: Artificial
<220> FEATURE:
<223> OTHER INFORMATION: synthetic oligonucleotide

<400> SEQUENCE: 22
tcgacgcaaa aacaggtcca cccgtacagg ttataacatg cgcagctttt gcaggcacta    60
tgacagg                                                             67

<210> SEQ ID NO 23
<211> LENGTH: 80
<212> TYPE: DNA
<213> ORGANISM: Artificial
<220> FEATURE:
<223> OTHER INFORMATION: synthetic oligonucleotide

<400> SEQUENCE: 23
ctaaaccctg ttgcgatcaa tgcgcatgtg ttgttcagga ctggggtcac caccgttgtc    60
gctgcagcga tatgcgtctg                                               80

<210> SEQ ID NO 24
<211> LENGTH: 88
<212> TYPE: DNA
<213> ORGANISM: Artificial
<220> FEATURE:
<223> OTHER INFORMATION: synthetic oligonucleotide

<400> SEQUENCE: 24
aattcagacg catatcgctg cagcgacaac ggtggtgacc ccagtcctga acaacacatg    60
cgcattgatc gcaacagggt ttagagct                                      88

<210> SEQ ID NO 25
<211> LENGTH: 53
<212> TYPE: DNA
<213> ORGANISM: Artificial
<220> FEATURE:
<223> OTHER INFORMATION: synthetic oligonucleotide

<400> SEQUENCE: 25

```
caaaagctgt atctgcgttg ttcaggactg gggtcaccac cgttgttttt gcg         53
```

\<210\> SEQ ID NO 26
\<211\> LENGTH: 61
\<212\> TYPE: DNA
\<213\> ORGANISM: Artificial
\<220\> FEATURE:
\<223\> OTHER INFORMATION: synthetic oligonucleotide

\<400\> SEQUENCE: 26

```
tcgacgcaaa acaacggtg gtgacccag tcctgaacaa cgcagataca gctttgcat    60
g                                                                 61
```

\<210\> SEQ ID NO 27
\<211\> LENGTH: 74
\<212\> TYPE: DNA
\<213\> ORGANISM: Artificial
\<220\> FEATURE:
\<223\> OTHER INFORMATION: synthetic oligonucleotide

\<400\> SEQUENCE: 27

```
ctaaaccctg ttgcgatcaa tgcagctgtg gtcgtaaaat cccgatccag tgtcgctgca   60
gcgatatgcg tctg                                                    74
```

\<210\> SEQ ID NO 28
\<211\> LENGTH: 82
\<212\> TYPE: DNA
\<213\> ORGANISM: Artificial
\<220\> FEATURE:
\<223\> OTHER INFORMATION: synthetic oligonucleotide

\<400\> SEQUENCE: 28

```
aattcagacg catatcgctg cagcgacact ggatcgggat tttacgacca cagctgcatt   60
gatcgcaaca gggtttagag ct                                           82
```

\<210\> SEQ ID NO 29
\<211\> LENGTH: 74
\<212\> TYPE: DNA
\<213\> ORGANISM: Artificial
\<220\> FEATURE:
\<223\> OTHER INFORMATION: synthetic oligonucleotide

\<400\> SEQUENCE: 29

```
ctaaaccctg ttgcgatcaa tgcggttgtg ctcgttctaa cctggacgaa tgtcgctgca   60
gcgatatgcg tctg                                                    74
```

\<210\> SEQ ID NO 30
\<211\> LENGTH: 82
\<212\> TYPE: DNA
\<213\> ORGANISM: Artificial
\<220\> FEATURE:
\<223\> OTHER INFORMATION: synthetic oligonucleotide

\<400\> SEQUENCE: 30

```
aattcagacg catatcgctg cagcgacatt cgtccaggtt agaacgagca caaccgcatt   60
gatcgcaaca gggtttagag ct                                           82
```

\<210\> SEQ ID NO 31
\<211\> LENGTH: 74
\<212\> TYPE: DNA
\<213\> ORGANISM: Artificial
\<220\> FEATURE:

<223> OTHER INFORMATION: synthetic oligonucleotide

<400> SEQUENCE: 31
ctaaaccctg ttgcgatcaa tgcggttgtc agcgtgctct gccgatcctg tgtcgctgca    60
gcgatatgcg tctg    74

<210> SEQ ID NO 32
<211> LENGTH: 82
<212> TYPE: DNA
<213> ORGANISM: Artificial
<220> FEATURE:
<223> OTHER INFORMATION: synthetic oligonucleotide

<400> SEQUENCE: 32
aattcagacg catatcgctg cagcgacaca ggatcggcag agcacgctga caaccgcatt    60
gatcgcaaca gggtttagag ct    82

<210> SEQ ID NO 33
<211> LENGTH: 74
<212> TYPE: DNA
<213> ORGANISM: Artificial
<220> FEATURE:
<223> OTHER INFORMATION: synthetic oligonucleotide

<400> SEQUENCE: 33
ctaaaccctg ttgcgatcaa tgccagtgtg gtcgtctgca catgaaaacc tgtcgctgca    60
gcgatatgcg tctg    74

<210> SEQ ID NO 34
<211> LENGTH: 82
<212> TYPE: DNA
<213> ORGANISM: Artificial
<220> FEATURE:
<223> OTHER INFORMATION: synthetic oligonucleotide

<400> SEQUENCE: 34
aattcagacg catatcgctg cagcgacagg ttttcatgtg cagacgacca cactggcatt    60
gatcgcaaca gggtttagag ct    82

<210> SEQ ID NO 35
<211> LENGTH: 67
<212> TYPE: DNA
<213> ORGANISM: Artificial
<220> FEATURE:
<223> OTHER INFORMATION: synthetic oligonucleotide

<400> SEQUENCE: 35
aattcctgtc atagtgcctg caaaagctgt atctgcgccc gtagtttgcc agctcaatgt    60
ttttgcg    67

<210> SEQ ID NO 36
<211> LENGTH: 67
<212> TYPE: DNA
<213> ORGANISM: Artificial
<220> FEATURE:
<223> OTHER INFORMATION: synthetic oligonucleotide

<400> SEQUENCE: 36
tcgacgcaaa acattgagc tggcaaacta cgggcgcaga tacagctttt gcaggcacta    60
tgacagg    67

```
<210> SEQ ID NO 37
<211> LENGTH: 74
<212> TYPE: DNA
<213> ORGANISM: Artificial
<220> FEATURE:
<223> OTHER INFORMATION: synthetic oligonucleotide

<400> SEQUENCE: 37
ctaaaccctg ttgcgatcaa tgcaactgta cgtactcaac ccctccacag tgtcgctgca      60
gcgatatgcg tctg                                                       74

<210> SEQ ID NO 38
<211> LENGTH: 82
<212> TYPE: DNA
<213> ORGANISM: Artificial
<220> FEATURE:
<223> OTHER INFORMATION: synthetic oligonucleotide

<400> SEQUENCE: 38
aattcagacg catatcgctg cagcgacact gtggaggggt tgagtacgta cagttgcatt      60
gatcgcaaca gggtttagag ct                                              82

<210> SEQ ID NO 39
<211> LENGTH: 51
<212> TYPE: DNA
<213> ORGANISM: Artificial
<220> FEATURE:
<223> OTHER INFORMATION: synthetic oligonucleotide

<400> SEQUENCE: 39
ctgtatctgc aaacgctcaa aatctcgtgg ctgtttttgc gtcgacatca c              51

<210> SEQ ID NO 40
<211> LENGTH: 51
<212> TYPE: DNA
<213> ORGANISM: Artificial
<220> FEATURE:
<223> OTHER INFORMATION: synthetic oligonucleotide

<400> SEQUENCE: 40
cgcaaaaaca gccacgagat tttgagcgtt tgcagataca gcttttgcat g              51

<210> SEQ ID NO 41
<211> LENGTH: 51
<212> TYPE: DNA
<213> ORGANISM: Artificial
<220> FEATURE:
<223> OTHER INFORMATION: synthetic oligonucleotide

<400> SEQUENCE: 41
ctgtatctgc tggtataatc aaatgacaac atgttttgc gtcgacatca c               51

<210> SEQ ID NO 42
<211> LENGTH: 51
<212> TYPE: DNA
<213> ORGANISM: Artificial
<220> FEATURE:
<223> OTHER INFORMATION: synthetic oligonucleotide

<400> SEQUENCE: 42
cgcaaaaaca tgttgtcatt tgattatacc agcagataca gcttttgcat g              51

<210> SEQ ID NO 43
<211> LENGTH: 51
<212> TYPE: DNA
```

<210> SEQ ID NO 43
<211> LENGTH: 51
<212> TYPE: DNA
<213> ORGANISM: Artificial
<220> FEATURE:
<223> OTHER INFORMATION: synthetic oligonucleotide

<400> SEQUENCE: 43
ctgtatctgc catcaacttg gcccgaattc atgttttgc gtcgacatca c    51

<210> SEQ ID NO 44
<211> LENGTH: 51
<212> TYPE: DNA
<213> ORGANISM: Artificial
<220> FEATURE:
<223> OTHER INFORMATION: synthetic oligonucleotide

<400> SEQUENCE: 44
cgcaaaaaca tgaattcggg ccaagttgat ggcagataca gcttttgcat g    51

<210> SEQ ID NO 45
<211> LENGTH: 51
<212> TYPE: DNA
<213> ORGANISM: Artificial
<220> FEATURE:
<223> OTHER INFORMATION: synthetic oligonucleotide

<400> SEQUENCE: 45
ctgtatctgc catccgtggg caccgtattc ttgttttgc gtcgacatca c    51

<210> SEQ ID NO 46
<211> LENGTH: 51
<212> TYPE: DNA
<213> ORGANISM: Artificial
<220> FEATURE:
<223> OTHER INFORMATION: synthetic oligonucleotide

<400> SEQUENCE: 46
cgcaaaaaca agaatacggt gcccacggat ggcagataca gcttttgcat g    51

<210> SEQ ID NO 47
<211> LENGTH: 51
<212> TYPE: DNA
<213> ORGANISM: Artificial
<220> FEATURE:
<223> OTHER INFORMATION: synthetic oligonucleotide

<400> SEQUENCE: 47
ctgtatctgc aatcttcatt atcttcaaca gtgttttgc gtcgacatca c    51

<210> SEQ ID NO 48
<211> LENGTH: 51
<212> TYPE: DNA
<213> ORGANISM: Artificial
<220> FEATURE:
<223> OTHER INFORMATION: synthetic oligonucleotide

<400> SEQUENCE: 48
cgcaaaaaca ctgttgaaga taatgaagat tgcagataca gcttttgcat g    51

<210> SEQ ID NO 49
<211> LENGTH: 51
<212> TYPE: DNA
<213> ORGANISM: Artificial
<220> FEATURE:
<223> OTHER INFORMATION: synthetic oligonucleotide

<400> SEQUENCE: 49
ctgtatctgc acaccgtctc tttatcgccc gtgttttgc gtcgacatca c    51

```
<210> SEQ ID NO 50
<211> LENGTH: 51
<212> TYPE: DNA
<213> ORGANISM: Artificial
<220> FEATURE:
<223> OTHER INFORMATION: synthetic oligonucleotide

<400> SEQUENCE: 50
cgcaaaaaca cgggcgataa agagacggtg tgcagataca gcttttgcat g          51

<210> SEQ ID NO 51
<211> LENGTH: 51
<212> TYPE: DNA
<213> ORGANISM: Artificial
<220> FEATURE:
<223> OTHER INFORMATION: synthetic oligonucleotide

<400> SEQUENCE: 51
ctgtatctgc ttacagatc aatctaaacc gtgttttgc gtcgacatca c             51

<210> SEQ ID NO 52
<211> LENGTH: 51
<212> TYPE: DNA
<213> ORGANISM: Artificial
<220> FEATURE:
<223> OTHER INFORMATION: synthetic oligonucleotide

<400> SEQUENCE: 52
cgcaaaaaca cggtttagat tgatctgtaa ggcagataca gcttttgcat g           51

<210> SEQ ID NO 53
<211> LENGTH: 51
<212> TYPE: DNA
<213> ORGANISM: Artificial
<220> FEATURE:
<223> OTHER INFORMATION: synthetic oligonucleotide

<400> SEQUENCE: 53
ctgtatctgc gttacaacat caatgggcat gtgttttgc gtcgacatca c            51

<210> SEQ ID NO 54
<211> LENGTH: 51
<212> TYPE: DNA
<213> ORGANISM: Artificial
<220> FEATURE:
<223> OTHER INFORMATION: synthetic oligonucleotide

<400> SEQUENCE: 54
cgcaaaaaca catgcccatt gatgttgtaa cgcagataca gcttttgcat g           51

<210> SEQ ID NO 55
<211> LENGTH: 51
<212> TYPE: DNA
<213> ORGANISM: Artificial
<220> FEATURE:
<223> OTHER INFORMATION: synthetic oligonucleotide

<400> SEQUENCE: 55
ctgtatctgc cgcgcatcac cgtatgattg gtgttttgc gtcgacatca c            51

<210> SEQ ID NO 56
<211> LENGTH: 51
<212> TYPE: DNA
<213> ORGANISM: Artificial
<220> FEATURE:
```

<223> OTHER INFORMATION: synthetic oligonucleotide

<400> SEQUENCE: 56
cgcaaaaaca ccaatcatac ggtgatgcgc ggcagataca gcttttgcat g          51

<210> SEQ ID NO 57
<211> LENGTH: 51
<212> TYPE: DNA
<213> ORGANISM: Artificial
<220> FEATURE:
<223> OTHER INFORMATION: synthetic oligonucleotide

<400> SEQUENCE: 57
ctgtatctgc tcaacacaaa aaattccgca atgttttgc gtcgacatca c            51

<210> SEQ ID NO 58
<211> LENGTH: 51
<212> TYPE: DNA
<213> ORGANISM: Artificial
<220> FEATURE:
<223> OTHER INFORMATION: synthetic oligonucleotide

<400> SEQUENCE: 58
cgcaaaaaca ttgcggaatt ttttgtgttg agcagataca gcttttgcat g           51

<210> SEQ ID NO 59
<211> LENGTH: 51
<212> TYPE: DNA
<213> ORGANISM: Artificial
<220> FEATURE:
<223> OTHER INFORMATION: synthetic oligonucleotide

<400> SEQUENCE: 59
ctgtatctgc acacaatttc gctctgcaac atgttttgc gtcgacatca c            51

<210> SEQ ID NO 60
<211> LENGTH: 51
<212> TYPE: DNA
<213> ORGANISM: Artificial
<220> FEATURE:
<223> OTHER INFORMATION: synthetic oligonucleotide

<400> SEQUENCE: 60
cgcaaaaaca tgttgcagag cgaaattgtg tgcagataca gcttttgcat g           51

<210> SEQ ID NO 61
<211> LENGTH: 51
<212> TYPE: DNA
<213> ORGANISM: Artificial
<220> FEATURE:
<223> OTHER INFORMATION: synthetic oligonucleotide

<400> SEQUENCE: 61
ctgtatctgc ccggatcatg ttccgcatct tgttttgc gtcgacatca c             51

<210> SEQ ID NO 62
<211> LENGTH: 51
<212> TYPE: DNA
<213> ORGANISM: Artificial
<220> FEATURE:
<223> OTHER INFORMATION: synthetic oligonucleotide

<400> SEQUENCE: 62
cgcaaaaaca aagatgcgga acatgatccg ggcagataca gcttttgcat g           51

<210> SEQ ID NO 63
<211> LENGTH: 51
<212> TYPE: DNA
<213> ORGANISM: Artificial
<220> FEATURE:
<223> OTHER INFORMATION: synthetic oligonucleotide

<400> SEQUENCE: 63
ctgtatctgc tcaggctttc cgctttctac atgttttgc gtcgacatca c           51

<210> SEQ ID NO 64
<211> LENGTH: 51
<212> TYPE: DNA
<213> ORGANISM: Artificial
<220> FEATURE:
<223> OTHER INFORMATION: synthetic oligonucleotide

<400> SEQUENCE: 64
cgcaaaaaca tgtagaaagc ggaaagcctg agcagataca gcttttgcat g           51

<210> SEQ ID NO 65
<211> LENGTH: 56
<212> TYPE: DNA
<213> ORGANISM: Artificial
<220> FEATURE:
<223> OTHER INFORMATION: synthetic oligonucleotide

<400> SEQUENCE: 65
tcaatgcgca tgtgaagaga tctggactat gctttgccgg tgttccgata tgcgtc      56

<210> SEQ ID NO 66
<211> LENGTH: 57
<212> TYPE: DNA
<213> ORGANISM: Artificial
<220> FEATURE:
<223> OTHER INFORMATION: synthetic oligonucleotide

<400> SEQUENCE: 66
cggaacaccg gcaaagcata gtccagatct cttcacatgc gcattgatcg caacagg     57

<210> SEQ ID NO 67
<211> LENGTH: 59
<212> TYPE: DNA
<213> ORGANISM: Artificial
<220> FEATURE:
<223> OTHER INFORMATION: synthetic oligonucleotide

<400> SEQUENCE: 67
caaaagctgt gcttgtgaag agatctggac tatgctttgc ttttgcgtcg acatcacgg   59

<210> SEQ ID NO 68
<211> LENGTH: 59
<212> TYPE: DNA
<213> ORGANISM: Artificial
<220> FEATURE:
<223> OTHER INFORMATION: synthetic oligonucleotide

<400> SEQUENCE: 68
acgcaaaagc aaagcatagt ccagatctct tcacaagcac agcttttgca tgcactatg   59

<210> SEQ ID NO 69
<211> LENGTH: 56
<212> TYPE: DNA
<213> ORGANISM: Artificial
<220> FEATURE:
<223> OTHER INFORMATION: synthetic oligonucleotide -continued

<400> SEQUENCE: 69
tcaatgcgca tgttgggccc ttactgtcaa acatgccgg tgttccgata tgcgtc        56

<210> SEQ ID NO 70
<211> LENGTH: 57
<212> TYPE: DNA
<213> ORGANISM: Artificial
<220> FEATURE:
<223> OTHER INFORMATION: synthetic oligonucleotide

<400> SEQUENCE: 70
cggaacaccg gcatgttttg acagtaaggg cccaacatgc gcattgatcg caacagg      57

<210> SEQ ID NO 71
<211> LENGTH: 59
<212> TYPE: DNA
<213> ORGANISM: Artificial
<220> FEATURE:
<223> OTHER INFORMATION: synthetic oligonucleotide

<400> SEQUENCE: 71
caaaagctgt gcttgttggg cccttactgt caaaacatgc ttttgcgtcg acatcacgg    59

<210> SEQ ID NO 72
<211> LENGTH: 59
<212> TYPE: DNA
<213> ORGANISM: Artificial
<220> FEATURE:
<223> OTHER INFORMATION: synthetic oligonucleotide

<400> SEQUENCE: 72
acgcaaaagc atgttttgac agtaagggcc caacaagcac agcttttgca tgcactatg    59

<210> SEQ ID NO 73
<211> LENGTH: 56
<212> TYPE: DNA
<213> ORGANISM: Artificial
<220> FEATURE:
<223> OTHER INFORMATION: synthetic oligonucleotide

<400> SEQUENCE: 73
tcaatgcgca tgtcttacag tactgtggac tacatgccgg tgttccgata tgcgtc       56

<210> SEQ ID NO 74
<211> LENGTH: 57
<212> TYPE: DNA
<213> ORGANISM: Artificial
<220> FEATURE:
<223> OTHER INFORMATION: synthetic oligonucleotide

<400> SEQUENCE: 74
cggaacaccg gcatgtagtc cacagtactg taagacatgc gcattgatcg caacagg      57

<210> SEQ ID NO 75
<211> LENGTH: 59
<212> TYPE: DNA
<213> ORGANISM: Artificial
<220> FEATURE:
<223> OTHER INFORMATION: synthetic oligonucleotide

<400> SEQUENCE: 75
caaaagctgt gcttgtctta cagtactgtg gactacatgc ttttgcgtcg acatcacgg    59

<210> SEQ ID NO 76
<211> LENGTH: 59

```
<212> TYPE: DNA
<213> ORGANISM: Artificial
<220> FEATURE:
<223> OTHER INFORMATION: synthetic oligonucleotide

<400> SEQUENCE: 76
acgcaaaagc atgtagtcca cagtactgta agacaagcac agcttttgca tgcactatg      59

<210> SEQ ID NO 77
<211> LENGTH: 56
<212> TYPE: DNA
<213> ORGANISM: Artificial
<220> FEATURE:
<223> OTHER INFORMATION: synthetic oligonucleotide

<400> SEQUENCE: 77
tcaatgcgca tgtactcttt ggaacagatc tccttgccgg tgttccgata tgcgtc         56

<210> SEQ ID NO 78
<211> LENGTH: 57
<212> TYPE: DNA
<213> ORGANISM: Artificial
<220> FEATURE:
<223> OTHER INFORMATION: synthetic oligonucleotide

<400> SEQUENCE: 78
cggaacaccg gcaaggagat ctgttccaaa gagtacatgc gcattgatcg caacagg        57

<210> SEQ ID NO 79
<211> LENGTH: 59
<212> TYPE: DNA
<213> ORGANISM: Artificial
<220> FEATURE:
<223> OTHER INFORMATION: synthetic oligonucleotide

<400> SEQUENCE: 79
caaaagctgt gcttgtactc tttggaatcg atctccttgc ttttgcgtcg acatcacgg      59

<210> SEQ ID NO 80
<211> LENGTH: 59
<212> TYPE: DNA
<213> ORGANISM: Artificial
<220> FEATURE:
<223> OTHER INFORMATION: synthetic oligonucleotide

<400> SEQUENCE: 80
acgcaaaagc aaggagatcg attccaaaga gtacaagcac agcttttgca tgcactatg      59

<210> SEQ ID NO 81
<211> LENGTH: 56
<212> TYPE: DNA
<213> ORGANISM: Artificial
<220> FEATURE:
<223> OTHER INFORMATION: synthetic oligonucleotide

<400> SEQUENCE: 81
tcaatgcgca tgtacaaaca tcgattctac tccttgccgg tgttccgata tgcgtc         56

<210> SEQ ID NO 82
<211> LENGTH: 57
<212> TYPE: DNA
<213> ORGANISM: Artificial
<220> FEATURE:
<223> OTHER INFORMATION: synthetic oligonucleotide

<400> SEQUENCE: 82
```
cggaacaccg gcaaggagta gaatcgatgt ttgtacatgc gcattgatcg caacagg        57

<210> SEQ ID NO 83
<211> LENGTH: 59
<212> TYPE: DNA
<213> ORGANISM: Artificial
<220> FEATURE:
<223> OTHER INFORMATION: synthetic oligonucleotide

<400> SEQUENCE: 83
caaaagctgt gcttgcacaa acatcgattc tactccttgt ttttgcgtcg acatcacgg       59

<210> SEQ ID NO 84
<211> LENGTH: 59
<212> TYPE: DNA
<213> ORGANISM: Artificial
<220> FEATURE:
<223> OTHER INFORMATION: synthetic oligonucleotide

<400> SEQUENCE: 84
acgcaaaaac aaggagtaga atcgatgttt gtgcaagcac agcttttgca tgcactatg       59

<210> SEQ ID NO 85
<211> LENGTH: 56
<212> TYPE: DNA
<213> ORGANISM: Artificial
<220> FEATURE:
<223> OTHER INFORMATION: synthetic oligonucleotide

<400> SEQUENCE: 85
tcaatgcgca tgtacaaaaa tcgatcgtac tccttgccgg tgttccgata tgcgtc          56

<210> SEQ ID NO 86
<211> LENGTH: 57
<212> TYPE: DNA
<213> ORGANISM: Artificial
<220> FEATURE:
<223> OTHER INFORMATION: synthetic oligonucleotide

<400> SEQUENCE: 86
cggaacaccg gcaaggagta cgatcgattt ttgtacatgc gcattgatcg caacagg        57

<210> SEQ ID NO 87
<211> LENGTH: 59
<212> TYPE: DNA
<213> ORGANISM: Artificial
<220> FEATURE:
<223> OTHER INFORMATION: synthetic oligonucleotide

<400> SEQUENCE: 87
caaaagctgt gcttgcacaa aaatcgatcg tactccttgt ttttgcgtcg acatcacgg       59

<210> SEQ ID NO 88
<211> LENGTH: 59
<212> TYPE: DNA
<213> ORGANISM: Artificial
<220> FEATURE:
<223> OTHER INFORMATION: synthetic oligonucleotide

<400> SEQUENCE: 88
acgcaaaaac aaggagtacg atcgattttt gtgcaagcac agcttttgca tgcactatg       59

<210> SEQ ID NO 89
<211> LENGTH: 56
<212> TYPE: DNA
<213> ORGANISM: Artificial

```
<220> FEATURE:
<223> OTHER INFORMATION: synthetic oligonucleotide

<400> SEQUENCE: 89
tcaatgcgca tgtcacctgc agacaactga aacatgccgg tgttccgata tgcgtc         56

<210> SEQ ID NO 90
<211> LENGTH: 57
<212> TYPE: DNA
<213> ORGANISM: Artificial
<220> FEATURE:
<223> OTHER INFORMATION: synthetic oligonucleotide

<400> SEQUENCE: 90
cggaacaccg gcatgtttca gttgtctgca ggtgacatgc gcattgatcg caacagg        57

<210> SEQ ID NO 91
<211> LENGTH: 59
<212> TYPE: DNA
<213> ORGANISM: Artificial
<220> FEATURE:
<223> OTHER INFORMATION: synthetic oligonucleotide

<400> SEQUENCE: 91
caaaagctgt gcttgccacc tgcagacaac tgaaacatgt ttttgcgtcg acatcacgg      59

<210> SEQ ID NO 92
<211> LENGTH: 59
<212> TYPE: DNA
<213> ORGANISM: Artificial
<220> FEATURE:
<223> OTHER INFORMATION: synthetic oligonucleotide

<400> SEQUENCE: 92
acgcaaaaac atgtttcagt tgtctgcagg tggcaagcac agcttttgca tgcactatg      59

<210> SEQ ID NO 93
<211> LENGTH: 56
<212> TYPE: DNA
<213> ORGANISM: Artificial
<220> FEATURE:
<223> OTHER INFORMATION: synthetic oligonucleotide

<400> SEQUENCE: 93
tcaatgcgca tgtggctact tcatccatc gatttgccgg tgttccgata tgcgtc          56

<210> SEQ ID NO 94
<211> LENGTH: 57
<212> TYPE: DNA
<213> ORGANISM: Artificial
<220> FEATURE:
<223> OTHER INFORMATION: synthetic oligonucleotide

<400> SEQUENCE: 94
cggaacaccg gcaaatcgat gggatgaagt agccacatgc gcattgatcg caacagg        57

<210> SEQ ID NO 95
<211> LENGTH: 59
<212> TYPE: DNA
<213> ORGANISM: Artificial
<220> FEATURE:
<223> OTHER INFORMATION: synthetic oligonucleotide

<400> SEQUENCE: 95
caaaagctgt gcttgcggct acttcatccc atcgatttgt ttttgcgtcg acatcacgg      59
```

<210> SEQ ID NO 96
<211> LENGTH: 59
<212> TYPE: DNA
<213> ORGANISM: Artificial
<220> FEATURE:
<223> OTHER INFORMATION: synthetic oligonucleotide

<400> SEQUENCE: 96
acgcaaaaac aaatcgatgg gatgaagtag ccgcaagcac agcttttgca tgcactatg      59

<210> SEQ ID NO 97
<211> LENGTH: 56
<212> TYPE: DNA
<213> ORGANISM: Artificial
<220> FEATURE:
<223> OTHER INFORMATION: synthetic oligonucleotide

<400> SEQUENCE: 97
tcaatgcgca tgtttacgta tccttgctaa caaatgccgg tgttccgata tgcgtc         56

<210> SEQ ID NO 98
<211> LENGTH: 57
<212> TYPE: DNA
<213> ORGANISM: Artificial
<220> FEATURE:
<223> OTHER INFORMATION: synthetic oligonucleotide

<400> SEQUENCE: 98
cggaacaccg gcatttgtta gcaaggatac gtaaacatgc gcattgatcg caacagg        57

<210> SEQ ID NO 99
<211> LENGTH: 59
<212> TYPE: DNA
<213> ORGANISM: Artificial
<220> FEATURE:
<223> OTHER INFORMATION: synthetic oligonucleotide

<400> SEQUENCE: 99
caaaagctgt gcttgcttac gtatccttgc taacaaatgt ttttgcgtcg acatcacgg      59

<210> SEQ ID NO 100
<211> LENGTH: 59
<212> TYPE: DNA
<213> ORGANISM: Artificial
<220> FEATURE:
<223> OTHER INFORMATION: synthetic oligonucleotide

<400> SEQUENCE: 100
acgcaaaaac atttgttagc aaggatacgt aagcaagcac agcttttgca tgcactatg      59

<210> SEQ ID NO 101
<211> LENGTH: 60
<212> TYPE: DNA
<213> ORGANISM: Artificial
<220> FEATURE:
<223> OTHER INFORMATION: synthetic oligonucleotide

<400> SEQUENCE: 101
gcgatcaatg cgcctgcaga actcaaccat atcctttatg tcggtgttcc gatatgcgtc     60

<210> SEQ ID NO 102
<211> LENGTH: 60
<212> TYPE: DNA
<213> ORGANISM: Artificial
<220> FEATURE:
<223> OTHER INFORMATION: synthetic oligonucleotide

<400> SEQUENCE: 102
ggaacaccga cataaaggat atggttgagt tctgcaggcg cattgatcgc aacagggttt        60

<210> SEQ ID NO 103
<211> LENGTH: 59
<212> TYPE: DNA
<213> ORGANISM: Artificial
<220> FEATURE:
<223> OTHER INFORMATION: synthetic oligonucleotide

<400> SEQUENCE: 103
caaaagctgt gcctgcagaa cacaaccta cccactttgt ttttgcgtcg acatcacgg        59

<210> SEQ ID NO 104
<211> LENGTH: 59
<212> TYPE: DNA
<213> ORGANISM: Artificial
<220> FEATURE:
<223> OTHER INFORMATION: synthetic oligonucleotide

<400> SEQUENCE: 104
acgcaaaaac aaagtgggta aggttgtgtt ctgcaggcac agcttttgca tgcactatg        59

<210> SEQ ID NO 105
<211> LENGTH: 59
<212> TYPE: DNA
<213> ORGANISM: Artificial
<220> FEATURE:
<223> OTHER INFORMATION: synthetic oligonucleotide

<400> SEQUENCE: 105
caaaagctgt gcctgcctgt taacacctac tcttaactgt ttttgcgtcg acatcacgg        59

<210> SEQ ID NO 106
<211> LENGTH: 59
<212> TYPE: DNA
<213> ORGANISM: Artificial
<220> FEATURE:
<223> OTHER INFORMATION: synthetic oligonucleotide

<400> SEQUENCE: 106
acgcaaaaac agttaagagt aggtgttaac aggcaggcac agcttttgca tgcactatg        59

<210> SEQ ID NO 107
<211> LENGTH: 57
<212> TYPE: DNA
<213> ORGANISM: Artificial
<220> FEATURE:
<223> OTHER INFORMATION: synthetic oligonucleotide

<400> SEQUENCE: 107
tcaatgcgca tgcgctcttc caactcattc taactgtcgg tgttccgata tgcgtct        57

<210> SEQ ID NO 108
<211> LENGTH: 57
<212> TYPE: DNA
<213> ORGANISM: Artificial
<220> FEATURE:
<223> OTHER INFORMATION: synthetic oligonucleotide

<400> SEQUENCE: 108
cggaacaccg acagttagaa tgagttggaa gagcgcatgc gcattgatcg caacagg        57

<210> SEQ ID NO 109

```
<211> LENGTH: 59
<212> TYPE: DNA
<213> ORGANISM: Artificial
<220> FEATURE:
<223> OTHER INFORMATION: synthetic oligonucleotide

<400> SEQUENCE: 109
caaaagctgt gcctgcgcgc ttcctacaca ctctaactgt ttttgcgtcg acatcacgg      59

<210> SEQ ID NO 110
<211> LENGTH: 59
<212> TYPE: DNA
<213> ORGANISM: Artificial
<220> FEATURE:
<223> OTHER INFORMATION: synthetic oligonucleotide

<400> SEQUENCE: 110
acgcaaaaac agttagagtg tgtaggaagc gcgcaggcac agcttttgca tgcactatg      59

<210> SEQ ID NO 111
<211> LENGTH: 59
<212> TYPE: DNA
<213> ORGANISM: Artificial
<220> FEATURE:
<223> OTHER INFORMATION: synthetic oligonucleotide

<400> SEQUENCE: 111
caaaagctgt gcctgccctt taggcctttg cccaccttgt ttttgcgtcg acatcacgg      59

<210> SEQ ID NO 112
<211> LENGTH: 59
<212> TYPE: DNA
<213> ORGANISM: Artificial
<220> FEATURE:
<223> OTHER INFORMATION: synthetic oligonucleotide

<400> SEQUENCE: 112
acgcaaaaac aaggtgggca aaggcctaaa gggcaggcac agcttttgca tgcactatg      59

<210> SEQ ID NO 113
<211> LENGTH: 56
<212> TYPE: DNA
<213> ORGANISM: Artificial
<220> FEATURE:
<223> OTHER INFORMATION: synthetic oligonucleotide

<400> SEQUENCE: 113
aagctgtatc tgctggaaca tcgattctac accttgtttt tgcgtcgaca tcacgg         56

<210> SEQ ID NO 114
<211> LENGTH: 56
<212> TYPE: DNA
<213> ORGANISM: Artificial
<220> FEATURE:
<223> OTHER INFORMATION: synthetic oligonucleotide

<400> SEQUENCE: 114
acgcaaaaac aaggtgtaga atcgatgttc cagcagatac agcttttgca tgcact         56

<210> SEQ ID NO 115
<211> LENGTH: 60
<212> TYPE: DNA
<213> ORGANISM: Artificial
<220> FEATURE:
<223> OTHER INFORMATION: synthetic oligonucleotide

<400> SEQUENCE: 115
```

```
gcgatcaatg catctgtact tggattgaca gtactccttg tcggtgttcc gatatgcgtc    60
```

<210> SEQ ID NO 116
<211> LENGTH: 60
<212> TYPE: DNA
<213> ORGANISM: Artificial
<220> FEATURE:
<223> OTHER INFORMATION: synthetic oligonucleotide

<400> SEQUENCE: 116

```
ggaacaccga caaggagtac tgtcaatcca agtacagatg cattgatcgc aacagggttt    60
```

<210> SEQ ID NO 117
<211> LENGTH: 56
<212> TYPE: DNA
<213> ORGANISM: Artificial
<220> FEATURE:
<223> OTHER INFORMATION: synthetic oligonucleotide

<400> SEQUENCE: 117

```
aagctgtatc tgcacatgga tcgatagtac tccttgtttt tgcgtcgaca tcacgg    56
```

<210> SEQ ID NO 118
<211> LENGTH: 56
<212> TYPE: DNA
<213> ORGANISM: Artificial
<220> FEATURE:
<223> OTHER INFORMATION: synthetic oligonucleotide

<400> SEQUENCE: 118

```
acgcaaaaac aaggtgtaga atcgatccat gtgcagatac agcttttgca tgcact    56
```

<210> SEQ ID NO 119
<211> LENGTH: 56
<212> TYPE: DNA
<213> ORGANISM: Artificial
<220> FEATURE:
<223> OTHER INFORMATION: synthetic oligonucleotide

<400> SEQUENCE: 119

```
aagctgtatc tgtacatgga tcgattggac accttgtttt tgcgtcgaca tcacgg    56
```

<210> SEQ ID NO 120
<211> LENGTH: 56
<212> TYPE: DNA
<213> ORGANISM: Artificial
<220> FEATURE:
<223> OTHER INFORMATION: synthetic oligonucleotide

<400> SEQUENCE: 120

```
acgcaaaaac aaggtgtcca atcgatccat gtacagatac agcttttgca tgcact    56
```

<210> SEQ ID NO 121
<211> LENGTH: 59
<212> TYPE: DNA
<213> ORGANISM: Artificial
<220> FEATURE:
<223> OTHER INFORMATION: synthetic oligonucleotide

<400> SEQUENCE: 121

```
caaaagctgc gcatgtgtta ctacagattg gatcgaatgt ttttgcgtcg acatcacgg    59
```

<210> SEQ ID NO 122
<211> LENGTH: 59
<212> TYPE: DNA

<213> ORGANISM: Artificial
<220> FEATURE:
<223> OTHER INFORMATION: synthetic oligonucleotide

<400> SEQUENCE: 122
acgcaaaaac attcgatcca atctgtagta acacatgcgc agcttttgca tgcactatg        59

<210> SEQ ID NO 123
<211> LENGTH: 61
<212> TYPE: DNA
<213> ORGANISM: Artificial
<220> FEATURE:
<223> OTHER INFORMATION: synthetic oligonucleotide

<400> SEQUENCE: 123
caaaagctgt gcctgcccaa cactttggac tcatatgtgt ttttgcgtcg acatcacgga        60
c                                                                      61

<210> SEQ ID NO 124
<211> LENGTH: 61
<212> TYPE: DNA
<213> ORGANISM: Artificial
<220> FEATURE:
<223> OTHER INFORMATION: synthetic oligonucleotide

<400> SEQUENCE: 124
acgcaaaaac acatatgagt ccaaagtgtt gggcaggcac agcttttgca tgcactatga        60
c                                                                      61

<210> SEQ ID NO 125
<211> LENGTH: 59
<212> TYPE: DNA
<213> ORGANISM: Artificial
<220> FEATURE:
<223> OTHER INFORMATION: synthetic oligonucleotide

<400> SEQUENCE: 125
caaaagctgc gcatgttact actctcaatt ccaccaatgt ttttgcgtcg acatcacgg         59

<210> SEQ ID NO 126
<211> LENGTH: 59
<212> TYPE: DNA
<213> ORGANISM: Artificial
<220> FEATURE:
<223> OTHER INFORMATION: synthetic oligonucleotide

<400> SEQUENCE: 126
acgcaaaaac attggtggaa ttgagagtag taacatgcgc agcttttgca tgcactatg        59

<210> SEQ ID NO 127
<211> LENGTH: 69
<212> TYPE: DNA
<213> ORGANISM: Artificial
<220> FEATURE:
<223> OTHER INFORMATION: synthetic oligonucleotide

<400> SEQUENCE: 127
caaaagctgt ctttgtccgg aaaacgataa cgtttctcct tgtaattgcg tcgacatcac        60
ggacttctg                                                              69

<210> SEQ ID NO 128
<211> LENGTH: 69
<212> TYPE: DNA
<213> ORGANISM: Artificial

```
<220> FEATURE:
<223> OTHER INFORMATION: synthetic oligonucleotide

<400> SEQUENCE: 128
tgtcgacgca attacaagga gaaacgttat cgttttccgg acaaagacag cttttgcatg      60
cactatgac                                                             69

<210> SEQ ID NO 129
<211> LENGTH: 47
<212> TYPE: DNA
<213> ORGANISM: Artificial
<220> FEATURE:
<223> OTHER INFORMATION: synthetic oligonucleotide

<400> SEQUENCE: 129
caaaagctgt gcttgtaaac acaacgtacg tcttttatgt ttttgcg                   47

<210> SEQ ID NO 130
<211> LENGTH: 55
<212> TYPE: DNA
<213> ORGANISM: Artificial
<220> FEATURE:
<223> OTHER INFORMATION: synthetic oligonucleotide

<400> SEQUENCE: 130
tcgacgcaaa aacataaaag acgtacgttg tgtttacaag cacagctttt gcatg          55

<210> SEQ ID NO 131
<211> LENGTH: 37
<212> TYPE: DNA
<213> ORGANISM: Artificial
<220> FEATURE:
<223> OTHER INFORMATION: synthetic oligonucleotide

<400> SEQUENCE: 131
gatccaggtg gagctgcttt agttgacgat gagagct                              37

<210> SEQ ID NO 132
<211> LENGTH: 29
<212> TYPE: DNA
<213> ORGANISM: Artificial
<220> FEATURE:
<223> OTHER INFORMATION: synthetic oligonucleotide

<400> SEQUENCE: 132
ctcatcgtca actaaagcag ctccacctg                                       29

<210> SEQ ID NO 133
<211> LENGTH: 70
<212> TYPE: DNA
<213> ORGANISM: Artificial
<220> FEATURE:
<223> OTHER INFORMATION: synthetic oligonucleotide

<400> SEQUENCE: 133
gatccaggtg aacctgaccc aactcctcca tctgatcctg gagaataccc agcttgggac      60
gatgagagct                                                            70

<210> SEQ ID NO 134
<211> LENGTH: 62
<212> TYPE: DNA
<213> ORGANISM: Artificial
<220> FEATURE:
<223> OTHER INFORMATION: synthetic oligonucleotide
```

<400> SEQUENCE: 134
ctcatcgtcc caagctgggt attctccagg atcagatgga ggagttgggt caggttcacc    60
tg    62

<210> SEQ ID NO 135
<211> LENGTH: 79
<212> TYPE: DNA
<213> ORGANISM: Artificial
<220> FEATURE:
<223> OTHER INFORMATION: synthetic oligonucleotide

<400> SEQUENCE: 135
gatccggcga acctgcgtct gtctaagctt ggcctgctta tgaaatcaga ccatcagcac    60
agcaatgacg atgagagct    79

<210> SEQ ID NO 136
<211> LENGTH: 71
<212> TYPE: DNA
<213> ORGANISM: Artificial
<220> FEATURE:
<223> OTHER INFORMATION: synthetic oligonucleotide

<400> SEQUENCE: 136
ctcatcgtca ttgctgtgct gatggtctga tttcataagc aggccaagct tagacagacg    60
caggttcgcc g    71

<210> SEQ ID NO 137
<211> LENGTH: 43
<212> TYPE: DNA
<213> ORGANISM: Artificial
<220> FEATURE:
<223> OTHER INFORMATION: synthetic oligonucleotide

<400> SEQUENCE: 137
gatccaaaat cagaccatca gcacagcaat gacgatgaga gct    43

<210> SEQ ID NO 138
<211> LENGTH: 35
<212> TYPE: DNA
<213> ORGANISM: Artificial
<220> FEATURE:
<223> OTHER INFORMATION: synthetic oligonucleotide

<400> SEQUENCE: 138
ctcatcgtca ttgctgtgct gatggtctga ttttg    35

<210> SEQ ID NO 139
<211> LENGTH: 205
<212> TYPE: DNA
<213> ORGANISM: Artificial
<220> FEATURE:
<223> OTHER INFORMATION: synthetic oligonucleotide

<400> SEQUENCE: 139
gatccaggag aaccggaccc aacgccccca agtgatccag gagagtatcc agcatgggat    60
tcaaatcaaa tttcacacaaa tgaaattgtg tatcataacg gtcagttatg gcaagcgaaa    120
tggtggacac aaaatcaaga gccaggtgac ccatacggtc cgtgggaacc actcaaatct    180
gacccagatt cagacgatga gagct    205

<210> SEQ ID NO 140
<211> LENGTH: 197

<212> TYPE: DNA
<213> ORGANISM: Artificial
<220> FEATURE:
<223> OTHER INFORMATION: synthetic oligonucleotide

<400> SEQUENCE: 140
ctcatcgtct gaatctgggt cagatttgag tggttcccac ggaccgtatg ggtcacctgg    60
ctcttgattt tgtgtccacc atttcgcttg ccataactga ccgttatgat acacaatttc   120
atttgtgtaa atttgatttg aatcccatgc tggatactct cctggatcac ttggggcgt   180 tgggtccggt tctcctg                                                  197

<210> SEQ ID NO 141
<211> LENGTH: 6
<212> TYPE: PRT
<213> ORGANISM: Artificial
<220> FEATURE:
<223> OTHER INFORMATION: synthetic linker peptide

<400> SEQUENCE: 141

Trp Gly Asp Pro His Tyr
1               5

<210> SEQ ID NO 142
<211> LENGTH: 6
<212> TYPE: PRT
<213> ORGANISM: Artificial
<220> FEATURE:
<223> OTHER INFORMATION: synthetic linker peptide

<400> SEQUENCE: 142

Asp Asn Asn Asp Pro Ile
1               5

<210> SEQ ID NO 143
<211> LENGTH: 6
<212> TYPE: PRT
<213> ORGANISM: Artificial
<220> FEATURE:
<223> OTHER INFORMATION: synthetic linker peptide

<400> SEQUENCE: 143

Val Val Ala Asp Pro Asn
1               5

<210> SEQ ID NO 144
<211> LENGTH: 37
<212> TYPE: DNA
<213> ORGANISM: Artificial
<220> FEATURE:
<223> OTHER INFORMATION: synthetic oligonucleotide

<400> SEQUENCE: 144
tggcgttcag caacatgagc gcgcaggctg atgatta                             37

<210> SEQ ID NO 145
<211> LENGTH: 37
<212> TYPE: DNA
<213> ORGANISM: Artificial
<220> FEATURE:
<223> OTHER INFORMATION: synthetic oligonucleotide

<400> SEQUENCE: 145
taatcatcag cctgcgcgct catgttgctg aacgcca                             37

```
<210> SEQ ID NO 146
<211> LENGTH: 128
<212> TYPE: DNA
<213> ORGANISM: Artificial
<220> FEATURE:
<223> OTHER INFORMATION: synthetic oligonucleotide

<400> SEQUENCE: 146
gacatcacgg acttctgcta tgagccatgt aaaccaagcg aggacgataa agagaactaa      60
aagcttaact cgaggttaac agaggacgga tttcctgaag gaaatccgtt ttttattt     120 taattaag                                                              128

<210> SEQ ID NO 147
<211> LENGTH: 130
<212> TYPE: DNA
<213> ORGANISM: Artificial
<220> FEATURE:
<223> OTHER INFORMATION: synthetic oligonucleotide

<400> SEQUENCE: 147
agctcttaat taaaaataaa aaaacggatt tccttcagga aatccgtcct ctgttaacct      60
cgagttaagc ttttagttct ctttatcgtc ctcgcttggt ttacatggct catagcagaa     120
gtccgtgatg                                                            130

<210> SEQ ID NO 148
<211> LENGTH: 23
<212> TYPE: DNA
<213> ORGANISM: Artificial
<220> FEATURE:
<223> OTHER INFORMATION: synthetic oligonucleotide

<400> SEQUENCE: 148
cagcaacatg agcgcgcagg ctg                                              23

<210> SEQ ID NO 149
<211> LENGTH: 59
<212> TYPE: DNA
<213> ORGANISM: Artificial
<220> FEATURE:
<223> OTHER INFORMATION: synthetic oligonucleotide

<400> SEQUENCE: 149
atcgtctgga tccggatagt gggggtctcc ccaagatgct gattctctta ttttttccc       59

<210> SEQ ID NO 150
<211> LENGTH: 59
<212> TYPE: DNA
<213> ORGANISM: Artificial
<220> FEATURE:
<223> OTHER INFORMATION: synthetic oligonucleotide

<400> SEQUENCE: 150
atcgtctgga tccggtatgg gatcattgtt gtcagatgct gattctctta ttttttccc       59

<210> SEQ ID NO 151
<211> LENGTH: 59
<212> TYPE: DNA
<213> ORGANISM: Artificial
<220> FEATURE:
<223> OTHER INFORMATION: synthetic oligonucleotide

<400> SEQUENCE: 151
atcgtctgga tccggggttgg gatctgcaac tacagatgct gattctctta ttttttccc      59
```

```
<210> SEQ ID NO 152
<211> LENGTH: 25
<212> TYPE: DNA
<213> ORGANISM: Artificial
<220> FEATURE:
<223> OTHER INFORMATION: synthetic oligonucleotide

<400> SEQUENCE: 152
gcataaggat gagtcatctg cagcg                                          25

<210> SEQ ID NO 153
<211> LENGTH: 57
<212> TYPE: DNA
<213> ORGANISM: Artificial
<220> FEATURE:
<223> OTHER INFORMATION: synthetic oligonucleotide

<400> SEQUENCE: 153
atcgtctgga tccggatagt gggggtctcc ccacggttct cctggatcag atggcgg       57

<210> SEQ ID NO 154
<211> LENGTH: 57
<212> TYPE: DNA
<213> ORGANISM: Artificial
<220> FEATURE:
<223> OTHER INFORMATION: synthetic oligonucleotide

<400> SEQUENCE: 154
atcgtctgga tccggtatgg gatcattgtt gtccggttct cctggatcag atggcgg       57

<210> SEQ ID NO 155
<211> LENGTH: 57
<212> TYPE: DNA
<213> ORGANISM: Artificial
<220> FEATURE:
<223> OTHER INFORMATION: synthetic oligonucleotide

<400> SEQUENCE: 155
atcgtctgga tccgggttgg gatctgcaac taccggttct cctggatcag atggcgg       57

<210> SEQ ID NO 156
<211> LENGTH: 9
<212> TYPE: PRT
<213> ORGANISM: Artificial
<220> FEATURE:
<223> OTHER INFORMATION: synthetic linker peptide

<400> SEQUENCE: 156

Trp Gly Asp Pro His Tyr Pro Asp Pro
1               5

<210> SEQ ID NO 157
<211> LENGTH: 9
<212> TYPE: PRT
<213> ORGANISM: Artificial
<220> FEATURE:
<223> OTHER INFORMATION: synthetic linker peptide

<400> SEQUENCE: 157

Asp Asn Asn Asp Pro Ile Pro Asp Pro
1               5

<210> SEQ ID NO 158
<211> LENGTH: 9
<212> TYPE: PRT
<213> ORGANISM: Artificial
```

```
<220> FEATURE:
<223> OTHER INFORMATION: synthetic linker peptide

<400> SEQUENCE: 158

Val Val Ala Asp Pro Asn Pro Asp Pro
1               5

<210> SEQ ID NO 159
<211> LENGTH: 24
<212> TYPE: PRT
<213> ORGANISM: Artificial
<220> FEATURE:
<223> OTHER INFORMATION: synthetic linker peptide

<400> SEQUENCE: 159

Ile Pro Pro Ser Asp Pro Thr Pro Pro Ser Asp Pro Gly Glu Pro Trp
1               5                   10                  15

Gly Asp Pro His Tyr Pro Asp Pro
            20

<210> SEQ ID NO 160
<211> LENGTH: 24
<212> TYPE: PRT
<213> ORGANISM: Artificial
<220> FEATURE:
<223> OTHER INFORMATION: synthetic linker peptide

<400> SEQUENCE: 160

Ile Pro Pro Ser Asp Pro Thr Pro Pro Ser Asp Pro Gly Glu Pro Asp
1               5                   10                  15

Asn Asn Asp Pro Ile Pro Asp Pro
            20

<210> SEQ ID NO 161
<211> LENGTH: 24
<212> TYPE: PRT
<213> ORGANISM: Artificial
<220> FEATURE:
<223> OTHER INFORMATION: synthetic linker peptide

<400> SEQUENCE: 161

Ile Pro Pro Ser Asp Pro Thr Pro Pro Ser Asp Pro Gly Glu Pro Val
1               5                   10                  15

Val Ala Asp Pro Asn Pro Asp Pro
            20

<210> SEQ ID NO 162
<211> LENGTH: 40
<212> TYPE: DNA
<213> ORGANISM: Artificial
<220> FEATURE:
<223> OTHER INFORMATION: synthetic oligonucleotide

<400> SEQUENCE: 162
gatccaggtg gagacgacga tgacaaagac gatgagagct                             40

<210> SEQ ID NO 163
<211> LENGTH: 32
<212> TYPE: DNA
<213> ORGANISM: Artificial
<220> FEATURE:
<223> OTHER INFORMATION: synthetic oligonucleotide

<400> SEQUENCE: 163
ctcatcgtct ttgtcatcgt cgtctccacc tg                                     32
```

<210> SEQ ID NO 164
<211> LENGTH: 34
<212> TYPE: DNA
<213> ORGANISM: Artificial
<220> FEATURE:
<223> OTHER INFORMATION: synthetic oligonucleotide

<400> SEQUENCE: 164
gatccaggtg ctgctcatta cgacgatgag agct                              34

<210> SEQ ID NO 165
<211> LENGTH: 26
<212> TYPE: DNA
<213> ORGANISM: Artificial
<220> FEATURE:
<223> OTHER INFORMATION: synthetic oligonucleotide

<400> SEQUENCE: 165
ctcatcgtcg taatgagcag cacctg                                       26

<210> SEQ ID NO 166
<211> LENGTH: 31
<212> TYPE: DNA
<213> ORGANISM: Artificial
<220> FEATURE:
<223> OTHER INFORMATION: synthetic oligonucleotide

<400> SEQUENCE: 166
gatccacgtg ctaaaagaga cgatgagagc t                                 31

<210> SEQ ID NO 167
<211> LENGTH: 23
<212> TYPE: DNA
<213> ORGANISM: Artificial
<220> FEATURE:
<223> OTHER INFORMATION: synthetic oligonucleotide

<400> SEQUENCE: 167
ctcatcgtct cttttagcac gtg                                          23

<210> SEQ ID NO 168
<211> LENGTH: 37
<212> TYPE: DNA
<213> ORGANISM: Artificial
<220> FEATURE:
<223> OTHER INFORMATION: synthetic oligonucleotide

<400> SEQUENCE: 168
gatccaggcg ctgcacacta caacgacgat gagagct                           37

<210> SEQ ID NO 169
<211> LENGTH: 29
<212> TYPE: DNA
<213> ORGANISM: Artificial
<220> FEATURE:
<223> OTHER INFORMATION: synthetic oligonucleotide

<400> SEQUENCE: 169
ctcatcgtcg ttgtagtgtg cagcgcctg                                    29

<210> SEQ ID NO 170
<211> LENGTH: 28
<212> TYPE: DNA
<213> ORGANISM: Artificial
<220> FEATURE:

<223> OTHER INFORMATION: synthetic oligonucleotide

<400> SEQUENCE: 170
gatccattcc ttgaagacga tgagagct                                28

<210> SEQ ID NO 171
<211> LENGTH: 20
<212> TYPE: DNA
<213> ORGANISM: Artificial
<220> FEATURE:
<223> OTHER INFORMATION: synthetic oligonucleotide

<400> SEQUENCE: 171
ctcatcgtct tcaaggaatg                                         20

<210> SEQ ID NO 172
<211> LENGTH: 29
<212> TYPE: DNA
<213> ORGANISM: Artificial
<220> FEATURE:
<223> OTHER INFORMATION: synthetic oligonucleotide

<400> SEQUENCE: 172
cccataccgg agccagacga tgagagctc                               29

<210> SEQ ID NO 173
<211> LENGTH: 32
<212> TYPE: DNA
<213> ORGANISM: Artificial
<220> FEATURE:
<223> OTHER INFORMATION: synthetic oligonucleotide

<400> SEQUENCE: 173
catcgtctgg ctccggtatg ggatcattgt tg                           32

<210> SEQ ID NO 174
<211> LENGTH: 21
<212> TYPE: PRT
<213> ORGANISM: Artificial
<220> FEATURE:
<223> OTHER INFORMATION: synthetic linker peptide

<400> SEQUENCE: 174

Asp Asn Asn Asp Pro Ile Pro Glu Pro Asp Asp Glu Ser Phe Asn Met
1               5                   10                  15

Pro Ile Pro Glu Pro
            20

<210> SEQ ID NO 175
<211> LENGTH: 58
<212> TYPE: DNA
<213> ORGANISM: Artificial
<220> FEATURE:
<223> OTHER INFORMATION: synthetic oligonucleotide

<400> SEQUENCE: 175
gatccaggcg ctgcacacta caaatcagac catcagcaca gcaatgacga tgagagct    58

<210> SEQ ID NO 176
<211> LENGTH: 50
<212> TYPE: DNA
<213> ORGANISM: Artificial
<220> FEATURE:
<223> OTHER INFORMATION: synthetic oligonucleotide

<400> SEQUENCE: 176
ctcatcgtca ttgctgtgct gatggtctga tttgtagtgt gcagcgcctg    50

<210> SEQ ID NO 177
<211> LENGTH: 46
<212> TYPE: DNA
<213> ORGANISM: Artificial
<220> FEATURE:
<223> OTHER INFORMATION: synthetic oligonucleotide

<400> SEQUENCE: 177
gatccaggcg ctgcacacta cgtagaattt caagacgatg agagct    46

<210> SEQ ID NO 178
<211> LENGTH: 38
<212> TYPE: DNA
<213> ORGANISM: Artificial
<220> FEATURE:
<223> OTHER INFORMATION: synthetic oligonucleotide

<400> SEQUENCE: 178
ctcatcgtct tgaaattcta cgtagtgtgc agcgcctg    38

<210> SEQ ID NO 179
<211> LENGTH: 18
<212> TYPE: PRT
<213> ORGANISM: Artificial
<220> FEATURE:
<223> OTHER INFORMATION: synthetic cleavage site

<400> SEQUENCE: 179

Asp Asn Asn Asp Pro Ile Pro Asp Pro Gly Ala Ala His Tyr Val Glu
1               5                   10                  15

Phe Gln

<210> SEQ ID NO 180
<211> LENGTH: 87
<212> TYPE: PRT
<213> ORGANISM: Artificial
<220> FEATURE:
<223> OTHER INFORMATION: synthetic fusion protein

<400> SEQUENCE: 180

Lys Ile Arg Glu Ser Ala Ser Asp Asn Asn Asp Pro Ile Pro Asp Pro
1               5                   10                  15

Asp Asp Glu Ser Ser Lys Pro Cys Cys Asp Gln Cys Ala Cys Thr Lys
                20                  25                  30

Ser Asn Pro Pro Gln Cys Arg Cys Ser Asp Met Arg Leu Asn Ser Cys
            35                  40                  45

His Ser Ala Cys Lys Ser Cys Ala Cys Tyr Asn Leu Tyr Gly Trp Thr
        50                  55                  60

Cys Phe Cys Val Asp Ile Thr Asp Phe Cys Tyr Glu Pro Cys Lys Pro
65                  70                  75                  80

Ser Glu Asp Asp Lys Glu Asn
                85

<210> SEQ ID NO 181
<211> LENGTH: 46
<212> TYPE: DNA
<213> ORGANISM: Artificial
<220> FEATURE:
<223> OTHER INFORMATION: synthetic oligonucleotide primer

<400> SEQUENCE: 181
aacatgagcg cgcaggctga tgacgcggca attcaacaaa cgttag        46

<210> SEQ ID NO 182
<211> LENGTH: 77
<212> TYPE: DNA
<213> ORGANISM: Artificial
<220> FEATURE:
<223> OTHER INFORMATION: synthetic oligonucleotide primer

<400> SEQUENCE: 182
tcgtctggat ccggtatggg atcattgttg tcaccagaac cactagttga tcctttaccg        60
ctggtcattt tttggtg        77

<210> SEQ ID NO 183
<211> LENGTH: 60
<212> TYPE: DNA
<213> ORGANISM: Artificial
<220> FEATURE:
<223> OTHER INFORMATION: synthetic oligonucleotide

<400> SEQUENCE: 183
tgcacttctc tgctttggtc tgttgaacgc agaggtcttg acaacaatga tcctattccg        60

<210> SEQ ID NO 184
<211> LENGTH: 60
<212> TYPE: DNA
<213> ORGANISM: Artificial
<220> FEATURE:
<223> OTHER INFORMATION: synthetic oligonucleotide

<400> SEQUENCE: 184
gatccggaat aggatcattg ttgtcaagac ctctgcgttc aacagaccaa agcagagaag        60

<210> SEQ ID NO 185
<211> LENGTH: 66
<212> TYPE: PRT
<213> ORGANISM: Glycine max

<400> SEQUENCE: 185

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu
65

<210> SEQ ID NO 186
<211> LENGTH: 71
<212> TYPE: PRT
<213> ORGANISM: Artificial
<220> FEATURE:
<223> OTHER INFORMATION: synthetic BBI-AV sequence

<400> SEQUENCE: 186

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Tyr Asn Leu Tyr Gly Trp Thr
            35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70

<210> SEQ ID NO 187
<211> LENGTH: 66
<212> TYPE: PRT
<213> ORGANISM: Artificial
<220> FEATURE:
<223> OTHER INFORMATION: synthetic BBIt-AV sequence

<400> SEQUENCE: 187

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Tyr Asn Leu Tyr Gly Trp Thr
            35                  40                  45

Cys Phe Cys Val Asp Ile Thr Asp Phe Cys Tyr Glu Pro Cys Lys Pro
    50                  55                  60

Ser Glu
65

<210> SEQ ID NO 188
<211> LENGTH: 48
<212> TYPE: DNA
<213> ORGANISM: Artificial
<220> FEATURE:
<223> OTHER INFORMATION: synthetic oligonucleotide

<400> SEQUENCE: 188
tcgacatcac ggacttctgc tatgaaccat gtaaaccaag cgagtaaa                48

<210> SEQ ID NO 189
<211> LENGTH: 48
<212> TYPE: DNA
<213> ORGANISM: Artificial
<220> FEATURE:
<223> OTHER INFORMATION: synthetic oligonucleotide

<400> SEQUENCE: 189 agctttttact cgcttggttt acatggttca tagcagaagt ccgtgatg               48

<210> SEQ ID NO 190
<211> LENGTH: 9
<212> TYPE: DNA
<213> ORGANISM: Artificial
<220> FEATURE:
<223> OTHER INFORMATION: synthetic polynucleotide

<400> SEQUENCE: 190 gctggtaaa                                                           9

<210> SEQ ID NO 191
<211> LENGTH: 3
<212> TYPE: PRT
<213> ORGANISM: Bacillus subtilis

<400> SEQUENCE: 191

Ala Gly Lys
1

<210> SEQ ID NO 192
<211> LENGTH: 40
<212> TYPE: DNA
<213> ORGANISM: Artificial
<220> FEATURE:
<223> OTHER INFORMATION: synthetic oligonucleotide primer

<400> SEQUENCE: 192
gcgcgcaggc agctggtaaa gatgattatt cagttgtaga        40

<210> SEQ ID NO 193
<211> LENGTH: 40
<212> TYPE: DNA
<213> ORGANISM: Artificial
<220> FEATURE:
<223> OTHER INFORMATION: synthetic oligonucleotide primer

<400> SEQUENCE: 193
aataatcatc tttaccagct gcctgcgcgc tcatgttgct        40

<210> SEQ ID NO 194
<211> LENGTH: 5625
<212> TYPE: DNA
<213> ORGANISM: Artificial
<220> FEATURE:
<223> OTHER INFORMATION: synthetic expression vector

<400> SEQUENCE: 194
gaattctcca ttttcttctg ctatcaaaat aacagactcg tgattttcca acgagctttt        60
caaaaaagcc tctgccccct tgcaaatcgga tgcctgtcta taaaattccc gatattggtt       120
aaacagcggc gcaatggcgg ccgcatctga tgtctttgct tggcgaatgt tcatcttatt       180
tcttcctccc tctcaataat ttttcattc tatccctttt ctgtaaagtt tattttcag         240
aatactttta tcatcatgct ttgaaaaaat atcacgataa tatccattgt tctcacggaa       300
gcacacgcag gtcatttgaa cgaatttttt cgacaggaat tgccgggac tcaggagcat        360
ttaacctaaa aaagcatgac atttcagcat aatgaacatt tactcatgtc tattttcgtt       420
cttttctgta tgaaaatagt tatttcgagt ctctacggaa atagcgagag atgatatacc       480
taaatagaga taaatcatc tcaaaaaaat gggtctacta aatattatt ccatctatta        540
caataaattc acagaatagt cttttaagta agtctactct gaattttttt aaaggagag        600
ggtaaagagt gagaagcaaa aaattgtgga tcagcttgtt gtttgcgtta acgttaatct       660
ttacgatggc gttcagcaac atgagcgcgc aggcagctgg taaagatgat tattcagttg       720
tagaggaaca tgggcaacta agtattagta acggtgaatt agtcaatgaa cgaggcgaac       780
aagttcagtt aaaagggatg agttcccatg gtttgcaatg gtacggtcaa tttgtaaact       840
atgaaagcat gaaatggcta agagatgatt ggggaataac tgtattccga gcagcaatgt       900
atacctcttc aggaggatat attgacgatc catcagtaaa ggaaaaagta aaagagactg       960
ttgaggctgc gatagacctt ggcatatatg tgatcattga ttggcatatc ctttcagaca      1020
atgacccgaa tatatataaa gaagaagcga aggatttctt tgatgaaatg tcagagttgt      1080
atggagacta tccgaatgtg atatacgaaa ttgcaaatga accgaatggt agtgatgtta      1140
cgtgggacaa tcaaataaaa ccgtatatcag aagaagtgat tccggttatt cgtgacaatg      1200
accctaataa cattgttatt gtaggtacag gtacatggag tcaggatgtc catcatgcag      1260

```
ccgataatca gcttgcagat cctaacgtca tgtatgcatt tcattttat gcaggaacac    1320
atggacaaaa tttacgagac caagtagatt atgcattaga tcaaggagca gcgatatttg   1380
ttagtgaatg ggggacaagt gcagctacag gtgatggtgg tgtgttttta gatgaagcac   1440
aagtgtggat tgactttatg gatgaaagaa atttaagctg ggccaactgg tctctaacgc   1500
ataaggatga gtcatctgca gcgttaatgc caggtgcaaa tccaactggt ggttggacag   1560
aggctgaact atctccatct ggtacatttg tgagggaaaa aataagagaa tcagcatctg   1620
acaacaatga tcccataccg gatccagacg atgagagctc taaaccctgt tgcgatcaat   1680
gcgcatgtac gaaatcaaat cctccacagt gtcggtgttc cgatatgcgt ctgaattcct   1740
gtcatagtgc ctgcaaaagc tgcgcatgtt ataacctgta cgggtggacc tgttttgcg    1800
tcgacatcac ggacttctgc tatgaaccat gtaaaccaag cgagtaaaag cttaactcga   1860
ggttaacaga ggacggattt cctgaaggaa atccgttttt ttattttaa ttaagagctt    1920
ggcgtaatca tggtcatagc tgtttcctgt gtgaaattgt tatccgctca caattccaca   1980
caacatacga gccggaaata agtgtaaag cctggggtgc ctaatgagtg agctaactca    2040
cattaattgc gttgcgctca ctgcccgctt tccagtcggg aaacctgtcg tgccagctgc   2100
attaatgaat cggccaacgc gcggggagag gcggtttgcg tattgggcgc tcttccgctt   2160
cctcgctcac tgactcgctg cgctcggtcg ttcggctgcg gcgagcggta tcagctcact   2220
caaaggcggt aatacggtta ccacagaat cagggataa cgcaggaaag aacatgtgag    2280
caaaaggcca gcaaaaggcc aggaaccgta aaaaggccgc gttgctggcg tttttccata   2340
ggctccgccc ccctgacgag catcacaaaa atcgacgctc aagtcagagg tggcgaaacc   2400
cgacaggact ataaagatac caggcgtttc ccctgaag ctcccgtgt cgctctcctg     2460
ttccgaccct gccgcttacc ggatacctgt ccgcctttct cccttcggga agcgtggcgc   2520
tttctcatag ctcacgctgt aggtatctca gttcggtgta ggtcgttcgc tccaagctgg   2580
gctgtgtgca cgaaccccc gttcagcccg accgctgcgc cttatccggt aactatcgtc    2640
ttgagtccaa cccggtaaga cacgacttat cgccactggc agcagccact ggtaacagga   2700
ttagcagagc gaggtatgta ggcggtgcta cagagttctt gaagtggtgg cctaactacg   2760
gctacactag aagaacagta tttggtatct gcgctctgct gaagccagtt accttcggaa   2820
aaagagttgg tagctcttga tccggcaaac aaaccaccgc tggtagcggt ggtttttttg   2880
tttgcaagca gcagattacg cgcagaaaaa aaggatctca agaagatcct ttgatctttt   2940
ctacggggtc tgacgctcag tggaacgaaa actcacgtta agggattttg gtcatgagat   3000
tatcaaaaag gatcttcacc tagatccttt taaattaaaa atgaagtttt aaatcaatct   3060
aaagtatata tgagtaaact tggtctgaca gttaccaatg cttaatcagt gaggcaccta   3120
tctcagcgat ctgtctattt cgttcatcca tagttgcctg actccccgtc gtgtagataa   3180
ctacgatacg ggagggctta ccatctggcc ccagtgctgc aatgataccg cgagacccac   3240
gctcaccggc tccagattta tcagcaataa accagccagc cggaagggcc gagcgcagaa   3300
gtggtcctgc aactttatcc gcctccatcc agtctattaa ttgttgccgg gaagctagag   3360
taagtagttc gccagttaat agtttgcgca acgttgttgc cattgctaca ggcatcgtgg   3420
tgtcacgctc gtcgtttggt atggcttcat tcagctccgg ttcccaacga tcaaggcgag   3480
ttacatgatc ccccatgttg tgcaaaaaag cggttagctc cttcggtcct ccgatcgttg   3540
tcagaagtaa gttggccgca gtgttatcac tcatggttat ggcagcactg cataattctc   3600
ttactgtcat gccatccgta agatgctttt ctgtgactgg tgagtactca accaagtcat   3660
```

```
tctgagaata gtgtatgcgg cgaccgagtt gctcttgccc ggcgtcaata cgggataata    3720
ccgcgccaca tagcagaact ttaaaagtgc tcatcattgg aaaacgttct tcggggcgaa    3780
aactctcaag gatcttaccg ctgttgagat ccagttcgat gtaacccact cgtgcaccca    3840
actgatcttc agcatctttt actttcacca gcgtttctgg gtgagcaaaa acaggaaggc    3900
aaaatgccgc aaaaaaggga ataagggcga cacggaaatg ttgaatactc atactcttcc    3960
tttttcaata ttattgaagc atttatcagg gttattgtct catgagcgga tacatatttg    4020
aatgtattta gaaaaataaa caaataggggttccgcgcac atttccccga aaagtgccac    4080
ctgacgtcta agaaaccatt attatcatga cattaaccta taaaaatagg cgtatcacga    4140 ggcccttcg tctcgcgcgt ttcggtgatg acggtgaaaa cctctgacac atgcagctcc    4200
cggagacggt cacagcttgt ctgtaagcgg atgccgggag cagacaagcc cgtcagggcg    4260
cgtcagcggg tgttggcggg tgtcggggct ggcttaacta tgcggcatca gagcagattg    4320
tactgagagt gcaccataga tctggagctg taatataaaa accttcttca actaacgggg    4380
caggttagtg acattagaaa accgactgta aaaagtacag tcggcattat ctcatattat    4440
aaaagccagt cattaggcct atctgacaat tcctgaatag agttcataaa caatcctgca    4500
tgataaccat cacaaacaga atgatgtacc tgtaaagata gcggtaaata tattgaatta    4560
cctttattaa tgaattttcc tgctgtaata atgggtagaa ggtaattact attattattg    4620
atatttaagt taaacccagt aaatgaagtc catggaataa tagaaagaga aaaagcattt    4680
tcaggtatag gtgttttggg aaacaatttc cccgaaccat tatatttctc tacatcagaa    4740
aggtataaat cataaaactc tttgaagtca ttctttacag gagtccaaat accagagaat    4800
gttttagata caccatcaaa aattgtataa agtggctcta acttatccca ataacctaac    4860
tctccgtcgc tattgtaacc agttctaaaa gctgtatttg agtttatcac ccttgtcact    4920
aagaaaataa atgcagggta aaatttatat ccttcttgtt ttatgtttcg gtataaaaca    4980
ctaatatcaa tttctgtggt tatactaaaa gtcgtttgtt ggttcaaata atgattaaat    5040
atctcttttc tcttccaatt gtctaaatca attttattaa agttcatttg atatgcctcc    5100
taaattttta tctaaagtga atttaggagg cttacttgtc tgctttcttc attagaatca    5160 atccttttt aaaagtcaat attactgtaa cataaatata tattttaaaa atatcccact    5220
ttatccaatt ttcgtttgtt gaactaatgg gtgctttagt tgaagaataa aagaccacat    5280
taaaaaatgt ggtcttttgt gttttttaa aggatttgag cgtagcgaaa atcctttc    5340 tttcttatct tgataataag ggtaactatt gccggatcgt cctcaggagt aggcgacatc    5400
gctaaataat gatctatgcg gtgtgaaata ccgcacagat gcgtaaggag aaaataccgc    5460
atcaggcgcc attcgccatt caggctgcgc aactgttggg aagggcgatc ggtgcgggcc    5520
tcttcgctat tacgccagct ggcgaaaggg ggatgtgctg caaggcgatt aagttgggta    5580
acgccagggt tttcccagtc acgacgttgt aaaacgacgg ccagt    5625
```

<210> SEQ ID NO 195
<211> LENGTH: 383
<212> TYPE: PRT
<213> ORGANISM: Artificial
<220> FEATURE:
<223> OTHER INFORMATION: synthetic BBPI fusion protein

<400> SEQUENCE: 195

Ala Gly Lys Asp Asp Tyr Ser Val Val Glu Glu His Gly Gln Leu Ser
1               5                   10                  15

```
Ile Ser Asn Gly Glu Leu Val Asn Glu Arg Gly Glu Gln Val Gln Leu
             20                  25                  30

Lys Gly Met Ser Ser His Gly Leu Gln Trp Tyr Gly Gln Phe Val Asn
         35                  40                  45

Tyr Glu Ser Met Lys Trp Leu Arg Asp Asp Trp Gly Ile Thr Val Phe
     50                  55                  60

Arg Ala Ala Met Tyr Thr Ser Gly Gly Tyr Ile Asp Asp Pro Ser
 65                  70                  75                  80

Val Lys Glu Lys Val Lys Glu Thr Val Glu Ala Ala Ile Asp Leu Gly
                 85                  90                  95

Ile Tyr Val Ile Ile Asp Trp His Ile Leu Ser Asp Asn Asp Pro Asn
            100                 105                 110

Ile Tyr Lys Glu Glu Ala Lys Asp Phe Phe Asp Glu Met Ser Glu Leu
            115                 120                 125

Tyr Gly Asp Tyr Pro Asn Val Ile Tyr Glu Ile Ala Asn Glu Pro Asn
        130                 135                 140

Gly Ser Asp Val Thr Trp Asp Asn Gln Ile Lys Pro Tyr Ala Glu Glu
145                 150                 155                 160

Val Ile Pro Val Ile Arg Asp Asn Asp Pro Asn Asn Ile Val Ile Val
                165                 170                 175

Gly Thr Gly Thr Trp Ser Gln Asp Val His His Ala Ala Asp Asn Gln
            180                 185                 190

Leu Ala Asp Pro Asn Val Met Tyr Ala Phe His Phe Tyr Ala Gly Thr
        195                 200                 205

His Gly Gln Asn Leu Arg Asp Gln Val Asp Tyr Ala Leu Asp Gln Gly
    210                 215                 220

Ala Ala Ile Phe Val Ser Glu Trp Gly Thr Ser Ala Ala Thr Gly Asp
225                 230                 235                 240

Gly Gly Val Phe Leu Asp Glu Ala Gln Val Trp Ile Asp Phe Met Asp
                245                 250                 255

Glu Arg Asn Leu Ser Trp Ala Asn Trp Ser Leu Thr His Lys Asp Glu
            260                 265                 270

Ser Ser Ala Ala Leu Met Pro Gly Ala Asn Pro Thr Gly Gly Trp Thr
        275                 280                 285

Glu Ala Glu Leu Ser Pro Ser Gly Thr Phe Val Arg Glu Lys Ile Arg
    290                 295                 300

Glu Ser Ala Ser Asp Asn Asn Asp Pro Ile Pro Asp Pro Asp Glu
305                 310                 315                 320

Ser Ser Lys Pro Cys Cys Asp Gln Cys Ala Cys Thr Lys Ser Asn Pro
                325                 330                 335

Pro Gln Cys Arg Cys Ser Asp Met Arg Leu Asn Ser Cys His Ser Ala
            340                 345                 350

Cys Lys Ser Cys Ala Cys Tyr Asn Leu Tyr Gly Trp Thr Cys Phe Cys
        355                 360                 365

Val Asp Ile Thr Asp Phe Cys Tyr Glu Pro Cys Lys Pro Ser Glu
    370                 375                 380

<210> SEQ ID NO 196
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
```

```
<222> LOCATION: (19)..(20)
<223> OTHER INFORMATION: n is a, c, g, or t

<400> SEQUENCE: 196
gatcccatac cggatccann sgatgagagc tctaaacc                              38

<210> SEQ ID NO 197
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 197
ccataccgga tccagacnns gagagctcta aaccctg                               37

<210> SEQ ID NO 198
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 198
cataccggat ccagacgatn nsagctctaa accctgttg                             39

<210> SEQ ID NO 199
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 199
cggatccaga cgatgagnns tctaaaccct gttgcgatc                             39

<210> SEQ ID NO 200
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 200
gatccagacg atgagagcnn saaaccctgt tgcgatcaat g                          41

<210> SEQ ID NO 201
<211> LENGTH: 37
<212> TYPE: DNA
<213> ORGANISM: Artificial
<220> FEATURE:
<223> OTHER INFORMATION: synthetic primer
<220> FEATURE:
```

```
<221> NAME/KEY: misc_feature
<222> LOCATION: (18)..(19)
<223> OTHER INFORMATION: n is a, c, g, or t

<400> SEQUENCE: 201
cagacgatga gagctctnns ccctgttgcg atcaatg                                37

<210> SEQ ID NO 202
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 202
gacgatgaga gctctaaann stgttgcgat caatgcgc                               38

<210> SEQ ID NO 203
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 203
gatgagagct ctaaacccnn stgcgatcaa tgcgcatg                               38

<210> SEQ ID NO 204
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 204
gagagctcta aaccctgtnn sgatcaatgc gcatgtac                               38

<210> SEQ ID NO 205
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 205
gctctaaacc ctgttgcnns caatgcgcat gtacgaaatc                             40

<210> SEQ ID NO 206
<211> LENGTH: 37
<212> TYPE: DNA
<213> ORGANISM: Artificial
<220> FEATURE:
<223> OTHER INFORMATION: synthetic primer
```

```
<220> FEATURE:
<221> NAME/KEY: misc_feature
<222> LOCATION: (18)..(19)
<223> OTHER INFORMATION: n is a, c, g, or t

<400> SEQUENCE: 206
ctaaaccctg ttgcgatnns tgcgcatgta cgaaatc                              37

<210> SEQ ID NO 207
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 207
ctaaaccctg ttgcgatcaa nnsgcatgta cgaaatcaaa tc                        42

<210> SEQ ID NO 208
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 208
cctgttgcga tcaatgcnns tgtacgaaat caaatcc                              37

<210> SEQ ID NO 209
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 209
gttgcgatca atgcgcanns acgaaatcaa atcctcc                              37

<210> SEQ ID NO 210
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 210
gcgatcaatg cgcatgtnns aaatcaaatc ctccacag                             38

<210> SEQ ID NO 211
<211> LENGTH: 38
<212> TYPE: DNA
<213> ORGANISM: Artificial
<220> FEATURE:
```

-continued

<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 211
gatcaatgcg catgtacgnn stcaaatcct ccacagtg         38

<210> SEQ ID NO 212
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 212
caatgcgcat gtacgaaann saatcctcca cagtgtcg         38

<210> SEQ ID NO 213
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 213
gcgcatgtac gaaatcanns cctccacagt gtcggtg         37

<210> SEQ ID NO 214
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 214
catgtacgaa atcaaatnns ccacagtgtc ggtgttc         37

<210> SEQ ID NO 215
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 215
gtacgaaatc aaatcctnns cagtgtcggt gttccgatat         40

<210> SEQ ID NO 216
<211> LENGTH: 38
<212> TYPE: DNA
<213> ORGANISM: Artificial

-continued

```
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 216
cgaaatcaaa tcctccanns tgtcggtgtt ccgatatg                               38

<210> SEQ ID NO 217
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 217
gaaatcaaat cctccacagn nscggtgttc cgatatgcg                              39

<210> SEQ ID NO 218
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 218
caaatcctcc acagtgtnns tgttccgata tgcgtctg                               38

<210> SEQ ID NO 219
<211> LENGTH: 43
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 219
caaatcctcc acagtgtcgg nnstccgata tgcgtctgaa ttc                         43

<210> SEQ ID NO 220
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 220
ctccacagtg tcggtgtnns gatatgcgtc tgaattc                                37

<210> SEQ ID NO 221
<211> LENGTH: 37
<212> TYPE: DNA
```

<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 221
cacagtgtcg gtgttccnns atgcgtctga attcctg                               37

<210> SEQ ID NO 222
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 222
cagtgtcggt gttccgatnn scgtctgaat tcctgtcata g                          41

<210> SEQ ID NO 223
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 223
gtcggtgttc cgatatgnns ctgaattcct gtcatag                               37

<210> SEQ ID NO 224
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 224
ggtgttccga tatgcgtnns aattcctgtc atagtgc                               37

<210> SEQ ID NO 225
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 225
gttccgatat gcgtctgnns tcctgtcata gtgcctg                               37

<210> SEQ ID NO 226
<211> LENGTH: 40

```
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 226
ccgatatgcg tctgaatnns tgtcatagtg cctgcaaaag                              40

<210> SEQ ID NO 227
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 227
gatatgcgtc tgaattccnn scatagtgcc tgcaaaag                                38

<210> SEQ ID NO 228
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 228
atatgcgtct gaattcctgt nnsagtgcct gcaaaagctg                              40

<210> SEQ ID NO 229
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 229
gtctgaattc ctgtcatnns gcctgcaaaa gctgcgc                                 37

<210> SEQ ID NO 230
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 230
ctgaattcct gtcatagtnn stgcaaaagc tgcgcatg                                38

<210> SEQ ID NO 231
```

```
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 231
gaattcctgt catagtgccn nsaaaagctg cgcatgttat aa                42

<210> SEQ ID NO 232
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 232
cctgtcatag tgcctgcnns agctgcgcat gttataac                    38

<210> SEQ ID NO 233
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 233
gtcatagtgc ctgcaaanns tgcgcatgtt ataacctg                    38

<210> SEQ ID NO 234
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 234
catagtgcct gcaaaagcnn sgcatgttat aacctgtac                   39

<210> SEQ ID NO 235
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 235
gtgcctgcaa aagctgcnns tgttataacc tgtacgg                     37
```

```
<210> SEQ ID NO 236
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 236
cctgcaaaag ctgcgcanns tataacctgt acgggtg                              37

<210> SEQ ID NO 237
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 237
gcaaaagctg cgcatgtnns aacctgtacg ggtggac                              37

<210> SEQ ID NO 238
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 238
caaaagctgc gcatgttatn nsctgtacgg gtggacctg                            39

<210> SEQ ID NO 239
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 239
gctgcgcatg ttataacnns tacgggtgga cctgtttttg                           40

<210> SEQ ID NO 240
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 240
gcgcatgtta taacctgnns gggtggacct gttttg                               37
```

<210> SEQ ID NO 241
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 241
catgttataa cctgtacnns tggacctgtt tttgcgtc                            38

<210> SEQ ID NO 242
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 242
gttataacct gtacgggnns acctgttttt gcgtcgac                            38

<210> SEQ ID NO 243
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 243
gttataacct gtacgggtgg nnstgttttt gcgtcgacat c                        41

<210> SEQ ID NO 244
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 244
ataacctgta cgggtggacc nnsttttgcg tcgacatcac                          40

<210> SEQ ID NO 245
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 245
ctgtacgggt ggacctgtnn stgcgtcgac atcacggac                           39

```
<210> SEQ ID NO 246
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 246
gtacgggtgg acctgttttn nsgtcgacat cacggacttc                            40

<210> SEQ ID NO 247
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 247
ggtggacctg tttttgcnns gacatcacgg acttctg                               37

<210> SEQ ID NO 248
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 248
ggacctgttt ttgcgtcnns atcacggact tctgctatg                             39

<210> SEQ ID NO 249
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 249 cctgttttttg cgtcgacnns acggacttct gctatgaac                            39

<210> SEQ ID NO 250
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 250
```
gtttttgcgt cgacatcnns gacttctgct atgaacc                                    37

<210> SEQ ID NO 251
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 251
gtttttgcgt cgacatcacg nnsttctgct atgaaccatg                                 40

<210> SEQ ID NO 252
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 252
gcgtcgacat cacggacnns tgctatgaac catgtaaac                                  39

<210> SEQ ID NO 253
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 253
gtcgacatca cggacttcnn statgaacca tgtaaacc                                   38

<210> SEQ ID NO 254
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 254
gacatcacgg acttctgcnn sgaaccatgt aaaccaag                                   38

<210> SEQ ID NO 255
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 255

```
catcacggac ttctgctatn nsccatgtaa accaagcgag                                    40

<210> SEQ ID NO 256
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 256
cggacttctg ctatgaanns tgtaaaccaa gcgagtaaaa                                    40

<210> SEQ ID NO 257
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 257
gacttctgct atgaaccann saaaccaagc gagtaaaag                                     39

<210> SEQ ID NO 258
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 258
cttctgctat gaaccatgtn nsccaagcga gtaaaagctt aa                                 42

<210> SEQ ID NO 259
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 259
gctatgaacc atgtaaanns agcgagtaaa agcttaac                                      38

<210> SEQ ID NO 260
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t
```

```
<400> SEQUENCE: 260
ctatgaacca tgtaaaccan nsgagtaaaa gcttaactc                                    39

<210> SEQ ID NO 261
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 261
gaaccatgta aaccaagcnn staaaagctt aactcgag                                     38

<210> SEQ ID NO 262
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 262
ggtttagagc tctcatcsnn tggatccggt atgggatc                                     38

<210> SEQ ID NO 263
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 263
cagggtttag agctctcsnn gtctggatcc ggtatgg                                      37

<210> SEQ ID NO 264
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 264
caacagggtt tagagctsnn atcgtctgga tccggtatg                                    39

<210> SEQ ID NO 265
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t
```

<400> SEQUENCE: 265
gatcgcaaca gggtttagas nnctcatcgt ctggatccg          39

<210> SEQ ID NO 266
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 266
cattgatcgc aacagggttt snngctctca tcgtctggat c          41

<210> SEQ ID NO 267
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 267
cattgatcgc aacagggsnn agagctctca tcgtctg          37

<210> SEQ ID NO 268
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 268
gcgcattgat cgcaacasnn tttagagctc tcatcgtc          38

<210> SEQ ID NO 269
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 269
catgcgcatt gatcgcasnn gggtttagag ctctcatc          38

<210> SEQ ID NO 270
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)

<223> OTHER INFORMATION: n is a, c, g, or t

<400> SEQUENCE: 270
gtacatgcgc attgatcsnn acagggttta gagctctc                                    38

<210> SEQ ID NO 271
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 271
gatttcgtac atgcgcattg snngcaacag ggtttagagc                                  40

<210> SEQ ID NO 272
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 272
gatttcgtac atgcgcasnn atcgcaacag ggtttag                                     37

<210> SEQ ID NO 273
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 273
gatttgattt cgtacatgcs nnttgatcgc aacagggttt ag                               42

<210> SEQ ID NO 274
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 274
ggatttgatt tcgtacasnn gcattgatcg caacagg                                     37

<210> SEQ ID NO 275
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature -continued
<222> LOCATION: (19)..(20)
<223> OTHER INFORMATION: n is a, c, g, or t

<400> SEQUENCE: 275
ggaggatttg atttcgtsnn tgcgcattga tcgcaac                              37

<210> SEQ ID NO 276
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 276
ctgtggagga tttgatttsn nacatgcgca ttgatcgc                             38

<210> SEQ ID NO 277
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 277
cactgtggag gatttgasnn cgtacatgcg cattgatc                             38

<210> SEQ ID NO 278
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 278
cgacactgtg gaggattsnn tttcgtacat gcgcattg                             38

<210> SEQ ID NO 279
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 279
caccgacact gtggaggsnn tgatttcgta catgcgc                              37

<210> SEQ ID NO 280
<211> LENGTH: 37
<212> TYPE: DNA
<213> ORGANISM: Artificial
<220> FEATURE:
<223> OTHER INFORMATION: synthetic primer
<220> FEATURE:

```
<221> NAME/KEY: misc_feature
<222> LOCATION: (19)..(20)
<223> OTHER INFORMATION: n is a, c, g, or t

<400> SEQUENCE: 280
gaacaccgac actgtggsnn atttgatttc gtacatg                                    37

<210> SEQ ID NO 281
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 281
atatcggaac accgacactg snnaggattt gatttcgtac                                 40

<210> SEQ ID NO 282
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 282
catatcggaa caccgacasn ntggaggatt tgatttcg                                   38

<210> SEQ ID NO 283
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 283
cgcatatcgg aacaccgsnn ctgtggagga tttgatttc                                  39

<210> SEQ ID NO 284
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 284
cagacgcata tcggaacasn nacactgtgg aggatttg                                   38

<210> SEQ ID NO 285
<211> LENGTH: 43
<212> TYPE: DNA
<213> ORGANISM: Artificial
<220> FEATURE:
<223> OTHER INFORMATION: synthetic primer
```

```
<220> FEATURE:
<221> NAME/KEY: misc_feature
<222> LOCATION: (22)..(23)
<223> OTHER INFORMATION: n is a, c, g, or t

<400> SEQUENCE: 285
gaattcagac gcatatcgga snnccgacac tgtggaggat ttg                    43

<210> SEQ ID NO 286
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 286
gaattcagac gcatatcsnn acaccgacac tgtggag                           37

<210> SEQ ID NO 287
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 287
caggaattca gacgcatsnn ggaacaccga cactgtg                           37

<210> SEQ ID NO 288
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 288
ctatgacagg aattcagacg snnatcggaa caccgacact g                      41

<210> SEQ ID NO 289
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 289
ctatgacagg aattcagsnn catatcggaa caccgac                           37

<210> SEQ ID NO 290
<211> LENGTH: 37
<212> TYPE: DNA
<213> ORGANISM: Artificial
<220> FEATURE:
```

<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 290
gcactatgac aggaattsnn acgcatatcg gaacacc                                37

<210> SEQ ID NO 291
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 291
caggcactat gacaggasnn cagacgcata tcggaac                                37

<210> SEQ ID NO 292
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 292
cttttgcagg cactatgaca snnattcaga cgcatatcgg                             40

<210> SEQ ID NO 293
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 293
cttttgcagg cactatgsnn ggaattcaga cgcatatc                               38

<210> SEQ ID NO 294
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 294
cagcttttgc aggcactsnn acaggaattc agacgcatat                             40

<210> SEQ ID NO 295
<211> LENGTH: 37
<212> TYPE: DNA
<213> ORGANISM: Artificial

```
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 295
gcgcagcttt tgcaggcsnn atgacaggaa ttcagac                              37

<210> SEQ ID NO 296
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 296
catgcgcagc ttttgcasnn actatgacag gaattcag                             38

<210> SEQ ID NO 297
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 297
ttataacatg cgcagctttt snnggcacta tgacaggaat tc                        42

<210> SEQ ID NO 298
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 298
gttataacat gcgcagctsn ngcaggcact atgacagg                             38

<210> SEQ ID NO 299
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 299
caggttataa catgcgcasn ntttgcaggc actatgac                             38

<210> SEQ ID NO 300
<211> LENGTH: 39
<212> TYPE: DNA
```

```
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 300
gtacaggtta taacatgcsn ngcttttgca ggcactatg                              39

<210> SEQ ID NO 301
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 301
ccgtacaggt tataacasnn gcagcttttg caggcac                                37

<210> SEQ ID NO 302
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 302
cacccgtaca ggttatasnn tgcgcagctt ttgcagg                                37

<210> SEQ ID NO 303
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 303
gtccacccgt acaggttsnn acatgcgcag cttttgc                                37

<210> SEQ ID NO 304
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 304
caggtccacc cgtacagsnn ataacatgcg cagcttttg                              39

<210> SEQ ID NO 305
<211> LENGTH: 40
```

```
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 305
caaaaacagg tccacccgta snngttataa catgcgcagc                                40

<210> SEQ ID NO 306
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 306
caaaaacagg tccacccsnn caggttataa catgcgc                                  37

<210> SEQ ID NO 307
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 307
gacgcaaaaa caggtccasn ngtacaggtt ataacatg                                 38

<210> SEQ ID NO 308
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 308
gtcgacgcaa aacaggtsn ncccgtacag gttataac                                  38

<210> SEQ ID NO 309
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 309
gatgtcgacg caaaaacasn nccacccgta caggttataa c                             41

<210> SEQ ID NO 310
```

```
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 310
gtgatgtcga cgcaaaasnn ggtccacccg tacaggttat                              40

<210> SEQ ID NO 311
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 311
gtccgtgatg tcgacgcasn nacaggtcca cccgtacag                               39

<210> SEQ ID NO 312
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 312
gaagtccgtg atgtcgacsn naaaacaggt ccacccgtac                              40

<210> SEQ ID NO 313
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 313
cagaagtccg tgatgtcsnn gcaaaaacag gtccacc                                 37

<210> SEQ ID NO 314
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 314
catagcagaa gtccgtgats nngacgcaaa aacaggtcc                               39
```

```
<210> SEQ ID NO 315
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 315
gttcatagca gaagtccgts nngtcgacgc aaaaacagg                    39

<210> SEQ ID NO 316
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 316
ggttcatagc agaagtcsnn gatgtcgacg caaaaac                      37

<210> SEQ ID NO 317
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 317
catggttcat agcagaasnn cgtgatgtcg acgcaaaaac                   40

<210> SEQ ID NO 318
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 318
gtttacatgg ttcatagcas nngtccgtga tgtcgacgc                    39

<210> SEQ ID NO 319
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 319
ggtttacatg gttcatasnn gaagtccgtg atgtcgac                     38
```

<210> SEQ ID NO 320
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 320
cttggtttac atggttcsnn gcagaagtcc gtgatgtc                                38

<210> SEQ ID NO 321
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 321
ctcgcttggt ttacatggsn natagcagaa gtccgtgatg                              40

<210> SEQ ID NO 322
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 322
ttttactcgc ttggtttaca snttcatag cagaagtccg                               40

<210> SEQ ID NO 323
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 323
cttttactcg cttggtttsn ntggttcata gcagaagtc                               39

<210> SEQ ID NO 324
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 324
ttaagctttt actcgcttgg snnacatggt tcatagcaga ag                           42

<210> SEQ ID NO 325
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 325
gttaagcttt tactcgctsn ntttacatgg ttcatagc                                38

<210> SEQ ID NO 326
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 326
gagttaagct tttactcsnn tggtttacat ggttcatag                               39

<210> SEQ ID NO 327
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 327
ctcgagttaa gcttttasnn gcttggttta catggttc                                38

<210> SEQ ID NO 328
<211> LENGTH: 26
<212> TYPE: DNA
<213> ORGANISM: Artificial
<220> FEATURE:
<223> OTHER INFORMATION: synthetic primer

<400> SEQUENCE: 328
ctatgcggca tcagagcaga ttgtac                                             26

<210> SEQ ID NO 329
<211> LENGTH: 214
<212> TYPE: DNA
<213> ORGANISM: Artificial
<220> FEATURE:
<223> OTHER INFORMATION: synthetic gene sequence

<400> SEQUENCE: 329
ggatccagac gatgagagct ctaaaccttg ttgcgatcaa tgcgcttgta caaaatcaaa        60
ccctccacaa tgtcgttgtt ctgatatgcg tttaaatagc tgtcattctg catgcaaatc       120
atgtgcttgc tataaccttt acggttggac atgtttctgc gtcgacatca ctgacttctg       180
ctatgaacca tgtaaacctt ctgaataaaa gctt                                   214

```
<210> SEQ ID NO 330
<211> LENGTH: 67
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (12)..(13)
<223> OTHER INFORMATION: n is a, c, g, or t

<400> SEQUENCE: 330
gtacaaaatc annscctcca caatgtcgtt gttctgatat gcgtttaaat agctgtcatt    60
ctgcatg                                                              67

<210> SEQ ID NO 331
<211> LENGTH: 59
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (51)..(52)
<223> OTHER INFORMATION: n is a, c, g, or t

<400> SEQUENCE: 331
cagaatgaca gctatttaaa cgcatatcag aacaacgaca ttgtggaggs nntgatttt     59

<210> SEQ ID NO 332
<211> LENGTH: 55
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (49)..(50)
<223> OTHER INFORMATION: n is a, c, g, or t

<400> SEQUENCE: 332
tcgacgcaga aacatgtcca accgtaaagg ttatagcaag cacatgasnn gcatg          55

<210> SEQ ID NO 333
<211> LENGTH: 47
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (2)..(3)
<223> OTHER INFORMATION: n is a, c, g, or t

<400> SEQUENCE: 333
cnnstcatgt gcttgctata acctttacgg ttggacatgt ttctgcg                   47

<210> SEQ ID NO 334
<211> LENGTH: 48
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (27)..(28)
<223> OTHER INFORMATION: n is a, c, g, or t

<400> SEQUENCE: 334
```
tcgacatcac tgacttctgc tatgaannst gtaaaccttc tgaataaa        48

<210> SEQ ID NO 335
<211> LENGTH: 22
<212> TYPE: DNA
<213> ORGANISM: Artificial
<220> FEATURE:
<223> OTHER INFORMATION: synthetic oligonucleotide

<400> SEQUENCE: 335
ttcatagcag aagtcagtga tg        22

<210> SEQ ID NO 336
<211> LENGTH: 23
<212> TYPE: DNA
<213> ORGANISM: Artificial
<220> FEATURE:
<223> OTHER INFORMATION: synthetic oligonucleotide

<400> SEQUENCE: 336
agcttttatt cagaaggttt aca       23

<210> SEQ ID NO 337
<211> LENGTH: 35
<212> TYPE: DNA
<213> ORGANISM: Artificial
<220> FEATURE:
<223> OTHER INFORMATION: synthetic oligonucleotide

<400> SEQUENCE: 337
gtacagtagc attgatcgca acaaggttta gagct      35

<210> SEQ ID NO 338
<211> LENGTH: 67
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (29)..(29)
<223> OTHER INFORMATION: n is a, c, g, or t

<400> SEQUENCE: 338
gtacaaaatc aaaccctcca caatgtgant gttctgatat gcgtttaaat agctgtcatt    60
ctgcatg      67

<210> SEQ ID NO 339
<211> LENGTH: 59
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (35)..(35)
<223> OTHER INFORMATION: n is a, c, g, or t

<400> SEQUENCE: 339
cagaatgaca gctatttaaa cgcatatcag aacantcaca ttgtggaggg tttgatttt     59

<210> SEQ ID NO 340
<211> LENGTH: 67
<212> TYPE: DNA
<213> ORGANISM: Artificial
<220> FEATURE:

<223> OTHER INFORMATION: synthetic oligonucleotide

<400> SEQUENCE: 340
gtacaaaatc aaaccctcca caatgtcgtt gtatggatat gcgtttaaat agctgtcatt    60
ctgcatg                                                              67

<210> SEQ ID NO 341
<211> LENGTH: 59
<212> TYPE: DNA
<213> ORGANISM: Artificial
<220> FEATURE:
<223> OTHER INFORMATION: synthetic oligonucleotide

<400> SEQUENCE: 341
cagaatgaca gctatttaaa cgcatatcca tacaacgaca ttgtggaggg tttgatttt     59

<210> SEQ ID NO 342
<211> LENGTH: 67
<212> TYPE: DNA
<213> ORGANISM: Artificial
<220> FEATURE:
<223> OTHER INFORMATION: synthetic oligonucleotide

<400> SEQUENCE: 342
gtacaaaatc aaaccctcca caatgtcgtt gttgggatat gcgtttaaat agctgtcatt    60
ctgcatg                                                              67

<210> SEQ ID NO 343
<211> LENGTH: 59
<212> TYPE: DNA
<213> ORGANISM: Artificial
<220> FEATURE:
<223> OTHER INFORMATION: synthetic oligonucleotide

<400> SEQUENCE: 343
cagaatgaca gctatttaaa cgcatatccc aacaacgaca ttgtggaggg tttgatttt     59

<210> SEQ ID NO 344
<211> LENGTH: 67
<212> TYPE: DNA
<213> ORGANISM: Artificial
<220> FEATURE:
<223> OTHER INFORMATION: synthetic oligonucleotide

<400> SEQUENCE: 344
gtacaaaatc aaaccctcca caatgtcgtt gtgbagatat gcgtttaaat agctgtcatt    60
ctgcatg                                                              67

<210> SEQ ID NO 345
<211> LENGTH: 59
<212> TYPE: DNA
<213> ORGANISM: Artificial
<220> FEATURE:
<223> OTHER INFORMATION: synthetic oligonucleotide

<400> SEQUENCE: 345
cagaatgaca gctatttaaa cgcatatctv cacaacgaca ttgtggaggg tttgatttt     59

<210> SEQ ID NO 346
<211> LENGTH: 67
<212> TYPE: DNA
<213> ORGANISM: Artificial
<220> FEATURE:
<223> OTHER INFORMATION: synthetic oligonucleotide

```
<400> SEQUENCE: 346
gtacaaaatc aaaccctcca caatgtcgtt gtmawgatat gcgtttaaat agctgtcatt      60
ctgcatg                                                               67

<210> SEQ ID NO 347
<211> LENGTH: 59
<212> TYPE: DNA
<213> ORGANISM: Artificial
<220> FEATURE:
<223> OTHER INFORMATION: synthetic oligonucleotide

<400> SEQUENCE: 347
cagaatgaca gctatttaaa cgcatatcwt kacaacgaca ttgtggaggg tttgatttt      59

<210> SEQ ID NO 348
<211> LENGTH: 67
<212> TYPE: DNA
<213> ORGANISM: Artificial
<220> FEATURE:
<223> OTHER INFORMATION: synthetic oligonucleotide

<400> SEQUENCE: 348
gtacaaaatc aaaccctcca caatgtcgtt gttctgattg gcgtttaaat agctgtcatt      60
ctgcatg                                                               67

<210> SEQ ID NO 349
<211> LENGTH: 59
<212> TYPE: DNA
<213> ORGANISM: Artificial
<220> FEATURE:
<223> OTHER INFORMATION: synthetic oligonucleotide

<400> SEQUENCE: 349
cagaatgaca gctatttaaa cgccaatcag aacaacgaca ttgtggaggg tttgatttt      59

<210> SEQ ID NO 350
<211> LENGTH: 67
<212> TYPE: DNA
<213> ORGANISM: Artificial
<220> FEATURE:
<223> OTHER INFORMATION: synthetic oligonucleotide

<400> SEQUENCE: 350
gtacaaaatc aaaccctcca caatgtcgtt gttctgatca ccgtttaaat agctgtcatt      60
ctgcatg                                                               67

<210> SEQ ID NO 351
<211> LENGTH: 35
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n is a, c, g, or t

<400> SEQUENCE: 351
tctgatgntc gtttaaatag ctgtcattct gcatg                                35

<210> SEQ ID NO 352
<211> LENGTH: 67
<212> TYPE: DNA
```

```
<213> ORGANISM: Artificial
<220> FEATURE:
<223> OTHER INFORMATION: synthetic oligonucleotide
<220> FEATURE:
<221> NAME/KEY: misc_feature
<222> LOCATION: (40)..(40)
<223> OTHER INFORMATION: n is a, c, g, or t

<400> SEQUENCE: 352
gtacaaaatc aaaccctcca caatgtcgtt gttctgatgn tcgtttaaat agctgtcatt    60
ctgcatg                                                              67

<210> SEQ ID NO 353
<211> LENGTH: 59
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (24)..(24)
<223> OTHER INFORMATION: n is a, c, g, or t

<400> SEQUENCE: 353
cagaatgaca gctatttaaa cgancatcag aacaacgaca ttgtggaggg tttgatttt     59

<210> SEQ ID NO 354
<211> LENGTH: 67
<212> TYPE: DNA
<213> ORGANISM: Artificial
<220> FEATURE:
<223> OTHER INFORMATION: synthetic oligonucleotide

<400> SEQUENCE: 354
gtacaaaatc aaaccctcca caatgtcgtt gttctgatwt tcgtttaaat agctgtcatt    60
ctgcatg                                                              67

<210> SEQ ID NO 355
<211> LENGTH: 59
<212> TYPE: DNA
<213> ORGANISM: Artificial
<220> FEATURE:
<223> OTHER INFORMATION: synthetic oligonucleotide

<400> SEQUENCE: 355
cagaatgaca gctatttaaa cgaawatcag aacaacgaca ttgtggaggg tttgatttt     59

<210> SEQ ID NO 356
<211> LENGTH: 67
<212> TYPE: DNA
<213> ORGANISM: Artificial
<220> FEATURE:
<223> OTHER INFORMATION: synthetic oligonucleotide

<400> SEQUENCE: 356
gtacaaaatc aaaccctcca caatgtcgtt gttctgatat gcgtattaat agctgtcatt    60
ctgcatg                                                              67

<210> SEQ ID NO 357
<211> LENGTH: 59
<212> TYPE: DNA
<213> ORGANISM: Artificial
<220> FEATURE:
<223> OTHER INFORMATION: synthetic oligonucleotide

<400> SEQUENCE: 357
```
cagaatgaca gctattaata cgcatatcag aacaacgaca ttgtggaggg tttgatttt    59

<210> SEQ ID NO 358
<211> LENGTH: 67
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (47)..(47)
<223> OTHER INFORMATION: n is a, c, g, or t

<400> SEQUENCE: 358
gtacaaaatc aaaccctcca caatgtcgtt gttctgatat gcgtganaat agctgtcatt    60
ctgcatg    67

<210> SEQ ID NO 359
<211> LENGTH: 59
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (17)..(17)
<223> OTHER INFORMATION: n is a, c, g, or t

<400> SEQUENCE: 359
cagaatgaca gctattntca cgcatatcag aacaacgaca ttgtggaggg tttgatttt    59

<210> SEQ ID NO 360
<211> LENGTH: 67
<212> TYPE: DNA
<213> ORGANISM: Artificial
<220> FEATURE:
<223> OTHER INFORMATION: synthetic oligonucleotide

<400> SEQUENCE: 360
gtacaaaatc aaaccctcca caatgtcgtt gttctgatat gcgtttaaat atgtgtcatt    60
ctgcatg    67

<210> SEQ ID NO 361
<211> LENGTH: 59
<212> TYPE: DNA
<213> ORGANISM: Artificial
<220> FEATURE:
<223> OTHER INFORMATION: synthetic oligonucleotide

<400> SEQUENCE: 361
cagaatgaca catatttaaa cgcatatcag aacaacgaca ttgtggaggg tttgatttt    59

<210> SEQ ID NO 362
<211> LENGTH: 67
<212> TYPE: DNA
<213> ORGANISM: Artificial
<220> FEATURE:
<223> OTHER INFORMATION: synthetic oligonucleotide

<400> SEQUENCE: 362
gtacaaaatc aaaccctcca caatgtcgtt gttctgatat gcgtttaaat kawtgtcatt    60
ctgcatg    67

<210> SEQ ID NO 363

```
<211> LENGTH: 59
<212> TYPE: DNA
<213> ORGANISM: Artificial
<220> FEATURE:
<223> OTHER INFORMATION: synthetic oligonucleotide

<400> SEQUENCE: 363
cagaatgaca wtmatttaaa cgcatatcag aacaacgaca ttgtggaggg tttgatttt      59

<210> SEQ ID NO 364
<211> LENGTH: 67
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (53)..(53)
<223> OTHER INFORMATION: n is a, c, g, or t

<400> SEQUENCE: 364
gtacaaaatc aaaccctcca caatgtcgtt gttctgatat gcgtttaaat cantgtcatt     60
ctgcatg                                                               67

<210> SEQ ID NO 365
<211> LENGTH: 59
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (11)..(11)
<223> OTHER INFORMATION: n is a, c, g, or t

<400> SEQUENCE: 365
cagaatgaca ntgatttaaa cgcatatcag aacaacgaca ttgtggaggg tttgatttt      59

<210> SEQ ID NO 366
<211> LENGTH: 67
<212> TYPE: DNA
<213> ORGANISM: Artificial
<220> FEATURE:
<223> OTHER INFORMATION: synthetic oligonucleotide

<400> SEQUENCE: 366
gtacaaaatc aaaccctcca caatgtcgtt gttctgatat gcgtttaaat agctgtcata     60
tcgcatg                                                               67

<210> SEQ ID NO 367
<211> LENGTH: 59
<212> TYPE: DNA
<213> ORGANISM: Artificial
<220> FEATURE:
<223> OTHER INFORMATION: synthetic oligonucleotide

<400> SEQUENCE: 367
cgatatgaca gctatttaaa cgcatatcag aacaacgaca ttgtggaggg tttgatttt      59

<210> SEQ ID NO 368
<211> LENGTH: 67
<212> TYPE: DNA
<213> ORGANISM: Artificial
<220> FEATURE:
<223> OTHER INFORMATION: synthetic oligonucleotide

<400> SEQUENCE: 368
```

```
gtacaaaatc aaaccctcca caatgtcgtt gttctgatat gcgtttaaat agctgtcatt    60
gggcatg                                                              67

<210> SEQ ID NO 369
<211> LENGTH: 59
<212> TYPE: DNA
<213> ORGANISM: Artificial
<220> FEATURE:
<223> OTHER INFORMATION: synthetic oligonucleotide

<400> SEQUENCE: 369
cccaatgaca gctatttaaa cgcatatcag aacaacgaca ttgtggaggg tttgattt     59

<210> SEQ ID NO 370
<211> LENGTH: 67
<212> TYPE: DNA
<213> ORGANISM: Artificial
<220> FEATURE:
<223> OTHER INFORMATION: synthetic oligonucleotide

<400> SEQUENCE: 370
gtacaaaatc aaaccctcca caatgtcgtt gttctgatat gcgtttaaat agctgtcatc    60 ragcatg                                                              67

<210> SEQ ID NO 371
<211> LENGTH: 59
<212> TYPE: DNA
<213> ORGANISM: Artificial
<220> FEATURE:
<223> OTHER INFORMATION: synthetic oligonucleotide

<400> SEQUENCE: 371
ctygatgaca gctatttaaa cgcatatcag aacaacgaca ttgtggaggg tttgattt     59

<210> SEQ ID NO 372
<211> LENGTH: 67
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (62)..(62)
<223> OTHER INFORMATION: n is a, c, g, or t

<400> SEQUENCE: 372
gtacaaaatc aaaccctcca caatgtcgtt gttctgatat gcgtttaaat agctgtcatg    60 angcatg                                                              67

<210> SEQ ID NO 373
<211> LENGTH: 59
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n is a, c, g, or t

<400> SEQUENCE: 373
cntcatgaca gctatttaaa cgcatatcag aacaacgaca ttgtggaggg tttgattt     59

<210> SEQ ID NO 374
```

```
<211> LENGTH: 55
<212> TYPE: DNA
<213> ORGANISM: Artificial
<220> FEATURE:
<223> OTHER INFORMATION: synthetic oligonucleotide

<400> SEQUENCE: 374
tcgacgcaga aacatgtcca accgtaaagg ttatagcaaw cacatgattt gcatg          55

<210> SEQ ID NO 375
<211> LENGTH: 47
<212> TYPE: DNA
<213> ORGANISM: Artificial
<220> FEATURE:
<223> OTHER INFORMATION: synthetic oligonucleotide

<400> SEQUENCE: 375
caaatcatgt gwttgctata acctttacgg ttggacatgt ttctgcg                   47

<210> SEQ ID NO 376
<211> LENGTH: 55
<212> TYPE: DNA
<213> ORGANISM: Artificial
<220> FEATURE:
<223> OTHER INFORMATION: synthetic oligonucleotide

<400> SEQUENCE: 376
tcgacgcaga aacatgtcca accgtaaagg ttatagcaak gacatgattt gcatg          55

<210> SEQ ID NO 377
<211> LENGTH: 47
<212> TYPE: DNA
<213> ORGANISM: Artificial
<220> FEATURE:
<223> OTHER INFORMATION: synthetic oligonucleotide

<400> SEQUENCE: 377
caaatcatgt cmttgctata acctttacgg ttggacatgt ttctgcg                   47

<210> SEQ ID NO 378
<211> LENGTH: 55
<212> TYPE: DNA
<213> ORGANISM: Artificial
<220> FEATURE:
<223> OTHER INFORMATION: synthetic oligonucleotide

<400> SEQUENCE: 378
tcgacgcaga aacatgtcca accgtaaagg ttatagcamy aacatgattt gcatg          55

<210> SEQ ID NO 379
<211> LENGTH: 47
<212> TYPE: DNA
<213> ORGANISM: Artificial
<220> FEATURE:
<223> OTHER INFORMATION: synthetic oligonucleotide

<400> SEQUENCE: 379
caaatcatgt trktgctata acctttacgg ttggacatgt ttctgcg                   47

<210> SEQ ID NO 380
<211> LENGTH: 55
<212> TYPE: DNA
<213> ORGANISM: Artificial
<220> FEATURE:
<223> OTHER INFORMATION: synthetic oligonucleotide

<400> SEQUENCE: 380
```

```
tcgacgcaat cacatgtcca accgtaaagg ttatagcaag cacatgattt gcatg      55

<210> SEQ ID NO 381
<211> LENGTH: 47
<212> TYPE: DNA
<213> ORGANISM: Artificial
<220> FEATURE:
<223> OTHER INFORMATION: synthetic oligonucleotide

<400> SEQUENCE: 381
caaatcatgt gcttgctata acctttacgg ttggacatgt gattgcg               47

<210> SEQ ID NO 382
<211> LENGTH: 55
<212> TYPE: DNA
<213> ORGANISM: Artificial
<220> FEATURE:
<223> OTHER INFORMATION: synthetic oligonucleotide

<400> SEQUENCE: 382
tcgacgcatk gacatgtcca accgtaaagg ttatagcaag cacatgattt gcatg      55

<210> SEQ ID NO 383
<211> LENGTH: 47
<212> TYPE: DNA
<213> ORGANISM: Artificial
<220> FEATURE:
<223> OTHER INFORMATION: synthetic oligonucleotide

<400> SEQUENCE: 383
caaatcatgt gcttgctata acctttacgg ttggacatgt cmatgcg               47

<210> SEQ ID NO 384
<211> LENGTH: 55
<212> TYPE: DNA
<213> ORGANISM: Artificial
<220> FEATURE:
<223> OTHER INFORMATION: synthetic oligonucleotide

<400> SEQUENCE: 384
tcgacgcakc tacatgtcca accgtaaagg ttatagcaag cacatgattt gcatg      55

<210> SEQ ID NO 385
<211> LENGTH: 47
<212> TYPE: DNA
<213> ORGANISM: Artificial
<220> FEATURE:
<223> OTHER INFORMATION: synthetic oligonucleotide

<400> SEQUENCE: 385
caaatcatgt gcttgctata acctttacgg ttggacatgt agmtgcg               47

<210> SEQ ID NO 386
<211> LENGTH: 95
<212> TYPE: DNA
<213> ORGANISM: Artificial
<220> FEATURE:
<223> OTHER INFORMATION: synthetic oligonucleotide

<400> SEQUENCE: 386
caaatcatgt gcttgctata acctttacgg ttggacatgt ttctgcgatg acatcactga 60
cttctgctat gaaccatgta aaccttctga ataaa                            95

<210> SEQ ID NO 387
```

```
<211> LENGTH: 103
<212> TYPE: DNA
<213> ORGANISM: Artificial
<220> FEATURE:
<223> OTHER INFORMATION: synthetic oligonucleotide

<400> SEQUENCE: 387 agctttatt cagaaggttt acatggttca tagcagaagt cagtgatgtc atcgcagaaa    60
catgtccaac cgtaaaggtt atagcaagca catgatttgc atg                    103

<210> SEQ ID NO 388
<211> LENGTH: 11
<212> TYPE: PRT
<213> ORGANISM: Glycine max

<400> SEQUENCE: 388

Cys Ile Cys Ala Leu Ser Tyr Pro Ala Gln Cys
1               5                   10

<210> SEQ ID NO 389
<211> LENGTH: 13
<212> TYPE: PRT
<213> ORGANISM: Artificial
<220> FEATURE:
<223> OTHER INFORMATION: synthetic peptide insert

<400> SEQUENCE: 389

Asp Asp Glu Pro Ser Lys Pro Cys Cys Asp Pro Asp Pro
1               5                   10

<210> SEQ ID NO 390
<211> LENGTH: 79
<212> TYPE: PRT
<213> ORGANISM: Artificial
<220> FEATURE:
<223> OTHER INFORMATION: synthetic BBI sequence

<400> SEQUENCE: 390

Asp Asp Glu Pro Ser Lys Pro Cys Cys Asp Pro Asp Pro Asp Glu
1               5                   10                  15

Ser Ser Lys Pro Cys Cys Asp Gln Cys Ala Cys Thr Lys Ser Asn Pro
            20                  25                  30

Pro Gln Cys Arg Cys Ser Asp Met Arg Leu Asn Ser Cys His Ser Ala
            35                  40                  45

Cys Lys Ser Cys Ala Cys Tyr Asn Leu Tyr Gly Trp Thr Cys Phe Cys
        50                  55                  60

Val Asp Ile Thr Asp Phe Cys Tyr Glu Pro Cys Lys Pro Ser Glu
65                  70                  75

<210> SEQ ID NO 391
<211> LENGTH: 88
<212> TYPE: PRT
<213> ORGANISM: Artificial
<220> FEATURE:
<223> OTHER INFORMATION: synthetic fusion BBI sequence

<400> SEQUENCE: 391

Asp Asn Asn Asp Pro Ile Pro Asp Pro Asp Asp Glu Pro Ser Lys Pro
1               5                   10                  15

Cys Cys Asp Pro Asp Pro Asp Asp Glu Ser Ser Lys Pro Cys Cys Asp
            20                  25                  30

Gln Cys Ala Cys Thr Lys Ser Asn Pro Pro Gln Cys Arg Cys Ser Asp
            35                  40                  45
```

```
Met Arg Leu Asn Ser Cys His Ser Ala Cys Lys Ser Cys Ala Cys Tyr
    50                  55                  60

Asn Leu Tyr Gly Trp Thr Cys Phe Cys Val Asp Ile Thr Asp Phe Cys
65                  70                  75                  80

Tyr Glu Pro Cys Lys Pro Ser Glu
                85
```

<210> SEQ ID NO 392
<211> LENGTH: 58
<212> TYPE: DNA
<213> ORGANISM: Artificial
<220> FEATURE:
<223> OTHER INFORMATION: synthetic oligonucleotide

<400> SEQUENCE: 392
gatccagatg acgaaccgag caaaccttgc tgtgatccag accctgacga tgagagct        58

<210> SEQ ID NO 393
<211> LENGTH: 50
<212> TYPE: DNA
<213> ORGANISM: Artificial
<220> FEATURE:
<223> OTHER INFORMATION: synthetic oligonucleotide

<400> SEQUENCE: 393
ctcatcgtca gggtctggat cacagcaagg tttgctcggt tcgtcatctg        50

<210> SEQ ID NO 394
<211> LENGTH: 253
<212> TYPE: DNA
<213> ORGANISM: Artificial
<220> FEATURE:
<223> OTHER INFORMATION: synthetic gene

<400> SEQUENCE: 394
ggatccagat gacgaaccga gcaaaccttg ctgtgatcca ccctgacg atgagagctc        60 taaaccctgt tgcgatcaat gcatttgtac gaaatcaaat cctccacagt gtcggtgttc       120
cgatatgcgt ccgaattcct gtcatagtgc ctgcaaaagc tgcaagtgtt ataacctgta      180
cgggtggacc tgtacatgcg ccgacatcac ggacttctgc tatgaaccat gtaaaccaag      240
cgagtaaaag ctt                                                         253

<210> SEQ ID NO 395
<211> LENGTH: 30
<212> TYPE: DNA
<213> ORGANISM: Artificial
<220> FEATURE:
<223> OTHER INFORMATION: synthetic primer

<400> SEQUENCE: 395
ctgttgcgat caatgcattt gtacgaaatc        30

<210> SEQ ID NO 396
<211> LENGTH: 42
<212> TYPE: DNA
<213> ORGANISM: Artificial
<220> FEATURE:
<223> OTHER INFORMATION: synthetic primer

<400> SEQUENCE: 396
ctgtacgggt ggacctgtac atgcgycgac atcacggact tc        42

<210> SEQ ID NO 397
<211> LENGTH: 28
<212> TYPE: DNA
<213> ORGANISM: Artificial
<220> FEATURE:
<223> OTHER INFORMATION: synthetic primer

<400> SEQUENCE: 397
gacctgtttt tgcgycgaca tcacggac                                28

<210> SEQ ID NO 398
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 398
ggatccagac gatgagagct ctaaaccctg ttgcgatcaa tgcgcatgta cgaaatcaaa     60
tcctccacag tgtcggtgtt ccgatatgcg tctgaattcc tgtcatagtg cctgcaaaag    120
ctgcgcatgt tataacctgt acgggtggac ctgtacatgc gccgacatca cggacttctg    180
ctatgaacca tgtaaaccaa gcgagtaaaa gctt                                214

<210> SEQ ID NO 399
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 399
ggatccagac gatgagagct ctaaaccctg ttgcgatcaa tgcatttgta cgaaatcaaa     60
tcctccacag tgtcggtgtc ttgatatgcg tctgaattcc tgtcatagtg cctgcaaaag    120
ctgcgcatgt tataacctgt acgggtggac ctgtacatgc gccgacatca cggacttctg    180
ctatgaacca tgtaaaccaa gcgagtaaaa gctt                                214

<210> SEQ ID NO 400
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 400
ggatccagac gatgagagct ctaaaccctg ttgcgatcaa tgcatttgta cgaaatcaaa     60
tcctccacag tgtcggtgtc ttgatatgcg tccgaattcc tgtcatagtg cctgcaaaag    120
ctgcgcatgt tataacctgt acgggtggac ctgtacatgc gccgacatca cggacttctg    180
ctatgaacca tgtaaaccaa gcgagtaaaa gctt                                214

<210> SEQ ID NO 401
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 401
ggatccagac gatgagagct ctaaaccctg ttgcgatcaa tgcatttgta cgaaatcaaa     60
tcctccacag tgtcggtgtc ttgatatgcg tccgaattcc tgtcatagtg cctgcaaaag    120

```
ctgcaagtgt tataacctgt acgggtggac ctgtacatgc gccgacatca cggacttctg    180
ctatgaacca tgtaaaccaa gcgagtaaaa gctt                                 214

<210> SEQ ID NO 402
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 402
ggatccagac gatgagagct ctaaaccctg ttgcgatcaa tgcatttgta cgaaatcaaa     60
tcctccacag tgtcggtgtc ttgatatgcg tctgaattcc tgtcatagtg cctgcaaaag    120
ctgcaagtgt tataacctgt acgggtggac ctgtacatgc gccgacatca cggacttctg    180
ctatgaacca tgtaaaccaa gcgagtaaaa gctt                                 214

<210> SEQ ID NO 403
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 403
ggatccagac gatgagagct ctaaaccctg ttgcgatcaa tgcatttgta cgaaatcaaa     60
tcctccacag tgtcggtgtt ccgatatgcg tccgaattcc tgtcatagtg cctgcaaaag    120
ctgcgcatgt tataacctgt acgggtggac ctgtacatgc gccgacatca cggacttctg    180
ctatgaacca tgtaaaccaa gcgagtaaaa gctt                                 214

<210> SEQ ID NO 404
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 404
ggatccagac gatgagagct ctaaaccctg ttgcgatcaa tgcatttgta cgaaatcaaa     60
tcctccacag tgtcggtgtt ccgatatgcg tccgaattcc tgtcatagtg cctgcaaaag    120
ctgcaagtgt tataacctgt acgggtggac ctgtacatgc gccgacatca cggacttctg    180
ctatgaacca tgtaaaccaa gcgagtaaaa gctt                                 214

<210> SEQ ID NO 405
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 405
ggatccagac gatgagagct ctaaaccctg ttgcgatcaa tgcatttgta cgaaatcaaa     60
tcctccacag tgtcggtgtt ccgatatgcg tctgaattcc tgtcatagtg cctgcaaaag    120
ctgcaagtgt tataacctgt acgggtggac ctgtacatgc gccgacatca cggacttctg    180
ctatgaacca tgtaaaccaa gcgagtaaaa gctt                                 214

<210> SEQ ID NO 406
<211> LENGTH: 214
```

<212> TYPE: DNA
<213> ORGANISM: Artificial
<220> FEATURE:
<223> OTHER INFORMATION: synthetic gene encoding BBPI variant

<400> SEQUENCE: 406

```
ggatccagac gatgagagct ctaaaccctg ttgcgatcaa tgcgcatgta cgaaatcaaa      60
tcctccacag tgtcggtgtc ttgatatgcg tctgaattcc tgtcatagtg cctgcaaaag     120
ctgcgcatgt tataacctgt acgggtggac ctgtacatgc gccgacatca cggacttctg     180
ctatgaacca tgtaaaccaa gcgagtaaaa gctt                                 214
```

<210> SEQ ID NO 407
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 407

```
ggatccagac gatgagagct ctaaaccctg ttgcgatcaa tgcgcatgta cgaaatcaaa      60
tcctccacag tgtcggtgtc ttgatatgcg tccgaattcc tgtcatagtg cctgcaaaag     120
ctgcgcatgt tataacctgt acgggtggac ctgtacatgc gccgacatca cggacttctg     180
ctatgaacca tgtaaaccaa gcgagtaaaa gctt                                 214
```

<210> SEQ ID NO 408
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 408

```
ggatccagac gatgagagct ctaaaccctg ttgcgatcaa tgcgcatgta cgaaatcaaa      60
tcctccacag tgtcggtgtc ttgatatgcg tccgaattcc tgtcatagtg cctgcaaaag     120
ctgcaagtgt tataacctgt acgggtggac ctgtacatgc gccgacatca cggacttctg     180
ctatgaacca tgtaaaccaa gcgagtaaaa gctt                                 214
```

<210> SEQ ID NO 409
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 409

```
ggatccagac gatgagagct ctaaaccctg ttgcgatcaa tgcgcatgta cgaaatcaaa      60
tcctccacag tgtcggtgtc ttgatatgcg tctgaattcc tgtcatagtg cctgcaaaag     120
ctgcaagtgt tataacctgt acgggtggac ctgtacatgc gccgacatca cggacttctg     180
ctatgaacca tgtaaaccaa gcgagtaaaa gctt                                 214
```

<210> SEQ ID NO 410
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 410

```
ggatccagac gatgagagct ctaaaccctg ttgcgatcaa tgcgcatgta cgaaatcaaa    60
tcctccacag tgtcggtgtt ccgatatgcg tccgaattcc tgtcatagtg cctgcaaaag   120
ctgcgcatgt tataacctgt acgggtggac ctgtacatgc gccgacatca cggacttctg   180
ctatgaacca tgtaaaccaa gcgagtaaaa gctt                               214
```

<210> SEQ ID NO 411
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 411

```
ggatccagac gatgagagct ctaaaccctg ttgcgatcaa tgcgcatgta cgaaatcaaa    60
tcctccacag tgtcggtgtt ccgatatgcg tccgaattcc tgtcatagtg cctgcaaaag   120
ctgcaagtgt tataacctgt acgggtggac ctgtacatgc gccgacatca cggacttctg   180
ctatgaacca tgtaaaccaa gcgagtaaaa gctt                               214
```

<210> SEQ ID NO 412
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 412

```
ggatccagac gatgagagct ctaaaccctg ttgcgatcaa tgcgcatgta cgaaatcaaa    60
tcctccacag tgtcggtgtt ccgatatgcg tctgaattcc tgtcatagtg cctgcaaaag   120
ctgcaagtgt tataacctgt acgggtggac ctgtacatgc gccgacatca cggacttctg   180
ctatgaacca tgtaaaccaa gcgagtaaaa gctt                               214
```

<210> SEQ ID NO 413
<211> LENGTH: 81
<212> TYPE: PRT
<213> ORGANISM: Artificial
<220> FEATURE:
<223> OTHER INFORMATION: synthetic BBPI sequence

<400> SEQUENCE: 413

```
Asp Pro Asp Asp Glu Pro Ser Lys Pro Cys Cys Asp Pro Asp Pro Asp
1               5                  10                  15

Asp Glu Ser Ser Lys Pro Cys Cys Asp Gln Cys Ile Cys Thr Lys Ser
            20                  25                  30

Asn Pro Pro Gln Cys Arg Cys Ser Asp Met Arg Pro Asn Ser Cys His
        35                  40                  45

Ser Ala Cys Lys Ser Cys Lys Cys Tyr Asn Leu Tyr Gly Trp Thr Cys
    50                  55                  60

Thr Cys Ala Asp Ile Thr Asp Phe Cys Tyr Glu Pro Cys Lys Pro Ser
65                  70                  75                  80

Glu
```

<210> SEQ ID NO 414
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 414

```
ggatccatgc gatgagagct ctaaaccttg ttgcgatcaa tgcatttgta ctaaatcaaa      60
ccctccacaa tgtcgttgtt ctgatatgcg tcctaattca tgtcattctg catgcaaatc     120
atgtaaatgc tataaccttt acggttggac atgtacatgc gcagatatca ctgacttctg     180
ctatgaacca tgtaaacctt ctgaataaaa gctt                                 214
```

<210> SEQ ID NO 415
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 415

```
ggatccagac gatgaggttt ctaaaccttg ttgcgatcaa tgcatttgta ctaaatcaaa      60
ccctccacaa tgtcgttgtt ctgatatgcg tcctaattca tgtcattctg catgcaaatc     120
atgtaaatgc tataaccttt acggttggac atgtacatgc gcagatatca ctgacttctg     180
ctatgaacca tgtaaacctt ctgaataaaa gctt                                 214
```

<210> SEQ ID NO 416
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 416

```
ggatccagac gatgagagcc ctaaaccttg ttgcgatcaa tgcatttgta ctaaatcaaa      60
ccctccacaa tgtcgttgtt ctgatatgcg tcctaatagc tgtcattctg catgcaaatc     120
atgtaaatgc tataaccttt acggttggac atgtacatgc gcagatatca ctgacttctg     180
ctatgaacca tgtaaacctt ctgaataaaa gctt                                 214
```

<210> SEQ ID NO 417
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 417

```
ggatccagac gatgagagct ctaaaccttg ttgcgatggc tgcatttgta ctaaatcaaa      60
ccctccacaa tgtcgttgtt ctgatatgcg tcctaattca tgtcattctg catgcaaatc     120
atgtaaatgc tataaccttt acggttggac atgtacatgc gcagatatca ctgacttctg     180
ctatgaacca tgtaaacctt ctgaataaaa gctt                                 214
```

<210> SEQ ID NO 418
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 418

```
ggatccagac gatgagagct ctaaaccttg ttgcgatcaa tgcctttgta ctaaatcaaa      60
ccctccacaa tgtcgttgtt ctgatatgcg tcctaattca tgtcattctg catgcaaatc     120
atgtaaatgc tataaccttt acggttggac atgtacatgc gcagatatca ctgacttctg     180
```

```
ctatgaacca tgtaaacctt ctgaataaaa gctt                                214
```

<210> SEQ ID NO 419
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 419

```
ggatccagac gatgagagct ctaaaccttg ttgcgatcaa tgcatttgta ctaaatcaaa     60
ccctccacaa tgtcgttgta gagatatgcg tcctaatagc tgtcattctg catgcaaatc    120
atgtaaatgc tataaccttt acggttggac atgtacatgc gcagatatca ctgacttctg    180
ctatgaacca tgtaaacctt ctgaataaaa gctt                                214
```

<210> SEQ ID NO 420
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 420

```
ggatccagac gatgagagct ctaaaccttg ttgcgatcaa tgcatttgta ctaaatcaaa     60
ccctccacaa tgtcgttgta gagatatgcg tcctaatgct tgtcattctg catgcaaatc    120
atgtaaatgc tataaccttt acggttggac atgtacatgc gcagatatca ctgacttctg    180
ctatgaacca tgtaaacctt ctgaataaaa gctt                                214
```

<210> SEQ ID NO 421
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 421

```
ggatccagac gatgagagct ctaaaccttg ttgcgatcaa tgcatttgta ctaaatcaaa     60
ccctccacaa tgtcgttgta gagatatgcg tcctaatcgc tgtcattctg catgcaaatc    120
atgtaaatgc tataaccttt acggttggac atgtacatgc gcagatatca ctgacttctg    180
ctatgaacca tgtaaacctt ctgaataaaa gctt                                214
```

<210> SEQ ID NO 422
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 422

```
ggatccagac gatgagagct ctaaaccttg ttgcgatcaa tgcatttgta ctaaatcaaa     60
ccctccacaa tgtcgttgtt ctgatagacg tcctaattca tgtcattctg catgcaaatc    120
atgtaaatgc tataaccttt acggttggac atgtacatgc gcagatatca ctgacttctg    180
ctatgaacca tgtaaacctt ctgaataaaa gctt                                214
```

<210> SEQ ID NO 423
<211> LENGTH: 214
<212> TYPE: DNA

-continued

<213> ORGANISM: Artificial
<220> FEATURE:
<223> OTHER INFORMATION: synthetic gene encoding BBPI variant

<400> SEQUENCE: 423
ggatccagac gatgagagct ctaaaccttg ttgcgatcaa tgcatttgta ctaaatcaaa 60
ccctccacaa tgtcgttgtt ctgatatgcg taaaaattca tgtcattctg catgcaaatc 120
atgtaaatgc tataaccttt acggttggac atgtacatgc gcagatatca ctgacttctg 180
ctatgaacca tgtaaacctt ctgaataaaa gctt 214

<210> SEQ ID NO 424
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 424
ggatccagac gatgagagct ctaaaccttg ttgcgatcaa tgcatttgta ctaaatcaaa 60
ccctccacaa tgtcgttgtt ctgatatgcg tcctaatgct tgtcattctg catgcaaatc 120
atgtaaatgc tataaccttt acggttggac atgtacatgc gcagatatca ctgacttctg 180
ctatgaacca tgtaaacctt ctgaataaaa gctt 214

<210> SEQ ID NO 425
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 425
ggatccagac gatgagagct ctaaaccttg ttgcgatcaa tgcatttgta ctaaatcaaa 60
ccctccacaa tgtcgttgtt ctgatatgcg tcctaataga tgtcattctg catgcaaatc 120
atgtaaatgc tataaccttt acggttggac atgtacatgc gcagatatca ctgacttctg 180
ctatgaacca tgtaaacctt ctgaataaaa gctt 214

<210> SEQ ID NO 426
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 426
ggatccagac gatgagagct ctaaaccttg ttgcgatcaa tgcatttgta ctaaatcaaa 60
ccctccacaa tgtcgttgtt ctgatatgcg tcctaatagc tgtcattctg catgcaaaaa 120
ctgtaaatgc tataaccttt acggttggac atgtacatgc gcagatatca ctgacttctg 180
ctatgaacca tgtaaacctt ctgaataaaa gctt 214

<210> SEQ ID NO 427
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 427
ggatccagac gatgagagct ctaaaccttg ttgcgatcaa tgcatttgta ctaaatcaaa 60

```
ccctccacaa tgtcgttgtt ctgatatgcg tcctaattca tgtcattctg catgcaaatc      120
atgtaaatgc tataacctttt acggttggac atgtaaatgc gcagatatca ctgacttctg     180
ctatgaacca tgtaaacctt ctgaataaaa gctt                                   214
```

<210> SEQ ID NO 428
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 428

```
ggatccagac gatgagagct ctaaaccttg ttgcgatcaa tgcatttgta ctaaatcaaa       60
ccctccacaa tgtcgttgtt ctgatatgcg tcctaattca tgtcattctg catgcaaatc      120
atgtaaatgc tataaccttt acggttggac atgtacatgc acagatatca ctgacttctg     180
ctatgaacca tgtaaacctt ctgaataaaa gctt                                   214
```

<210> SEQ ID NO 429
<211> LENGTH: 214
<212> TYPE: DNA
<213> ORGANISM: Artificial
<220> FEATURE:
<223> OTHER INFORMATION: synthetic gene encoding BBPI variant

<400> SEQUENCE: 429

```
ggatccagac gatgagagct ctaaaccttg ttgcgatcaa tgcatttgta ctaaatcaaa       60
ccctccacaa tgtcgttgtt ctgatatgcg tcctaatagc tgtcattctg catgcaaatc      120
atgtaaatgc tataaccttt acggttggac atgtacatgc gcagatatca ctgacttctg     180
ctatgaacca tgtaaacctg aagaataaaa gctt                                   214
```

<210> SEQ ID NO 430
<211> LENGTH: 12
<212> TYPE: PRT
<213> ORGANISM: Artificial
<220> FEATURE:
<223> OTHER INFORMATION: synthetic FGF-binding peptide

<400> SEQUENCE: 430

Cys Ala Cys Arg Thr Gln Pro Tyr Pro Leu Cys Phe
1               5                   10

<210> SEQ ID NO 431
<211> LENGTH: 11
<212> TYPE: PRT
<213> ORGANISM: Artificial
<220> FEATURE:
<223> OTHER INFORMATION: synthetic FGF-binding peptide

<400> SEQUENCE: 431

Cys Ile Cys Thr Trp Ile Asp Ser Thr Pro Cys
1               5                   10

<210> SEQ ID NO 432
<211> LENGTH: 68
<212> TYPE: PRT
<213> ORGANISM: Artificial
<220> FEATURE:
<223> OTHER INFORMATION: synthetic BBI variant

<400> SEQUENCE: 432

```
Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Arg Thr Gln Pro Tyr
        35                  40                  45

Pro Leu Cys Thr Cys Ala Asp Ile Thr Asp Phe Cys Tyr Glu Pro Cys
    50                  55                  60

Lys Pro Ser Glu
65
```

<210> SEQ ID NO 433
<211> LENGTH: 214
<212> TYPE: DNA
<213> ORGANISM: Artificial
<220> FEATURE:
<223> OTHER INFORMATION: synthetic gene

<400> SEQUENCE: 433

```
ggatccagac gatgagagct ctaaaccttg ttgcgatcaa tgcatttgta ctaaatcaaa      60
tcctccacaa tgtcgttgtt ctgatatgcg tcctaatagc tgtcattctg catgcaaatc     120
atgtgcttgc cgtactcaac catacccctct ttgtacatgc gcagacatca ctgacttctg    180
ctatgaacca tgtaaaccat ctgaataaaa gctt                                 214
```

<210> SEQ ID NO 434
<211> LENGTH: 68
<212> TYPE: PRT
<213> ORGANISM: Artificial
<220> FEATURE:
<223> OTHER INFORMATION: synthetic BBI variant

<400> SEQUENCE: 434

```
Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Thr Trp Ile Asp Ser
        35                  40                  45

Thr Pro Cys Thr Cys Ala Asp Ile Thr Asp Phe Cys Tyr Glu Pro Cys
    50                  55                  60

Lys Pro Ser Glu
65
```

<210> SEQ ID NO 435
<211> LENGTH: 214
<212> TYPE: DNA
<213> ORGANISM: Artificial
<220> FEATURE:
<223> OTHER INFORMATION: synthetic BBI variant

<400> SEQUENCE: 435

```
ggatccagac gatgagagct ctaaaccttg ttgcgatcaa tgcatttgta ctaaatcaaa      60
tcctccacaa tgtcgttgtt ctgatatgcg tcctaatagc tgtcattctg catgcaaatc     120
atgtgcttgc acttggattg attcaacacc atgtacatgc gcagacatca ctgacttctg    180
ctatgaacca tgtaaaccat ctgaataaaa gctt                                 214
```

<210> SEQ ID NO 436
<211> LENGTH: 13

```
<212> TYPE: PRT
<213> ORGANISM: Artificial
<220> FEATURE:
<223> OTHER INFORMATION: synthetic TGF-binding peptide

<400> SEQUENCE: 436

Cys Leu Cys Pro Glu Asn Ile Asn Val Leu Pro Cys Asn
1               5                   10

<210> SEQ ID NO 437
<211> LENGTH: 12
<212> TYPE: PRT
<213> ORGANISM: Artificial
<220> FEATURE:
<223> OTHER INFORMATION: synthetic TGF-binding peptide

<400> SEQUENCE: 437

Cys Ile Cys Lys His Asn Val Asp Trp Leu Cys Phe
1               5                   10

<210> SEQ ID NO 438
<211> LENGTH: 12
<212> TYPE: PRT
<213> ORGANISM: Artificial
<220> FEATURE:
<223> OTHER INFORMATION: synthetic TGF-binding peptide

<400> SEQUENCE: 438

Cys Ile Cys Trp Thr Gln His Ile His Asn Cys Phe
1               5                   10

<210> SEQ ID NO 439
<211> LENGTH: 50
<212> TYPE: DNA
<213> ORGANISM: Artificial
<220> FEATURE:
<223> OTHER INFORMATION: synthetic oligonucleotide

<400> SEQUENCE: 439
caaaagctgt ctttgtcctg aaaatattaa cgttcttcct tgtaactgcg               50

<210> SEQ ID NO 440
<211> LENGTH: 58
<212> TYPE: DNA
<213> ORGANISM: Artificial
<220> FEATURE:
<223> OTHER INFORMATION: synthetic oligonucleotide

<400> SEQUENCE: 440
tcgacgcagt tacaaggaag aacgttaata ttttcaggac aaagacagct tttgcatg     58

<210> SEQ ID NO 441
<211> LENGTH: 47
<212> TYPE: DNA
<213> ORGANISM: Artificial
<220> FEATURE:
<223> OTHER INFORMATION: synthetic oligonucleotide

<400> SEQUENCE: 441
caaatcatgc atttgttgga cacaacatat ccacaactgt ttttgcg                  47

<210> SEQ ID NO 442
<211> LENGTH: 55
<212> TYPE: DNA
<213> ORGANISM: Artificial
<220> FEATURE:
<223> OTHER INFORMATION: synthetic oligonucleotide
```

<400> SEQUENCE: 442
tcgacgcaaa aacagttgtg gatatgttgt gtccaacaaa tgcatgattt gcatg          55

<210> SEQ ID NO 443
<211> LENGTH: 69
<212> TYPE: PRT
<213> ORGANISM: Artificial
<220> FEATURE:
<223> OTHER INFORMATION: synthetic BBPI variant

<400> SEQUENCE: 443

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Pro Glu Asn Ile Asn
        35                  40                  45

Val Leu Pro Cys Thr Cys Ala Asp Ile Thr Asp Phe Cys Tyr Glu Pro
    50                  55                  60

Cys Lys Pro Ser Glu
65

<210> SEQ ID NO 444
<211> LENGTH: 217
<212> TYPE: DNA
<213> ORGANISM: Artificial
<220> FEATURE:
<223> OTHER INFORMATION: synthetic gene

<400> SEQUENCE: 444
ggatccagac gatgagagct ctaaaccttg ttgcgatcaa tgcatttgta ctaaatcaaa          60
tcctccacaa tgtcgttgtt ctgatatgcg tcctaatagc tgtcattctg catgcaaatc         120
atgtgcttgc ccagaaaaca tcaacgttct tccttgtaca tgcgcagaca tcactgactt         180
ctgctatgaa ccatgtaaac catctgaata aaagctt                                  217

<210> SEQ ID NO 445
<211> LENGTH: 68
<212> TYPE: PRT
<213> ORGANISM: Artificial
<220> FEATURE:
<223> OTHER INFORMATION: synthetic BBPI variant

<400> SEQUENCE: 445

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Lys His Asn Val Asp
        35                  40                  45

Trp Leu Cys Thr Cys Ala Asp Ile Thr Asp Phe Cys Tyr Glu Pro Cys
    50                  55                  60

Lys Pro Ser Glu
65

<210> SEQ ID NO 446
<211> LENGTH: 214
<212> TYPE: DNA
<213> ORGANISM: Artificial
<220> FEATURE:

-continued

<223> OTHER INFORMATION: synthetic gene

<400> SEQUENCE: 446

```
ggatccagac gatgagagct ctaaaccttg ttgcgatcaa tgcatttgta ctaaatcaaa      60
tcctccacaa tgtcgttgtt ctgatatgcg tcctaatagc tgtcattctg catgcaaatc     120
atgtgcttgc aaacataacg ttgattggct ttgtacatgc gcagacatca ctgacttctg     180
ctatgaacca tgtaaaccat ctgaataaaa gctt                                 214
```

<210> SEQ ID NO 447
<211> LENGTH: 68
<212> TYPE: PRT
<213> ORGANISM: Artificial
<220> FEATURE:
<223> OTHER INFORMATION: synthetic BBPI variant

<400> SEQUENCE: 447

```
Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Trp Thr Gln His Ile
        35                  40                  45

His Asn Cys Thr Cys Ala Asp Ile Thr Asp Phe Cys Tyr Glu Pro Cys
    50                  55                  60

Lys Pro Ser Glu
65
```

<210> SEQ ID NO 448
<211> LENGTH: 214
<212> TYPE: DNA
<213> ORGANISM: Artificial
<220> FEATURE:
<223> OTHER INFORMATION: synthetic gene

<400> SEQUENCE: 448

```
ggatccagac gatgagagct ctaaaccttg ttgcgatcaa tgcatttgta ctaaatcaaa      60
tcctccacaa tgtcgttgtt ctgatatgcg tcctaatagc tgtcattctg catgcaaatc     120
atgtgcttgc tggacacaac atatccacaa ctgtacatgc gcagacatca ctgacttctg     180
ctatgaacca tgtaaaccat ctgaataaaa gctt                                 214
```

<210> SEQ ID NO 449
<211> LENGTH: 63
<212> TYPE: PRT
<213> ORGANISM: Dolichos biflorus

<400> SEQUENCE: 449

```
Pro Ser Glu Ser Ser Lys Pro Cys Cys Asp Gln Cys Ala Cys Thr Lys
1               5                   10                  15

Ser Ile Pro Pro Gln Cys Arg Cys Thr Asp Val Arg Leu Asn Ser Cys
            20                  25                  30

His Ser Ala Cys Ser Ser Cys Val Cys Thr Phe Ser Ile Pro Ala Gln
        35                  40                  45

Cys Val Cys Val Asp Met Lys Asp Phe Cys Tyr Glu Pro Cys Lys
    50                  55                  60
```

<210> SEQ ID NO 450
<211> LENGTH: 67
<212> TYPE: PRT

<213> ORGANISM: Glycine max

<400> SEQUENCE: 450

Asp Glu Tyr Ser Lys Pro Cys Cys Asp Leu Cys Met Cys Thr Arg
1               5                   10                  15

Ser Met Pro Pro Gln Cys Ser Cys Glu Asp Ile Arg Leu Asn Ser Cys
            20                  25                  30

His Ser Asp Cys Lys Ser Cys Met Cys Thr Arg Ser Gln Pro Gly Gln
        35                  40                  45

Cys Arg Cys Leu Asp Thr Asn Asp Phe Cys Tyr Lys Pro Cys Lys Ser
    50                  55                  60

Arg Asp Asp
65

<210> SEQ ID NO 451
<211> LENGTH: 63
<212> TYPE: PRT
<213> ORGANISM: Torresea cearensis

<400> SEQUENCE: 451

Ser Ser Lys Trp Glu Ala Cys Cys Asp Arg Cys Ala Cys Thr Lys Ser
1               5                   10                  15

Ile Pro Pro Gln Cys His Cys Ala Asp Ile Arg Leu Asn Ser Cys His
            20                  25                  30

Ser Ala Cys Glu Ser Cys Ala Cys Thr His Ser Ile Pro Ala Gln Cys
        35                  40                  45

Arg Cys Phe Asp Ile Thr Asp Phe Cys Tyr Lys Pro Cys Ser Gly
    50                  55                  60

<210> SEQ ID NO 452
<211> LENGTH: 64
<212> TYPE: PRT
<213> ORGANISM: Artificial
<220> FEATURE:
<223> OTHER INFORMATION: synthetic BBdb-AV sequence

<400> SEQUENCE: 452

Asp Pro Ser Glu Ser Ser Lys Pro Cys Cys Asp Gln Cys Ala Cys Thr
1               5                   10                  15

Lys Ser Ile Pro Pro Gln Cys Arg Cys Thr Asp Val Arg Leu Asn Ser
            20                  25                  30

Cys His Ser Ala Cys Ser Cys Ala Cys Tyr Asn Leu Tyr Gly Trp
        35                  40                  45

Thr Cys Val Cys Val Asp Met Lys Asp Phe Cys Tyr Glu Pro Cys Lys
    50                  55                  60

<210> SEQ ID NO 453
<211> LENGTH: 69
<212> TYPE: PRT
<213> ORGANISM: Artificial
<220> FEATURE:
<223> OTHER INFORMATION: synthetic BBsb3-AV sequence

<400> SEQUENCE: 453

Asp Pro Asp Asp Glu Tyr Ser Lys Pro Cys Cys Asp Leu Cys Met Cys
1               5                   10                  15

Thr Arg Ser Met Pro Pro Gln Cys Ser Cys Glu Asp Ile Arg Leu Asn
20 25 30

Ser Cys His Ser Asp Cys Lys Ser Cys Ala Cys Tyr Asn Leu Tyr Gly
35 40 45

Trp Thr Cys Arg Cys Leu Asp Thr Asn Asp Phe Cys Tyr Lys Pro Cys
           50                  55                  60

Lys Ser Arg Asp Asp
 65

<210> SEQ ID NO 454
<211> LENGTH: 65
<212> TYPE: PRT
<213> ORGANISM: Artificial
<220> FEATURE:
<223> OTHER INFORMATION: synthetic BBtc-AV sequence

<400> SEQUENCE: 454

Asp Pro Ser Ser Lys Trp Glu Ala Cys Cys Asp Arg Cys Ala Cys Thr
 1               5                  10                  15

Lys Ser Ile Pro Pro Gln Cys His Cys Ala Asp Ile Arg Leu Asn Ser
            20                  25                  30

Cys His Ser Ala Cys Glu Ser Cys Ala Cys Tyr Asn Leu Tyr Gly Trp
        35                  40                  45

Thr Cys Arg Cys Phe Asp Ile Thr Asp Phe Cys Tyr Lys Pro Cys Ser
     50                  55                  60

Gly
 65

<210> SEQ ID NO 455
<211> LENGTH: 202
<212> TYPE: DNA
<213> ORGANISM: Artificial
<220> FEATURE:
<223> OTHER INFORMATION: synthetic gene

<400> SEQUENCE: 455
ggatccttct gagagctcta aaccatgctg tgatcaatgc gcttgtacaa aatctatccc      60
tccacaatgc cgttgcactg atgttcgtct taactcatgt cactctgcat gcagctcatg     120
cgcttgttac aacctttacg gttggacatg cgtttgcgtc gacatgaaag atttctgcta     180
cgaaccttgt aaataaaagc tt                                              202

<210> SEQ ID NO 456
<211> LENGTH: 217
<212> TYPE: DNA
<213> ORGANISM: Artificial
<220> FEATURE:
<223> OTHER INFORMATION: synthetic gene

<400> SEQUENCE: 456
ggatccagat gacgaatact ctaaaccttg ctgtgatctt tgcatgtgta cacgttctat      60
gccacctcaa tgctcatgtg aagacatccg ccttaactct tgccactcag attgcaaaag    120
ctgcgcttgt tacaaccttt acggttggac atgccgttgt ttagatacta acgatttctg    180
ctacaaacct tgcaaatctc gtgatgatta aaagctt                             217

<210> SEQ ID NO 457
<211> LENGTH: 260
<212> TYPE: DNA
<213> ORGANISM: Artificial
<220> FEATURE:
<223> OTHER INFORMATION: synthetic gene

<400> SEQUENCE: 457
ggatccttct tcaaaatggg aagcttgctg tgatcgttgc gcatgcacaa aatctatccc      60

```
tccacaatgc cactgcgctg atatccgtct taactcatgc cattctgcat gcgaaagctg    120
cgcttgttac aacctttacg gttggacatg ccgttgcttc gatatcactg atttctgtta   180
caaaccttgc tctggctaaa agcttaaaag gagaccgtta atctaaaatc attatttgag   240
gcccgagctt aaagcttaag                                               260
```

```
<210> SEQ ID NO 458
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 458

Lys Tyr Tyr Leu Tyr Trp Trp
1               5

<210> SEQ ID NO 459
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 459

Thr Leu Trp Lys Ser Tyr Trp
1               5

<210> SEQ ID NO 460
<211> LENGTH: 5
<212> TYPE: PRT
<213> ORGANISM: Artificial
<220> FEATURE:
<223> OTHER INFORMATION: synthetic VEGF binding peptide

<400> SEQUENCE: 460

Asp Leu Tyr Trp Trp
1               5

<210> SEQ ID NO 461
<211> LENGTH: 47
<212> TYPE: DNA
<213> ORGANISM: Artificial
<220> FEATURE:
<223> OTHER INFORMATION: synthetic oligonucleotide

<400> SEQUENCE: 461
caaatcttgc gcatgtaaat attaccttta ctggtggtgt ttttgcg                 47

<210> SEQ ID NO 462
<211> LENGTH: 55
<212> TYPE: DNA
<213> ORGANISM: Artificial
<220> FEATURE:
<223> OTHER INFORMATION: synthetic oligonucleotide

<400> SEQUENCE: 462
tcgacgcaaa aacaccacca gtaaaggtaa tatttacatg cgcaagattt gcatg        55

<210> SEQ ID NO 463
<211> LENGTH: 47
<212> TYPE: DNA
<213> ORGANISM: Artificial
<220> FEATURE:
<223> OTHER INFORMATION: synthetic oligonucleotide
```

-continued

<400> SEQUENCE: 463
caaatcttgc gcgtgcacac tttggaaatc ttactggtgt ttttgcg                47

<210> SEQ ID NO 464
<211> LENGTH: 55
<212> TYPE: DNA
<213> ORGANISM: Artificial
<220> FEATURE:
<223> OTHER INFORMATION: synthetic oligonucleotide

<400> SEQUENCE: 464
tcgacgcaaa aacaccagta agatttccaa agtgtgcacg cgcaagattt gcatg        55

<210> SEQ ID NO 465
<211> LENGTH: 47
<212> TYPE: DNA
<213> ORGANISM: Artificial
<220> FEATURE:
<223> OTHER INFORMATION: synthetic oligonucleotide

<400> SEQUENCE: 465
caaatcttgc atctgtaaat atgatcttta ctggtggtgt ttttgcg                47

<210> SEQ ID NO 466
<211> LENGTH: 55
<212> TYPE: DNA
<213> ORGANISM: Artificial
<220> FEATURE:
<223> OTHER INFORMATION: synthetic oligonucleotide

<400> SEQUENCE: 466
tcgacgcaaa aacaccacca gtaaagatca tatttacaga tgcaagattt gcatg        55

<210> SEQ ID NO 467
<211> LENGTH: 214
<212> TYPE: DNA
<213> ORGANISM: Artificial
<220> FEATURE:
<223> OTHER INFORMATION: synthetic gene

<400> SEQUENCE: 467
ggatccagac gatgagagct ctaaaccttg ttgcgatcaa tgcatctgta caaaatcaaa    60
ccctccacaa tgtcgttgta agatatgcg tcctaatagc tgtcattctg catgcaaatc   120
atgtatctgc aaatatgacc tttactggtg gtgtttctgc aaagacatca ctgacttctg   180
ctatgaacca tgtaaacctt ctgaataaaa gctt                              214

<210> SEQ ID NO 468
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 468

Ser Lys His Ser Gln Ile Thr
1               5

<210> SEQ ID NO 469
<211> LENGTH: 7
<212> TYPE: PRT
<213> ORGANISM: Artificial
<220> FEATURE:
<223> OTHER INFORMATION: synthetic VEGF binding peptide

```
<400> SEQUENCE: 469

Lys Thr Asn Pro Ser Gly Ser
1               5

<210> SEQ ID NO 470
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 470

Arg Pro Thr Gly His Ser Leu
1               5

<210> SEQ ID NO 471
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 471

Lys His Ser Ala Lys Ala Glu
1               5

<210> SEQ ID NO 472
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 472

Lys Pro Ser Ser Ala Ser Ser
1               5

<210> SEQ ID NO 473
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 473

Pro Val Thr Lys Arg Val His
1               5

<210> SEQ ID NO 474
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 474

Arg Tyr Trp Gln Asp Ile Pro
1               5

<210> SEQ ID NO 475
<211> LENGTH: 7
<212> TYPE: PRT
<213> ORGANISM: Artificial
<220> FEATURE:
<223> OTHER INFORMATION: synthetic TNF-binding peptide
```

```
<400> SEQUENCE: 475

Ala Pro Glu Pro Ile Leu Ala
1               5

<210> SEQ ID NO 476
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 476

Asp Met Ile Met Val Ser Ile
1               5

<210> SEQ ID NO 477
<211> LENGTH: 214
<212> TYPE: DNA
<213> ORGANISM: Artificial
<220> FEATURE:
<223> OTHER INFORMATION: synthetic gene

<400> SEQUENCE: 477
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc agcaaacact ctcaaattac ttgtaaatgc acagacatca ctgacttctg     180
ctatgaacca tgtaaacctt ctgaataaaa gctt                                 214

<210> SEQ ID NO 478
<211> LENGTH: 214
<212> TYPE: DNA
<213> ORGANISM: Artificial
<220> FEATURE:
<223> OTHER INFORMATION: synthetic gene

<400> SEQUENCE: 478
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc aaaacaaacc caagcggttc ttgtaaatgc acagacatca ctgacttctg     180
ctatgaacca tgtaaacctt ctgaataaaa gctt                                 214

<210> SEQ ID NO 479
<211> LENGTH: 214
<212> TYPE: DNA
<213> ORGANISM: Artificial
<220> FEATURE:
<223> OTHER INFORMATION: synthetic gene

<400> SEQUENCE: 479
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc agaccaactg gtcacagcct ttgtaaatgc acagacatca ctgacttctg     180
ctatgaacca tgtaaacctt ctgaataaaa gctt                                 214

<210> SEQ ID NO 480
<211> LENGTH: 214
<212> TYPE: DNA
<213> ORGANISM: Artificial
<220> FEATURE:
<223> OTHER INFORMATION: synthetic gene
```

```
<400> SEQUENCE: 480
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc aaacacagcg ctaaagcaga atgtaaatgc acagacatca ctgacttctg     180
ctatgaacca tgtaaacctt ctgaataaaa gctt                                 214

<210> SEQ ID NO 481
<211> LENGTH: 214
<212> TYPE: DNA
<213> ORGANISM: Artificial
<220> FEATURE:
<223> OTHER INFORMATION: synthetic gene

<400> SEQUENCE: 481
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc aaaccaagct ctgcttcatc ttgtaaatgc acagacatca ctgacttctg     180
ctatgaacca tgtaaacctt ctgaataaaa gctt                                 214

<210> SEQ ID NO 482
<211> LENGTH: 214
<212> TYPE: DNA
<213> ORGANISM: Artificial
<220> FEATURE:
<223> OTHER INFORMATION: synthetic gene

<400> SEQUENCE: 482
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc ccagttacta aaagagtaca ctgtaaatgc acagacatca ctgacttctg     180
ctatgaacca tgtaaacctt ctgaataaaa gctt                                 214

<210> SEQ ID NO 483
<211> LENGTH: 214
<212> TYPE: DNA
<213> ORGANISM: Artificial
<220> FEATURE:
<223> OTHER INFORMATION: synthetic gene

<400> SEQUENCE: 483
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
atgtgcttgc agatactggc aagatattcc atgtaaatgc acagacatca ctgacttctg     180
ctatgaacca tgtaaacctt ctgaataaaa gctt                                 214

<210> SEQ ID NO 484
<211> LENGTH: 214
<212> TYPE: DNA
<213> ORGANISM: Artificial
<220> FEATURE:
<223> OTHER INFORMATION: synthetic gene

<400> SEQUENCE: 484
ggatccagac gatgagagct ctaaaccttg ttgcgatcaa tgcatctgta caaaatcaaa      60
ccctccacaa tgtcgttgta gagatgctcg tcctaatgca tgtcattctg catgcaaatc     120
```

```
atgtgcttgc gcaccagaac ctattcttgc ttgtaaatgc acagacatca ctgacttctg    180
ctatgaacca tgtaaacctt ctgaataaaa gctt                                 214

<210> SEQ ID NO 485
<211> LENGTH: 214
<212> TYPE: DNA
<213> ORGANISM: Artificial
<220> FEATURE:
<223> OTHER INFORMATION: synthetic gene

<400> SEQUENCE: 485
ggatccagac gatgagagct ctaaaccttg ttgcgatcaa tgcatctgta caaaatcaaa     60
ccctccacaa tgtcgttgta gagatgctcg tcctaatgca tgtcattctg catgcaaatc    120
atgtgcttgc gatatgatta tggttagcat ctgtaaatgc acagacatca ctgacttctg    180
ctatgaacca tgtaaacctt ctgaataaaa gctt                                 214

<210> SEQ ID NO 486
<211> LENGTH: 214
<212> TYPE: DNA
<213> ORGANISM: Artificial
<220> FEATURE:
<223> OTHER INFORMATION: synthetic gene

<400> SEQUENCE: 486
ggatccagac gatgagagct ctaaaccttg ttgcgatcaa tgcatctgta caaaatcaaa     60
ccctccacaa tgtcgttgta gagatgctcg tcctaatgca tgtcattctg catgcaaatc    120
atgtcactgc tataaccttt acggttggac atgtaaatgc acagacatca ctgacttctg    180
ctatgaacca tgtaaacctt ctgaataaaa gctt                                 214

<210> SEQ ID NO 487
<211> LENGTH: 214
<212> TYPE: DNA
<213> ORGANISM: Artificial
<220> FEATURE:
<223> OTHER INFORMATION: synthetic gene

<400> SEQUENCE: 487
ggatccagac gatgagagct ctaaaccttg ttgcgatcaa tgcatctgta caaaatcaaa     60
ccctccacaa tgtcgttgta aagatgctcg tagaaatgaa tgtcattctg catgcaaatc    120
atgtaaatgc tataaccttt acggttggac atgtcaatgc aagacatca ctgacttctg     180 ctatgaacca tgtaaacctt ctgaataaaa gctt                                 214

<210> SEQ ID NO 488
<211> LENGTH: 214
<212> TYPE: DNA
<213> ORGANISM: Artificial
<220> FEATURE:
<223> OTHER INFORMATION: synthetic gene

<400> SEQUENCE: 488
ggatccagac gatgagagct ctaaaccttg ttgcgatcaa tgcatctgta caaaatcaaa     60
ccctccacaa tgtcgttgta aagatagacg tgaaaatgct tgtcattctg catgcaaatc    120
atgtcactgc tataaccttt acggttggac atgtagatgc aaagacatca ctgacttctg    180
ctatgaacca tgtaaacctt ctgaataaaa gctt                                 214

<210> SEQ ID NO 489
<211> LENGTH: 214
```

-continued

```
<212> TYPE: DNA
<213> ORGANISM: Artificial
<220> FEATURE:
<223> OTHER INFORMATION: synthetic gene

<400> SEQUENCE: 489
ggatccagac gatgagagct ctaaaccttg ttgcgatcaa tgcatctgta caaaatcaaa     60
ccctccacaa tgtcgttgta aagatgctcg tagaaatgct tgtcattctg catgcaaatc    120
atgtcactgc tataaccttt acggttggac atgtagatgc ttagacatca ctgacttctg    180
ctatgaacca tgtaaacctt ctgaataaaa gctt                                214

<210> SEQ ID NO 490
<211> LENGTH: 214
<212> TYPE: DNA
<213> ORGANISM: Artificial
<220> FEATURE:
<223> OTHER INFORMATION: synthetic gene

<400> SEQUENCE: 490
ggatccagac gatgagagct ctaaaccttg ttgcgatcaa tgcatctgta caaaatcaaa     60
ccctccacaa tgtcgttgta aagatcaacg tcctaatgaa tgtcattctg catgcaaatc    120
atgtcactgc tataaccttt acggttggac atgtagatgc caagacatca ctgacttctg    180
ctatgaacca tgtaaacctt ctgaataaaa gctt                                214

<210> SEQ ID NO 491
<211> LENGTH: 68
<212> TYPE: PRT
<213> ORGANISM: Artificial
<220> FEATURE:
<223> OTHER INFORMATION: synthetic variant VEGF-binding protein BBPI

<400> SEQUENCE: 491

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Ser Lys His Ser Gln
        35                  40                  45

Ile Thr Cys Lys Cys Thr Asp Ile Thr Asp Phe Cys Tyr Glu Pro Cys
    50                  55                  60

Lys Pro Ser Glu
65

<210> SEQ ID NO 492
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 492

Thr Leu His Trp Trp Val Thr
1               5

<210> SEQ ID NO 493
<211> LENGTH: 7
<212> TYPE: PRT
<213> ORGANISM: Artificial
<220> FEATURE:
<223> OTHER INFORMATION: synthetic VEGF binding peptide
```

```
<400> SEQUENCE: 493

Pro Tyr Lys Ala Ser Phe Tyr
1               5

<210> SEQ ID NO 494
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 494

Pro Leu Arg Thr Ser His Thr
1               5

<210> SEQ ID NO 495
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 495

Glu Ala Thr Pro Arg Asp Thr
1               5

<210> SEQ ID NO 496
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 496

Asn Pro Leu His Thr Leu Ser
1               5

<210> SEQ ID NO 497
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 497

Lys His Glu Arg Ile Trp Ser
1               5

<210> SEQ ID NO 498
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 498

Ala Thr Asn Pro Pro Pro Met
1               5

<210> SEQ ID NO 499
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 499
```

Ser Thr Thr Ser Pro Asn Met
1               5

<210> SEQ ID NO 500
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 500

Ala Asp Arg Ser Phe Arg Tyr
1               5

<210> SEQ ID NO 501
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 501

Pro Lys Ala Asp Ser Lys Gln
1               5

<210> SEQ ID NO 502
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 502

Pro Asn Gln Ser His Leu His
1               5

<210> SEQ ID NO 503
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 503

Ser Gly Ser Glu Thr Trp Met
1               5

<210> SEQ ID NO 504
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 504

Ala Leu Ser Ala Pro Tyr Ser
1               5

<210> SEQ ID NO 505
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 505

```
Lys Met Pro Thr Ser Lys Val
1               5
```

<210> SEQ ID NO 506
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 506

```
Ile Thr Pro Lys Arg Pro Tyr
1               5
```

<210> SEQ ID NO 507
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 507

```
Lys Trp Ile Val Ser Glu Thr
1               5
```

<210> SEQ ID NO 508
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 508

```
Pro Asn Ala Asn Ala Pro Ser
1               5
```

<210> SEQ ID NO 509
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 509

```
Asn Val Gln Ser Leu Pro Leu
1               5
```

<210> SEQ ID NO 510
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 510

```
Thr Leu Trp Pro Thr Phe Trp
1               5
```

<210> SEQ ID NO 511
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 511

```
Asn Leu Trp Pro His Phe Trp
```

-continued

```
1               5

<210> SEQ ID NO 512
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 512

Ser Leu Trp Pro Ala Phe Trp
1               5

<210> SEQ ID NO 513
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 513

Ser Leu Trp Pro His Phe Trp
1               5

<210> SEQ ID NO 514
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 514

Ala Pro Trp Asn Ser His Ile
1               5

<210> SEQ ID NO 515
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 515

Ala Pro Trp Asn Leu His Ile
1               5

<210> SEQ ID NO 516
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 516

Leu Pro Ser Trp His Leu Arg
1               5

<210> SEQ ID NO 517
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 517

Pro Thr Ile Leu Glu Trp Tyr
1               5
```

-continued

<210> SEQ ID NO 518
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 518

Thr Leu Tyr Pro Gln Phe Trp
1               5

<210> SEQ ID NO 519
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 519

His Leu Ala Pro Ser Ala Val
1               5

<210> SEQ ID NO 520
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 520

Lys Tyr Tyr Leu Ser Trp Trp
1               5

<210> SEQ ID NO 521
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 521

Trp Tyr Thr Leu Tyr Lys Trp
1               5

<210> SEQ ID NO 522
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 522

Thr Tyr Arg Leu Tyr Trp Trp
1               5

<210> SEQ ID NO 523
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 523

Arg Tyr Ser Leu Tyr Tyr Trp
1               5

```
<210> SEQ ID NO 524
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 524

Tyr Tyr Leu Tyr Tyr Trp Lys
1               5

<210> SEQ ID NO 525
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 525

Asn Tyr Gln Leu Tyr Gly Trp
1               5

<210> SEQ ID NO 526
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 526

Thr Lys Trp Pro Ser Tyr Trp
1               5

<210> SEQ ID NO 527
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 527

Thr Leu Trp Lys Ser Tyr Trp
1               5

<210> SEQ ID NO 528
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 528

Pro Leu Trp Pro Ser Tyr Trp
1               5

<210> SEQ ID NO 529
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 529

Arg Leu Trp Pro Ser Tyr Trp
1               5
```

```
<210> SEQ ID NO 530
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 530

Thr Leu Trp Pro Lys Tyr Trp
1               5

<210> SEQ ID NO 531
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 531

Lys Tyr Asp Leu Tyr Trp Trp
1               5

<210> SEQ ID NO 532
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 532

Arg Tyr Asp Leu Tyr Trp Trp
1               5

<210> SEQ ID NO 533
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 533

Asp Tyr Arg Leu Tyr Trp Trp
1               5

<210> SEQ ID NO 534
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 534

Asp Tyr Lys Leu Tyr Trp Trp
1               5

<210> SEQ ID NO 535
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 535

Glu Tyr Lys Leu Tyr Trp Trp
1               5

<210> SEQ ID NO 536
```

```
<211> LENGTH: 7
<212> TYPE: PRT
<213> ORGANISM: Artificial
<220> FEATURE:
<223> OTHER INFORMATION: synthetic VEGF binding peptide

<400> SEQUENCE: 536

Arg Tyr Pro Leu Tyr Trp Trp
1               5

<210> SEQ ID NO 537
<211> LENGTH: 9
<212> TYPE: PRT
<213> ORGANISM: Artificial
<220> FEATURE:
<223> OTHER INFORMATION: synthetic FGF-binding peptide

<400> SEQUENCE: 537

Cys Tyr Gly Leu Pro Phe Thr Arg Cys
1               5

<210> SEQ ID NO 538
<211> LENGTH: 9
<212> TYPE: PRT
<213> ORGANISM: Artificial
<220> FEATURE:
<223> OTHER INFORMATION: synthetic FGF-binding peptide

<400> SEQUENCE: 538

Cys Glu Glu Ile Trp Thr Met Leu Cys
1               5

<210> SEQ ID NO 539
<211> LENGTH: 9
<212> TYPE: PRT
<213> ORGANISM: Artificial
<220> FEATURE:
<223> OTHER INFORMATION: synthetic FGF-binding peptide

<400> SEQUENCE: 539

Cys Trp Ala Leu Thr Val Lys Thr Cys
1               5

<210> SEQ ID NO 540
<211> LENGTH: 9
<212> TYPE: PRT
<213> ORGANISM: Artificial
<220> FEATURE:
<223> OTHER INFORMATION: synthetic FGF-binding peptide

<400> SEQUENCE: 540

Cys Leu Thr Val Leu Trp Thr Thr Cys
1               5

<210> SEQ ID NO 541
<211> LENGTH: 9
<212> TYPE: PRT
<213> ORGANISM: Artificial
<220> FEATURE:
<223> OTHER INFORMATION: synthetic FGF-binding peptide

<400> SEQUENCE: 541

Cys Thr Leu Trp Asn Arg Ser Pro Cys
1               5

<210> SEQ ID NO 542
<211> LENGTH: 9
```

```
<212> TYPE: PRT
<213> ORGANISM: Artificial
<220> FEATURE:
<223> OTHER INFORMATION: synthetic FGF-binding peptide

<400> SEQUENCE: 542

Cys His Tyr Leu Leu Thr Asn Tyr Cys
1               5

<210> SEQ ID NO 543
<211> LENGTH: 9
<212> TYPE: PRT
<213> ORGANISM: Artificial
<220> FEATURE:
<223> OTHER INFORMATION: synthetic FGF-binding peptide

<400> SEQUENCE: 543

Cys Arg Ile His Leu Ala His Lys Cys
1               5

<210> SEQ ID NO 544
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 544

Thr Asn Ile Asp Ser Thr Pro
1               5

<210> SEQ ID NO 545
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 545

His Leu Gln Thr Thr Glu Thr
1               5

<210> SEQ ID NO 546
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 546

Ser Leu Asn Asn Leu Thr Val
1               5

<210> SEQ ID NO 547
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 547

Thr Asn Ile Asp Ser Thr Pro
1               5

<210> SEQ ID NO 548
<211> LENGTH: 7
<212> TYPE: PRT
```

```
<213> ORGANISM: Artificial
<220> FEATURE:
<223> OTHER INFORMATION: synthetic FGF-binding peptide

<400> SEQUENCE: 548

Thr Asn Ile Asp Ser Thr Pro
1               5

<210> SEQ ID NO 549
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 549

Leu Arg Ile Leu Ala Asn Lys
1               5

<210> SEQ ID NO 550
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 550

Leu Leu Thr Pro Thr Leu Asn
1               5

<210> SEQ ID NO 551
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 551

Ala Leu Pro Thr His Ser Asn
1               5

<210> SEQ ID NO 552
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 552

Thr Asn Ile Asp Ser Thr Pro
1               5

<210> SEQ ID NO 553
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 553

Leu Cys Arg Arg Phe Glu Asn
1               5

<210> SEQ ID NO 554
<211> LENGTH: 7
<212> TYPE: PRT
<213> ORGANISM: Artificial
```

-continued

```
<220> FEATURE:
<223> OTHER INFORMATION: synthetic FGF-binding peptide

<400> SEQUENCE: 554

Thr Asn Ile Asp Ser Thr Pro
1               5

<210> SEQ ID NO 555
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 555

Thr Asn Ile Asp Ser Thr Pro
1               5

<210> SEQ ID NO 556
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 556

His Leu Gln Thr Thr Glu Thr
1               5

<210> SEQ ID NO 557
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 557

Pro Leu Gly Leu Cys Pro Pro
1               5

<210> SEQ ID NO 558
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 558

Gly Tyr Phe Ile Pro Ser Ile
1               5

<210> SEQ ID NO 559
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 559

Thr Lys Ile Asp Ser Thr Pro
1               5

<210> SEQ ID NO 560
<211> LENGTH: 7
<212> TYPE: PRT
<213> ORGANISM: Artificial
<220> FEATURE:
```

-continued

<223> OTHER INFORMATION: synthetic FGF-binding peptide

<400> SEQUENCE: 560

His Leu Gln Thr Thr Glu Thr
1               5

<210> SEQ ID NO 561
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 561

Trp Asn Ile Asp Ser Thr Pro
1               5

<210> SEQ ID NO 562
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 562

Thr Trp Ile Asp Trp Thr Pro
1               5

<210> SEQ ID NO 563
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 563

Cys Val Thr Thr Asp Trp Ile Glu Cys
1               5

<210> SEQ ID NO 564
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 564

Cys Tyr Tyr Ser Gln Phe His Gln Cys
1               5

<210> SEQ ID NO 565
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 565

Cys Pro Thr Leu Trp Thr His Met Cys
1               5

<210> SEQ ID NO 566
<211> LENGTH: 21
<212> TYPE: PRT
<213> ORGANISM: Artificial
<220> FEATURE:
<223> OTHER INFORMATION: synthetic TGF-binding peptide -continued

```
<400> SEQUENCE: 566

Gln Ser Ala Cys Ile Val Tyr Tyr Val Gly Arg Lys Pro Lys Val Glu
1               5                   10                  15

Cys Ala Ser Ser Asp
            20

<210> SEQ ID NO 567
<211> LENGTH: 21
<212> TYPE: PRT
<213> ORGANISM: Artificial
<220> FEATURE:
<223> OTHER INFORMATION: synthetic TGF-binding peptide

<400> SEQUENCE: 567

Gln Ser Ala Cys Ile Leu Tyr Tyr Ile Gly Lys Thr Pro Lys Ile Glu
1               5                   10                  15

Cys Ala Ser Ser Asp
            20

<210> SEQ ID NO 568
<211> LENGTH: 21
<212> TYPE: PRT
<213> ORGANISM: Artificial
<220> FEATURE:
<223> OTHER INFORMATION: synthetic TGF-binding peptide

<400> SEQUENCE: 568

Gln Ser Ala Cys Ile Leu Tyr Tyr Val Gly Arg Thr Pro Lys Val Glu
1               5                   10                  15

Cys Ala Ser Ser Asp
            20

<210> SEQ ID NO 569
<211> LENGTH: 12
<212> TYPE: PRT
<213> ORGANISM: Artificial
<220> FEATURE:
<223> OTHER INFORMATION: synthetic TGF-binding peptide

<400> SEQUENCE: 569

Leu Cys Pro Glu Asn Asp Asn Val Ser Pro Cys Tyr
1               5                   10

<210> SEQ ID NO 570
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 570

Lys His Asn Val Arg Leu Leu
1               5

<210> SEQ ID NO 571
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 571

Asn Asp Thr Pro Ser Tyr Phe
1               5
```

```
<210> SEQ ID NO 572
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 572

Ala Lys Leu Tyr Ala Gly Ser
1               5

<210> SEQ ID NO 573
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 573

Arg Gly Pro Ala His Ser Leu
1               5

<210> SEQ ID NO 574
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 574

Asn Ser Leu Ala Glu Arg Arg
1               5

<210> SEQ ID NO 575
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 575

His Pro Leu Ala Ser Pro His
1               5

<210> SEQ ID NO 576
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 576

Gln Pro Trp Asn Lys Leu Lys
1               5

<210> SEQ ID NO 577
<211> LENGTH: 7
<212> TYPE: PRT
<213> ORGANISM: Artificial
<220> FEATURE:
<223> OTHER INFORMATION: synthetic TGF-binding peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 577
```

```
Ala Trp Leu Xaa Ile Pro Tyr
1               5

<210> SEQ ID NO 578
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 578

Pro Thr Lys Pro Ala Gln Gln
1               5

<210> SEQ ID NO 579
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 579

Pro Ser Leu Asn Arg Pro Gln
1               5

<210> SEQ ID NO 580
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 580

His His Ala Arg Gln Glu Trp
1               5

<210> SEQ ID NO 581
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 581

Arg His His Thr Pro Gly Pro
1               5

<210> SEQ ID NO 582
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 582

Ala Ser Ala Ile Asn Pro His
1               5

<210> SEQ ID NO 583
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 583
```

```
Trp Thr Pro Lys Pro Thr Gln
1               5
```

<210> SEQ ID NO 584
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 584

```
Ala Thr Phe Pro Asn Gln Ser
1               5
```

<210> SEQ ID NO 585
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 585

```
Ala Ser Thr Val Gly Gly Leu
1               5
```

<210> SEQ ID NO 586
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 586

```
Thr Met Leu Pro Tyr Arg Pro
1               5
```

<210> SEQ ID NO 587
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 587

```
Ala Trp His Ser Pro Ser Val
1               5
```

<210> SEQ ID NO 588
<211> LENGTH: 6
<212> TYPE: PRT
<213> ORGANISM: Artificial
<220> FEATURE:
<223> OTHER INFORMATION: synthetic TNF-binding peptide

<400> SEQUENCE: 588

```
Thr Gln Ser Phe Ser Ser
1               5
```

<210> SEQ ID NO 589
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 589

```
Thr His Lys Asn Thr Leu Arg
```

```
1               5

<210> SEQ ID NO 590
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 590

Gly Gln Thr His Phe His Val
1               5

<210> SEQ ID NO 591
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 591

Leu Pro Ile Leu Thr Gln Thr
1               5

<210> SEQ ID NO 592
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 592

Ser Ile Leu Pro Val Ser His
1               5

<210> SEQ ID NO 593
<211> LENGTH: 6
<212> TYPE: PRT
<213> ORGANISM: Artificial
<220> FEATURE:
<223> OTHER INFORMATION: synthetic TNF-binding peptide

<400> SEQUENCE: 593

Ser Gln Pro Ile Pro Ile
1               5

<210> SEQ ID NO 594
<211> LENGTH: 7
<212> TYPE: PRT
<213> ORGANISM: Artificial
<220> FEATURE:
<223> OTHER INFORMATION: synthetic TNF-binding peptide

<400> SEQUENCE: 594

Gln Pro Leu Arg Lys Leu Pro
1               5

<210> SEQ ID NO 595
<211> LENGTH: 68
<212> TYPE: PRT
<213> ORGANISM: Artificial
<220> FEATURE:
<223> OTHER INFORMATION: synthetic BBPI variant

<400> SEQUENCE: 595

Asp Pro Asp Asp Glu Ser Ser Lys Pro Cys Cys Asp Gln Cys Ala Cys
1               5                   10                  15
```

Thr Lys Ser Asn Pro Pro Gln Cys Arg Cys Ser Asp Met Arg Leu Asn
            20                  25                  30

Ser Cys His Ser Ala Cys Lys Ser Cys Ala Cys Tyr Asn Leu Tyr Gly
            35                  40                  45

Trp Thr Cys Thr Cys Ala Asp Ile Thr Asp Phe Cys Tyr Glu Pro Cys
            50                  55                  60

Lys Pro Ser Glu
65

<210> SEQ ID NO 596
<211> LENGTH: 68
<212> TYPE: PRT
<213> ORGANISM: Artificial
<220> FEATURE:
<223> OTHER INFORMATION: synthetic BBPI variant

<400> SEQUENCE: 596

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Leu Asp Met Arg Leu Asn
            20                  25                  30

Ser Cys His Ser Ala Cys Lys Ser Cys Ala Cys Tyr Asn Leu Tyr Gly
            35                  40                  45

Trp Thr Cys Thr Cys Ala Asp Ile Thr Asp Phe Cys Tyr Glu Pro Cys
            50                  55                  60

Lys Pro Ser Glu
65

<210> SEQ ID NO 597
<211> LENGTH: 68
<212> TYPE: PRT
<213> ORGANISM: Artificial
<220> FEATURE:
<223> OTHER INFORMATION: synthetic BBPI variant

<400> SEQUENCE: 597

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Leu Asp Met Arg Pro Asn
            20                  25                  30

Ser Cys His Ser Ala Cys Lys Ser Cys Ala Cys Tyr Asn Leu Tyr Gly
            35                  40                  45

Trp Thr Cys Thr Cys Ala Asp Ile Thr Asp Phe Cys Tyr Glu Pro Cys
            50                  55                  60

Lys Pro Ser Glu
65

<210> SEQ ID NO 598
<211> LENGTH: 68
<212> TYPE: PRT
<213> ORGANISM: Artificial
<220> FEATURE:
<223> OTHER INFORMATION: synthetic BBPI variant

<400> SEQUENCE: 598

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Leu Asp Met Arg Pro Asn
            20                  25                  30

-continued

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 599
<211> LENGTH: 68
<212> TYPE: PRT
<213> ORGANISM: Artificial
<220> FEATURE:
<223> OTHER INFORMATION: synthetic BBPI variant

<400> SEQUENCE: 599

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Leu Asp Met Arg Leu Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 600
<211> LENGTH: 68
<212> TYPE: PRT
<213> ORGANISM: Artificial
<220> FEATURE:
<223> OTHER INFORMATION: synthetic BBPI variant

<400> SEQUENCE: 600

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 601
<211> LENGTH: 68
<212> TYPE: PRT
<213> ORGANISM: Artificial
<220> FEATURE:
<223> OTHER INFORMATION: synthetic BBPI variant

<400> SEQUENCE: 601

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys

Lys Pro Ser Glu
65

<210> SEQ ID NO 602
<211> LENGTH: 68
<212> TYPE: PRT
<213> ORGANISM: Artificial
<220> FEATURE:
<223> OTHER INFORMATION: synthetic BBPI variant

<400> SEQUENCE: 602

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Leu Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 603
<211> LENGTH: 68
<212> TYPE: PRT
<213> ORGANISM: Artificial
<220> FEATURE:
<223> OTHER INFORMATION: synthetic BBPI variant

<400> SEQUENCE: 603

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Leu Asp Met Arg Leu Asn
            20                  25                  30

Ser Cys His Ser Ala Cys Lys Ser Cys Ala Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 604
<211> LENGTH: 68
<212> TYPE: PRT
<213> ORGANISM: Artificial
<220> FEATURE:
<223> OTHER INFORMATION: synthetic BBPI variant

<400> SEQUENCE: 604

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Leu Asp Met Arg Pro Asn
            20                  25                  30

Ser Cys His Ser Ala Cys Lys Ser Cys Ala Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 605
<211> LENGTH: 68
<212> TYPE: PRT
<213> ORGANISM: Artificial
<220> FEATURE:
<223> OTHER INFORMATION: synthetic BBPI variant

<400> SEQUENCE: 605

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Leu Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 606
<211> LENGTH: 68
<212> TYPE: PRT
<213> ORGANISM: Artificial
<220> FEATURE:
<223> OTHER INFORMATION: synthetic BBPI variant

<400> SEQUENCE: 606

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Leu Asp Met Arg Leu Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 607
<211> LENGTH: 68
<212> TYPE: PRT
<213> ORGANISM: Artificial
<220> FEATURE:
<223> OTHER INFORMATION: synthetic BBPI variant

<400> SEQUENCE: 607

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Ala Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 608
<211> LENGTH: 68

-continued

```
<212> TYPE: PRT
<213> ORGANISM: Artificial
<220> FEATURE:
<223> OTHER INFORMATION: synthetic BBPI variant

<400> SEQUENCE: 608

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 609
<211> LENGTH: 68
<212> TYPE: PRT
<213> ORGANISM: Artificial
<220> FEATURE:
<223> OTHER INFORMATION: synthetic BBPI variant

<400> SEQUENCE: 609

Asp Pro Asp Asp Glu Ser Ser Lys Pro Cys Cys Asp Gln Cys Ala Cys
1               5                   10                  15

Thr Lys Ser Asn Pro Pro Gln Cys Arg Cys Ser Asp Met Arg Leu Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 610
<211> LENGTH: 11
<212> TYPE: PRT
<213> ORGANISM: Artificial
<220> FEATURE:
<223> OTHER INFORMATION: synthetic VEGF binding peptide

<400> SEQUENCE: 610

Cys Ala Cys Tyr Asn Leu Tyr Gly Trp Thr Cys
1               5                   10

<210> SEQ ID NO 611
<211> LENGTH: 68
<212> TYPE: PRT
<213> ORGANISM: Artificial
<220> FEATURE:
<223> OTHER INFORMATION: synthetic BBPI variant

<400> SEQUENCE: 611

Asp Pro Asp Asp Glu Val Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45
```

-continued

```
Trp Thr Cys Thr Cys Ala Asp Ile Thr Asp Phe Cys Tyr Glu Pro Cys
    50                  55                  60

Lys Pro Ser Glu
65

<210> SEQ ID NO 612
<211> LENGTH: 68
<212> TYPE: PRT
<213> ORGANISM: Artificial
<220> FEATURE:
<223> OTHER INFORMATION: synthetic BBPI variant

<400> SEQUENCE: 612

Asp Pro Asp Asp Glu Val Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 613
<211> LENGTH: 68
<212> TYPE: PRT
<213> ORGANISM: Artificial
<220> FEATURE:
<223> OTHER INFORMATION: synthetic BBPI variant

<400> SEQUENCE: 613

Asp Pro Asp Asp Glu Ser Pro Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 614
<211> LENGTH: 68
<212> TYPE: PRT
<213> ORGANISM: Artificial
<220> FEATURE:
<223> OTHER INFORMATION: synthetic BBPI variant

<400> SEQUENCE: 614

Asp Pro Asp Asp Glu Ser Ser Lys Pro Cys Cys Asp Gly Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
```

<210> SEQ ID NO 615
<211> LENGTH: 68
<212> TYPE: PRT
<213> ORGANISM: Artificial
<220> FEATURE:
<223> OTHER INFORMATION: synthetic BBPI variant

<400> SEQUENCE: 615

Asp Pro Asp Asp Glu Ser Ser Lys Pro Cys Cys Asp Gln Cys Leu Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys P

```
<211> LENGTH: 68
<212> TYPE: PRT
<213> ORGANISM: Artificial
<220> FEATURE:
<223> OTHER INFORMATION: synthetic BBPI variant

<400> SEQUENCE: 618

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Met Arg Pro Asn
            20                  25                  30

Arg Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 619
<211> LENGTH: 68
<212> TYPE: PRT
<213> ORGANISM: Artificial
<220> FEATURE:
<223> OTHER INFORMATION: synthetic BBPI variant

<400> SEQUENCE: 619

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Arg Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 620
<211> LENGTH: 68
<212> TYPE: PRT
<213> ORGANISM: Artificial
<220> FEATURE:
<223> OTHER INFORMATION: synthetic BBPI variant

<400> SEQUENCE: 620

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Lys Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 621
<211> LENGTH: 68
<212> TYPE: PRT
<213> ORGANISM: Artificial
<220> FEATURE:
```

<223> OTHER INFORMATION: synthetic BBPI variant

<400> SEQUENCE: 621

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ala Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 622
<211> LENGTH: 68
<212> TYPE: PRT
<213> ORGANISM: Artificial
<220> FEATURE:
<223> OTHER INFORMATION: synthetic BBPI variant

<400> SEQUENCE: 622

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Arg Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 623
<211> LENGTH: 68
<212> TYPE: PRT
<213> ORGANISM: Artificial
<220> FEATURE:
<223> OTHER INFORMATION: synthetic BBPI variant

<400> SEQUENCE: 623

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Asn Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Ser Glu
65

<210> SEQ ID NO 624
<211> LENGTH: 68
<212> TYPE: PRT
<213> ORGANISM: Artificial
<220> FEATURE:
<223> OTHER INFORMATION: synthetic BBPI variant

<400> SEQUENCE: 624

```
Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Lys Cys Ala Asp Ile Thr Asp Phe Cys Tyr Glu Pro Cys
    50                  55                  60

Lys Pro Ser Glu
65

<210> SEQ ID NO 625
<211> LENGTH: 68
<212> TYPE: PRT
<213> ORGANISM: Artificial
<220> FEATURE:
<223> OTHER INFORMATION: synthetic BBPI variant

<400> SEQUENCE: 625

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Thr Asp Ile Thr Asp Phe Cys Tyr Glu Pro Cys
    50                  55                  60

Lys Pro Ser Glu
65

<210> SEQ ID NO 626
<211> LENGTH: 68
<212> TYPE: PRT
<213> ORGANISM: Artificial
<220> FEATURE:
<223> OTHER INFORMATION: synthetic BBPI variant

<400> SEQUENCE: 626

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Ser Asp Met Arg Pro Asn
            20                  25                  30

Ser Cys His Ser Ala Cys Lys Ser Cys Lys Cys Tyr Asn Leu Tyr Gly
        35                  40                  45

Trp Thr Cys Thr Cys Ala Asp Ile Thr Asp Phe Cys Tyr Glu Pro Cys
    50                  55                  60

Lys Pro Glu Glu
65

<210> SEQ ID NO 627
<211> LENGTH: 68
<212> TYPE: PRT
<213> ORGANISM: Artificial
<220> FEATURE:
<223> OTHER INFORMATION: synthetic BBPI variant

<400> SEQUENCE: 627

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
```

-continued

```
                20                  25                  30
Ala Cys His Ser Ala Cys Lys Ser Cys His Cys Tyr Asn Leu Tyr Gly
            35                  40                  45

Trp Thr Cys Lys Cys Thr Asp Ile Thr Asp Phe Cys Tyr Glu Pro Cys
        50                  55                  60

Lys Pro Ser Glu
65

<210> SEQ ID NO 628
<211> LENGTH: 68
<212> TYPE: PRT
<213> ORGANISM: Artificial
<220> FEATURE:
<223> OTHER INFORMATION: synthetic BBPI variant

<400> SEQUENCE: 628

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Lys Asp Ala Arg Arg Asn
            20                  25                  30

Glu Cys His Ser Ala Cys Lys Ser Cys Lys Cys Tyr Asn Leu Tyr Gly
            35                  40                  45

Trp Thr Cys Gln Cys Gln Asp Ile Thr Asp Phe Cys Tyr Glu Pro Cys
        50                  55                  60

Lys Pro Ser Glu
65

<210> SEQ ID NO 629
<211> LENGTH: 68
<212> TYPE: PRT
<213> ORGANISM: Artificial
<220> FEATURE:
<223> OTHER INFORMATION: synthetic BBPI variant

<400> SEQUENCE: 629

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Lys Asp Arg Arg Glu Asn
            20                  25                  30

Ala Cys His Ser Ala Cys Lys Ser Cys His Cys Tyr Asn Leu Tyr Gly
            35                  40                  45

Trp Thr Cys Arg Cys Lys Asp Ile Thr Asp Phe Cys Tyr Glu Pro Cys
        50                  55                  60

Lys Pro Ser Glu
65

<210> SEQ ID NO 630
<211> LENGTH: 68
<212> TYPE: PRT
<213> ORGANISM: Artificial
<220> FEATURE:
<223> OTHER INFORMATION: synthetic BBPI variant

<400> SEQUENCE: 630

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Lys Asp Ala Arg Arg Asn
            20                  25                  30

Ala Cys His Ser Ala Cys Lys Ser Cys His Cys Tyr Asn Leu Tyr Gly
            35                  40                  45
```

```
Trp Thr Cys Arg Cys Leu Asp Ile Thr Asp Phe Cys Tyr Glu Pro Cys
 50                  55                  60

Lys Pro Ser Glu
 65

<210> SEQ ID NO 631
<211> LENGTH: 68
<212> TYPE: PRT
<213> ORGANISM: Artificial
<220> FEATURE:
<223> OTHER INFORMATION: synthetic BBPI variant

<400> SEQUENCE: 631

Asp Pro Asp Asp Glu Ser Ser Lys Pro Cys Cys Asp Gln Cys Ile Cys
  1               5                  10                  15

Thr Lys Ser Asn Pro Pro Gln Cys Arg Cys Lys Asp Gln Arg Pro Asn
             20                  25                  30

Glu Cys His Ser Ala Cys Lys Ser Cys His Cys Tyr Asn Leu Tyr Gly
         35                  40                  45

Trp Thr Cys Arg Cys Gln Asp Ile Thr Asp Phe Cys Tyr Glu Pro Cys
 50                  55                  60

Lys Pro Ser Glu
 65

<210> SEQ ID NO 632
<211> LENGTH: 68
<212> TYPE: PRT
<213> ORGANISM: Artificial
<220> FEATURE:
<223> OTHER INFORMATION: synthetic BBPI variant

<400> SEQUENCE: 632

Asp Pro Asp Asp Glu Ser Ser Lys Pro Cys Cys Asp Gln Cys Ile Cys
  1               5                  10                  15

Thr Lys Ser Asn Pro Pro Gln Cys Arg Cys Arg Asp Ala Arg Pro Asn
             20                  25                  30

Ala Cys His Ser Ala Cys Lys Ser Cys Ala Cys Lys Thr Asn Pro Ser
         35                  40                  45

Gly Ser Cys Lys Cys Thr Asp Ile Thr Asp Phe Cys Tyr Glu Pro Cys
 50                  55                  60

Lys Pro Ser Glu
 65

<210> SEQ ID NO 633
<211> LENGTH: 68
<212> TYPE: PRT
<213> ORGANISM: Artificial
<220> FEATURE:
<223> OTHER INFORMATION: synthetic BBPI variant

<400> SEQUENCE: 633

Asp Pro Asp Asp Glu Ser Ser Lys Pro Cys Cys Asp Gln Cys Ile Cys
  1               5                  10                  15

Thr Lys Ser Asn Pro Pro Gln Cys Arg Cys Arg Asp Ala Arg Pro Asn
             20                  25                  30

Ala Cys His Ser Ala Cys Lys Ser Cys Ala Cys Arg Pro Thr Gly His
         35                  40                  45

Ser Leu Cys Lys Cys Thr Asp Ile Thr Asp Phe Cys Tyr Glu Pro Cys
 50                  55                  60
```

Lys Pro Ser Glu
65

<210> SEQ ID NO 634
<211> LENGTH: 68
<212> TYPE: PRT
<213> ORGANISM: Artificial
<220> FEATURE:
<223> OTHER INFORMATION: synthetic BBPI variant

<400> SEQUENCE: 634

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Lys His Ser Ala Lys
        35                  40                  45

Ala Glu Cys Lys Cys Thr Asp Ile Thr Asp Phe Cys Tyr Glu Pro Cys
    50                  55                  60

Lys Pro Ser Glu
65

<210> SEQ ID NO 635
<211> LENGTH: 68
<212> TYPE: PRT
<213> ORGANISM: Artificial
<220> FEATURE:
<223> OTHER INFORMATION: synthetic BBPI variant

<400> SEQUENCE: 635

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Lys Pro Ser Ser Ala
        35                  40                  45

Ser Ser Cys Lys Cys Thr Asp Ile Thr Asp Phe Cys Tyr Glu Pro Cys
    50                  55                  60

Lys Pro Ser Glu
65

<210> SEQ ID NO 636
<211> LENGTH: 68
<212> TYPE: PRT
<213> ORGANISM: Artificial
<220> FEATURE:
<223> OTHER INFORMATION: synthetic BBPI variant

<400> SEQUENCE: 636

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Pro Val Thr Lys Arg
        35                  40                  45

Val His Cys Lys Cys Thr Asp Ile Thr Asp Phe Cys Tyr Glu Pro Cys
    50                  55                  60

Lys Pro Ser Glu
65

```
<210> SEQ ID NO 637
<211> LENGTH: 68
<212> TYPE: PRT
<213> ORGANISM: Artificial
<220> FEATURE:
<223> OTHER INFORMATION: synthetic BBPI variant

<400> SEQUENCE: 637

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Arg Tyr Trp Gln Asp
        35                  40                  45

Ile Pro Cys Lys Cys Thr Asp Ile Thr Asp Phe Cys Tyr Glu Pro Cys
    50                  55                  60

Lys Pro Ser Glu
65

<210> SEQ ID NO 638
<211> LENGTH: 68
<212> TYPE: PRT
<213> ORGANISM: Artificial
<220> FEATURE:
<223> OTHER INFORMATION: synthetic BBPI variant

<400> SEQUENCE: 638

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Ala Pro Glu Pro Ile
        35                  40                  45

Leu Ala Cys Lys Cys Thr Asp Ile Thr Asp Phe Cys Tyr Glu Pro Cys
    50                  55                  60

Lys Pro Ser Glu
65

<210> SEQ ID NO 639
<211> LENGTH: 68
<212> TYPE: PRT
<213> ORGANISM: Artificial
<220> FEATURE:
<223> OTHER INFORMATION: synthetic BBPI variant

<400> SEQUENCE: 639

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
            20                  25                  30

Ala Cys His Ser Ala Cys Lys Ser Cys Ala Cys Asp Met Ile Met Val
        35                  40                  45

Ser Ile Cys Lys Cys Thr Asp Ile Thr Asp Phe Cys Tyr Glu Pro Cys
    50                  55                  60

Lys Pro Ser Glu
65

<210> SEQ ID NO 640
<211> LENGTH: 68
<212> TYPE: PRT
<213> ORGANISM: Artificial
```

```
<220> FEATURE:
<223> OTHER INFORMATION: synthetic BBIt-VEGK

<400> SEQUENCE: 640

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Arg Asp Ala Arg Pro Asn
                20                  25                  30

Ala Cys His Ser Ala Cys Lys Ser Cys Ala Cys Lys Tyr Tyr Leu Tyr
            35                  40                  45

Trp Trp Cys Lys Cys Thr Asp Ile Thr Asp Phe Cys Tyr Glu Pro Cys
        50                  55                  60

Lys Pro Ser Glu
65

<210> SEQ ID NO 641
<211> LENGTH: 68
<212> TYPE: PRT
<213> ORGANISM: Artificial
<220> FEATURE:
<223> OTHER INFORMATION: synthetic BBIt-VEGT

<400> SEQUENCE: 641

Asp Pro Asp Asp Glu Ser Ser Lys Pro Cys Cys Asp Gln Cys Ile C

Asp Pro Asp Asp Glu Ser Ser Lys Pro Cys Cys Asp Gln Cys Ile Cys
1               5                   10                  15

Thr Lys Ser Asn Pro Pro Gln Cys Arg Cys Lys Asp Met Arg Pro Asn
            20                  25                  30

Ser Cys His Ser Ala Cys Lys Ser Cys Ile Cys Lys Tyr Asp Leu Tyr
        35                  40                  45

Trp Trp Cys Phe Cys Lys Asp Ile Thr Asp Phe Cys Tyr Glu Pro Cys
        50                  55                  60

Lys Pro Ser Glu
65

<210> SEQ ID NO 644
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 644

Cys His Gly Tyr Asp Arg Ala Pro Cys
1               5

<210> SEQ ID NO 645
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 645

Cys Phe Ala Pro Ala Asp Gln Ala Cys
1               5

<210> SEQ ID NO 646
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 646

Cys Ile Pro Ser Arg Phe Ile Thr Cys
1               5

<210> SEQ ID NO 647
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 647

Cys His Gly His Thr Lys Leu Ala Cys
1               5

<210> SEQ ID NO 648
<211> LENGTH: 9
<212> TYPE: PRT
<213> ORGANISM: Artificial
<220> FEATURE:
<223> OTHER INFORMATION: synthetic TGF-binding peptide

<400> SEQUENCE: 648

Cys Asn Gly Lys Ser Lys Leu Ala Cys

-continued

<210> SEQ ID NO 649
<211> LENGTH: 15
<212> TYPE: PRT
<213> ORGANISM: Glycine max

<400> SEQUENCE: 649

Asp Asp Glu Ser Ser Lys Pro Cys Cys Asp Gln Cys Ala Cys Thr
1               5                   10                  15

<210> SEQ ID NO 650
<211> LENGTH: 15
<212> TYPE: PRT
<213> ORGANISM: Glycine max

<400> SEQUENCE: 650

Ser Ser Lys Pro Cys Cys Asp Gln Cys Ala Cys Thr Lys Ser Asn
1               5                   10                  15

<210> SEQ ID NO 651
<211> LENGTH: 15
<212> TYPE: PRT
<213> ORGANISM: Glycine max

<400> SEQUENCE: 651

Pro Cys Cys Asp Gln Cys Ala Cys Thr Lys Ser Asn Pro Pro Gln
1               5                   10                  15

<210> SEQ ID NO 652
<211> LENGTH: 15
<212> TYPE: PRT
<213> ORGANISM: Glycine max

<400> SEQUENCE: 652

Asp Gln Cys Ala Cys Thr Lys Ser Asn Pro Pro Gln Cys Arg Cys
1               5                   10                  15

<210> SEQ ID NO 653
<211> LENGTH: 15
<212> TYPE: PRT
<213> ORGANISM: Glycine max

<400> SEQUENCE: 653

Ala Cys Thr Lys Ser Asn Pro Pro Gln Cys Arg Cys Ser Asp Met
1               5                   10                  15

<210> SEQ ID NO 654
<211> LENGTH: 15
<212> TYPE: PRT
<213> ORGANISM: Glycine max

<400> SEQUENCE: 654

Lys Ser Asn Pro Pro Gln Cys Arg Cys Ser Asp Met Arg Leu Asn
1               5                   10                  15

<210> SEQ ID NO 655
<211> LENGTH: 15
<212> TYPE: PRT
<213> ORGANISM: Glycine max

<400> SEQUENCE: 655

Pro Pro Gln Cys Arg Cys Ser Asp Met Arg Leu Asn Ser Cys His
1               5                   10                  15

```
<210> SEQ ID NO 656
<211> LENGTH: 15
<212> TYPE: PRT
<213> ORGANISM: Glycine max

<400> SEQUENCE: 656

Cys Arg Cys Ser Asp Met Arg Leu Asn Ser Cys His Ser Ala Cys
1               5                   10                  15

<210> SEQ ID NO 657
<211> LENGTH: 15
<212> TYPE: PRT
<213> ORGANISM: Glycine max

<400> SEQUENCE: 657

Ser Asp Met Arg Leu Asn Ser Cys His Ser Ala Cys Lys Ser Cys
1               5                   10                  15

<210> SEQ ID NO 658
<211> LENGTH: 15
<212> TYPE: PRT
<213> ORGANISM: Glycine max

<400> SEQUENCE: 658

Arg Leu Asn Ser Cys His Ser Ala Cys Lys Ser Cys Ile Cys Ala
1               5                   10                  15

<210> SEQ ID NO 659
<211> LENGTH: 15
<212> TYPE: PRT
<213> ORGANISM: Glycine max

<400> SEQUENCE: 659

Ser Cys His Ser Ala Cys Lys Ser Cys Ile Cys Ala Leu Ser Tyr
1               5                   10                  15

<210> SEQ ID NO 660
<211> LENGTH: 15
<212> TYPE: PRT
<213> ORGANISM: Glycine max

<400> SEQUENCE: 660

Ser Ala Cys Lys Ser Cys Ile Cys Ala Leu Ser Tyr Pro Ala Gln
1               5                   10                  15

<210> SEQ ID NO 661
<211> LENGTH: 15
<212> TYPE: PRT
<213> ORGANISM: Glycine max

<400> SEQUENCE: 661

Lys Ser Cys Ile Cys Ala Leu Ser Tyr Pro Ala Gln Cys Phe Cys
1               5                   10                  15

<210> SEQ ID NO 662
<211> LENGTH: 15
<212> TYPE: PRT
<213> ORGANISM: Glycine max

<400> SEQUENCE: 662

Ile Cys Ala Leu Ser Tyr Pro Ala Gln Cys Phe Cys Val Asp Ile
1               5                   10                  15

<210> SEQ ID NO 663
```

```
<211> LENGTH: 15
<212> TYPE: PRT
<213> ORGANISM: Glycine max

<400> SEQUENCE: 663

Leu Ser Tyr Pro Ala Gln Cys Phe Cys Val Asp Ile Thr Asp Phe
1               5                   10                  15

<210> SEQ ID NO 664
<211> LENGTH: 15
<212> TYPE: PRT
<213> ORGANISM: Glycine max

<400> SEQUENCE: 664

Pro Ala Gln Cys Phe Cys Val Asp Ile Thr Asp Phe Cys Tyr Glu
1               5                   10                  15

<210> SEQ ID NO 665
<211> LENGTH: 15
<212> TYPE: PRT
<213> ORGANISM: Glycine max

<400> SEQUENCE: 665

Cys Phe Cys Val Asp Ile Thr Asp Phe Cys Tyr Glu Pro Cys Lys
1               5                   10                  15

<210> SEQ ID NO 666
<211> LENGTH: 15
<212> TYPE: PRT
<213> ORGANISM: Glycine max

<400> SEQUENCE: 666

Val Asp Ile Thr Asp Phe Cys Tyr Glu Pro Cys Lys Pro Ser Glu
1               5                   10                  15

<210> SEQ ID NO 667
<211> LENGTH: 15
<212> TYPE: PRT
<213> ORGANISM: Glycine max

<400> SEQUENCE: 667

Thr Asp Phe Cys Tyr Glu Pro Cys Lys Pro Ser Glu Asp Asp Lys
1               5                   10                  15

<210> SEQ ID NO 668
<211> LENGTH: 15
<212> TYPE: PRT
<213> ORGANISM: Glycine max

<400> SEQUENCE: 668

Phe Cys Tyr Glu Pro Cys Lys Pro Ser Glu Asp Asp Lys Glu Asn
1               5                   10                  15

<210> SEQ ID NO 669
<211> LENGTH: 305
<212> TYPE: PRT
<213> ORGANISM: Bacillus subtilis

<400> SEQUENCE: 669

Asp Asp Tyr Ser Val Val Glu Glu His Gly Gln Leu Ser Ile Ser Asn
1               5                   10                  15

Gly Glu Leu Val Asn Glu Arg Gly Glu Gln Val Gln Leu Lys Gly Met
                20                  25                  30

Ser Ser His Gly Leu Gln Trp Tyr Gly Gln Phe Val Asn Tyr Glu Ser
```

```
                35                  40                  45
Met Lys Trp Leu Arg Asp Asp Trp Gly Ile Thr Val Phe Arg Ala Ala
     50                  55                  60

Met Tyr Thr Ser Ser Gly Gly Tyr Ile Asp Asp Pro Ser Val Lys Glu
 65                  70                  75                  80

Lys Val Lys Glu Thr Val Glu Ala Ala Ile Asp Leu Gly Ile Tyr Val
                 85                  90                  95

Ile Ile Asp Trp His Ile Leu Ser Asp Asn Asp Pro Asn Ile Tyr Lys
                100                 105                 110

Glu Glu Ala Lys Asp Phe Phe Asp Glu Met Ser Glu Leu Tyr Gly Asp
            115                 120                 125

Tyr Pro Asn Val Ile Tyr Glu Ile Ala Asn Glu Pro Asn Gly Ser Asp
        130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Ala Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Asn Pro Thr Gly Gly Trp Thr Glu Ala Glu
        275                 280                 285

Leu Ser Pro Ser Gly Thr Phe Val Arg Glu Lys Ile Arg Glu Ser Ala
    290                 295                 300

Ser
305

<210> SEQ ID NO 670
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 670

Arg Thr Gln Pro Tyr Pro Leu
1               5

<210> SEQ ID NO 671
<211> LENGTH: 7
<212> TYPE: PRT
<213> ORGANISM: Artificial
<220> FEATURE:
<223> OTHER INFORMATION: synthetic FGF-binding peptide

<400> SEQUENCE: 671

Thr Trp Ile Asp Ser Thr Pro
1               5
```

-continued

<210> SEQ ID NO 672
<211> LENGTH: 8
<212> TYPE: PRT
<213> ORGANISM: Artificial
<220> FEATURE:
<223> OTHER INFORMATION: synthetic TGF-binding peptide

<400> SEQUENCE: 672

Pro Glu Asn Ile Asn Val Leu Pro
1 5

<210> SEQ ID NO 673
<211> LENGTH: 7
<212> TYPE: PRT
<213> ORGANISM: Artificial
<220> FEATURE:
<223> OTHER INFORMATION: synthetic TGF-binding peptide

<400> SEQUENCE: 673

Lys His Asn Val Asp Trp Leu
1 5

<210> SEQ ID NO 674
<211> LENGTH: 8
<212> TYPE: PRT
<213> ORGANISM: Artificial
<220> FEATURE:
<223> OTHER INFORMATION: synthetic TGF-binding peptide

<400> SEQUENCE: 674

Trp Thr Gln His Ile His Asn Cys
1 5

<210> SEQ ID NO 675
<211> LENGTH: 7
<212> TYPE: PRT
<213> ORGANISM: Glycine max

<400> SEQUENCE: 675

Ala Leu Ser Tyr Pro Ala Gln
1 5

<210> SEQ ID NO 676
<211> LENGTH: 7
<212> TYPE: PRT
<213> ORGANISM: Artificial
<220> FEATURE:
<223> OTHER INFORMATION: synthetic VEGF binding protein

<400> SEQUENCE: 676

Tyr Asn Leu Tyr Gly Trp Thr
1 5

<210> SEQ ID NO 677
<211> LENGTH: 63
<212> TYPE: PRT
<213> ORGANISM: Artificial
<220> FEATURE:
<223> OTHER INFORMATION: synthetic BBdb-AV sequence

<400> SEQUENCE: 677

Pro Ser Glu Ser Ser Lys Pro Cys Cys Asp Gln Cys Ala Cys Thr Lys
1 5 10 15

Ser Ile Pro Pro Gln Cys Arg Cys Thr Asp Val Arg Leu Asn Ser Cys
20 25 30

His Ser Ala Cys Ser Ser Cys Ala Cys Tyr Asn Leu Tyr Gly Trp Thr
        35                  40                  45
Cys Val Cys Val Asp Met Lys Asp Phe Cys Tyr Glu Pro Cys Lys
    50                  55                  60

<210> SEQ ID NO 678
<211> LENGTH: 66
<212> TYPE: PRT
<213> ORGANISM: Artificial
<220> FEATURE:
<223> OTHER INFORMATION: synthetic MM007-PT-BBIt-FGF-5

<400> SEQUENCE: 678

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Arg Thr Gln Pro Tyr Pro Leu
        35                  40                  45

Cys Phe Cys Val Asp Ile Thr Asp Phe Cys Tyr Glu Pro Cys Lys Pro
    50                  55                  60

Ser Glu
65

<210> SEQ ID NO 679
<211> LENGTH: 66
<212> TYPE: PRT
<213> ORGANISM: Artificial
<220> FEATURE:
<223> OTHER INFORMATION: synthetic FGFps2-PT-BBIt-FGF5

<400> SEQUENCE: 679

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Thr Trp Ile Asp Ser Thr Pro
        35                  40                  45

Cys Phe Cys Val Asp Ile Thr Asp Phe Cys Tyr Glu Pro Cys Lys Pro
    50                  55                  60

Ser Glu
65

<210> SEQ ID NO 680
<211> LENGTH: 67
<212> TYPE: PRT
<213> ORGANISM: Artificial
<220> FEATURE:
<223> OTHER INFORMATION: synthetic PEN3-PT-BBIt-TGFBI

<400> SEQUENCE: 680

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Pro Glu Asn Ile Asn Val Leu
        35                  40                  45

Pro Cys Phe Cys Val Asp Ile Thr Asp Phe Cys Tyr Glu Pro Cys Lys
    50                  55                  60

Pro Ser Glu

<210> SEQ ID NO 681
<211> LENGTH: 68
<212> TYPE: PRT
<213> ORGANISM: Artificial
<220> FEATURE:
<223> OTHER INFORMATION: synthetic WTQ-PT-TGFBI

<400> SEQUENCE: 681

```
Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Trp Thr Gln His Ile His Asn
        35                  40                  45

Cys Phe Cys Phe Cys Val Asp Ile Thr Asp Phe Cys Tyr Glu Pro Cys
    50                  55                  60

Lys Pro Ser Glu
65
```

<210> SEQ ID NO 682
<211> LENGTH: 66
<212> TYPE: PRT
<213> ORGANISM: Artificial
<220> FEATURE:
<223> OTHER INFORMATION: synthetic MM0021W-PT-TGFBI

<400> SEQUENCE: 682

```
Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Lys His Asn Val Asp Trp Leu
        35                  40                  45

Cys Phe Cys Val Asp Ile Thr Asp Phe Cys Tyr Glu Pro Cys Lys Pro
    50                  55                  60

Ser Glu
65
```

<210> SEQ ID NO 683
<211> LENGTH: 67
<212> TYPE: PRT
<213> ORGANISM: Artificial
<220> FEATURE:
<223> OTHER INFORMATION: synthetic BBsb3-AV sequence

<400> SEQUENCE: 683

```
Asp Asp Glu Tyr Ser Lys Pro Cys Cys Asp Leu Cys Met Cys Thr Arg
1               5                   10                  15

Ser Met Pro Pro Gln Cys Ser Cys Glu Asp Ile Arg Leu Asn Ser Cys
            20                  25                  30

His Ser Asp Cys Lys Ser Cys Ala Cys Tyr Asn Leu Tyr Gly Trp Thr
        35                  40                  45

Cys Arg Cys Leu Asp Thr Asn Asp Phe Cys Tyr Lys Pro Cys Lys Ser
    50                  55                  60

Arg Asp Asp
65
```

<210> SEQ ID NO 684

-continued

```
<211> LENGTH: 63
<212> TYPE: PRT
<213> ORGANISM: Artificial
<220> FEATURE:
<223> OTHER INFORMATION: synthetic BBtc-AV sequence

<400> SEQUENCE: 684

Ser Ser Lys Trp Glu Ala Cys Cys Asp Arg Cys Ala Cys Thr Lys Ser
1               5                   10                  15

Ile Pro Pro Gln Cys His Cys Ala Asp Ile Arg Leu Asn Ser Cys His
                20                  25                  30

Ser Ala Cys Glu Ser Cys Ala Cys Tyr Asn Leu Tyr Gly Trp Thr Cys
            35                  40                  45

Arg Cys Phe Asp Ile Thr Asp Phe Cys Tyr Lys Pro Cys Ser Gly
        50                  55                  60

<210> SEQ ID NO 685
<211> LENGTH: 10
<212> TYPE: PRT
<213> ORGANISM: Glycine max

<400> SEQUENCE: 685

Ile Cys Ala Leu Ser Tyr Pro Ala Gln Cys
1               5                   10
```

PERSONAL CARE COMPOSITIONS COMPRISING MODIFIED VARIANT BOWMAN BIRK PROTEASE INHIBITORS

FIELD OF THE INVENTION

The present invention relates to compositions that comprise modified variant Bowman Birk Protease Inhibitor proteins (BBPIs). The modified variant BBPIs comprise peptides that bind target proteins, and that are further modified to have greater protease inhibitory activity and/or be produced at greater yields than the unmodified BBPIs. The invention encompasses the compositions comprising the modified variant BBPIs, and the methods for making and using the compositions in personal care.

BACKGROUND OF THE INVENTION

Proteases are involved in a wide variety of biological processes. Disruption of the balance between proteases and protease inhibitors is often associated with pathologic tissue destruction.

Various studies have focused on the role of proteases in tissue injury, and it is thought that the balance between proteinases and proteinase inhibitors is a major determinant in maintaining tissue integrity. Serine proteinases from inflammatory cells, including neutrophils, are implicated in various inflammatory disorders, such as pulmonary emphysema, arthritis, atopic dermatitis and psoriasis. These and other inflammatory conditions are often associated with dysregulated levels of cytokines.

Proteases also degrade the vascular basement membrane and participate in the remodeling of the extracellular matrix to facilitate cell migration and invasion to promote tumor angiogenesis. Proteases release angiogenic growth factors bound to the extracellular matrix and to generate chemotactically active fragments derived from extracellular matrix components, which in turn exert chemotactic and mitogenic, modulatory activates on endothelial cells, smooth muscle cells and fibroblasts to participate in angiogenic processes. The list of protein factors angiogenically active in vivo includes fibroblast growth factors, Angiogenin, Angiopoietin-1, EGF, HGF, NPY, VEGF, TNF-alpha, TGF-beta, PD-ECGF, PDGF, IGF, IL8, and Growth hormone. Risks associated with current cytokine blocking agents include serious infections, anaphylaxis, and lupus-like syndrome. In addition, there is observed loss of clinical benefit after the drugs are stopped, and a small proportion of patients develop antibodies to the biological agents, which is likely to limit their efficacy with repeated use.

Synthetic and natural protease inhibitors have been shown to inhibit tumor promotion in vivo and in vitro. Previous research investigations have indicated that certain protease inhibitors belonging to a family of structurally-related proteins classified as serine protease inhibitors or SERPINS, are known to inhibit several proteases including trypsin, cathepsin G, thrombin, tissue kallikrein, as well as neutrophil elastase. The SERPINS are extremely effective at preventing/suppressing carcinogen-induced transformation in vitro and carcinogenesis in animal model systems. Systemic delivery of purified protease inhibitors reduces joint inflammation and cartilage and bone destruction as well.

Topical administration of protease inhibitors finds use in such conditions as atopic dermatitis, a common form of inflammation of the skin, which may be localized to a few patches or involve large portions of the body. The depigmenting activity of protease inhibitors and their capability to prevent ultraviolet-induced pigmentation have been demonstrated both in vitro and in vivo. Paine et al., Journal of Investigative Dermatology 116:587-595 [2001]. Also, protease inhibitors have been found to help wound healing (http://www.sciencedaily.com/releases/2000/10/001002071718.htm). Secretory leukocyte protease inhibitor was demonstrated to reverse the tissue destruction and speed the wound healing process when applied topically. In addition, serine protease inhibitors can also help to reduce pain in lupus erythematosus patients (See U.S. Pat. No. 6,537,968).

Naturally occurring protease inhibitors can be found in a variety of foods such as cereal grains (oats, barley, and maize), Brussels sprouts, onion, beetroot, wheat, finger millet, and peanuts. One source of interest is the soybean. The average level in soybeans is around 1.4 percent and 0.6 percent for Kunitz and Bowman-Birk respectively, two of the most important protease inhibitors. These low levels make it impractical to isolate the natural protease inhibitor for clinical applications.

Thus, there is a need for a method to produce large quantities of protease inhibitors that have desired characteristics of protein therapeutics, and for compositions that effectively deliver the protease inhibitor in a usable form.

The compositions and methods according to the invention fulfill some of the above needs and in particular offer an advantage in providing protease inhibitors that specifically target the activity of cytokines involved in pathologic and non-pathologic processes.

SUMMARY OF THE INVENTION

The present invention relates to compositions that comprise modified variant Bowman Birk Protease Inhibitor proteins (BBPIs). The modified variant BBPIs comprise peptides that bind target proteins, and that are further modified to have greater protease inhibitory activity and/or be produced at greater yields than the unmodified BBPIs. The invention encompasses the compositions comprising the modified variant BBPIs, and the methods for making and using the compositions in personal care.

In one embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a binding peptide that is chosen from a vascular endothelial growth factor (VEGF) binding peptide, a fibroblast growth factor-5 (FGF5) binding peptide, a transforming growth factor β (TGFβ) binding peptide and a tumor necrosis factor α (TNFα) variant peptide. In some embodiments, the modified variant BBPI binds a target protein chosen from VEGF, FGF5, TGFβ and TNFα. In some embodiments, the BBPI scaffold is chosen from BBI (SEQ ID NO:13), BBIt (SEQ ID NO:185), BBI-AV (SEQ ID NO:186), BBIt-AV (SEQ ID NO:187), BBIt-VEGK (SEQ ID NO:640), BBIt-VEGT (SEQ ID NO:641), BBIt-VEGKD (SEQ ID NO:642), BBdb (SEQ ID NO:449), BBsb3 (SEQ ID NO:450), BBtc (SEQ ID NO:451), BBdb-AV (SEQ ID NO:452), BBsb3-AV (SEQ ID NO:453) and BBtc-AV (SEQ ID NO:454).

In other embodiments, the modified variant BBPI of the invention comprises a combination of amino acid substitutions chosen from the following combinations: 50T-52A, 25L-50T-52A, 29P-50T-52A, 40K-50T-52A, 13I-25L-50T-52A, 13I-29P-50T-52A, 13I-40K-50T-52A, 25L-29P-50T-

52A, 25L-40K-50T-52A, 29P-40K-50T-52A, 13I-25K-29P-52K, 13I-25L-29P-50T-52A, 13I-29P-40K-50T-52A, 13I-25K-40K-50T-52A, 25L-29P-40K-50T-52A, 13L-29P-40K-50T-52A, 13I-29K-40K-50T-52A, 13I-29P-40K-50K-52A, 13I-29P-40K-50T-52A, 13I-25L-29P-40K-50T-52A, D1C-13I-29P-40K-50T-52A, S4V-13I-29P-40K-50T-52A, S5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, 13I-29P-40K-50T-52A-65E, 13L-25R-29P-31A-40K-50T-52A, 13L-25R-29P-31R-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q.

In another embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding binding peptide that is chosen from the following VEGF-binding peptides: ACYNLYGWTC (SEQ ID NO:9), KYYLYWW (SEQ ID NO:458), TLWKSYW (SEQ ID NO:459), DLYWW (SEQ ID NO:460), SKHSQIT (SEQ ID NO:468) KTNPSGS (SEQ ID NO:469) RPTGHSL (SEQ ID NO:470), KHSAKAE (SEQ ID NO:471) KPSSASS (SEQ ID NO:472), PVTKRVH (SEQ ID NO:473), TLHWWVT (SEQ ID NO:492), PYKASFY (SEQ ID NO:493), PLRTSHT (SEQ ID NO:494), EATPROT (SEQ ID NO:495), NPLHTLS (SEQ ID NO:496), KHERIWS (SEQ ID NO:497), ATNPPPM (SEQ ID NO:498), STTSPNM (SEQ ID NO:499), ADRSFRY (SEQ ID NO:500), PKADSKQ (SEQ ID NO:501), PNQSHLH (SEQ ID NO:502), SGSETWM (SEQ ID NO:503), ALSAPYS (SEQ ID NO:504), KMPTSKV (SEQ ID NO:505), ITPKRPY (SEQ ID NO:506), KWIVSET (SEQ ID NO:507), PNANAPS (SEQ ID NO:508), NVQSLPL (SEQ ID NO:509), TLWPTFW (SEQ ID NO:510), NLWPHFW (SEQ ID NO:511), SLWPAFW (SEQ ID NO:512), SLWPHFW (SEQ ID NO:513), APWNSHI (SEQ ID NO:514), APWNLHI (SEQ ID NO:515), LPSWHLR (SEQ ID NO:516), PTILEWY (SEQ ID NO:517), TLYPQFW (SEQ ID NO:518), HLAPSAV (SEQ ID NO:519), KYYLSWW (SEQ ID NO:520), WYTLYKW (SEQ ID NO:521), TYRLYWW (SEQ ID NO:522), RYSLYYW (SEQ ID NO:523), YYLYYWK (SEQ ID NO:524), NYQLYGW (SEQ ID NO:525), TKWPSYW (SEQ ID NO:226), TLWKSYW (SEQ ID NO:527), PLWPSYW (SEQ ID NO:528), RLWPSYW (SEQ ID NO:529), TLWPKYW (SEQ ID NO:530), KYDLYWW (SEQ ID NO:531), RYDLYWW (SEQ ID NO:532), DYRLYWW (SEQ ID NO:533), DYKLYWW (SEQ ID NO:534), EYKLYWW (SEQ ID NO:535), and RYPLYWW (SEQ ID NO:536).

In another embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a FGF-binding binding peptide that is chosen from the following FGF-binding peptides: CACRTQPYPLCF (MM007; SEQ ID NO:430), CICTWID-STPC (PS2; SEQ ID NO:431), CYGLPFTRC (SEQ ID NO:537), CEEIWTMLC (SEQ ID NO:538), CWALTVKTC (SEQ ID NO:539), CLTVLWTTC (SEQ ID NO:540), CTLWNRSPC (SEQ ID NO:541), CHYLLTNYC (SEQ ID NO:542), CRIHLAHKC (SEQ ID NO:543), TNIDSTP (SEQ ID NO:544), HLQTTET (SEQ ID NO:545), SLNNLTV (SEQ ID NO:546), TNIDSTP (SEQ ID NO:547), TNIDSTP (SEQ ID NO:548), LRILANK (SEQ ID NO:549), LLTPTLN (SEQ ID NO:550), ALPTHSN (SEQ ID NO:551), TNIDSTP (SEQ ID NO:552), LCRRFEN (SEQ ID NO:553), TNIDSTP (SEQ ID NO:554), TNIDSTP (SEQ ID NO:555), HLQTTET (SEQ ID NO:556), PLGLCPP (SEQ ID NO:557), GYFIPSI (SEQ ID NO:558), TKIDSTP (SEQ ID NO:559), HLQTTET (SEQ ID NO:560), WNIDSTP (SEQ ID NO:561), TWIDWTP (SEQ ID NO:562), RTQPYPL (SEQ ID NO:670) and TWIDSTP (SEQ ID NO:671).

In another embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding binding peptide that is chosen from the following TGF-binding peptides: CLCPENINVLPCN (PEN3; SEQ ID NO:436), CICKHNVDWLCF (MMO21W; SEQ ID NO:437), CICWTQHIHNCF (WTQ; SEQ ID NO:438), CVTTDWIEC (SEQ ID NO:563), CYYSQFHQC (SEQ ID NO:564), CPTLWTHMC (SEQ ID NO:565), QSACIVYYVGRKP-KVECASSD (SEQ ID NO:566), QSACILYYIGKTPK-IECASSD (SEQ ID NO:567), QSACILYYVGRTPKVE-CASSD (SEQ ID NO:568), acetyl-LCPENDNVSPCY-cohn2 (SEQ ID NO:569), KHNVRLL (SEQ ID NO:570), NDTPSYF (SEQ ID NO:571), AKLYAGS (SEQ ID NO:572), RGPAHSL (SEQ ID NO:573), NSLAERR (SEQ ID NO:574), HPLASPH (SEQ ID NO:575), QPWNKLK (SEQ ID NO:576), AWLr/Mipy (SEQ ID NO:577), PTK-PAQQ (SEQ ID NO:578), PSLNRPQ (SEQ ID NO:579), HHARQEW (SEQ ID NO:580), RHHTPGP (SEQ ID NO:581), ASAINPH (SEQ ID NO:582), CHGYDRAPC (SEQ ID NO:644), CFAPADQAC (SEQ ID NO:645), CIPSRFITC (SEQ ID NO:646), CHGHTKLAC (SEQ ID NO:647), CNGKSKLAC (SEQ ID NO:648), PENINVLP (SEQ ID NO:672), KHNVDWL (SEQ ID NO:673) and WTQHIHNC (SEQ ID NO:674).

In another embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding binding peptide that is chosen from the following TNF-binding peptides: RYWQDIP (T1; SEQ ID NO:474), APEPILA (T2; SEQ ID NO:475), DMIMVSI (T3; SEQ ID NO:476), WTPKPTQ (SEQ ID NO:583), ATFPNQS (SEQ ID NO:584), ASTVGGL (SEQ ID NO:585), TMLPYRP (SEQ ID NO:586), AWHSPSV (SEQ ID NO:587), TQSFSS (SEQ ID NO:588), THKNTLR (SEQ ID NO:589), GQTHFHV (SEQ ID NO:590), LPILTQT (SEQ ID NO:591), SILPVSH (SEQ ID NO:592), SQPIPI (SEQ ID NO:593), and QPLRKLP (SEQ ID NO:594).

In another embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a binding peptide that is chosen from a vascular endothelial growth factor (VEGF) binding peptide, a fibroblast growth factor-5 (FGF5) binding peptide, a transforming growth factor β (TGFβ) binding peptide and a tumor necrosis factor α (TNFα) variant peptide, and that is present in an amount ranging from about 0.0001% to about 5% by weight based on the total weight of the composition. In some embodiments, the modified variant BBPI comprised in the personal care composition of the invention, has greater trypsin inhibitory activity and production yield than the corresponding unmodified precursor variant inhibitor of said BBPI.

In other embodiments, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding peptide that is chosen from SEQ ID NOS:9, 458, 459, 460, 468, 469, 470, 471, 472 and 473. In some embodiments, the scaffold of the modified variant BBPI is the BBIt-AV of SEQ ID NO:187. In other embodiments, the modified variant BBPI comprised in the personal care composition of the invention comprises a combination of amino acid substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the personal care composition comprises a VEGF-binding BBPI (VEGF-BBPI) that is chosen from SEQ ID NOS: 601, 602, 627, 628, 630, 631, 643, 491, 632, 633, 634, 635, and 636. In some embodiments, the personal care composition is a skin care composition selected from the group consisting of skin creams, lotions, sprays, emulsions, colloidal suspensions, foams, aerosols, liquids, gels, sera, and solids. In other embodiments, the skin care composition is chosen from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, sunscreens, dipilatories, hair growth inhibitors and radioprotectives. Typically, the radioprotective is a sunscreen that is chosen from non-water-resistant sunscreens, very water-resistant sunscreens, and water-in-silicone sunscreens. The skin care compositions may optionally include topically applied over-the-counter compositions, anti-fungal treatments, anti-acne treatments, skin protectants, sunscreens, deodorants, and antiperspirants. In some embodiments, the cosmetic compositions of the invention comprise at least one pigment. Such cosmetic compositions include pressed powder formulations, and foundations. Cosmetic foundation compositions can be chosen from water-in-oil foundations, water-in-silicone foundations, oil-in-water foundations, anhydrous makeup sticks, and cream-to-powder foundations.

In other embodiments, the invention provides for a skin care composition for treating an angiogenic skin disorder. Said skin care composition comprises a Bowman Birk Protease Inhibitor (BBPI) having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding peptide that is chosen from SEQ ID NOS:9, 458, 459, 460, 468, 469, 470, 471, 472 and 473.

In other embodiments, the personal care composition is used for improving the appearance and/or condition of skin in a subject suffering from a skin disorder chosen from psoriasis, scleroderma, venous ulcers, acne, rosacea, warts, eczema, hemangiomas and lymphangiogenesis.

In other embodiments, the invention provides for a skin care composition for treating an angiogenic skin disorder. The skin care composition comprises a Bowman Birk Protease Inhibitor (BBPI) having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding peptide that is chosen from SEQ ID NOS:9, 458, 459, 460, 468, 469, 470, 471, 472 and 473. The hair care composition can be in the form of shampoos, conditioners, hair styling compositions, hair colorants, permanent wave formulations, creams, gels, mousses, sprays, emulsions, colloidal suspensions, liquids, foams, and solids. In some embodiments, the hair care composition may also include a radiopretective. Examples of radioprotectives include sunscreens selected from non-water-resistant sunscreens, very water-resistant sunscreens, and water-in-silicone sunscreens. The hair care composition can be used to prevent hair growth.

In other embodiments, the invention provides for a method for inhibiting hair growth by providing a personal composition that comprises a BBPI having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding peptide that is chosen from SEQ ID NOS:9, 458, 459, 460, 468, 469, 470, 471, 472 and 473; and applying the composition to a subject in an area where inhibition of hair growth is desired. For example, the composition can be applied to inhibit facial hair, underarm hair, leg hair, torso hair, arm hair and head hair growth. In some embodiments, the method uses a personal care composition that comprises a VEGF-BBPI chosen from SEQ ID NOS: 601, 602, 627, 628, 630, 631, 643, 491, 632, 633, 634, 635, and 636.

In other embodiments, the invention provides a method for improving the appearance and/or condition of the skin of a subject suffering from an angiogenic skin disorder by providing a personal composition that comprises a BBPI having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a VEGF-binding peptide that is chosen from SEQ ID NOS:9, 458, 459, 460, 468, 469, 470, 471, 472 and 473; and applying the composition to the skin of the subject. The angiogenic skin disorder can be chosen from psoriasis, scleroderma, venous ulcers, acne, rosacea, warts, eczema, hemangiomas and lymphangiogenesis. In some embodiments, the method uses a personal care composition that comprises a VEGF-BBI chosen from SEQ ID NOS:601, 602, 627, 628, 630, 631, 643, 491, 632, 633, 634, 635, and 636.

In other embodiments, the invention provides a personal care composition that comprises a Bowman Birk Protease Inhibitor (BBPI) having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of the BBPI is a an FGF-binding peptide chosen from SEQ ID NOS: 430 and 431. In some embodiments, the scaffold of the BBPI is the BBIt-AV of SEQ ID NO:187. In other embodiments, the modified variant BBPI comprised in the personal care composition of the invention comprises a combination of amino acid substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the personal care composition comprises modified variant BBPI that is an FGF-binding BBPI (FGF-BBPI) is chosen from SEQ ID NOS:432 and 434.

In some embodiments, the invention provides for a hair care composition comprising a Bowman Birk Protease Inhibitor (BBPI) having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of the BBPI is a an FGF-binding peptide chosen from SEQ ID NOS: 430 and 431. The hair care composition can be in the form of shampoos, conditioners, hair styling compositions, hair colorants, permanent wave formulations, creams, gels, mousses, sprays, emulsions, colloidal suspensions, liquids, foams, and solids. In some embodiments, the hair care composition may also include a radiopretective. Examples of radioprotectives include sunscreens selected from non-water-resistant sunscreens, very water-resistant sunscreens, and water-in-silicone sunscreens. The hair care composition can be used to promote hair growth.

In another embodiment, the invention provides for a method for promoting hair growth by providing a personal care composition that comprises a Bowman Birk Protease Inhibitor (BBPI) having an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of the BBPI is a an FGF-binding peptide chosen from SEQ ID NOS: 430 and 431; and applying the hair composition to a subject in an area where hair growth is desired. For example, the composition can be applied to promote the growth of facial hair, underarm hair, leg hair, torso hair, arm hair and head hair growth. In some embodiments, the hair growth-promoting personal care composition can be used to treat a condition that involves hair loss. For example, conditions that involve hair loss and that can be treated using the hair care composition of the invention include inflammatory alopecias, pseudopelade, scleroderma, tick bites, lichen planus, psoriasis, lupus, seborrheic dermatitis, loose hair syndrome, hemochromatosis, androgenic alopecia, and alopecia greata. In some embodiments, the personal care composition that can be used to promote hair growth comprises an FGF-binding (FGF-BBPI) chosen from SEQ ID NOS:432 and 434.

In another embodiments, the invention the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding peptide that is chosen from SEQ ID NOS:436, 437, 438, 672, 673, and 674. In some embodiments, the scaffold of the BBPI is the BBIt-AV of SEQ ID NO:187. In other embodiments, the modified variant BBPI comprised in the personal care composition of the invention comprises a combination of amino acid substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the personal care composition comprises a modified variant BBPI that is a TGF-binding BBPI (TGF-BBPI) is chosen from SEQ ID NOS:443, 445 and 447. In some embodiments, the personal care composition is capable of promoting hair growth.

In other embodiments, the invention the invention provides for a hair care or a skin care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding peptide that is chosen from SEQ ID NOS:436, 437, 438, 672, 673, and 674. The hair or skin care composition can be in the form of shampoos, conditioners, hair styling compositions, hair colorants, permanent wave formulations, creams, gels, mousses, sprays, emulsions, colloidal suspensions, liquids, foams, and solids. In some embodiments, when the composition is a skin care composition, it can be in the form of moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, sunscreens, and radioprotectives. The skin care composition can optionally further include topically applied over-the-counter compositions, anti-fungal treatments, anti-acne treatments, skin protectants, sunscreens, deodorants, and antiperspirants. The radioprotectives included in the skin or hair care composition are sunscreens that can be selected from non-water-resistant sunscreens, very water-resistant sunscreens, and water-in-silicone sunscreens.

In other embodiments, the invention provides for a cosmetic composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding peptide that is chosen from SEQ ID NOS:436, 437, 438, 672, 673, and 674. Examples of cosmetic compositions include mascaras, eyeliners, pressed powder formulations, and foundations.

In other embodiments, the invention provides for a hair care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding peptide that is chosen from SEQ ID NOS:436, 437, 438, 672, 673, and 674, and that further comprises a radioprotective. Examples of radioprotectives that can be included in the hair care composition are sunscreens such as very water-resistant sunscreens, and water-in-silicone sunscreens. The hair care composition is capable of promoting hair growth.

In another embodiment, the invention provides for a method for promoting hair growth by providing a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding peptide that is chosen from SEQ ID NOS:436, 437, 438, 672, 673, and 674; and applying the composition to a subject in an area where hair growth is desired. For example, the composition can be applied to promote the growth of facial hair, underarm hair, leg hair, torso hair, arm hair and head hair growth. In some embodiments, the hair growth-promoting personal care composition can be used to treat a condition that involves hair loss. For example, conditions that involve hair loss and that can be treated using the hair care composition of the invention include inflammatory alopecias, pseudopelade, scleroderma, tick bites, lichen planus, psoriasis, lupus, seborrheic dermatitis, loose hair syndrome, hemochromatosis, androgenic alopecia, and alopecia greata. In some embodiments, the personal care composition that can be used to promote hair growth comprises a modified variant TGF-BBPI chosen from SEQ ID NOS: 443, 445 and 447.

In another embodiment, the invention provides for a method for improving the appearance and/or condition of the skin of a subject suffering from skin disorder by providing a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TGF-binding peptide that is chosen from SEQ ID NOS:436, 437, 438, 672, 673, and 674; and applying the composition to the subject. In some embodiments, the skin disorders that can be treated with the composition include psoriasis, scleroderma, and skin cancer. In some embodiments, the personal care composition comprises a TGF-BBPI chosen from modified variant TGF-BBPI chosen from SEQ ID NOS:443, 445 and 447.

In another embodiment, the invention provides for a personal care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TNF-binding peptide that is chosen from SEQ ID NOS: 474, 475 and 476. In some embodiments, the scaffold of the BBPI is the BBIt-AV of SEQ ID NO:187. In other embodiments, the modified variant BBPI comprised in the personal care composition of the invention comprises a combination of amino acid substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the personal care composition comprises a modified variant BBPI that is a TNF-BBPI is chosen from SEQ ID NOS:637, 638 and 639. The personal care composition can be used to promote hair growth.

In another embodiment, the invention provides for a hair care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TNF-binding peptide that is chosen from SEQ ID NOS: 474, 475 and 476. In some embodiments, the hair care composition is capable of promoting hair growth in a subject suffering from psoriasis. The hair care composition can be in the form of shampoos, conditioners, hair styling compositions, hair colorants, permanent wave formulations, creams, gels, mousses, sprays, emulsions, colloidal suspensions, liquids, foams, and solids. In some embodiments, the hair care composition further comprises a radioprotective. Examples of radioprotectives include sunscreens such as non-water-resistant sunscreens, very water-resistant sunscreens, and water-in-silicone sunscreens. In some embodiments, the hair care composition is capable of promoting hair growth.

In another embodiment, the invention provides for a skin care composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TNF-binding peptide that is chosen from SEQ ID NOS: 474, 475 and 476. The skin care composition can be used to improve the appearance and/or condition of the skin of a subject suffering from psoriasis or scleroderma. In some embodiments, the skin care composition can be in the form of skin creams, lotions, sprays, emulsions, colloidal suspensions, foams, aerosols, liquids, gels, sera, and solids. Alternatively, the skin care composition is in the form of moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, and radioprotectives. Optionally, the skin care composition further comprises topically applied over-the-counter compositions, anti-fungal treatments, anti-acne treatments, skin protectants, sunscreens, deodorants, and antiperspirants.

In another embodiment, the invention provides for a cosmetic composition that comprises a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TNF-binding peptide that is chosen from SEQ ID NOS: 474, 475 and 476. The cosmetic composition is selected from mascaras, eyeliners, pressed powder formulations, and foundations. In some embodiments, the cosmetic composition is a cosmetic composition that comprises at least one pigment. A cosmetic composition that comprises at least one pigment is a mascara, and the mascara is selected from non-waterproof mascaras, waterproof mascaras, volumizing mascaras, lengthening mascaras, curling mascaras, anhydrous waterproof mascaras, water-based mascaras, and eyelash or eyebrow treatments. In other embodiments, the cosmetic composition is a cosmetic composition selected from a pressed powder formulation selected from loose powders, blushes, eye shadows, and bronzing powders.

In yet other embodiments, the cosmetic composition is a foundation selected from water-in-oil foundations, water-in-silicone foundations, oil-in-water foundations, anhydrous makeup sticks, and cream-to-powder foundations.

In another embodiment, the invention provides for a method for promoting hair growth of a subject suffering from psoriasis that includes the steps of providing a personal care composition comprising a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TNF-binding peptide that is chosen from SEQ ID NOS: 474, 475 and 476; and applying the composition to the subject in an area in which promotion of hair growth is desired.

For example, the composition can be applied to promote the growth of facial hair, underarm hair, leg hair, torso hair, arm hair and head hair growth. In some embodiments, the personal care composition that can be used to promote hair growth comprises a modified TNF-BBPI chosen from SEQ ID NOS: 637, 638 and 639.

In another embodiment, the invention provides for a method for improving the appearance and/or condition of the skin of a subject suffering from psoriasis that includes the steps of providing a personal care composition comprising a modified variant Bowman Birk Protease Inhibitor (BBPI) that comprises an amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, and in which the second protease inhibitory loop of the scaffold of said BBPI is a TNF-binding peptide that is chosen from SEQ ID NOS: 474, 475 and 476; and applying the composition to the skin of the subject. In some embodiments, the method comprises providing a personal care composition that comprises a modified TNF-BBPI chosen from SEQ ID NOS: 637, 638 and 639.

BRIEF DESCRIPTION OF THE DRAWINGS

FIG. 1A-D provides the DNA and amino acid sequences of the aprE-BCE103-BBI-Histag expression cassette (EcoRI-HindIII) cloned into the pJM103 integration vector (SEQ ID NOS:1 and 2).

FIG. 3 provides the DNA and amino acid sequences of 12BBIck81 from the BCE103 fusion site (at the BamHI) to the end of the gene (SEQ ID NOS:3 and 4). The CK37281 peptide sequence (ACYNLYGWTC (SEQ ID NO:9) is inserted into both the trypsin and chymotrypsin inhibitory loops.

In this Figure, 37 C=no additions, BME=2-mercaptoethanol, Cys=cysteine, Glut=reduced glutathione, DTT=dithiothreitol.

Figure 5:
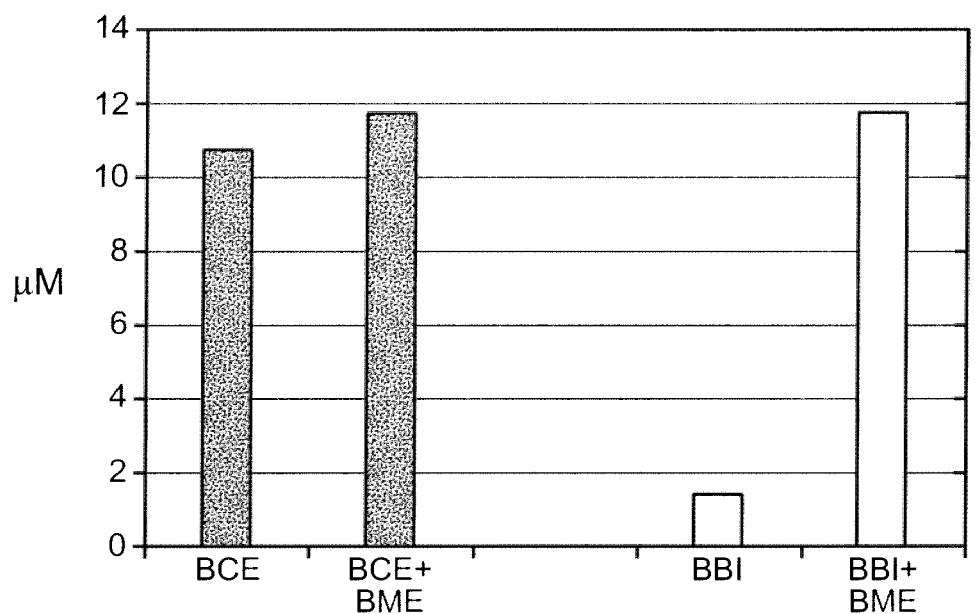

FIG. 5 provides a graph showing the activation of 2BBIck81 with 2-mercaptoethanol (BME) after partial purification of the BCE-Ink2-2BBck81 fusion protein by ion exchange chromatography. The concentrations (□M) of BCE (black bars) and 2BBIck81 (white bars) measured by activity assays are shown before and after treatment with 3 mM 2-mercaptoethanol (BME).

Figure 6:
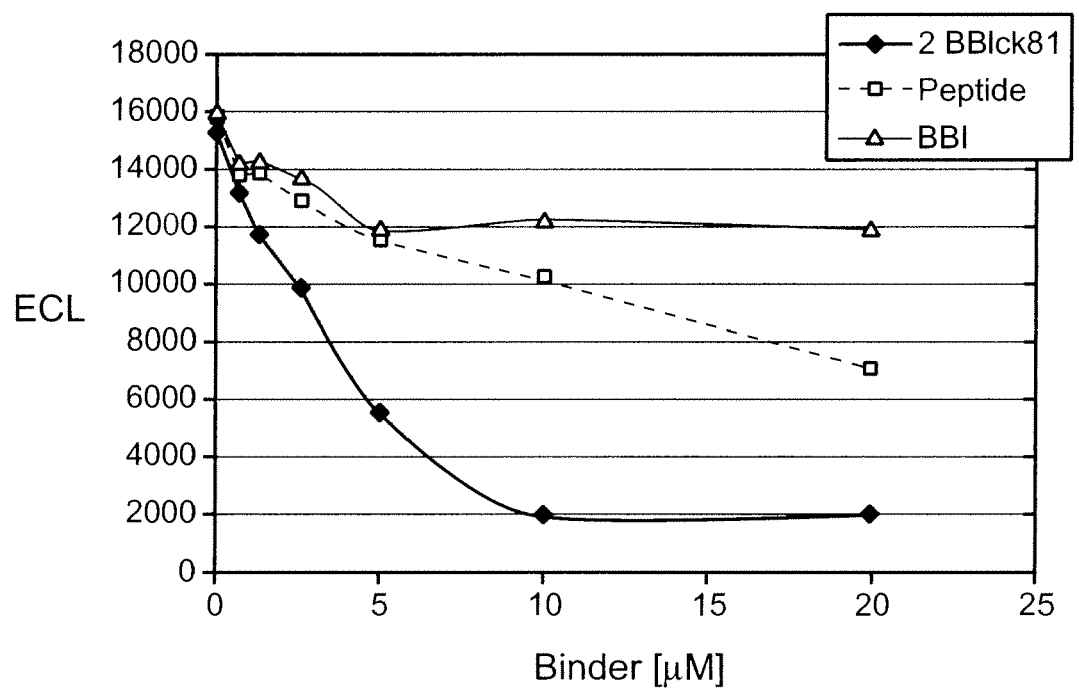

FIG. 6 provides a graph showing results from a competition analysis of 2BBIck81 versus anti-VegF antibody for binding to VegF in a BioVeris assay. The binding competition with the CK37281 peptide is shown for comparison and the binding with the wild-type BBI is included as a negative control.

FIG. 7A-D provides the sequence of the synthetic DNA fragment carrying the H. insolens PDI (hiPDI) that was inserted into the B. subtilis BBI expression vector (using the BssHII and SacI sites), as well as the amino acid sequence (SEQ ID NOS:5 and 6).

FIG. 8A-D provides the DNA and amino acid sequences of the aprE-cutinase expression cassette that was ligated into the EcoRI-BamHI sites of p2JM103-Ink2-2BBIck81 (SEQ ID NOS:7 and 8).

Figure 9:
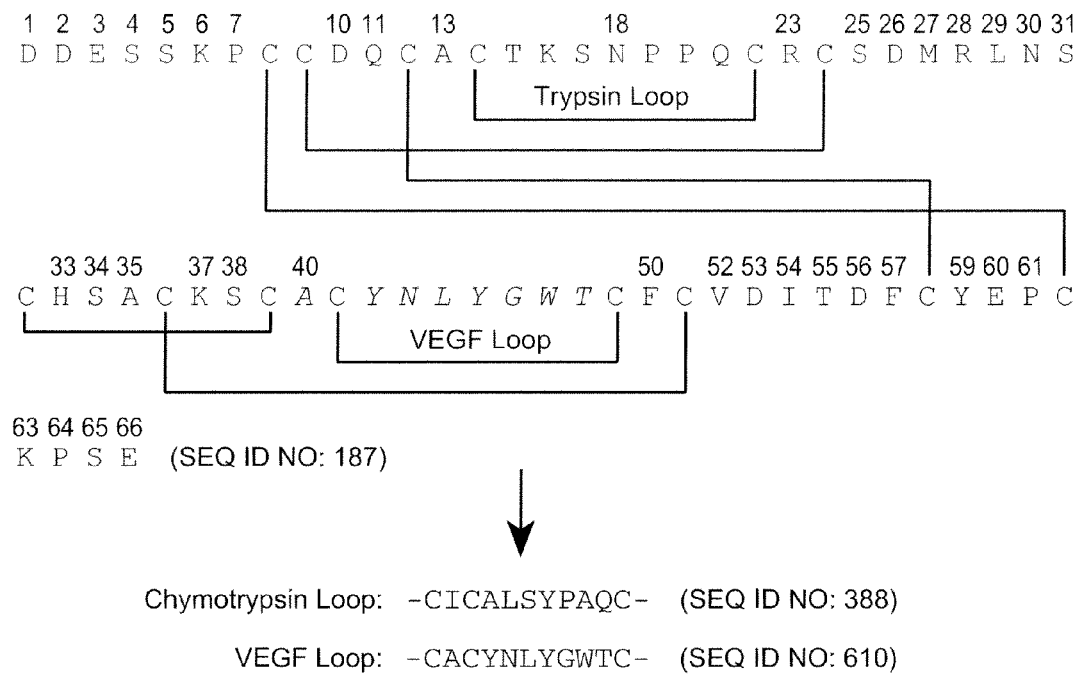

FIG. 9 provides the amino acid sequence of the unmodified BBIt-AV protein (SEQ ID NO:187). Site-saturation libraries were constructed at all the numbered amino acids. The trypsin inhibitory loop and the VEGF binding peptide loop (in italics) are indicated and disulfide bonds are shown by the connecting lines. At the bottom, the sequence of the VEGF binding peptide is compared to the chymotrypsin inhibitory loop in sBBI that it replaces. The downward arrow indicates the potential protease cleavage site between the $P_1$ and $P_1'$ residues of the chymotrypsin reactive site.

Figure 10:
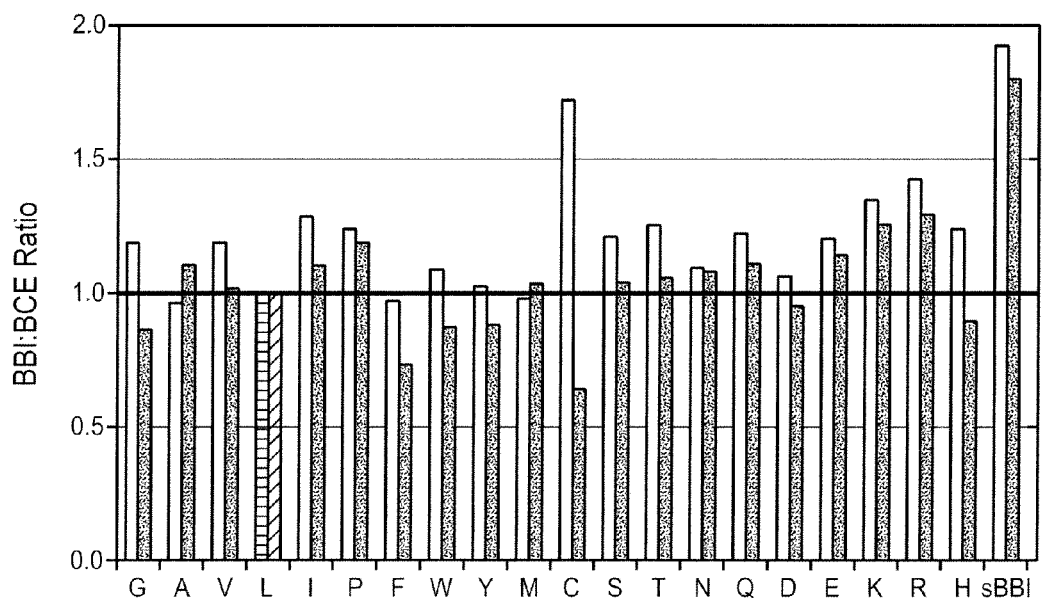

FIG. 10 provides the relative BBI:BCE activity ratios for each amino acid substitution made at position 29. The ratios were averaged from quadruplicate cultures grown in microtiter plates in the absence (white bars) or presence (black bars) of 2-mercaptoethanol. The activity ratios for sBBI are included for comparison as a positive control. The ratios were normalized to the value determined for the wild-type amino acid in BBIt-AV (SEQ ID NO:187) (indicated by a horizontal line), leucine, that is shown in the absence (horizontally lined bar) or in the presence (diagonally lined bar) of 2-mercaptoethanol.

Figure 11A:
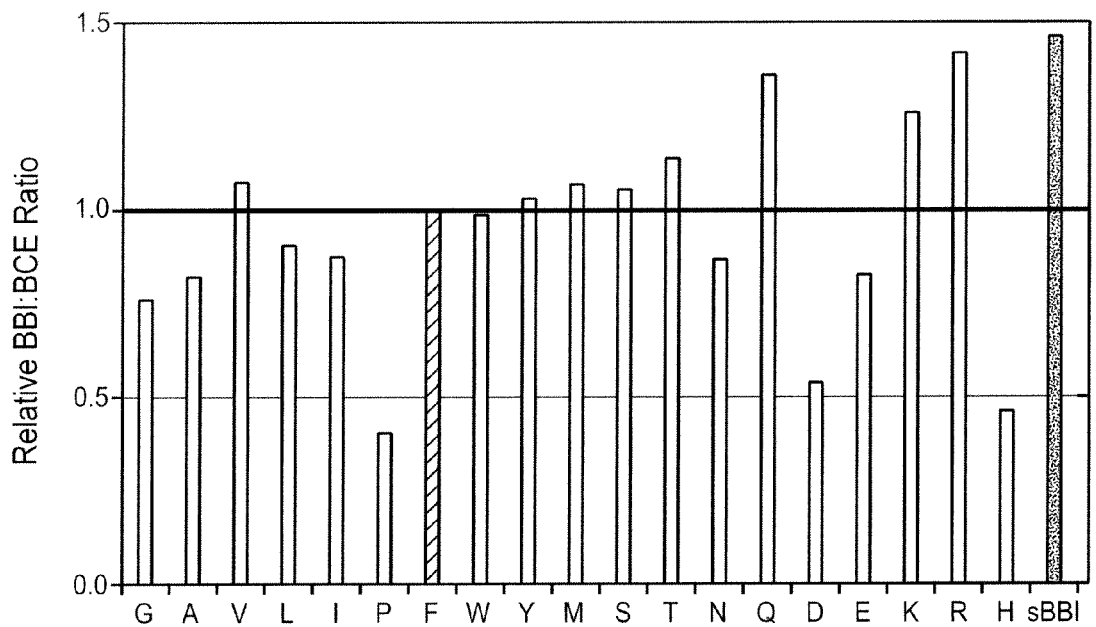
Figure 11B:
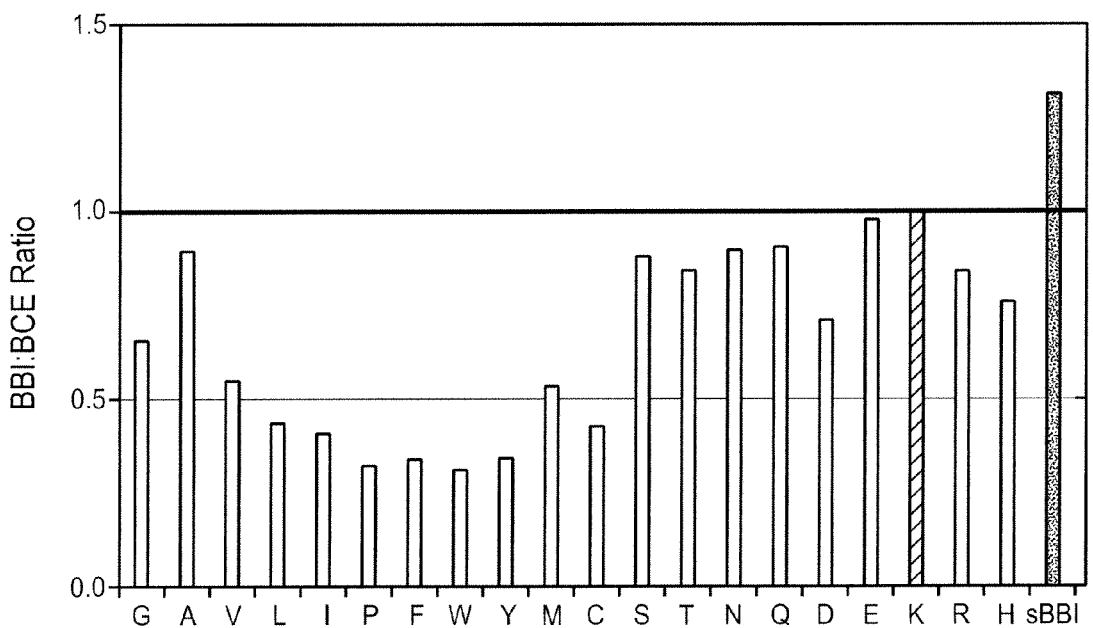

FIGS. 11A-B respectively provide the relative BBI:BCE activity ratios for the amino acid substitutions made at position 50 (A) and position 37 (B) (white bars). The ratios were averaged from quadruplicate cultures in the presence of 2-mercaptoethanol. The activity ratios for sBBI are included as a positive control for comparison (black bars). The ratios are normalized to the value (indicated by a horizontal line) determined for the wild-type amino acids in BBIt-AV (SEQ ID NO:187) and is shown with diagonally lined bars.

Figure 12:
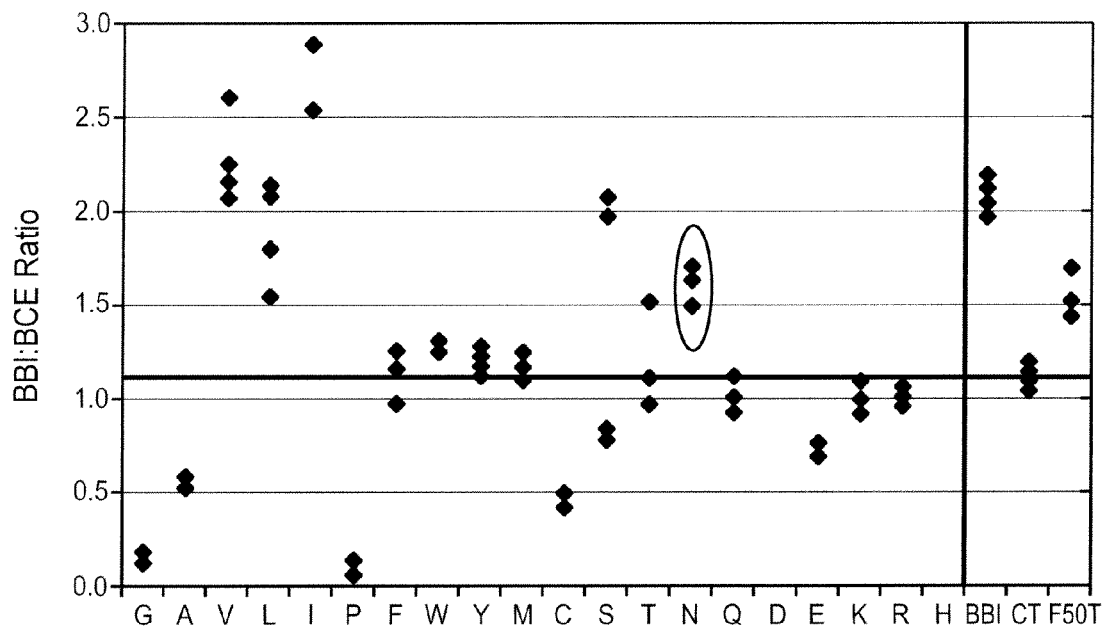

FIG. 12 provides the relative BBI:BCE activity ratios for the amino acid substitutions at the $P_2'$ position (residue 18 in FIG. 9, SEQ ID NO:187) in the trypsin inhibitory loop. The ratios were determined in quadruplicate in the presence of 2-mercaptoethanol (individual data points shown). The activity ratios for sBBI (BBI; SEQ ID NO:13), BBIt-AV (CT; SEQ ID NO:187) and BBIt-AV-F50T (F50T) are shown on the right side of the horizontal line and were added for comparison. The ratios are normalized to the value (shown by a horizontal line) determined for BBIt-AV (CT).

Figure 13:
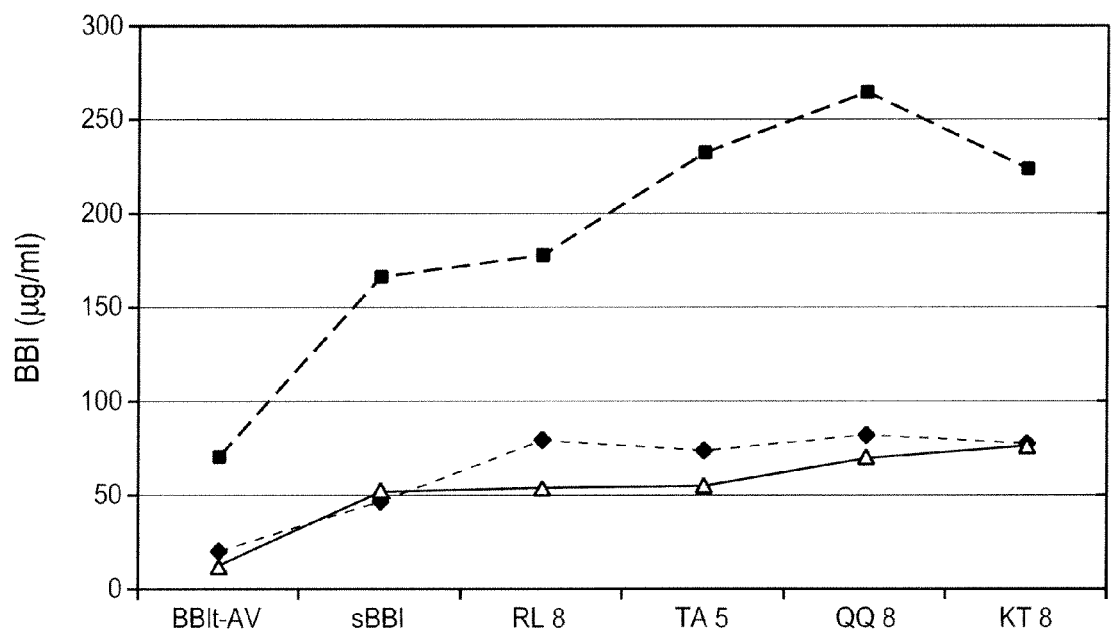

FIG. 13 provides a comparison of the production of three BBIt-AVs containing combinations of 8 amino acid substitutions: octuple variant BBIt-AV-A13I-S25K-M27A-L29R-

S31A-A40H-F50R-V52L (RL8; SEQ ID NO:630), BBIt-AV-A13I-S25K-M27A-L29R-S31E-A40K-F50Q-V52Q (QQ8; SEQ ID NO:628), and BBIt-AV-A13I-S25R-M27A-L29P-S31A-A40H-F50K-V52T (KT8; SEQ ID NO:627). The amount of active BBI species was determined by trypsin inhibition after growth (♦), after activation with 2-mercaptoethanol (■) and after acid/heat treatment (▲). BBIt-AV, the quintuple variant BBIt-AV-A13I-L29P-A40K-F50T-V52A (TA5; SEQ ID NO:601) and sBBI are included for comparison.

Figure 14:
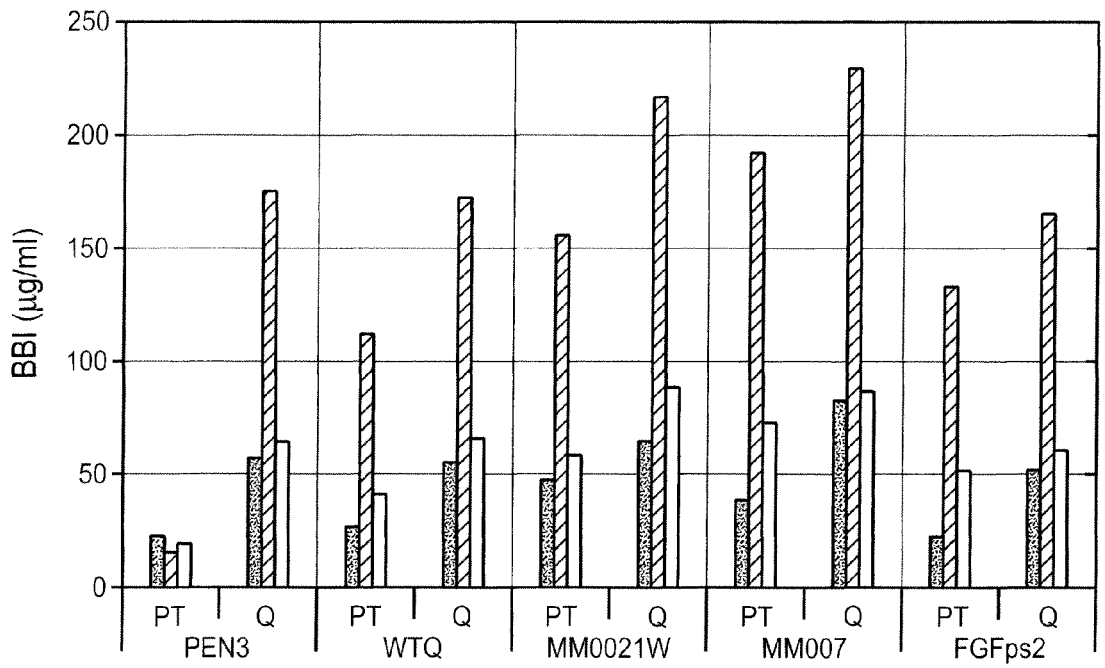

FIG. 14 provides a comparison of the active BBI species (by trypsin inhibition) after growth (black bars), after activation with 2-mercaptoethanol (diagonally lined bars) and after acid/heat treatment (white bars) of different binding peptides (three TGFβ and two FGF5 binders) in the precursor variant BBPI scaffold (designated parent (PT)) versus the modified variant BBIt-AV-A13I-L29P-F50T-V52A scaffold (Q; SEQ ID NO:600). In all scaffolds, the binding peptides replaced the chymotrypsin inhibitory loop. PEN3 (SEQ ID NO:436), WTQ (SEQ ID NO:438) and MM021W (SEQ ID NO:437) are TGFβ binding peptides, and MM007 (SEQ ID NO:430) and FGFps2 (SEQ ID NO:431) are FGF5 binding peptides.

FIG. 15 provides the amino acid sequences of the variant Bowman Birk Inhibitor scaffolds from *Dolichos biflorus* (BBdb-AV, SEQ ID NO:452), the variant protease inhibitor IV or D-II (BBsb3-AV, SEQ ID NO:453) from *Glycine max* (soybean), and from *Torresea (Amburana) cearensis* (BBtc-AV, SEQ ID NO:454) in which the chymotrypsin loop is replaced with a VEGF-binding peptide, that are aligned to the sequence of the variant BBI, BBIt-AV (SEQ ID NO:187). The differences from the BBIt-AV sequence between C9 and C58 are shown underlined in bold font. In all scaffolds, the CK3781 binding peptide (ACYNLYGWT; SEQ ID NO:9) replaces the second protease inhibitory loop.

Figure 16:
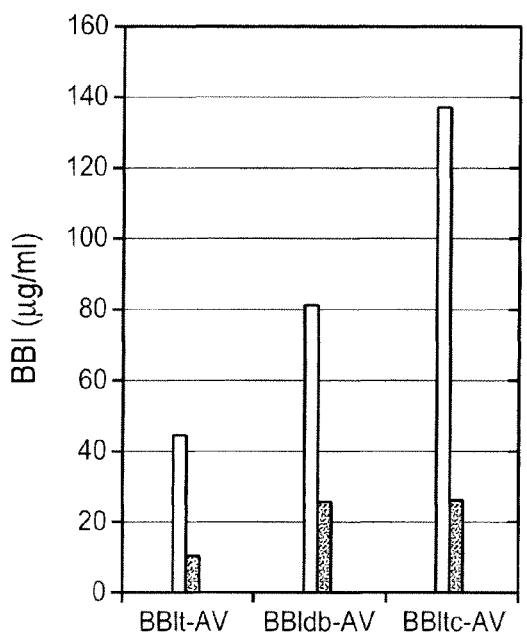

FIG. 16 provides a comparison of the active BBI concentration (by trypsin inhibition) of BBIt-AV, BBdb-AV and BBtc-AV after activation with 2-mercaptoethanol (white bars) and after acid/heat treatment (black bars).

FIG. 17 provides an alignment of unmodified variant BBIt-AV, (SEQ ID NO:187), BBdb-AV, (SEQ ID NO:452), BBsb3-AV (SEQ ID NO:453) and BBtc-AV (SEQ ID NO:454) and the corresponding unmodified precursor BBIt (SEQ ID NO:187), BBsb3 (SEQ ID NO:449), BBtc (SEQ ID NO:450) and BBdb (SEQ ID NO:451) BBPIs. The star symbol (*) identifies the invariant conserved C residues. The numbered residues identify the amino acids that are substituted to generate the modified variant BBPIs of the invention.

FIG. 18 Identification of T-cell epitopes in wild type BBI. (A) The stimulation indices (SI) values for all 71 donors were averaged and are shown, with standard deviations in error bars. (B) The percent responders to each peptide in the 20 wt BBI peptide set are shown.

DETAILED DESCRIPTION OF THE INVENTION

The present invention relates to compositions that comprise modified variant Bowman Birk Protease Inhibitor proteins (BBPIs). The modified variant BBPIs comprise peptides that bind target proteins, and that are further modified to have greater protease inhibitory activity and/or be produced at greater yields than the unmodified BBPIs. The invention encompasses the compositions comprising the modified variant BBPIs, and the methods for making and using the compositions in personal care.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

5.1 Definitions

As used herein, the terms "isolated" and "purified" refer to a nucleic acid or amino acid (or other component) that is removed from at least one component with which it is naturally associated.

As used herein, the term "modified" when referring to a protease inhibitor (PI) e.g. Bowman Birk Protease Inhibitor (BBPI), refers to a BBPI having an amino acid sequence that is derived from the amino acid sequence of an unmodified "precursor" or "parent" BBPI protein. The unmodified precursor BBPI can be a naturally-occurring or wild-type protein, or a variant BBPI. The amino acid sequence of the modified protein is "derived" from the precursor protein amino acid sequence by the substitution, deletion or insertion of one or more amino acids of the region of the precursor amino acid sequence. In some embodiments, at least one amino acid is substituted to generate the modified protease inhibitor. In some embodiments, the parent protease inhibitor is a variant BBPI, which contains a trypsin and/or chotrypsin loop(s) that has been replaced with a variant sequence. Substitution of at least one amino acid of a variant precursor BBPI generates a modified variant BBPI protease inhibitor. In some embodiments, the modified variant PI comprises an amino acid substitution at least at one position equivalent to positions 1, 4, 5, 11, 13, 18, 25, 27, 29, 31, 38, 40, 50, 52, and 65 of SEQ ID NO:187 (DDESSKPCCDQCACTKSNP-PQCRCSDMRLNSCHSACKSCACYNLYG-WTCFCVDITD FCYEPCKPSE: SEQ ID NO:187). In other embodiments, the modified variant PI comprises a combination of substitutions as described herein. In yet other embodiments, the modified variant PI comprises an insertion. Such modifications are of the "precursor DNA sequence" which encodes the amino acid sequence of the precursor protease inhibitor rather than manipulation of the precursor protease inhibitor per se. The modified protease inhibitors herein encompass the substitution of any of the nineteen naturally occurring amino acids at any one of the amino acid residues in regions other than the reactive loops e.g. trypsin and/or chymotrypsin loops(s). The polynucleotides that encode the modified sequence are referred to as "modified polynucleotides", and the polynucleotides that encode the precursor protease inhibitor are referred to as "precursor polynucleotides".

As used herein, the term "protease inhibitor" (PI) herein refers to and is used interchangeably with Bowman Birk Protease Inhibitor (BBPI), which is a cysteine-rich protease inhibitor as described, for example, by Prakash et al. [J mol Evol 42:560-569 (1996)].

As used herein, the term "scaffold" refers to a BBPI protein sequence into which a variant sequence is introduced. In some embodiments, the scaffold is a variant scaffold, which has either the first protease inhibitory loop e.g. the trypsin loop, and/or the second protease inhibitory loop e.g. the chymotrypsin replaced with a binding peptide sequence. In other embodiments, the scaffold is a wild type BBPI scaffold The term "modified variant scaffold" refers to a variant scaffold that comprises modifications e.g. amino acid substitutions or insertions in the backbone of the BBPI scaffold.

As used herein, the term "backbone" when used in reference to a variant BBPI scaffold refers to the portion of the variant BBPI that is outside of the binding peptide sequence that has been introduced to replace the first and/or second protease inhibitory loop i.e. the trypsin and/or chymotrypsin loop. For example, the backbone of the variant BBPI of SEQ ID NO:187 refers to amino acids 1-40 and 50-66 i.e. the amino acids N-terminal and C-terminal to the invariant cysteine residues at amino acid positions 41 and 49, which bracket the VEGF binding sequence that was introduced to replace the chymotrypsin loop found in the wild type BBPI i.e. BBI of SEQ ID NO:13 (DDESSKPCCDQCACTKSNP-PQCRCSDMRLNSCHSACKSCICALSY-PAQCFCVDITDF CYEPCKPSEDDKEN; SEQ ID NO:13). In some embodiments, the scaffold has at least 80%, at least 85%, at least 90%, at least 95%, at least 98%, or at least 99% identity to the scaffold of the BBIt of SEQ ID NO:187.

As used herein, the terms "binding peptide", "binding sequence", "variant sequence" and "variant peptide" are used interchangeably, and refer to the short polypeptide sequence(s) that replace the first and/or second protease inhibitory loops of protease inhibitor e.g. Bowman Birk Inhibitor The binding peptide does not need to be of the same length as the protease inhibitory loop sequence it is replacing in the scaffold, and it differs from the protease inhibitory loop sequence of the wild-type BBPI by at least two amino acids. In some embodiments, replacing the first and/or second protease inhibitory loop e.g. trypsin and/or chymotrypsin loops of a precursor protease inhibitor alters the sequence that is equivalent to that spanning amino acids 15 to 21 (truypsin loop) and/or the sequence that is equivalent to that spanning amino acids 42 to 48 (chymotrypsin loop) of a wild-type e.g. SEQ ID NO:13 or variant SEQ ID NO:187 BBPI. The binding peptide sequence is heterologous to that of the protease inhibitor. Binding peptides bind to target proteins.

A "VEGF binding peptide", an "FGF binding peptide", a "TGF binding peptide" and a "TNF binding peptide" herein refer to a peptide sequence that binds VEGF, FGF5, TGFβ and TNFα, respectively.

A "VEGF composition", an "FGF composition", a "TGF composition" and a "TNF composition" herein refer to a composition e.g. a personal care composition, which comprises a VEGF-BBPI, an FGF-BBPI, a TGF-BBPI and a TGF-BBPI, respectively.

A "compound" when used in reference to a formulation described herein, refers to a modified variant BBPI e.g. a VEGF-BBPI, an FGF-BBPI, a TGF-BBPI or a TNF-BBPI. A formulation may include more than one type of modified variant BBPI i.e. the formulation may comprise a VEGF-BBPI and a TNF-BBPI, or any other combination of the four types of BBPIs disclosed herein.

The term "a" when used in reference to a modified variant BBPI comprised in a personal care composition, herein refers to a modified variant BBPI having a particular sequence. "a", in this context does not limit the number of modified variant BBPI molecules that are needed in the personal care composition.

The terms "chymotrypsin loop" and "second protease inhibitory loop" are herein used interchangeably and refer to the sequence of amino acids that spans the amino acid sequence that corresponds to the second reactive site loop of a protease inhibitor of the Bowman Birk family. For example, the second protease inhibitory loop of the wild-type BBPI inhibitor from *Glycine max* i.e. BBI of SEQ ID NO:13 is the peptide sequence that spans the second reactive site loop encompassed by cysteine 10 and cysteine 11 (see Prakash et al. supra). C10 and C11 encopass an amino acid sequence that is equivalent to that which spans from amino acid 42 to amino acid 48 in the variant BBIt-AV of SEQ ID NO:187 (FIG. 9). The second protease inhibitory loop or chymotrypsin loop of a variant BBPI e.g. BBIt-AV of SEQ ID NO:187, corresponds to the amino acid sequence that spans amino acids 42-48 encompassed by the cysteines at positions 41 and 49, which are the cysteine residues equivalent to C10 and C11 as described by Prakash et al. While the amino acid sequence of second protease inhibitory loop of the wild-type BBI of SEQ ID NO:13 is a chymotrypsin inhibitory peptide, the second protease inhibitory loop of the variant BBIt-AV of SEQ ID NO:187 is a VEGF-binding peptide. Thus, the terms "chymotrypsin loop" or "second protease inhibitory loop" herein refer to the position of the loop and do not intend to imply that the sequence between C10 and C11 imparts protease inhibitory activity to a variant BBPI. Similarly, the terms "trypsin loop" and "first protease inhibitory loop" are herein used interchangeably and refer to the sequence of amino acids that spans the amino acid sequence that corresponds to the first reactive site loop of a protease inhibitor of the Bowman Birk family. For example, the second protease inhibitory loop of the wild-type BBPI inhibitor from *Glycine max* i.e. BBI of SEQ ID NO:13 is the peptide sequence that spans the second reactive site loop encompassed by cysteine 4 and cysteine 5 (see Prakash et al. supra). C4 and C5 encopass an amino acid sequence that is equivalent to that which spans from amino acid 15 to amino acid 21 in the variant BBIt-AV of SEQ ID NO:187 (FIG. 9).

As used herein, the term "target protein" refers to protein (e.g., enzyme, hormone, etc.), whose action would be blocked by the binding of the variant peptide. In some embodiments, the variant peptide binds the target protein when the peptide replaces the trypsin and/or chymotrypsin loop of a BBPI.

As used herein, "substituted" and "substitutions" refer to replacement(s) of an amino acid residue or nucleic acid base in a parent sequence. In some embodiments, the substitution involves the replacement of a naturally occurring residue or base. In some embodiments, two or more amino acids are substituted to generate a modified BBPI that comprises a combination of amino acid substitutions. In some embodiments, combinations of substitutions are denoted by the amino acid position at which the substitution is made. For example, a combination denoted by 25-50-52 means that three amino acids at positions 25, 50 and 52 are substituted. In other embodiments, the combination of substitutions is denoted by the amino acid position and the amino acid resulting from the substitution. For example, a modified BBPI that comprises the combination of substitutions 13I-25L-50T-52A is a modified BBPI wherein the amino acid at position 13 has been substituted with an isolucine, the amino acid at position 25 has been substituted with a leucine, the amino acid at position 50 has been substituted with a threonine, and the amino acid at position 52 has been substituted with an alanine. Amino acid positions are positions equivalent to the numbered positions in the BBPI of SEQ ID NO:187. In some embodiments, the combination of substitutions is given in the context of the scaffold in which the substitutions are made. For example, the modified variant BBPI of SEQ ID NO:601 is also referred to as BBIt-AV-13I-29P-40K-50T-52A, indicating that the BBIt-AV scaffold (SEQ ID NO:187) has been modified to contain the resulting substitutions at amino acids 13, 29, 40, 50, and 52. In some embodiments, the original and substituted amino acid are indicated e.g. the modified variant BBPI of SEQ ID NO:601 can be referred to as BBIt-AV-A13I-L29P-A40K-F50T-V52A.

As used herein, "modification" and "modify" refer to any change(s) in an amino acid or nucleic acid sequence, including, but not limited to deletions, insertions, interruptions, and substitutions. In some embodiments, the modification involves the replacement of a naturally occurring residue or base. In other embodiments, the modification comprises a combination of at least one amino acid substitution. In yet other embodiments, the modification comprises an insertion with or without the insertion being combined with at least one amino acid substitution.

As used herein, the term "equivalent" when used in reference to an amino acid residue or the position of an amino acid residue in a BBPI refers to the position of an amino acid residue in a modified BBPI that corresponds in position in the primary sequence of the unmodified precursor BBPI. In order to establish the position of equivalent amino acid positions in a BBPI, the amino acid sequence of the BBPI that is modified is directly compared to the BBPI of SEQ ID NO:187, and in particular to the cysteine residues that are known to be invariant in protease inhibitors of the Bowman Birk Inhibitor family (Prakash et al. supra). After aligning the conserved cysteine residues, allowing for insertions and deletions in order to maintain alignment (i.e. avoiding the elimination of conserved cysteine residues through arbitrary deletion or insertion), the residues at positions equivalent to particular amino acid positions in the sequence of the BBPI of SEQ ID NO:187 are defined. Alignment of conserved cysteine residues preferably should conserve 100% of such residues. For example, in FIG. 17 the amino acid sequences of variant and wild-type BBPIs are aligned to provide the maximum amount of homology between amino acid sequences. A comparison of these sequences shows that the invariant cysteine residues are conserved. While the primary sequence is the preferred structure for determining the position of equivalent amino acids in the BBPIs of the invention, equivalent residues may also be identified by determining homology at the level of tertiary structure for a protein BBPI protein.

Equivalent amino acid positions are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis. The crystal structure of the Bowman Birk inhibitor from soybean has been determined (Hwang et al. J Biol. Chem. 10; 252(3):1099-101 [1977], Wei et al., J Biol. Chem. 10; 254 (11):4892-4 [1979], Voss et al. Eur J. Biochem. 15; 242(1): 122-31 [1996]) and can be used as outlined above to determine equivalent amino acid positions on the level of tertiary structure.

As used herein, "fusion polypeptides," "fusion proteins," and "fusion analogs" encode from the amino-terminus a signal peptide functional as a secretory sequence functional in a host cell, a secreted polypeptide or portion thereof normally secreted from a host cell, a cleavable linker polypeptide and a desired polypeptide. In some embodiments, the fusion polypeptides include a spacer peptide positioned between the secretory sequence and a secreted polypeptide. In some embodiments, the fusion protein is processed by host cell enzymes (e.g., a protease), to yield the desired protein free from the other protein sequences in the fusion protein. As used herein, the terms "fusion analog," "fusion polypeptide," and "fusion protein" are used interchangeably.

As used herein, the term "activity" refers to any activity associated with a particular protein, such as enzymatic activity associated with a protease. In some embodiments, the activity is biological activity. In further embodiments, activity encompasses binding of proteins to receptors which results in measurable downstream effects (e.g., VEGF binding to its cognate receptor). "Biological activity" refers to any activity that would normally be attributed to that protein by one skilled in the art.

As used herein, "protease inhibitory activity" refers to the activity of a BBPI in inhibiting the proteolytic activity of a protease i.e. inhibiting the ability of a protease to hydrolyze peptides or substrates having peptide linkages.

As used herein, the term "expression" refers to the process by which a polypeptide is produced based on the nucleic acid sequence of a gene. The process includes both transcription and translation.

The term "production" with reference to a BBPI, encompasses the two processing steps of a full-length protease including: 1. the removal of the signal peptide, which is known to occur during protein secretion; and 2. the removal of the pro region, which creates the active mature form of the BBPI and which is known to occur during the maturation process (Wang et al., Biochemistry 37:3165-3171 (1998); Power et al., Proc Natl Acad Sci USA 83:3096-3100 (1986)).

As used herein, the term "production yield" refers to the level at which an unmodified and/or modified variant protease inhibitor e.g. a variant BBPI is produced. The greater the production yield, the greater the level or amount of protease inhibitor that is produced.

As used herein, the term "efficient production" herein to the production of a protein e.g. a modified variant BBPI, and implies that said protein is produced at a level that is greater than that of an unmodified or precursor variant BBPI.

As used herein, the term "substantially pure" when applied to the proteins or fragments thereof of the present invention means that the proteins are essentially free of other substances to an extent practical and appropriate for their intended use. In particular, the proteins are sufficiently pure and are sufficiently free from other biological constituents of the host cells so as to be useful in, for example, protein sequencing, and/or producing pharmaceutical preparations.

As used herein, the term "substantially free" encompasses preparations of the desired polypeptide having less than about 20% (by dry weight) other proteins (i.e., contaminating protein), less than about 10% other proteins, less than about 5% other proteins, or less than about 1% other proteins.

As used herein, the terms "polynucleotide", "nucleic acid molecule" and "nucleic acid sequence" include sequences of any form of nucleic acid, including, but not limited to RNA, DNA and cDNA molecules. It will be understood that, as a result of the degeneracy of the genetic code, a multitude of nucleotide sequences encoding a given protein may be produced.

As used herein, the terms "DNA construct", "polynucleotide construct" and "transforming DNA" are used interchangeably to refer to DNA used to introduce sequences into a host cell or organism. The DNA may be generated in vitro by PCR or any other suitable technique(s) known to those in the art. In some embodiments, the DNA construct comprises a sequence of interest (e.g., a modified sequence). In some embodiments, the sequence is operably linked to additional elements such as control elements (e.g., promoters, etc.). In some embodiments, the DNA construct comprises sequences homologous to the host cell chromosome. In other embodiments, the DNA construct comprises non-homologous sequences. Once the DNA construct is assembled in vitro it may be used to mutagenize a region of the host cell chromosome (i.e., replace an endogenous sequence with a heterologous sequence).

As used herein, the term "heterologous DNA sequence" refers to a DNA sequence that does not naturally occur in a host cell. In some embodiments, a heterologous DNA sequence is a chimeric DNA sequence that is comprised of parts of different genes, including regulatory elements.

As used herein, the term "heterologous protein" refers to a protein or polypeptide that does not naturally occur in the host cell i.e. it is encoded by a heterologous sequence.

As used herein, "homologous protein" refers to a protein or polypeptide native or naturally occurring in a cell.

As used herein, the term "vector" refers to a polynucleotide construct designed to introduce nucleic acids into one or more cell types. Vectors include cloning vectors, expression vectors, shuttle vectors, and plasmids. In some embodiments, the polynucleotide construct comprises a DNA sequence encoding a modified variant BBPI.

As used herein, the term "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those of skill in the art.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus, Plenum Publishing Corp., pages* 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein, "percent (%) sequence identity" or "percent homology" when used in reference to a polynucleotide or to a polypeptide sequence is defined as the percentage of nucleotide or amino acid residues in a candidate sequence that are identical with the nucleotide or amino acid residues of a sequence disclosed herein. The percent identity shared by polynucleotide or polypeptide sequences is determined by direct comparison of the sequence information between the molecules by aligning the sequences and determining the identity by methods known in the art. In some embodiments, the alignment includes the introduction of gaps in the sequences to be aligned. In addition, for sequences which contain either more or fewer nucleotides or amino acids than those of the candidate polynucleotide or polypeptide sequences, it is understood that the percentage of homology will be determined based on the number of homologous nucleotides or amino acids in relation to the total number of nucleotides or amino acids. Thus, for example, homology of sequences shorter than those of the sequences identified herein will be determined using the number of nucleosites or amino acids in the shorter sequence. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the protein is essentially the same as that designated for the Bowman Birk family of protease inhibitors. Additionally, analogous proteins include at least 60%, 65%, 70%, 75%, 80%, 85%, 90%, 95%, 97%, 98%, 99% or 100% sequence identity with the sequence of the variant BBPI of SEQ ID NO:187. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). A preferred method utilizes the BLASTN module of WU-BLAST-2 set to the default parameters, with overlap span and overlap fraction set to 1 and 0.125, respectively.

A "host cell" refers to a suitable cell from a cell that serves as a host for an expression vector comprising DNA according to the present invention. A suitable host cell may be a naturally occurring or wild-type host cell, or it may be an altered host cell. In one embodiment, the host cell is a Gram positive microorganism. In some preferred embodiments, the term refers to cells in the genus *Bacillus*.

As used herein, "*Bacillus* sp." includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

As used herein, a "promoter sequence" refers to a DNA sequence which is recognized by the bacterial host for expression purposes. In preferred embodiments, it is operably linked to a DNA sequence encoding the fusion polypeptide. Such linkage comprises positioning of the promoter with respect to the translation initiation codon of the DNA sequence encoding the fusion DNA sequence. In particularly preferred embodiments, the promoter sequence contains transcription and translation control sequences which mediate the expression of the fusion DNA sequence.

As used herein, a nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Operably linked DNA sequences are usually contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "personal care composition" refers to a product for application to the skin, hair, nails, oral cavity and related membranes for the purposes of improving, cleaning, beautifying, treating, and/or caring for these surfaces and membranes. In some embodiments, the personal care composition is in the form of an emulsified vehicle, such as a nutrient cream or lotion, a stabilized gel or dispersioning system, such as skin softener, a nutrient emulsion, a nutrient cream, a massage cream, a treatment serum, a liposomal delivery system, a topical facial pack or mask, a surfactant-based cleansing system such as a shampoo or body wash, an aerosolized or sprayed dispersion or emulsion, a hair or skin conditioner, styling aid, or a pigmented product such as makeup in liquid, cream, solid, anhydrous or pencil form. However, it is not intended that the present invention be limited to any particular form, as various forms find use in the present invention.

Personal care products can be classified/described as cosmetic, over-the-counter ("OTC") compounds that find use in personal care applications (e.g., cosmetics, skin care, oral care, hair care, nail care). In some embodiments, the modified variant BBPI is added to a personal care composition such as a hair care composition, a skin care composition, a nail care composition, a cosmetic composition, or any combinations thereof.

As used herein, "skin care composition" refers to compositions that are applied to skin in order to provide beneficial properties, including but not limited to wrinkle minimizing, wrinkle removal, decoloring, coloring, skin softening, skin smoothing, depilation, cleansing, etc. In some particularly preferred embodiments, the present invention provides skin care compositions that improve skin tone. In these embodiments, the improvement comprises lessening of wrinkles, smoothing skin texture, modifying skin coloration, and other desired cosmetic benefits. In further embodiments, the skin care composition is in a form selected from the group consisting of body washes, moisturizing body washes, deodorant body washes, antimicrobial cleansers, skin protecting treatments, body lotions, facial creams, moisturizing creams, facial cleansing emulsions, surfactant-based facial cleansers, facial exfoliating gels, facial toners, exfoliating creams, facial masks, after shave lotions, balms, and/or radioprotective compositions (e.g., sunscreens).

As used herein, "cosmetic composition" refers to compositions that find use in the cosmetics. The Food Drug and Cosmetic Act (FD&C Act) definition is used herein. Thus, cosmetics are defined by their intended use, as articles intended to be rubbed, poured, sprinkled, or sprayed on, introduced into, or otherwise applied to the human body for cleansing, beautifying, promoting attractiveness, or altering appearance. These compositions provide non-therapeutic benefits and are not regulated as pharmaceuticals. However, in some situations, cosmetic compositions are incorporated into pharmaceutical compositions to provide cosmetic benefits (e.g., products that treat skin or hair diseases, but also contain cosmetic compositions for their coloring or other benefits). Cosmetic compositions include makeup compositions as defined herein. Also, it is intended that the present invention encompass the use of cosmetics on animals other than humans.

As used herein, the terms "pharmaceutical compositions" and "therapeutic compositions" refer to compositions such as drugs that provide medical benefits, rather than solely cosmetic benefits. In the United States, pharmaceutical and therapeutic compositions are approved by the Food and Drug Administration for treatment and/or prevention of particular conditions.

As used herein, the term "drug" is defined as it is in the FD&C Act definition. Thus, drugs are defined as articles intended for use in the diagnosis, cure, mitigation, treatment or prevention of disease, and articles (other than food) intended to affect the structure or any function of the body of man or other animals.

As used herein, "leave-on" refers to a composition that is applied to a subject and not removed (e.g., cleansed by washing, rinsing, etc.) for a period of typically at least several hours (e.g., 4-12 hours) before the area exposed to the composition is cleansed.

As used herein, a "rinse-off" composition is a composition that is applied and cleansed (e.g., by washing, rinsing, etc.) soon after its application (generally within about 30 minutes of application). In some preferred embodiments, rinse-off compositions are formulated so as to deposit an effective amount of active(s) on the area treated.

As used herein, the term "cosmetic benefit" refers to a desired cosmetic change that results from the administration of a personal care composition. Cosmetic benefits include but are not limited to improvements in the condition of skin, hair, nails, and the oral cavity. In preferred embodiments, at least one cosmetic benefit is provided by the skin care, hair care, nail care, and makeup compositions of the present invention.

As used herein, "cosmetically acceptable" refers to materials that are suitable for use in contact with tissues of humans and/or other animals, without undue toxicity, incompatibility, instability, irritation, allergic responses, etc., commensurate with a reasonable benefit/risk ratio.

As used herein, the terms "pigment," "color pigment," and "dye" used in reference to the compositions of the present invention encompasses any compound that provides a color to the composition and/or imparts a color to the surface (e.g., skin and/or hair) to which the composition is applied.

The term "radioprotective" refers to a substance capable of blocking or filtering. UV radiation sunscreens and sunblocks.

As used herein, "improving the appearance and/or condition of skin" refers to any benefit achieved through use of the personal care compositions of the present invention. Examples of benefits include but are not limited to reducing the reducing imperfections and/or blemishes in skin color, including lightening hyperpigmented regions of skin and/or evening skin pigmentation, relieving dryness, eliminating rough, dry spots, improving the skin's ability to retain moisture and/or protect itself from environmental stresses, reducing the appearance of fine lines and wrinkles, improving appearance and skin tone, increasing skin firmness and/or suppleness, decreasing sagging of skin, increasing skin glow and clarity, increasing the skin renewal process, and/or removing vellus hair. Improving the visual appearance of skin also encompasses regulating wrinkles, atrophy, skin lightening, skin darkening, skin smoothness, and/or reducing the visual appearance of pores. In some embodiments, improving the appearance and/or condition of the skin results in skin improvements due to the treatment of a skin disorder with the personal care composition of the invention.

The term "angiogenesis" refers to the biological processes which result in the development of blood vessels and/or increase in the vascularization of tissue in an organism.

The terms "angiogenic disease," "angiogenic disorder," and "angiogenic skin disorder," are used in reference to a disorder, generally a skin disorder or related disorder which occurs as a consequence of or which results in increased vascularization in tissue. Oftentimes, the etiology of the angiogenic disease is unknown. However, whether angiogenesis is an actual cause of a disease state or is simply a condition of the disease state is unimportant, but the inhibition of angiogenesis in treating or reversing the disease state or condition is an important aspect of the present invention. Thus, it is not intended that the present invention be limited to any particular mechanisms of action. Examples of angiogenic skin disorders which are suitable for treatment utilizing compounds of the present invention include, but are not limited to psoriasis, acne, rosacea, warts, eczema, hemangiomas and lymphangiogenesis, Sturge-Weber syndrome, neurofibromatosis, tuberous sclerosis, chronic inflammatory disease, and arthritis. Any skin disorder which has as a primary or secondary characterization, increased vascularization, is considered an angiogenic skin disorder herein. Thus, the personal care compositions comprising VEGF-binding BBPIs (VEGF-BB-PIs) provided by the present invention find use in treatment of a wide variety of angiogenic skin disorders and/or conditions.

The term "rosacea" is used to describe acne, rosacea, or erythematosa characterized by vascular and follicular dilation typically involving the nose and contiguous portions of the cheeks. Rosacea may vary from very mild but persistent erythema to extensive hyperplasia of the sebaceous glands with deep-seated papules and pustules and be accompanied by telangiectasia at the affected erythematous sites. This condition is also referred to as "hypertrophic rosacea" or "rhinophyma," depending upon the severity of the condition. It is intended that the term encompass all of the various forms of the condition.

The term "psoriasis" is used to describe a skin condition which is characterized by the eruption of circumscribed, discrete and confluent, reddish, silvery-scaled maculopapules. Although it is not intended that the present invention be limited to any particular body area, psoriatic lesions typically occur on the elbows, knees, scalp and trunk. Microscopically, these lesions demonstrate characteristic parakeratosis and elongation of rete ridges.

The term "acne" is used to describe a condition of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolescence due to an overactive sebaceous apparatus which is believed to be affected by hormonal activity.

The term "eczema" is a generic term used to describe acute or chronic inflammatory conditions of the skin, typically erythematous, edematous, papular, vesicular and/or crusting. These conditions are often followed by lichenification, scaling and occasionally, by duskiness of the erythema and, infrequently, hyperpigmentation. Eczema is often accompanied by the sensation of itching and burning. Eczema vesicles form due to intraepidermal spongiosis. Eczema is sometimes referred to colloquially as "tetter," "dry tetter," and "scaly tetter." There are numerous subcategories of eczema, all of which are treated by one or more of the compounds according to the present invention.

The term "hemangioma" refers to a benign self-involuting tumour of endothelial cells (the cells that line blood vessels). Hemangiomas are connected to the circulatory system and filled with blood. The appearance depends on location. If they are on the surface of the skin they look like a ripe strawberry, if they are just under the skin they present as a bluish swelling. Sometimes they grow in internal organs such as the liver or larynx. Approximately 80% are located on the face and neck, with the next most prevalent location being the liver. The personal care compositions of the invention are intended to treat hemangiomas of the skin i.e. hemangiomas that are on the surface of the skin and hemangiomas that are just under the skin.

The term "scleroderma" herein refers to a chronic disease characterized by excessive deposits of collagen in the skin or other organs. Scleroderma affects the skin, and in more serious cases it can affect the blood vessels and internal organs. The most evident symptom is usually the hardening of the skin and associated scarring. The skin may appear tight, reddish or scaly. Blood vessels may also be more visible. A significant player in the process is transforming growth factor (TGFβ). Topical treatment for the skin changes of scleroderma do not alter the disease course, but may improve pain and ulceration.

As used herein, "hair care composition" refers to compositions that are applied to hair to provide beneficial properties such as thickening, thinning, coloring, decoloring, cleansing, conditioning, softening, shaping, etc. In some embodiments, the hair care composition is in a form selected from the group consisting of shampoos, conditioners, anti-dandruff treatments, styling aids, styling conditioners, hair repair or treatment sera, lotions, creams, pomades, and chemical treatments. In other embodiments, the styling aids are selected from the group consisting of sprays, mousses, rinses, gels, foams, and combinations thereof. In further embodiments, the chemical treatments are selected from the group consisting of permanent waves, relaxers, and permanents, semipermanents, temporary color treatments and combinations thereof.

As used herein, "inhibiting hair growth" and "inhibition of hair growth" refer to an observed lessening of hair length and/or thickness. Thus, in some preferred embodiments, application of a personal care composition of the present invention provides a benefit in lessening hair length and/or thickness as compared to an area in which a personal care composition of the present invention has not been applied. In some embodiments, the observed reduction of hair growth and/or thickness is a range from less than 1% to more than 99%, as compared to untreated areas, while in other embodiments, the observed reduction is from about 100% to about 90%, from about 90% to about 80%, from about 80% to about 70%, from about 70% to about 60%, from about 60% to about 50%, from about 50% to about 40%, from about 40% to about 30%, from about 30% to about 20%, from about 20% to about 10%, from about 10% to about 1%. Indeed, it is not intended that the term be limited to any particular percentage reduction, as long as the reduction is observable by visual (i.e., by eye) or other means. It is also intended that the term encompass "preventing hair growth" to any degree, as described above. It is not intended that the term be limited to the complete prevention of hair growth (i.e., there is no observed growth of hair).

The terms "dermatological inflammatory disorder" or "inflammatory skin disorder" refer to skin condition associated with inflammation of the skin. In some embodiments, the inflammatory skin disorder is a disorder associated with elevated levels of inflammatory cytokines e.g. TNFα.

As used herein, in some embodiments, the term "compound" refers to the BBPI comprised in the personal care compositions of the invention.

The term "effective amount" is used throughout the specification to describe concentrations or amounts of compounds according to the present invention which may be used to produce a favorable change in the disease or condition treated, e.g. whether that change is hair growth, prevention of hair growth or for ameliorating a condition caused or associated with a disorder. As used herein, "safe and effective amount" refers to a sufficient amount of a material that significantly induces a positive modification to the area upon which the material is applied and also does not result in the production of serious side effects (at a reasonable risk/benefit ratio). The safe and effective amount of the material may vary with the particular skin or other body part being treated, the age of the subject being treated, the severity of the condition being treated, the duration of treatment, the nature of concurrent therapy, the specific material used, the particular carrier utilized, etc. Those of skill in the art are capable of adjusting the concentration of the personal care compositions provided herein for the desired application of the compositions.

As used herein, "active" (and "actives") refers to a composition that imparts a benefit to a subject being treated. For example, in some embodiments, the present invention provides personal care compositions comprising a modified variant BBPI, e.g. modified variant VEGF-BBPI, a "primary active" which functions to provide benefit to the area to which it is applied. Thus, in some embodiments, the modified variant VEGF-BBPI is present in skin care formulations and serves to treat the skin of subjects suffering from an angiogenic skin disorder. It is not intended that the term be limited to VEGF-BBPI, as there are additional constituents present in the personal care compositions of the present invention which impart benefits. In some embodiments, these additional constituents are encompassed by the designation "secondary actives." Primary and secondary actives are collectively referred to as "actives" herein. Other "primary actives" provided by the invention include FGF-BBPIs, TGF-BBPIs and TNF-BBPIs.

As used herein, "vitamin B3 compound" means a compound having the formula:

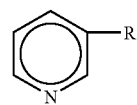

wherein R is —CONH2 (i.e., niacinamide), —COOH (i.e., nicotinic acid) or —CH$_2$OH (i.e., nicotinyl alcohol); derivatives thereof; and salts of any of the foregoing.

As used herein, "non-vasodilating" means that an ester does not commonly yield a visible flushing response after application to the skin in the subject compositions. It is contemplated that the majority of the general population would not experience a visible flushing response, although such compounds may cause vasodilation not visible to the naked eye.

As used herein, "retinoid" includes all natural and/or synthetic analogs of Vitamin A and/or retinol-like compounds which possess the biological activity of Vitamin A in/on the skin, as well as the geometric isomers and stereoisomers of these compounds. However, it is not intended that the term be limited to these compounds, as the term encompasses vitamin A alcohol (retinol) and its derivatives such as vitamin A aldehyde (retinal), vitamin A acid (retinoic acid) and vitamin A esters (e.g., retinyl acetate, retinyl propionate and retinyl palmitate), etc. It is further intended that the term encompass all-trans-retinoic acids and 13-cis-retinoic acids. It is also intended that the term encompass compositions that are encapsulated, as well as provided for use in various forms. The terms "retinol" and "retinal" preferably comprise the all-trans compounds. The retinoid preferably used for the formulation of the present invention is all-trans-retinol, generally referred to as "retinol" herein.

As used herein, "carotenoid" is used in reference to β-carotene, lycopene, lutein, astaxanthin, zeaxanthin, cryptoxanthin, citranaxanthin, canthaxanthin, bixin, β-apo-4-carotenal, β-apo-8-carotenal, β-apo-8-carotenoic esters, alone, as well as in combination. Carotenoids which are preferably used are β-carotene, lycopene, lutein, astaxanthin, zeaxanthin, citranaxanthin and canthaxanthin. In some embodiments, carotenoids are utilized in crystalline form, as well as in formulations, including but not limited to dry powders (See e.g., dry powders, as described in EP 0 065 193; hereby incorporated by reference). In some embodiments, the preferred use in the case of lycopene, astaxanthin and canthaxanthin is of lycopene-, astaxanthin- and canthaxanthin-containing dry powders, for example LYCOVIT®, LUCANTIN® Pink and LUCANTIN® Red (10% dry powders respectively of lycopene, astaxanthin and canthaxanthin, commercially available from BASF AG, Ludwigshafen, Germany. As used herein, the term "dispersed phase" is used as by those of skill in the art of emulsion technology as the phase that exists as small particles or droplets suspended in and surrounded by a continuous phase. The dispersed phase is also known as the "internal" or "discontinuous" phase.

As used herein, "penetration enhancers" refer to compositions that facilitate penetration through the upper stratum corneum barrier to the deeper skin layers. Examples of penetration enhancers include, but are not limited to, propylene glycol, azone, ethoxydiglycol, dimethyl isosorbide, urea, ethanol, dimethyl sulfoxide, microemulsions, liposomes, and nanoemulsions.

As used herein, the terms "emulsifier" and "surfactant" refer to compounds that disperse and suspend the dispersed phase within the continuous phase of a material. Surfactants find particular use in products intended for skin and/or hair cleansing. In particular embodiments, the term "surfactant(s)" is used in reference to surface-active agents, whether used as emulsifiers or for other surfactant purposes such as skin cleansing.

In various embodiments, the present invention also includes "protectants" such as UV absorbers (e.g., octyl methoxycinnamate, benzophenone-3, titanium dioxide, and octyl salicylate); film-forming agents (e.g., VP/Eicosene copolymer); cosmeceutical agents (e.g., peptides and proteins, alpha hydroxy acids, and retinol and retinoic acid derivatives); antioxidants (e.g., tocopherol and derivatives thereof and ascorbic acid and derivatives thereof); vitamins (e.g., B, D, K and their derivatives); antiperspirant actives (e.g., aluminum hydroxide and zirconium hydroxide); depilating agents (e.g., thioglycolate salts); anti-acne agents (e.g., salicylic acid and benzoyl peroxide); abrasives and exfoliants (e.g., silicates, pumice, and polyethylene); and extracts of plant, fruit, vegetable and/or marine sources.

As used herein, the term "bioactivity" refers to a cause and effect relationship between a composition and a biological system. Thus, the term is used as by those skilled in the art of biotechnology and biological sciences as the phrase that describes a cause and effect relationship between a molecular composition and living biological matter (e.g., tissue, cells, etc.).

As used herein as a noun, the term "bioactive" refers a composition that exhibits bioactivity upon administration to living biological matter (e.g., tissue, cells, etc.). The term is used synonymously with "bioactive compound."

As used herein, "silicone gum" means high molecular weight silicones having an average molecular weight in excess of about 200,000 and preferably from about 200,000 to about 4,000,000. It is intended that the definition encompass non-volatile polyalkyl and polyaryl siloxane gums.

As used herein, a "composition comprising a modified variant BBPI" refers broadly to any composition containing the given modified variant BBPI. The composition may be in any form, particularly a form that is suitable for administration.

As used herein, a compound is said to be "in a form suitable for administration" when the compound may be administered to a human or other animal by any desired route (e.g., topical, oral, etc.).

As used herein, "safe and effective amount" refers to a sufficient amount of a material that significantly induces a positive modification to the area upon which the material is applied and also does not result in the production of serious side effects (at a reasonable risk/benefit ratio). The safe and effective amount of the material may vary with the particular skin or other body part being treated, the age of the subject being treated, the severity of the condition being treated, the duration of treatment, the nature of concurrent therapy, the specific material used, the particular carrier utilized, etc. Those of skill in the art are capable of adjusting the concentration of the personal care compositions provided herein for the desired application of the compositions.

5.2 Bowman Birk Protease Inhibitor Scaffolds

Bowman Birk Protease Inhibitor proteins (BBPI) are a kinetically and structurally well-characterized family of small proteins (60-90 residues), and have been found only in the seed of monocotyledous and dicotyledonous plants, and have not been identified in any other part of the plant (See e.g., Birk, Int. J. Pept. Protein Res., 25:113-131 [1985]). The sequences of many wild-type BBPI scaffolds have been determined from both monocotyledonous and dicotyledonous seeds, and have been analyzed (Prakash et al., J mol Evol 42:560-569 [1996]). They typically have a symmetrical structure of two tricyclic domains each containing an independent binding loop, although some have one domain and some have more than two domains. The major ~8 kDa Bowman Birk Inhibitor isolated from soybeans (BBI) has two separate reactive site loops, loop I inhibits proteases having trypsin-like specificity and loop II inhibits proteases with chymotrypsinlike specificity (See e.g., Chen et al., J. Biol. Chem., 267: 1990-1994 [1992]; Werner and Wemmer, Biochem., 31:999-1010 [1992]; Lin et al., Eur. J. Biochem., 212:549-555 [1993]; Voss et al., Eur. J. Biochem., 242:122-131 [1996]; and Billings et al., Pro. Natl. Acad. Sci., 89:3120-3124 [1992]). These binding regions each contain a "canonical loop" structure, which is a motif found in a variety of serine proteinase inhibitors (Bode and Huber, Eur. J. Biochem., 204:433-451 [1992]). In some embodiments, wild-type BBPI scaffolds serve as wild-type precursor BBPI scaffolds from which variant and modified variant BBPI scaffolds are derived.

In some embodiments, the present invention provides for variant BBPI scaffolds in which the tryspin (loop I) and/or chymotrypsin loop(s) (loop II) is replaced by a variant peptide. In some embodiments, the trypsin loop is replaced with a variant peptide resulting in a variant BBPI that retains chymotrypsin inhibitory activity (CIA). In other embodiments, the chymotrypsin loop is replaced with a variant peptide to generate a variant BBPI that retains trypsin inhibitory activity (TIA). In yet other embodiments, both the trypsin and the chymotrypsin loops of the BBPI are each replaced with a variant peptide. Non-limiting examples of BBPI scaffolds in which the trypsin and/or chymotrypsin loop is replaced with a variant peptide sequence include wild-type and unmodified variant scaffolds. Examples of wild-type precursor scaffolds include but are not limited to the scaffolds disclosed by Prakash (supra), such as the scaffold of the soybean inhibitor from *Glycine max*

(BBI; SEQ ID NO:13) or the mature and truncated form thereof (SEQ ID NO:185; DDESSKPCCDQCACTKSN-PPQCRCSDMRLNSCHSACKSCICALSY-PAQCFCVDITDF CYEPCKPSE), the inhibitor from *Dolichos biflorus*

(BBdb; SEQ ID NO:449; PSESSKPCCDQCACTKSIP-PQCRCTDVRLNSCHSACSSCVCTFSI-PAQCVCVDMKDFC YEPCK; the soybean inhibitor D-II from *Glycine max*

(BBsb3; SEQ ID NO:450; DDEYSKPCCDLCMCTRSMP-PQCSCEDIRLNSCHSDCKSCMCTRSQPGQCRCLDT NDFCYKPCKSRDD) and the inhibitor from *Torresea (Amburana) cearensis*

(BBtc; SEQ ID NO:451; SSKWEACCDRCACTKSIP-PQCHCADIRLNSCHSACESCACTHSI-PAQCRCFDITDFCYK PCSG). Examples of unmodified variant precursor scaffolds include but are not limited to scaffolds in which the chymotrypsin loop has been replaced with a VEGF binding variant sequence include the BBI-AV (SEQ ID NO:186; DDESSKPCCDQCACTKSNP-PQCRCSDMRLNSCHSACKSCACYNLYG-WTCFCVDITDF CYEPCKPSEDDKEN), BBIt-AV (SEQ ID NO:187; DDESSKPCCDQCACTKSNP-PQCRCSDMRLNSCHSACKSCACYNLYG-WTCFCVDITDF CYEPCKPSE), BBdb-AV (SEQ ID NO:452; DPSESSKPCCDQCACTK-SIPPQCRCTDVRLNSCHSACSSCACYN-LYGWTCVCVDMKD FCYEPCK), BBsb3-AV (SEQ ID NO:453; DPDDEYSKPCCDLCMC-TRSMPPQCSCEDIRLNSCHSDCKSCA-CYNLYGWTCRCLDT NDFCYKPCKSRDD), and BBtc-AV (SEQ ID NO:454; DPSSKWEACCDRCACTK-SIPPQCHCADIRLNSCHSACESCACYN-LYGWTCRCFDITDF CYKPCSG), BBIt-VEGK (SEQ ID NO:640; DPDDESSKPC-CDQCICTKSNPPQCRCRDARPNACH-SACKSCACKYYLYWWCKCTDIT DFCYEPCKPSE), BBIt-VEGT (SEQ ID NO:641; DPDDESSKPC-CDQCICTKSNPPQCRCRDARPNACH-SACKSCACTLWKSYW CKCTDITDFCYEPCKPSE) and BBIt-VEGKD (SE ID NO:642; DPDDESSKPC-CDQCICTKSNPPQCRCRDARPNACH-SACKSCACKYDLYWWCKCTDIT DFCYEPCKPSE).

In some embodiments, unmodified variant precursor scaffolds are variant scaffolds in which a variant peptide replaces the chymotrypsin loop of the wild-type BBPI and which also introduces a substitution of the amino acid at the position equivalent to position 40 of the BBPI of SEQ ID NO:187. For example, the unmodified variant BBPI scaffold of SEQ ID NO:187 (BBIt-AV) was derived from the wild-type precursor scaffold of SEQ ID NO:185 by replacing the chymotrypsin loop of SEQ ID NO:185 with the VEGF variant peptide of SEQ ID NO:9, which introduces an amino acid substitution I40A in addition to replacing the chymotrypsin loop. The unmodified variant BBPI of SEQ ID NO:187 is modified to generate a modified variant BBPI, which in addition to the replaced chymotrypsin loop, comprises at least one amino acid substitution as described below.

Although numerous isoforms of BBI have been characterized, SEQ ID NO:13 is an example of the amino acid sequence of the wild-type BBI scaffold used in some embodiments comprising approximately 71 amino acid residues (See Example 1). In some embodiments, the invention provides for BBPI scaffolds e.g. SEQ ID NO:11, that include the pro region, while in other embodiments, the invention provides for BBI scaffolds from which the pro peptide has been removed e.g. SEQ ID NO:185. In yet other embodiments, the invention provides for BBI scaffolds from which up to 10 amino acids have been removed from the N- or C-terminus. In some embodiments, the invention provides for BBI scaffolds from which up to 5 e.g. SEQ ID NO:187. It will be appreciated that truncations of the BBI scaffold will not destroy the ability of the BBI to bind the target protein.

In soybeans, BBPIs e.g. BBI is produced as a pro-protein with an N-terminal pro-peptide that is 19 amino acids in length. Thus, in some embodiments, BBI is produced with all or at least a portion of the propeptide. In some embodiments, BBI is truncated, with as many as 10 amino acid residues being removed from either the N- or C-terminal. For example, upon seed desiccation, some BBPI molecules have the C-terminal 9 or 10 amino acid residues removed. Thus, proteolysis is generally highly tolerated prior to the initial disulfide and just after the terminal disulfide bond, the consequences of which are usually not detrimental to the binding to target protein. However, it will be appreciated that any one of the isoforms or truncated forms a BBPI find use in various embodiments of the present invention. In some embodiments, the truncated form of BBPI that finds use in the present invention is the variant BBIt in which the chymotrypsin loop is replaced with a variant sequence as described below.

5.3 Variant BBPIs

As indicated above, BBPIs have binding loops (i.e. trypsin and chymotrypsin loops) that inhibit proteases. The present invention provides variant BBPIs, which are derived from wild-type or from unmodified variant BBPI precursor scaffolds in which one or more reactive sites (e.g., Loop I (trypsin) and/or Loop II (chymotrypsin) of BBPIs have been replaced with variant peptides that bind a target protein. Non-limiting examples of target proteins that are bound by variant peptides comprised in the BBPIs of the invention include various cytokines, including cytokines of the tumor necrosis factor (TNF) family, particularly TNF-α; cytokines of the transforming growth factor family, particularly TGFβ; cytokines of the fibroblast growth factor family (FGF), particularly FGF-5, and cytokines of the vascular endothelial growth factor (VEGF) family, particularly VEGF-A. In addition, variant peptides that replace one or both loops of the BBPIs of the invention include peptides that interact with inhibitors of the complement pathway such as C2, C3, C4 or C5 inhibitors, Compstatin, and other proteins of interest. Indeed, it is not intended that the present invention be limited to any particular sequence substituted into either of these loops, as any suitable sequence finds use in the present invention.

In some embodiments, the trypsin and/or chymotrypsin loop(s) of the BBPI precursor scaffold is replaced with variant sequence that binds VEGF to generate variant VEGF-BBPI proteins. In some embodiments, the variant BBPI is derived from a wild-type or an unmodified variant BBPI precursor scaffold chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds.

In some embodiments, the VEGF variant sequences include, but are not limited to VEGF-binding peptides disclosed in U.S. application Ser. Nos. 09/832,723 and 10/984, 270, including peptides ACYNLYGWTC (SEQ ID NO:9), KYYLYWW (SEQ ID NO:458), TLWKSYW (SEQ ID NO:459), DLYWW (SEQ ID NO:460), SKHSQIT (SEQ ID NO:468) KTNPSGS (SEQ ID NO:469) RPTGHSL (SEQ ID NO:470), KHSAKAE (SEQ ID NO:471) KPSSASS (SEQ ID NO:472), PVTKRVH (SEQ ID NO:473), TLHWWVT (SEQ ID NO:492), PYKASFY (SEQ ID NO:493), PLRTSHT (SEQ ID NO:494), EATPROT (SEQ ID NO:495), NPLHTLS (SEQ ID NO:496), KHERIWS (SEQ ID NO:497), ATNPPPM (SEQ ID NO:498), STTSPNM (SEQ ID NO:499), ADRSFRY (SEQ ID NO:500), PKADSKQ (SEQ ID NO:501), PNQSHLH (SEQ ID NO:502), SGSETWM (SEQ ID NO:503), ALSAPYS (SEQ ID NO:504), KMPTSKV (SEQ ID NO:505), ITPKRPY (SEQ ID NO:506), KWIVSET (SEQ ID NO:507), PNANAPS (SEQ ID NO:508), NVQSLPL (SEQ ID NO:509), TLWPTFW (SEQ ID NO:510), NLWPHFW (SEQ ID NO:511), SLWPAFW (SEQ ID NO:512), SLWPHFW (SEQ ID NO:513), APWNSHI (SEQ ID NO:514), APWNLHI (SEQ ID NO:515), LPSWHLR (SEQ ID NO:516), PTILEWY (SEQ ID NO:517), TLYPQFW (SEQ ID NO:518), and HLAPSAV (SEQ ID NO:519). In some other embodiments, the VEGF variant sequences include, but are not limited to VEGF-binding peptides disclosed in U.S. application Ser. No. 11/919,717, including peptides KYYLSWW (SEQ ID NO:520), WYTLYKW (SEQ ID NO:521), TYRLYWW (SEQ ID NO:522), RYSLYYW (SEQ ID NO:523), YYLYYWK (SEQ ID NO:524), NYQLYGW (SEQ ID NO:525), TKWPSYW (SEQ ID NO:226), TLWKSYW (SEQ ID NO:527), PLWPSYW (SEQ ID NO:528), RLWPSYW (SEQ ID NO:529), TLWPKYW (SEQ ID NO:530), KYDLYWW (SEQ ID NO:531), RYDLYWW (SEQ ID NO:532), DYRLYWW (SEQ ID NO:533), DYKLYWW (SEQ ID NO:534), EYKLYWW (SEQ ID NO:535), and RYPLYWW (SEQ ID NO:536).

In some embodiments, the trypsin and/or chymotrypsin loop(s) of the BBPI precursor scaffold is replaced with variant sequences that interact with FGF5 to generate variant FGF-BBPI proteins. In some embodiments, the variant BBPI is derived from a wild-type or an unmodified variant BBPI precursor scaffold chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds.

In some embodiments, the trypsin and/or chymotrypsin loop(s) of the BBPI precursor scaffold is replaced with variant sequences that interact with FGF5. In some embodiments, the FGF5 variant sequences include, but are not limited to FGF5-binding peptides disclosed in U.S. application Ser. Nos. 10/984,410 and 12/033,848, including peptides CACRTQPYPLCF (MM007; SEQ ID NO:430), CICTWIDSTPC (PS2; SEQ ID NO:431), CYGLPFTRC (SEQ ID NO:537), CEEIWTMLC (SEQ ID NO:538), CWALTVKTC (SEQ ID NO:539), CLTVLWTTC (SEQ ID NO:540), CTLWNRSPC (SEQ ID NO:541), CHYLLTNYC (SEQ ID NO:542), CRIHLAHKC (SEQ ID NO:543), TNIDSTP (SEQ ID NO:544), HLQTTET (SEQ ID NO:545), SLNNLTV (SEQ ID NO:546), TNIDSTP (SEQ ID NO:547), TNIDSTP (SEQ ID NO:548), LRILANK (SEQ ID NO:549), LLTPTLN (SEQ ID NO:550), ALPTHSN (SEQ ID NO:551), TNIDSTP (SEQ ID NO:552), LCRRFEN (SEQ ID NO:553), TNIDSTP (SEQ ID NO:554), TNIDSTP (SEQ ID NO:555), HLQTTET (SEQ ID NO:556), PLGLCPP (SEQ ID NO:557), GYFIPSI (SEQ ID NO:558), TKIDSTP (SEQ ID NO:559), HLQTTET (SEQ ID NO:560), WNIDSTP (SEQ ID NO:561), TWIDWTP (SEQ ID NO:562), RTQPYPL (SEQ ID NO:670) and TWIDSTP (SEQ ID NO:671).

In some embodiments, the trypsin and/or chymotrypsin loop(s) of the BBPI precursor scaffold is replaced with variant sequences that interact with TGFβ to generate variant TGF-BBPIs. In some embodiments, the variant BBPI is derived from a wild-type or an unmodified variant BBPI precursor scaffold chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds.

In some embodiments, the trypsin and/or chymotrypsin loop(s) of the BBPI precursor scaffold is replaced with variant sequences that interact with TGFβ. In some embodiments, the TGFβ variant sequences include, but are not limited to TGFβ-binding peptides disclosed in U.S. application Ser. No. 10/581,142, including peptides CLCPENINVLPCN (PEN3; SEQ ID NO:436), CICKHNVDWLCF (MMO21W; SEQ ID NO:437), CICWTQHIHNCF (WTQ; SEQ ID NO:438), CVTTDWIEC (SEQ ID NO:563), CYYSQFHQC (SEQ ID NO:564), CPTLWTHMC (SEQ ID NO:565), QSACIVYYVGRKPKVECASSD (SEQ ID NO:566), QSACILYYIGKTPKIECASSD (SEQ ID NO:567), QSACILYYVGRTPKVECASSD (SEQ ID NO:568), acetyl-LCPENDNVSPCY-cohn2 (SEQ ID NO:569), KHNVRLL (SEQ ID NO:570), NDTPSYF (SEQ ID NO:571), AKLYAGS (SEQ ID NO:572), RGPAHSL (SEQ ID NO:573), NSLAERR (SEQ ID NO:574), HPLASPH (SEQ ID NO:575), QPWNKLK (SEQ ID NO:576), AWLr/Mipy (SEQ ID NO:577), PTKPAQQ (SEQ ID NO:578), PSLNRPQ (SEQ ID NO:579), HHARQEW (SEQ ID NO:580), RHHTPGP (SEQ ID NO:581), ASAINPH (SEQ ID NO:582), CHGYDRAPC (SEQ ID NO:644), CFAPADQAC (SEQ ID NO:645), CIPSRFITC (SEQ ID NO:646), CHGHTKLAC (SEQ ID NO:647), CNGKSKLAC (SEQ ID NO:648), PENINVLP (SEQ ID NO:672), KHNVDWL (SEQ ID NO:673) and WTQHIHNC (SEQ ID NO:674).

In some embodiments, the trypsin and/or chymotrypsin loop(s) of the BBPI precursor scaffold is replaced with variant sequences that interact with TNFα to generate variant TNF-BBPIs. In some embodiments, the variant BBPI is derived from a wild-type or an unmodified variant BBPI precursor scaffold chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea* (*Amburana*) *cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds.

In some embodiments, the trypsin and/or chymotrypsin loop(s) of the BBPI precursor scaffold is replaced with variant sequences that bind TNFα. In some embodiments, the TNFα binding sequences include, but are not limited to TNF-binding peptides disclosed in U.S. application Ser. No. 10/968,732, including peptides RYWQDIP (T1; SEQ ID NO:474), APEPILA (T2; SEQ ID NO:475), DMIMVSI (T3; SEQ ID NO:476), WTPKPTQ (SEQ ID NO:583), ATFPNQS (SEQ ID NO:584), ASTVGGL (SEQ ID NO:585), TMLPYRP (SEQ ID NO:586), AWHSPSV (SEQ ID NO:587), TQSFSS (SEQ ID NO:588), THKNTLR (SEQ ID NO:589), GQTHFHV (SEQ ID NO:590), LPILTQT (SEQ ID NO:591), SILPVSH (SEQ ID NO:592), SQPIPI (SEQ ID NO:593), and QPLRKLP (SEQ ID NO:594).

In some embodiments, the variant BBPIs further comprises a peptide insert that is positioned at the N-terminus of the modified variant BBPI. In some embodiments, the peptide insert comprises a sequence of between 1 and 15 amino acids. In other embodiments, the peptide insert comprises a sequence between 5 and 10 amino acids. In some embodiments, the peptide insert comprises the peptide of SEQ ID NO:389 (DDEPSKPCCDPDP; SEQ ID NO:389). Examples of modified variant BBPIs that comprise the peptide insert of SEQ ID NO:389 are the modified variant 4D13BBIt-AV of (DDEPSKPCCDPDPDDESSKPCCDQ-CACTKSNPPQCRCSDMRLNSCHSACKSCACY NLYG-WTCFCVDITDFCYEPCKPSE; SEQ ID NO:390), and the modified variant BBIt-AV-4D13-13I-29P-40K-50T-52A of SEQ ID NO: 413 (DPDDEPSKPCCDPDPDDESSKPC-CDQCICTKSNPPQCRCSDMRPNSCHSACKSCKC YNLYGWTCTCADITDFCYEPCKPSE; SEQ ID NO:413).

In some embodiments, variant sequences are selected by various methods known in the art, including but not limited to phage display and other suitable screening methods. For example, a random peptide gene library is fused with phage PIII gene so the peptide library will be displayed on the surface of the phage. Subsequently, the phage display library is exposed to the target protein and washed with buffer to remove non-specific binding (this process is sometimes referred to as panning). Finally, the binding phage and PCR the DNA sequence for the peptide encoded are isolated.

In most embodiments, one of the loops is replaced with a variant sequence i.e., peptides often 3 to 14 amino acids in length, with 5 to 10 amino acids being preferred, to generate the variant BBPI. Longer sequences find use in the present invention, as long as they provide the binding and/or inhibition desired. In addition, peptides suitable for use as replacements of the binding loop(s) preferably adopt a functional conformation when contained within a constrained loop (i.e., a loop formed by the presence of a disulfide bond between two cysteine residues). In some specific embodiments, the peptides are between 7 and 9 amino acids in length. In other embodiments, the variant sequences are peptides of 10 amino acids in length.

5.4 Modified Variant BBPI Protiens 5.4.1 Modified Variant BBPIS: Single Amino Acid Substitutions In some embodiments, the invention provides for modified variant BBPIs, which are variant BBPIs that further comprise at least one amino acid substitution in the backbone of the BBPI. Thus, in some embodiments, modified variant BBPIs are variant BBPIs that contain trypsin and/or chymotrypsin loop(s) that have been replaced by a variant sequence that binds to a target protein, and that are further altered by comprising at least one amino acid substitution C-terminal and/or N-terminal to the replaced loop. Thus, in some embodiments, modified variant BBPIs are the variant BBPIs described in section 5.4 in which the trypsin and/or chymotrypsin loop(s) has been replaced by a variant peptide, but that further comprise a substituted amino acid at least at one position equivalent to a position chosen from positions equivalent to positions 1, 4, 5, 11, 13, 18, 25, 27, 29, 31, 38, 40, 50, 52, 55, and 65 of SEQ ID NO:187, as described in section 5.4.

An amino acid residue of a modified variant BBPI is at an equivalent to the position of a residue of a precursor BBPI if it is homologous (i.e. corresponding in position in primary structure) to a specific residue. In order to establish homology to primary structure, the amino acid sequence of a precursor BBPI is directly compared to the primary amino acid sequence, and particularly to the set of cysteine residues known to be conserved in BBPIs for which the sequence is known. FIG. 17 shows the conserved cysteine residues among exemplary wild type and variant precursor BBPIs described herein. Equivalent residues that are substituted in the modified variant BBPIs of the invention are numbered.

The precursor BBPI may be a naturally-occurring BBPI or a variant BBPI. Specifically, such modified variant BBPIs have an amino acid sequence not found in nature, which is derived by replacement of the trypsin and/or chymotrypsin loop of a precursor BBPI and by replacement of at least one amino acid residue of a precursor BBPI with a different amino acid. In some embodiments, the substitution of the at least one amino acid generates a modified variant BBPI that has a greater protease inhibitory activity than that of the unmodified variant precursor BBPI. In other embodiments, substitution of the at least one amino acid generates a modified variant BBPI that has a greater protease inhibitory activity and production yield than that of the unmodified variant precursor BBPI.

Thus, a modified variant BBPI is derived by substituting at least one amino acid in the backbone of any one variant BBPI scaffold as recited herein. In some embodiments, the isolated modified variant Bowman Birk Protease Inhibitor (BBPI) contains a variant peptide that replaces the chymotrypsin loop of the BBPI scaffold and further comprises a substituted amino acid at least at one amino acid position chosen from positions equivalent to 1, 4, 5, 11, 13, 18, 25, 27, 29, 31, 38, 40, 50, 52, 55, and 65 of the variant BBI of SEQ ID NO:187. In other embodiments, the isolated modified variant Bowman Birk Protease Inhibitor (BBPI) contains a variant peptide that replaces the trypsin loop of the BBPI scaffold and further comprises a substituted amino acid at least at one amino acid position chosen from positions equivalent to 1, 4, 5, 11, 13, 18, 25, 27, 29, 31, 38, 40, 50, 52, 55, and 65 of the variant BBI of SEQ ID NO:187. In yet other embodiments, the isolated modified variant Bowman Birk Protease Inhibitor (BBPI) contains a variant peptide that replaces the trypsin and the chymotrypsin loop of the BBPI scaffold and further comprises a substituted amino acid at least at one amino acid position chosen from positions equivalent to 1, 4, 5, 11, 13, 18, 25, 27, 29, 31, 38, 40, 50, 52, 55, and 65 of the variant BBI of SEQ ID NO:187. In some embodiments, the BBPI scaffold chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SEQ ID NO:642). In some embodiments, the variant peptide comprised in the modified variant BBPI is chosen from a VEGF-binding peptide, an FGF-5-binding peptide, a TGFβ-binding peptide and a TNFα-binding peptide. In some embodiments, the VEGF-binding sequences include, but are not limited to VEGF-binding peptides disclosed in U.S. application Ser. Nos. 09/832,723 and 10/984,270, including peptides ACYNLYGWTC (SEQ ID NO:9), KYYLYWW (SEQ ID NO:458), TLWKSYW (SEQ ID NO:459), DLYWW (SEQ ID NO:460), SKHSQIT (SEQ ID NO:468) KTNPSGS (SEQ ID NO:469) RPTGHSL (SEQ ID NO:470), KHSAKAE (SEQ ID NO:471) KPSSASS (SEQ ID NO:472), PVTKRVH (SEQ ID NO:473), TLHWWVT (SEQ ID NO:492), PYKASFY (SEQ ID NO:493), PLRTSHT (SEQ ID NO:494), EATPROT (SEQ ID NO:495), NPLHTLS (SEQ ID NO:496), KHERIWS (SEQ ID NO:497), ATNPPPM (SEQ ID NO:498), STTSPNM (SEQ ID NO:499), ADRSFRY (SEQ ID NO:500), PKADSKQ (SEQ ID NO:501), PNQSHLH (SEQ ID NO:502), SGSETWM (SEQ ID NO:503), ALSAPYS (SEQ ID NO:504), KMPTSKV (SEQ ID NO:505), ITPKRPY (SEQ ID NO:506), KWIVSET (SEQ ID NO:507), PNANAPS (SEQ ID NO:508), NVQSLPL (SEQ ID NO:509), TLWPTFW (SEQ ID NO:510), NLWPHFW (SEQ ID NO:511), SLWPAFW (SEQ ID NO:512), SLWPHFW (SEQ ID NO:513), APWNSHI (SEQ ID NO:514), APWNLHI (SEQ ID NO:515), LPSWHLR (SEQ ID NO:516), PTILEWY (SEQ ID NO:517), TLYPQFW (SEQ ID NO:518), and HLAPSAV (SEQ ID NO:519). In some other embodiments, the VEGF variant sequences include, but are not limited to VEGF-binding peptides disclosed in U.S. application Ser. No. 11/919,717, including peptides KYYLSWW (SEQ ID NO:520), WYTLYKW (SEQ ID NO:521), TYRLYWW (SEQ ID NO:522), RYSLYYW (SEQ ID NO:523), YYLYYWK (SEQ ID NO:524), NYQLYGW (SEQ ID NO:525), TKWPSYW (SEQ ID NO:226), TLWKSYW (SEQ ID NO:527), PLWPSYW (SEQ ID NO:528), RLWPSYW (SEQ ID NO:529), TLWPKYW (SEQ ID NO:530), KYDLYWW (SEQ ID NO:531), RYDLYWW (SEQ ID NO:532), DYRLYWW (SEQ ID NO:533), DYKLYWW (SEQ ID NO:534), EYKLYWW (SEQ ID NO:535), and RYPLYWW (SEQ ID NO:536).

In other embodiments, the FGF5-binding sequences include, but are not limited to FGF5-binding peptides disclosed in U.S. application Ser. No. 10/984,410 and 12/033,848, including peptides CACRTQPYPLCF (MM007; SEQ ID NO:430), CICTWIDSTPC (PS2; SEQ ID NO:431), CYGLPFTRC (SEQ ID NO:537), CEEIWTMLC (SEQ ID NO:538), CWALTVKTC (SEQ ID NO:539), CLTVLWTTC (SEQ ID NO:540), CTLWNRSPC (SEQ ID NO:541), CHYLLTNYC (SEQ ID NO:542), CRIHLAHKC (SEQ ID NO:543), TNIDSTP (SEQ ID NO:544), HLQTTET (SEQ ID NO:545), SLNNLTV (SEQ ID NO:546), TNIDSTP (SEQ ID NO:547), TNIDSTP (SEQ ID NO:548), LRILANK (SEQ ID NO:549), LLTPTLN (SEQ ID NO:550), ALPTHSN (SEQ ID NO:551), TNIDSTP (SEQ ID NO:552), LCRRFEN (SEQ ID NO:553), TNIDSTP (SEQ ID NO:554), TNIDSTP (SEQ ID NO:555), HLQTTET (SEQ ID NO:556), PLGLCPP (SEQ ID NO:557), GYFIPSI (SEQ ID NO:558), TKIDSTP (SEQ ID NO:559), HLQTTET (SEQ ID NO:560), WNIDSTP (SEQ ID NO:561), TWIDWTP (SEQ ID NO:562), RTQPYPL (SEQ ID NO:670) and TWIDSTP (SEQ ID NO:671).

In other embodiments, the variant peptide is a TGF-β-binding peptide is chosen from TGFβ-binding sequences that include, but are not limited to TGFβ-binding peptides disclosed in U.S. application Ser. No. 10/581,142, including peptides CLCPENINVLPCN (PEN3; SEQ ID NO:436), CICKHNVDWLCF (MMO21W; SEQ ID NO:437), CICWTQHIHNCF (WTQ; SEQ ID NO:438), CVTTDWIEC (SEQ ID NO:563), CYYSQFHQC (SEQ ID NO:564), CPTLWTHMC (SEQ ID NO:565), QSACIVYYVGRKP-KVECASSD (SEQ ID NO:566), QSACILYYIGKTPK-IECASSD (SEQ ID NO:567), QSACILYYVGRTPKVE-CASSD (SEQ ID NO:568), acetyl-LCPENDNVSPCY-cohn2 (SEQ ID NO:569), KHNVRLL (SEQ ID NO:570), NDTPSYF (SEQ ID NO:571), AKLYAGS (SEQ ID NO:572), RGPAHSL (SEQ ID NO:573), NSLAERR (SEQ ID NO:574), HPLASPH (SEQ ID NO:575), QPWNKLK (SEQ ID NO:576), AWLr/Mipy (SEQ ID NO:577), PTK-PAQQ (SEQ ID NO:578), PSLNRPQ (SEQ ID NO:579), HHARQEW (SEQ ID NO:580), RHHTPGP (SEQ ID NO:581), ASAINPH (SEQ ID NO:582), CHGYDRAPC (SEQ ID NO:644), CFAPADQAC (SEQ ID NO:645), CIPSRFITC (SEQ ID NO:646), CHGHTKLAC (SEQ ID NO:647), CNGKSKLAC (SEQ ID NO:648), PENINVLP (SEQ ID NO:672), KHNVDWL (SEQ ID NO:673) and WTQHIHNC (SEQ ID NO:674).

In yet other embodiments, the variant peptide is a TNFα-binding peptide is chosen from TNFα binding sequences that include, but are not limited to TNF-binding peptides disclosed in U.S. application Ser. No. 10/968,732, including peptides RYWQDIP (T1; SEQ ID NO:474), APEPILA (T2; SEQ ID NO:475), DMIMVSI (T3; SEQ ID NO:476), WTPKPTQ (SEQ ID NO:583), ATFPNQS (SEQ ID NO:584), ASTVGGL (SEQ ID NO:585), TMLPYRP (SEQ ID NO:586), AWHSPSV (SEQ ID NO:587), TQSFSS (SEQ ID NO:588), THKNTLR (SEQ ID NO:589), GQTHFHV (SEQ ID NO:590), LPILTQT (SEQ ID NO:591), SILPVSH (SEQ ID NO:592), SQPIPI (SEQ ID NO:593), and QPLRKLP (SEQ ID NO:594).

In some embodiments, the at least one amino acid substitution contained at least one equivalent to a position chosen from positions equivalent to positions 1, 4, 5, 11, 13, 18, 25, 27, 29, 31, 38, 40, 50, 52, 55, and 65 of SEQ ID NO:187 result in the following substituted amino acids. In one embodiment, the substituted amino acid at the amino acid position equivalent to position 1 of SEQ ID NO:187 is chosen from A and C. In another embodiment, the substituted amino acid at the amino acid position equivalent to position 4 of SEQ ID NO:187 is V. In another embodiment, the substituted amino acid at the amino acid position equivalent to position 5 of SEQ ID NO:187 is chosen from P, and A. In another embodiment, the substituted amino acid at the amino acid position equivalent to position 11 of SEQ ID NO:187 is G. In another embodiment, the substituted amino acid at the amino acid position equivalent to position 13 of SEQ ID NO:187 is chosen from Y, I, F, M, L, V, K, and R. In another embodiment, the substituted amino acid at the amino acid position equivalent to position 18 of SEQ ID NO:187 include 1, V and L. In another embodiment, the substituted amino acid at the amino acid position equivalent to position 25 of SEQ ID NO:187 is chosen from K, N, W, I, A and R. In another embodiment, the substituted amino acid at the amino acid position equivalent to position 27 of SEQ ID NO:187 include R, K, V, A, and Q. In another embodiment, the substituted amino acid at the amino acid position equivalent to position 29 of SEQ ID NO:187 is chosen from R, K, and P. In another embodiment, the substituted amino acid at the amino acid position equivalent to position 31 of SEQ ID NO:187 is chosen from Q, H, E, A, R, W, K and T. In another embodiment, the substituted amino acid at the amino acid position equivalent to position 38 of SEQ ID NO:187 is chosen from N, K and R. In another embodiment, the substituted amino acid at the amino acid position equivalent to position 40 of SEQ ID NO:187 is chosen from H, K, Q, R, and Y. In another embodiment, the substituted amino acid at the amino acid position equivalent to position 50 of SEQ ID NO:187 is chosen from R, Q, K, T, V, M, and S. In another embodiment, the substituted amino acid at the amino acid position equivalent to position 52 of SEQ ID NO:187 is chosen from K, T, R, Q, L, H, A, M, S and E. In another embodiment, the substituted amino acid at the amino acid position equivalent to position 55 of SEQ ID NO:187 is M. In another embodiment, the substituted amino acid at the amino acid position equivalent to position 65 of SEQ ID NO:187 is chosen from E, Q, and D. In some embodiments, a single amino acid substitution made in a variant BBPI results in a modified variant BBPI that has a greater protease inhibitory activity than that of the precursor unmodified variant BBPI. In some embodiments, a single amino acid substitution generates a modified variant BBPI that has greater trypsin inhibitory activity (TIA) than the unmodified precursor variant BBPI; while in other embodiments, a single amino acid substitution generates a modified variant BBPI that has greater chymotrypsin inhibitory activity (CIA) than the unmodified precursor variant BBPI.

In one embodiment, the modified variant BBPI is the variant BBI of SEQ ID NO:187 (BBIt-AV; FIG. 9), which contains a VEGF variant peptide in place of the chymotrypsin loop, and which is further modified to contain an amino acid substitution at least at one position chosen from positions 1, 4, 5, 11, 13, 18, 25, 27, 29, 31, 38, 40, 50, 52, 55, and 65 of SEQ ID NO:187 to generate a modified variant BBI. Any one of the single amino acid substitutions described above and made in the variant BBIt-AV BBPI of SEQ ID NO:187 generated modified variant BBIt-AV BBPIs that have greater trypsin inhibitory activity than the unmodified precursor variant BBIt-AV (SEQ ID NO:187; see Example 10).

5.4.2 Modified Variant BBPIs: Combinations of Amino Acid Substitutions

The invention encompasses modified variant BBPIs comprising at least two, at least three, at least four, at least five, at least six, at least seven, at least eight, at least nine, at least ten, at least eleven, at least twelve, at least thirteen, at least fourteen, at least fifteen and at least sixteen amino acid substitutions. In some embodiments, the at least two, at least three, at least four, at least five, at least six, at least seven, at least eight amino, at least nine, at least ten, at least eleven, at least twelve, at least thirteen, at least fourteen, at least fifteen and at least sixteen acid substitutions generate modified variant BBPIs that have greater TIA than the unmodified precursor variant BBPI. In other embodiments, the at least two, at least three, at least four, at least five, at least six, at least seven, at least eight, amino acid substitutions generate modified variant BBPIs that have greater TIA and production yield than the unmodified precursor variant BBPI.

In some embodiments, the modified variant BBPI comprises a combination of two amino acid substitutions at amino acids at positions equivalent to positions 50 and 52 of SEQ ID NO:187. In some embodiments, the combination of two amino acid substitutions is 50T-52A. The invention provides for any one of the variant BBPI scaffolds described in Section 5.3 and further comprising the combination of the two amino acid substitutions 50T-52A, as described in section 5.4. In one embodiment, the chymotrypsin loop of the variant scaffold is a VEGF variant peptide e.g. SEQ ID NO:9, and the variant scaffold is altered further to comprise a combination of three amino acid substitutions at positions equivalent to positions 13, 50 and 52 of SEQ ID NO:187 to generate a modified variant BBPI scaffold. In one embodiment, the modified variant BBPI comprising a combination of two amino acid substitutions is the modified variant BBIt-AV-F50T-V52A of SEQ ID NO: 595 (DPDDESSKPCCDQCACTKSNP-PQCRCSDMRLNSCHSACKSCACYNLYGWTCTCADI TDFCYEPCKPSE; SEQ ID NO:595).

In some embodiments, the modified variant BBPI comprises a combination of three amino acid substitutions at amino acids at positions equivalent to positions 13, 50 and 52 of SEQ ID NO:187. In some embodiments, the combination of three amino acid substitutions is chosen from a combination of substitutions at positions 25-50-52, 29-50-52, 40-50-52, and 13-50-52. In some embodiments, the combination of three amino acid substitutions is chosen from 25L-50T-52A, 29P-50T-52A, 40K-50T-52A and 13I-50T-52A. The invention provides for any one of the variant BBPI scaffolds described in Section 5.3 and further comprising the combination of the three amino acid substitutions chosen from 25L-50T-52A, 29P-50T-52A, 40K-50T-52A and 13I-50T-

52A, as described in section 5.4. In one embodiment, the chymotrypsin loop of the variant scaffold is a VEGF variant peptide e.g. SEQ ID NO:9, and the variant scaffold is altered further to comprise a combination of three amino acid substitutions at positions equivalent to positions 13, 50 and 52 of SEQ ID NO:187 to generate a modified variant BBPI scaffold. In one embodiment, the modified variant BBPI comprising a combination of three amino acid substitutions is chosen from the modified variant BBIt-AV-S25L-F50T-V52A of SEQ ID NO: 603 (DPDDESSKPCCDQCACTKSNPPQCR-CLDMRLNSCHSACKSCACYNLYGWTCTCADI TDF-CYEPCKPSE; SEQ ID NO:603), the modified variant BBIt-AV-L29P-F50T-V52A of SEQ ID NO:607 (DPDDESSKPCCDQCACTKSNPPQCRCSD-MRPNSCHSACKSCACYNLYGWTCTCADI TDF-CYEPCKPSE; SEQ ID NO:607), and the modified variant BBIt-AV-A40K-F50T-V52A of SEQ ID NO:609 (DPD-DESSKPCCDQCACTKSNPPQCRCSDM-RLNSCHSACKSCKCYNLYGWTCTCADI TDF-CYEPCKPSE; SEQ ID NO:609).

In some embodiments, the modified variant BBPI comprises a combination of four amino acid substitutions at amino acids at positions equivalent to positions 13, 29, 50 and 52 of SEQ ID NO:187. In some embodiments, the combination of four amino acid substitutions is chosen from a combination of substitutions at positions 13-25-50-52, 13-29-50-52, 25-29-50-52, 13-40-50-52, 25-40-50-52, and 29-40-50-52. In some embodiments, the combination of four amino acid substitutions is chosen from 13I-25L-50T-52A, 13I-29P-50T-52A, 25L-29P-50T-52A, 13I-40K-50T-52A, 25L-40K-50T-52A, and 29P-40K-50T-52A. The invention provides for any one of the variant BBPI scaffolds described in Section 5.3 and further comprising the combination of the four amino acid substitutions chosen from 13I-25L-50T-52A, 13I-29P-50T-52A, 25L-29P-50T-52A, 13I-40K-50T-52A, 25L-40K-50T-52A, and 29P-40K-50T-52A, as described in section 5.4. In one embodiment, the chymotrypsin loop of the variant scaffold is a VEGF variant peptide chosen from SEQ ID NO:9 and 460, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-AV-A13I-S25L-F50T-V52A of SEQ ID NO:596 (DPDDESSKPCCDQCICTKSNPPQCRCLD-MRLNSCHSACKSCACYNLYGWTCTCADIT DFCYEPCKPSE; SEQ ID NO:596), the modified variant BBIt-AV-A13I-L29P-F50T-V52A of SEQ ID NO:600 (DPD-DESSKPCCDQCICTKSNPPQCRCSDMRP-NSCHSACKSCACYNLYGWTCTCADI TDF-CYEPCKPSE; SEQ ID NO:600), the modified variant BBIt-AV-A13I-A40K-F50T-V52A of SEQ ID NO:602 (DPDDESSKPCCDQCICTKSNPPQCRCSD-MRLNSCHSACKSCKCYNLYGWTCTCADIT DFCYEPCKPSE; SEQ ID NO:602), the modified variant BBIt-AV-S25L-L29P-F50T-V52A of SEQ ID NO:604 (DP-DDESSKPCCDQCACTKSNPPQCRCLDMR-PNSCHSACKSCACYNLYGWTCTCADI TDF-CYEPCKPSE; SEQ ID NO:604), the modified variant BBIt-AV-S25L-A40K-F50T-V52A of SEQ ID NO:606 (DPDDESSKPCCDQCACTKSNPPQCRCLD-MRLNSCHSACKSCKCYNLYGWTCTCADI TDF-CYEPCKPSE; SEQ ID NO:606), the modified variant BBIt-AV-L29P-A40K-F50T-V52A of SEQ ID NO:608 (DPDDESSKPCCDQCACTKSNPPQCRCSD-MRPNSCHSACKSCKCYNLYGWTCTCADI TDF-CYEPCKPSE; SEQ ID NO:608), and the modified variant BBIt-VEGKD-A13I-S25K-L29P-V52K of SEQ ID NO:643 (DPDDESSKPCCDQCICTKSNPPQCRC KDMRPN-SCHSACKSCICKYDLYWWCFCKDITDFCYEPCKPS E; SEQ ID NO:643). In another embodiment, the chymotrypsin loop of the variant scaffold is an FGF5 variant peptide chosen from SEQ ID NOS:430 and 431, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-MM007-Q-A13I-L29P-F50T-V52A of SEQ ID NO:432, and the modified variant BBIt-FGFps2-Q-A13I-L29P-F50T-V52A of SEQ ID NO:434. In another embodiment, the chymotrypsin loop of the variant scaffold is a TGFβ variant peptide chosen from SEQ ID NOS:436, 437, 438, 672, 673, and 674 and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-PEN3-Q-A13I-L29P-F50T-V52A of SEQ ID NO:443, the modified variant BBIt-MM021W-Q-A13I-L29P-F50T-V52A of SEQ ID NO:445, and the modified variant BBIt-WTQ-Q-A13I-L29P-F50T-V52A of SEQ ID NO:447.

In some embodiments, the modified variant BBPI comprises a combination of five amino acid substitutions at amino acids at positions equivalent to positions 13, 29, 40, 50 and 52 of SEQ ID NO:187. In some embodiments, the combination of five amino acid substitutions is chosen from a combination of substitutions at positions 13-25-29-50-52, 13-29-40-50-52, 13-25-40-50-52, 25-29-40-50-52, and 13-29-40-50-52. In some embodiments, the combination of five amino acid substitutions is chosen from 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A and 13I-29P-40K-50T-52T. The invention provides for any one of the variant BBPI scaffolds described in Section 5.3 and further comprising the combination of the five amino acid substitutions chosen from 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A and 13I-29P-40K-50T-52T, as described in section 5.4. In one embodiment, the chymotrypsin loop of the variant scaffold is a VEGF variant peptide of SEQ ID NO:9, and the variant scaffold is altered further to comprise a combination of five amino acid substitutions at positions equivalent to positions 13, 29, 40, 50 and 52 of SEQ ID NO:187 to generate a modified variant BBPI scaffold. In one embodiment, the modified variant BBPI comprising a combination of five amino acid substitutions is chosen from the modified variant BBIt-AV-A13I-S25L-L29P-F50T-V52A of SEQ ID NO:597 (DPDDESSKPCCDQCICTKSNPPQCRCLD-MRPNSCHSACKSCACYNLYGWTCTCADIT DFCYEPCKPSE; SEQ ID NO:597), the modified variant BBIt-AV-A13I-L29P-A40K-F50T-V52A of SEQ ID NO:599 (DPDDESSKPCCDQCICTKSNPPQCRCLD-MRLNSCHSACKSCKCYNLYGWTCTCADIT DFCYEPCKPSE; SEQ ID NO:599), the modified variant BBIt-AV-A13I-S25L-A40K-F50T-V52A of SEQ ID NO:601

(DPDDESSKPCCDQCICTKSNPPQCRCSD-MRPNSCHSACKSCKCYNLYGWTCTCADI TDF-CYEPCKPSE; SEQ ID NO:601), the modified variant BBIt-AV-S25L-L29P-A40K-F50T-V52A of SEQ ID NO:605 (DPDDESSKPCCDQCACTKSNPPQCRCLD-MRPNSCHSACKSCKCYNLYGWTCTCADI TDF-CYEPCKPSE; SEQ ID NO:605), the modified variant BBIt-AV-A13L-L29P-A40K-F50T-V52A of SEQ ID NO:615 (DPDDESSKPCCDQCLCTKSNPPQCRCSD-MRPNSCHSACKSCKCYNLYGWTCTCADI TDF-CYEPCKPSE; SEQ ID NO:615), the modified variant BBIt-AV-A13I-L29K-A40K-F50T-V52A of SEQ ID NO:620 (DPDDESSKPCCDQCICTKSNPPQCRCSD-MRKNSCHSACKSCKCYNLYGWTCTCADI TDF-CYEPCKPSE; SEQ ID NO:620), the modified variant BBIt-AV-A13I-L29P-A40K-F50K-V52A of SEQ ID NO:624 (DPDDESSKPCCDQCICTKSNPPQCRCSD-MRPNSCHSACKSCKCYNLYGWTCKCADI TDF-CYEPCKPSE; SEQ ID NO:624), and the modified variant BBIt-AV-A13I-L29P-A40K-F50T-V52T of SEQ ID NO:625 (DPDDESSKPCCDQCICTKSNPPQCRCSD-MRPNSCHSACKSCKCYNLYGWTCTCTDI TDF-CYEPCKPSE; SEQ ID NO:625).

In some embodiments, the modified variant BBPI comprises a combination of six amino acid substitutions at amino acids at positions equivalent to positions 13, 25, 29, 40, 50 and 52 of SEQ ID NO:187. In some embodiments, the combination of six amino acid substitutions is chosen from a combination of substitutions at positions 13-25-29-40-50-52, 1-13-29-40-50-52, 4-13-29-40-50-52, 5-13-29-40-50-52, 11-13-29-40-50-52, 13-25-29-40-50-52, 13-27-29-40-50-52, 13-29-31-40-50-52, 13-29-31-40-50-52, 13-29-38-40-50-52, and 13-29-38-40-50-52. In some embodiments, the combination of six amino acid substitutions is chosen from 13I-25L-29P-40K-50T-52A, 1C-13I-29P-40K-50T-52A, 4V-13I-29P-40K-50T-52A, 5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, and 13I-29P-38N-40K-50T-52A. The invention provides for any one of the variant BBPI scaffolds described in Section 5.3 and further comprising the combination of the six amino acid substitutions chosen from 13I-25L-29P-40K-50T-52A, 1C-13I-29P-40K-50T-52A, 4V-13I-29P-40K-50T-52A, 5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, and 13I-29P-38N-40K-50T-52A, as described in section 5.4. In one embodiment, the chymotrypsin loop of the variant scaffold is a VEGF variant peptide of SEQ ID NO:9, and the variant scaffold is altered further to comprise a combination of six amino acid substitutions at positions equivalent to positions 13, 25, 29, 40, 50 and 52 of SEQ ID NO:187 to generate a modified variant BBPI scaffold. In one embodiment, the modified variant BBPI comprising a combination of six amino acid substitutions is chosen from the modified variant BBIt-AV-A13I-S25L-L29P-A40K-F50T-V52A of SEQ ID NO:598 (DPD-DESSKPCCDQCICTKSNPPQCRCLDMRPNSCHSACK-SCKCYNLYGWTCTCADIT DFCYEPCKPSE; SEQ ID NO:598), the modified variant BBIt-AV-D1C-A13I-L29P-A40K-F50T-V52A of SEQ ID NO:611 (DPDDEVSKPC-CDQCICTKSNPPQCRCSDMRPN-SCHSACKSCKCYNLYGWTCTCADI TDFCYEPCKPSE; SEQ ID NO:611), the modified variant BBIt-AV-S4V-A13I-L29P-A40K-F50T-V52A of SEQ ID NO:612 (DPD-DEVSKPCCDQCICTKSNPPQCRCSDMRP-NSCHSACKSCKCYNLYGWTCTCADI TDF-CYEPCKPSE; SEQ ID NO:612), the modified variant BBIt-AV-S5P-A13I-L29P-A40K-F50T-V52A of SEQ ID NO:613 (DPDDESPKPCCDQCICTKSNPPQCRCSD-MRPNSCHSACKSCKCYNLYGWTCTCADI TDF-CYEPCKPSE; SEQ ID NO:613), the modified variant BBIt-AV-Q11G-A13I-L29P-A40K-F50T-V52A of SEQ ID NO:614 (DPDDESSKPCCDGCICTKSNPPQCRCSD-MRPNSCHSACKSCKCYNLYGWTCTCADI TDF-CYEPCKPSE; SEQ ID NO:614), the modified variant BBIt-AV-A13I-S25R-L29P-A40K-F50T-V52A- of SEQ ID NO:616 (DPDDESSKPCCDQCICTKSNPPQCRCRD-MRPNSCHSACKSCKCYNLYGWTCTCADI TDF-CYEPCKPSE; SEQ ID NO:616), the modified variant BBIt-AV-A13I-M27R-L29P-A40K-F50T-V52A of SEQ ID NO:619 (DPDDESSKPCCDQCICTKSNPPQCRCS-DRRPNSCHSACKSCKCYNLYGWTCTCADIT DFCYEPCKPSE; SEQ ID NO:619), the modified variant BBIt-AV-A13I-L29P-S31A-A40K-F50T-V52A of SEQ ID NO:621 (DPDDESSKPCCDQCICTKSNPPQCRCSD-MRPNACHSACKSCKCYNLYGWTCTCADI TDF-CYEPCKPSE; SEQ ID NO:621), the modified variant BBIt-AV-A13I-L29P-S31R-A40K-F50T-V52A of SEQ ID NO:622 (DPDDESSKPCCDQCICTKSNPPQCRCSD-MRPNRCHSACKSCKCYNLYGWTCTCADI TDF-CYEPCKPSE; SEQ ID NO:622), the modified variant BBIt-AV-A13I-L29P-S38N-A40K-F50T-V52A of SEQ ID NO:623 (DPDDESSKPCCDQCICTKSNPPQCRCSD-MRPNSCHSACKNCKCYNLYGWTCTCADI TDF-CYEPCKPSE; SEQ ID NO:623), and the modified variant BBIt-AV-A13I-L29P-S38N-A40K-F50T-V52A of SEQ ID NO:626 (DPDDESSKPCCDQCICTKSNPPQCRCSD-MRPNSCHSACKSCKCYNLYGWTCTCADI TDF-CYEPCKPEE; SEQ ID NO:626).

In some embodiments, the modified variant BBPI comprises a combination of seven amino acid substitutions at amino acids at positions equivalent to positions 13, 25, 29, 31, 40, 50 and 52 of SEQ ID NO:187. In some embodiments, the combination of seven amino acid substitutions is chosen from a combination of substitutions at positions 13-25-29-31-40-50-52, 13-25-29-31-40-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, and 13-25-27-29-31-50-52. In some embodiments, the combination of seven amino acid substitutions is chosen from 13L-25R-29P-31A-40K-50T-52A, 13L-25R-29P-31R-40K-50T-52A, and 13I-25R-27A-29P-31A-50K-52T. The invention provides for any one of the variant BBPI scaffolds described in Section 5.3 and further comprising the combination of the six amino acid substitutions chosen from 13L-25R-29P-31A-40K-50T-52A, 13L-25R-29P-31R-40K-50T-52A, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, and 13I-25R-27A-29P-31A-50K-52T, as described in section 5.4. In one embodiment, the chymotrypsin loop of the variant scaffold is a VEGF variant peptide of SEQ ID NO:9, and the variant scaffold is altered further to comprise a combination of seven amino acid substitutions at positions equivalent to positions 13, 25, 29, 31, 40, 50 and 52 of SEQ ID NO:187 to generate a modified variant BBPI scaffold. In one embodiment, the modified variant BBPI comprising a combination of seven amino acid substitutions is chosen from the modified variant BBIt-AV-A13I-S25R-L29P-S31A-A40K-F50T-V52A of SEQ ID NO:617 (DPDDESSKPCCDQCICTKSNPPQCRCRD-MRPNACHSACKSCKCYNLYGWTCTC ADITDF-CYEPCKPSE ; SEQ ID NO:617), the modified variant BBIt-AV-A13I-S25R-L29P-S31R-A40K-F50T-V52A of SEQ ID NO:618 (DPDDESSKPCCDQCICTKSNPPQCRCRD-MRPNRCHSACKSCKCYNLYGWTCTC ADITDF-CYEPCKPSE; SEQ ID NO:618), the modified variant of BBIt-VEGF-V1-A13I-S25R-M27A-L29P-S31A-F50K-V52T SEQ ID NO:491 (DPDDESSKPCCDQ CICTKSNP-PQCRCRDARPNACHSACKSCACSKHSQITCK CTDIT-DFCYEPCKPSE; SEQ ID NO:491), the modified variant BBIt-VEGF-V2-A13I-S25R-M27A-L29P-S31A-F50K-V52T of SEQ ID NO:632 (D PDDE SSKPCCDQCICTKSN-PPQCRCRDARPNACHSACKSCACK TNPSGSCKCT-DITDFCYEPCKPSE:SEQ ID NO:632),the modified variant BBIt-VEGF-V3-A13I-S25R-M27A-L29P-S31A-F50K-V52T of SEQ ID NO:633 (DPDDESSKPCCDQCICTKSN-PPQCRCRDARPNACHSAC KSCACRPTGHSLCKCT-DITDFCYEPCKPSE; SEQ ID NO:633), the modified variant BBIt-VEGF-V4-A1311-S25R-M27A-L29P-S31A-F50K-V52T of SEQ ID NO:634 (DPDDESSKPC-CDQCICTKSNPPQCRCRDARP NACHSACKSCACKH-SAKAECKCTDITDFCYEPCKPSE; SEQ ID NO:634), the modified variant BBIt-VEGF-V5-A13I-S25R-M27A-L29P-S31A-F50K-V52T of SEQ ID NO:635 (DPDDESSKPC-CDQCICTKSNPPQC RCRDARPNACHSACK-SCACKPSSASSCKCTDITDFCYEP CKPSE; SEQ ID NO:635 ), the modified variant BBIt-VEGF-V6-A13I-S25R -M27A-L29P-S31A-F50K-V52T of SEQ ID NO:636 (DPDDESSKPCCDQCICTKS NPPQCRCRDARPNACH-SACKSCACPVTKRVHCKCTDITD FCYEPCKPSE; SEQ ID NO:636), the modified variant BBIt-TNFα-T1-A13I-S25R-M27A-L29P-S31A-F50K-V52T of SEQ ID NO:637 (DPDDESSKPC CD QCICTKSNPPQCRCRDARPNACH-SACKSCACRYWQDIPC KCTDITDFCYEPCKPSE; SEQ ID NO:637), the modified variant BBIt-TNFα-T2-A13I-25 R-M27A-L29P-S31A-F50K-V52T of SEQ ID NO:638 (DP-DDE SSKPCCDQCICTKSNPPQCRCRDARPN-ACHSACKSCACA PEPILACKCTDITDFCYEPCKPSE; SEQ ID NO:638),and the modified variant BBIt-TNFα-T3-A13-S25R-M27A-L29P-S31A-F50K-V52T of SEQ ID NO:639 (DPDDESSKPCCDQCICTKSNPPQCRCRD-ARPNACHSACKSCACDMIMVSICKCTDI TDF-CYEPCKPSE; SEQ ID NO:639).

In some embodiments, the modified variant BBPI comprises a combination of eight amino acid substitutions at amino acids at positions equivalent to positions 13, 25, 27, 29, 31, 40, 50 and 52 of SEQ ID NO:187. In some embodiments, the combination of eight amino acid substitutions is chosen from a combination of substitutions at positions 13-25-27-29-31-40-50-52, 13-25-27-29-31-40-50-52, 13-25-27-29-31-40-50-52, 13-25-27-29-31-40-50-52, and 13-25-27-29-31-40-50-52. In some embodiments, the combination of eight amino acid substitutions is chosen from combinations 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q. The invention provides for any one of the variant BBPI scaffolds described in Section 5.3 and further comprising the combination of the eight amino acid substitutions chosen from combinations 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q, as described in section 5.4. In one embodiment, the chymotrypsin loop of the variant scaffold is a VEGF variant peptide of SEQ ID NO:9, and the variant scaffold is altered further to comprise a combination of seven amino acid substitutions at positions equivalent to positions 13, 25, 27, 29, 31, 40, 50 and 52 of SEQ ID NO:187 to generate a modified variant BBPI scaffold. In one embodiment, the modified variant BBPI comprising a combination of eight amino acid substitutions is chosen from the modified variant BBIt-AV-A13I-S25R-M27A-L29P-S31A-A40H-F50K-V52T of SEQ ID NO:627 (DPDDESSKPCCDQCICTKSNPPQ CRCRDAR-PNACHSACKSCHCYNLYGWTCKCTDITDFCYEPC KPSE; SEQ ID NO:627; KT8), the modified variant of BBIt-AV-A13I-S25K-M27A-L29R-S31E-A40K-F50Q-V52Q of SEQ ID NO:628 (DPDDESSKPCCDQCICT KSNP-PQCRCKDARRNECHSACKSCKCYNLYG-WTCQCQDIT DFCYEPCKPSE; SEQ ID NO:628; QQ8), the modified variant BBIt-AV-A13I-S25K-M27R-L29E-S31A-A40H-F50R-V52K of SEQ ID NO:629 (DPD-DESSKPCC DQCICTKSNPPQCRCKDRRENACHSACK-SCHCYNLYGWTC RCKDITDFCYEPCKPSE; SEQ ID NO:629; RK8), the modified variant BBIt-AV-A13I-S25K-M27A-L29R-S31A-A40H-F50R-V52L of SEQ ID NO:630 (DPDDESS KPCCDQCICTKSNPPQCRCKDARRNACH-SACKSCHCYNLY GWTCRCLDITDFCYEPCKPSE; SEQ ID NO: 630; RL8) and the modified variant BBIt-AV-A13I-S25K-M27Q-L29P-S31E-A40H-F50R-V52Q of SEQ ID NO:631 (D PDDESSKPCCDQCICTKSNPPQCRCK-DQRPNECHSACKSC HCYNLYGWTCRCQDITDF-CYEPCKPSE; SEQ ID NO:631; RQ8).

The invention further provides for modified variant BBPIs that comprise any one combination of the amino acid substitutions described above and that have greater protease inhibitory activity than the unmodified precursor variant BBPI. In some embodiments, modified variant BBPIs which contain a variant peptide in place of the chymotrypsin loop of the corresponding precursor unmodified BBPI have greater trypsin inhibitory activity (TIA) than that of the precursor unmodified BBPI scaffold. In other embodiments, modified variant BBPIs which contain a variant peptide in place of the trypsin loop of the corresponding precursor unmodified BBPI have greater chymotrypsin inhibitory activity (TIA) than that of the precursor unmodified BBPI scaffold.

As shown in the Examples, substitutions of at least one amino acid in the backbone of the variant BBPI generates a modified variant BBPI that has a greater production yield that the unmodified variant BBPI. In some embodiments, BBPIs that comprise a combination of two, three, four, five, six, seven or eight amino acid substitutions have a greater production yield than the unmodified precursor BBPI. Thus, the invention provides for modified variant BBPIs that comprise any one combination of the amino acid substitutions described above and that have greater production yield (PY) than the unmodified precursor variant BBPIs. In yet other embodiments, the invention provides for modified variant BBPIs that comprise any one combination of the amino acid substitutions described above and that have greater trypsin inhibitory activity and greater production yield than the TIA and PY of the unmodified precursor variant BBPIs.

In some embodiments, the modified variant BBPIs further comprise a peptide insert that is positioned at the N-terminus of the modified variant BBPI. In some embodiments, the peptide insert comprises a sequence of between 1 and 15 amino acids. In other embodiments, the peptide insert comprises a sequence between 5 and 10 amino acids. In some embodiments, the peptide insert comprises the peptide of SEQ ID NO:389 (DDEPSKPCCDPDP; SEQ ID NO:389). Examples of modified variant BBPIs that the peptide insert of SEQ ID NO:389 are the modified variant 4D13BBIt-AV of (DDEPSKPCCDPDPDDESSKPCCDQ-CACTKSNPPQCRCSDMRLNSCHSACKSCACY NLYGWTCFCVDITDFCYEPCKPSE; SEQ ID NO:390), and the modified variant BBIt-AV-4D13-13I-29P-40K-50T-52A of SEQ ID NO: 413 (DPDDEPSKPCCDPDPDDESSKPC-CDQCICTKSNPPQCRCSDMRPNSCHSACKSCKC YNLYGWTCTCADITDFCYEPCKPSE; SEQ ID NO:413).

5.4.3 BBPI Fusion Proteins

In some embodiments, each modified variant BBPI is expressed as fusion protein comprising a catalytic domain, a cleavage site and the BBPI scaffold. The catalytic domain is chosen from cellulase, cutinase, and disulfide isomerase. In some embodiments, the catalytic domain comprised in the BBPI fusion protein is the cellulase catalytic domain of SEQ ID NO:669

(SEQ ID NO: 669)
ddysvveehgqlsisngelvnergeqvqlkgmsshglqwygqfvnyesmk wlrddwgitvfraamytssggyiddpsvkekvketveaaidlgiyviidw hilsdndpniykeeakdffdemselygdypnviyeianepngsdvtwdnq ikpyaeevipvirdndpnnivivgtgtwsqdvhhaadnqladpnvmyafh fyagthgqnlrdqvdyaldqgaaifvsewgtsaatgdggvfldeaqvwid fmdernlswanwslthkdessaalmpganptggwteaelspsgtfvreki resas The fusion protein is processed by a protease or acid/heat treatment to liberate the modified variant BBPI. In some embodiments, the fusion protein further comprises at least one linker sequence. In some embodiments, the linker sequence is selected from the group consisting of SEQ ID NOS:141-143. Although cleavage of the fusion polypeptide to release the modified variant BBPI will often be useful, it is not necessary. Modified variant BBPIs expressed and secreted as fusion proteins surprisingly retain their function.

The modified variant BBPI fusion proteins are each expressed by the host bacterial cell from a fusion polynucleotide sequence. Such fusion polynucleotide sequences are assembled in proper reading frame from the 5' terminus to 3' terminus in the order of first, second, third and fourth polynucleotide sequences. As so assembled, the polynucleotide sequence encodes a "fusion polypeptide" encoding from its amino-terminus 1. a signal peptide functional as a secretory sequence in a bacterial species, 2. a secreted polypeptide or portion thereof normally secreted from a bacterial species e.g. cellulase or portion thereof, 3. a cleavable linker peptide and a 4. desired polypeptide (e.g., a modified variant BBPI). In some embodiments, the above-defined fusion polynucleotide sequence further comprises a polynucleotide encoding a portion of a propeptide that functions as a spacer between the first and second polynucleotide sequences of a fusion protein. The function of the spacer is intended to increase the distance between the first and second encoded polypeptides. In some embodiments, the spacer sequence is 1-10 amino acids long. In other embodiments, the above-defined fusion polynucleotide sequence further comprises a polynucleotide encoding a peptide insert between the linker peptide and the modified variant BBPI. In some embodiments, the peptide insert comprises a sequence of between 1 and 15 amino acids. In other embodiments, the peptide insert comprises a sequence between 5 and 10 amino acids. In some embodiments, the peptide insert comprises the peptide of SEQ ID NO:389.

Various methods are known to those in the art for the production of fusion proteins (See e.g., U.S. Pat. Nos. 5,411,873, 5,429,950, and 5,679,543, all of which are incorporated by reference herein). Thus, it is intended that any suitable method will find use in the present invention.

5.5 Bowman Birk Protease Inhibitor Polnucleotides

To the extent that the present invention depends on the production of fusion proteins, it relies on routine techniques in the field of recombinant genetics. Basic texts disclosing the general methods of use in this invention include Sambrook et al., Molecular Cloning, A Laboratory Manual ((2nd ed.) [1989]); Kriegler, Gene Transfer and Expression: A Laboratory Manual (1990); and Ausubel et al., (eds.), Current Protocols in Molecular Biology (1994).

The invention provides for compositions including polynucleotide constructs, vectors and host cells that enable the expression of modified variant BBPIs. The polynucleotide constructs of the invention comprise a promoter sequence and a fusion polynucleotide sequence that encodes a fusion protein comprising a modified variant BBPI. As described above, the fusion polynucleotide sequence comprises a catalytic domain, a cleavage site and the BBPI scaffold. Natural or synthetic polynucleotide fragments encoding a BBPI may be incorporated into the polynucleotide constructs. The at least one amino acid substitution introduced into a variant BBPI is generated by means of site saturation mutagenesis in at least one codon. In alternative embodiments, the at least one amino acid substitution is encoded by DNA oligonucleotides that contain the encoding sequence, and that are annealed and ligated into the protease inhibitor DNA sequence. The desired DNA sequence is then isolated and used in the methods provided herein.

In some embodiments, the polynucleotide constructs of the invention comprise polynucleotide sequences that encode a modified variant BBPI that shares at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 92% amino acid sequence identity, at least about 95% amino acid sequence identity, at least about 97% amino acid sequence identity, at least about 98% amino acid sequence identity, and at least about 99% amino acid sequence identity with the amino acid sequence of the unmodified precursor variant BBPI and has greater protease inhibitory activity than the unmodified precursor variant BBPI. The invention further provides for polynucleotides encoding modified variant BBPIs that comprise any one combination of the amino acid substitutions described above and that have greater protease inhibitory activity e.g. trypsin inhibitory activity, than the unmodified precursor variant BBPI.

In some embodiments, the polynucleotide constructs of the invention comprise a polynucleotide sequence that may be codon optimized for expression of a modified variant BBPI in the host cell used. Since codon usage tables listing the usage of each codon in many cells are known in the art (See, e.g., Nakamura et al., Nucl. Acids Res., 28:292 [2000]) or readily derivable, such nucleic acids can be readily designed giving the amino acid sequence of a protein to be expressed.

The invention also encompasses polynucleotide constructs that comprise coding sequences encoding modified variant BBPI proteins that are related by being structurally and/or functionally similar. In some embodiments, a modified variant BBPI is derived from a naturally-occurring BBPI belonging to a different genus and/or species. In some embodiments, related proteins are provided from the same species. Indeed, it is not intended that the present invention be limited to related proteins from any particular source(s). In addition, the term "related proteins" encompasses tertiary structural homologs and primary sequence homologs. For example, the present invention encompasses such homologues including but not limited to such BBPI proteins such as those described by Prakash et al. (J mol Evol 42:560-569 [1996]).

In some embodiments, the promoter sequence comprised in the polynucleotide constructs of the invention is operably linked to the BBPI-encoding polynucleotide. Exemplary promoters include both constitutive promoters and inducible promoters. Such promoters are well known to those of skill in the art. Those skilled in the art are also aware that a natural promoter can be modified by replacement, substitution, addition or elimination of one or more nucleotides without changing its function. The practice of the present invention encompasses and is not constrained by such alterations to the promoter. The choice of promoter used in the genetic construct is within the knowledge of one skilled in the art.

In some embodiments, the promoter sequence may be obtained from a bacterial source. In some embodiments, the promoter sequence may be obtained from a Gram-positive bacterium such as a *Bacillus* strain (e.g., *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*); or a *Streptomyces* strain (e.g., *Streptomyces lividans* or *Streptomyces murinus*); or from a gram negative bacterium (e.g., *E. coli* or *Pseudomonas* sp.).

The promoter can be any DNA sequence having transcription activity in the host organism of choice and can be derived from genes that are homologous or heterologous to the host organism. Examples of suitable promoters that can be used to express a modified variant BBPI in a bacterial host include, but are not limited to the promoter of the lac operon of *E. coli*, the *Streptomyces coelicolor* agarase gene dagA promoters, the promoters of the *Bacillus licheniformis* α-amylase gene (amyL), the aprE promoter of *Bacillus subtilis*, the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.-derived promoter including the P170 promoter. When the gene encoding the compound is expressed in a bacterial species such as *E. coli*, a suitable promoter can be selected, for example, from a bacteriophage promoter including a T7 promoter and a phage lambda promoter. For transcription in a fungal species, examples of useful promoters are those derived from the genes encoding the *Aspergillus oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, and *A. nidulans* acetamidase. Examples of suitable promoters for the expression in a yeast species include but are not limited to the Gal 1 and Gal 10 promoters of *Saccharomyces cerevisiae* and the *Pichia pastoris* AOX1 or AOX2 promoters.

The invention also encompasses promoter sequences that have been mutated to increase the activity of the promoter when compared to the activity of the corresponding wild-type promoter resulting in the expression of the modified variant BBPI protein. Thus, it is understood that variants of the sequences that define the *B. subtilis* AprE promoter find use in the constructs of the invention. Methods for creating promoter variants in *Bacillus* sp. are well known in the art (See e.g., Helmann et al., 2002. RNA polymerase and sigma factors, pp 289-312 In A. L. Sonenshein, J. A. Hoch and R. Losick (ed), *Bacillus subtilis* and its closest relatives: from genes to cells. American Society for Microbiology, Washington, D.C.) It is not intended that the present invention be limited to any particular promoter, as any suitable promoter known to those skilled in the art finds use with the present invention.

In embodiments, in addition to a promoter sequence, the polynucleotide construct also contains a transcription termination region downstream of the structural gene to provide for efficient termination. In some embodiments, the termination region is obtained from the same gene as the promoter sequence, while in other embodiments it is obtained from another gene. The selection of suitable transcription termination signals is well-known to those of skill in the art.

5.6 Bowman Birk Protease Inhibitor Vectors

The invention provides vectors comprising the polynucleotide constructs of the invention. The vectors are introduced into a host cell to express the modified variant BBPI proteins of the invention. Any vector may be used as long as it is replicable and viable in the cells into which it is introduced. Large numbers of suitable vectors and promoters are known to those of skill in the art, and are commercially available. Appropriate cloning and expression vectors are also described in various references known to those in the art (See e.g., Sambrook et al., supra and Ausubel et al., supra, expressly incorporated by reference herein). The appropriate BBPI-encoding DNA sequence is inserted into a plasmid or vector (collectively referred to herein as "vectors") by any suitable method. In general, the DNA sequence is inserted into an appropriate restriction endonuclease site(s) by standard procedures known to those in the art.

Appropriate vectors are typically equipped with a selectable marker-encoding nucleic acid sequence, insertion sites, and suitable control elements, such as termination sequences. In some embodiments, the vectors comprise regulatory sequences, including, for example, control elements (i.e., promoter and terminator elements or 5' and/or 3' untranslated regions), effective for expression of the coding sequence in host cells (and/or in a vector or host cell environment in which a modified soluble protein coding sequence is not normally expressed), operably linked to the coding sequence. Large numbers of suitable vectors and promoters are known to those of skill in the art, many of which are commercially available and known to those in the art. The choice of the proper selectable marker will depend on the host cell. Appropriate markers for different bacterial hosts are well known in the art. Typical selectable marker genes encode proteins that (a) confer resistance to antibiotics or other toxins (e.g., ampicillin, methotrexate, tetracycline, neomycin mycophenolic acid, puromycin, zeomycin, or hygromycin; or (b) complement an auxotrophic mutation or a naturally occurring nutritional deficiency in the host strain.

In some embodiments, expression of a fusion BBPI polypeptide results from the expression of one or more copies of the corresponding fusion polypeptide-encoding polynucleotide that is present on a multicopy/replicating plasmid that has been introduced into a host cell. In some embodiments, the vector is a multicopy/replicating plasmid vector which forms an extrachromosomal self-replicating genetic element that expresses a fusion BBPI protein in the host cell. Typically, the vector is a plasmid vector, which carries a selectable marker gene that allows for ease of selecting the host cells that contain the plasmid. Vectors that replicate autonomously in a host cell include vectors that comprise an origin of replication, which enables the vector to replicate autonomously in the *Bacillus* cell. Examples of bacterial origins of replication are the origins of replication of plasmids pBR322, pUC19, pACYC177, and pACYC184 permitting replication in *E. coli*, and pUB110, pC194, pE194, pTA1060, and pAMβ1 permitting replication in *Bacillus*. The origin of replication may be one having a mutation to make its function temperature-sensitive in the *Bacillus* cell (See, e.g., Ehrlich, Proceedings of the National Academy of Sciences USA 75:1433 [1978]). Additional bacterial expression vectors that find use in the present invention include bacteriophages λ and M13, and fusion expression systems such as MBP, GST, and LaZ. In further embodiments, epitope tags are added to recombinant proteins, in order to provide convenient methods of isolation (e.g., c-myc).

In some embodiments, the expression of a BBPI fusion polypeptide results from the expression of at least one copy of a BBPI fusion-encoding polynucleotide that is integrated into the genome of the host cell. Thus, in some embodiments, the invention provides a BBPI encoding polynucleotide construct that is incorporated into an integrating vector. Thus, when the vector is introduced into the host cell, it is integrated into the genome and replicated together with the genome into which it has integrated. Multiple copies of the BBPI gene can be integrated at several positions in the genome of the host cell. Alternatively, an amplifiable expression cassette carrying a sequence encoding a BBPI fusion protein and a selectable marker (e.g., an antimicrobial resistance marker, such as a gene coding chloramphenicol acetyl transferase) can be integrated in the genome via a single cross-over event and then amplified by challenging the transformed host cell with increasing concentrations of the appropriate antimicrobial (e.g., chloramphenicol).

5.7 Bowman Birk Protease Inhibitor Host Cells

In one embodiment, the invention provides for a host cell transformed with an expression vector comprising a polynucleotide sequence encoding a modified variant BBPI. After the expression vector is introduced into the host cells, the transformed host cells are cultured under conditions favoring expression of gene encoding the desired BBPI fusion protein. Large batches of transformed cells can be cultured as described above. Finally, product is recovered from the culture using techniques known in the art.

Methods for introducing DNA into *Bacillus* cells involving plasmid constructs and transformation of plasmids into bacterial host cells are well known. In some embodiments, the plasmids are subsequently isolated from *E. coli* and transformed into *Bacillus*. However, it is not essential to use intervening microorganisms such as *E. coli*, and in some embodiments, a DNA construct or vector is directly introduced into a *Bacillus* host. Those of skill in the art are well aware of suitable methods for introducing polynucleotide sequences into *Bacillus* cells (See e.g., Ferrari et al., "Genetics," in Harwood et al. (ed.), *Bacillus, Plenum Publishing Corp.* [1989], pages 57-72; Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; Chang et al., Mol. Gen. Genet., 168:11-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; and McDonald, J. Gen. Microbiol., 130:203 [1984]). Indeed, such methods as transformation, including protoplast transformation and congression, transduction, and protoplast fusion are known and suited for use in the present invention. Methods of transformation are particularly preferred to introduce a DNA construct provided by the present invention into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell without insertion into a plasmid or vector. Such methods include, but are not limited to electroporation, insertion of naked DNA or liposomes and the like. In additional embodiments, DNA constructs are co-transformed with a plasmid, without being inserted into the plasmid. In further embodiments, a selective marker is deleted from the altered *Bacillus* strain by methods known in the art (See, Stahl et al., J. Bacteriol., 158:411-418 [1984]; and Palmeros et al., Gene 247:255-264 [2000]).

Methods known in the art to transform *Bacillus*, include such methods as plasmid marker rescue transformation, which involves the uptake of a donor plasmid by competent cells carrying a partially homologous resident plasmid (Contente et al., Plasmid 2:555-571 [1979]; Haima et al., Mol. Gen. Genet., 223:185-191 [1990]; Weinrauch et al., J. Bacteriol., 154:1077-1087 [1983]; and Weinrauch et al., J. Bacteriol., 169:1205-1211 [1987]). In this method, the incoming donor plasmid recombines with the homologous region of the resident "helper" plasmid in a process that mimics chromosomal transformation.

Other methods involving transformation by protoplast transformation are well known in the art (See e.g., Chang and Cohen, Mol. Gen. Genet., 168:111-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; McDonald J. Gen. Microbiol., 130:203 [1984]; and Bakhiet et al., 49:577 [1985]). In addition, Mann et al., (Mann et al., Curr. Microbiol., 13:131-135 [1986]) describe transformation of *Bacillus* protoplasts, and Holubova (Holubova, Microbiol., 30:97 [1985]) describe methods for introducing DNA into protoplasts using DNA-containing liposomes. In some embodiments, marker genes are used in order to indicate whether or not the gene of interest is present in the host cell. In some embodiments, the BBPI fusion polynucleotide sequence contained in the vector of the invention encodes for a BBPI fusion protein having SEQ ID NO:195. In addition to these methods, in other embodiments, host cells are directly transformed. In "direct transformation," an intermediate cell is not used to amplify, or otherwise process, the modified polynucleotide prior to introduction into the host (i.e., *Bacillus*) cell. Introduction of the modified polynucleotide into the host cell includes those physical and chemical methods known in the art to introduce modified polynucleotide into a host cell without insertion into a plasmid or vector. Such methods include but are not limited to the use of competent cells, as well as the use of "artificial means" such as calcium chloride precipitation, electroporation, etc. to introduce DNA into cells. Thus, the present invention finds use with naked DNA, liposomes and the like.

Examples of suitable bacterial host organisms are Gram positive species, including, but not limited to members of the *Bacillus* species, which Bacillaceae, (e.g., *B. subtilis, B. licheniformis, B. lentus, B. brevis, B. stearothermophilus, B. alkalophilus, B. amyloliquefaciens, B. clausii, B. halodurans, B. coagulans, B. circulans, B. lautus, B. megaterium* and *B. thuringiensis*), *Streptomyces* species (e.g., *S. murinus* and *S. lividans*) lactic acid bacteria (e.g., *Lactococcus* spp. such as

*Lactococcus* lactis; *Lactobacillus* spp. including *Lactobacillus reuteri; Leuconostoc* spp.; *Pediococcus* spp.; and *Streptococcus* spp. Alternatively, strains of Gram-negative species belonging to Enterobacteriaceae (e.g., *E. coli*) or members of the Pseudomonadaceae find use in the present invention.

In some embodiments, a suitable yeast host organism is selected from various biotechnologically useful yeasts species, including but not limited to *Pichia* sp., *Hansenula* sp or *Kluyveromyces, Yarrowinia, Saccharomyces* (e.g., *Saccharomyces cerevisiae*), Schizosaccharomyce (e.g., *S. pombe*). In some embodiments, strains of the methylotrophic yeast species *Pichia pastoris* are used as the host organism, while in other embodiments, the host organism is a *Hansenula* species. Suitable host organisms among filamentous fungi include species of *Aspergillus* (e.g., *A. niger, A. oryzae*, *A. tubigensis*, *A. awamori* and *Aspergillus nidulans*). Alternatively, strains of *Fusarium* species (e.g. *F. oxysporum*) and *Rhizomucor* (e.g., *Rhizomucor miehei*) find used as the host organism. Additional suitable strains include, but are not limited to *Thermomyces* and *Mucor* species.

Accessory proteins such as thiol-disulfide oxidoreductases or chaperones find use in some embodiments, as they may be beneficial to help fold the secretory protein into its active conformation. Thiol-disulsfide oxidoreductases and protein disulfide isomerases catalyze the formation of the correct disulfide bonds in the protein. Overexpression of the bdbDC operon in *B. subtilis* has been shown to be beneficial for the production of a protein with disulfide bonds (See e.g., Meima et al., J. Biol. Chem., 277:6994-7001, [2002]). Chaperones help the secretory protein to fold by binding to exposed hydrophobic regions in the unfolded states and preventing unfavourable interactions and prolyl-peptidyl cis-trans isomerases assist in formation of the proper conformation of the peptide chain adjacent to proline residues.

In some embodiments of the present invention, the host cells are transformed with an expression vector encoding at least one thiol-disulfide oxidoreductase or chaperone. It is not intended that the present invention be limited to any particular thiol-disulfide oxidoreductase or chaperone, as any suitable thiol-disulfide oxidoreductase or chaperone known to those skilled in the art will find use in the present invention.

In some embodiments of the present invention, and as described further below, the fraction of properly folded secretory protein is increased by the addition of chemicals to the growth medium that reduce/oxidize disulfide bonds, and/or alter the general redox potential, and/or chemicals that alter solvent properties thus affecting protein conformation and aggregation. In particularly preferred embodiments, a reagent that reduces disulfide bonds, such as 2-mercaptoethanol (βME), is preferred to increase the fraction of correctly folded protein. However, in other embodiments and depending on the medium used, other disulfide reducing or oxidizing agents (e.g., DTT, TCEP, reduced and oxidized glutathione, cysteine, cystine, cysteamine, thioglycolate, $S_2O_3^{2-}$, $S_2O_4^{2-}$, $S_2O_5^{2-}$, $SO_3^{2-}$, $S_2O_7^{2-}$, Cu+, etc.), either used alone or in combination, find use in the present invention. It is contemplated that other adjuvants that alter solvent properties, (e.g., urea, DMSO, TWEEN®-80, etc.), either added to the growth medium alone or preferably in combination with disulfide reducing/oxidizing agents, such as BME, will also increase the fraction of correctly folded secretory protein and find use in various embodiments of the present invention. In some preferred embodiments, the BME is used at concentrations ranging from 0.5 to 4 mM, while in other embodiments, the concentrations range from 0.1 mM to 10 mM. Indeed, those of skill in the art know how to select the best growth medium and growth conditions to optimize the effects of the added thiol reducing/oxidizing agents and/or other adjuvants, as well as the concentration of thio reducing/oxidizing agents and/or other adjuvants to use. It is not intended that the present invention be limited to any particular disulfide reducing/oxidizing agent or adjuvant, as any suitable reagents known to those skilled in the art find use in the present invention.

5.7.1 Fermentation Parameters

The present invention relies on fermentation procedures for culturing bacterial species. Fermentation procedures for production of heterologous proteins by bacterial species are well known in the art. Culturing is accomplished in a growth medium comprising an aqueous mineral salts medium, organic growth factors, the carbon and energy source material, molecular oxygen (for aerobic and facultative bacteria), and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation medium.

Various culture media find use in the present invention, as known to those of skill in the art. However, standard bacterial culture media find use in the present invention. In some preferred media formulations, the media include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

In some embodiments, the fermentation reaction involves an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth of aerobic and to a lesser extent, facultative organisms.

Although the aeration rate can vary over a considerable range, aeration generally is conducted at a rate which is in the range of about 0.5 to 10, preferably about 0.5 to 7, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates.

At the same time, this is balanced by the fact that high atmospheric pressures do increase equipment and operating costs.

The fermentation temperature can vary somewhat, but for most bacterial species used in the present invention, the temperature generally will be within the range of about 20° C. to 40° C., generally preferably in the range of about 28° C. to 37° C., depending on the strain of microorganism chosen, as known to those skilled in the art.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. However, pH range optima for certain microorganisms are dependent on the media employed to some extent, as well as the particular microorganism, and thus change somewhat with change in media as known to those skilled in the art.

While the average retention time of the fermentation admixture in the fermentor can vary considerably, depending in part on the fermentation temperature and culture employed, as known in the art.

In some embodiments, the fermentation is preferably conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily removed. It may be a problem, however, in the case of non-water-soluble substrates, and require added product-treatment steps such as suitable washing steps. The time needed to reach this limiting substrate level is not critical and may vary with the particular microorganism and fermentation process being conducted. However, it is well known in the art how to determine the carbon source concentration in the fermentation medium and whether or not the desired level of carbon source has been achieved.

Although in some embodiments, the fermentation is conducted as a batch or continuous operation, fed batch operation is generally preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium into the fermentor. Indeed, each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible, but more importantly to obtain the highest production of the desired protein per unit volume.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though in some embodiments, the 15L Biolafitte (Saint-Germain-en-Laye, France) is preferred.

5.8 Protein Separation

In some embodiments, host cells transformed with polynucleotide sequences encoding modified proteases are cultured under conditions suitable for the expression and recovery of the encoded protein from cell culture. The protein produced by a recombinant host cell comprising a fusion BBPI of the present invention is secreted into the culture media. In some embodiments, the secreted fusion BBPI is recovered.

In some embodiments, the present invention provides methods of separating a desired protein from its fusion analog. It is contemplated that the methods described herein will find use in the separation of the modified variant BBPI from the fusion analog.

The collection and purification of the desired fusion BBPI protein from the fermentation broth can also be achieved using procedures known to those of skill in the art. The fermentation broth will generally contain cellular debris, including cells, various suspended solids and other biomass contaminants, as well as the desired protein product, which are preferably removed from the fermentation broth by means known in the art. Suitable processes for such removal include conventional solid-liquid separation techniques (e.g., centrifugation, filtration, dialysis, microfiltration, rotary vacuum filtration, or other known processes), to produce a cell-free filtrate. In some embodiments, it is preferable to further concentrate the fermentation broth or the cell-free filtrate prior to the purification and/or crystallization process using techniques such as ultrafiltration, evaporation and/or precipitation.

Precipitating the proteinaceous components of the supernatant or filtrate may be accomplished by means of a salt (e.g., ammonium sulfate) or low pH (typically less than 3), followed by purification by a variety of chromatographic procedures (e.g., ion exchange chromatography, affinity chromatography, hydrophobic interaction chromatography, hydrophobic charge induction chromatography etc.) or similar art recognized procedures. It is not intended that the present invention be limited to any particular separation method, as it is contemplated that any method will find use in the present invention.

In certain preferred embodiments, when the expressed desired polypeptide is secreted from the bacterial cells, the polypeptide is purified from the growth media. In preferred embodiments, the expression host cells are removed from the media before purification of the polypeptide (e.g. by centrifugation).

When the expressed recombinant desired polypeptide is not secreted from the host cell, the host cell is preferably disrupted and the polypeptide released into an aqueous "extract" which is the first stage of purification. Preferably, the expression host cells are collected from the media before the cell disruption (e.g. by centrifugation). The cell disruption may be performed by using any suitable means known in the art, such as by lysozyme or beta-glucanase digestion or by forcing the cells through high pressure (See e.g., Scobes, Protein Purification, Second edition, Springer-Verlag)

In some embodiments, other recombinant constructions include the addition of purification facilitating domains to the nucleotide sequence encoding a modified variant BBPI polypeptide domain which facilitates purification of the soluble proteins (Kroll D J et al (1993) DNA Cell Biol 12:441-53). In some embodiments, the addition of six histidine residues (i.e., a "His Tag") to the C-terminus of the modified variant BBPI is used as an aid in the purification of the desired protein and its fusion analog. Use of the His tags as a purification aid is well known in the art (See e.g., Hengen, TIBS 20:285-286 [1995]). The 6× his-tagged proteins are easily purified using Immobilized Metal ion Affinity Chromatography (IMAC), as known to those skilled in the art. Other purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

Thus, any method suitable for recovering the fusion BBPIs of the present invention finds use in the present invention. Indeed, it is not intended that the present invention be limited to any particular purification method.

For some applications, it is of great importance that the protease inhibitors produced using the present invention be highly pure (e.g., having a purity of more than 99%). This is particularly true whenever the desired protein is to be used as a therapeutic, but is also necessary for other applications. The methods described herein provide a way of producing substantially pure desired proteins. The desired proteins described herein are useful in pharmaceutical and personal care compositions. However, it is contemplated that proteins of varying purity levels will be produced using the methods of the present invention and it is not intended that the proteins produced using the present invention be limited to any particular level of purity.

5.8.1 Activation of BBPI During Purification: Protease Inhibitory Activity

In some embodiments of the present invention, after growth during the purification process, the activity of the protein i.e. the protease inhibitory activity, is increased by the addition of chemicals that reduce/oxidize disulfide bonds and/or alter the general redox potential, and/or chemicals that alter solvent properties thus affecting protein conformation and aggregation. In some particularly preferred embodiments, addition of a reagent that reduces disulfide bonds, such as 2-mercaptoethanol, is used to increase activity of the protein. However, as those skilled in the art appreciate, depending purity and buffer composition, other disulfide reducing or oxidizing agents (e.g., DTT, TCEP, reduced and oxidized glutathione, cysteine, cystine, cysteamine, thioglycolate, $S_2O_3^{2-}$, $S_2O_4^{2-}$, $S_2O_5^{2-}$, $SO_3^{2-}$, $S_2O_7^{2-}$, Cu+, protein disulfide isomerases, protein thiol-disulfide oxidoreductases, etc.), either used alone or in combination, find use in the present invention. Other adjuvants, which alter solvent properties, (e.g. ethanolamine, DMSO, TWEEN®-80, arginine, urea, etc.), are either added alone or preferably in combination with disulfide reducing/oxidizing agents, such as βME, during the purification process also find use in the present invention by increasing the activity of the protein. In certain preferred embodiments, partially purified protein is diluted in buffer (in some particularly preferred embodiments, a zwitterionic buffer with TWEEN®-80 at basic pH) and activated with βME and a disulfide oxidizing agent (in alternative preferred embodiments, oxidized glutathione or sodium sulfite).

In addition, it is contemplated that conditions will be screened in order to determine the optimal activation of the BBPI protein, if desired. For example, various βME concentrations (0.1-10 mM), oxidizing agent concentrations (0 to ½0 to 20 times the βME concentration) pH (7.5-9.5), temperatures (15-40° C.), dilutions (1-20 fold), incubation times (12-72 h), aeration (incubations under inert gas to vigorous mixing under oxygen containing gases), buffer types (Tris, CHES, CAPS, Tricine, TAPS, other zwitterionic buffers, etc.), buffer concentrations (0.1-1 M), and the addition of various adjuvants known to alter solvent properties thereby affecting protein conformation and aggregation (e.g., ethanolamine, DMSO, TWEEN®-80, arginine, urea, etc.) are tested in order to determine the optimum conditions for the expression system used. It is not intended that the present invention be limited to any particular disulfide reducing/oxidizing agent, dilution, temperature, pH, buffer type or composition, or adjuvant, as any suitable reagents known to those skilled in the art find use in the present invention.

Optimal activation of BBPIs by thiol reducing agents and/or oxidizing agents is monitored by measuring an increase in the protease inhibitory activity of the unmodified variant BBPI. Trypsin inhibitory activity is the protease inhibitory that is assayed in variant BBPIs in which the chymotrypsin loop has been replaced by a variant peptide, while chymotrypsin inhibitory activity is the protease inhibitory that is assayed in variant BBPIs in which the trypsin loop has been replaced by a variant peptide. In some embodiments, the effect of at least one amino acid substitution on the trypsin inhibitory activity of a modified BBPI is assayed and compared to the trypsin inhibitory activity of the unmodified precursor BBPI.

In some embodiments, modified variant BBPIs comprising at least one amino acid substitution have greater trypsin inhibitory activity than that of the unmodified precursor BBPI. In some embodiments, the single amino acid substitution that generates a modified variant BBPI having a greater TIA than the unmodified precursor is chosen from equivalent to a position chosen from positions equivalent to positions 1, 4, 5, 11, 13, 18, 25, 27, 29, 31, 38, 40, 50, 52, 55, and 65 of SEQ ID NO:187 result in the following substituted amino acids. In one embodiment, the substituted amino acid at the amino acid position equivalent to position 1 of SEQ ID NO:187 is chosen from A and C. In another embodiment, the substituted amino acid at the amino acid position equivalent to position 4 of SEQ ID NO:187 is V. In another embodiment, the substituted amino acid at the amino acid position equivalent to position 5 of SEQ ID NO:187 is chosen from P, and A. In another embodiment, the substituted amino acid at the amino acid position equivalent to position 11 of SEQ ID NO:187 is G. In another embodiment, the substituted amino acid at the amino acid position equivalent to position 13 of SEQ ID NO:187 is chosen from Y, I, F, M, L, V, K, and R. In another embodiment, the substituted amino acid at the amino acid position equivalent to position 18 of SEQ ID NO:187 include 1, V and L. In another embodiment, the substituted amino acid at the amino acid position equivalent to position 25 of SEQ ID NO:187 is chosen from K, N, W, I, A and R. In another embodiment, the substituted amino acid at the amino acid position equivalent to position 27 of SEQ ID NO:187 include R, K, V, A, and Q. In another embodiment, the substituted amino acid at the amino acid position equivalent to position 29 of SEQ ID NO:187 is chosen from R, K, and P. In another embodiment, the substituted amino acid at the amino acid position equivalent to position 31 of SEQ ID NO:187 is chosen from Q, H, E, A, R, W, K and T. In another embodiment, the substituted amino acid at the amino acid position equivalent to position 38 of SEQ ID NO:187 is chosen from N, K and R. In another embodiment, the substituted amino acid at the amino acid position equivalent to position 40 of SEQ ID NO:187 is chosen from H, K, Q, R, and Y. In another embodiment, the substituted amino acid at the amino acid position equivalent to position 50 of SEQ ID NO:187 is chosen from R, Q, K, T, V, M, and S. In another embodiment, the substituted amino acid at the amino acid position equivalent to position 52 of SEQ ID NO:187 is chosen from K, T, R, Q, L, H, A, M, S and E. In another embodiment, the substituted amino acid at the amino acid position equivalent to position 55 of SEQ ID NO:187 is M. In another embodiment, the substituted amino acid at the amino acid position equivalent to position 65 of SEQ ID NO:187 is chosen from E, Q, and D.

In some embodiments, the modified variant BBPI that have greater TIA and PY than the corresponding precursor unmodified BBPIs each comprise a combination of two amino acid substitutions at amino acids at positions equivalent to positions 50 and 52 of SEQ ID NO:187. In some embodiments, the combination of two amino acid substitutions is 50T-52A. The invention provides for any one of the variant BBPI scaffolds described in Section 5.3 and further comprising the combination of the two amino acid substitutions 50T-52A, as described in section 5.4. In one embodiment, the chymotrypsin loop of the variant scaffold is a VEGF variant peptide e.g. SEQ ID NO:9, and the variant scaffold is altered further to comprise a combination of three amino acid substitutions at positions equivalent to positions 13, 50 and 52 of SEQ ID NO:187 to generate a modified variant BBPI scaffold. In one embodiment, the modified variant BBPI comprising a combination of two amino acid substitutions is the modified variant BBIt-AV-F50T-V52A of SEQ ID NO:595.

In some embodiments, the modified variant BBPI that have greater TIA and PY than the corresponding precursor unmodified BBPIs each comprise a combination of three amino acid substitutions at amino acids at positions equivalent to positions 13, 50 and 52 of SEQ ID NO:187. In some embodiments, the combination of three amino acid substitutions is chosen from a combination of substitutions at positions 25-50-52, 29-50-52, 40-50-52, and 13-50-52. In some embodiments, the combination of three amino acid substitutions is chosen from 25L-50T-52A, 29P-50T-52A, 40K-50T-52A and 13I-50T-52A. The invention provides for any one of the variant BBPI scaffolds described in 5.3 and further comprising the combination of the three amino acid substitutions chosen from 25L-50T-52A, 29P-50T-52A, 40K-50T-52A and 13I-50T-52A, as described in section 5.4. In one embodiment, the chymotrypsin loop of the variant scaffold is a VEGF variant peptide e.g. SEQ ID NO:9, and the variant scaffold is altered further to comprise a combination of three amino acid substitutions at positions equivalent to positions 13, 50 and 52 of SEQ ID NO:187 to generate a modified variant BBPI scaffold. In one embodiment, the modified variant BBPI comprising a combination of three amino acid substitutions is chosen from the modified variant BBIt-AV-S25L-F50T-V52A of SEQ ID NO: 603, the modified variant BBIt-AV-L29P-F50T-V52A of SEQ ID NO:607, and the modified variant BBIt-AV-A40K-F50T-V52A of SEQ ID NO:609.

In some embodiments, the modified variant BBPI that have greater TIA than the corresponding precursor unmodified BBPIs each comprise a combination of four amino acid substitutions at amino acids at positions equivalent to positions 13, 29, 50 and 52 of SEQ ID NO:187. In some embodiments, the combination of four amino acid substitutions is chosen from a combination of substitutions at positions 13-25-50-52, 13-29-50-52, 25-29-50-52, 13-40-50-52, 25-40-50-52, and 29-40-50-52. In some embodiments, the combination of four amino acid substitutions is chosen from 13I-25L-50T-52A, 13I-29P-50T-52A, 25L-29P-50T-52A, 13I-40K-50T-52A, 25L-40K-50T-52A, and 29P-40K-50T-52A. The invention provides for any one of the variant BBPI scaffolds described in Section 5.3 and further comprising the combination of the four amino acid substitutions chosen from 13I-25L-50T-52A, 13I-29P-50T-52A, 25L-29P-50T-52A, 13I-40K-50T-52A, 25L-40K-50T-52A, and 29P-40K-50T-52A, as described in section 5.4. In one embodiment, the chymotrypsin loop of the variant scaffold is a VEGF variant peptide chosen from SEQ ID NO:9 and 460, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-AV-A13I-S25L-F50T-V52A of SEQ ID NO:596, the modified variant BBIt-AV-A13I-L29P-F50T-V52A of SEQ ID NO:600, the modified variant BBIt-AV-A13I-A40K-F50T-V52A of SEQ ID NO:602, the modified variant BBIt-AV-S25L-L29P-F50T-V52A of SEQ ID NO:604, the modified variant BBIt-AV-S25L-A40K-F50T-V52A of SEQ ID NO:606, the modified variant BBIt-AV-L29P-A40K-F50T-V52A of SEQ ID NO:608, and the modified variant BBIt-VEGKD-A13I-S25K-L29P-V52K of SEQ ID NO:643. In another embodiment, the chymotrypsin loop of the variant scaffold is an FGF5 variant peptide chosen from SEQ ID NOS:433 and 434, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-MM007-Q-A13I-L29P-F50T-V52A of SEQ ID NO:432, and the modified variant BBIt-FGFps2-Q-A13I-L29P-F50T-V52A of SEQ ID NO:434. In another embodiment, the chymotrypsin loop of the variant scaffold is a TGFβ variant peptide chosen from SEQ ID NOS:436, 437 and 438, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-PEN3-Q-A13I-L29P-F50T-V52A of SEQ ID NO:443, the modified variant BBIt-MM021W-Q-A13I-L29P-F50T-V52A of SEQ ID NO:445, and the modified variant BBIt-WTQ-Q-A13I-L29P-F50T-V52A of SEQ ID NO:447.

In some embodiments, the modified variant BBPI that have greater TIA than the corresponding precursor unmodified BBPIs each comprise a combination of five amino acid substitutions at amino acids at positions equivalent to positions 13, 29, 40, 50 and 52 of SEQ ID NO:187. In some embodiments, the combination of five amino acid substitutions is chosen from a combination of substitutions at positions 13-25-29-50-52, 13-29-40-50-52, 13-25-40-50-52, 25-29-40-50-52, 13-29-40-50-52, 13-29-40-50-52, 13-29-40-50-52 and 13-29-40-50-52. In some embodiments, the combination of five amino acid substitutions is chosen from 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A and 13I-29P-40K-50T-52T. The invention provides for any one of the variant BBPI scaffolds described in Section 5.3 and further comprising the combination of the five amino acid substitutions chosen from 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A and 13I-29P-40K-50T-52T, as described in section 5.4. In one embodiment, the chymotrypsin loop of the variant scaffold is a VEGF variant peptide of SEQ ID NO:9, and the variant scaffold is altered further to comprise a combination of five amino acid substitutions at positions equivalent to positions 13, 29, 40, 50 and 52 of SEQ ID NO:187 to generate a modified variant BBPI scaffold. In one embodiment, the modified variant BBPI comprising a combination of five amino acid substitutions is chosen from the modified variant BBIt-AV-A13I-S25L-L29P-F50T-V52A of SEQ ID NO:597, the modified variant BBIt-AV-A13I-L29P-A40K-F50T-V52A of SEQ ID NO:599, the modified variant BBIt-AV-A13I-S25L-A40K-F50T-V52A of SEQ ID NO:601, the modified variant BBIt-AV-S25L-L29P-A40K-F50T-V52A of SEQ ID NO:605, the modified variant BBIt-AV-A13L-L29P-A40K-F50T-V52A of SEQ ID NO:615, the modified variant BBIt-AV-A13I-L29K-A40K-F50T-V52A of SEQ ID NO:620, the modified variant BBIt-AV-A13I-L29P-A40K-F50K-V52A of SEQ ID NO:624, and the modified variant BBIt-AV-A13I-L29P-A40K-F50T-V52T of SEQ ID NO:625.

In some embodiments, the modified variant BBPI that have greater TIA than the corresponding precursor unmodified BBPIs each comprise a combination of six amino acid substitutions at amino acids at positions equivalent to positions 13, 25, 29, 40, 50 and 52 of SEQ ID NO:187. In some embodiments, the combination of six amino acid substitutions is chosen from a combination of substitutions at positions 13-25-29-40-50-52, 1-13-29-40-50-52, 4-13-29-40-50-52, 5-13-29-40-50-52, 11-13-29-40-50-52, 13-25-29-40-50-52, 13-27-29-40-50-52, 13-29-31-40-50-52, 13-29-31-40-50-52, 13-29-38-40-50-52, and 13-29-38-40-50-52. In some embodiments, the combination of six amino acid substitutions is chosen from 13I-25L-29P-40K-50T-52A, 1C-13I-29P-40K-50T-52A, 4V-13I-29P-40K-50T-52A, 5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, and 13I-29P-38N-40K-50T-52A. The invention provides for any one of the variant BBPI scaffolds described in Section 5.3 and further comprising the combination of the six amino acid substitutions chosen from 13I-25L-29P-40K-50T-52A, 1C-13I-29P-40K-50T-52A, 4V-13I-29P-40K-50T-52A, 5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, and 13I-29P-38N-40K-50T-52A, as described in section 5.4. In one embodiment, the chymotrypsin loop of the variant scaffold is a VEGF variant peptide of SEQ ID NO:9, and the variant scaffold is altered further to comprise a combination of six amino acid substitutions at positions equivalent to positions 13, 25, 29, 40, 50 and 52 of SEQ ID NO:187 to generate a modified variant BBPI scaffold. In one embodiment, the modified variant BBPI comprising a combination of six amino acid substitutions is chosen from the modified variant BBIt-AV-A13I-S25L-L29P-A40K-F50T-V52A of SEQ ID NO:598, the modified variant BBIt-AV-D1C-A13I-L29P-A40K-F50T-V52A of SEQ ID NO:611, the modified variant BBIt-AV-S4V-A13I-L29P-A40K-F50T-V52A of SEQ ID NO:612, the modified variant BBIt-AV-S5P-A13I-L29P-A40K-F50T-V52A of SEQ ID NO:613, the modified variant BBIt-AV-Q11G-A13I-L29P-A40K-F50T-V52A of SEQ ID NO:614, the modified variant BBIt-AV-A13I-S25R-L29P-A40K-F50T-V52A- of SEQ ID NO:616, the modified variant BBIt-AV-A13I-M27R-L29P-A40K-F50T-V52A of SEQ ID NO:619, the modified variant BBIt-AV-A13I-L29P-S31A-A40K-F50T-V52A of SEQ ID NO:621, the modified variant BBIt-AV-A13I-L29P-S31R-A40K-F50T-V52A of SEQ ID NO:622, the modified variant BBIt-AV-A13I-L29P-S38N-A40K-F50T-V52A of SEQ ID NO:623, and the modified variant BBIt-AV-A13I-L29P-S38N-A40K-F50T-V52A of SEQ ID NO:626.

In some embodiments, the modified variant BBPI that have greater TIA than the corresponding precursor unmodified BBPIs each comprise a combination of seven amino acid substitutions at amino acids at positions equivalent to positions 13, 25, 29, 31, 40, 50 and 52 of SEQ ID NO:187. In some embodiments, the combination of seven amino acid substitutions is chosen from a combination of substitutions at positions 13-25-29-31-40-50-52, 13-25-29-31-40-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, and 13-25-27-29-31-50-52. In some embodiments, the combination of seven amino acid substitutions is chosen from 13L-25R-29P-31A-40K-50T-52A, 13L-25R-29P-31R-40K-50T-52A, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, and 13I-25R-27A-29P-31A-50K-52T. The invention provides for any one of the variant BBPI scaffolds described in Section 5.3 and further comprising the combination of the six amino acid substitutions chosen from 13L-25R-29P-31A-40K-50T-52A, 13L-25R-29P-31R-40K-50T-52A, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, and 13I-25R-27A-29P-31A-50K-52T, as described in section 5.4. In one embodiment, the chymotrypsin loop of the variant scaffold is a VEGF variant peptide of SEQ ID NO:9, and the variant scaffold is altered further to comprise a combination of seven amino acid substitutions at positions equivalent to positions 13, 25, 29, 31, 40, 50 and 52 of SEQ ID NO:187 to generate a modified variant BBPI scaffold. In one embodiment, the modified variant BBPI comprising a combination of seven amino acid substitutions is chosen from the modified variant BBIt-AV-A13I-S25R-L29P-S31A-A40K-F50T-V52A of SEQ ID NO:617, the modified variant BBIt-AV-A13I-S25R-L29P-S31R-A40K-F50T-V52A of SEQ ID NO:618, the modified variant of BBIt-VEGF-V1-A13I-S25R-M27A-L29P-S31A-F50K-V52T SEQ ID NO:491, the modified variant BBIt-VEGF-V2-A13I-S25R-M27A-L29P-S31A-F50K-V52T of SEQ ID NO:632, the modified variant BBIt-VEGF-V3-A13I-S25R-M27A-L29P-S31A-F50K-V52T of SEQ ID NO:633, the modified variant BBIt-VEGF-V4-A13I-S25R-M27A-L29P-S31A-F50K-V52T of SEQ ID NO:634, the modified variant BBIt-VEGF-V5-A13I-S25R-M27A-L29P-S31A-F50K-V52T of SEQ ID NO:635, the modified variant BBIt-VEGF-V6-A13I-S25R-M27A-L29P-S31A-F50K-V52T of SEQ ID NO:636, the modified variant BBIt-TNFa-T1-A13I-S25R-M27A-L29P-S31A-F50K-V52T of SEQ ID NO:637, the modified variant BBIt-TNFa-T2-A13I-S25R-M27A-L29P-S31A-F50K-V52T of SEQ ID NO:638, and the modified variant BBIt-TNFa-T3-A13I-S25R-M27A-L29P-S31A-F50K-V52T of SEQ ID NO:639.

In some embodiments, the modified variant BBPI that have greater TIA than the corresponding precursor unmodified BBPIs each comprise a combination of eight amino acid substitutions at amino acids at positions equivalent to positions 13, 25, 27, 29, 31, 40, 50 and 52 of SEQ ID NO:187. In some embodiments, the combination of eight amino acid substitutions is chosen from a combination of substitutions at positions 13-25-27-29-31-40-50-52, 13-25-27-29-31-40-50-52, 13-25-27-29-31-40-50-52, 13-25-27-29-31-40-50-52, and 13-25-27-29-31-40-50-52. In some embodiments, the combination of eight amino acid substitutions is chosen from combinations 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q. The invention provides for any one of the variant BBPI scaffolds described in Section 5.3 and further comprising the combination of the eight amino acid substitutions chosen from combinations 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q, as described in section 5.4. In one embodiment, the chymotrypsin loop of the variant scaffold is a VEGF variant peptide of SEQ ID NO:9, and the variant scaffold is altered further to comprise a combination of seven amino acid substitutions at positions equivalent to positions 13, 25, 27, 29, 31, 40, 50 and 52 of SEQ ID NO:187 to generate a modified variant BBPI scaffold. In one embodiment, the modified variant BBPI comprising a combination of eight amino acid substitutions is chosen from the modified variant BBIt-AV-A13I-S25R-M27A-L29P-S31A-A40H-F50K-V52T of SEQ ID NO:627, the modified variant of BBIt-AV-A13I-S25K-M27A-L29R-S31 E-A40K-F50Q-V52Q of SEQ ID NO:628, the modified variant BBIt-AV-A13I-S25K-M27R-L29E-S31A-A40H-F50R-V52K of SEQ ID NO:629, the modified variant BBIt-AV-A13I-S25K-M27A-L29R-S31A-A40H-F50R-V52L of SEQ ID NO:630, and the modified variant BBIt-AV-A13I-S25K-M27Q-L29P-S31E-A40H-F50R-V52Q of SEQ ID NO:631.

In some embodiments, the modified variant BBPI that have greater TIA than the corresponding precursor unmodified BBPIs each further comprise a peptide insert that is positioned at the N-terminus of the modified variant BBPI. In some embodiments, the peptide insert comprises a sequence of between 1 and 15 amino acids. In other embodiments, the peptide insert comprises a sequence between 5 and 10 amino acids. In some embodiments, the peptide insert comprises the peptide of SEQ ID NO:389 (DDEPSKPCCDPDP; SEQ ID NO:389). Examples of modified variant BBPIs that the peptide insert of SEQ ID NO:389 are the modified variant 4D13BBIt-AV of SEQ ID NO:390 (DDEPSKPCCDPDPD-DESSKPCCDQCACTKSNPPQCRCSDM-RLNSCHSACKSCACY NLYGWTCFCVDITDF-CYEPCKPSE; SEQ ID NO:390), and the modified variant BBIt-AV-4D13-13I-29P-40K-50T-52A of SEQ ID NO: 413.

One measure of enhancement in trypsin and/or chymotrypsin inhibitory activity can be determined as the increase in an enzymatic activity ratio i.e. BCE:BBPI, in the modified variant BBPI when compared to that of the unmodified variant BBPI. The BCE:BBPI enzymatic activity ratio is the ratio of BBPI protease inhibitory activity e.g. trypsin inhibitory activity, to the BCE i.e. cellulase enzymatic activity. The ratio of the unmodified variant BBPI is assigned a value of 1. A ratio equal or greater than 1 for a modified variant BBPI indicates that the modified variant BBPI has a greater protease inhibitory activity e.g. trypsin inhibitory activity than that of the unmodified precursor BBPI. In some embodiments, the activity ratio of the modified variant BBPI is at least 1, at least about 1.05, about at least about 1.1, at least about 1.2, at least about 1.3, at least about 1.4, at least about 1.5, at least about 1.6, at least about 1.7, at least about 1.8. at least about 1.9, and at least about 2. In other embodiments, the activity ratio is at least about 2.1, at least about 2.2, at least about 2.3, at least about 2.4, at least about 2.5, at least about 2.6, at least about 2.7, at least about 2.8, at least about 2.9 and at least about 3. In yet other embodiments, the activity ratio is at least about 3.5, at least about 4.0, and at least about 5. Thus, in some embodiments, the protease inhibitory activity e.g. protease inhibitory activity, of the modified variant BBPI greater than that of the corresponding unmodified precursor BBPI by at least about 0.5%, about 1.0%, about 1.5%, about 2.0%, about 2.5%, about 3.0%, about 4.0%, about 5.0%, about 8.0%, about 10%, about 15%, about 20%, about 25%, about 30%, about 40%, about 50%, at least about 60%, at least about 70%, at least about 80%, at least about 90%, at least about 100% or more. In other embodiments, the protease inhibitory activity e.g. protease inhibitory activity, of the modified variant BBPI greater than that of the corresponding unmodified precursor BBPI by at least about 110%, 120%, 130%, 140%, 150%, 160%, 170%, 180%, 190%, and up to at least about 200%.

In other embodiments, modified variant BBPIs comprising a combination of amino acid substitutions have greater trypsin inhibitory activity than that of the unmodified precursor BBPI. In some embodiments, the at least two, at least three, at least four, at least five, at least six, at least seven, and at least eight amino acid substitutions generate modified variant BBPIs that have greater TIA than the unmodified precursor variant BBPI. All modified variant BBPIs comprising a combination of amino acid substitutions as described in section 5.4 have greater trypsin inhibitory activity than the corresponding unmodified precursor BBPIs.

5.8.2 BBPI Production Yield

In some embodiments, the amino acid substitutions made in the precursor variant BBPI are assessed for the ability of the resulting modified variant BBPI to have a greater production yield that is greater than that at which the unmodified precursor BBPI is produced i.e. the modified variant BBPI is produced at a level that is greater than that at which the unmodified precursor BBPI is produced. In some embodiments, the invention provides for modified variant BBPIs comprising a combination of amino acid substitutions as described in section 5.4 that have greater protease inhibitory activity e.g. trypsin inhibitory activity, and greater production yield than the corresponding unmodified precursor BBPIs.

Modified variant BBPIs that have greater TIA and PY than the corresponding precursor unmodified BBPIs each comprise at least two, at least three, at least four, at least five, at least six, at least seven, and at least eight amino acid substitutions (see Examples 12, 13, 14 and 15).

In some embodiments, the modified variant BBPI that have greater TIA and PY than the corresponding precursor unmodified BBPIs each comprise a combination of two amino acid substitutions at amino acids at positions equivalent to positions 50 and 52 of SEQ ID NO:187. In some embodiments, the combination of two amino acid substitutions is 50T-52A. The invention provides for any one of the variant BBPI scaffolds described in Section 5.3 and further comprising the combination of the two amino acid substitutions 50T-52A, as described in section 5.4. In one embodiment, the chymotrypsin loop of the variant scaffold is a VEGF variant peptide e.g. SEQ ID NO:9, and the variant scaffold is altered further to comprise a combination of three amino acid substitutions at positions equivalent to positions 13, 50 and 52 of SEQ ID NO:187 to generate a modified variant BBPI scaffold. In one embodiment, the modified variant BBPI comprising a combination of two amino acid substitutions is the modified variant BBIt-AV-F50T-V52A of SEQ ID NO: 6595.

In some embodiments, the modified variant BBPI that have greater TIA and PY than the corresponding precursor unmodified BBPIs each comprise a combination of three amino acid substitutions at amino acids at positions equivalent to positions 13, 50 and 52 of SEQ ID NO:187. In some embodiments, the combination of three amino acid substitutions is chosen from a combination of substitutions at positions 25-50-52, 29-50-52, 40-50-52, and 13-50-52. In some embodiments, the combination of three amino acid substitutions is chosen from 25L-50T-52A, 29P-50T-52A, 40K-50T-52A and 13I-50T-52A. The invention provides for any one of the variant BBPI scaffolds described in Section 5.3 and further comprising the combination of the three amino acid substitutions chosen from 25L-50T-52A, 29P-50T-52A, 40K-50T-52A and 13I-50T-52A, as described in section 5.4. In one embodiment, the chymotrypsin loop of the variant scaffold is a VEGF variant peptide e.g. SEQ ID NO:9, and the variant scaffold is altered further to comprise a combination of three amino acid substitutions at positions equivalent to positions 13, 50 and 52 of SEQ ID NO:187 to generate a modified variant BBPI scaffold. In one embodiment, the modified variant BBPI comprising a combination of three amino acid substitutions is chosen from the modified variant BBIt-AV-S25L-F50T-V52A of SEQ ID NO: 603, the modified variant BBIt-AV-L29P-F50T-V52A of SEQ ID NO:607, and the modified variant BBIt-AV-A40K-F50T-V52A of SEQ ID NO:609.

In some embodiments, the modified variant BBPI that have greater TIA and PY than the corresponding precursor unmodified BBPIs each comprise a combination of four amino acid substitutions at amino acids at positions equivalent to positions 13, 29, 50 and 52 of SEQ ID NO:187. In some embodiments, the combination of four amino acid substitutions is chosen from a combination of substitutions at positions 13-25-50-52, 13-29-50-52, 25-29-50-52, 13-40-50-52, 25-40-50-52, and 29-40-50-52. In some embodiments, the combination of four amino acid substitutions is chosen from 13I-25L-50T-52A, 13I-29P-50T-52A, 25L-29P-50T-52A, 13I-40K-50T-52A, 25L-40K-50T-52A, and 29P-40K-50T-52A. The invention provides for any one of the variant BBPI scaffolds described in Section 5.3 and further comprising the combination of the four amino acid substitutions chosen from 13I-25L-50T-52A, 13I-29P-50T-52A, 25L-29P-50T-52A, 13I-40K-50T-52A, 25L-40K-50T-52A, and 29P-40K-50T-52A, as described in section 5.4. In one embodiment, the chymotrypsin loop of the variant scaffold is a VEGF variant peptide chosen from SEQ ID NO:9 and 460, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-AV-A13I-S25L-F50T-V52A of SEQ ID NO:596, the modified variant BBIt-AV-A13I-L29P-F50T-V52A of SEQ ID NO:600, the modified variant BBIt-AV-A13I-A40K-F50T-V52A of SEQ ID NO:602, the modified variant BBIt-AV-S25L-L29P-F50T-V52A of SEQ ID NO:604, the modified variant BBIt-AV-S25L-A40K-F50T-V52A of SEQ ID NO:606, the modified variant BBIt-AV-L29P-A40K-F50T-V52A of SEQ ID NO:608, and the modified variant BBIt-VEGKD-A13I-S25K-L29P-V52K of SEQ ID NO:643. In another embodiment, the chymotrypsin loop of the variant scaffold is an FGF5 variant peptide chosen from SEQ ID NOS:430 and 431, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-MM007-Q-A13I-L29P-F50T-V52A of SEQ ID NO:432, and the modified variant BBIt-FGFps2-Q-A13I-L29P-F50T-V52A of SEQ ID NO:434. In another embodiment, the chymotrypsin loop of the variant scaffold is a TGFβ variant peptide chosen from SEQ ID NOS:436, 437 and 438, and the variant scaffold is altered further to comprise a combination of four amino acid substitutions at positions equivalent to positions 13, 29, 50 and 52 of SEQ ID NO:187 to generate a modified variant BBPI scaffold. In one embodiment, the modified variant BBPI comprising a combination of four amino acid substitutions is chosen from the modified variant BBIt-PEN3-Q-A13I-L29P-F50T-V52A of SEQ ID NO:443, the modified variant BBIt-MM021W-Q-A13I-L29P-F50T-V52A of SEQ ID NO:445, and the modified variant BBIt-WTQ-Q-A13I-L29P-F50T-V52A of SEQ ID NO:447.

In some embodiments, the modified variant BBPI that have greater TIA and PY than the corresponding precursor unmodified BBPIs each comprise a combination of five amino acid substitutions at amino acids at positions equivalent to positions 13, 29, 40, 50 and 52 of SEQ ID NO:187. In some embodiments, the combination of five amino acid substitutions is chosen from a combination of substitutions at positions 13-25-29-50-52, 13-29-40-50-52, 13-25-40-50-52, 25-29-40-50-52, 13-29-40-50-52, 13-29-40-50-52, 13-29-40-50-52 and 13-29-40-50-52. In some embodiments, the combination of five amino acid substitutions is chosen from 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A and 13I-29P-40K-50T-52T. The invention provides for any one of the variant BBPI scaffolds described in Section 5.3 and further comprising the combination of the five amino acid substitutions chosen from 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A and 13I-29P-40K-50T-52T, as described in section 5.4. In one embodiment, the chymotrypsin loop of the variant scaffold is a VEGF variant peptide of SEQ ID NO:9, and the variant scaffold is altered further to comprise a combination of five amino acid substitutions at positions equivalent to positions 13, 29, 40, 50 and 52 of SEQ ID NO:187 to generate a modified variant BBPI scaffold. In one embodiment, the modified variant BBPI comprising a combination of five amino acid substitutions is chosen from the modified variant BBIt-AV-A13I-S25L-L29P-F50T-V52A of SEQ ID NO:597, the modified variant BBIt-AV-A13I-L29P-A40K-F50T-V52A of SEQ ID NO:599, the modified variant BBIt-AV-A13I-S25L-A40K-F50T-V52A of SEQ ID NO:601, the modified variant BBIt-AV-S25L-L29P-A40K-F50T-V52A of SEQ ID NO:605, the modified variant BBIt-AV-A13L-L29P-A40K-F50T-V52A of SEQ ID NO:615, the modified variant BBIt-AV-A13I-L29K-A40K-F50T-V52A of SEQ ID NO:620, the modified variant BBIt-AV-A13I-L29P-A40K-F50K-V52A of SEQ ID NO:624, and the modified variant BBIt-AV-A13I-L29P-A40K-F50T-V52T of SEQ ID NO:625.

In some embodiments, the modified variant BBPI that have greater TIA and PY than the corresponding precursor unmodified BBPIs each comprise a combination of six amino acid substitutions at amino acids at positions equivalent to positions 13, 25, 29, 40, 50 and 52 of SEQ ID NO:187. In some embodiments, the combination of six amino acid substitutions is chosen from a combination of substitutions at positions 13-25-29-40-50-52, 1-13-29-40-50-52, 4-13-29-40-50-52, 5-13-29-40-50-52, 11-13-29-40-50-52, 13-25-29-40-50-52, 13-27-29-40-50-52, 13-29-31-40-50-52, 13-29-31-40-50-52, 13-29-38-40-50-52, and 13-29-38-40-50-52. In some embodiments, the combination of six amino acid substitutions is chosen from 13I-25L-29P-40K-50T-52A, 1C-13I-29P-40K-50T-52A, 4V-13I-29P-40K-50T-52A, 5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, and 13I-29P-38N-40K-50T-52A. The invention provides for any one of the variant BBPI scaffolds described in Section 5.3 and further comprising the combination of the six amino acid substitutions chosen from 13I-25L-29P-40K-50T-52A, 1C-13I-29P-40K-50T-52A, 4V-13I-29P-40K-50T-52A, 5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, and 13I-29P-38N-40K-50T-52A, as described in section 5.4. In one embodiment, the chymotrypsin loop of the variant scaffold is a VEGF variant peptide of SEQ ID NO:9, and the variant scaffold is altered further to comprise a combination of six amino acid substitutions at positions equivalent to positions 13, 25, 29, 40, 50 and 52 of SEQ ID NO:187 to generate a modified variant BBPI scaffold. In one embodiment, the modified variant BBPI comprising a combination of six amino acid substitutions is chosen from the modified variant BBIt-AV-A13I-S25L-L29P-A40K-F50T-V52A of SEQ ID NO:598, the modified variant BBIt-AV-D1C-A13I-L29P-A40K-F50T-V52A of SEQ ID NO:611, the modified variant BBIt-AV-S4V-A13I-L29P-A40K-F50T-V52A of SEQ ID NO:612, the modified variant BBIt-AV-S5P-A13I-L29P-A40K-F50T-V52A of SEQ ID NO:613, the modified variant BBIt-AV-Q11G-A13I-L29P-A40K-F50T-V52A of SEQ ID NO:614, the modified variant BBIt-AV-A13I-S25R-L29P-A40K-F50T-V52A- of SEQ ID NO:616, the modified variant BBIt-AV-A13I-M27R-L29P-A40K-F50T-V52A of SEQ ID NO:619, the modified variant BBIt-AV-A13I-L29P-S31A-A40K-F50T-V52A of SEQ ID NO:621, the modified variant BBIt-AV-A13I-L29P-S31R-A40K-F50T-V52A of SEQ ID NO:622, the modified variant BBIt-AV-A13I-L29P-S38N-A40K-F50T-V52A of SEQ ID NO:623, and the modified variant BBIt-AV-A13I-L29P-S38N-A40K-F50T-V52A of SEQ ID NO:626.

In some embodiments, the modified variant BBPI that have greater TIA and PY than the corresponding precursor unmodified BBPIs each comprise a combination of seven amino acid substitutions at amino acids at positions equivalent to positions 13, 25, 29, 31, 40, 50 and 52 of SEQ ID NO:187. In some embodiments, the combination of seven amino acid substitutions is chosen from a combination of substitutions at positions 13-25-29-31-40-50-52, 13-25-29-31-40-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, 13-25-27-29-31-50-52, and 13-25-27-29-31-50-52. In some embodiments, the combination of seven amino acid substitutions is chosen from 13L-25R-29P-31A-40K-50T-52A, 13L-25R-29P-31R-40K-50T-52A, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, and 13I-25R-27A-29P-31A-50K-52T. The invention provides for any one of the variant BBPI scaffolds described in Section 5.3 and further comprising the combination of the six amino acid substitutions chosen from 13L-25R-29P-31A-40K-50T-52A, 13L-25R-29P-31R-40K-50T-52A, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, 13I-25R-27A-29P-31A-50K-52T, and 13I-25R-27A-29P-31A-50K-52T, as described in section 5.4. In one embodiment, the chymotrypsin loop of the variant scaffold is a VEGF variant peptide of SEQ ID NO:9, and the variant scaffold is altered further to comprise a combination of seven amino acid substitutions at positions equivalent to positions 13, 25, 29, 31, 40, 50 and 52 of SEQ ID NO:187 to generate a modified variant BBPI scaffold. In one embodiment, the modified variant BBPI comprising a combination of seven amino acid substitutions is chosen from the modified variant BBIt-AV-A13I-S25R-L29P-S31A-A40K-F50T-V52A of SEQ ID NO:617, the modified variant BBIt-AV-A13I-S25R-L29P-S31R-A40K-F50T-V52A of SEQ ID NO:618, the modified variant of BBIt-VEGF-V1-A13I-S25R-M27A-L29P-S31A-F50K-V52T SEQ ID NO:491, the modified variant BBIt-VEGF-V2-A13I-S25R-M27A-L29P-S31A-F50K-V52T of SEQ ID NO:632, the modified variant BBIt-VEGF-V3-A13I-S25R-M27A-L29P-S31A-F50K-V52T of SEQ ID NO:633, the modified variant BBIt-VEGF-V4-A13I-S25R-M27A-L29P-S31A-F50K-V52T of SEQ ID NO:634, the modified variant BBIt-VEGF-V5-A13I-S25R-M27A-L29P-S31A-F50K-V52T of SEQ ID NO:635, the modified variant BBIt-VEGF-V6-A13I-S25R-M27A-L29P-S31A-F50K-V52T of SEQ ID NO:636, the modified variant BBIt-TNFα-T1-A13I-S25R-M27A-L29P-S31A-F50K-V52T of SEQ ID NO:637, the modified variant BBIt-TNFα-T2-A13I-S25R-M27A-L29P-S31A-F50K-V52T of SEQ ID NO:638, and the modified variant BBIt-TNFα-T3-A13I-S25R-M27A-L29P-S31A-F50K-V52T of SEQ ID NO:639.

In some embodiments, the modified variant BBPI that have greater TIA and PY than the corresponding precursor unmodified BBPIs each comprise a combination of eight amino acid substitutions at amino acids at positions equivalent to positions 13, 25, 27, 29, 31, 40, 50 and 52 of SEQ ID NO:187. In some embodiments, the combination of eight amino acid substitutions is chosen from a combination of substitutions at positions 13-25-27-29-31-40-50-52, 13-25-27-29-31-40-50-52, 13-25-27-29-31-40-50-52, 13-25-27-29-31-40-50-52, and 13-25-27-29-31-40-50-52. In some embodiments, the combination of eight amino acid substitutions is chosen from combinations 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q. The invention provides for any one of the variant BBPI scaffolds described in Section 5.3 and further comprising the combination of the eight amino acid substitutions chosen from combinations 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q, as described in section 5.4. In one embodiment, the chymotrypsin loop of the variant scaffold is a VEGF variant peptide of SEQ ID NO:9, and the variant scaffold is altered further to comprise a combination of seven amino acid substitutions at positions equivalent to positions 13, 25, 27, 29, 31, 40, 50 and 52 of SEQ ID NO:187 to generate a modified variant BBPI scaffold. In one embodiment, the modified variant BBPI comprising a combination of eight amino acid substitutions is chosen from the modified variant BBIt-AV-A13I-S25R-M27A-L29P-S31A-A40H-F50K-V52T of SEQ ID NO:627, the modified variant of BBIt-AV-A13I-S25K-M27A-L29R-S31E-A40K-F50Q-V52Q of SEQ ID NO:628, the modified variant BBIt-AV-A13I-S25K-M27R-L29E-S31A-A40H-F50R-V52K of SEQ ID NO:629, the modified variant BBIt-AV-A13I-S25K-M27A-L29R-S31A-A40H-F50R-V52L of SEQ ID NO:630, and the modified variant BBIt-AV-A13I-S25K-M27Q-L29P-S31E-A40H-F50R-V52Q of SEQ ID NO:631.

In some embodiments, the modified variant BBPIs further comprise a peptide insert that is positioned at the N-terminus of the modified variant BBPI. In some embodiments, the peptide insert comprises a sequence of between 1 and 15 amino acids. In other embodiments, the peptide insert comprises a sequence between 5 and 10 amino acids. In some embodiments, the peptide insert comprises the peptide of SEQ ID NO:389. Examples of modified variant BBPIs that the peptide insert of SEQ ID NO:389 are the modified variant 4D13BBIt-AV of SEQ ID NO:390, and the modified variant BBIt-AV-4D13-13I-29P-40K-50T-52A of SEQ ID NO: 413.

The invention further provides for modified variant BBPIs that have greater TIA and PY than the corresponding precursor unmodified BBPIs each comprise any one combination of the amino acid substitutions described above and that have greater protease inhibitory activity than the unmodified precursor variant BBPI. In some embodiments, modified variant BBPIs which contain a variant peptide in place of the chymotrypsin loop of the corresponding precursor unmodified BBPI have greater trypsin inhibitory activity (TIA) than that of the precursor unmodified BBPI scaffold. In other embodiments, modified variant BBPIs which contain a variant peptide in place of the trypsin loop of the corresponding precursor unmodified BBPI have greater chymotrypsin inhibitory activity (TIA) than that of the precursor unmodified BBPI scaffold.

As shown in the Examples, substitutions of at least one amino acid in the backbone of the variant BBPI generates a modified variant BBPI that has a greater production yield that the unmodified variant BBPI. In some embodiments, BBPIs that comprise a combination of two, three, four, five, six, seven or eight amino acid substitutions have a greater production yield than the unmodified precursor BBPI. Thus, the invention provides for modified variant BBPIs that comprise any one combination of the amino acid substitutions described above and that have greater production yield (PY) than the unmodified precursor variant BBPIs. In yet other embodiments, the invention provides for modified variant BBPIs that comprise any one combination of the amino acid substitutions described above and that have greater trypsin inhibitory activity and greater production yield than the TIA and PY of the unmodified precursor variant BBPIs.

In some embodiments, the modified variant BBPIs that have greater TIA and PY than the corresponding precursor unmodified BBPIs each comprise further comprise a peptide insert that is positioned at the N-terminus of the modified variant BBPI. In some embodiments, the peptide insert comprises a sequence of between 1 and 15 amino acids. In other embodiments, the peptide insert comprises a sequence between 5 and 10 amino acids. In some embodiments, the peptide insert comprises the peptide of SEQ ID NO:389. Examples of modified variant BBPIs include the modified variant 4D13BBIt-AV of SEQ ID NO:390, and the modified variant BBIt-AV-4D13-13I-29P-40K-50T-52A of SEQ ID NO: 413.

One measure of enhancement in production yield can be determined as the increase in the level of free BBPI following cleavage of the BBPI from the C-terminus of the BCE core. As described above, in some embodiments, the BBPI fusion proteins can be cleaved using proteases or by chemical means. In other embodiments, the BBPI can be cleaved from the BBPI fusion protein by acid/heat treatment, which cleaves the A-P bonds present in the CBD linker that joins the BCE to the BBPI. In yet other embodiments, the BBPI fusion proteins can be cleaved using glutamyl endopeptidase I from *B. licheniformis*. In some embodiments, the enhancement in production yield of a modified variant BBPI is measured as the increase in the level of free modified variant BBPI following activation of the fusion BBPI and following acid heat treatment of the BBPI fusion protein, when compared to the level of free unmodified precursor BBPI that was subjected to the same treatment. In other embodiments, the enhancement in production yield of a modified variant BBPI is measured as the increase in the level of free modified variant BBPI without activation of the fusion BBPI and following acid heat treatment of the BBPI fusion protein, when compared to the level of the corresponding free unmodified precursor BBPI that was subjected to the same treatment. In some embodiments, the free modified variant BBPI has a greater production yield and a greater TIA than the corresponding precursor BBPI.

In some embodiments, the production yield of the modified variant BBPI is greater than that of the corresponding unmodified precursor BBPI by at least about 0.5%, about 1.0%, about 1.5%, about 2.0%, about 2.5%, about 3.0%, about 4.0%, about 5.0%, about 8.0%, about 10%, about 15%, about 20%, about 25%, about 30%, about 40%, about 50%, at least about 60%, at least about 70%, at least about 80%, at least about 90%, at least about 100% or more. In other embodiments, the production yield of the modified variant BBPI is greater than that of the corresponding unmodified precursor BBPI by at least about 110%, 120%, 130%, 140%, 150%, 160%, 170%, 180%, 190%, and up to at least about 200%.

6. Personal Care Compositions

6.0.1 Personal Care Compositions Comprising Modified Variant BBPIs

The present invention provides personal care compositions comprising at least one modified variant BBPI for medical and nonmedical conditions. In some embodiments, the present invention provides personal care compositions and the methods of their use. In some embodiments, the invention provides personal care compositions for use in the skin care. In other embodiments, the personal care compositions are for use in hair care. In some embodiments, the personal care compositions for use in skin care include cosmetic compositions. In other embodiments, the personal care compositions of the invention are for use in the treatment of various disorders.

As described in greater detail herein, the present invention provides compositions for use in numerous aspects of personal care, including but not limited to hair and skin care, as well as cosmetics (e.g., make-up). For example, the present invention provides compositions that find use in daily personal care, skin care, sun care (e.g., sunscreens, as well as tanners), hair care (e.g., shampoos, leave-on and/or rinse off conditioners, hair tonics, hair sprays, gels, foams, mousses, setting products, hair colorants, permanent formulations, other styling and cleaning products, etc.), after-sun care for skin, hair and lips, oral care (e.g., toothpastes and gels, mouthwashes, rinses, etc.), bathing (e.g., washes, shower soaps, bath soaps, salts, pearls, etc.), skin lighteners, cleansing treatments for skin conditions (e.g., pimples, acne, skin toners, etc.), depilatories, wet wipes, deodorants, antiperspirants, facial masks, shaving (e.g., shaving creams, gels, etc.), after-shave, skin peeling (e.g., exfoliants), intimate care products (e.g., feminine hygiene products), personal fresheners, and foot care. The present invention also provides compositions that find use in cosmetics (e.g., foundations, mascara, eye shadows, eye liners, lipsticks, lip glosses, blushers, etc.). In addition, the present invention provides personal care compositions for use in ameliorating a hair condition associated with a disorder. In other embodiments, the personal care composition are for use in ameliorating a skin condition associated with a disorder. It is contemplated that the compositions of the present invention will find use various forms, including but not limited to solids, liquids, colloidal suspensions, emulsions, oils, gels, aerosols, foams, powders, pump sprays, etc., as well as being used in conjunction with items such as wet wipes, etc. Indeed, it is contemplated that the present invention will find use in any suitable form for the intended use(s).

In some embodiments, the personal care composition comprises a modified variant BBPI comprising a variant peptide and at least one amino acid substitution, as described in section 5.4.1 above. In other embodiments, the personal care composition comprises a modified variant BBPI comprising a variant peptide and a combination of amino acid substitutions, as described in section 5.4.2 above. In some embodiments, the personal care composition comprises a modified variant BBPI in which the equivalent chymotrypsin loop is a VEGF-binding peptide. In other embodiments, the personal care composition comprises a modified variant BBPI in which the equivalent chymotrypsin loop is an FGF5 binding peptide. In other embodiments, the personal care composition comprises a modified variant BBPI in which the equivalent chymotrypsin loop is a TGFβ binding peptide. In yet other embodiments, the personal care composition comprises a modified variant BBPI in which the equivalent chymotrypsin loop is a TNFα binding peptide. In some embodiments, the modified variant BBPI comprises from about 0.0001 weight percent to about 5 weight percent of the personal care composition, while in alternative embodiments, the modified variant BBPI comprises from about 0.001 weight percent to about 0.5 weight percent of the personal care composition, and in yet additional embodiments, the modified variant BBPI comprises from about 0.01 weight percent to about 1 weight percent of the personal care composition.

6.0.2 Personal Care Compositions Comprising Modified Variant VEGF-BBPIs

VEGF plays a central role in promoting angiogenesis as well as influencing diverse cell functions including cell survival, proliferation and the generation of nitric oxide and prostacyclin (Zachary et al., Cardiovasc Res, 49: 568-81 [2001]). The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (See, Siemeister et al., [1998]). In fact, monoclonal antibodies against VEGF have been shown to inhibit human tumor xenograft growth and ascites formation in mice (See, Kim et al., [1993]; Asano et al., [1998]; Mesiano et al., [1998]; Luo et al., [1998a] and [1998b]; and Borgstrom et al., [1996] and [1998]).

Angiogenesis, involving VEGF and RTKs is not only involved in cancer development, as many other diseases or conditions affecting different physiological systems are angiogenesis-dependent, such as arthritis and atherosclerotic plaques (bone and ligaments), diabetic retinopathy, neovascular glaucoma, macular degeneration, ocular herpes, trachoma and corneal graft neovascularization (eye) and angiofibroma. VEGF expression is upregulated in the hyperplastic epidermis of psoriasis patients (Detmar and Yeo et al. [1995]), and in other skin diseases characterized by enhanced angiogenesis including, scleroderma, rosacea, hemangioma, contact dermatitis, and hypertrophic scarring of the skin. Targeted overexpression of VEGF in the epidermis of transgenic mice was reported to result in enhanced skin vascularization with equal numbers of tortuous and leaky blood vessels (See e.g., Brown et al., [1998]). Also, chronic synthesis of VEGF in mouse skin leads to the first histologically equivalent murine model of human psoriasis (Xia et al., [2003]) that is reversible by binding agents specific for VEGF. In addition, ultraviolet radiation induces VEGF production in keratinocytes and enhances cutaneous angiogenesis (Kim et al., Soc. Investigative Dermatol. 126:2697 [2006]; Blaudshun et al., FEBS Let. 474:195-200; [2000]; Kosmadaki et al., FASEB J. 17:446-8 [2003]).

In addition, the expression of VEGF in the outer root sheath of murine hair follicles was found to be temporally and spatially associated with capillary proliferation during anagen. Transgenic overexpression of VEGF in the outer root sheath increased perifollicular vascularization and led to accelerated hair growth following depilation and the growth of larger hairs (Yano et al. J Clin Invest 107: 409-17 [2001]).

Thus, VEGF is involved in the vascularization associated with pathologic and non-pathologic conditions.

The invention provides for personal skin care and/or hair care compositions that comprise a modified variant VEGF-BBPI. The VEGF-BBPIs comprised in the personal care compositions of the invention are modified variant BBPIs in which the equivalent chymotrypsin loop of the precursor scaffold of the VEGF-BBPI has been replaced by a VEGF variant peptide, and which further comprise at least one amino acid substitution as described in sections 5.4.1 and 5.4.2. In some embodiments of the present invention, binding of the modified variant VEGF-BBPI to VEGF prevents VEGF from increasing perifollicular vascularization and inhibits the VEGF from promoting hair growth. In other embodiments, binding of the modified variant VEGF-BBPI to VEGF prevents VEGF from increasing vascularization of the skin in a subject suffering from an angiogenic skin disorder e.g. hemangioma and lichen planus. In yet other embodiments, binding of the modified variant VEGF-BBPI to VEGF prevents VEGF from promoting disregulated angiogenesis associated with inflammatory skin disorders including psoriasis, scleroderma, venous ulcers, acne, rosacea, warts, eczema, and lymphangiogenesis. However, it is not intended that the present invention be limited to any particular mechanism.

In some embodiments, the personal care composition comprises a VEGF-BBPI in which the chymotrypsin loop is a VEGF-binding peptide chosen from U.S. application Ser.

Nos. 09/832,723 and 10/984,270, including peptides ACYN-LYGWTC (SEQ ID NO:9), KYYLYWW (SEQ ID NO:458), TLWKSYW (SEQ ID NO:459), DLYWW (SEQ ID NO:460), SKHSQIT (SEQ ID NO:468) KTNPSGS (SEQ ID NO:469) RPTGHSL (SEQ ID NO:470), KHSAKAE (SEQ ID NO:471) KPSSASS (SEQ ID NO:472), PVTKRVH (SEQ ID NO:473), TLHWWVT (SEQ ID NO:492), PYKASFY (SEQ ID NO:493), PLRTSHT (SEQ ID NO:494), EATPROT (SEQ ID NO:495), NPLHTLS (SEQ ID NO:496), SKHERIWS (SEQ ID NO:497), ATNPPPM (SEQ ID NO:498), STTSPNM (SEQ ID NO:499), ADRSFRY (SEQ ID NO:500), PKADSKQ (SEQ ID NO:501), PNQSHLH (SEQ ID NO:502), SGSETWM (SEQ ID NO:503), ALSAPYS (SEQ ID NO:504), KMPTSKV (SEQ ID NO:505), ITPKRPY (SEQ ID NO:506), KWIVSET (SEQ ID NO:507), PNANAPS (SEQ ID NO:508), NVQSLPL (SEQ ID NO:509), TLWPTFW (SEQ ID NO:510), NLWPHFW (SEQ ID NO:511), SLWPAFW (SEQ ID NO:512), SLW-PHFW (SEQ ID NO:513), APWNSHI (SEQ ID NO:514), APWNLHI (SEQ ID NO:515), LPSWHLR (SEQ ID NO:516), PTILEWY (SEQ ID NO:517), TLYPQFW (SEQ ID NO:518), and HLAPSAV (SEQ ID NO:519). In some other embodiments, the VEGF variant sequences include, but are not limited to VEGF-binding peptides disclosed in U.S. application Ser. No. 11/919,717, including peptides KYYLSWW (SEQ ID NO:520), WYTLYKW (SEQ ID NO:521), TYRLYWW (SEQ ID NO:522), RYSLYYW (SEQ ID NO:523), YYLYYWK (SEQ ID NO:524), NYQLYGW (SEQ ID NO:525), TKWPSYW (SEQ ID NO:226), TLWKSYW (SEQ ID NO:527), PLWPSYW (SEQ ID NO:528), RLWPSYW (SEQ ID NO:529), TLWPKYW (SEQ ID NO:530), KYDLYWW (SEQ ID NO:531), RYDLYWW (SEQ ID NO:532), DYRLYWW (SEQ ID NO:533), DYK-LYWW (SEQ ID NO:534), EYKLYWW (SEQ ID NO:535), and RYPLYWW (SEQ ID NO:536). In other embodiments, the VEGF binding peptide is chosen from SEQ ID NOS:9, 458, 459, 460, 468, 469, 470, 471, 472 and 473.

The scaffold in which the variant VEGF peptide is introduced to replace the chymotrypsin loop is chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds. In some embodiments, the scaffold of the VEGF-BBPI is that of SEQ ID NO:187.

In some embodiments, the backbone of the modified variant VEGF-BBPI comprises at least one amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, as described in section 5.4.1.

In other embodiments, the backbone of the modified variant VEGF-BBPI comprises a combination of amino acid substitutions chosen from a combination two, three, four, five, six, seven or eight amino acid substitutions as recited above in section 5.4.2.

In other embodiments, the backbone of the modified variant VEGF-BBPI comprises a combination of amino acid substitutions chosen from a combination of amino acid substitutions chosen from 13I-29P-50T-52A, 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L.

In some embodiments, the personal care compositions of the invention comprise a modified variant BBPI in which the equivalent chymotrypsin loop of the precursor scaffold is replaced with a VEGF variant peptide chosen from SEQ ID NOS:9, 458, 459, 460, 468, 469, 470, 471, 472 and 473, wherein the scaffold is that of SEQ ID NO:187, and which comprises a combination of amino acid substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the personal care compositions comprise a VEGF-BBPI chosen from the VEGF-BBPIs of SEQ ID NOS: 601, 602, 627, 628, 629, 630, 631, 643, 491, 632, 633, 634, 635 and 636.

In some embodiments, the invention provides a personal care composition comprising a VEGF-BBPI that binds to VEGF. In alternative embodiments, the binding of the VEGF-BBPI to VEGF blocks the downstream activity of VEGF. In some embodiments, the composition is capable of modulating angiogenesis.

In some embodiments, the personal care composition comprises a modified variant BBPI-VEGF for use in skin care. In some embodiments, the skin care compositions are for cosmetic use in improving the appearance of skin. In other embodiments, the skin care compositions are for therapeutic use in improving the appearance of skin in a subject suffering from a skin disorder. In some embodiments, the skin disorder is an angiogenic skin disorder. In additional embodiments, the skin disorder is at least one chosen from psoriasis, scleroderma, venous ulcers, acne, rosacea, warts, eczema, hemangiomas and lymphangiogenesis. In some embodiments, the skin disorder is rosacea. In other embodiments, the skin disorder is psoriasis.

In one embodiment, the personal skin care composition comprising a VEGF-BBPI is chosen from skin creams, lotions, sprays, emulsions, colloidal suspensions, foams, aerosols, liquids, gels, sera, and solids. In another embodiment, the personal care composition is a skin care composition selected from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, hair growth inhibitors, and radioprotectives. Radioprotectives are chosen from non-water-resistant sunscreens, very water-resistant sunscreens, and water-in-silicone sunscreens.

In one embodiment, the personal care skin care composition comprising a VEGF-BBPI is comprises topically applied over-the-counter compositions, anti-fungal treatments, anti-acne treatments, skin protectants, sunscreens, deodorants, and antiperspirants. In other embodiments, the skin care composition is capable of lightening skin tone, reducing redness, preventing skin tone darkening or preventing color development.

The present invention also provides personal care compositions that are cosmetic compositions. In some preferred embodiments, the cosmetic compositions comprising a VEGF-BBPI are chosen from pressed powder formulations and foundations. In some preferred embodiments, the cosmetic compositions comprise at least one pigment.

In yet additional embodiments, the makeup compositions are pressed powder formulations selected from loose powders, blushes, and bronzing powders. In still further embodiments, the makeup compositions are foundations selected from water-in-oil foundations, water-in-silicone foundations, oil-in-water foundations, anhydrous makeup sticks, and cream-to-powder foundations.

In some embodiments, the personal skin care compositions comprise a modified variant VEGF-BBPI, as set forth herein, and a physiologically acceptable carrier or excipient. Preferably, the VEGF-BBPI is present in an amount of about 0.0001% to about 5% by weight based on the total weight of the composition. Also preferably, the VEGF-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In some other embodiments, the invention provides a personal care composition that comprises a modified variant VEGF-BBPI for use in hair care.

In some embodiments, the hair care compositions find use in inhibiting hair growth. In other embodiments, inhibition of hair growth comprises hair removal for treatment of at least one disease or condition for which decreased hair growth is desirable. In some embodiments, inhibition and/or removal comprises depilation. In some embodiments, the hair is selected from the group consisting of facial hair, leg hair, arm hair, and torso hair.

In one embodiment, the hair care composition is selected from the group consisting of shampoos, conditioners, hair styling compositions, hair colorants, permanent wave formulations, creams, gels, mousses, sprays, emulsions, colloidal suspensions, liquids, foams, and solids. In some embodiments, the hair care composition further comprises a radioprotective. As described for the personal skin care compositions the radioprotective is a sunscreen chosen from non-water-resistant sunscreens, very water-resistant sunscreens, and water-in-silicone sunscreens. In other embodiments, the radioprotective is a sunscreen chosen from non-water-resistant sunscreens, very water-resistant sunscreens, and water-in-silicone sunscreens.

In some embodiments, the personal hair care compositions comprise a modified variant VEGF-BBPI, as set forth herein, and a physiologically acceptable carrier or excipient. Preferably, the VEGF-BBPI is present in an amount of about 0.0001% to about 5% by weight based on the total weight of the composition. Also preferably, the VEGF-BBPI is present in an amount of about 0.001% to about 1% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In other embodiments, the personal care compositions of the invention are for use in the treatment of various diseases associated with elevated levels of VEGF.

The present invention also provides methods for inhibiting hair growth of a subject, comprising the steps of providing the personal care VEGF hair care composition of the present invention; providing a subject to be treated; and applying the composition to the subject in an area in which inhibition of hair growth is desired. In some embodiments, the inhibition of hair growth comprises inhibiting the growth of the subject's hair, wherein the hair to be inhibited is selected from the group consisting of facial air, underarm hair, leg hair, torso hair, and arm hair, and head hair. In additional embodiments, the method for inhibiting hair growth using a VEGF hair care composition of the invention comprises a personal care composition comprising a VEGF-BBPI having an amino acid sequence chosen from SEQ ID NOS SEQ ID NOS:601, 602, 627, 628, 629, 630, 631, 643, 491, 632, 633, 634, 635 and 636.

In another embodiment, the invention provides a method for improving the appearance and/or condition of skin in a subject suffering from a skin disorder, comprising providing the personal care composition of the present invention; providing a subject to be treated; and applying the composition to the affected skin of the subject. In some embodiments, the skin disorder is chosen from psoriasis, venous ulcers, acne, rosacea, warts, eczema, hemangiomas, cutaneous lichen planus, and lymphangiogenesis, etc. In some particularly preferred embodiments, the skin disorder is rosacea. In other embodiments, the skin disorder is psoriasis. In additional embodiments, the method for improving the appearance and/or condition of skin in a subject suffering from a skin disorder using a VEGF skin care composition of the invention comprises a personal care composition comprising a VEGF-BBPI having an amino acid sequence chosen from SEQ ID NOS: 601, 602, 627, 628, 629, 630, 631, 643, 491, 632, 633, 634, 635 and 636.

6.0.3 Personal Care Compositions Comprising Modified Variant FGF-5-BBPIs

The Fibroblast Growth Factor (FGF) family is a superfamily of growth factors containing at least 23 members, many of which are potent regulators of cell proliferation, differentiation and cell function. All of the FGFs have a conserved 120 amino acid core. Members of the family share conserved cysteine residues and 30-50% sequence homology at the amino acid level. The molecular weight of the FGFs ranges from 7 kDa for FGF-1 to 38 kDa for FGF-5. The length of the proteins is from 60 amino acids in the case of an FGF-1 splice variant to 288 amino acids for FGF-2. Binding to heparin is an essential step required for an FGF factor to interact with cell surface receptors. FGF5 is a secreted signaling protein consisting of 268 amino acids with a 17 amino acid signal sequence and a 251 amino acid mature peptide. The human gene also gives rise to a glycosylated alternate splice form that is 18 kDa in size and 123 amino acid in length. The murine homologue of FGF-5 was cloned and found to be 84% homologous to the human protein at the amino acid sequence level. Human FGF-5 consists of three exons and maps to chromosome 4q21 and cross-reacts with murine FGF-5.

Formation of hair follicles involves a complex series of steps: growth (anagen), regression (catagen), rest (telogen) and shedding (exogen). FGF-5 has been implicated as one of the major drivers of the transition from anagen to catagen in the hair cycle. Expression of FGF-5 is detected in hair follicles from wild-type mice and is localized to the outer root sheath during the anagen phase. Mice homozygous for a predicted null allele of FGF-5, fgf5neo, have abnormally long hair (See, Hebert et al., Cell 78: 1017-25 [1994]). The phenotype appears identical to that of mice homozygous for the spontaneous mutation angora (go). Recently, partial FGF-5 sequences, FGF5S, thought to compete with FGF-5 in binding to the receptor have been identified, (See, Ito et al., J. Cell Physiol., 197:272-83 [2003]).

The invention provides personal hair care compositions that comprises at least one modified variant FGF-BBPI for use in promoting hair growth and/or preventing hair loss. In one embodiment, the invention provides FGF-BBPI compositions for personal skin care. In other embodiments, the invention provides FGF-BBPI compositions for hair care. The FGF-BBPIs comprised in the personal care compositions of the invention are modified variant BBPIs in which the equivalent chymotrypsin loop of the precursor scaffold of the FGF-5-BBPI has been replaced by an FGF-5 variant peptide, and which further comprise at least one amino acid substitution as described in sections 5.4.1 and 5.4.2. In the present invention, binding of the modified variant FGF-BBPI to FGF-5 prevents FGF-5 from interacting with its cognate receptor and inhibits transition from the anagen to the catagen promoting hair growth and preventing hair loss. However, it is not intended that the present invention be limited to any particular mechanism.

In some embodiments, personal care composition comprises at least one FGF-BBPI in which the chymotrypsin loop is an FGF-5 variant peptide chosen from CACRTQPYPLCF (MM007; SEQ ID NO:430), CICTWIDSTPC (PS2; SEQ ID NO:431), CYGLPFTRC (SEQ ID NO:537), CEEIWTMLC (SEQ ID NO:538), CWALTVKTC (SEQ ID NO:539), CLTVLWTTC (SEQ ID NO:540), CTLWNRSPC (SEQ ID NO:541), CHYLLTNYC (SEQ ID NO:542), CRIHLAHKC (SEQ ID NO:543), TNIDSTP (SEQ ID NO:544), HLQTTET (SEQ ID NO:545), SLNNLTV (SEQ ID NO:546), TNIDSTP (SEQ ID NO:547), TNIDSTP (SEQ ID NO:548), LRILANK (SEQ ID NO:549), LLTPTLN (SEQ ID NO:550), ALPTHSN (SEQ ID NO:551), TNIDSTP (SEQ ID NO:552), LCRRFEN (SEQ ID NO:553), TNIDSTP (SEQ ID NO:554), TNIDSTP (SEQ ID NO:555), HLQTTET (SEQ ID NO:556), PLGLCPP (SEQ ID NO:557), GYFIPSI (SEQ ID NO:558), TKIDSTP (SEQ ID NO:559), HLQTTET (SEQ ID NO:560), WNIDSTP (SEQ ID NO:561), TWIDWTP (SEQ ID NO:562), RTQPYPL (SEQ ID NO:670) and TWIDSTP (SEQ ID NO:671). In other embodiments, the FGF variant peptide is chosen from SEQ ID NOS: SEQ ID NOS:430, 431, 670 and 671.

The scaffold in which the variant FGF peptide is introduced to replace the chymotrypsin loop is chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds. In some embodiments, the scaffold of the VEGF-BBPI is that of SEQ ID NO:187.

In some embodiments, the backbone of the modified variant FGF-BBPI comprises at least one amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, as recited in section 5.4.1. In other embodiments, the backbone of the modified variant FGF-BBPI comprises a combination of amino acid substitutions chosen from a combination two, three, four, five, six, seven or eight amino acid substitutions as recited above in section 5.4.2. In other embodiments, the backbone of the modified variant FGF-BBPI comprises a combination of amino acid substitutions chosen from a combination of amino acid substitutions chosen from 13I-29P-50T-52A, 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the combination of substitutions is 13I-29P-50T-52A.

In some embodiments, the personal care compositions of the invention comprise an FGF-BBPI in which the equivalent chymotrypsin loop of the precursor scaffold is replaced with an FGF variant peptide chosen from SEQ ID NOS:433 and 434, wherein the scaffold is that of SEQ ID NO:187, and which comprises the combination of amino acid substitutions 13I-40K-50T-52A. Thus, in some embodiments, the personal care compositions comprise a FGF-BBPI chosen from the FGF-BBPIs of SEQ ID NOS:439 and 441.

In some embodiments, the invention provides a personal care composition comprising a FGF-BBPI that binds to FGF. In alternative embodiments, the binding of the FGF-BBPI to FGF blocks the downstream activity of FGF. In some embodiments, the composition is capable of promoting hair growth.

In some embodiments, the personal care composition comprising a modified variant BBPI-FGF is for use in skin care. In some embodiments, the skin care compositions are cosmetic compositions for use in promoting hair growth. In some embodiments, the skin care compositions are for use in promoting hair growth in a subject suffering from a disease or condition that involves hair loss. In some of these embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia greata, cancer, conditions that affect defective hair fiber production, and environmental factors that affect hair production. In a preferred embodiment, the disease is androgenic alopecia or alopecia areata.

In one embodiment, the personal care composition comprising an FGF-BBPI is a skin care composition is chosen from skin creams, lotions, sprays, emulsions, colloidal suspensions, foams, aerosols, liquids, gels, sera, and solids. In another embodiment, the personal care composition is a skin care composition selected from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, hair growth inhibitors, and radioprotectives. Radioprotectives are chosen from non-water-resistant sunscreens, very water-resistant sunscreens, and water-in-silicone sunscreens.

In one embodiment, the personal skin care composition comprising an FGF-BBPI is a skin care composition comprising topically applied over-the-counter compositions, antifungal treatments, anti-acne treatments, skin protectants, sunscreens, deodorants, and antiperspirants.

In some embodiments, the personal skin care compositions comprise a modified variant VEGF-BBPI, as set forth herein, and a physiologically acceptable carrier or excipient. Preferably, the VEGF-BBPI is present in an amount of about 0.0001% to about 5% by weight based on the total weight of the composition. Also preferably, the VEGF-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In other embodiments, the invention provides a personal care composition comprising a modified variant FGF-BBPI for use in hair care.

In some embodiments, the hair care compositions find use in promoting hair growth. In other embodiments, modulation comprises promoting hair growth in a subject suffering from a disease or condition that involves hair loss. In some of these embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia greata, cancer, conditions that affect defective hair fiber production, and environmental factors that affect hair production. In a preferred embodiment, the disease is androgenic alopecia or alopecia greata.

In one embodiment, the hair care composition is selected from the group consisting of shampoos, conditioners, hair styling compositions, hair colorants, permanent wave formulations, creams, gels, mousses, sprays, emulsions, colloidal suspensions, liquids, foams, and solids. In some embodiments, the hair care composition further comprises a radioprotective. As described for the personal skin care compositions the radioprotective is a sunscreen chosen from non-water-resistant sunscreens, very water-resistant sunscreens, and water-in-silicone sunscreens. In other embodiments, the radioprotective is a sunscreen chosen from non-water-resistant sunscreens, very water-resistant sunscreens, and water-in-silicone sunscreens.

In some embodiments, the personal hair care compositions comprise a modified variant FGF-BBPI, as set forth herein, and a physiologically acceptable carrier or excipient. Preferably, the FGF-BBPI is present in an amount of about 0.0001% to about 5% by weight based on the total weight of the composition. Also preferably, the FGF-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In other embodiments, the personal care FGF-BBPI compositions of the invention are for use in the treatment of various diseases associated with elevated levels of FGF.

The present invention also provides methods for promoting hair growth of a subject, comprising the steps of providing the personal care FGF composition of the present invention; providing a subject to be treated; and applying the composition to the subject in an area in which promotion of hair growth is desired. In some embodiments, the FGF composition is a skin care composition. In other embodiments, the FGF composition is a hair composition. In some embodiments, promotion of hair growth comprises promoting the growth of the subject's hair, wherein the hair growth to be promoted is chosen from facial air, underarm hair, leg hair, torso hair, and arm hair, and head hair. In additional embodiments, the method for promoting hair growth using an FGF hair care composition of the invention comprises applying a personal care composition comprising an FGF-BBPI having an amino acid sequence chosen from SEQ ID NOS:439 and 441.

6.0.4 Personal Care Compositions Comprising Modified Variant TGFβ-BBPIs

Proteins of the Transforming Growth Factor-β (TGFβ) family are synthesized by almost all cells. The TGFβs are a group of stable, multifunctional polypeptide growth factors whose activities include, among other things, context-specific inhibition and stimulation of cell proliferation, control of the extracellular matrix, degradation and control of mesenchymal-epithelial interactions during embryogenesis, mediation of cell and tissue responses to injury, control of carcinogenesis and modulation of immune responses. TGFβ-1 is synthesized by virtually all cells (with only a few exceptions). TGFβ-1 has been found in the highest concentration in human platelets and mammalian bone. TGFβ-1 has many functions including suppression of cell proliferation, enhancement of extracellular matrix deposition and physiological immunosuppression. TGFβ-1 has also been determined to be biologically active in hair follicle development. Human TGFβ-1 is a 25.0 kDa protein with subunits that contain approximately 112 amino acids per subunit. Two different receptor proteins are involved in TGFβ-1 binding and signaling, namely TGF-RβII and TGF-RβI. TGFβ-2 is expressed in a variety of cells, including keratinocytes, fibroblasts, osteoclasts, thymic epithelium, skeletal muscle cells, prostatic epithelium, bronchial epithelium, neurons and astrocytes, visceral smooth muscle, macrophages and various other cells. TGFβ-2 has many fundamental activities, including function as a growth inhibitor for most cells, an enhancer for deposition of the extracellular matrix, and immunosuppression. The mature region is 71% identical to TGFβ-1, 80% identical to TGFβ-3, and 97% identical to the mouse homologue of the same protein at the amino acid level. TGFβ-2 dimerizes with formation of disulfide bonds between the 'pro' regions and disulfide bonds between the mature regions. TGFβ-2 is synthesized as a pre-procytokine with a 19 amino acid signal sequence, a 283 pro-region and a 112 mature amino acid segment. The receptor for TGFβ-2 forms a heterotetrameric complex of two type I signal-transduction receptors and two type II ligand-binding receptors.

Formation of hair follicles involves a complex series of steps: growth (anagen), regression (catagen), rest (telogen) and shedding (exogen) (See, Stenn and Paus, Physiol. Rev, Exp. Dermatol., 8:229-233 [1999]). TGFβs have been implicated as one of the major drivers of the transition from anagen to catagen in the hair cycle (See e.g., Foitzik et al, FASEB J., 5:752-760 [2000]; and Soma et al. J. Infect. Dis., J. Invest. Dermatol., 118:993-9997 [2002]), and TGFβ2 is both a required and sufficient inducer of murine hair follicle morphogenesis (See, Foitzik et al., Develop. Biol., 212:278-289 [1999]). Conditional TGFβ-1 expression in transgenic mice demonstrates that one can induce alopecia reversibly (See, Liu et al., Proc. Natl. Acad. Sci. USA 98:9139-9144 [2001]). In addition, TGFβ-1 mutants have been associated with the delay of catagen onset in mice (See, Foitzik et al, [2000], supra). Recently, it has been shown that catagen can be delayed through the use of TGFβ-2 antibodies (See, Soma et al., [2002], supra). Finally, androgens that induce TGFβ-1 production in balding dermal papilla cells can inhibit epithelial cell growth (Inui et al., FASEB J., 14:1967-1969 [2002]).

TGFβ is also a potent stimulus of connective tissue accumulation, and is implicated in the pathogenesis of scleroderma and other fibrotic disorders (Blobe et al., N Engl J Med 342:1350-1358 [2000]). Scleroderma is a chronic autoimmune disease characterized by early inflammation and vascular injury, followed by progressive fibrosis of the skin and other organs (Kissin and Korn, Rheum Dis Clin North Am 29:351-369 [2003]). The most evident symptom is usually the hardening of the skin and associated scarring.

TGFβ has also been implicated in the formation of skin tumors (Li et al., Molecular Carcinogenesis 45:389-396 [2006]). The TGFβ signaling pathway is one of the most important mechanisms in the maintenance of epithelial homeostasis. Alterations leading to either the repression or enhancement of this pathway have been shown to affect cancer development. Although TGFβ inhibits growth of normal epithelial cells, it is paradoxically overexpressed in many epithelial cancers. It has been postulated that TGFβ acts as a tumor suppressor at the early stages of carcinogenesis, but overexpression of TGFβ at late stages of carcinogenesis may be a critical factor for tumor invasion and metastasis.

The invention provides personal care compositions that comprise a modified variant TGF-BBPI. The TGFβ-BBPI comprised in the personal care compositions of the invention is a modified variant TGFβ-BBPI in which the chymotrypsin loop of the precursor scaffold of the TGF-BBPI has been replaced by a TGFβ variant peptide, and which further comprise at least one amino acid substitution as described in sections 5.4.1 and 5.4.2. In some embodiments, binding of the modified variant TGF-BBPI to TGFβ1 and/or TGFβ2 prevents TGFβ1 and/or TGFβ2 from interacting with its cognate receptor and inhibits transition from the anagen to the catagen to promote hair growth and preventing hair loss. In other embodiments, binding of the modified variant TGF-BBPI to TGFβ1 and/or TGFβ2 prevents TGFβ1 and/or TGFβ2 from interacting with its cognate receptor to prevent fibrosis of the skin that is characteristic of scleroderma. In other embodiments, binding of the modified variant TGF-BBPI to TGFβ1 and/or TGFβ2 prevents TGFβ1 and/or TGFβ2 from interacting with its cognate receptor to prevent progression of benign to malignant skin lesions. However, it is not intended that the present invention be limited to any particular mechanism.

In some embodiments, the TGFβ variant peptide comprised in the TGFβ-BBPI is chosen from CLCPENINV-LPCN (PEN3; SEQ ID NO:436), CICKHNVDWLCF (MMO21W; SEQ ID NO:437), CICWTQHIHNCF (WTQ; SEQ ID NO:438), CVTTDWIEC (SEQ ID NO:563), CYYSQFHQC (SEQ ID NO:564), CPTLWTHMC (SEQ ID NO:565), QSACIVYYVGRKPKVECASSD (SEQ ID NO:566), QSACILYYIGKTPKIECASSD (SEQ ID NO:567), QSACILYYVGRTPKVECASSD (SEQ ID NO:568), acetyl-LCPENDNVSPCY-cohn2 (SEQ ID NO:569), KHNVRLL (SEQ ID NO:570), NDTPSYF (SEQ ID NO:571), AKLYAGS (SEQ ID NO:572), RGPAHSL (SEQ ID NO:573), NSLAERR (SEQ ID NO:574), HPLASPH (SEQ ID NO:575), QPWNKLK (SEQ ID NO:576), AWLr/Mipy (SEQ ID NO:577), PTKPAQQ (SEQ ID NO:578), PSLNRPQ (SEQ ID NO:579), HHARQEW (SEQ ID NO:580), RHHTPGP (SEQ ID NO:581), ASAINPH (SEQ ID NO:582), CHGYDRAPC (SEQ ID NO:644), CFAPADQAC (SEQ ID NO:645), CIPSRFITC (SEQ ID NO:646), CHGHTKLAC (SEQ ID NO:647), CNGKSKLAC (SEQ ID NO:648), PENINVLP (SEQ ID NO:672), KHNVDWL (SEQ ID NO:673), and WTQHIHNC (SEQ ID NO:674). SEQ ID NOS:644-648 are TGFβ1-binding peptides, while SEQ ID NOS:463, 437, 438, 563-582 are TGFβ2-binding peptides.

In other embodiments, the TGFβ variant peptide is chosen from SEQ ID NOS: SEQ ID NOS:436, 437 and 438.

The scaffold in which the variant TGFβ peptide is introduced to replace the equivalent chymotrypsin loop is chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds. In some embodiments, the scaffold of the VEGF-BBPI is that of SEQ ID NO:187.

In some embodiments, the backbone of the modified variant TGFβ-BBPI comprises at least one amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, as recited in section 5.4.1.

In other embodiments, the backbone of the modified variant TGFβ-BBPI comprises a combination of amino acid substitutions chosen from a combination two, three, four, five, six, seven or eight amino acid substitutions as recited above in section 5.4.2.

In other embodiments, the backbone of the modified variant TGFβ-BBPI comprises a combination of amino acid substitutions chosen from a combination of amino acid substitutions chosen from 13I-29P-50T-52A, 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L. In some embodiments, the combination of substitutions is 13I-29P-50T-52A. In some embodiments, the personal care compositions of the invention comprise a BBPI in which the equivalent chymotrypsin loop of the precursor scaffold is replaced with a TGFβ variant peptide chosen from SEQ ID NOS: 436, 437, 438, 672, 673, and 674, wherein the scaffold is that of SEQ ID NO:187, and which comprises the combination of amino acid substitutions 13I-29P-50T-52A. In some embodiments, the personal care compositions comprise a FGF-BBPI chosen from the TGFβ-BB-PIs of SEQ ID NOS:443, 445 and 447.

In some embodiments, the invention provides a personal care composition comprising a TGFβ-BBPI that binds to TGFβ1 and/or TGFβ2. In alternative embodiments, the binding of the TGFβ-BBPI to TGFβ blocks the downstream activity of TGFβ. In some embodiments, the composition is capable of promoting hair growth.

In some embodiments, the personal care composition comprising a modified variant TGF-BBPI is for use in skin care. In some embodiments, the skin care compositions are cosmetic compositions for use in promoting hair growth.

In some embodiments, the skin care compositions are for use in promoting hair growth in a subject suffering from a disease or condition that involves hair loss. In some of these embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia greata, cancer, conditions that affect defective hair fiber production, and environmental factors that affect hair production. In a preferred embodiment, the disease is androgenic alopecia or alopecia greata.

In other embodiments, the personal care composition comprising a modified variant TGF-BBPI is for use in improving the appearance and/or condition of the skin of a subject suffering from scleroderma. In yet other embodiments, the personal care composition comprising a modified variant TGF-BBPI is for use in improving the appearance and/or condition of the skin of a subject suffering from skin cancer.

In one embodiment, the personal care composition comprising a TGFβ-BBPI is a skin care composition is chosen from skin creams, lotions, sprays, emulsions, colloidal suspensions, foams, aerosols, liquids, gels, sera, and solids. In another embodiment, the personal care composition is a skin care composition selected from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, hair growth inhibitors, and radioprotectives. Radioprotectives are chosen from non-water-resistant sunscreens, very water-resistant sunscreens, and water-in-silicone sunscreens.

In one embodiment, the personal care composition comprising a TGFβ-BBPI is a skin care composition comprising topically applied over-the-counter compositions, anti-fungal treatments, anti-acne treatments, skin protectants, sunscreens, deodorants, and antiperspirants.

The present invention also provides personal care compositions that are cosmetic compositions. In some preferred embodiments, the cosmetic compositions are selected from mascaras, pressed powder formulations, and foundations. In some preferred embodiments, the makeup compositions comprise at least one pigment.

In some preferred embodiments, the makeup composition comprising at least one pigment is a mascara selected from non-waterproof mascaras, waterproof mascaras, volumizing mascaras, lengthening mascaras, curling mascaras, anhydrous waterproof mascaras, water-based mascaras, and eyelash or eyebrow treatments.

In yet additional embodiments, the makeup compositions are pressed powder formulations selected from loose powders, blushes, eye shadows, and bronzing powders. In still further embodiments, the makeup compositions are foundations selected from water-in-oil foundations, water-in-silicone foundations, oil-in-water foundations, anhydrous makeup sticks, and cream-to-powder foundations.

In some embodiments, the personal skin care compositions comprise a modified variant TGF-BBPI, as set forth herein, and a physiologically acceptable carrier or excipient. Preferably, the TGF-BBPI is present in an amount of about 0.0001% to about 5% by weight based on the total weight of the composition. Also preferably, the TGF-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In other embodiments, the invention provides a personal care composition that comprises a modified variant TGF-BBPI for use in hair care. In some embodiments, the hair care composition is for use in promoting hair growth.

In some embodiments, the hair care compositions find use in promoting hair growth. In other embodiments, modulation comprises promoting hair growth in a subject suffering from a disease or condition that involves hair loss. In some of these embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia greata, cancer, conditions that affect defective hair fiber production, and environmental factors that affect hair production. In a preferred embodiment, the disease is androgenic alopecia or alopecia greata.

In one embodiment, the hair care composition is selected from the group consisting of shampoos, conditioners, hair styling compositions, hair colorants, permanent wave formulations, creams, gels, mousses, sprays, emulsions, colloidal suspensions, liquids, foams, and solids. In some embodiments, the hair care composition further comprises a radioprotective. As described for the personal skin care compositions the radioprotective is a sunscreen chosen from non-water-resistant sunscreens, very water-resistant sunscreens, and water-in-silicone sunscreens. In other embodiments, the radioprotective is a sunscreen chosen from non-water-resistant sunscreens, very water-resistant sunscreens, and water-in-silicone sunscreens.

In some embodiments, the personal hair care compositions comprise a modified variant TGFβ-BBPI, as set forth herein, and a physiologically acceptable carrier or excipient. Preferably, the TGFβ-BBPI is present in an amount of about 0.0001% to about 5% by weight based on the total weight of the composition. Also preferably, the TGFβ-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In other embodiments, the personal care TGF-BBPI compositions of the invention are for use in the treatment of various diseases associated with elevated levels of TGFβ1 and/or TGFβ2.

The present invention also provides methods for promoting hair growth of a subject, comprising the steps of providing the personal care TGF composition of the present invention; providing a subject to be treated; and applying the composition to the subject in an area in which promotion of hair growth is desired. In some embodiments, the TGF composition is a skin care composition. In other embodiments, the FGF composition is a hair composition. In some embodiments, promotion of hair growth comprises promoting the growth of the subject's hair, wherein the hair growth to be promoted is chosen from facial air, underarm hair, leg hair, torso hair, and arm hair, and head hair. In additional embodiments, the method for promoting hair growth using an TGF hair care composition of the invention comprises applying a personal care composition comprising a TGF-BBPI having an amino acid sequence chosen from SEQ ID NOS:443, 445 and 447.

In another embodiment, the invention provides a method for improving the appearance and/or condition of skin in a subject suffering from a skin disorder, comprising providing the personal skin care composition of the present invention; providing a subject to be treated; and applying the composition to the affected skin of the subject. In some embodiments, the skin disorder is chosen from psoriasis, scleroderma and skin cancer. In additional embodiments, the method for improving the appearance and/or condition of skin in a subject suffering from a skin disorder using a TGF skin care composition of the invention comprises a personal care composition comprising a TGF-BBPI having an amino acid sequence chosen from SEQ ID NOS: 443, 445 and 447.

6.0.5 Personal Care Compositions Comprising Modified Variant TNFα-BBPIs

Proteins of the Tissue Necrosis Factor (TNF) family are members of a large cytokine family. Tissue Necrosis Factor alpha (TNFα) is a prototypic member of the TNF family of ligands. It is produced by various immune cells, and plays a key role in immune-mediated inflammatory diseases.

TNFα is synthesized by T-lymphocytes, B cells, synoviocytes, fibroblasts, and macrophages initially as a 26 kD protein. Later it is cleaved by TNFα converting enzyme (the metalloproteinase, ADAMS 17) into a monomeric 17-kD molecule. Three of these molecules form, under physiologic conditions, a non-covalently bound, cone-shaped homotrimer that cross-links membrane-bound receptors that exist in 2 isoforms: TNF receptor I (TNF-RI) and TNF receptor II (TNF-RII). Its natural function is to stimulate the recruitment of neutrophils and monocytes to sites of infection and to activate these cells to eradicate microbes, exerting its function by binding to its corresponding TNF receptor on the surface of numerous cell types. It activates the vascular endothelium locally, causing vasodilation and increased permeability. Vascular endothelium adhesion molecules (ICAM-1, VCAM-1, E-selectin) and MHC class II are upregulated leading to recruitment of proinflammatory cells, and induction of immunoglobulins, and complement. Platelets become activated and "stickier," causing small vessel occlusion, and containment of infections. In addition, it induces macrophages and endothelial cells to secrete chemokines and promotes apoptosis of target cells. TNFα has a potent paracrine function, inducing (via a NFκB-mediated mechanism) the secretion of pro-inflammatory cytokines such as IL-1, IL-6, and GM-CSF, and also stimulates the production of various chemokines, including RANTES, IL-8, MCP-1, and MIP-1α. Finally, TNFα plays a role in angiogenesis, which is critical to the growth and propagation of the rheumatoid synovium.

Immune-mediated inflammatory diseases (IMIDs) are triggered by an abnormal production of pro-inflammatory cytokines, including TNFα. These diseases include: rheumatoid arthritis (RA), inflammatory bowel disease (IBD) such as Crohn's disease, chronic plaque psoriasis, psoriatic arthritis, vasculitis, and ankylosing spondylitis.

New developments in the treatment of immune-mediated inflammatory diseases have arisen from basic research in cytokine expression and signaling that identified two key players in the pathophysiology of several diseases in this category: TNFα and interleukin interleukin-1 (IL-1). For example, both cytokines have been found to be elevated in the serum, synovium, and synovial fluid of patients with RA. Moreover, TNFα and IL-1 are capable of inducing and augmenting joint damage in experimental models of arthritis. Such findings led to the development of strategies to block/antagonize their effects, and specific targeting by biological agents has become possible in the recent years. This first generation of products includes monoclonal antibodies (mAb) and soluble receptor fusion proteins, all acting to compete with receptor for binding of the cytokine.

To date, the US FDA has approved three TNFα inhibitors/blocking agents for clinical use in the treatment of several IMIDs, including psoriasis and psoriatic arthritis. They are: Etanercept (Enbrel®, Amgen-Wyeth), a fully human chimeric protein of TNF receptor II fused to the Fc component of human IgG1, Infliximab (Remicade®, Centocor), a chimeric monoclonal antibody, and Adalimumab (Humira®, Abbott) a fully human IgG1 anti-TNFα monoclonal antibody. The proven initial efficacy and safety profile of these agents has to be weighed against the concerns for declining efficacy over time, the high cost of these biopharmaceutical agents and the limitations imposed by the current needle delivery for these agents.

An animal model developed by Boyman and colleagues (Boyman et al., J. Exp. Med. 199:731-736 [2004]) demonstrated the essential role for resident T-cells and TNFα in the spontaneous development of psoriasis. In this model, symptomless pre-psoriatic human skin lesions are grafted onto transgenic AGR129 mice. The group showed that blocking of T cells lead to inhibition of psoriasis development. It also showed that application of neutralizing anti-human TNFα monoclonal antibody (Infliximab, i.v.) or TNF receptor fusion protein (Etanercept, s.c.) led to dramatic inhibition of psoriatic phenotype development. These results have served to support the notion that TNFα antagonists have a direct effect in IMIDs disease development.

Unfortunately, more than one third of patients suffering from any of the approved IMIDs indications do not benefit clinically from anti-TNF treatment (Wong et al., Clin. Immunol. 126:121-136 [2008]). Efforts continue in the development of novel therapeutics to address this medical area. There are a number of "smart" TNFα antagonists currently in clinical trials, including: various anti-TNF monoclonal antibodies, pegylated antibody fragments or truncated TNF receptor molecules. In addition, a small-molecule inhibitor that promotes TNFα subunit disassembly of the trimeric cytokine has shown promising in vitro results (He et al., Science 310:1022-1025 [2005]) but no further clinical development has been reported.

Psoriasis is a common skin disorder that affects approximately 2.8 percent of the population (Linden and Weinstein Am. J. Med. 107:595-605 [1999]). An estimated 4.5 million people in the US suffer from psoriais and 1.5 million have moderate to severe plaque psoriasis. The disease is characterized by chronic inflammation of the skin. This inflammation helps drive the formation of red, itchy skin plaques that are often painful and disfiguring. TNF-α plays a critical role in their formation and continued existence because it induces synthesis if IL-1 and IL-8, the triggers of inflammation. TNF-α concentrations are higher in psoriatic lesions than in unaffected skin of psoriatic patients and tend to decline with clearing of the lesions after effective therapy (Mussi et al., J. Biol. Regul. Homeost. Agents 11:115-118 [1997]). TNF-α also promotes keratinocyte proliferation and angiogenesis (Asadullah et al., Drugs today 35:913-924 [1999]), and thus inhibiting this cytokine should halt the disease at multiple stages.

Traditionally, first-line treatment of moderate psoriasis has consisted of topical agents because they are often less invasive than systemic therapy, with a low incidence of the most serious side effects, such as renal or hepatic failure (Kincaid (2005) Drug discovery today 10:884). Some agents such as: antithyroid thioureylenes, propylthiouracil and methimazole, are effective in the treatment of patients with psoriasis with a significant number of patients showing clearing or near clearing of their lesions after a several weeks of treatment. Systemic treatment with the new anti-TNFα biologics: Enbrel, Remicade, and Humira, has been approved for moderate to severe chronic plaque psoriasis. Patients treated with such agents very often show marked improvement in their disease with major clearing in several instances (Chaudhari et al., Lancet 357:1842-1847 [2001]; Leonardi et al., N. Engl. J. Med. 349:2014-2022 [2003]). But present day therapy of the disease is not particularly satisfactory and the many therapies currently in use are associated with significant cumulative toxicity (Gottlieb et al., J Am Acad Dermatol. 48:829-835 [2003]). Risks associated with TNFα blocking agents include serious infections, malignancies, anaphylaxis, hepatitis B reactivation, demyelinating disease, cytopenias, heart failure, and lupus-like syndrome. In addition, there is observed loss of clinical benefit after the drugs are stopped, and a small proportion of patients develop antibodies to the biological agents which is likely to limit their efficacy with repeated use.

Proteins such as the engineered modified variant BBPIs which are much smaller in size and thus presumed to be much less immunogenic should significantly reduce concerns about development of neutralizing antibodies in patients. BBPI molecules, because of their reduced molecular weight in comparison to antibodies or proteins fusions, will likely be more amenable to delivery via a topical route, or via less invasive systemic administrations like subcutaneous injections or needleless delivery methods.

The invention provides personal care compositions comprising a modified variant TNF-BBPI for use in skin and/or hair care. In some embodiments, the personal care composition comprising a TNF-BBPI is used for promoting hair growth and/or improving the condition of the skin of a subject suffering from a dermatological inflammatory disorder. In some embodiments, the inflammatory skin disorder is chosen from dermatitis, eczema, psoriasis, acne, rosacea and hives.

In some embodiments, the dermatological inflammatory disorder is psoriasis. Thus, the invention provides for personal skin care and/or hair care compositions. The TNF-BBPIs comprised in the personal care compositions of the invention are modified variant BBPIs in which the equivalent chymotrypsin loop of the precursor scaffold of the TNF-5-BBPI has been replaced by a TNF variant peptide, and which further comprise at least one amino acid substitution as described in sections 5.4.1 and 5.4.2. In the present invention, binding of the modified variant TNF-BBPI to TNFα diverts TNFα from interacting with its cognate receptor and inhibits the TNFα-induced inflammation of the scalp and preventing hair loss. In some embodiments, binding of the modified variant TNF-BBPI to TNFα diminishes the inflammation of the skin and improves the condition of the skin in a subject suffering from a dermatological inflammatory disorder recited herein e.g. psoriasis. However, it is not intended that the present invention be limited to any particular mechanism.

In some embodiments, the TNF variant peptide comprised in the TNF-BBPI composition is chosen from RYWQDIP (T1; SEQ ID NO:474), APEPILA (T2; SEQ ID NO:475), DMIMVSI (T3; SEQ ID NO:476), WTPKPTQ (SEQ ID NO:583), ATFPNQS (SEQ ID NO:584), ASTVGGL (SEQ ID NO:585), TMLPYRP (SEQ ID NO:586), AWHSPSV (SEQ ID NO:587), TQSFSS (SEQ ID NO:588), THKNTLR (SEQ ID NO:589), GQTHFHV (SEQ ID NO:590), LPILTQT (SEQ ID NO:591), SILPVSH (SEQ ID NO:592), SQPIPI (SEQ ID NO:593), and QPLRKLP (SEQ ID NO:594). In other embodiments, the TNF variant peptide is chosen from SEQ ID NOS:483, 484 AND 485.

The scaffold in which the variant TNF peptide is introduced to replace the equivalent chymotrypsin loop is chosen from the scaffolds of the soybean inhibitor from *Glycine max* (BBI; SEQ ID NO:13) or the mature and truncated form thereof (SEQ ID NO:185), the inhibitor from *Dolichos biflorus* (BBdb; SEQ ID NO:449), the soybean inhibitor D-II from *Glycine max* (BBsb3; SEQ ID NO:450), the inhibitor from *Torresea (Amburana) cearensis* (BBtc; SEQ ID NO:451), the BBI-AV scaffold of (SEQ ID NO:186), the BBIt-AV scaffold of (SEQ ID NO:187), the BBdb-AV scaffold of (SEQ ID NO:452), the BBsb3-AV scaffold of (SEQ ID NO:453), the BBtc-AV scaffold of (SEQ ID NO:454), the BBIt-VEGK scaffold of (SEQ ID NO:640), the BBIt-VEGT scaffold of (SEQ ID NO:641) and the BBIt-VEGKD scaffold of (SE ID NO:642). In addition, any wild-type BBPI precursor scaffolds, such as those disclosed by Prakash et al. (supra), may be used to generate variant BBPI scaffolds. In some embodiments, the scaffold of the VEGF-BBPI is that of SEQ ID NO:187. In some embodiments, the backbone of the modified variant TNF-BBPI comprises at least one amino acid substitution at least at one amino acid position chosen from positions equivalent to 1, 4, 5, 11, 13, 18, 25, 27, 29, 31, 38, 40, 50, 52, 55, and 65 of the variant BBI of SEQ ID NO:187, as recited in section 5.4.1. In other embodiments, the backbone of the modified variant TNF-BBPI comprises a combination of amino acid substitutions chosen from a combination two, three, four, five, six, seven or eight amino acid substitutions as recited above in section 5.4.2.

In other embodiments, the backbone of the modified variant TNF-BBPI comprises a combination of amino acid substitutions chosen from a combination of amino acid substitutions chosen from 13I-29P-50T-52A, 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27A-29R-31A-40H-50R-52L at equivalent positions in SEQ ID NO:187.

In some embodiments, the personal care compositions of the invention comprises a BBPI in which the equivalent chymotrypsin loop of the precursor scaffold is replaced with a TNF variant peptide chosen from SEQ ID NOS:474, 475 And 476, wherein the scaffold is that of SEQ ID NO:187, and which comprises a combination of amino acid substitutions 13I-25R-27A-29P-31A-50K-52T.

In some embodiments, the personal care compositions comprise a TNF-BBPI chosen from the TNF-BBPIs of SEQ ID NOS:647, 648, and 649.

In some embodiments, the invention provides a personal care composition comprising a TNF-BBPI that binds to TNF. In alternative embodiments, the binding of the TNF-BBPI to TNF blocks the downstream activity of TNF. In some embodiments, the composition is capable of modulating inflammation.

In some embodiments, the personal care composition comprising a modified variant BBPI-TNF is for use in skin care. In some embodiments, the skin care compositions are for use in improving the appearance and/or condition of skin in a subject suffering from a skin disorder. Thus, in some embodiments, the personal care compositions for use in skin care include cosmetic compositions. In some embodiments, the skin disorder is an inflammatory skin disorder. In some embodiments, the inflammatory skin disorder is psoriasis.

In one embodiment, the personal care composition comprising a TNF-BBPI is a skin care composition is chosen from skin creams, lotions, sprays, emulsions, colloidal suspensions, foams, aerosols, liquids, gels, sera, and solids. In another embodiment, the personal care composition is a skin care composition selected from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, hair growth inhibitors, and radioprotectives. Radioprotectives are chosen from non-water-resistant sunscreens, very water-resistant sunscreens, and water-in-silicone sunscreens.

In one embodiment, the personal care composition comprising a TNF-BBPI is a skin care composition comprising topically applied over-the-counter compositions, anti-fungal treatments, anti-acne treatments, skin protectants, sunscreens, deodorants, and antiperspirants. In other embodiments, the skin care composition is capable of lightening skin tone, reducing redness, preventing skin tone darkening or preventing color development.

The present invention also provides personal care compositions that are cosmetic compositions. In some preferred embodiments, the cosmetic compositions are selected from mascaras, pressed powder formulations, and foundations. In some preferred embodiments, the makeup compositions comprise at least one pigment.

In some preferred embodiments, the makeup composition comprising at least one pigment is a mascara selected from non-waterproof mascaras, waterproof mascaras, volumizing mascaras, lengthening mascaras, curling mascaras, anhydrous waterproof mascaras, water-based mascaras, and eyelash or eyebrow treatments.

In yet additional embodiments, the makeup compositions are pressed powder formulations selected from loose powders, blushes, eye shadows, and bronzing powders. In still further embodiments, the makeup compositions are foundations selected from water-in-oil foundations, water-in-silicone foundations, oil-in-water foundations, anhydrous makeup sticks, and cream-to-powder foundations.

In some embodiments, the personal skin care compositions comprise a modified variant TNF-BBPI, as set forth herein, and a physiologically acceptable carrier or excipient. Preferably, the TNF-BBPI is present in an amount of about 0.0001% to about 5% by weight based on the total weight of the composition. Also preferably, the TNF-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In other embodiments, the invention provides a personal care composition comprising a modified variant BBPIs that comprises a TNF variant peptide (TNF-BBPI) for use in hair care.

In some embodiments, the hair care compositions find use in improving the appearance and/or condition of scalp skin in patients suffering from psoriasis.

In one embodiment, the hair care composition is selected from the group consisting of shampoos, conditioners, hair styling compositions, hair colorants, permanent wave formulations, creams, gels, mousses, sprays, emulsions, colloidal suspensions, liquids, foams, and solids.

In some embodiments, the hair care composition further comprises a radioprotective. As described for the personal skin care compositions the radioprotective is a sunscreen chosen from non-water-resistant sunscreens, very water-resistant sunscreens, and water-in-silicone sunscreens. In other embodiments, the radioprotective is a sunscreen chosen from non-water-resistant sunscreens, very water-resistant sunscreens, and water-in-silicone sunscreens.

In some embodiments, the personal hair care compositions comprise a modified variant VEGF-BBPI, as set forth herein, and a physiologically acceptable carrier or excipient. Preferably, the VEGF-BBPI is present in an amount of about 0.0001% to about 5% by weight based on the total weight of the composition. Also preferably, the VEGF-BBPI is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

6.1.1 Formulations

In additional preferred embodiments, the present invention provides cosmetic and/or pharmaceutical compositions comprising at least one modified variant BBPI, as set forth herein, and a physiologically acceptable carrier or excipient. Preferably, the compound is present in an amount of about 0.0001% to about 5% by weight, based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup. Preferably, the carrier is at least compound selected from the group consisting of water, propylene glycol, ethanol, propanol, glycerol, butylene glycol and polyethylene glycol.

It is contemplated that the present invention will find use in numerous personal care compositions. It is not intended that the present invention be limited to any particular format or type of composition. The following description provides exemplary, not limiting compositions comprising the following invention.

Emulsions comprises one group of customary, commonly-used cosmetics. The term "emulsion" is generally used in reference to a heterogeneous system of two liquids which are immiscible or miscible only to a limited extent with one another, which are usually referred to as "phases." One phase is typically in the form of droplets (i.e., the "dispersed," "discontinuous" or "internal" phase), while the other liquid forms a continuous (i.e., "coherent" or "external") phase. Less common forms of application include multiple emulsions (i.e. those in which the droplets of the dispersed [or discontinuous] phase, comprise for their part droplets of a further dispersed phase, such as water/oil/water [W/O/W] emulsions and oil/water/oil [O/W/O] emulsions).

If the oil phase is finely distributed in the water phase, then this is an oil-in-water emulsion (O/W emulsion; e.g. milk). The basic character of an O/W emulsion is determined by the water. These emulsions are generally less greasy on the skin, are rather matting, and absorb more rapidly into the skin than W/O (water-in-oil) emulsions.

Those of skill in the art are familiar with a large number of options of formulating stable W/O preparations for cosmetic and/or dermatological uses, including such formulations as creams and ointments, which are spreadable in the range from room temperature to skin temperature, as well as lotions and milks, which are more flowable in this temperature range.

The stability of emulsions is dependent on their viscosity, in particular on the viscosity of the external phase. An emulsion becomes unstable when the finely dispersed particles collect together to form relatively large aggregates, and the droplets which are in contact coalesce. This process is referred to as "coalescence." The more viscous the external phase of the emulsion, the slower the process of coalescence. Emulsions of "liquid" (=flowable) consistency are used in various cosmetics (e.g., skin care lotions, cleansing lotions, face lotions, hand lotions, etc.). These compositions generally have a viscosity of from about 2000 mPa·s to about 10,000 mPa·s. The stability of flowable emulsions is deserving of particular attention since the considerably greater mobility of the particles promotes more rapid coalescence.

It is known that liquid emulsions typically presently in use generally comprise thickeners and are not stable toward relatively high electrolyte concentrations. This is manifested in phase separation of the compositions. However, in some embodiments, it is desirable to use certain electrolytes (e.g., water-soluble UV filters), in order to be able to utilize the other physical, chemical or physiological properties thereof. Although in many cases appropriate choice of the emulsifier system can provide remedies to a certain extent, other disadvantages then arise just as often.

For example, some disadvantages result due to the fact that emulsifiers, like ultimately any chemical substance, may trigger allergic reactions or reactions based on oversensitivity (i.e., hypersensitivity) of the user. The use of customary cosmetic emulsifiers is generally entirely without risk, although for some individuals, "hypoallergenic" compositions are necessary and/or preferred. Indeed, in some particularly sensitive individuals, certain dermatoses are triggered by exposure to certain emulsifiers and simultaneous exposure to sunlight. Thus, as known to those in the art, in some compositions, particular emulsifiers are less preferred and/or are avoided.

It is possible to prepare emulsifier-free preparations. For example, some preparations have an oily phase which contains dispersed water droplets (i.e., it is similar to a W/O emulsion). Such systems are sometimes called "hydrodispersions" or "oleodispersions," depending upon which is the disperse phase and which is the continuous phase.

For cosmetic technology, it is, however, neither necessary nor possible to dispense with emulsifiers altogether, especially since there is a certain choice of particularly mild emulsifiers.

In some liposomal embodiments, the liposomes comprise water and one or more ingredients capable of forming lipid bilayer vesicles that can hold one or more functional or active ingredient(s). Non-limiting examples of ingredients capable of forming lipid bilayer vesicles include: phospholipids, hydrogenated phosphatidylcholine, lecithin, cholesterol and sphingolipids. Preferred liposomes include, without limitation: a) lipoid liposome 0003 (composed of water and lecithin and glycerin); b) lipoid liposome 0300 (composed of water and phosphatidylcholine); c) lipoid liposome 0111 (composed of water, *Ginkgo biloba* leaf extract, denatured alcohol, hydrogenated lecithin and cholesterol); d) anti-irritant liposomes (composed of water, cola acuminata seed extract, bisabolol and phospholipids); e) vitamin C and E liposomes (composed of water, phospholipids, tocopheryl acetate and ascorbyl palmitate); f) firming liposomes (composed of water, butylene glycol, pyrus malus (Apple) fruit extract, phospholipids, tocopheryl acetate and carbomer); and g) moisturizing liposomes (composed of water, sodium PCA, tocopheryl acetate, xanthan gum, arginine, lysine, glycine and proline).

In other embodiments, the personal care composition of the present invention further comprise at least one active ingredient in addition to the scaffolds provide herein. There are numerous active ingredients known to those of skill in the art that find use in the personal care compositions of the present invention. Indeed, it is contemplated that any suitable active ingredient or combination of suitable active ingredients will find use in the present invention (See e.g., McCutcheon's Functional Materials, North American and International Editions, published by MC Publishing Co. [2003]). For example, in some embodiments, the personal care compositions herein comprise a skin care active ingredient at a level from about 0.0001% to about 20%, by weight of the composition. In another embodiment, the personal care compositions comprise a skin care active ingredient from about 0.001% to about 0.5%, by weight of the composition. In yet another embodiment, the personal care compositions comprise a skin care active ingredient from about 0.01% to about 2%, by weight of the composition.

Non-limiting examples of functional or active ingredients that can be delivered via liposomes include: vitamins and their derivatives, antioxidants, proteins and peptides, keratolytic agents, bioflavinoids, terpenoids, phytochemicals, and extracts of plant, marine or fermented origin. In a preferred embodiment, the composition further comprises a skin care or hair care active. Active ingredients can include any of a wide variety of ingredients such as are known in the art. (See e.g., McCutcheon's Functional Materials, North American and International Editions, (2003), published by MC Publishing Co.). Preferably, such actives include but are not limited to antioxidants, such as tocopheryl and ascorbyl derivatives, bioflavinoids, terpenoids, synthetics and the like, vitamins and vitamin derivatives, hydroxyl- and polyhydroxy acids and their derivatives, such as AHAs and BHAs and their reaction products, peptides and polypeptides and their derivatives, such as glycopeptides and lipophilized peptides, heat shock proteins and cytokines, enzymes and enzymes inhibitors and their derivatives, such as proteases, MMP inhibitors, catalases, glucose oxydase and superoxide dismutase, amino acids and their derivatives, bacterial, fungal and yeast fermentation products and their derivatives, including mushrooms, algae and seaweed and their derivatives, phytosterols and plant and plant part extracts and their derivatives and phospholipids and their derivatives, anti-dandruff agents such as zinc pyrithione and delivery systems containing them, as provided herein and/or known in the art.

In some preferred embodiments, the skin care active is selected from the group consisting of a Vitamin B3 component, panthenol, Vitamin E, Vitamin E acetate, retinol, retinyl propionate, retinyl palmitate, retinoic acid, Vitamin C, theobromine, alpha-hydroxyacid, farnesol, phytrantriol, salicylic acid, palmityl peptapeptide-3 and mixtures thereof. In some preferred embodiments, the Vitamin B3 component is niacinamide. In some embodiments, the compositions provided herein comprise a skin care active at a level from about 0.0001% to about 20%, preferably from about 0.001% to about 0.5%, more preferably from about 0.01% to about 1%, by weight.

Exemplary derivatives of the foregoing vitamin B3 compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Suitable esters of nicotinic acid include nicotinic acid esters of C1-C22, preferably C1-C16, more preferably C1-C6 alcohols. In these embodiments, the alcohols are suitably straight-chain or branched chain, cyclic or acyclic, saturated or unsaturated (including aromatic), and substituted or unsubstituted. The esters are preferably non-vasodilating.

Non-vasodilating esters of nicotinic acid include tocopherol nicotinate and inositol hexanicotinate; tocopherol nicotinate are preferred. A more complete description of vitamin B3 compounds is provided in WO 98/22085. Preferred vitamin B3 compounds include niacinamide and tocopherol nicotinate.

In additional embodiments, the skin care active comprises at least one retinoid. The retinoid is preferably retinol, retinol esters (e.g., C2-C22 alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources (e.g., Sigma and Boehringer Mannheim). Preferred retinoids include retinol, retinyl palmitate, retinyl acetate, retinyl proprionate, retinal, retinoic acid and combinations thereof. More preferred are retinol, retinoic propionate, retinoic acid and retinyl palmitate. In some embodiments, the retinoid is included as a substantially pure material, while in other embodiments, it is provided as an extract obtained by suitable physical and/or chemical isolation from natural (e.g., plant) sources. When a retinoid is included in the compositions herein, it preferably comprises from about 0.005% to about 2%, preferably from about 0.01% to about 1% retinoid. Retinol is preferably used in an amount of from about 0.01% to about 0.15%; retinol esters are preferably used in an amount of from about 0.01% to about 2% (e.g., about 1%).

In still further embodiments of the present invention, antioxidants are incorporated in the personal care compositions. It is contemplated that any suitable antioxidants will find use in the personal care compositions of the present invention. Suitable antioxidants include, but are not limited to amino acids (e.g., glycine, histidine, tyrosine, and tryptophan) and derivatives thereof, imidazoles (e.g. urocanic acid) and derivatives thereof, peptides (e.g., D,L-carnosine, D-carnosine, and L-carnosine) and derivatives thereof (e.g., anserine), carotenoids, carotenes (e.g., α-carotene, β-carotene, and γ-lycopene) and derivatives thereof, chlorogenic acid and derivatives thereof, aurothioglucose, propylthiouracil and other thiols (e.g., thioredoxin, glutathione, cysteine, cystine, cystamine and the glycosyl, N-acetyl, methyl, ethyl, propyl, amyl, butyl and lauryl, palmitoyl, oleyl, g-linoleyl, cholesteryl and glyceryl esters thereof) and salts thereof, dilauryl thiodipropionate, distearyl thiodipropionate, thiodipropionic acid and derivatives thereof (e.g., esters, ethers, peptides, lipids, nucleotides, nucleosides and salts), and sulfoximine compounds (e.g. buthionine sulfoximines, homocysteine sulfoximine, buthionine sulfones, penta-, hexa-, and heptathionine sulfoximine) in very small tolerated doses (e.g., typically pmol to mmol/kg), chelating agents (e.g., α-hydroxy fatty acids, palmitic acid, phytic acid, and lactoferrin), α-hydroxy acids (e.g. citric acid, lactic acid, and malic acid), humic acid, bile acid, bile extracts, bilirubin, biliverdin, EDTA, EGTA and derivatives thereof, unsaturated fatty acids and derivatives thereof (e.g., linolenic acids, linoleic acid, oleic acid), folic acid and derivatives thereof, furfurylidenesorbitol and derivatives thereof, ubiquinone and ubiquinol and derivatives thereof, vitamin C and derivatives thereof (e.g., sodium ascorbyl phosphate, ascorbyl palmitate, Mg ascorbyl phosphate, and ascorbyl acetate), tocopherols and derivatives (e.g., vitamin E acetate), coniferyl benzoate of benzoin resin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g., ZnO, ZnSO4), selenium and derivatives thereof (e.g., selenomethionine), stilbenes and derivatives thereof (e.g., stilbene oxide, trans-stilbene oxide) and the derivatives thereof (e.g., salts, esters, ethers, sugars, nucleotides, nucleosides, peptides and lipids) of said active ingredients which are suitable for the intended use of the particular embodiment(s) of the present invention.

In some embodiments, the concentration of one or more antioxidant in the compositions of the present invention is preferably from about 0.001 to about 30% by weight, particularly preferably from about 0.05 to about 20% by weight, and more preferably from about 1 to about 10% by weight, based on the total weight of the preparation. In additional embodiments, in which vitamin E and/or its derivatives are utilized as anti-oxidant(s), the preferred range is from about 0.001 to about 10% by weight, based on the total weight of the formulation. However, it is not intended that the present invention be limited to any specific antioxidant concentration(s), as various concentrations will find use in the various embodiments of the present invention.

In yet some additional embodiments, the active ingredient(s) is/are catechins, bile esters of catechins, and/or aqueous or organic extracts from plants or sections of plants which have a content of catechins or bile esters of catechins (e.g., the leaves of the Theaceae plant family, in particular of the species *Camellia sinensis* [green tea]). Their typical ingredients (e.g., polyphenols or catechins, caffeine, vitamins, sugars, minerals, aminoacids, lipids) find particular use in some embodiments of the present invention.

In some embodiments, catechins find use in the present invention. Catechins are a group of compounds which are regarded as hydrogenated flavones or anthocyanidines, and are derivatives of "catechin" (catechol, 3,3',4',5,7-flavanpentol, 2-(3,4-dihydroxyphenyl)chroman-3,5,7-triol). Epicatechin ((2R,3R)-3,3',4',5,7-flavanpentol) is also an active ingredient that finds use in some embodiments of the present invention.

In yet additional embodiments, plant extracts with a content of catechin, in particular extracts of green tea (e.g., extracts from leaves of the plants of the genus *Camellia*, in particular those used for tea, such as *C. sinensis*, *C. assamica*, *C. taliensis*. and *C. irrawadiensis* and hybrids of these species with other species, such as *C. japonica*) find use in some personal care compositions of the present invention.

In some further embodiments, preferred active ingredients include polyphenols and catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin, and (−)-epigallocatechin gallate.

In some additional embodiments of the compositions of the present invention flavone and its derivatives (also often collectively called "flavones") find used. These compounds have the following basic structure (substitution positions are shown):

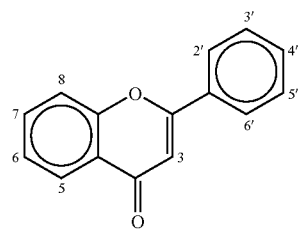

Some of the more important flavones which find use in some personal care compositions of the present invention are provided below. However, it is not intended that the present invention be limited to any particular flavone.

FLAVONES

| | OH Substitution Positions | | | | | | | |
|---|---|---|---|---|---|---|---|---|
| | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones are usually present in glycosylated form.

In some further embodiments, the personal care compositions of the present invention comprise at least one flavonoids having generic structural formula:

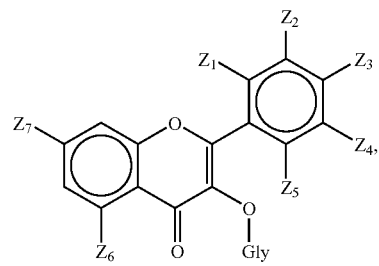

where $Z_1$ to $Z_7$, independently of one another, are chosen from the group consisting of H, OH, alkoxy and hydroxyalkoxy, where the alkoxy and hydroxyalkoxy groups can be branched or unbranched and have 1 to 18 carbon atoms, and where Gly is chosen from the group of mono- and oligoglycoside radicals.

In some alternative embodiments, the personal care compositions of the present invention comprise at least one flavonoids having the generic structural formula:

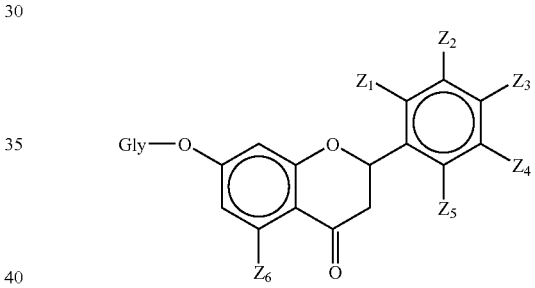

where $Z_1$ to $Z_6$, independently of one another, are chosen from the group consisting of H, OH, alkoxy and hydroxyalkoxy, where the alkoxy and hydroxyalkoxy groups may be branched or unbranched and have 1 to 18 carbon atoms, where Gly is chosen from the group mono and oligoglycoside radicals.

In some preferred embodiments, the composition has the generic structural formula

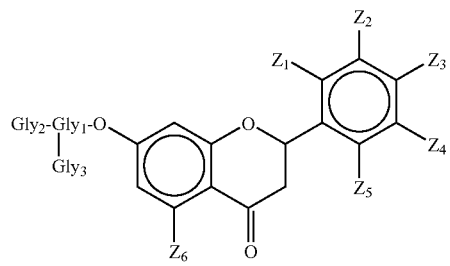

where $Gly_1$, $Gly_2$ and $Gly_3$, independently of one another, are monoglycoside radicals. $Gly_2$ and $Gly_3$ may also, individually or together, represent saturations by hydrogen atoms. In some preferred embodiments, $Gly_1$, $Gly_2$ and $Gly_3$, independently of one another, are selected from the group of hexosyl radicals, in particular the rhamnosyl radicals and glucosyl radicals. However, hexosyl radicals, for example allosyl, altrosyl, galactosyl, gulosyl, idosyl, mannosyl and talosyl, also find use in some embodiments of the present invention. In yet additional embodiments, pentosyl radicals find use in some personal care compositions of the present invention.

In some embodiments, $Z_1$ to $Z_5$ are, independently of one another, advantageously chosen from the group consisting of H, OH, methoxy, ethoxy and 2-hydroxyethoxy, and the flavone glycosides have the structure:

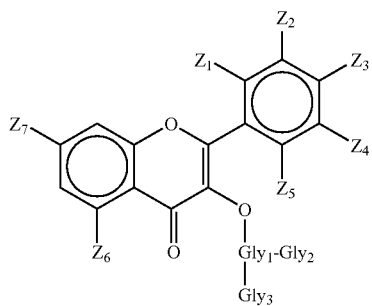

In some embodiments, the flavone glycosides provided in some of the personal care compositions of the present invention have the following structure:

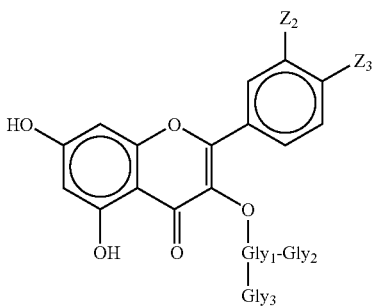

where $Gly_1$, $Gly_2$ and $Gly_3$, independently of one another, are monoglycoside radicals. $Gly_2$ and $Gly_3$ can also, individually or together, represent saturations by hydrogen atoms. In alternative embodiments, $Gly_1$, $Gly_2$ and $Gly_3$, independently of one another, are selected from the group of hexosyl radicals, in particular of rhamnosyl radicals and glucosyl radicals. However, other hexosyl radicals, for example allosyl, altrosyl, galactosyl, gulosyl, idosyl, mannosyl and talosyl, find use in some embodiments of the present invention. In addition, in some embodiments, pentosyl radicals find use in the present invention. In some preferred embodiments, the personal care compositions of the present invention comprise one or more flavone glucoside selected from the group consisting of a-glucosylrutin, a-glucosylmyricetin, a-glucosylisoquercitrin, a-glucosylisoquercetin and a-glucosylquercitrin. In some particularly preferred embodiments, the flavone glucoside is a-glucosylrutin.

In yet some additional embodiments, the personal care compositions of the present invention comprise at least one naringin (e.g., aurantin, naringenin-7-rhamno-glucoside), hesperidin 3',5,7-trihydroxy-4'-methoxyflavanone-7-rutinoside, hesperidoside, hesperetin-7-O-rutinoside), rutin (3,3',4', 5,7-pentahydroxyflavone-3-rutinoside, quercetin-3-rutinoside, sophorin, birutan, rutabion, taurutin, phytomelin, melin), troxerutin (3,5-dihydroxy-3',4',7-tris(2-hydroxyethoxy)flavone-3-(6-O-(6-deoxy-a-L-mannopyranosyl)-b-D-lucopyranoside)), monoxerutin (3,3',4',5-tetrahydroxy-7-(2-hydroxyethoxy)flavone-3-(6-O-(6-deoxy-a-L-mannopyranosyl)-b-D-glucopyranoside)),dihydrorobinetin (3,3',4',5',7-pentahydroxyflavanone), taxifolin (3,3',4',5,7-pentahydroxyflavanone), eriodictyol-7-glucoside (3',4',5,7-tetrahydroxyflavanone-7 glucoside), flavanomarein (3',4',7, 8-tetrahydroxyflavanone-7 glucoside), and/or isoquercetin (3,3',4',5,7-pentahydroxyflavanone-3-(b-D-glucopyranoside). In some yet further embodiments, the active ingredient is selected from the group consisting of ubiquinones and plastoquinones. Ubiquinones are characterized by the structural formula:

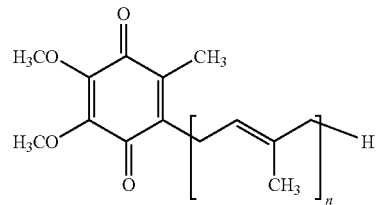

Ubiquinones are the most widespread and the most investigated bioquinones. Ubiquinones are referred to, depending on the number of isoprene units linked in the side chain, as Q-1, Q-2, Q-3 etc., or according to the number of carbon atoms, as U-5, U-10, U-15 etc. They preferably arise with certain chain lengths (e.g. in some microorganisms and yeasts where n=6). In most mammals, including humans, Q10 predominates. Coenzyme Q10 finds particular use in some embodiments of the present invention. Its structural formula is:

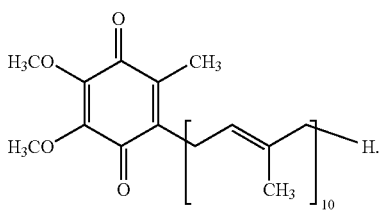

Plastoquinones have the general structural formula:

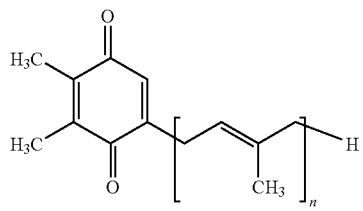

Plastoquinones differ in the number n of isoprene radicals and are referred to accordingly (e.g. PQ-9 [n=9]). In addition, other plastoquinones with varying substituents on the quinone ring exist in some embodiments.

In yet additional embodiments, the present invention provides preparations suitable for use as deodorants and/or antiperspirants. It is contemplated that any of the active ingredients which commonly find use in such preparations will also find use in various embodiments of the present invention. Additional components that are commonly used in such preparations also find use in various embodiments of the present invention. Examples of such actives and inactive compounds include, but are not limited to odor maskers (e.g., perfumes), odor absorber (e.g., phyllosilicates described in DE-P 40 09 347); as well as montmorillonite, kaolinite, illite, beidellite, nontronite, saponite, hectorite, bentonite, smectite, and zinc salts of ricinoleic acid. In some embodiments of the present invention, the range of active ingredients (i.e., one or more compounds) in such preparations is preferably from about 0.001 to about 30% by weight; more preferably from about 0.05 to about 20% by weight; and most particularly in the range of from about 1 to about 10% by weight, based on the total weight of the preparation.

In some embodiments, the compositions of the present invention comprise safe and effective amounts of a dermatologically acceptable carrier that is suitable for topical application to the skin or hair within which the essential materials and optional other materials are incorporated to enable the essential materials and optional components to be delivered to the skin or hair at an appropriate concentration. Thus, in some embodiments, the carrier acts as a diluent, dispersant, solvent or the like for the essential components, ensuring that these components can be applied and distributed evenly over the selected target at an appropriate concentration.

In further embodiments, an effective amount of one or more compounds described herein is also be included in compositions to be applied to keratinous materials such as nails and hair, including but not limited to those useful as hair spray compositions, hair styling compositions, hair shampooing and/or conditioning compositions, compositions applied for the purpose of hair growth regulation and compositions applied to the hair and scalp for the purpose of treating seborrhoea, dermatitis and/or dandruff.

In yet additional embodiments, an effective amount of one or more compounds described herein is included in compositions suitable for topical application to the skin or hair. These compositions are provided in any suitable form, including but not limited to creams, lotions, gels, suspensions dispersions, microemulsions, nanodispersions, microspheres, hydrogels, emulsions (e.g., oil-in-water and water-in-oil, as well as multiple emulsions), and multilaminar gels and the like (See e.g., Schlossman et al., The Chemistry and Manufacture of Cosmetics, [1998], incorporated by reference, herein). In some embodiments, the compositions are formulated as aqueous or silicone compositions, while in other embodiments they are formulated as emulsions of one or more oil phases in an aqueous continuous phase (or an aqueous phase in an oil phase).

The type of carrier utilized in the present invention depends on the type of product form desired for the composition. The carrier can be solid, semi-solid or liquid. Suitable carriers include liquids, semi-solids (e.g., creams, lotions, gels, sticks, ointments, and pastes), sprays and mousses. Preferably the carrier is in the form of a lotion, cream or a gel, more preferably one which has a sufficient thickness or yield point to prevent the particles from sedimenting. In some embodiments, the carrier is inert, while in other embodiments it provides dermatological benefits. In some embodiments, the carrier is applied directly to the skin and/or hair, while in other embodiments, it is applied via a woven or non-woven wipe or cloth. In yet other embodiments, it is in the form of a patch, mask or wrap. In still further embodiments, it is aerosolized or otherwise sprayed or pumped onto the skin and/or hair. The carrier chosen is physically and chemically compatible with the essential components described herein, and should not unduly impair stability, efficacy or other use benefits associated with the compositions of the present invention.

Preferred carriers contain a dermatologically acceptable, hydrophilic diluent. Suitable hydrophilic diluents include water, organic hydrophilic diluents such as $C_2$-$C_{10}$, preferably $C_2$-$C_6$, preferably, $C_3$-$C_6$ monohydric alcohols and low molecular weight glycols and polyols, including propylene glycol, polyethylene glycol polypropylene glycol, glycerol, butylene glycol, 1,2,4-butanetriol, sorbitol esters, 1,2,6-hexametriol, pentylene glycol, hexylene glycol, sorbitol esters, ethoxylated ethers, propoxylated ethers, and combinations thereof. The diluent is preferably liquid. Water is a preferred diluent. The composition preferably comprises at least about 20% of the hydrophilic diluent.

In some embodiments, suitable carriers also comprise an emulsion comprising a hydrophilic phase, especially an aqueous phase, and a hydrophobic phase (e.g., a lipid, oil or oily material). As well known to those skilled in the art, the hydrophilic phase is dispersed in the hydrophobic phase, or vice versa, to form respectively hydrophilic or hydrophobic dispersed and continuous phases, depending on the composition of ingredients. The term "dispersed phase" is a term well-known to one skilled in the art of emulsion technology, used in reference to the phase which exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 60% (preferably about 1% to about 30%) of the dispersed hydrophobic phase and from about 1% to about 99% (preferably from about 10% to about 90%) of the continuous hydrophilic phase, while water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase.

In further embodiments, the carrier also includes one or more components that facilitate penetration through the upper stratum corneum barrier to the lower levels of the skin. Examples of penetration enhancers include, but are not limited to, propylene glycol, azone, ethoxydiglycol, dimethyl isosorbide, urea, ethanol and dimethyl sulfoxide, as well as microemulsions, liposomes and nanoemulsions.

In some additional embodiments, the compositions of the present invention comprise humectants which are preferably present at a level of from about 0.01% to about 20%, preferably from about 0.1% to about 15% and preferably from about 0.5% to about 10%. Preferred humectants include, but are not limited to, compounds selected from polyhydric alcohols, sorbitol, glycerol, urea, betaine, D-panthenol, DL-panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6, -triol, guanidine or its derivatives, and mixtures thereof.

Suitable polyhydric alcohols for use herein include, but are not limited to polyalkylene glycols and preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3- butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols of the present invention are selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Suitable humectants useful herein are sodium 2-pyrrolidone-5-carboxylate (NaPCA), guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; betaine, panthenol and derivatives thereof; and mixtures thereof.

In some embodiments, at least part (up to about 5% by weight of composition) of a humectant is incorporated into the compositions of the present invention in the form of an admixture with a particulate cross-linked hydrophobic acrylate or methacrylate copolymer, itself preferably present in an amount of from about 0.1% to about 10%, which can be added either to the aqueous or disperse phase. This copolymer is particularly valuable for reducing shine and controlling oil while helping to provide effective moisturization benefits and is described in further detail in WO96/03964, incorporated herein by reference.

In some embodiments, the oil-in-water and water-in-oil compositions of the present invention comprise from about 0.05% to about 20%, preferably from about 1% to about 15%, preferably from about 2% to about 10%, preferably from about 2% to about 5% of a dermatologically acceptable emollient. Emollients tend to lubricate the skin, increase the smoothness and suppleness of the skin, prevent or relieve dryness of the skin and/or protect the skin. Emollients are typically water-immiscible, oily or waxy materials and emollients can confer aesthetic properties to a topical composition. A wide variety of suitable emollients are known (See e.g., Sagarin, Cosmetics, Science and Technology, 2nd Edition, Vol. 1, pp. 32-43 [1972]; and WO 00/24372), and find use herein, contains numerous examples of materials suitable as emollients. Additional emollients include, but are not limited to the following:

i) Straight and branched chain hydrocarbons having from about 7 to about 40 carbon atoms, such as mineral oils, dodecane, squalane, cholesterol, hydrogenated polyisobutylene, isohexadecane, isoeicosane, isooctahexacontane, isohexapentacontahectane, and the C7-C40 isoparaffins, which are C7-C40 branched hydrocarbons. Suitable branched chain hydrocarbons for use herein are selected from isopentacontaoctactane, petrolatum and mixtures thereof;

ii) C1-C30 fatty acid esters of C1-C30 carboxylic acids, $C_{12-15}$ alkyl benzoates and of C2-C30 dicarboxylic acids, e.g. isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof also find use in the present invention;

iii) C1-C30 mono- and poly-esters of sugars and related materials. These esters are derived from a sugar or polyol moiety and one or more carboxylic acid moieties. Depending on the constituent acid and sugar, these esters can be in either liquid or solid form at room temperature. Examples include: glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester. Other materials include cottonseed oil or soybean oil fatty acid esters of sucrose. Other examples of such materials are described in WO 96/16636, incorporated by reference herein;

iv) Vegetable oils and hydrogenated vegetable oils. Examples of vegetable oils and hydrogenated vegetable oils include safflower oil, grapeseed oil, coconut oil, cottonseed oil, menhaden oil, palm kernel oil, palm oil, peanut oil, soybean oil, rapeseed oil, linseed oil, rice bran oil, pine oil, nut oil, sesame oil, sunflower seed oil, partially and fully hydrogenated oils from the foregoing sources and mixtures thereof;

v) Soluble or colloidally-soluble moisturizing agents. Examples include hyaluronic acid and chondroitin sulfate.

The term "lipid" is often used as a generic term to refer to fats, oils, waxes and the like. In addition, the terms "oil phase" and "lipid phase" are also used synonymously. However, oils and fats differ from one another in their polarity, which is difficult to define. It has been proposed to adopt the interfacial tension toward water as a measure of the polarity index of an oil or of an oily phase. Thus, it is contemplated that the interfacial tension be regarded as a suitable measure of the polarity of a given oil component. The "interfacial tension" is the force which acts on an imaginary line one meter in length in the interface between two phases. In this measurement, the lower the interfacial tension between the oily phase and water, the greater the polarity of the oily phase being analyzed. The physical unit for this interfacial tension is conventionally calculated from the force/length relationship and is usually expressed in mN/m (millinewtons divided by meters). It has a positive sign if it endeavours to reduce the interface. In the converse case, it has a negative sign. As used herein, lipids are regarded as "polar," if their interfacial tension toward water is less than 30 mN/m.

"Polar oils" include those from the group of lecithins and of fatty acid triglycerides, namely the triglycerol esters of saturated and/or unsaturated, branched and/or unbranched alkane carboxylic acids having a chain length of from 8 to 24, in particular 12 to 18, carbon atoms. In some embodiments, the fatty acid triglycerides are chosen from the group consisting of synthetic, semi-synthetic and natural oils (e.g., olive oil, sunflower oil, soya oil, groundnut oil, rapeseed oil, almond oil, palm oil, coconut oil, castor oil, wheatgerm oil, grapeseed oil, thistle oil, evening primrose oil, *macadamia* nut oil and the like). However, is it not intended that the present invention be limited to compositions that contain particular polar oils. Additional examples of polar oils that find use in the present invention include the group of esters of saturated and/or unsaturated, branched and/or unbranched alkane carboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. In some embodiments, such ester oils are chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters (e.g., jojoba oil).

In addition, in some embodiments, the oily phase is chosen from the group consisting of dialkyl ethers, as well as saturated or unsaturated, and branched or unbranched alcohols. In some particularly preferred embodiments, the oily phase of the compositions of the preferred embodiments also contains $C_{12-15}$-alkyl benzoate, while in alternative embodiments, the preferred embodiments contains only the latter. In yet additional embodiments, the oil phase is chosen from the group of Guerbet alcohols (i.e., the group of alcohols named after Marcel Guerbet who first described their preparation). These alcohols are formed according to the equation:

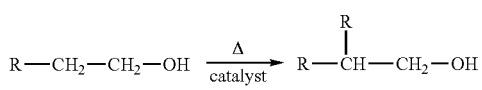

by oxidation of an alcohol to an aldehyde, by aldol condensation of the aldehyde, elimination of water from the aldol and hydrogenation of the allyl aldehyde. Guerbet alcohols are liquid even at low temperatures and result in virtually no skin irritations. Thus, they find use as fatting, superfatting and also refatting constituents in skincare and hair care compositions. Indeed, the use of Guerbet alcohols is known in the cosmetic art. In these applications, the species are generally characterized as having the following structure:

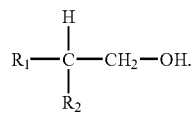

In this structure, $R_1$ and $R_2$ are usually unbranched alkyl radicals. In some preferred embodiments of the present invention the following Guerbet alcohols in which $R_1$ is propyl, butyl, pentyl, hexyl, heptyl or octyl and/or $R_2$ is hexyl, heptyl, octyl, nonyl, decyl, undecyl, dodecyl, tridecyl or tetradecyl find use in the present invention. In additional embodiments, preferred Guerbet alcohols include 2-butyloctanol with the following chemical structure:

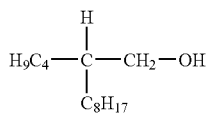

which is commercially available, for example, under the trade name ISOFOL® 12 (Condea Chemie GmbH), and 2-hexyldecanol with the following chemical structure:

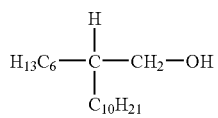

which is commercially available, for example, under the trade name ISOFOL® 16 (Condea Chemie GmbH).

In additional embodiments, mixtures of Guerbet alcohols find use in compositions of the present invention. For example, mixtures of 2-butyloctanol and 2-hexyldecanol find use in some embodiments. The total amount of Guerbet alcohols in the finished cosmetic or dermatological preparations is selected from the of range up to about 25.0% by weight, preferably about 0.5 to about 15.0% by weight, based on the total weight of the preparations. However, it is not intended that the present invention be limited to any particular concentration nor range of concentrations, as those of skill in the art know how to prepare compositions having suitable concentrations for the desired compositions and their use(s). In addition, it is contemplated that any mixtures of oil and/or wax components will find use in the present invention. For example, in some embodiments, waxes (e.g., cetyl palmitate) find use as the sole lipid component of the oil phase. In additional embodiments, nonpolar oils (e.g., those which are chosen from the group of branched and unbranched hydrocarbons and hydrocarbon waxes, in particular VASELINE® [i.e., petrolatum], paraffin oil, squalane and squalene, polyolefins and hydrogenated polyisobutenes find use in the present invention. In some embodiments containing polyolefins, polydecenes are the preferred substances.

Fatty and/or wax components which find use in embodiments of the present invention include but are not limited to vegetable waxes, animal waxes, mineral waxes and petrochemical waxes. Examples which particularly preferred waxes include candelilla wax, carnauba wax, japan wax, esparto grass wax, cork wax, guaruma wax, rice germ oil wax, sugar cane wax, berry wax, ouricury wax, montan wax, jojoba wax, shea butter, beeswax, shellac wax, spermaceti, lanolin (wool wax), uropygial grease, ceresin, ozokerite (earth wax), paraffin waxes and microcrystalline waxes.

Additional fatty and/or wax components that find use in the present invention include chemically modified waxes and/or synthetic waxes (e.g., those commercially available under the trade names SYNCROWAX® HRC [glyceryl tribehenate] and SYNSCROWAX® AW 1C [$C_{18}$-$C_{36}$ fatty acid], which are available from CRODA GmbH), and montan ester waxes, Sasol waxes, hydrogenated jojoba waxes, synthetic or modified beeswaxes (e.g., dimethicone copolyol beeswax and/or $C_{30-50}$ alkyl beeswax), polyalkylene waxes, polyethylene glycol waxes, as well as chemically modified fats (e.g., hydrogenated vegetable oils, such as hydrogenated castor oil and/or hydrogenated coconut fatty glycerides), triglycerides (e.g., trihydroxystearin, fatty acids, fatty acid esters, and glycol esters, such as, $C_{20}$-$C_{40}$-alkyl stearate, $C_{20}$-$C_{40}$-alkylhydroxystearoyl stearate and/or glycol montanate). In further embodiments, the present invention comprises certain organosilicone compounds, which have similar physical properties to the specified fatty and/or wax components (e.g., stearoxytrimethylsilane). In additional embodiments, the fatty and/or wax components are provided individually, while in still further embodiments, they are provided as a mixture. Indeed, it is intended that any desired mixture of such oil and/or wax components will find use in various embodiments of the present invention.

In some embodiments, the oily phase is selected from the group consisting of 2-ethylhexyl isostearate, octyldodecanol, isotridecyl isononanoate, isoeicosane, 2-ethylhexyl cocoate, $C_{12}$-$C_{15}$-alkyl benzoate, caprylic/capric triglyceride, and dicaprylyl ether. In alternative embodiments, mixtures of various oily phases are provided, including but not limited to mixtures comprising one or more of octyldodecanol, caprylic/capric triglyceride, dicaprylyl ether, $C_{12}$-$C_{15}$-alkyl benzoate, 2-ethylhexyl isostearate, isotridecyl isononanoate. The following table provides a list of lipids which find use alone or in combination with other lipids in various embodiments of the present invention. The corresponding interfacial tensions toward water are given in the last column. However, it is not intended that the present invention be limited to these specific components, as other components find use in various embodiments of the present invention, including mixtures of greater or lesser polar components and the like.

LIPIDS

| Trade name | INCI name | (m/Nm) |
|---|---|---|
| ISOFOL ® 14 T | Butyl Decanol + Hexyl Decanol + Hexyl Octanol + Butyl Octanol | 27.6 |
| ISOFOL ® 16 | Hexyl Decanol | 24.3 |
| EUTANOL ® G | Octyldodecanol | 24.8 |
| CETIOL ® OE | Dicaprylyl Ether | 22.1 |
| MIGLYOL ® 812 | Caprylic/Capric Triglyceride | 21.3 |
| CEGESOFT ® C24 | Octyl Palmitate | 23.1 |
| Isopropyl stearate | Isopropyl Stearate | 21.9 |
| ESTOL ® 1540 EHC | Octyl Octanoate | 30.0 |
| FINSOLV ® TN | $C_{12}$-$C_{15}$ Alkyl Benzoate | 21.8 |
| CETIOL ® SN | Cetearyl Isononanoate | 28.6 |
| DERMOFEEL ® BGC | Butylene Glycol Dicaprylate/Dicapate | 21.5 |
| TRIVENT ® OCG | Tricaprylin | 20.2 |
| MOD | Octyldodeceyl Myristate | 22.1 |
| COSMACOL ® ETI | Di-$C_{12}$-$C_{13}$ Alkyl Tartrate | 29.4 |
| MIGLYCOL ® 829 | Caprylic/Capric Diglyceryl Succinate | 29.5 |
| PRISORINE ® 2036 | Octyl Isostearate | 29.7 |
| TEGOSOFT ® SH | Stearyl Heptanoate | 28.7 |
| ABIL ® Wax 9840 | Cetyl Dimethicone | 25.1 |
| CETIOL ® LC | Coco-Caprylate/Caprate | 24.8 |
| IPP | Isopropyl Palmitate | 22.5 |
| LUVITOL ® EHO | Cetearyl Octanoate | 28.6 |
| CETIOL ® 868 | Octyl Stearate | 28.4 |

In some embodiments, some or all of the oil phase of the preparations are selected from the group consisting of cyclic and/or linear silicones which are also often referred to as "silicone oils." In some embodiments, these silicones or silicone oils are present as monomers which are generally characterized by structural elements as follows:

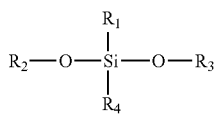

Silicones having two or more siloxyl units which find use in some embodiments of the present invention are generally characterized by structural elements as follows:

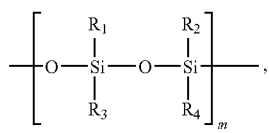

where the silicon atoms may be substituted by identical or different alkyl radicals and/or aryl radicals, which are represented in general terms by the radicals $R_1$ to $R_4$, where the number of different radicals is not necessarily limited to 4 and may assume values from 2 to 200,000.

Cyclic silicones to be used advantageously according to the invention are generally characterized by the structural elements as follows:

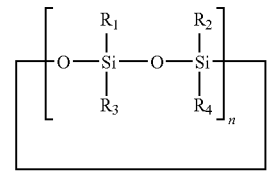

where the silicon atoms may be substituted by identical or different alkyl radicals and/or aryl radicals, which are represented here in general terms by the radicals $R_1$ to $R_4$, where the number of different radicals is not necessarily limited to 4. n can assume values of 3/2 to 20. Fractional values for "n" take into consideration that uneven numbers of siloxyl groups may be present in the cycle.

In some embodiments, phenyltrimethicone is selected as silicone oil. Other silicone oils suitable for use in various embodiments of the present invention include, but are not limited to dimethicone, phenyldimethicone, cyclomethicone (octamethylcyclotetrasiloxane), hexamethylcyclotrisiloxane, polydimethylsiloxane, poly(methylphenylsiloxane), cetyldimethicone, and behenoxydimethicone. In alternative embodiments, mixtures of these compounds find use in the present invention, including but not limited to mixtures of cyclomethicone and isotridecyl isononanoate, and mixtures of cyclomethicone and 2-ethylhexyl isostearate. It yet additional embodiments, silicone oils of similar constitution, such as the compounds referred to above whose organic side chains have been derivatized (e.g., polyethoxylated and/or polypropoxylated) find use in the present invention. These include, but are not limited to such compounds as polysiloxane-polyalkyl-polyether copolymers such as cetyldimethicone copolyol (i.e., cetyldimethicone copolyol (and) polyglyceryl-4 isostearate (and) hexyl laurate). Indeed, it is not intended that the present invention be limited to any specific silicone oil nor mixture of silicone oils, as various oils find use in various embodiments of the present invention.

In additional embodiments, water in oil (W/O) emulsions find use in the present invention. In some embodiments, W/O emulsifiers are used with or without additional co-emulsifiers. In still further embodiments, W/O emulsions of the present further comprise one or more emulsifiers, including, but not limited to one or more of the following compounds: lecithin, lanolin, microcrystalline wax (*Cera microcristallina*) in a mixture with paraffin oil (*Paraffinum liquidum*), ozokerite, hydrogenated castor oil, polyglyceryl-3 oleate, wool wax acid mixtures, wool wax alcohol mixtures, pentaerythrithyl isostearate, polyglyceryl-3 diisostearate, beeswax (*Cera alba*) and stearic acid, sodium dihydroxycetylphosphate in a mixture with isopropyl hydroxycetyl ether, methylglucose dioleate, methylglucose dioleate in a mixture with hydroxystearate and beeswax, mineral oil in a mixture with petrolatum and ozokerite and glyceryl oleate and lanolin alcohol, petrolatum in a mixture with ozokerite and hydrogenated castor oil and glyceryl isostearate and polyglyceyl-3 oleate, PEG-7 hydrogenated castor oil, ozokerite and hydrogenated castor oil, polyglyceryl-4 isostearate, polyglyceryl-4 isostearate in a mixture with cetyldimethicone copolyol and hexyl laurate, laurylmethicone copolyol, cetyldimethicone copolyol, acrylate/$C_{10}$-$C_{30}$-alkyl acrylate crosspolymer, Poloxamer 101, polyglyceryl-2 dipolyhydroxystearate, polyglyceryl-3 diisostearate, polyglyceryl-4 dipolyhydroxystearate, PEG-30 dipolyhydroxystearate, diisostearoyl polyglyceryl-3 diisostearate, polyglyceryl-2 dipolyhydroxystearate, polyglyceryl-3 dipolyhydroxystearate, polyglyceryl-4 dipolyhydroxystearate, polyglyceryl-3 dioleate.

In yet additional embodiments of the present invention, W/O emulsions of the present invention comprise one or more coemulsifiers, including, but not limited to the following: glyceryl stearate in a mixture with ceteareth-20, ceteareth-25, ceteareth-6 in a mixture with stearyl alcohol, cetylstearyl alcohol in a mixture with PEG-40 castor oil and sodium cetylstearyl sulfate, triceteareth-4 phosphate, sodium cetylstearyl sulfate, lecithin trilaureth-4 phosphate, laureth-4 phosphate, stearic acid, propylene glycol stearate SE, PEG-25 hydrogenated castor oil, PEG-54 hydrogenated castor oil, PEG-6 caprylic/capric glycerides, glyceryl oleate in a mixture with propylene glycol, ceteth-2, ceteth-20, polysorbate 60, glyceryl stearate in a mixture with PEG-100 stearate, laureth-4, ceteareth-3, isostearyl glyceryl ether, cetylstearyl alcohol in a mixture with sodium cetylstearyl sulfate, laureth-23, steareth-2, glyceryl stearate in a mixture with PEG-30 stearate, PEG-40 stearate, glycol distearate, PEG-22 dodecyl glycol copolymer, polyglyceryl-2 PEG-4 stearate, ceteareth-20, methylglucose sesquistearate, steareth-10, PEG-20 stearate, steareth-2 in a mixture with PEG-8 distearate, steareth-21, steareth-20, isosteareth-20, PEG-45/dodecyl glycol copolymer, methoxy-PEG-22/dodecyl glycol copolymer, PEG-20 glyceryl stearate, PEG-8 beeswax, polyglyceryl-2 laurate, isostearyl diglyceryl succinate, stearamidopropyl PG dimonium chloride phosphate, glyceryl stearate SE, ceteth-20, triethyl citrate, PEG-20 methylglucose sesquistearate, ceteareth-12, glyceryl stearate citrate, cetyl phosphate, triceteareth-4 phosphate, trilaureth-4 phosphate, polyglyceryl methylglucose distearate, potassium cetyl phosphate, isosteareth-10, polyglyceryl-2 sesquiisostearate, ceteth-10, oleth-20, isoceteth-20, glyceryl stearate in a mixture with ceteareth-20, ceteareth-12, cetylstearyl alcohol and cetyl palmitate, cetylstearyl alcohol in a mixture with PEG-20 stearate, PEG-30 stearate, PEG-40 stearate, and PEG-100 stearate.

In yet additional embodiments in which the oil phase of the preparations consists at least partially of silicone oils, silicone emulsifiers find use. In some embodiments, the silicone emulsifiers are selected from the group of interface-active substances, alkylmethicone copolyols, and/or alkyl dimethicone copolyols, particularly from the group of compounds characterized by the following chemical structure:

8842, ABIL® B 8843, ABIL® B 8847, ABIL® B 8851, ABIL® B 8852, ABIL® B 8863, ABIL® B 8873, and ABIL® B 88183, all of which are commercially available from Th. Goldschmidt AG). An additional example of an interface-active substances which finds use in the present invention includes cetyldimethicone copolyol (ABIL® EM 90), as well as cyclomethiconedimethicone copolyol (ABIL® EM 97), both of which are commercially available from Th. Goldschmidt AG. An additional emulsifier which has proven useful in various compositions that finds use in embodiments of the present invention is laurylmethicone copolyol (Dow Corning® 5200 Formulation Aid), which is commercially available from Dow Corning Ltd.

In preferred embodiments of the present invention, the total amount of emulsifiers used in the personal care compositions (e.g., cosmetic or skin care preparations) are present in the range from about 0.1 to about 10.0% by weight, preferably about 0.5 to about 5.0% by weight, based on the total weight of the preparations. However, it is not intended that the present invention be limited to any specific concentration of emulsifier and/or co-emulsifier, as various embodiments of the present invention have different preferred concentrations and/or concentration ranges.

In some embodiments, the present invention provides emulsions in various forms, including skin protection creams, skin lotions, cosmetic milks, sunscreen creams, and sun protection milks. In some preferred embodiments, these compositions comprise fats, oils, waxes, and/or other fatty substances, as well as water, and one or more emulsifiers as are customarily used for such a type of formulation.

In addition to the liquid and somewhat more solid emulsions of the cosmetic cleansing lotions and/or cleansing creams of the present invention, the present invention also provides sprayable cleansing preparations ("cleansing sprays"), which are used, for example, for removing make-up or as mild washing lotion. In addition, these cleansing sprays find use in applications for treatment of blemished skin. These cleansing preparations also find use as "rinse-off preparations" (i.e., products which are rinsed off the skin following application).

In addition to the above constituents, various embodiments of the present invention include additional components, such as auxiliaries and additives, including but not limited to bodying agents, fillers, perfume, dyes, emulsifiers, additional active ingredients (e.g., vitamins and proteins), light protection agents, stabilizers, insect repellents, alcohol, self-tanning substances, water, salts, antimicrobials, proteases, and/or

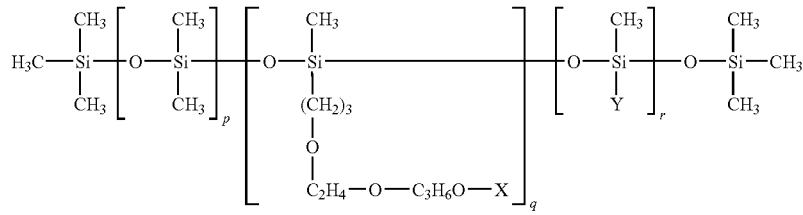

in which X and Y, independently of one another, are chosen from the group H and the branched and unbranched alkyl groups, acyl groups and alkoxy groups having 1 to 24 carbon atoms, p is a number from 0 to 200, q is a number from 1 to 40, and r is a number from 1 to 100. Some examples of silicone emulsifiers which find use in the present invention include, but are not limited to dimethicone copolyols (e.g., ABIL® B keratinase, etc. Indeed, it is not intended that the present invention be limited to any particular components, as long as the active component comprising a scaffold and a peptide is included. It is further contemplated that the present invention will find use in numerous and various medicinal preparations.

In some embodiments, the compositions of the present invention contain an emulsifier and/or surfactant, generally to help disperse and suspend the disperse phase within the continuous aqueous phase. A surfactant may also be useful if the product is intended for skin or hair cleansing. For convenience hereinafter, "emulsifiers" are encompassed by the term "surfactants." Thus, as used herein, the term "surfactant(s)" refers to surface active agents, whether used as emulsifiers or for other surfactant purposes such as skin cleansing. Known, including conventional surfactants find use in the present invention, provided that the selected agent is chemically and physically compatible with essential components of the composition and provides the desired characteristics (See e.g., WO 00/24372). Suitable surfactants include non-silicone derived materials, silicone-derived materials, and mixtures thereof.

In further embodiments, the compositions of the present invention comprise preferably from about 0.05% to about 30%, more preferably from about 0.5% to 15%, and most preferably from about 1% to 10% of a surfactant or mixture of surfactants. The exact surfactant or surfactant mixture chosen depends upon the pH of the composition, the other components present and the desired final product aesthetics.

Among the nonionic surfactants that are useful herein are those that can be broadly defined as condensation products of long chain alcohols (e.g., C8-30 alcohols), with sugar or starch polymers (e.g., glycosides). Other useful nonionic surfactants include the condensation products of alkylene oxides with fatty acids (i.e., alkylene oxide esters of fatty acids). These materials have the general formula RCO(X)nOH wherein R is a C10-30 alkyl group, X is —OCH2CH2- (i.e., derived from ethylene glycol or oxide) or —OCH2CHCH3- (i.e., derived from propylene glycol or oxide) and n is an integer from about 6 to about 200. Other nonionic surfactants are the condensation products of alkylene oxides with 2 moles of fatty acids (i.e., alkylene oxide diesters of fatty acids). These materials have the general formula RCO(X)nOOCR wherein R is a C10-30 alkyl group, X is —OCH2CH2- (i.e., derived from ethylene glycol or oxide) or —OCH2CHCH3- (i.e., derived from propylene glycol or oxide) and n is an integer from about 6 to about 100. In some embodiments, an emulsifier for use herein is preferably a fatty acid ester blend based on a mixture of sorbitan fatty acid ester and sucrose fatty acid ester, especially a blend of sorbitan stearate and sucrose cocoate. Further suitable examples include a mixture of cetearyl alcohols and cetearyl glucosides. However, it is not intended that the present invention be limited to any particular emulsifier, as various suitable emulsifiers are known in the art.

In additional embodiments, the hydrophilic surfactants useful herein alternatively or additionally include any of a wide variety of cationic, anionic, zwitterionic, and amphoteric surfactants such as are known in the art (See, e.g., McCutcheon's, Emulsifiers and Detergents, North American and International Editions, MC Publishing Co. [2003]; U.S. Pat. No. 5,011,681 U.S. Pat. No. 4,421,769; and U.S. Pat. No. 3,755,560).

In some additional embodiments, interface- and/or surface-active agents are included in some personal care compositions of the present invention, including but not limited to cationic emulsifiers (e.g., quaternary surfactants).

Quaternary surfactants that contain at least one N atom which is covalently bonded to 4 alkyl or aryl groups. This leads, irrespective of the pH, to a positive charge. Alkylbetain, alkylamidopropylbetain and alkylamidopropylhydroxysultaine are examples of quaternary surfactants that find use in some embodiments of the present invention.

The cationic surfactants provided in some embodiments of the present invention also include, but are not limited to quaternary ammonium compounds, in particular benzyltrialkylammonium chlorides or bromides (e.g., benzyldimethylstearylammonium chloride), alkyltrialkylammonium salts (e.g., cetyltrimethylammonium chloride or bromide), alkyldimethylhydroxyethylammonium chlorides or bromides, dialkyldimethylammonium chlorides or bromides, alkylamidoethyltrimethylammonium ether sulfates, alkylpyridinium salts (e.g., lauryl- or cetylpyrimidinium chloride), imidazoline derivatives, and compounds with a cationic character, such as amine oxides (e.g., alkyldimethylamine oxides or alkylaminoethyldimethylamine oxides). In some preferred embodiments, cetyltrimethylammonium salts find use in some personal care compositions of the present invention.

In yet additional embodiments, cationic polymers (e.g., JAGUAR® C 162 [hydroxypropyl guar hydroxypropyltrimonium chloride]), modified magnesium aluminum silicates (e.g., quaternium-18-hectorite, which is commercially available (e.g., BENTONE® 38; Rheox), and/or stearalkonium hectorite, which is commercially available (e.g., SOFTISAN® gel; Hüls AG) find use in some personal care compositions of the present invention. However, it is not intended that the present invention be limited to any particular cationic polymer.

In some yet further embodiments, some compositions of the present invention comprise oil thickeners in order to improve the tactile properties of emulsions. Preferred oil thickeners include, but are not limited to other solids (e.g., hydrophobic silicon oxides of the AEROSIL® type, which are available from Degussa AG). Examples of advantageous AEROSIL® oxide grades include AEROSIL® OX50, AEROSIL® 130, AEROSIL® 150, AEROSIL® 200, AEROSIL® 300, AEROSIL® 380, AEROSIL® MOX 80, AEROSIL® MOX 170, AEROSIL® COK 84, AEROSIL® R 202, AEROSIL® R 805, AEROSIL® R 812, AEROSIL® R 972, AEROSIL® R 974 and AEROSIL® R976.

In some additional embodiments, some personal care compositions of the present invention comprise at least one "metal soap" (i.e., a salt of a higher fatty acid, with the exception of alkali metal salt), which are function as oil thickeners. Examples of such metal soaps include, but are not limited to aluminum stearate, zinc stearate and/or magnesium stearate.

A variety of anionic surfactants are also useful herein (See e.g., U.S. Pat. No. 3,929,678). Exemplary anionic surfactants include, but are not limited to alkoyl isethionates (e.g., C12-C30), alkyl and alkyl ether sulfates and salts thereof, alkyl and alkyl ether phosphates and salts thereof, alkyl methyl taurates (e.g., C12-C30), and soaps (e.g., substituted alkylamine and alkali metal salts, e.g., sodium or potassium salts) of fatty acids.

Amphoteric and zwitterionic surfactants are also useful herein. Examples of preferred amphoteric and zwitterionic surfactants which find use in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably C8-C18) and one contains an anionic water solubilizing group (e.g., carboxy, sulfonate, sulfate, phosphate, or phosphonate). Examples, include but are not limited to alkyl imino acetates and iminodialkanoates and aminoalkanoates, imidazolinium and ammonium derivatives. Other suitable amphoteric and zwitterionic surfactants are those selected from the group consisting of betaines, sultaines, hydro-xysultaines, and branched and unbranched alkanoyl sarcosinates, and mixtures thereof.

In some further embodiments, some personal care compositions comprise at least one amphoteric and/or zwitterionic surfactant (e.g., cocamidopropylbetain) and/or moisturizer (e.g. betain). Examples of amphoteric surfactants that find use in such embodiments of the present invention include but are not limited to acyl/dialkylethylenediamine (e.g., sodium acylamphoacetate), disodium acylamphodipropionate, disodium alkylamphodiacetate, sodium acylamphohydroxypropylsulfonate, disodium acylamphodiacetate, sodium acylamphopropionate, N-alkylamino acids, for example aminopropylalkylglutamide, alkylaminopropionic acid, sodium alkylimidodipropionate, and lauroamphocarboxyglycinate.

In some embodiments, the amount of surface- or interface-active substances (one or more compounds) in the preparations is preferably between about 0.001 and about 30% by weight, and more preferably between about 0.05 and about 20% by weight, in most preferably between about 1 and about 10% by weight, based on the total weight of the preparation.

In some yet additional embodiments, the active ingredients (one or more compounds) comprise at least one lipophilic active ingredient. In some embodiments, these lipophilic active ingredients are selected from the group consisting of acetylsalicylic acid, atropine, azulene, hydrocortisone and derivatives thereof (e.g., hydrocortisone-17-valerate), B vitamins, D vitamins, vitamin $B_1$, vitamin $B_{12}$, vitamin $D_1$, retinoid, bisabolol, unsaturated fatty acids (e.g., the essential fatty acids often also referred to as "vitamin F"), γ-linolenic acid, oleic acid, eicosapentenoic acid, docosahexenoic acid and derivatives thereof, chloramphenicol, caffeine, prostaglandins, thymol, camphor, extracts or other products of a vegetable and animal origin (e.g. evening primrose oil, borrage oil or currant seed oil, fish oils, cod-liver oil), and ceramides and ceramide-like compounds, etc. In some embodiments, the active ingredient(s) are refatting substances (e.g., purcellin oil, EUCERIT® and/or NEROCERIT®).

In further embodiments, some emulsions of the present invention include a silicone containing emulsifier or surfactant. A wide variety of silicone emulsifiers find use herein. These silicone emulsifiers are typically organically modified organopolysiloxanes, also known to those skilled in the art as silicone surfactants. Useful silicone emulsifiers include, but are not limited to dimethicone copolyols. These materials are polydimethyl siloxanes which have been modified to include polyether side chains such as polyethylene oxide chains, polypropylene oxide chains, mixtures of these chains and polyether chains containing moieties derived from both ethylene oxide and propylene oxide. Other examples include alkyl-modified dimethicone copolyols (i.e., compounds which contain C2-C30 pendant side chains). Still other useful dimethicone copolyols include materials having various cationic, anionic, amphoteric, and zwitterionic pendant moieties.

In some embodiments, the compositions of the present invention comprise at least one polymeric thickening agent. The polymeric thickening agents useful herein preferably have a number average molecular weight of greater than about 20,000, more preferably greater than about 50,000, and most preferably greater than about 100,000. In some embodiments, the compositions of the present invention comprise from about 0.01% to about 10%, preferably from about 0.1% to about 8% and more preferably from about 0.2% to about 5% by weight of the composition of the polymeric thickening agent or mixtures thereof.

Preferred polymer thickening agents for use herein include, but are not limited to non-ionic thickening agents and anionic thickening agents or mixtures thereof. Suitable non-ionic thickening agents include, but are not limited to polyacrylamide polymers, crosslinked poly(N-vinylpyrrolidones), polysaccharides, natural or synthetic gums, polyvinylpyrrolidone and polyvinylalcohol. Suitable anionic thickening agents include, but are not limited to acrylic acid/ethyl acrylate copolymers, carboxyvinyl polymers and crosslinked copolymers of alkyl vinyl ethers and maleic anhydride. Commercially available thickeners (e.g., Carbopol; Noveon) find use in some embodiments of the present invention. Suitable Carbopol resins may be hydrophobically modified, and other suitable resins are described in WO98/22085, or mixtures thereof.

In some embodiments of the present invention, the water phase has a gel character which, in addition to an effective content of compounds and solvents (as appropriate) preferably comprises water, further organic and/or inorganic thickeners, and/or hydrocolloids.

In some embodiments, inorganic thickeners are selected from the group consisting of modified, unmodified, naturally occurring, and synthetic phyllosilicates. Although it is generally preferable to use pure components, in some embodiments, mixtures of different modified and/or unmodified phyllosilicates find use in various compositions of the present invention. As generally known in the art, phyllosilicates are silicates and alumosilicates in which the silicate or aluminate units are linked together via three Si—O— or Al—O— bonds and form a wavy sheet or layer structure. The fourth Si—O— or Al—O— valence is saturated by cations. Relatively weak electrostatic interactions (e.g. hydrogen bridge bonds), exist between the individual layers. The layer structure is largely defined by strong, covalent bonds. The stochiometry of the sheet silicates is $(Si_2O_5^{2-})$ for pure silicate structures and $(Al_mSi^{2-}_mO_5^{(2+m)-})$ for alumosilicates, wherein "m" is a number greater than zero and less than 2. In some embodiments in which alumosilicates are present in the absence of pure silicates, each $Si^{4+}$ group replaced by $Al^{3+}$ requires another singly charged cation to neutralize the charge. The charge balance is preferably evened out by $H^+$, alkali metal ions or alkaline earth metal ions. In alternative embodiments, aluminum is used as a counterion. In contrast to the alumosilicates, these compounds are referred to as "aluminum silicates." "Aluminum alumosilicates," in which aluminum is present both in the silicate network, and also as counterion, also find use in some embodiments of the present invention.

Phyllosilicates are well known in the art (See e.g., Hollemann et al., Lehrbuch der Anorganischen Chemie [Textbook of Inorganic Chemistry], 91st-100th Ed., Walter de Gruyter—Verlag [1985]; Remy, Lehrbuch der Anorganischen Chemie, $12^{th}$ Ed., Akademische Verlagsgesellschaft, Leipzig [1965]). The layer structure of montmorillonite is also known (See, Römpps Chemie-Lexikon, Franckh'sche Verlagshandlung, W. Keller & Co., Stuttgart, $8^{th}$ Ed., [1985], p. 2668 f). Examples of phyllosilicates include the following (montmorillonite is the main mineral comprising the naturally-occurring bentonites);

| | |
|---|---|
| Montmorillonite often simplified: | $Na_{0.33}((Al_{1.67}Mg_{0.33})(OH)_2(Si_4O_{10}))$ <br> $Al_2O_3·4SiO_2·H_2O·nH_2O$ or <br> $Al_2[(OH)_2/Si_4O_{10}]·n\,H_2O$ |
| Kaolinite | $Al_2(OH)_4(Si_2O_5)$ |
| Illite | $(K,H_3O)_y(Mg_3(OH)_2(Si_{4-y}Al_yO_{10}))$ or <br> $(K,H_3O)_y(Al_2(OH)_2(Si_{4-y}Al_yO_{10}))$ <br> where y = 0.7-0.9 |
| Beidellite | $(Ca,Na)_{0.3}(Al_2(OH)_2(Al_{0.5}Si_{3.5}O_{10}))$ |
| Nontronite | $Na_{0.33}(Fe_2(OH)_2(Al_{0.33}Si_{3.67}O_{10}))$ |
| Saponite | $(Ca,Na)_{0.33}((Mg,Fe)_3(OH)_2(Al_{0.33}Si_{3.67}O_{10}))$ |
| Hectorite | $Na_{0.33}((Mg,Li)_3(OH,F)_2(Si_4O_{10}))$ |

In some preferred embodiments, inorganic gel formers including but not limited to aluminum silicates, such as the montmorillonites (bentonites, hectorites and derivatives thereof, such as quaternium-18 bentonite, quaternium-18 hectorites, stearalkonium bentonites and stearalkonium hectorites), and also magnesium-aluminum silicates (VEEGUM® grades), and sodium-magnesium silicates (LAPONITE® grades) find use in the present invention.

Montmorillonites represent clay minerals which are a type of dioctahedral smectites, and are masses which swell in water, but do not become plastic. The layer packets in the three-layer structure of the montmorillonites can swell as a result of reversible incorporation of water (in a 2- to 7-fold amount) and other substances, such as, for example, alcohols, glycols, pyridine, picoline, ammonium compounds, hydroxy-aluminosilicate ions etc. The chemical formula given above provides just an approximation of the formula, as montmorillonites have a large capacity for ion exchange. For example, Al can be replaced by Mg, $Fe^{2+}$, $Fe^{3+}$, Zn, Pb (e.g., from harmful substances in waste waters), Cr, Cu and other elements. The resulting negative charge of the octahedral layers is compensated for by the presence of cations, in particular $Na^+$ (i.e., sodium montmorillonite) and $Ca^{2+}$ (i.e., calcium montmorillonite, a compound that is only swellable to a very small extent) in interlayer positions.

In alternative embodiments, synthetic magnesium silicates and/or bentonites find use in the present invention, including but not limited to such commercially available compounds as OPTIGEL® (Sud-Chemie). As indicated above, in some embodiments, aluminum silicates such as the commercially available VEEGUM® (R.T. Vanderbilt Comp., Inc), find use in the present invention. Various VEEGUM® grades which find use in various embodiments of the present invention are provided below.

| VEEGUM® Grades | | | | | |
|---|---|---|---|---|---|
| | Regular Grade | HV | K | HS | S-728 |
| $SiO_2$ | 55.5 | 56.9 | 64.7 | 69.0 | 65.3 |
| MgO | 13.0 | 13.0 | 5.4 | 2.9 | 3.3 |
| $Al_2O_3$ | 8.9 | 10.3 | 14.8 | 14.7 | 17.0 |
| $Fe_2O_3$ | 1.0 | 0.8 | 1.5 | 1.8 | 0.7 |
| CaO | 2.0 | 2.0 | 1.1 | 1.3 | 1.3 |
| $Na_2O$ | 2.1 | 2.8 | 2.2 | 2.2 | 3.8 |
| $K_2O$ | 1.3 | 1.3 | 1.9 | 0.4 | 0.2 |
| Ashing loss | 11.1 | 12.6 | 7.6 | 5.5 | 7.5 |

The above products swell in water to form viscous gels, which have an alkaline reaction. The organophilization of montmorillonite or bentonites (exchange of the interlayer cations for quaternary alkylammonium ions) produces products (bentones) which are preferably used for dispersion in organic solvents and oils, fats, ointments, inks, surface coatings and in detergents.

BENTONE® is a trade name for various neutral and chemically inert gelling agents which are constructed from long-chain, organic ammonium salts and specific types of montmorillonite. BENTONE® gelling agents swell in organic media, which cause the media to also swell. The gels are resistant to diluted acids and alkalis, although they partially lose their gelling properties upon prolonged contact with strong acids and alkalis. Because of their organophilic character, BENTONE® gelling agents are only wettable by water with difficulty. There are various BENTONE® gelling agent grades commercially available, including those sold by Kronos Titan: BENTONE® 27, an organically modified montmorillonite; BENTONE® 34 (dimethyldioctylammonium bentonite; prepared in accordance with U.S. Pat. No. 2,531,427, incorporated herein by reference, which because of its lipophilic groups, swells more readily in lipophilic medium than in water); BENTONE® 38, an organically modified montmorillonite, available as a cream-colored to white powder; BENTONE® LT, a purified clay mineral; BENTONE® Gel MIO, an organically modified montmorillonite which is supplied as a very fine suspension in mineral oil (SUS-71) (10% bentonite, 86.7% mineral oil and 3.3% wetting agent); BENTONE® Gel IPM, an organically modified bentonite which is suspended in isopropyl myristate (10% bentonite, 86.7% isopropylmyristate, 3.3% wetting agent); BENTONE® Gel CAO, an organically modified montmorillonite which is taken up in castor oil (10% bentonite, 86.7% castor oil and 3.3% wetting agent); BENTONEE Gel Lantrol, an organically modified montmorillonite which, in paste form, is intended for the further processing, in particular for the preparation, of cosmetic compositions; 10% bentonite, 64.9 LANTROL® (wool wax oil), 22.0 isopropyl myristate, 3.0 wetting agent and 0.1 propyl p-hydroxybenzoate; BENTONE® Gel Lan I, a 10% strength BENTONE® 27 paste in a mixture of wool wax USP and isopropyl palmitate; BENTONE® Gel Lan II, a bentonite paste in pure liquid wool wax; BENTONE® Gel NV, a 15% strength BENTONE® 27 paste in dibutyl phthalate; BENTONE® Gel OMS, a bentonite paste in Shellsol T; BENTONE® Gel OMS 25, a bentonite paste in isoparaffinic hydrocarbons (IDOPAR® H); and BENTONE® Gel IPP, a bentonite paste in isopropyl palmitate.

"Hydrocolloid" is the technological abbreviation for the more correct name "hydrophilic colloid." Hydrocolloids are macromolecules which have a largely linear structure and intermolecular forces of interaction which permit secondary and primary valence bonds between the individual molecules to form a recticular structure. Some hydrocolloids are water-soluble natural or synthetic polymers which, in aqueous systems, form gels or viscous solutions. These compounds increase the viscosity of water by either binding water molecules (hydration), or by absorbing and encapsulating the water into their interwoven macromolecules, while restricting the mobility of water. These water-soluble polymers represent a large group of natural and synthetic polymers that are chemically very different, but which share a common feature in their solubility in water or aqueous media. A prerequisite for this is that these polymers have a number of hydrophilic groups sufficient for solubility in water and are not too greatly crosslinked. These hydrophilic groups can be nonionic, anionic or cationic in nature, for example as follows:

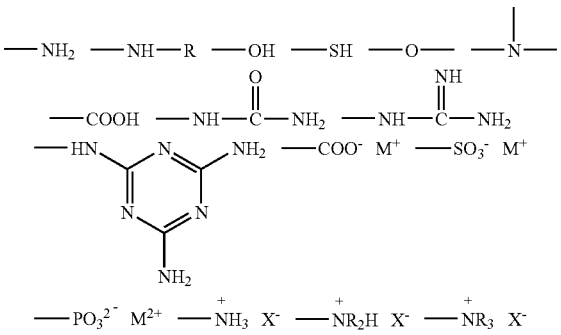

-continued

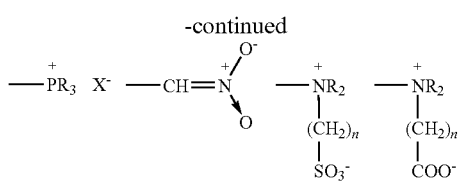

In some preferred embodiments, the group of the cosmetically and dermatologically relevant hydrocolloids are divided into the following groups: organic, natural compounds (e.g., agar agar, carrageen, tragacanth, gum arabic, alginates, pectins, polyoses, guar flour, carob bean flour, starch, dextrins, gelatins, and casein); organic, modified natural substances (e.g., carboxymethylcellulose and other cellulose ethers, hydroxyethylcellulose and hydroxypropylcellulose and microcristalline cellulose); organic, completely synthetic compounds (e.g., polyacrylic and polymethacrylic compounds, vinyl polymers, polycarboxylic acids, polyethers, polyimines, polyamides, and polyurethanes); and inorganic compounds (e.g., polysilicic acids, clay minerals, such as montmorillonites, zeolites, and silicas).

In alternative embodiments, ethylcelluloses find use in compositions of the present invention as stabilizers. Ethylcelluloses are characterized by the following structure. In this structure, the Rs are either ethyl groups or hydrogen atoms.

ferred embodiments, AVICEL® RC-591 (a modified microcristalline cellulose which is made up of 89% microcrystalline cellulose and 11% sodium carboxymethylcellulose) finds use in the present invention.

Additional hydrocolloids that find use in the present invention include methylcelluloses (i.e., methylesters of cellulose). These compounds are characterized by the following structural formula

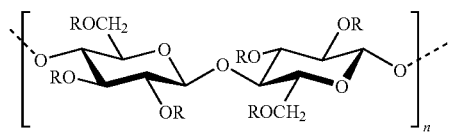

in which R can be a hydrogen or a methyl group.

Cellulose mixed ethers (generally referred to as methylcelluloses, which contain, in addition to a predominating content of methyl groups, also 2-hydroxyethyl, 2-hydroxypropyl or 2-hydroxybutyl groups) also find use in some embodiments of the present invention. In some preferred embodiments, hydroxypropyl)methyl-celluloses (e.g., METHOCEL® E4M; Dow Chemical Co.) find use in the present invention.

In yet further embodiments sodium carboxymethylcellulose (i.e., the sodium salt of the glycolic ether of cellulose, for

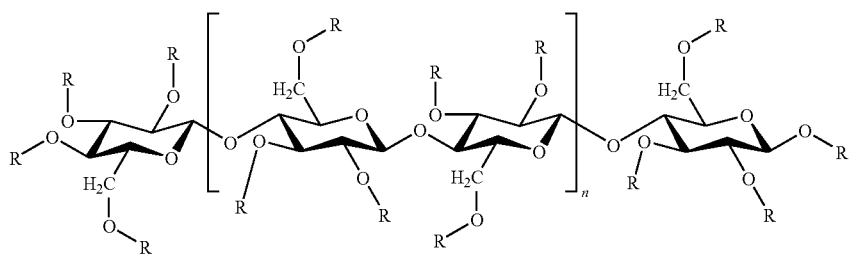

In some preferred embodiments, the degree of ethylation in the ethylcellulose is from about 2.0 to about 3.0, corresponding to about 40 to about 55%, and more preferably about 48.0 to about 49.5% ethylation. The average molecular mass is preferably chosen such that the viscosity of an approximately 5% strength solution in a mixture of 80 parts of toluene and 20 parts of ethanol at 25° C. is 3 to 110 mPas, and more preferably 9 to 11 mPas. In some particularly preferred embodiments, the average molar mass is from about 100,000 to about 400,000 g/mol. In some preferred embodiments, the ethylcellulose concentration in compositions of the present invention ranges from about 0.1 to about 10% by weight, based on the total weight of the preparations. Various ethylcelluloses find use in the present invention, including but not limited to those that are commercially available (e.g., ETHOCEL® Standard 10 Premium; Dow Chemicals).

In yet additional embodiments, microcristalline cellulose finds use as hydrocolloid in compositions of the present invention. Various microcrystalline cellulose preparations find use in the present invention, including but not limited to those that are commercially available (e.g., AVICEL®, such as AVICEL® RC-591, as well as AVICEL® RC/CL; AVICEL® CE-15; and AVICEL® 500; FMC Corporation Food and Pharmaceutical Products). In some particularly pre-which R in the above structural formula may be hydrogen and/or $CH_2$—COONa) finds use in the present invention. In some preferred embodiments, sodium carboxymethylcellulose, also sometimes referred to as "cellulose gum" (e.g., NATROSOL® Plus 330 CS; Aqualon) finds use in the present invention.

In additional embodiments, xanthan (CAS No. 11138-66-2), (i.e., xanthan gum), an anionic heteropolysaccharide generally formed by fermentation from maize sugar and isolated as potassium salt finds use in the present invention. It is produced by *Xanthomonas campestris* and some other species under aerobic conditions and has a molecular weight of from $2\times10^6$ to $24\times10^6$. Xanthan is formed from a chain having cellulose with side chains. The structure of the subgroups consists of glucose, mannose, glucuronic acid, acetate and pyruvate. The number of pyruvate units determines the viscosity of the xanthan.

In still further embodiments, carrageen is used as a gel former in compositions of the present invention. This compound is an extract from North Atlantic red algae (*Florideae; Chondrus crispus* and *Gigartina stellata*) that has a structure similar to that of agar. The term "carrageen" is frequently used in reference to a dried algae product and "carrageenan" is used in reference to the extract thereof. The carrageen precipitated from the hot-water extract of the algae is a colorless to sand-colored powder with a molecular weight range from about 100,000 to about 800,000 and a sulfate content of about 25%. Carrageen, which is very readily soluble in warm water, forms a thixotropic gel upon cooling, even if the water content is 95-98%. The rigidity of the gel is effected by the double helix structure of the carrageen.

In the case of carrageenan, three principle constituents are differentiated. The gel-forming "κ fraction" consists of D-galactose 4-sulfate and 3,6-anhydro-α-D-galactose, which has alternate glycoside bonds in the 1,3- and 1,4 position (in contrast, agar contains 3,6-anhydro-α-L-galactose). The non-gelling "λ fraction" is composed of 1,3-glycosidically linked D-galactose 2-sulfate and 1,4-bonded D-galactose-2,6-disulfate radicals, and is readily soluble in cold water. Finally, "☐-carrageenan," composed of D-galactose 4-sulfate in 1,3 bond and 3,6-anhydro-α-D-galactose 2-sulfate in 1,4 bond, is both water-soluble and also gel-forming. The nature of any cations which are present ($K^+$, $NH_4^+$, $Na^+$, $Mg^{2+}$, $Ca^{2+}$) also influences the solubility of the carrageens.

In yet additional embodiments, chitosan (i.e., partially deacylated chitin) finds use in various compositions of the present invention. Chitosan has film-forming properties and is characterized as having a silky feel on the skin. One disadvantage for some uses, is its severe stickiness on the skin which occurs in temporarily (usually) during application. Due to this stickiness, some preparations are not acceptable to consumers. However, chitosan finds use in some preparations, including hair care compositions, as it is better than chitin in thickening and/or stabilizing, as well as improving the adhesion and water resistance of polymeric films. The use of chitosan is well-known to those of skill in the personal care art (See e.g., Fiedler, *Lexikon der Hilfsstoffe für Pharmazie, Kosmetik und anqrenzende Gebiete*, [Lexikon of auxiliaries for pharmacy, cosmetics and related fields], $3^{rd}$ edition, Editio Cantor, Aulendorf, [1989], p. 293). Chitosan is characterized by the following structural formula:

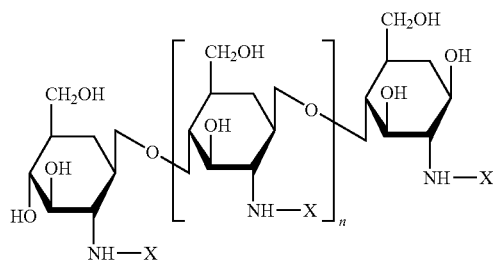

where n assumes values up to about 10 000, and X is either the acetyl radical or hydrogen. Chitosan forms by deacetylation and partial depolymerization (hydrolysis) of chitin, which is characterized by the structural formula

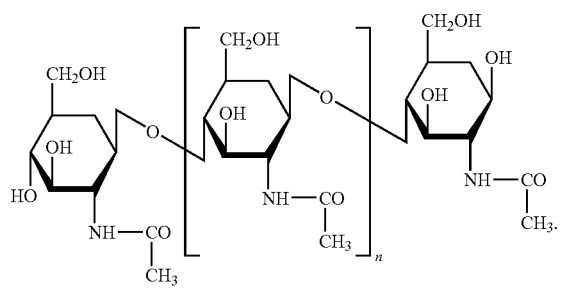

Chitin is an essential constituent of the arthropod (e.g. insects, crabs, and spiders) ectoskeleton, and is also found in the connective and/or supporting tissues of other organisms (e.g. mollusks, algae, and fungi). In the region of about pH<6, chitosan is positively charged and in that range is also soluble in aqueous systems. It is incompatible with anionic raw materials. For this reason, in order to prepare chitosan-containing oil-in-water emulsions, the use of nonionic emulsifiers is appropriate (See e.g., EP 776 657). In some preferred embodiments, the compositions of the present invention contain at least one chitosans with a degree of deacetylation of at least about >25%, and more preferably, a range of more than about 55 to about 99% (as determined by means of $^1$H-NMR). In some embodiments, chitosans of molecular weights between about 10,000 and about 1,000,000, in particular those with molecular weights between 100,000 and 1,000, 000 (determined by means of gel permeation chromatography) find use in the present invention.

In yet further embodiments, polyacrylates find use as gelling agents in some compositions of the present invention. Suitable polyacrylates include but are not limited to acrylate-alkyl acrylate copolymers, in particular those chosen from the group of carbomers or CARBOPOL® copolymers (B. F. Goodrich Co.). In particular, the acrylate-alkyl acrylate copolymers that find use in some embodiments of the present invention have the following structure:

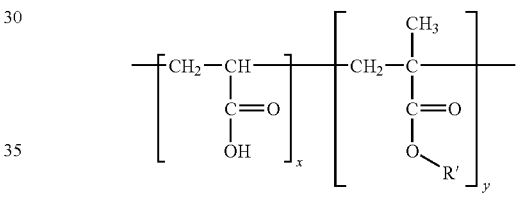

where R' is a long-chain alkyl radical, and x and y represent numbers which symbolize the respective stoichiometric proportion of each of the comonomers.

In some embodiments, acrylate copolymers and/or acrylate-alkyl acrylate copolymers, include but are not limited to those that are commercially available (e.g., CARBOPOL® 1382, CARBOPOL® 981, and CARBOPOL® 5984; B. F. Goodrich Co., and in particular, polyacrylates from the group of CARBOPOL grades 980, 981, 1382, 2984, 5984 and Carbomer 2001). In additional embodiments, copolymers of $C_{10-30}$-alkyl acrylates and one or more monomers of acrylic acid, of methacrylic acid or esters thereof which are crosslinked with an allyl ether of sucrose or an allyl ether of pentaerythrito find use in some embodiments of the present invention.

Compounds which carry the INCI name "Acrylates/$C_{10-30}$ Alkyl Acrylate Crosspolymer" also find use in some embodiments of the present invention. In some embodiments, commercially available polymers (e.g., PEMULEN® TR1 and PEMULEN® TR2; B. F. Goodrich Co.) find use in some embodiments of the present invention, although it is not intended that the present invention be limited to any specific acrylate-containing composition.

In yet additional embodiments, compounds which carry the INCI name "ammonium acryloyldimethyltaurates/vinylpyrrolidone copolymers" find use in the present invention. These ammonium acryloyldimethyl taurate/vinylpyrrolidone copolymers have the empirical formula $[C_7H_{16}N_2SO_4]_n$ $[C_6H_9NO]_m$, which corresponds to the following structure:

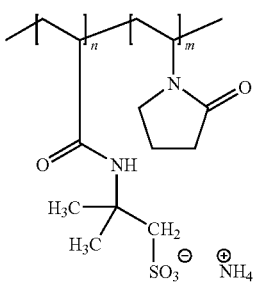

Preferred species of this compound are listed in Chemical Abstracts under the Registry numbers 58374-69-9, 13162-05-5 and 88-12-0, and are commercially available (e.g., ARISTOFLEX®; Clariant GmbH). However, it is not intended that the present invention be limited to any particular species. In yet additional embodiments of the present invention, copolymers/crosspolymers comprising acryloyldimethyl taurate (e.g., SIMUGEL® EG and SIMUGEL® EG; Seppic S.A.) find use in some compositions of the present invention.

Additional completely synthetic hydrocolloids that find use in the present invention include, but are not limited to anionic polyurethanes which are soluble or dispersible in water and which are advantageously obtainable from:

Aa) at least one compound which contains two or more active hydrogen atoms per molecule, Ab) at least one diol containing acid or salt groups, and Ac) at least one diisocyanate.

In some preferred embodiments, the component Aa) is, in particular, a diol, aminoalcohol, diamine, polyesterol, polyetherol with a number-average molecular weight of in each case up to 3000, or mixtures thereof, where up to 3 mol % of said compounds may be replaced by triols or triamines. Preference is given to diols and polyesterdiols. In particular, the component Aa) comprises at least 50% by weight, based on the total weight of the component Aa), of a polyesterdiol. Suitable polyesterdiols are all those which are customarily used for the preparation of polyurethanes, in particular the reaction products of phthalic acid and diethylene glycol, isophthalic acid and 1,4-butanediol, isophthalic acid/adipic acid and 1,6-hexanediol, and adipic acid and ethylene glycol or 5-NaSO$_3$-isophthalic acid, phthalic acid, adipic acid and 1,6-hexanediol.

Examples of diols which find use in some embodiments of the present invention include, but are not limited to ethylene glycol, propylene glycol, butylene glycol, neopentyl glycol, polyetherols (e.g., polyethylene glycols having molecular weights up to 3000), block copolymers of ethylene oxide and propylene oxide with number-average molecular weights of up to 3000, and block copolymers of ethylene oxide, propylene oxide and butylene oxide which contain the copolymerized alkylene oxide units in randomly distributed manner or in the form of blocks. Preference is given to ethylene glycol, neopentyl glycol, di-, tri-, tetra-, penta- or hexaethylene glycol. Other diols which find use include poly(α-hydroxycarboxylic acid)diols.

Suitable aminoalcohols that find use in some embodiments of the present invention include but are not limited to 2-aminoethanol, 2-(N-methylamino)ethanol, 3-aminopropanol, and 4-aminobutanol.

In some embodiments, diamines such as ethylenediamine, propylenediamine, 1,4-diaminobutan, 1,6-diaminohexane, and α,ω-diamines which can be prepared by amination of polyalkylene oxides with ammonia find use in some compositions of the present invention.

Component Ab) is, in particular, dimethylolpropanoic acid or a compound with the formula:

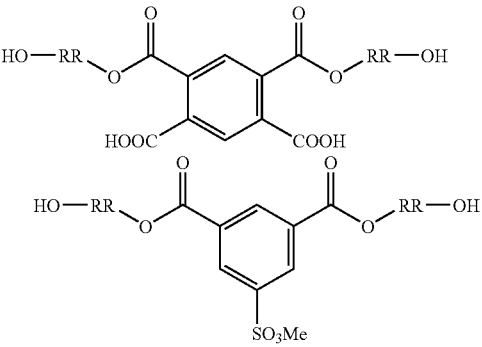

where RR is in each case a C$_2$-C$_{18}$-alkylene group and Me is Na or K.

Component Ac) is, in particular, hexamethylene diisocyanate, isophorone diisocyanate, methyldiphenyl isocyanate (MDI), and/or tolylene diisocyanate.

In some embodiments, the polyurethanes are obtained by reacting the compounds of groups Aa) and Ab) under an inert-gas atmosphere in an inert solvent at temperatures of from 70 to 130° C. with the compounds of group Ac). This reaction can be carried out, where appropriate, in the presence of chain extenders in order to prepare polyurethanes with relatively high molecular weights. As is customary in the preparation of polyurethanes, the components [(Aa)+(Ab)]:Ac are advantageously used in the molar ratio of from 0.8 to 1.1:1. The acid number of the polyurethanes is determined by the composition and the concentration of the compounds of component (Ab) in the mixture of components (Aa) and (Ab).

In some embodiments, the polyurethanes have K values according to H. Fikentscher (determined in 0.1% strength by weight solutions in N-methylpyrrolidone at 25° C. and pH 7) of from about 15 to about 100, and preferably about 25 to about 50. The K value (i.e., "intrinsic viscosity"), is a parameter which is easy to determine by means of viscosity measurements of polymer solutions and is therefore frequently used in the industrial sector for characterizing polymers. Polyurethanes containing acid groups that find use in some embodiments of the present invention include, but are not limited to polyurethanes that are water-soluble or dispersible without the aid of emulsifiers after partial or complete neutralization. The salts of the polyurethanes generally have better solubility or dispersibility in water than the unneutralized polyurethanes. Bases which find use for the neutralization of the polyurethanes include alkali metal bases (e.g., sodium hydroxide solution, potassium hydroxide solution, soda, sodium hydrogencarbonate, potassium carbonate or potassium hydrogen carbonate) and alkaline earth metal bases (e.g., calcium hydroxide, calcium oxide, magnesium hydroxide or magnesium carbonate, and ammonia and amines). In some embodiments, 2-amino-2-methylpropanol, diethylaminopropylamine and triisopropanolamine find particular use in the neutralization of the polyurethanes containing acid groups. In yet additional embodiments, the neutralization of the polyurethanes containing acid groups is carried out using mixtures of two or more bases (e.g. mixtures of sodium hydroxide solution and triisopropanolamine). Depending on the intended use, neutralization is partial (e.g.

about 20 to about 40%) or complete (i.e., 100%). These polymers and their preparation are described in more detail in DE-A-42 25 045, incorporated herein by reference.

B. Water-soluble or -dispersible cationic polyurethanes and polyureas of:
 Ba) at least one diisocyanate, which may have already been reacted beforehand with one or more compounds which contain two or more active hydrogen atoms per molecule, and
 Bb) at least one diol, primary or secondary amino alcohol, primary or secondary diamine or primary or secondary triamine with one or more tertiary, quaternary or protonated tertiary amino nitrogen atoms.

Preferred diisocyanates are as given above under A). Compounds with two or more active hydrogen atoms are diols, aminoalcohols, diamines, polyesterols, polyamidediamines and polyetherols. Suitable compounds of this type are as given above under A).

The polyurethanes are prepared as described above under A). Charged cationic groups can be produced in the polyureas from the tertiary amino nitrogen atoms present either by protonation, (e.g., with carboxylic acids, such as lactic acid), or by quaternization (e.g. with alkylating agents, such as $C_1$ to $C_4$-alkyl halides) or sulfates. Examples of such alkylating agents include, but are not limited to ethyl chloride, ethyl bromide, methyl chloride, methyl bromide, dimethyl sulfate and diethyl sulfate. These polymers and their preparation are described in more detail in DE-A-42 41 118, which is incorporated herein by reference.

C. Linear polyurethanes with carboxylate groups of:
 Ca) a 2,2-hydroxymethyl-substituted carboxylic acid of the formula

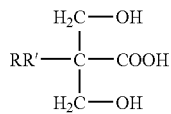

in which RR' is a hydrogen atom or a $C_1$-$C_{20}$-alkyl group, which is used in an amount which suffices for about 0.35 to about 2.25 milliequivalents of carboxyl groups to be present in the polyurethane per g of polyurethane,
 Cb) about 10 to about 90% by weight, based on the weight of the polyurethane, of one or more organic compounds with not more than two active hydrogen atoms and
 Cc) one or more organic diisocyanates.

In some preferred embodiments, the carboxyl groups present in the polyurethane are, finally, at least partially neutralized with a suitable base. These polymers and their preparation are described in EP-A-619 111, incorporated herein by reference.

D. Carboxyl-containing polycondensation products of anhydrides of tri- or tetracarboxylic acids and diols, diamines or aminoalcohols (polyesters, polyamides or polyester amides). These polymers and their preparation are described in more detail in DE-A-42 24 761, incorporated herein by reference.

E. Polyacrylates and polymethacrylates, as are described in more detail in DE-A-43 14 305, 36 27 970 and 29 17 504, all of which are incorporated herein by reference.

The polymers used in some embodiments of the present invention have a K value of from about 15 to about 100, and more preferably from about 25 to about 50. The polymers are generally present in the composition in an amount in the range from about 0.2 to about 20% by weight, based on the total weight of the compositions. The salt is used in an amount effective for improving the exchangeability of the polymers. The salt is generally used in an amount of from about 0.02 to about 10% by weight, and more preferably from about 0.05 to about 5% by weight, and in particular, from about 0.1 to about 3% by weight, based on the total weight of the composition.

The total amount of one or more hydrocolloids in some embodiments of the personal care compositions of the present invention is less than about 5% by weight, preferably between about 0.05 and about 3.0% by weight, and more preferably between about 0.1 and about 1.0% by weight, based on the total weight of the preparations.

In some embodiments, the present compositions comprise at least one silicone oil phase. Silicone oil phase(s) generally comprises from about 0.1% to about 20%, preferably from about 0.5% to about 10%, and more preferably from about 0.5% to about 5%, of the composition. The silicone oil phase preferably comprises one or more silicone components.

In some embodiments, silicone components are fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. Volatile, as well as non-volatile silicone fluids find use herein. Silicone fluids generally have an average molecular weight of less than about 200,000. In preferred embodiments, suitable silicone fluids have a molecular weight of about 100,000 or less, preferably about 50,000 or less, and more preferably about 10,000 or less. Preferably the silicone fluid is selected from silicone fluids having a weight average molecular weight in the range from about 100 to about 50,000 and preferably from about 200 to about 40,000. Typically, silicone fluids have a viscosity ranging from about 0.65 to about 600,000 mm2s-1, preferably from about 0.65 to about 10,000 mm2.s-1 at 25° C. The viscosity can be measured by means of a glass capillary viscometer as set forth in Dow Corning Corporate Test Method CTM0004, Jul. 29, 1970. Suitable polydimethyl siloxanes that can be used herein include commercially available compounds (e.g., from the General Electric Company and Dow Corning). Also useful are essentially non-volatile polyalkylarylsiloxanes, for example, polymethylphenylsiloxanes, having viscosities of about 0.65 to 30,000 mm2s-1 at 25° C. (General Electric Company or from Dow Corning). Cyclic polydimethylsiloxanes suitable for use herein are those having a ring structure incorporating from about 3 to about 7 (CH3)2SiO moieties, preferably about 5 or more.

In additional embodiments, silicone gums find use herein. In some preferred embodiments, a silicone oil phase comprises a silicone gum or a mixture of silicones including the silicone gum. Typically, silicone gums have a viscosity at 25° C. in excess of about 1,000,000 mm2s-1. The silicone gums include dimethicones as known in the art (See e.g., U.S. Pat. No. 4,152,416; and Noll, Chemistry and Technology of Silicones, Academic Press, New York [1968]). Silicone gums such as those described in General Electric Silicone Rubber Product Data Sheets SE 30, SE 33, SE 54 and SE 76, also find use in the present invention. Specific examples of silicone gums include polydimethylsiloxane, (polydimethylsiloxane) (methylvinylsiloxane) copolymer, poly(dimethylsiloxane) (diphenyl)(methylvinylsiloxane) copolymer and mixtures thereof. Preferred silicone gums for use herein are silicone gums having a molecular weight of from about 200,000 to about 4,000,000 selected from dimethiconol, dimethicone copolyol, dimethicone and mixtures thereof.

In some embodiments, a silicone phase herein preferably comprises a silicone gum incorporated into the composition as part of a silicone gum-fluid blend. When the silicone gum is incorporated as part of a silicone gum-fluid blend, the silicone gum preferably constitutes from about 5% to about 40%, especially from about 10% to 20% by weight of the silicone gum-fluid blend. Suitable silicone gum-fluid blends herein are mixtures consisting essentially of:

(i) a silicone having a molecular weight of from about 200,000 to about 4,000,000 selected from dimethiconol, fluorosilicone and dimethicone and mixtures thereof; and (ii) a carrier which is a silicone fluid, the carrier having a viscosity from about 0.65 $mm^2s^{-1}$ to about 100 $mm^2s^{-1}$, wherein the ratio of i) to ii) is from about 10:90 to about 20:80 and wherein said silicone gum-based component has a final viscosity of from about 100 $mm^2s^{-1}$ to about 100,000 $mm^2s^{-1}$, preferably from 500 $mm^2s^{-1}$ to about 10,000 $mm^2s^{-1}$.

Further silicone components suitable for use in a silicone oil phase herein include crosslinked polyorganosiloxane polymers, optionally dispersed in a fluid carrier. In general, when present the crosslinked polyorganosiloxane polymers, together with its carrier (if present) comprises from about 0.1% to about 20%, preferably from about 0.5% to about 10%, and more preferably from about 0.5% to about 5% of the composition. Such polymers comprise polyorganosiloxane polymers crosslinked by a crosslinking agent (See e.g., WO98/22085). Examples of suitable polyorganosiloxane polymers for use herein include, but are not limited to methyl vinyl dimethicone, methyl vinyl diphenyl dimethicone and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment (See e.g., WO98/22085). Suitable polydiorganosiloxane-polyalkylene copolymers are available commercially under the tradenames BELSIL® from Wacker-Chemie GmbH. A particularly preferred copolymer fluid blend for use herein includes Dow Corning DC3225C which has the CTFA designation Dimethicone/Dimethicone copolyol.

In further embodiments, compositions of the present invention comprise an organic sunscreen. In some embodiments, suitable sunscreens have UVA absorbing properties, while others have UVB absorbing properties, and still others comprise a mixture thereof. The exact amount of the sunscreen active varies, depending upon the desired Sun Protection Factor (i.e., the "SPF") of the composition, as well as the desired level of UV protection. SPF is a commonly used measure of photoprotection of a sunscreen against erythema. The SPF is defined as a ratio of the ultraviolet energy required to produce minimal erythema on protected skin to that required to produce the same minimal erythema on unprotected skin in the same individual. Amounts of the sunscreen used are preferably from about 2% to about 20%, and more preferably from about 4% to about 14%. Suitable sunscreens include, but are not limited to those approved for use in the United States, Japan, Europe and Australia. The compositions of the present invention preferably comprise an SPF of about 2 to about 30, preferably about 4 about 30, and more preferably about 4 to about 15.

In some embodiments, the compositions of the present invention comprise one or more UVA absorbing sunscreen actives that absorb UV radiation having a wavelength of from about 320 nm to about 400 nm. Suitable UVA absorbing sunscreen actives include, but are not limited to dibenzoylmethane (See e.g., Lowe and Shaath (eds.), Sunscreens: Development, Evaluation, and Regulatory Aspects, Marcel Dekker, Inc.) derivatives, anthranilate derivatives such as methylanthranilate and homomethyl, 1-N-acetylanthranilate, and mixtures thereof. The UVA absorbing sunscreen active is preferably present in an amount sufficient to provide broad spectrum UVA protection either independently, or in combination with, other UV protective actives which may be present in the composition.

Suitable UVA sunscreen actives include dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane, 2,6-dimethyl-4'-tert-butyl-4'methoxydibenzoylmethane, and mixtures thereof. Preferred dibenzoyl sunscreen actives include those selected from 4-(1,1-dimethylethyl)-4'-methoxydibenzoylmethane, 4-isopropyldibenzoylmethane, and mixtures thereof. A preferred sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or "avobenzone," is commercially available under the names of Parsol® 1789 from Givaudan Roure (International) S. A., and Eusolex® 9020 from Merck & Co., Inc. The sunscreen 4-isoproplydibenzoylmethane, which is also known as isopropyldibenzoylmethane, is commercially available from Merck under the name of Eusolex® 8020.

In some embodiments, the compositions of the present invention further include one or more UVB sunscreen actives that absorb(s) UV radiation having a wavelength of about 290 nm to about 320 nm. The compositions comprise an amount of the UVB sunscreen active that is safe and effective in providing UVB protection either independently, or in combination with, other UV protective actives which may be present in the compositions. The compositions comprise from about 0.1% to about 20%, preferably from about 0.1% to about 12%, and more preferably from about 0.5% to about 8% by weight, of each UVB absorbing organic sunscreen, or as mandated by the relevant regulatory authority(s).

A variety of UVB sunscreen actives are suitable for use herein (See e.g., U.S. Pat. No. 5,087,372; U.S. Pat. No. 5,073,371; U.S. Pat. No. 5,073,372; U.S. Pat. No. 4,937,370; and U.S. Pat. No. 4,999,186). Preferred UVB sunscreen actives are selected from 2-ethylhexyl-2-cyano-3,2-ethylhexyl N,N-dimethyl-p-aminobenzoate, p-amino-benzoic acid, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 3-diphenylacrylate, 2-phenyl-benzimidazole-5-sulphonic acid (PBSA), cinnamate esters and their derivatives such as 2-ethylhexyl-p-methoxycinnamate, salicylate esters and their derivatives such as triethanolamine salicylate, ethylhexyl salicylate, octyldimethyl para-aminobenzoic acid, camphor derivatives and their derivatives, and mixtures thereof. Preferred organic sunscreen actives include 2-ethylhexyl-2-cyano-3,3-diphenylacrylate, 2-phenyl-benzimidazole-5-sulphonic acid (PBSA), octyl-p-methoxycinnamate, and mixtures thereof. Salt and acid neutralized forms of the acidic sunscreens are also useful herein.

Thus, in some embodiments, the present invention provides compositions comprising any organic UV-A and UV-B filter, for example but not limited to the following:

| Nr. | Compound | CAS-Nr. (=Acid) |
|---|---|---|
| 1 | 4-Aminobenzoicacid | 150-13-0 |
| 2 | 3-(4'-Trimethylammonium)-benzylidenbornan-2-on-methylsulfate | 52793-97-2 |
| 3 | 3,3,5-Trimethyl-cyclohexyl-salicylate (Homosalatum) | 118-56-9 |
| 4 | 2-Hydroxy-4-methoxy-benzophenon (Oxybenzonum) | 131-57-7 |
| 5 | 2-Phenylbenzimidazol-5-sulfonic acid and their Calcium-, Sodium- and Triethanolaminosalts | 27503-81-7 |
| 6 | 3,3'-(1,4-Phenylendimethin)-bis(7,7-dimethyl-2-oxobicyclo[2.2.1]heptan-1-methansolfonicacid) and salts thereof | 90457-82-2 |
| 7 | 4-Bis(polyethoxy)amino-benzoesaurepolyethoxy-ethylester | 113010-52-9 |
| 8 | 4-Dimethylamino-benzoicacid-2-ethylhexylester | 21245-02-3 |
| 9 | Salicylicacid-2-ethylhexylester | 118-60-5 |
| 10 | 4-Methoxy-cinnamicacid-2-isoamylester | 71617-10-2 |
| 11 | 4-Methoxy-cinnamicacid-2-ethylhexylester | 5466-77-3 |
| 12 | 2-Hydroxy-4-methoxy-benzophenon-5-sulfonicacid-(Sulisobenzonum) and the sodiumsalt | 4065-45-6 |
| 13 | 3-(4'-Sulfobenzyliden)-bornan-2-on and salts thereof | 58030-58-6 |
| 14 | 3-Benzylidenbornan-2-on | 16087-24-8 |
| 15 | 1-(4'-Isopropylphenyl)-3-phenylpropan-1,3-dion | 63260-25-9 |
| 16 | 4-Isopropylbenzylsalicylat | 94134-93-7 |
| 17 | 3-Imidazol-4-yl-acrylicacid und ihr Ethylester | 104-98-3 |
| 18 | 2-Cyano-3,3-diphenylacricacidethylester | 5232-99-5 |
| 19 | 2-Cyano-3,3-diphenylacrylicacid-2'-ethylhexylester | 6197-30-4 |
| 20 | Menthyl-o-aminobenzoat oder: 5-Methyl-2-(1-methylethyl)-2-aminobenzoat | 134-09-8 |
| 21 | Glyceryl p-aminobenzoat oder: 4-Aminobenzoicacid-1-glyceryl-ester | 136-44-7 |
| 22 | 2,2'-Dihydroxy-4-methoxybenzophenon (Dioxybenzone) | 131-53-3 |
| 23 | 2-Hydroxy-4-methoxy-4-methylbenzophenon (Mexenon) | 1641-17-4 |
| 24 | Triethanolamin Salicylat | 2174-16-5 |
| 25 | Dimethoxyphenylglyoxalsaure oder: 3,4-dimethoxy-phenyl-glyoxal-saures Natrium | 4732-70-1 |
| 26 | 3-(4'Sulfobenzyliden)-bornan-2-on und seine Salze | 56039-58-8 |
| 27 | 4-tert.-Butyl-4'-methoxy-dibenzoylmethan | 70356-09-1 |
| 28 | 2,2',4,4'-Tetrahydroxybenzophenon | 131-55-5 |
| 29 | 2,2'-Methylen-bis-[6-(2H-benzotriazol-2-yl)-4-(1,1,3,3,-tetramethylbutyl)phenol] | 103597-45-1 |
| 30 | 2,2'-(1,4-Phenylen)-bis-1H-benzimidazol-4,6-disulfonicacid, Sodiumsalt | 180898-37-7 |
| 31 | 2,4-bis-[4-(2-Ethylhexyloxy)-2-hydroxy]phenyl-6-(4-methoxyphenyl)-(1,3,5)-triazin | 187393-00-6 |
| 32 | 3-(4-Methylbenzyliden)-campher | 36861-47-9 |
| 33 | 4-Bis(polyethoxy)paraaminobenzoicacidpolyethoxyethylester | 113010-52-9 |
| 34 | 2,4-Dihydroxybenzophenon | 131-56-6 |
| 35 | 2,2'-Dihydroxy-4,4'-dimethoxybenzophenon-5,5'-disodiumsulfonat | 3121-60-6 |
| 36 | Benzoicacid, 2-[4-(diethylamino)-2-hydroxybenzoyl]-, hexylester | 302776-68-7 |
| 37 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 38 | 1,1-[(2,2'-Dimethylpropoxy)carbonyl]-4,4-diphenyl-1,3-butadien | 363602-15-7 |

In some embodiments, at least one agent is added to any of the compositions useful in the present invention to stabilize the UVA sunscreen to prevent it from photo-degrading on exposure to UV radiation and thereby maintaining its UVA protection efficacy. A wide range of compounds are reported to have these stabilizing properties and should be chosen to complement both the UVA sunscreen and the composition as a whole (See e.g., U.S. Pat. Nos. 5,972,316; 5,968,485; 5,935,556; 5,827,508; and WO 00/06110). Preferred examples of stabilizing agents for use in the present invention include 2-ethylhexyl-2-cyano-3,3-diphenylacrylate, ethyl-2-cyano-3,3-diphenylacrylate, 2-ethylhexyl-3,3-diphenylacrylate, ethyl-3,3-bis(4-methoxyphenyl)acrylate, diethylhexyl 2,6 napthalate and mixtures thereof (Symrise Chemical Company).

In some preferred embodiments, the present invention provides cosmetic and/or topical dermatological preparations suitable for use as skin protection creams, cleansing milks, sun screen lotions, nourishing creams, day creams, night creams etc. In some embodiments, the present invention finds use a components of drug (i.e., pharmaceutical) compositions. In additional embodiments, the present invention finds use in decorative cosmetics (e.g., make-up formulations).

In some particularly preferred embodiments, the present invention provides sunscreens useful in cosmetic and/or skin care preparations. In addition to the active ingredient used according to the embodiments of the present invention, in some embodiments, these preparations preferably additionally comprise at least one broadband filter and/or at least one UVA filter substance and/or at least one UVB filter substance and/or at least one inorganic pigment.

In yet further embodiments, the present invention provides personal care compositions which have UV protection components, but which are not primarily sunscreens. For example, in some embodiments, UV-A and/or UV-B filter substances are incorporated into day creams and/or hair care compositions.

In additional embodiments, the personal care compositions of the present invention comprise cosmetically active ingredients, auxiliaries and/or additives, as are customarily used in such preparations (e.g., antioxidants, preservatives, bacteriocides, perfumes, antifoams, dyes, pigments which have a coloring action, thickeners, surface-active substances, emulsifiers, emollients, moisturizers and/or humectants, fats, oils, waxes or other customary constituents of a cosmetic or dermatological formulation, such as alcohols, polyols, polymers, foam stabilizers, electrolytes, organic solvents or silicone derivatives). Indeed it is contemplated that various compounds will find use in the various embodiments of the present invention, as appropriate for the product and the user.

In some embodiments, at least one agent is added to any of the compositions useful in the present invention to improve the skin substantivity of those compositions, particularly to enhance their resistance to being washed off by water or rubbed off. Examples include, but are not limited to, acrylates/$C_{12-22}$ alkylmethacrylate copolymer, acrylate/acrylate copolymer, dimethicone, dimethiconol, graft-copoly (dimethylsiloxane/1-butyl methacrylate), lauryl dimethicone, PVP/Hexadecane copolymer, PVP/Eicosene copolymer, tricontanyl PVP and trimethoxysiloxysilicate.

In addition to organic sunscreens, in some embodiments, the compositions of the present invention additionally comprise inorganic physical sunblocks (See e.g., TFA International Cosmetic Ingredient Dictionary, $6^{th}$ Edition, pp. 1026-28 and 1103 [1995]; Sayre et al., J. Soc. Cosmet. Chem., 41:103-109 [1990]; and Lowe et al., supra). Preferred inorganic physical sunblocks include zinc oxide and titanium dioxide and mixtures thereof.

When used in preferred embodiments, the physical sunblocks are present in an amount such that the present compositions are transparent on the skin (i.e., non-whitening), preferably from about 0.5% to about 20%, preferably from about 0.5% to about 10%, and more preferably from about 0.5% to 5% by weight. When titanium dioxide is used, it can have an anatase, rutile or amorphous structure. Manufacturers of micronized grade titanium dioxide and zinc oxide for sunscreen use include, but are not limited to Tayca Corporation, Uniqema, Shinetsu Chemical Corporation, Kerr-McGee, Nanophase, Nanosource, Sachtleben, Elementis, and BASF Corporation, as well as their distribution agents and those companies that further process the material for sunscreen use. Physical sunblock particles (e.g., titanium dioxide and zinc oxide) can be uncoated or coated with a variety of materials including but not limited to amino acids, aluminum compounds such as alumina, aluminum stearate, aluminum laurate, and the like; carboxylic acids and their salts (e.g., stearic acid and its salts); phospholipids, such as lecithin; organic silicone compounds; inorganic silicone compounds such as silica and silicates and mixtures thereof. In some preferred embodiments, the compositions of the present invention comprise from about 0.1% to about 15%, preferably from about 0.1% to about 7%, and more preferably from about 0.5% to about 5%, by weight, of inorganic sunscreen.

In addition to the deleterious effects of some emulsifiers, exposure to other factors is known to harm skin and hair. For example, the harmful effect of the ultraviolet portion of solar radiation on the skin is generally known. While rays having a wavelength of less than 290 nm (i.e., the UVC region) are absorbed by the ozone layer in the earth's atmosphere, rays in the range between 290 nm and 320 nm (i.e., the UVB region), cause erythema, simple sunburn or even burns of varying severity. The erythema activity maximum of sunlight is given as the relatively narrow region around 308 nm.

Numerous compounds are known to provide protection against harmful UVB radiation. Most commonly, these compounds are derivatives of 3-benzylidenecamphor, of 4-aminobenzoic acid, of cinnamic acid, of salicylic acid, of benzophenone, and of 2-phenyl-benzimidazole.

It is also important to have available filter substances for the range between about 320 nm and about 400 nm, the UVA region, since its rays can also cause damage. For a long time it was incorrectly assumed that the long-wave UV-A radiation having a wavelength of between 320 nm and 400 nm had only a negligible biological action and that, accordingly, the UV-B rays were responsible for most photodamage to the human skin. However, numerous recent studies have shown that UV-A radiation is much more harmful than UV-B radiation with regard to the triggering of photodynamic, specifically phototoxic, reactions and chronic changes in the skin. In addition, the harmful effects of UV-B radiation can be further intensified by exposure to UV-A radiation.

It has been shown that UV-A radiation by itself and under very normal everyday conditions, is sufficient to damage collagen and elastin fibers, which are of essential importance for the structure and strength of the skin, within a short period. This leads to chronic light-induced changes in the skin, such that the skin prematurely "ages." The clinical appearance of skin aged by light typically includes increased wrinkles and lines, and an irregular, furrowed relief. In addition, the skin areas affected by light-induced skin aging often show irregular pigmentation. In some cases, brown patches, keratoses, carcinomas, or malignant melanomas arise. Skin prematurely aged as a result of everyday UV exposure is also characterized has having lowered activity of the Langerhans cells and slight, chronic inflammation.

Approximately 90% of the ultraviolet radiation which reaches the Earth consists of UV-A rays. While amount of UV-B radiation reaching Earth varies widely depending on numerous factors (e.g., time of year and day and/or degree of latitude), the UV-A radiation levels that reach Earth remain relatively constant on a daily basis, irrespective of the time of year and day or geographical factors. Additionally, the majority of UV-A radiation penetrates the living epidermis, while about 70% of the UV-B rays are retained by the horny layer. Preventive protection against UV-A rays, for example by applying light protection filter substances in the form of a cosmetic or dermatological formulation to the skin, is therefore of fundamental importance.

In general, the light absorption behavior of light protection filter substances is very well known and documented, largely due to the fact that most industrialized countries have positive lists for the use of such substances, which impose very strict standards on the documentation that accompanies each product which incorporates these substances. For the concentration of the substances in the finished formulations, the absorbance values provide a guide, since interaction with substances within the skin or the surface of the skin itself often presents variables that may impact how well the compositions perform on each individual. However, it is usually difficult to estimate beforehand, how uniformly and thickly the filter substance is distributed in and on the horny layer of the skin.

To test UV-A protection performance, use is usually made of the IPD method (IPD 5 immediate pigment darkening) known to those in the art. This method is similar to the determination of the sun protection factor, and provides a method which indicates how much longer skin protected with the light protection composition can be irradiated with UV-A radiation before the pigmentation which occurs is the same as that produced for unprotected skin.

Another test method which has become established throughout Europe is the Australian standard AS/NZS 2604: 1997. In this method, the absorption of the preparation in the UV-A region is measured. In order to satisfy the standard, the preparation must absorb at least 90% of the UV-A radiation in the region 320-360 nm.

Of concern in the formulation of sunscreen compositions is that the use concentration of known light protection filter substances which also exhibit high filter action in the UV-A region are often limited by the very fact that they are combined with other substances which are in the form of solids. Thus, there are certain formulation difficulties associate with achieving relatively high sun protection factors and UV-A protection performance. However, those of skill in the art are generally aware of means to overcome and/or compensate for these difficulties.

As light protection filter substances are generally expensive and some light protection filter substances are additionally difficult to incorporate into cosmetic and/or dermatological preparations in relatively high concentrations, some embodiments of the present invention were designed to provide simple and cost-effective preparations which, despite having unusually low concentrations of conventional UV-A light protection filter substances, nevertheless achieve acceptable or even high UV-A protection performance.

However, as known in the art, UV radiation can also lead to photochemical reactions which produce products that interfere with the skin's metabolism. These photochemical reaction products are predominantly free-radical compounds (e.g., hydroxyl radicals). Undefined free-radical photoproducts which form in the skin itself can also exhibit uncontrolled secondary reactions as a result of their high reactivity. However, singlet oxygen, a non-free-radical excited state of the oxygen molecule, can also arise during UV irradiation, as can short-lived epoxides and many others. Singlet oxygen, for example, differs from normal triplet oxygen (free-radical ground state) by virtue of its increased reactivity. However, excited, reactive "free-radical" triplet states of the oxygen molecule also exist. Thus, in order to prevent these reactions, antioxidants and/or free-radical scavengers find use in cosmetic and/or dermatological formulations.

The compounds which are commonly used as light protection agents in cosmetic and/or dermatological light protection formulations are generally characterized as providing good light protection. However, they have the disadvantage that it is sometimes difficult to incorporate them into the desired formulations in a satisfactory manner.

As indicated above, the sun protection factor (SPF) indicates how much longer the skin protected with the light protection composition can be irradiated before the erythema reaction which occurs is the same as for unprotected skin (i.e., ten times as long compared with unprotected skin for an SPF=10). Consumers are very aware of the meaning of "SPF" and choose skin and/or hair care products based on the SPF values indicated on products. Consumers expect to receive reliable information from manufacturers regarding the sun protection factor, largely due to increased public awareness of the association between excess sun exposure and skin cancer, as well as premature aging. In addition, in some parts of the world, the degradation of the ozone layer is a major concern. Depending upon the skin type and the sun exposure expected, consumers choose products with a lower or a higher SPF. However, there appears to be a tendency for consumers to select relatively high SPF factors, particularly for products to be applied to children and those with fair skin. In some embodiments, the present invention provides compositions with relatively low concentrations of conventional light protection filter substances, yet with SPF values that are acceptable to consumers.

In some preferred embodiments, the basic constituents of the sunscreen preparations provided by the present invention include: water or aqueous solutions; aqueous ethanolic solutions; natural oils and/or chemically modified natural oils and/or synthetic oils; fats, waxes and other natural and synthetic fatty substances, preferably esters of fatty acids with alcohols of low carbon number (e.g., with isopropanol, propylene glycol or glycerol), or esters of fatty alcohols with alkanoic acids of low carbon number or with fatty acids; alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products. In alternatively preferred embodiments, mixtures of two or more of these constituents find use in the present invention.

In some preferred embodiments, the composition of the present invention also includes preservatives. Such preservatives include, but are not limited to pentylene glycol, ethylene diamine tetra acetate (EDTA) and their salts, chlorhexidine (and its diacetate, dihydrochloride, digluconate derivatives), 1,1,1-trichloro-2-methyl-2-propanol, parachloro metaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde (e.g., 37% aqueous solution, with 10-15% methanol to avoid polymerization), glutaraldehyde, dimethylidantoin, imidazolidinyl urea, 5-Chloro-2-methyl-4-isothiazolin-3-one, ortho-phenylphenol, 4-hydroxybenzoic acid esters (e.g., "paraben") and its methyl-, ethyl-, propyl-, isopropyl-, butyl-, and isobutyl-esters, trichlosan, 2-phenoxyethanol, phenyl mercuric acetate, borate, nitrate, quaternium-15, salicylate, salicylic acid and its salts, calcium, calcium sorbate, sorbic acid and its salts, iodopropanyl butylcarbamate zinc pyrithione, benzyl alcohol, 5-bromo-5-nitro-1,3-dioxane, 2-bromo-2-nitropropane-1,3-diol, benzoic acid and its salts, sulfites, bisulfites, phenoxyethanol, chloroxylenol, diazolidinyl urea, methylparabens, propylparabens, isoproplyparabens, isobutylparabens, butylparabens, ethylparaben, phenoxyethanol PG, and benzalkonium chloride.

In still further embodiments, preservatives, such as those used in food and feed applications find use in various compositions of the present invention. The following table provides a list of such compounds, as well as the E number for each compound. However, it is not intended that the present invention be limited to these specific preservatives, as it is contemplated that additional preservatives will find use in various embodiments of the present invention.

| Examples of Food Grade Preservatives That Find Use in Embodiments of the Present Invention | |
|---|---|
| 200 | Sorbic acid |
| 201 | Sodium sorbate |
| 202 | Potassium sorbate |
| 203 | Calcium sorbate |
| 210 | Benzoic acid |
| 211 | Sodium benzoate |
| 212 | Potassium benzoate |
| 213 | Calcium benzoate |
| 214 | Ethyl p-hydroxybenzoate |

-continued

Examples of Food Grade Preservatives That Find Use in Embodiments of the Present Invention

| | |
|---|---|
| 215 | p-hydroxybenzoic ethyl ester Na salt |
| 216 | n-propyl p-hydroxybenzoate |
| 217 | p-hydroxybenzoic-n-propyl ester Na salt |
| 218 | methyl p-hydroxybenzoate |
| 219 | p-hydroxybenzoic methyl ester Na salt |
| 220 | Sulfur dioxide |
| 221 | Sodium sulfite |
| 222 | Sodium hydrogensulfite |
| 223 | Sodium disulfite |
| 224 | Potassium disulfite |
| 226 | Calcium sulfite |
| 227 | Calcium hydrogen sulfite |
| 228 | Potassium hydrogen sulfite |
| 230 | Biphenyl (Diphenyl) |
| 231 | Orthophenylphenol |
| 232 | Sodium orthophenylphenoxide |
| 233 | Thiabendazole |
| 235 | Natamycin |
| 236 | Formic acid |
| 237 | Sodium formate |
| 238 | Calcium formate |
| 239 | Hexamethylenetetramine |
| 249 | Potassium nitrite |
| 250 | Sodium nitrite |
| 251 | Sodium nitrate |
| 252 | Potassium nitrate |
| 280 | Propionic acid |
| 281 | Sodium propionate |
| 282 | Calcium propionate |
| 283 | Potassium propionate |
| 290 | Carbon dioxide |

Additional preservatives that find use in various embodiments include but are not limited to dibromodicyanobutane (2-bromo-2-bromomethylglutarodinitrile), 3-iodo-2-propinylbutylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol, and formaldehyde donors. Further preservatives that find use in various embodiments of the present invention include phenyl hydroxyalkyl ethers, in particular the compounds known as "phenoxyethanol," due to their bactericidal and fungicidal effects on a number of microorganisms.

A variety of optional ingredients such as neutralizing agents, perfumes and perfume solubilizing agents, and coloring agents, also find use in some of the compositions herein. It is preferred that any additional ingredients enhance the skin softness/smoothness benefits of the product. In addition it is preferred that any such ingredients do not negatively impact the aesthetic properties of the product.

Other optional materials include keratolytic agents, as well as water-soluble and/or solubilizable preservatives preferably at a level of from about 0.1% to about 5% (e.g., Germall 115, methyl, ethyl, propyl and butyl esters of hydroxybenzoic acid, benzyl alcohol, DMDM hydantoin iodopropanyl butylcarbanate available under the trade name Glydant Plus from Lonza; EDTA, EUXYL® K400, Bromopol (2-bromo-2-nitropropane-1,3-diol) and phenoxypropanol); anti-bacterials (e.g., IRGASAN®) and phenoxyethanol (preferably at levels of from about 0.1% to about 5%); as well as soluble or colloidally-soluble moisturizing agents such as hyaluronic acid, chondroitin sulfate, and starch-grafted sodium polyacrylates (e.g., SANWET® IM-1000, IM-1500 and IM-2500, available from Celanese Superabsorbent Materials, Portsmith, Va., See e.g., U.S. Pat. No. 4,076,663; vitamins such as vitamin A, vitamin C, vitamin E and derivatives thereof and building blocks thereof such as phytantriol, and vitamin K and components thereof such as the fatty alcohol dodecatrienol; alpha and beta hydroxyacids; aloe vera; sphingosines and phytosphingosines, cholesterol; skin whitening agents; N-acetyl cysteine; colouring agents; antibacterial agents such as TCC/TCS, also known as triclosan and trichlorocarbon; perfumes and perfume solubilizers. Examples of alpha hydroxy acids include glycolic acid, lactic acid, malic acid, citric acid, glycolic acid in conjunction with ammonium glycolate, alpha-hydroxy ethanoic acid, alpha-hydroxyoctanoic acid, alpha-hydroxycaprylic acid, hydroxycaprylic acid, mixed fruit acid, tri-alpha hydroxy fruit acids, triple fruit acid, sugar cane extract, alpha hydroxy and botanicals, 1-alpha hydroxy acid and glycomer in crosslinked fatty acids (e.g., alpha nutrium). Preferred examples of alpha hydroxy acids are glycolic acid and lactic acid. It is preferred that alpha hydroxy acids are used in levels of up to about 10%. It is not intended that the present invention be limited to any particular compound derived from any particular source, as any suitable additive compound, whether obtained from natural sources or through synthesis in the laboratory find use in the present invention.

Other optional materials include water-soluble or solubilizable preservatives preferably at a level of from about 0.1% to about 5% each, such as Germall 115, methyl, ethyl, propyl and butyl esters of hydroxybenzoic acid, benzyl alcohol, DMDM hydantoin iodopropanyl butylcarbanate available under the trade name Glydant Plus from Lonza, EDTA, Euxyl® K400, Bromopol (2-bromo-2-nitropropane-1,3-diol), pentylene glycol and phenoxypropanol; anti-bacterials such as Irgasan™ and phenoxyethanol (preferably at levels of from 0.1% to about 5%). Antibacterial agents such as TCC/TCS, also known as triclosan and trichlorocarbon are also useful in compositions of the present invention.

Yet other antimicrobial agents are likewise suitable for use in various embodiments of the present invention, including but not limited to 2,4,4'-trichloro-2'-hydroxydiphenyl ether (i.e., IRGASAN®), 1,6-di(4-chlorophenylbiguanido)hexane (i.e., CHLORHEXIDIN), 3,4,4'-trichlorocarbanilide, quaternary ammonium compounds, oil of cloves, mint oil, thyme oil, triethyl citrate, FARNESOL® (3,7,11-trimethyl-2,6,10-dodecatrien-1-ol) and the active ingredients and/or active ingredient combinations described in DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004, DE-196 34 019, DE-42 29 737, DE-42 37 081, DE-43 24 219, DE-44 29 467, DE-44 23 410, and DE-195 16 705, all of which are hereby incorporated by reference. In still further embodiments, sodium hydrogencarbonate is also included in some compositions of the present invention. However, it is not intended that the present invention be limited to any particular antimicrobial nor combination of anti-microbial, as various compounds having such effects will find use in various embodiments of the present invention.

In additional embodiments of the personal care compositions of the present invention, compounds such as anti-irritants and/or anti-inflammatory actives are included. In some embodiments, batyl alcohol (a-octadecyl glyceryl ether), selachyl alcohol (a-9-octadecenyl glyceryl ether), chimyl alcohol (a-hexadecyl glyceryl ether), bisabolol, and/or panthenol are included. However, it is not intended that the present invention be limited to the incorporation of any specific anti-irritant(s) and/or anti-inflammatory(ies), as various compounds suitable for such applications find use in the present invention.

Neutralizing agents suitable for use in neutralizing acidic group containing hydrophilic gelling agents herein include sodium hydroxide, potassium hydroxide, ammonium hydroxide, monoethanolamine, diethanolamine, amino methyl propanol, tris-buffer and triethanolamine.

Other optional materials that find use in the present invention include any of the numerous functional and/or active ingredients known to those skilled in the art (See e.g., McCutcheon's Functional Materials, North American and International Editions, MC Publishing Co. [2003]) As indicated above, non-limiting examples include keratolytic agents; soluble or colloidally-soluble moisturizing agents such as hyaluronic acid and chondroitin sulfate; vitamins such as vitamin A, vitamin C, vitamin E, vitamin K and derivatives thereof and building blocks thereof; phytantriol; fatty alcohols such as dodecatrienol; alpha and beta hydroxy-acids; aloe vera; sphingosines and phytosphingosines, cholesterol; skin whitening agents; N-acetyl cysteine; coloring agents; Examples of alpha hydroxy acids include glycolic acid, lactic acid, malic acid, and citric acid (whether derived synthetically or from natural sources and whether used alone or in combination) and their esters or relevant buffered combinations. Other examples of alpha-hydroxy acids include: alpha-hydroxy ethanoic acid, alpha-hydroxyoctanoic acid, alpha-hydroxycaprylic acid, and hydroxycaprylic acid. Preferred examples of alpha hydroxy acids include glycolic acid and lactic acid. It is preferred that alpha hydroxy acids are used in levels of up to about 10%.

Optional materials include pigments that, where water-insoluble, contribute to and are included in the total level of oil phase ingredients. Pigments suitable for use in the compositions of the present invention can be organic and/or inorganic. Also included within the term "pigment" are materials having a low color or luster, such as matte finishing agents, light scattering agents, and formulation aids such as micas, seracites, and carbonate salts. Further examples of suitable pigments include titanium dioxide, iron oxides, glutamate iron oxides, zinc oxide, bismuth oxychloride, ultramarine blue (all of which may be either pre-dispersed and/or pre-coated or not) D&C dyes and lakes, FD&C colors, natural color additives such as carmine, and mixtures thereof. Depending upon the type of composition, a mixture of pigments is usually used in preferred embodiments of the present invention. Preferred pigments for use herein from the viewpoint of moisturization, skin feel, skin appearance and emulsion compatibility are treated pigments. In some embodiments, the pigments are treated with compounds, including but not limited to amino acids, silicones, lecithin and ester oils.

In some embodiments, the present invention provides compositions comprising pigments, including, but not limited to inorganic pigments based on metaloxides and/or other in water slightly soluble or insoluble metal compounds such as zinc oxides (ZnO), titanium (TiO$_2$), iron (e.g., Fe$_2$O$_3$), zirconium (ZrO$_2$), silica (SiO$_2$), manganese (e.g., MnO), aluminium (Al$_2$O$_3$), cer (e.g., Ce$_2$O$_3$), and mixed compositions of these oxides, as well as blends thereof. In some preferred embodiments, the metaloxides are microfine, while in alternative preferred embodiments, the metaloxides are pigment grade. In yet additional embodiments, the pigments are "coated" such that they are surface treated. In some preferred embodiments, the coating comprises a thin, hydrophobic film layer, while in other embodiments, the coating comprises a thin, hydrophilic film layer.

As used herein, the terms "pigment," "color pigment," and "dye" used in reference to the compositions of the present invention encompasses any compound that provides a color to the composition and/or imparts a color to the surface (e.g., skin and/or hair) to which the composition is applied. In some embodiments, the dyes and pigments are chosen from the list of cosmetic colorants provided by the Cosmetics Directive or the EC. In most cases, these dyes and pigments are identical to the dyes approved for foods. Preferred pigments/dyes include for example, titanium dioxide, mica, iron oxides (e.g., Fe$_2$O$_3$, Fe$_3$O$_4$, FeO(OH)) and/or tin oxide. Advantageous pigments/dyes include for example, carmine, Berlin blue, chrome oxide green, ultramarine blue and/or manganese violet. In some preferred embodiments, the pigments/dyes include, but are not limited to those in the following table. The Colour Index Numbers (CIN) those known in the art (See, Society of Dyers and Colourists, *Rowe Colour Index,* 3rd Edition, Bradford, England, [1971]).

| CHEMICAL OR OTHER NAME | CIN | COLOR |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamido-1'-phenylazo)-3-hydroxy-5''-chloro-2'',4''-dimethoxy-2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfo)-1-hydroxynaphthalene-4-sulfonic acid | 14700 | red |

-continued

| CHEMICAL OR OTHER NAME | CIN | COLOR |
|---|---|---|
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfo-4-chloro-5-carboxy-1-phenylazo)-2-hydroxynaphthalene | 15525 | red |
| 1-(3-Methylphenylazo-4-sulfo)-2-hydroxynaphthalene | 15580 | red |
| 1-(4',(8')-Sulfonaphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthyl-carboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2",4"-dimethyl)bisphenylazo-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4"-(4"-Sulfo-1"-phenylazo)-7'-sulfo-1'-naphthylazo]-1-hydroxy-7-aminonaphthalene-3,6-di-sulfonic acid | 27755 | black |
| 4'-[(4"-Sulfo-1"-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotinaldehyde ($C_{30}$) | 40820 | orange |
| trans-Apo-8'-carotinic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4"-bis(diethylamino)triphenylcarbinol | 42051 | blue |
| 4-[(4-N-Ethyl-p-sulfobenzylamino)phenyl(4-hydroxy-2-sulfophenyl)(methylene)-1-(N-ethyl-N-p-sulfobenzyl)-2,5-cyclohexadienimine] | 42053 | green |
| Acid Blue 7 | 42080 | blue |
| (N-Ethyl-p-sulfobenzylamino)phenyl(2-sulfophenyl)methylene-(N-ethyl-N-p-sulfobenzyl)$D^{2,5}$-cyclohexadienimine | 42090 | blue |
| Acid Green 9 | 42100 | green |
| Diethyldisulfobenzyldi-4-amino-2-chloro-di-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4"-(N-diethyl)amino-2-methyl-N-ethyl-N-m-sulfobenzylfuchsonimmonium | 42735 | blue |
| 4'-(N-Dimethyl)amino-4"-(N-phenyl)aminonaphtho-N-dimethyl-fuchsonimmonium | 44045 | blue |
| 2-Hydroxy-3,6-disulfo-4,4'-bisdimethylaminonaphtho-fuchsonimmonium | 44090 | green |
| Acid Red 52 | 45100 | red |
| 3-(2'-Methylphenylamino)-6-(2'-methyl-4'-sulfophenylamino)-9-(2"-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |

-continued

| CHEMICAL OR OTHER NAME | CIN | COLOR |
|---|---|---|
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone,calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated Phthalocyanines | 74260 | green |
| Natural Yellow 6,19; Natural Red 1 | 75100 | yellow |
| Bixin, Nor-Bixin | 75120 | orange |
| Lycopene | 75125 | yellow |
| trans-alpha-, beta- and gamma-carotene | 75130 | orange |
| Keto- and/or hydroxyl derivates of carotene | 75135 | yellow |
| Guanine or pearlizing agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of chlorophylls and Chlorophyllins | 75810 | green |
| Aluminum | 77000 | white |
| Hydrated alumina | 77002 | white |
| Hydrous aluminum silicates | 77004 | white |
| Ultramarine | 77007 | blue |
| Pigment Red 101 und 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide, hydrated | 77492 | yellow |
| Iron oxide | 77499 | black |
| Mixtures of iron (II) and iron(III)hexacyano-ferrate | 77510 | blue |
| Pigment White 18 | 77713 | white |
| Manganese ammonium diphosphate | 77742 | violet |
| Manganese phosphate; $Mn_3(PO_4)_2 \square$ 7 H20 | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)-isoalloxazine, lactoflavine | | yellow |
| Sugar coloring | | brown |
| Capsanthin, capsorubin | | orange |
| Betanin | | red |
| Benzopyrylium salts, Anthocyans | | red |
| Aluminum, zinc, magnesium and calcium stearate | | white |
| Bromothymol blue | | blue |
| Bromocresol green | | green |
| Acid Red 195 | | red |

In yet further embodiments, compositions of the present invention further comprise one or more substances from the following group: 2,4-dihydroxyazobenzene, 1-(2'-chloro-4'-nitro-1'-phenylazo)-2-hydroxynaphthalene, Ceres Red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5,7-tetrabromofluorescein, 3',4',5',6'-tetrachloro-2,4,5,7-tetrabromofluorescein and its aluminum salt, aluminum salt of 2,4,5,7-tetraiodofluorescein, aluminum salt of quinophthalone disulfonic acid, aluminum salt of indigo disulfonic acid, red and black iron oxide (CIN: 77 491 (red) and 77 499 (black)), iron oxide hydrate (CIN: 77 492), manganese ammonium diphosphate and titanium dioxide.

In yet further embodiments, oil-soluble natural dyes, such as, for example, paprika extracts, β-carotene or cochenille find use in the present invention.

In yet additional embodiments, gel cream compositions of the present invention comprise pearlescent pigments. In some preferred embodiments, various pearlescent pigments find use in the present invention, including but not limited to "natural pearlescent pigments" (e.g., "pearl essence" [guanine/hypoxanthine mixed crystals from fish scales], "mother of pearl" [ground mussel shells]), and "monocrystalline pearlescent pigments" (e.g., bismuth oxychloride [BiOCl]); and "layer substrate pigments" (e.g. mica/metal oxide).

Bases for pearlescent pigments include, but are not limited to pulverulent pigments, castor oil dispersions of bismuth oxychloride and/or titanium dioxide, bismuth oxychloride and/or titanium dioxide on mica. The luster pigment listed under CIN 77163, for example, is particularly advantageous.

An additional group of pearlescent pigments based on mica/metal oxide find particular use in the present invention is provided below.

| GROUP | COATING/LAYER THICKNESS | COLOR |
|---|---|---|
| Silver-white pearlescent pigments | $TiO_2$: 40-60 nm | silver |
| Interference pigments | $TiO_2$: 60-80 nm | yellow |
|  | $TiO_2$: 80-100 nm | red |
|  | $TiO_2$: 100-140 nm | blue |
|  | $TiO_2$: 120-160 nm | green |
| Color luster pigments | $Fe_2O_3$ | bronze |
|  | $Fe_2O_3$ | copper |
|  | $Fe_2O_3$ | red |
|  | $Fe_2O_3$ | red-violet |
|  | $Fe_2O_3$ | red-green |
|  | $Fe_2O_3$ | black |
| Combination pigments | $TiO_2/Fe_2O_3$ | gold shades |
|  | $TiO_2/Cr_2O_3$ | green |
|  | $TiO_2$/Berlin blue | deep blue |
|  | $TiO_2$/carmine | red |

In some preferred embodiments, the pearlescent pigments available from Merck under the trade names Timiron, Colorona or Dichrona find use in the present invention. However, it is not intended that the present invention be limited to the specific pigments listed herein. Indeed, pearlescent pigments that find use in the present invention are obtainable from numerous sources. For example, other substrates apart from mica can be coated with further metal oxides, such as, for example, silica and the like. $SiO_2$ particles coated with, for example, $TiO_2$ and $Fe_2O_3$ ("ronaspheres"), which are sold by Merck and are particularly suitable for the optical reduction of fine lines find use in the present invention.

In alternative embodiments, the substrate (e.g., mica) is not included. In some preferred embodiments, particular preference is given to pearlescent pigments prepared using $SiO_2$. Such pigments, which may also additionally have goniochromatic effects, are available, for example, under the trade name Sicopearl Fantastico, available from BASF.

In additional embodiments, pigments obtained from Engelhard/Mearl based on calcium sodium borosilicate which have been coated with titanium dioxide also find use. These are available under the name Reflecks. In addition to the color, as a result of their particle size of from 40 nm to 180 mm, they have a glitter effect.

In yet further embodiments, effect pigments which are available under the trade name Metasomes Standard/Glitter in various colors (yellow, red, green, blue) from Flora Tech find use in the compositions of the present invention. The glitter particles are present here in the mixtures with various auxiliaries and dyes (such as, for example, the dyes with the Colour Index (CI) Numbers 19140, 77007, 77289, 77491).

In some embodiments, the dyes and pigments are present either individually or in a mixture. In alternative embodiments, they are mutually coated with one another, different coating thicknesses generally giving rise to different color effects. In some embodiments, the total amount of dyes and color-imparting pigments is chosen from a range of concentrations (e.g., from about 0.1% by weight to about 30% by weight; preferably from about 0.5 to about 15% by weight; and most preferably from about 1.0 to about 10% by weight, in each case based on the total weight of the preparations).

In preferred embodiments, the pH of the compositions herein is in the range from about 3.5 to about 10, preferably from about 4 to about 8, and more preferably from about 5 to about 7, wherein the pH of the final composition is adjusted by addition of acidic, basic or buffer salts as necessary, depending upon the composition of the forms and the pH-requirements of the compounds.

The compositions of the present invention are prepared by standard techniques well known to those skilled in the art. In general the aqueous phase and/or the oil phase are prepared separately, with materials of similar phase partitioning being added in any order. If the final product is an emulsion, the two phases are then combined with vigorous stirring and/or homogenization as necessary, to reduce the size of the internal phase droplets. Any ingredients in the formulation with high volatility, or which are susceptible to hydrolysis or decomposition at high temperatures, are added with gentle stirring towards the end of the process, post emulsification if applicable. Dosage frequency and amount will depend upon the desired performance criteria.

In some embodiments of the present invention, method of decreasing VEGF activity are provided. In these embodiments, the methods comprise applying to an organism in need thereof an effective amount of any one of the compounds set forth herein. In additional preferred embodiments, the present invention provides compounds for treatment of an organism in need thereof, including humans and other animals.

In some still further embodiments, the present invention comprises at least one creatine and/or creatine derivative. Creatine has the following structure:

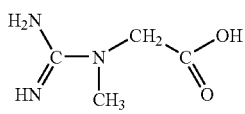

In some preferred embodiments of the personal care compositions of the present invention creatine phosphate, creatine sulfate, creatine acetate, creatine ascorbate, and/or derivatives esterified at the carboxyl group with mono- or polyfunctional alcohols find use.

In some additional embodiments, the personal care compositions of the present invention contain L-carnitine [3-hydroxy-4-(trimethylammonio)butyrobetaine]. Acylcarnitines have the following general structure:

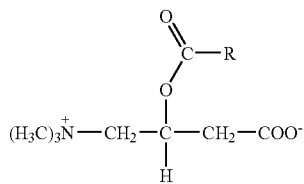

where R is chosen from the group of branched and unbranched alkyl radicals having up to 10 carbon atoms, and find use in some embodiments of the present invention. In some preferred embodiments, propionylcarnitine and/or acetylcarnitine find use. Both enantiomers (D and L form), as well as mixtures and racemates of the D- and L-forms find use in some personal care compositions of the present invention.

In some further embodiments, the active ingredients of the present invention include, but are not limited to sericoside, pyridoxol, vitamin K, biotin, and aroma substances. In addition, it is not intended that the active ingredients present in the personal care compositions of the present invention be limited to any particular constituent and/or mixture(s) of actives. Indeed, it is intended that various actives and mixtures of actives will find use in various embodiments of the present invention. It is also not intended that the concentration(s) of such actives be limited to any particular level. In some embodiments, the concentration is from about 0.001 to about 30% by weight, while in other embodiments it is from about 0.05 to about 20% by weight, and in still further embodiments, it is from about 0.1 to about 10% by weight, based on the total weight of the preparation. It is further contemplated that those of skill in the art will formulate personal care compositions of the present invention with active(s) concentrations that are suitable for the intended use of the compositions.

The yet further embodiments, the present invention provides methods for the preparation of the compositions of the present invention. In some embodiments, these methods include combining and heating the constituents of the oil phase and/or the water phase separately, and then combining them together with stirring. In some preferred embodiments, the phases are homogenized. In some particularly preferred embodiments, the compositions are stirred with moderate to high input of energy, advantageously using a gear rim dispersing machine at a rotary number up to at most 10000 rpm (preferably in the range from about 2500 to about 7700 rpm).

6.2 Experimental

The present invention is described in further detail in the following Examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention In the experimental disclosure which follows, the following abbreviations apply PI (proteinase inhibitor), BBI (Bowman-Birk Inhibitor from *Glycine max* Acc. No. P01055), BBI-AV (Bowman-Birk Inhibitor Anti-VegF), STI (Soybean Trypsin inhibitor from *Glycine max*); VEGF and VegF (vascular endothelial growth factor); BBdb (Bowman Birk Inhibitor from *Dolichos biflorus* Acc. No. AAK97765), BBsb3 (Bowman Birk Inhibitor from *Glycine max* (soybean) protease inhibitor IV or D-II), and BBtc (Bowman Birk Inhibitor from *Torresea cearensis*), FGF-5 (fibroblast growth factor 5), TGFβ (Transforming growth factor β), TNFα (Tumor necrosis factor α), ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG (polyethylene glycol); PCR (polymerase chain reaction); RT-PCR (reverse transcription PCR); SDS (sodium dodecyl sulfate); Tris (tris(hydroxymethyl) aminomethane); HEPES (N-[2-Hydroxyethyl]piperazine-N-[2-ethanesulfonic acid]); HBS (HEPES buffered saline); SDS (sodium dodecylsulfate); bME, BME and βME (beta-mercaptoethanol or 2-mercaptoethanol); Tris-HCl (tris[Hydroxymethyl]aminomethane-hydrochloride); Tricine (N-[tris-(hydroxymethyl)-methyl]-glycine); CHES (2-(N-cyclohexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); Glut and GSH (reduced glutathione); GSSG (oxidized glutathione); TCEP (Tris[2-carboxyethyl]phosphine); Ci (Curies) mCi (milliCuries); μCi (microCuries); TLC (thin layer achromatography); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information); Applied Biosystems (Applied Biosystems, Foster City, Calif.); Clontech (CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); BioVeris (BioVeris Corp., Gaithersburg, Md.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); and Microsoft (Microsoft, Inc., Redmond, Wash.).

EXAMPLE 1

Production of BCE103-BBI Fusion Proteins in *B. subtilis*

In this Example, experiments conducted to produce BCE103-BBI fusion proteins in *B. subtilis* are described. The DNA sequence of the synthetic gene (Operon Technologies) coding for the pro-BBI protein with a C-terminal hexa-histidine tag used in these experiments is:

(SEQ ID NO: 10)
AACCTGCGTCTGTCTAAGCTTGGCCTGCTTATGAAATCAGACCATCAGCA

CAGCAATGACGATGAGAGCTCTAAACCCTGTTGCGATCAATGCGCATGTA

CGAAATCAAATCCTCCACAGTGTCGGTGTTCCGATATGCGTCTGAATAGC

TGTCATAGTGCATGCAAAAGCTGTATCTGCGCCCTGAGTTATCCAGCTCA

ATGTTTTTGCGTCGACATCACGGACTTCTGCTATGAGCCATGTAAACCAA

GCGAGGACGATAAAGAGAACCATCATCACCATCACCAT

The protein sequence of pro-BBI with a C-terminal hexa-histidine tagged coded for by the above synthetic gene is:

(SEQ ID NO: 11)
NLRLSKLGLLMKSDHQHSNDDESSKPCCDQCACTKSNPPQCRCSDMRLNS

CHSACKSCICALSYPAQCFCVDITDFCYEPCKPSEDDKENHHHHHH

The portion of the DNA sequence of the synthetic gene that codes for the major mature form of BBI is:

(SEQ ID NO: 12)
GACGATGAGAGCTCTAAACCCTGTTGCGATCAATGCGCATGTACGAAATC

AAATCCTCCACAGTGTCGGTGTTCCGATATGCGTCTGAATAGCTGTCATA

GTGCATGCAAAAGCTGTATCTGCGCCCTGAGTTATCCAGCTCAATGTTTT

TGCGTCGACATCACGGACTTCTGCTATGAGCCATGTAAACCAAGCGAGGA

CGATAAAGAGAAC

The protein sequence of the major mature form of BBI coded by the above synthetic gene is:

(SEQ ID NO: 13)
DDESSKPCCDQCACTKSNPPQCRCSDMRLNSCHSACKSCICALSYPAQCF

CVDITDFCYEPCKPSEDDKEN

The PCR primers used to amplify the BBI gene for fusion to the BCE103 cellulase expression cassette in the pJ103 vector were:

BBIfusion_FW:
(SEQ ID NO: 14)
5' CAGCACGGATCCAGACGATGAGAGCTCTAAACCC 3'

BBIHindIII_RV:
(SEQ ID NO: 15)
5' CTGCAGAAGCTTAAAAATAAAAAAACGGATTTCCTTCAGGAAATCCG
TCCTCTGTTAACTTTTAGTTCTCTTTATCGTCCTCGC 3'

BBIHIS-HindIII_RV:
(SEQ ID NO: 16)
5' CTGCAGAAGCTTAAAAATAAAAAAACGGATTTCCTTCAGGAAATCCG
TCCTCTGTTAACTTTTAATGGTGATGGTGATGATGGTTCTC 3'

Figure 2:
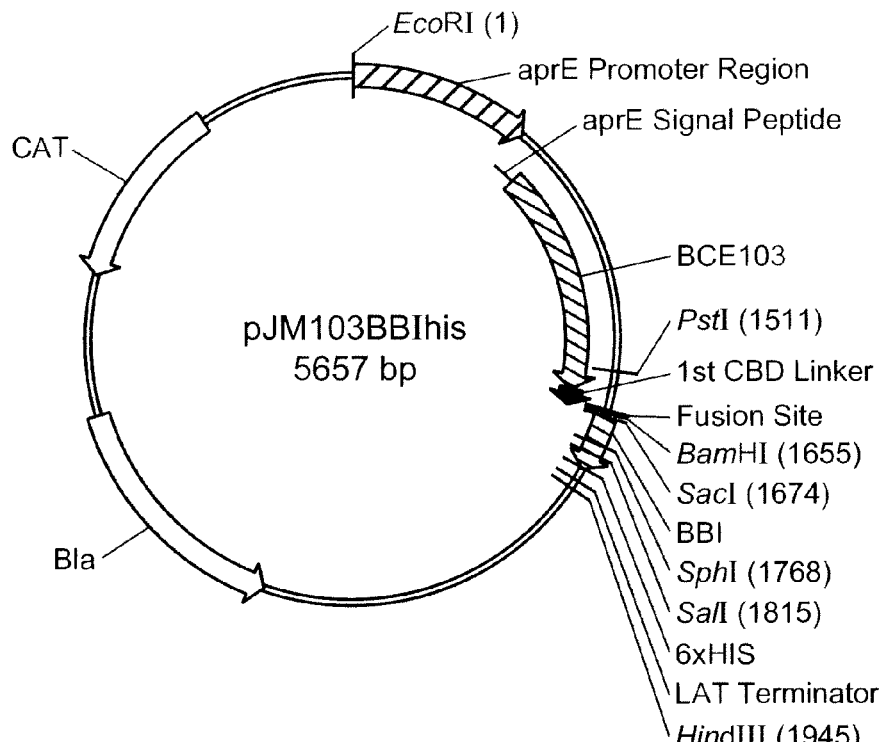
FIG. 2 provides a schematic map of the pJM103BBIhis expression vector.

The sequence of the aprE-BCE103-BBI-HisTag expression cassette (EcoRI-HindIII) that was cloned into the pJM103 integration vector is provided in FIG. 1. A schematic plasmid map of the pJM103BBIHis expression vector is provided in FIG. 2.

The alkaline cellulase (BCE103) gene (See, van Soligen, U.S. Pat. No. 6,063,611, hereby incorporated by reference) fused to the *B. subtilis* aprE promoter and signal sequence, was cloned from pUCAPR103 (Shaw et al., J. Mol. Biol., 320:303-309 [2002]) as an EcoRI-BamHI fragment (i.e., a fragment that carries the coding sequence of the BCE103 catalytic domain and first cellulose binding domain linker only) into pJM103 (Perego, "Integrational vectors for genetic manipulation in *Bacillus subtilis*" In, *Bacillus subtilis* and Other Gram-positive Bacteria: Biochemistry, Physiology, and Molecular Genetics, Sonenshein, Hoch, and Losick (eds), American Society for Microbiology, Washington D.C., pp. 615-624 [1993]). A gene encoding the soybean Bowman-Birk protease inhibitor (BBI) (Swiss-Prot Accession # P01055; See, Odani and Ikenaka, J. Biochem., 71: 839-848 [1972]) with a C-terminal hexa-histidine tag (His-Tag) was synthesized by Operon Technologies (See, DNA sequence above). The BBI gene was amplified by PCR with primers (all primers were synthesized by MWG Biotech, Oligos Etc., or Operon Technologies) that generated a 5' BamHI site in the correct reading frame with the BCE103 gene, and at the 3' end introduced a strong transcriptional terminator (LAT, from the *Bacillus licheniformis* α-amylase gene) after the end of the BBI gene with a 3' HindIII site for cloning into the pJM103 vector.

PCR fragments with or without a C-terminal His-Tag were generated with the primers BBIfusion_FW (SEQ ID NO:14) and BBIHISHindIII_RV (SEQ ID NO:16), or BBIfusion_FW (SEQ ID NO:14) and BBI-HindIII_RV (SEQ ID NO:15), respectively, using the synthetic BBI gene as a template. Unless indicated otherwise, PCR reactions were typically performed on a thermocycler for 30 cycles with High Fidelity Platinum Taq polymerase (Invitrogen) according to the instructions of the supplier (with an annealing temperature of 55° C.). The PCR fragments were cloned as BamHI-HindIII fragments into pJM103 carrying the aprE-BCE103 expression cassette. The correct gene sequence was verified by DNA sequencing.

Thus, as shown in FIG. 1, the N-terminus of the mature coding region of the BBI gene (with or without the His-Tag) was fused in frame to the C-terminal coding region of the first CBD (cellulose binding domain) linker sequence coded by the BCE103 cellulase gene. Thereby, the two CBD's of BCE103 (Shaw et al., supra) are replaced by BBI in the final expression vectors, pJM103BBI or pJM103BBIhis (See, FIG. 2). The aprE promoter controls the expression of the BCE103-BBI gene fusions (See, Ferrari et al., J. Bact., 170: 289-295 [1988]; and Henner et al., J. Bact., 170: 296-300 [1988]).

Competent *Bacillus subtilis* cells, BG3934comK (degUHY32, oppA, ΔspoIIE3501, ΔaprE, ΔnprE, Δepr, ΔispA, Δbpr, amyE::xylRPxylAcomK-phleo), were transformed with the expression plasmids, pJM103BBI or pJM103BBIhis. The bacteria were made competent by the induction of the comK gene under control of a xylose inducible promoter (Hahn et al., Mol. Microbiol., 21:763-775 [1996]). The transformants were selected on Luria Broth agar (LA) plates containing 5 μg/ml chloramphenicol. To increase the expression by gene amplification, colonies were streaked and grown several times on LA plates with 25 μg/ml chloramphenicol until the growth rate with the antibiotic was similar to growth rate in the absence of chloramphenicol. The BCE103-BBI fusion protein was produced by growth in shake flasks at 37° C. in TSB medium (Tryptone Soya Broth from OXOID, 30 g/L) or in MBD medium, a MOPS based defined medium. MBD medium was made essentially as described (Neidhardt et al., J. Bacteriol., 119: 736-747 [1974]), except $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1 M $CaCl_2$, and 10 ml of 0.5 M sodium citrate.

BCE103-BBI fusion protein could be easily visualized in samples from cell free supernatants (after 24 h of growth in TSB medium or 48 h in MBD medium) as the major protein band on SDS-PAGE gels (10% NuPAGE in MES buffer, run as described by the manufacturer, Invitrogen) running at ~44 kDa by using standard protein stains (e.g. GelCode Blue Stain Reagent; Pierce). The identity of the BCE103-BBI fusion protein was verified by immunoblots of SDS-PAGE gels using the protocols supplied by the manufacturer (BM Chromogenic Western Blotting Kit; Roche Applied Science using an anti-HisTag antibody or an anti-BCE103 cellulase polyclonal antibody for detection).

To determine the BCE103 activity, cellulase degradation was assessed qualitatively on LA cellulase indicator plates (with 1% carboxymethylcellulose stained with 0.2% Congo Red, or with 0.5% azo-CM-cellulose, Megazyme), or quantitatively by a direct assay in Assay Buffer (100 mM Tris pH 8.6, 0.005% Tween-80) on the culture broth using a the synthetic substrate, 4-nitrophenyl □-D-cellobioside (Sigma), using methods known in the art (See e.g., van Tilbeurgh et al., Meth. Enzymol., 160:45-59 [1988]).

Trypsin inhibitory assays were performed in Assay Buffer to determine the BBI activity. Specifically, a standard curve was generated by making eleven 1:1 serial dilutions (100 μL BBI+100 μL Assay Buffer) of a 2 μg/mL standard BBI solution. The BBI standard was purified from a 1 mg/ml Trypsin-Chymotrypsin Inhibitor (Sigma Cat. #T-9777) solution in 20 mM MES pH 6.0 using a hydrophobic interaction column (POROS HP2, Phenyl column, Applied Biosystems). The column was equilibrated with 20 mM MES pH 6.0, loaded with 5 mg of the inhibitor, washed with the equilibration buffer, and then the BBI was eluted with water. Unknown BBI samples to be tested in the inhibitory assay were diluted as necessary, so that two or more data points would fall within the standard curve (usually 1:10, 1:100, 1:200, 1:1000, 1:2000 sample dilutions were tested and then the dilutions fine tuned if necessary). Each diluted BBI standard or sample, 20 μL, was added to 80 μL of 50 ng/ml bovine pancreatic trypsin (Worthington) (made by diluting a stock 1 mg/mL trypsin solution into Assay Buffer). For convenience, the standards and samples were arrayed in 96 well microtiter plates. The reactions were mixed and incubated 15 min at 25° C. After the incubation, 100 μL of the 0.5 mg/ml trypsin substrate (diluted in Assay Buffer from a 100 mg/ml solution in DMSO), Suc-AAPR-pNA (succinyl-Ala-Ala-Pro-Arg-para-nitroanilide, Bachem), was added, mixed and the OD ($A_{405}$) was monitored for 15 min, with 1 time point recorded every 12 sec using a Spectra Max 250 (Molecular Devices). The data points were used to determine the Vmax for each reaction. The standard curve was generated by plotting Vmax versus BBI concentration and was fitted to a four-parameter curve. All data fitting was done using software supplied by the manufacturer (Molecular Devices). The BBI concentration of the unknown samples was calculated from the standard curve. Alternatively, the BBI activity was measured using the same protocol but by determining bovine pancreatic chymotrypsin (Worthington) inhibition (chymotrypsin was used at the same concentration as trypsin and chymotrypsin activity was measured by adding 100 μL of a 0.4 mg/ml chymotrypsin substrate, succinyl-Ala-Ala-Pro-Phe-para-nitroanilide, Bachem).

Titers from shake flask runs (500 ml MBD medium in 2.8 L Fernbach 6 baffled flasks, 37° C., 225 rpm, harvested 60 h after of growth) typically ranged from 0.4-0.9 mg/ml BCE activity and 40-150 μg/ml BBI trypsin inhibitory activity. However, it is contemplated that titers likely could be improved further by optimizing the bacterial strain, culture medium and growth conditions (aeration, temperature, time of harvest, etc.).

In addition to the BCE103 fusion to wild-type BBI, fusion proteins to BBI variants and fusion proteins with various linkers between BCE103 and BBI were produced using the methods outlined above, as described in the following Examples. In addition, fusion proteins were also produced when the BBI was fused to the $2^{nd}$ CBD linker (BCE-cbdD-BBI; See, Example 4) making it possible to use the $1^{st}$ CBD to aid in the purification process.

EXAMPLE 2

Production of Peptides Substituted into the BBI Reactive Site Loops as BCE103-BBI Fusion Proteins In this Example, experiments conducted to produce peptides substituted into the BBI reactive site loops as BCE103-BBI fusion proteins are described. The primers, as well as other sequences used in the various steps of these experiments are provided below. The sequence of 12BBIck81 from the BCE103 fusion site (at the BamHI) to the end of the gene is provided in FIG. 3. The CK37281 peptide sequences (ACYNLYGWTC (SEQ ID NO:9) are inserted into both the trypsin and chymotrypsin inhibitory loops.

The primers used to introduce an EcoRI site in the BBI gene using QuikChange® site-directed mutagenesis (Stratagene) were:

```
BowBeco-F
5'-GATATGCGTCTGAATTCCTGTCATAGTGCAT (SEQ ID NO: 17)

BowBeco-R
5'-ATGCACTATGACAGGAATTCAGACGCATATC (SEQ ID NO: 18)
```

The sequences of the DNA oligonucleotides that were annealed and cloned in the BBI gene (SacI-EcoRI) to replace the trypsin inhibitory loop with the VegF binding peptide CK37281 were:

```
1BBck81+
                                    (SEQ ID NO: 19)
5'-CTAAACCCTGTTGCGATCAATGCGCATGTTATAATTTGTATGGGTGG
ACTTGTCGCTGCAGCGATATGCGTCTG

1BBck81-
                                    (SEQ ID NO: 20)
5'-AATTCAGACGCATATCGCTGCAGCGACAAGTCCACCCATACAAATTA
TAACATGCGCATTGATCGCAACAGGGTTTAGAGCT
```

The sequences of the DNA oligonucleotides that were annealed and cloned in the BBI gene (EcoRI-SalI) to replace the chymotrypsin inhibitory loop with the VegF binding peptide CK37281 were:

```
2BBck81+
                                    (SEQ ID NO: 21)
5'-AATTCCTGTCATAGTGCCTGCAAAAGCTGCGCATGTTATAACCTGTA
CGGGTGGACCTGTTTTTGCG

2BBck81-
                                    (SEQ ID NO: 22)
5'-TCGACGCAAAAACAGGTCCACCCGTACAGGTTATAACATGCGCAGCT
TTTGCAGGCACTATGACAGG
```

The DNA sequences of the oligonucleotide pairs used to make cassettes to introduce peptides into the trypsin (SacI and EcoRI restriction sites) or chymotypsin (EcoRI and SalI restriction sites) reactive site loops of the synthetic BBI gene are provided below. These peptide coding sequences were then moved into the p2JM103BBI expression vector as SacI-SalI fragments.

```
Comstatin (1st loop)
                                    (SEQ ID NO: 23)
CTAAACCCTGTTGCGATCAATGCGCATGTTGTTCAGGACTGGGGTCAC
CACCGTTGTCGCTGCAGCGATATGCGTCTG
and
                                    (SEQ ID NO: 24)
AATTCAGACGCATATCGCTGCAGCGACAACGGTGGTGACCCCAGTCCTGA
ACAACACATGCGCATTGATCGCAACAGGGTTTAGAGCT Comstatin (2nd loop)
                                    (SEQ ID NO: 25)
CAAAAGCTGTATCTGCGTTGTTCAGGACTGGGGTCACCACCGTTGTTTTT
GCG
and
                                    (SEQ ID NO: 26)
TCGACGCAAAAACAACGGTGGTGACCCCAGTCCTGAACAACGCAGATACA
GCTTTTGCATG C2c (1st loop)
                                    (SEQ ID NO: 27)
CTAAACCCTGTTGCGATCAATGCAGCTGTGGTCGTAAAATCCCGATCCAG
TGTCGCTGCAGCGATATGCGTCTG
and
                                    (SEQ ID NO: 28)
AATTCAGACGCATATCGCTGCAGCGACACTGGATCGGGATTTTACGACCA
CAGCTGCATTGATCGCAACAGGGTTTAGAGCT C3c (1st loop)
                                    (SEQ ID NO: 29)
CTAAACCCTGTTGCGATCAATGCGGTTGTGCTCGTTCTAACCTGGACGAA
TGTCGCTGCAGCGATATGCGTCTG
and
                                    (SEQ ID NO: 30)
AATTCAGACGCATATCGCTGCAGCGACATTCGTCCAGGTTAGAACGAGCA
CAACCGCATTGATCGCAACAGGGTTTAGAGCT C4c (1st loop)
                                    (SEQ ID NO: 31)
CTAAACCCTGTTGCGATCAATGCGGTTGTCAGCGTGCTCTGCCGATCCTG
TGTCGCTGCAGCGATATGCGTCTG
and
                                    (SEQ ID NO: 32)
AATTCAGACGCATATCGCTGCAGCGACACAGGATCGGCAGAGCACGCTGA
CAACCGCATTGATCGCAACAGGGTTTAGAGCT C5c (1st loop)
CTAAACCCTGTTGCGATCAATGCCAGTGTGGTCGTCTGCACATGAAAACC
TGTCGCTGCAGCGATATGCGTCTG
and
                                    (SEQ ID NO: 34)
AATTCAGACGCATATCGCTGCAGCGACAGGTTTTCATGTGCAGACGACCA
CACTGGCATTGATCGCAACAGGGTTTAGAGCT Xa1 (2nd loop)
                                    (SEQ ID NO: 35)
AATTCCTGTCATAGTGCCTGCAAAAGCTGTATCTGCGCCCGTAGTTTGCC
AGCTCAATGTTTTTGCG
and
                                    (SEQ ID NO: 36)
TCGACGCAAAAACATTGAGCTGGCAAACTACGGGCGCAGATACAGCTTTT
GCAGGCACTATGACAGG hSCC1 (1st loop)
                                    (SEQ ID NO: 37)
CTAAACCCTGTTGCGATCAATGCAACTGTACGTACTCAACCCCTCCACAG
TGTCGCTGCAGCGATATGCGTCTG
and
                                    (SEQ ID NO: 38)
AATTCAGACGCATATCGCTGCAGCGACACTGTGGAGGGGTTGAGTACGTA
CAGTTGCATTGATCGCAACAGGGTTTAGAGCT
```

The DNA sequences of oligonucleotide primer pairs used to introduce peptide sequences into the trypsin or chymotrypsin reactive site loops using a QuikChange® II XL site-directed mutagenesis kit (Stratagene) are provided below. The reactions were performed as outlined by the manufacturer and described in this Example. Twenty cycles were performed with extensions of 6 minutes at 68° C., denaturations of 50 s at 95° C., and annealings at 55° C. for 50 s. After the cycles, a final extension was performed at 68° C. for 20 minutes.

1A (2^nd loop)

(SEQ ID NO: 39)
CTGTATCTGCAAACGCTCAAAATCTCGTGGCTGTTTTTGCGTCGACATCAC and (SEQ ID NO: 40)
CGCAAAAACAGCCACGAGATTTTGAGCGTTTGCAGATACAGCTTTTGCATG 2B (2^nd loop)

(SEQ ID NO: 41)
CTGTATCTGCTGGTATAATCAAATGACAACATGTTTTTGCGTCGACATCAC and (SEQ ID NO: 42)
CGCAAAAACATGTTGTCATTTGATTATACCAGCAGATACAGCTTTTGCATG 4A (2^nd loop)

(SEQ ID NO: 43)
CTGTATCTGCCATCAACTTGGCCCGAATTCATGTTTTTGCGTCGACATCAC and (SEQ ID NO: 44)
CGCAAAAACATGAATTCGGGCCAAGTTGATGGCAGATACAGCTTTTGCATG 5A (2^nd loop)

(SEQ ID NO: 45)
CTGTATCTGCCATCCGTGGGCACCGTATTCTTGTTTTTGCGTCGACATCAC and (SEQ ID NO: 46)
CGCAAAAACAAGAATACGGTGCCCACGGATGGCAGATACAGCTTTTGCATG 6-1A (2^nd loop)

(SEQ ID NO: 47)
CTGTATCTGCAATCTTCATTATCTTCAACAGTGTTTTTGCGTCGACATCAC and (SEQ ID NO: 48)
CGCAAAAACACTGTTGAAGATAATGAAGATTGCAGATACAGCTTTTGCATG 7A (2^nd loop)

(SEQ ID NO: 49)
CTGTATCTGCACACCGTCTCTTTATCGCCCGTGTTTTTGCGTCGACATCAC and (SEQ ID NO: 50)
CGCAAAAACACGGGCGATAAAGAGACGGTGTGCAGATACAGCTTTTGCATG 8B (2^nd loop)

(SEQ ID NO: 51)
CTGTATCTGCCTTACAGATCAATCTAAACCGTGTTTTTGCGTCGACATCAC and (SEQ ID NO: 52)
CGCAAAAACACGGTTTAGATTGATCTGTAAGGCAGATACAGCTTTTGCATG 9A (2^nd loop)

(SEQ ID NO: 53)
CTGTATCTGCGTTACAACATCAATGGGCATGTGTTTTTGCGTCGACATCAC and (SEQ ID NO: 54)
CGCAAAAACACATGCCCATTGATGTTGTAACGCAGATACAGCTTTTGCATG 10B (2^nd loop)

(SEQ ID NO: 55)
CTGTATCTGCCGCGCATCACCGTATGATTGGTGTTTTTGCGTCGACATCAC and (SEQ ID NO: 56)
CGCAAAAACACCAATCATACGGTGATGCGCGGCAGATACAGCTTTTGCATG 11-1A (2^nd loop)

(SEQ ID NO: 57)
CTGTATCTGCTCAACACAAAAAATTCCGCAATGTTTTTGCGTCGACATCAC and (SEQ ID NO: 58)
CGCAAAAACATTGCGGAATTTTTTGTGTTGAGCAGATACAGCTTTTGCATG 12B (2^nd loop)

(SEQ ID NO: 59)
CTGTATCTGCACACAATTTCGCTCTGCAACATGTTTTTGCGTCGACATCAC and (SEQ ID NO: 60)
CGCAAAAACATGTTGCAGAGCGAAATTGTGTGCAGATACAGCTTTTGCATG 13A (2^nd loop)

(SEQ ID NO: 61)
CTGTATCTGCCCGGATCATGTTCCGCATCTTTGTTTTTGCGTCGACATCAC and (SEQ ID NO: 62)
CGCAAAAACAAAGATGCGGAACATGATCCGGGCAGATACAGCTTTTGCATG 15-1A (2^nd loop)

(SEQ ID NO: 63)
CTGTATCTGCTCAGGCTTTCCGCTTTCTACATGTTTTTGCGTCGACATCAC and (SEQ ID NO: 64)
CGCAAAAACATGTAGAAAGCGGAAAGCCTGAGCAGATACAGCTTTTGCATG 1A6 (1^st loop)

(SEQ ID NO: 65)
TCAATGCGCATGTGAAGAGATCTGGACTATGCTTTGCCGGTGTTCCGATATGCGTC and (SEQ ID NO: 66)
CGGAACACCGGCAAAGCATAGTCCAGATCTCTTCACATGCGCATTGATCGCAACAG 1A6 (2^nd loop)

(SEQ ID NO: 67)
CAAAAGCTGTGCTTGTGAAGAGATCTGGACTATGCTTTGCTTTTGCGTCGACATCACGG and (SEQ ID NO: 68)
ACGCAAAAGCAAAGCATAGTCCAGATCTCTTCACAAGCACAGCTTTTGCATGCACTATG 1C2 (1^st loop)

(SEQ ID NO: 69)
TCAATGCGCATGTTGGGCCCTTACTGTCAAAACATGCCGGTGTTCCGATATGCGTC and (SEQ ID NO: 70)
CGGAACACCGGCATGTTTTGACAGTAAGGGCCCAACATGCGCATTGATCG
CAACAGG 1C2 (2nd loop)
(SEQ ID NO: 71)
CAAAAGCTGTGCTTGTTGGGCCCTTACTGTCAAAACATGCTTTTGCGTCG
ACATCACGG
and (SEQ ID NO: 72)
ACGCAAAAGCATGTTTTGACAGTAAGGGCCCAACAAGCACAGCTTTTGCA
TGCACTATG 2E2 (1st loop)
(SEQ ID NO: 73)
TCAATGCGCATGTCTTACAGTACTGTGGACTACATGCCGGTGTTCCGATA
TGCGTC
and (SEQ ID NO: 74)
CGGAACACCGGCATGTAGTCCACAGTACTGTAAGACATGCGCATTGATCG
CAACAGG 2E2 (2nd loop)
(SEQ ID NO: 75)
CAAAAGCTGTGCTTGTCTTACAGTACTGTGGACTACATGCTTTTGCGTCG
ACATCACGG
and (SEQ ID NO: 76)
ACGCAAAAGCATGTAGTCCACAGTACTGTAAGACAAGCACAGCTTTTGCA
TGCACTATG 2E5 (1st loop)
(SEQ ID NO: 77)
TCAATGCGCATGTACTCTTTGGAACAGATCTCCTTGCCGGTGTTCCGATA
TGCGTC
and (SEQ ID NO: 78)
CGGAACACCGGCAAGGAGATCTGTTCCAAAGAGTACATGCGCATTGATCG
CAACAGG 2E5 (2nd loop)
(SEQ ID NO: 79)
CAAAAGCTGTGCTTGTACTCTTTGGAATCGATCTCCTTGCTTTTGCGTCG
ACATCACGG
and (SEQ ID NO: 80)
ACGCAAAAGCAAGGAGATCGATTCCAAAGAGTACAAGCACAGCTTTTGCA
TGCACTATG FGFns (1st loop)
(SEQ ID NO: 81)
TCAATGCGCATGTACAAACATCGATTCTACTCCTTGCCGGTGTTCCGATA
TGCGTC
and (SEQ ID NO: 82)
CGGAACACCGGCAAGGAGTAGAATCGATGTTTGTACATGCGCATTGATCG
CAACAGG FGFns (2nd loop)
(SEQ ID NO: 83)
CAAAAGCTGTGCTTGCACAAACATCGATTCTACTCCTTGTTTTGCGTCG
ACATCACGG
and (SEQ ID NO: 84)
ACGCAAAAACAAGGAGTAGAATCGATGTTTGTGCAAGCACAGCTTTTGCA
TGCACTATG FGFkr (1st loop)
(SEQ ID NO: 85)
TCAATGCGCATGTACAAAAATCGATCGTACTCCTTGCCGGTGTTCCGATA
TGCGTC
and (SEQ ID NO: 86)
CGGAACACCGGCAAGGAGTACGATCGATTTTTGTACATGCGCATTGATCG
CAACAGG FGFkr (2nd loop)
(SEQ ID NO: 87)
CAAAAGCTGTGCTTGCACAAAAATCGATCGTACTCCTTGTTTTGCGTCG
ACATCACGG
and (SEQ ID NO: 88)
ACGCAAAAACAAGGAGTACGATCGATTTTTGTGCAAGCACAGCTTTTGCA
TGCACTATG FGFhI (1st loop)
(SEQ ID NO: 89)
TCAATGCGCATGTCACCTGCAGACAACTGAAACATGCCGGTGTTCCGATA
TGCGTC
and (SEQ ID NO: 90)
CGGAACACCGGCATGTTTCAGTTGTCTGCAGGTGACATGCGCATTGATCG
CAACAGG FGFhI (2nd loop)
(SEQ ID NO: 91)
CAAAAGCTGTGCTTGCCACCTGCAGACAACTGAAACATGTTTTTGCGTCG
ACATCACGG
and (SEQ ID NO: 92)
ACGCAAAAACATGTTTCAGTTGTCTGCAGGTGGCAAGCACAGCTTTTGCA
TGCACTATG FGFgy (1st loop)
(SEQ ID NO: 93)
TCAATGCGCATGTGGCTACTTCATCCCATCGATTTGCCGGTGTTCCGATA
TGCGTC
and (SEQ ID NO: 94)
CGGAACACCGGCAAATCGATGGGATGAAGTAGCCACATGCGCATTGATCG
CAACAGG FGFgy (2nd loop)
(SEQ ID NO: 95)
CAAAAGCTGTGCTTGCGGCTACTTCATCCCATCGATTTGTTTTGCGTCG
ACATCACGG
and (SEQ ID NO: 96)
ACGCAAAAACAAATCGATGGGATGAAGTAGCCGCAAGCACAGCTTTTGCA
TGCACTATG MM005 (1st loop)
(SEQ ID NO: 97)
TCAATGCGCATGTTTACGTATCCTTGCTAACAAATGCCGGTGTTCCGATA
TGCGTC
and (SEQ ID NO: 98)
CGGAACACCGGCATTTGTTAGCAAGGATACGTAAACATGCGCATTGATCG
CAACAGG MM005 (2nd loop)
(SEQ ID NO: 99)
CAAAAGCTGTGCTTGCTTACGTATCCTTGCTAACAAATGTTTTGCGTCG
ACATCACGG
and (SEQ ID NO: 100)
ACGCAAAAACATTTGTTAGCAAGGATACGTAAGCAAGCACAGCTTTTGCA
TGCACTATG MM007 (1st loop)
(SEQ ID NO: 101)
GCGATCAATGCGCCTGCAGAACTCAACCATATCCTTTATGTCGGTGTTCC
GATATGCGTC
and (SEQ ID NO: 102)
GGAACACCGACATAAAGGATATGGTTGAGTTCTGCAGGCGCATTGATCGC
AACAGGGTTT MM007 (2nd loop)
(SEQ ID NO: 103)
CAAAAGCTGTGCCTGCAGAACACAACCTTACCCACTTTGTTTTTGCGTCG
ACATCACGG
and (SEQ ID NO: 104)
ACGCAAAAACAAAGTGGGTAAGGTTGTGTTCTGCAGGCACAGCTTTTGCA
TGCACTATG MM009 (2nd loop)
(SEQ ID NO: 105)
CAAAAGCTGTGCCTGCCTGTTAACACCTACTCTTAACTGTTTTTGCGTCG
ACATCACGG
and (SEQ ID NO: 106)
ACGCAAAAACAGTTAAGAGTAGGTGTTAACAGGCAGGCACAGCTTTTGCA
TGCACTATG MM010 (1st loop)
(SEQ ID NO: 107)
TCAATGCGCATGCGCTCTTCCAACTCATTCTAACTGTCGGTGTTCCGATA
TGCGTCT
and (SEQ ID NO: 108)
CGGAACACCGACAGTTAGAATGAGTTGGAAGAGCGCATGCGCATTGATCG
CAACAGG MM010 (2nd loop)
(SEQ ID NO: 109)
CAAAAGCTGTGCCTGCGCGCTTCCTACACACTCTAACTGTTTTTGCGTCG
ACATCACGG
and (SEQ ID NO: 110)
ACGCAAAAACAGTTAGAGTGTGTAGGAAGCGCGCAGGCACAGCTTTTGCA
TGCACTATG MM017 (2nd loop)
(SEQ ID NO: 111)
CAAAAGCTGTGCCTGCCCTTTAGGCCTTTGCCCACCTTGTTTTTGCGTCG
ACATCACGG
and (SEQ ID NO: 112)
ACGCAAAAACAAGGTGGGCAAAGGCCTAAAGGGCAGGCACAGCTTTTGCA
TGCACTATG FGFps1 (2nd loop)
(SEQ ID NO: 113)
AAGCTGTATCTGCTGGAACATCGATTCTACACCTTGTTTTTGCGTCGACA
TCACGG
and (SEQ ID NO: 114)
ACGCAAAAACAAGGTGTAGAATCGATGTTCCAGCAGATACAGCTTTTGCA
TGCACT FGFps2 (1st loop)
(SEQ ID NO: 115)
GCGATCAATGCATCTGTACTTGGATTGACAGTACTCCTTGTCGGTGTTCC
GATATGCGTC
and (SEQ ID NO: 116)
GGAACACCGACAAGGAGTACTGTCAATCCAAGTACAGATGCATTGATCGC
AACAGGGTTT FGFps2 (2nd loop)
(SEQ ID NO: 117)
AAGCTGTATCTGCACATGGATCGATAGTACTCCTTGTTTTTGCGTCGACA
TCACGG
and (SEQ ID NO: 118)
ACGCAAAAACAAGGTGTAGAATCGATCCATGTGCAGATACAGCTTTTGCA
TGCACT FGFpsB (2nd loop)
(SEQ ID NO: 119)
AAGCTGTATCTGTACATGGATCGATTGGACACCTTGTTTTTGCGTCGACA
TCACGG
and (SEQ ID NO: 120)
ACGCAAAAACAAGGTGTCCAATCGATCCATGTACAGATACAGCTTTTGCA
TGCACT 1A8 (2nd loop)
(SEQ ID NO: 121)
CAAAAGCTGCGCATGTGTTACTACAGATTGGATCGAATGTTTTTGCGTCG
ACATCACGG
and (SEQ ID NO: 122)
ACGCAAAAACATTCGATCCAATCTGTAGTAACATGCGCAGCTTTTGCA
TGCACTATG 1A12 (2nd loop)
(SEQ ID NO: 123)
CAAAAGCTGTGCCTGCCCAACACTTTGGACTCATATGTGTTTTTGCGTCG
ACATCACGGAC
and (SEQ ID NO: 124)
ACGCAAAAACACATATGAGTCCAAAGTGTTGGGCAGGCACAGCTTTTGCA
TGCACTATGAC 1E11 (2nd loop)
(SEQ ID NO: 125)
CAAAAGCTGCGCATGTTACTACTCTCAATTCCACCAATGTTTTTGCGTCG
ACATCACGG
and (SEQ ID NO: 126)
ACGCAAAAACATTGGTGGAATTGAGAGTAGTAACATGCGCAGCTTTTGCA
TGCACTATG TGFps1 (2nd loop)
(SEQ ID NO: 127)
CAAAAGCTGTCTTTGTCCGGAAAACGATAACGTTTCTCCTTGTAATTGCG
TCGACATCACGGACTTCTG
and (SEQ ID NO: 128)
TGTCGACGCAATTACAAGGAGAAACGTTATCGTTTTCCGGACAAAGACAG
CTTTTGCATGCACTATGAC The DNA sequences of the oligonucleotide pair used to make the cassette to introduce the MM021 peptide into the chymotrypsin reactive site loops of the p2JM103-Ink2-BBI expression vector are provided below. The cassette was ligated into the SphI and SalI restriction sites in the vector.

MM021 (2nd loop)
(SEQ ID NO: 129)
CAAAAGCTGTGCTTGTAAACACAACGTACGTCTTTTATGTTTTTGCG
and (SEQ ID NO: 130)
TCGACGCAAAAACATAAAAGACGTACGTTGTGTTTACAAGCACAGCTTTT
GCATG Libraries made of cysteine constrained peptides are popular reagents (e.g. the commercially available PhD-C7C Phage Display Peptide Library Kit; NEB) for selecting peptides that bind to substrates of interest. BBI has two cysteine constrained reactive site loops that are structurally similar to the peptide loops displayed in various methods used to select peptide binders. So, once a cysteine constrained binding peptide has been selected, BBI is suitable for use as a scaffold to present the peptide in a binding reaction.

Figure 4:
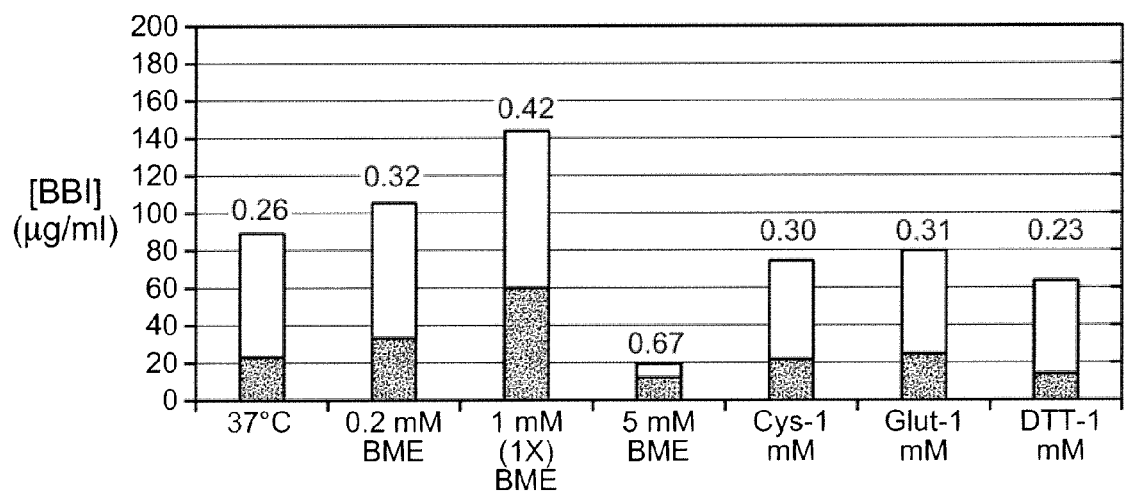
FIG. 4 provides a graph showing titers of active versus inactive 2BBIck81 with various thiol reducing agents added at the given concentrations during the growth of the culture. The white portion of the bars represents the amount of active 2BBIck81 (determined by trypsin inhibition) and the black portion of the bars represents the amount of inactive 2BBIck81 (determined from BCE103 a ctivity and assumes BCE103 and 2BBIck 81 are produced in 1:1 molar ratio). The fraction of active 2BBIck81 is indicated at the top of the bars.

The VEGF binding peptide CK37281 (See e.g., co-pending U.S. Provisional Patent Application Ser. No. 60/520,403, filed Nov. 13, 2003, incorporated herein by reference) was grafted into BBI by replacing the trypsin, chymotrypsin, or both reactive site loops, with the CK37281 peptide sequence (ACYNLYGWTC) (SEQ ID NO:9) by using DNA oligonucleotide cassettes. To facilitate the construction, an EcoRI site was introduced in the coding region of the BBI gene (custom synthesized by Operon Technologies; See, Example [1]) between the trypsin and chymotrypsin reactive site loops by QuikChange® site-directed mutagenesis, using methods described by the manufacturer (Stratagene) using the primers BowBeco-F and BowBeco-R, shown above (0.5 μmol of each primer was used in the QuikChange® reaction; after an initial denaturation step of 97° C. for 3 minutes, 18 PCR cycles of 68° C. for 12 minutes, 95° C. for 30 seconds and 55° C. for one minute, followed by a final extension reaction for 15 minutes at 68° C.).

To replace the trypsin inhibitory peptide loop, two DNA oligonucleotides (IBBCK81+ and 1 BBCk81−) were annealed and ligated into the SacI and EcoRI restriction sites. Likewise, to replace the chymotrypsin inhibitory peptide loop, EcoRI and SalI sites were used for insertion of a DNA cassette made by annealing the oligonucleotides (2BBck81+ and 2BBck81−). The CK37281 peptide was grafted into both loops by inserting the CK37281 peptide in the chymotrypsin loop (using the oligonucleotides (2BBck81+ and 2BBck81−) after the trypsin loop was first replaced by the CK37281 peptide. BBI with the CK37281 peptide in the trypsin loop (1 BBIck81) was moved into the pJM103BBI expression vector as a SacI-SphI fragment. BBI with the CK37281 in the chymotrypsin loop (2BBIck81), or both loops (12BBIck81), was moved into pJM103BBI as SacI-SalI fragments. The correct sequences were verified by DNA sequencing (the sequence of 12BBIck81 gene is shown in FIG. 3). The resulting vectors, pJM103-1 BBIck81, pJM103-2BBIck81, or pJM103-12BBIck81, were used to transform *B. subtilis* BG3934comK, and the production of the BCE fusion proteins was determined as in Example 1 above.

The fusion protein running at ~44 kDa was detected by SDS-PAGE to be the major protein present in the cell free broth. Although in some cases, there was significant degradation (up to 50%) of the BBI moiety (especially after >48 h of growth in MBD medium), as observed by the presence of a prominent protein band running at 34 kDa corresponding to the BCE103 catalytic core. In these cases, the titers of the BCE103 cellulase were similar to that measured with fusions to the wild-type BBI (Example 1), but the activity of the BBI (trypsin inhibition with 2BBIck81, or chymotrypsin inhibition with 1 BBIck81) was generally about two fold less.

To reduce the proteolytic degradation of BBI variants during growth (i.e. decrease the amount of BCE103 cellulase core present on SDS-PAGE gels in comparison to the fusion protein), a *Bacillus subtilis* strain with nine protease genes deleted, BG6006 (degU$^{HY}$32, oppA, ΔspollE3501, ΔaprE, ΔnprE, Δepr, ΔispA, Δbpr, Δvpr ΔwprA, Δmpr-ybjF, ΔnprB, amyE::xylRPxylAcomK-ermC), was used as an expression host, and the growth temperature (35° C.) and aeration (200 rpm) were reduced. With these changes, a major fusion protein band (~44 kDa) was observed on SDS-PAGE gels with an insignificant band present at the molecular weight expected for the BCE catalytic core protein (~34 kDa).

In addition to the CK37281 peptide, a number of other cysteine constrained peptides were produced when substituted into the trypsin and/or chymotrypsin reactive site loops of BBI fused to the C-terminus of the BCE103 cellulase. Specific examples included:

(1) Peptides designed or selected as complement antagonists, compstatin introduced into the 1$^{st}$ or 2$^{nd}$ reactive site loops (See, Sahu et al., J. Immunol., 157: 884-891, [1996]), C2c (1$^{st}$ loop), C3c (1$^{st}$ loop), C4c (1$^{st}$ loop) and C5c (1$^{st}$ loop); or peptides selected in a Factor B binding reaction 1B, 2B, 4A, 5A, 6-1A, 7A, 8B, 9A, 10B, 11-1A, 12B, 13A, and 15-1A (all in 2$^{nd}$ loop);

(2) Peptides designed to bind to the proteases Factor Xa or stratum corenum chymotrypsin, Xa1 (2$^{nd}$ loop) or hSCC1 (1$^{st}$ loop), respectively;

(3) Peptides selected in FGF5 binding reactions 1A6 (1$^{st}$ or 2$^{nd}$ loop), 1C2 (1$^{st}$ or 2$^{nd}$ loop), 2E2 (1$^{st}$ or 2$^{nd}$ loop), 2E5 (1$^{st}$, 2$^{nd}$ or both loops), FGFns (1$^{st}$ or 2$^{nd}$ loop), FGFkr (1$^{st}$ or 2$^{nd}$ loop), FGFhl (1$^{st}$ or 2$^{nd}$ loop), FGFgy (1$^{st}$ or 2$^{nd}$ loop), MM005 (1$^{st}$ or 2$^{nd}$ loop), MM007 (1$^{st}$, 2$^{nd}$ or both loops), MM009 (2$^{nd}$ loop), MM010 (1$^{st}$, 2$^{nd}$ or both loops), MM017 (2$^{nd}$ loop), FGFps1 (2$^{nd}$ loop), FGFps2 (1$^{st}$, 2$^{nd}$ or both loops), and FGFpsB (2$^{nd}$ loop); and (4) Peptides selected in TGFβ-L binding reactions 1A8 (2$^{nd}$ loop), 1A12 (2$^{nd}$ loop), 1E11 (2$^{nd}$ loop), TGFps1 (2$^{nd}$ loop), and MM021 (2$^{nd}$ loop).

The oligonucleotides used to introduce these peptides into either the trypsin (1$^{st}$ loop) or chymotrypsin (2$^{nd}$ loop) reactive site loops, and methods used to graft these peptides into BBI, are provided above. In all cases, fusion proteins were produced as determined by SDS-PAGE gels. However, with some substituted peptides, the amount of intact fusion protein was increased by reducing the proteolytic degradation as described above for the CK37281 substituted peptide.

EXAMPLE 3

Activation of BBI By Thiol Reducing/Oxidizing Agents

After growth, the activity of the BBI (by trysin or chymotrypsin inhibition) is typically some 5-20 times lower than what would be expected from the activity of the BCE103 cellulase measured in the cell free supernatants (the two molecules should be present at a 1:1 molar ratio in the fusion protein). An increase in the activity of BBI (measured by either trypsin or chymotrypsin inhibition) in the BCE103-BBI fusion protein can be routinely obtained by adding BME, typically concentrations of 1-4 mM added to the MBD growth medium about 14 h after inoculation. The trypsin or chymotrypsin inhibitory activity of BBI in the fusion protein is also lower than expected when binding peptides (e.g. VegF binding peptide CK37281) replace the chymotrypsin or trypsin reactive site loop, respectively. As with the wild-type BBI, the inhibitory activity can be increased by treatment with bME. Unexpectedly, other thiol reducing agents (e.g., cysteine, reduced glutathione, DL-dithiothreitol and Tris[2-carboxyethyl]phosphine) had small or negligible effects on the activation of BBI during growth in these experiments. Also, additions of antioxidants (e.g., ascorbic acid or DL-α-tocopherol acetate) or other adjuvants to the growth medium (e.g., isoleucine, soybean oil, Tween-80), or growth at 30° C. did not significantly improve the BCE103:BBI activity ratio.

Specifically, to determine the BBI activation during growth, cultures of *B. subtilis* BG6006 transformed with p2JM103-E3-2BBIck81 (See, Example 4, below) were grown in 40 ml MBD medium in 250 ml shake flasks at 37° C. for 13 h. Then, the thiol reducing agents indicated on the graph in FIG. 4 were added and cell supernatants harvested after 62 h of growth. The reagents 2-mercaptoethanol (BME), cysteine (Cys), reduced glutathione (Glut), and DL-dithiothreitol (DTT) were added to the growth medium to the final concentrations indicated on the graph provided in FIG. 4. Concentrations of 5 mM BME can result in better BCE103: BBI activity ratios but typically result in an overall decrease in both BCE103 and BBI titers (see FIG. 4), at least partially due to the reduction in bacterial growth caused by the added reagent. Titers of BCE103 and 2BBIck81 were determined using the assays described in Example 1.

BBI activation was also achieved after partial purification of the fusion proteins (e.g. BCE-Ink2-2BBIck81, see Example 4 below) by Q-Sepharose ion exchange chromatography.

The fusion protein was purified from cell free broth obtained from shake flasks or fermentor runs. The broth was filtered, diluted five to ten fold in water and the pH adjusted to pH 7.5-8.0. The diluted sample was loaded onto a column packed with Q-Sepharose resin (GE Healthcare). The column was washed with 50 mM Tris pH 7.5 and then washed again in the same buffer containing 300 mM NaCl. The fusion protein was eluted in the same buffer with 700 mM NaCl.

To activate the BBI, the pooled fusion protein fractions were diluted ten fold in Assay Buffer then treated with 2 mM BME and 0.2 mM oxidized glutathione (GSSG) with constant mixing on a stir plate or rocker platform for about 24 h at room temperature. The BBI could generally be activated to about 70-100% of the expected trypsin inhibitory activity based on the measured concentration of the BCE103 cellulase. Although the activation method outlined above generally yielded the best results, in some cases, in order to maximize the activation of a given sample, screens were performed in 96-well plates to determine the optimal conditions. Initially, the typical conditions screened were the dilution in Assay Buffer (e.g., a 2-50 fold dilution series), BME concentration (e.g., series between 0.5-5 mM) and oxidized glutathione concentration (e.g. 0 mM then a series of 1/20 to 1/2 the BME concentration).

The activation of the fusion protein BCE-Ink2-2BBIck81 is shown in FIG. 5. In this specific example, the fusion protein from a Q-Sepharose purification was diluted 1:10 in Dulbecco's PBS (Mediatech) with 0.005% TWEEN®-80. Beta-mercaptoethanol was added to a final concentration of 3 mM and incubated overnight at room temperature on a rocker. The sample was further incubated at room temperature for about 60 h with vigorous stirring on a magnetic stir plate. The titers of the BCE103 and 2BBIck81 (before and after βME treatment) were determined by cellulase assays and trypsin inhibitory assays, respectively.

In some embodiments, such as for activating BBI or it variants in cell free broth from large volume fermentations, it is desirable to reduce the dilution and βME concentration in the activation reaction. This can be accomplished by using higher concentrations of buffer (500 mM Tris pH 8.6), or changing to zwitterionic buffers such as CHES (also CAPS, Tricine, TAPS, and other suitable zwitterionic buffers). For example, cell free broth (or fusion protein fractions purified by ion exchange chromatography) was diluted 1:1 in 375 mM CHES pH 8.6 with 0.005% TWEEN®-80 then activated with 1 mM BME and 10 mM $Na_2SO_3$ and incubated with stirring at room temperature for about 24 h. BBI or its variants, as BCE103 cellulase fusion proteins, were routinely activated by this method to 70-100% of the expected value (based on BCE103 cellulase activities).

EXAMPLE 4

Release of Free BBI/Variants by Cleavage of the BCE103-BBI Fusion Proteins

This Example describes experiments developed to release free BBI or its variants by cleavage of the BCE103-BBI fusion proteins.

The sequences of the DNA oligonucleotide pairs that were annealed and ligated into the BamHI and SacI sites of pJM103-BBI to generate potential cleavage sites during culture growth between the BCE103 catalytic domain and BBI are provided below.

```
BCEsubBBI
(a subtilisin-type sensitive peptide sequence)
                                          (SEQ ID NO: 131)
GATCCAGGTGGAGCTGCTTTAGTTGACGATGAGAGCT
and (SEQ ID NO: 132)
CTCATCGTCAACTAAAGCAGCTCCACCTG BCEcbdLBBI (a portion of the 1$^{st}$ CBD)
                                          (SEQ ID NO: 133)
GATCCAGGTGAACCTGACCCAACTCCTCCATCTGATCCTGGAGAATACCC
AGCTTGGGACGATGAGAGCT
and (SEQ ID NO: 134)
CTCATCGTCCCAAGCTGGGTATTCTCCAGGATCAGATGGAGGAGTTGGGT
CAGGTTCACCTG BCEproBBI (the entire pro peptide of BBI)
                                          (SEQ ID NO: 135)
GATCCGGCGAACCTGCGTCTGTCTAAGCTTGGCCTGCTTATGAAATCAGA
CCATCAGCACAGCAATGACGATGAGAGCT
and (SEQ ID NO: 136)
CTCATCGTCATTGCTGTGCTGATGGTCTGATTTCATAAGCAGGCCAAGCT
TAGACAGACGCAGGTTCGCCG BCEshortproBBI
(a C-terminal portion of the pro peptide of BBI)
                                          (SEQ ID NO: 137)
GATCCAAAATCAGACCATCAGCACAGCAATGACGATGAGAGCT
and (SEQ ID NO: 138)
CTCATCGTCATTGCTGTGCTGATGGTCTGATTTTG
```

The sequences of the DNA oligonucleotide pair that was annealed and ligated into the BamHI and SacI sites of p2JM103-BBI to fuse BBI to the 2$^{nd}$ CBD linker of BCE103 cellulase are provided below.

```
BCEcbdDBBI
                                          (SEQ ID NO: 139)
GATCCAGGAGAACCGGACCCAACGCCCCCAAGTGATCCAGGAGAGTATCC
AGCATGGGATTCAAATCAAATTTACACAAATGAAATTGTGTATCATAACG
GTCAGTTATGGCAAGCGAAATGGTGGACACAAAATCAAGAGCCAGGTGAC
CCATACGGTCCGTGGGAACCACTCAAATCTGACCCAGATTCAGACGATGA
GAGCT
and (SEQ ID NO: 140)
CTCATCGTCTGAATCTGGGTCAGATTTGAGTGGTTCCCACGGACCGTATG
GGTCACCTGGCTCTTGATTTTGTGTCCACCATTTCGCTTGCCATAACTGA
CCGTTATGATACACAATTTCATTTGTGTAAATTTGATTTGAATCCCATGC
TGGATACTCTCCTGGATCACTTGGGGGCGTTGGGTCCGGTTCTCCTG
```

The peptide sequences susceptible to acid cleavage between aspartic acid and proline residues are provided below.

```
Linker 1 - WGDPHY (SEQ ID NO: 141) (Lidell et al.,
J. Biol. Chem. 278: 13944-51 [2003])

Linker 2 - DNNDPI (SEQ ID NO: 142) (Segalas et al.,
FEBS Lett., 371: 171-175 [1995'9 )

Linker 3 - VVADPN (SEQ ID NO: 143) (Kemperman et
al., Appl. Env. Microbiol., 69: 1589-1597 [2003])
```

Oligonucleotide primers used to introduce a BssHII site into pJM103BBI by QuikChange® site-directed mutagenesis are provided below.

```
BCEbss-F
                                      (SEQ ID NO: 144)
5'-TGGCGTTCAGCAACATGAGCGCGCAGGCTGATGATTA BCEbss-R
                                      (SEQ ID NO: 145)
5'-TAATCATCAGCCTGCGCGCTCATGTTGCTGAACGCCA
```

Sequences of the DNA oligonucleotides that were annealed as a cassette (SalI-HindIII) to introduce HindIII and XhoI sites after the stop codon of BBI, to introduce a PacI site after the LAT, and remove the original HindIII site are provided below.

```
BCEterm+
                                      (SEQ ID NO: 146)
5'-GACATCACGGACTTCTGCTATGAGCCATGTAAACCAAGCGAGGACGA
TAAAGAGAACTAAAAGCTTAACTCGAGGTTAACAGAGGACGGATTTCCTG
AAGGAAATCCGTTTTTTTATTTTTAATTAAG BCEterm-
                                      (SEQ ID NO: 147)
5'-AGCTCTTAATTAAAAATAAAAAAACGGATTTCCTTCAGGAAATCCGT
CCTCTGTTAACCTCGAGTTAAGCTTTTAGTTCTCTTTATCGTCCTCGCTT
GGTTTACATGGCTCATAGCAGAAGTCCGTGATG
```

PCR primers used to generate the acid labile linkers provided above (i.e., Linker 1, Linker 2, and Linker 3) inserted between the BCE103 catalytic domain and BBI are provided below.

```
BCE103coreBssHII_FW
                                      (SEQ ID NO: 148)
5'-CAGCAACATGAGCGCGCAGGCTG linkerWGDPHY_RV
                                      (SEQ ID NO: 149)
5'-ATCGTCTGGATCCGGATAGTGGGGGTCTCCCCAAGATGCTGATTCTC
TTATTTTTTCCC linkerDNNDPI_RV
                                      (SEQ ID NO: 150)
5'-ATCGTCTGGATCCGGTATGGGATCATTGTTGTCAGATGCTGATTCTC
TTATTTTTTCCC linkerVVADPN_RV
                                      (SEQ ID NO: 151)
5'-ATCGTCTGGATCCGGGTTGGGATCTGCAACTACAGATGCTGATTCTC
TTATTTTTTCCC
```

PCR primers used to generate the acid labile linkers provided above (i.e., Linker 1, Linker 2, and Linker 3) inserted into the 1st CBD linker.

```
BCE103corePstI_FW
                                      (SEQ ID NO: 152)
GCATAAGGAT GAGTCATCTG CAGCG LplusWGDPHY_RV
                                      (SEQ ID NO: 153)
5'-ATCGTCTGGATCCGGATAGTGGGGGTCTCCCCACGGTTCTCCTGGAT
CAGATGGCGG LplusDNNDPI_RV
                                      (SEQ ID NO: 154)
5'-ATCGTCTGGATCCGGTATGGGATCATTGTTGTCCGGTTCTCCTGGAT
CAGATGGCGG LplusVVADPN_RV
                                      (SEQ ID NO: 155)
5'-ATCGTCTGGATCCGGGTTGGGATCTGCAACTACCGGTTCTCCTGGAT
CAGATGGCGG
```

Protein sequence of the acid labile linkers inserted between the BCE103 catalytic domain and BBI are provided below. The acid labile linkers are shown in bold type and the sequences from the first CBD domain are underlined.

Linker 1
BCE-WGDPHY-PDP-BBI (SEQ ID NO: 156)

Linker 2
BCE-DNNDPI-PDP-BBI (SEQ ID NO: 157)

Linker 3
BCE-VVADPN-PDP-BBI (SEQ ID NO: 158)

LinkerPlus 1
BCE-IPPSDPTPPSDPGEP-WGDPHY-PDP-BBI (SEQ ID NO: 159)

LinkerPlus 2
BCE-IPPSDPTPPSDPGEP-DNNDPI-PDP-BBI (SEQ ID NO: 160)

LinkerPlus 3
BCE-IPPSDPTPPSDPGEP-VVADPN-PDP-BBI (SEQ ID NO: 161)

The sequences of the DNA oligonucleotide pairs that were annealed and ligated into the BamHI and SacI sites of pJM103-BBI to generate potential cleavage sites between the BCE103 catalytic domain and BBI during the purification process are provided below.

```
BCEentBBI (Enteropeptidase cleaveage site)
                                      (SEQ ID NO: 162)
GATCCAGGTGGAGACGACGATGACAAAGACGATGAGAGCT
and
                                      (SEQ ID NO: 163)
CTCATCGTCTTTGTCATCGTCGTCTCCACCTG BCEgenen1BBI (Genenase I cleavage site)
                                      (SEQ ID NO: 164)
GATCCAGGTGCTGCTCATTACGACGATGAGAGCT
and
                                      (SEQ ID NO: 165)
CTCATCGTCGTAATGAGCAGCACCTG
```

The sequences of the DNA oligonucleotide pairs that were annealed and ligated into the BamHI and SacI sites of pJM103-Ink2-1 BBIck81 to generate potential cleavage sites between the BCE103 catalytic domain and BBI during the purification process are provided below.

```
BCEfurinBBI (Furin/Blisterase cleavage site)
                                        (SEQ ID NO: 166)
GATCCACGTGCTAAAAGAGACGATGAGAGCT
and (SEQ ID NO: 167)
CTCATCGTCTCTTTTAGCACGTG BCEgenen2BBI (Genenase I cleavage site)
                                        (SEQ ID NO: 168)
GATCCAGGCGCTGCACACTACAACGACGATGAGAGCT
and (SEQ ID NO: 169)
CTCATCGTCGTTGTAGTGTGCAGCGCCTG BCEfleBBI (Mpr cleavage site)
                                        (SEQ ID NO: 170)
GATCCATTCCTTGAAGACGATGAGAGCT
and (SEQ ID NO: 171)
CTCATCGTCTTCAAGGAATG
```

```
                                      -continued
BCEgenen4BBI
                                        (SEQ ID NO: 177)
GATCCAGGCGCTGCACACTACGTAGAATTTCAAGACGATGAGAGCT
and (SEQ ID NO: 178)
CTCATCGTCTTGAAATTCTACGTAGTGTGCAGCGCCTG
```

The protein sequence of a Genenase I sensitive cleavage site (also acid and Mpr sensitive) inserted between the BCE103 catalytic domain and BBI was DNNDPIPDP-GAAHYVEFQ (SEQ ID NO:179). The Genenase I site (Gen4 Linker) is in bold type (cleavage occurs between the tyrosine and valine) (NEB) and Linker 2 is underlined. Cleavage by Mpr can also occur after the glutamic acid that follows the valine in the Gen4 linker. The sequence used herein was BCE-SEQ ID NO:179)-BBI Cleavage sites in the BCE103-lnk2-2BBIck81 fusion protein are indicated below. The C-terminal seven amino acids of the BCE103 catalytic domain (underlined), linker 2 sequence (bold type), and 2BBIck81 sequences are shown. The acid/heat labile Asp-Pro bonds are indicated with solid headed arrows and the Mpr sensitive bonds after glutamic acids are indicated with line headed arrows.

(SEQ ID NO: 180)

KIRESASDNNDPIPDPDDESSKPCCDQCACTKSNPPQCRCSDMRLNSCHSACK
SCACYNLYGWTCFCVDITDFCYEPCKPSEDDKEN

Sequences of the oligonucleotide primer pairs used to introduce the E and E3 linkers in Linker 2 by QuikChange site-directed mutagenensis (Stratagene) are provided below.

```
BCE-EInk-BBI (Mpr cleavage site)
CCCATACCGGAGCCAGACGATGAGAGCTC    (SEQ ID NO: 172)
and

CATCGTCTGGCTCCGGTATGGGATCATTGTTG (SEQ ID NO: 173)
```

The protein sequence of the E3 linker between the BCE103 catalytic domain and BBI was DNNDPIPEPDDESFN-MPIPEP (SEQ ID NO:174). In this sequence, the E Linker is underlined and the sequence generated by faulty recombination in E. coli is shown in bold type. Cleavage by Mpr (or V8 protease) can occur after any of the three glutamic acids present in the E3 Linker. Thus, the structure was BCE-(SEQ ID NO:174)-BBI.

The sequences of the DNA oligonucleotide pairs that were annealed and ligated into the BamHI and SacI sites of p2JM103-Ink2-2BBIck81 to generate potential Genenase I cleavage sites between the BCE103 catalytic domain and BBI are provided below.

```
BCEgenen3BBI
                                        (SEQ ID NO: 175)
GATCCAGGCGCTGCACACTACAAATCAGACCATCAGCACAGCAATGACGA
TGAGAGCT
and (SEQ ID NO: 176)
CTCATCGTCATTGCTGTGCTGATGGTCTGATTTGTAGTGTGCAGCGCCTG
```

In order to isolate free BBI or its variants, the BBI moiety needs to be cleaved from the BCE103-BBI fusion protein. In some embodiments, this is accomplished during growth, by proteases intrinsically produced by B. subtilis. In some alternative embodiments, this cleavage occurs after growth, during the purification process (e.g. by acid/heat or proteolytic cleavage). Linkers potentially susceptible to cleavage during growth were designed (See, above, sub, cbdL, pro, shortpro, and cbdD) and cloned into the pJM103BBI or p2JM103BBI expression vectors as BamHI-SacI cassettes. The production of fusion protein versus BCE103 catalytic domain was analyzed on SDS-PAGE gels as described in Example 1.

Little cleavage of the fusion protein was observed for all these linkers except with the pro linker, which was nearly completely cleaved so that very little intact fusion protein was observed on gels, although there was a large band corresponding to the BCE103 catalytic core. Unfortunately, this cleavage during growth resulted in negligible BBI activity measured in cell free supernatants and no BBI band could be identified on SDS-PAGE gels. Although it is not intended that the present invention be limited to any particular mechanism or theory, it is possible that the BBI is particularly sensitive to proteolytic degradation in its inactive form. Thus, cleavage during the purification process after activation is generally preferred.

In some embodiments, the bonds between aspartic acid and proline residues are cleaved by heat treatment at acidic pH as known in the art (See e.g., Landon, Meth. Enzymol., 47:145-149 [1977]). The 1$^{st}$ CBD linker in the BCE103 cellulase has three Asp-Pro dipeptide sequences (See, FIG. 1) with the potential to be cleaved by acid/heat treatment. However, cleavage by acid/heat treatment at these sites was found to be inefficient. Protein sequences that are especially labile to acid/heat have been described in the literature, three of such sequences are WGDPHY (SEQ ID NO:141), DNNDPI (SEQ ID NO:142), and VVADPN (SEQ ID NO:143) (i.e., Linkers 1, 2 and 3).

Before these acid labile linkers were introduced into the BCE103-BBI expression vector, pJM103BBI, a BssHII site was introduced by QuikChange® XL (Stratagene) mutagenesis (using the manufacturer's methods; and described in Example 2 above, except 8 minute extension and 1 minute denaturation steps were used) in the aprE signal sequence coding region using the oligonucleotide primers BCEbss-F and BCEbss-R (provided above). Then, HindIII and XhoI sites were inserted in front of the LAT terminator (after the BBI stop codon) and a PacI site was added after the terminator (the original HindIII site after the LAT terminator was removed) by inserting an oligonucleotide cassette (BCEterm+ and BCEterm−; provided above) into the SalI and the original HindIII sites. This new vector was called "p2JM103BBI."

The acid labile linker fragments were generated by PCR, using forward primer BCE103coreBssHII_FW with each of the reverse primers, linker WGDPHY_R, linker DNNDPI_RV, or linkerVVADPN_RV (the sequences of which are all provided above) and p2JM103BBI as the template (see Example 1 for the PCR protocol). The PCR fragments of 970 bp were digested with BamHI and PstI, the 154 bp fragments encoding the acid linker fragments were isolated from an agarose gel after electrophoresis, and ligated into the p2JM103 vector digested with BamHI and PstI that had also been purified from a gel. The linker sequences in the final expression vectors, p2JM103lnk1-BBI, p2JM103lnk2-BBI and p2JM103lnk3-BBI, were verified by DNA sequencing.

Competent *B. subtilis* strain BG3934comK or BG6006 were transformed with the plasmids, colonies selected on 5 µg/ml chloramphenicol LA plates and amplified to 25 µg/ml chloramphenicol as described in Example 1.

Similarly, the acid labile linkers were inserted into the first CBD linker. Specifically, PCR fragments were generated using the forward primer BCE103corePstI_FW with the reverse primers LplusWGDPHY_RV, LplusDNNDPI_RV, or LplusVVADPN_RV (See above, for the sequences) with p2JM103BBI as a template. The PCR fragments of about 150 bp were digested with BamHI and PstI, purified and ligated to the p2JM103BBI vector digested with BamHI and PstI. The correct sequences were verified by DNA sequencing and the plasmids p2JM103 plInk1-BBI, p2JM103 plInk2-BBI and p2JM103 plInk3-BBI were used to transform *B. subtilis* strains as described above.

After growth in MBD medium, the fusion proteins were purified by ion exchange chromatography essentially as described above (See, Example 2). The fusion protein was cleaved by treatment at 55° C. for 16 h in 10% formic acid. The BCE103 catalytic domain precipitated during the acid treatment and was removed by centrifugation. The free BBI in the supernatant was dried overnight on a SpeedVac. The sample was suspended in 50 mM Tris pH 8 before loading on the SDS-PAGE gel. By analysis of the protein stained SDS-PAGE gels, it was observed that acid cleavage was much more efficient in the fusion proteins where Linker 2 was inserted between the BCE103 catalytic domain and BBI (BCE-DNNDPI-PDP-BBI). This linker was found to be cleaved in a couple of hours at 75° C. in 20 mM glycine pH 2.

In alternative embodiments, the fusion protein was cleaved by treatment with a protease during the purification process. Linkers were designed with cleavage sites for glutamic acid specific proteases (e.g., Mpr or V8 protease), Furin/blisterase, Genenase I, and Enteropeptidase (Enterokinase). These linkers were introduced as oligonucleotide cassettes (See above, for the sequences) between the BCE103 catalytic core and BBI in the expression vector using the BamHI and SacI sites (See, FIG. 1). In the coding region of the original expression vector (pJM103BBI), there is a glutamic acid residue in the $1^{st}$ CBD domain and at the third residue in BBI (See, FIG. 1), which is contemplated to be susceptible to cleavage by glutamic acid specific proteases such as *B. subtilis* Mpr (BsMpr) or V8 protease. However, neither BsMpr nor V8 protease were found to cleave the BCE-BBI fusion protein very efficiently at these sites. Thus, it was necessary to design other linkers that were susceptible to cleavage by these proteases.

The six acid labile linkers described above were tested for cleavage by BsMpr. These fusion proteins were cleaved by treatment for 16 h with 16 µg of BsMpr at room temperature. After cleavage, the BCE103 catalytic domain was precipitated by the addition of 10% formic acid and removed by centrifugation. The free BBI in the supernatant was dried overnight on a SpeedVac. The sample was suspended in 50 mM Tris pH 8, before loading on the SDS-PAGE. Similar to the acid cleavage, the BCE-DNNDPI-PDP-BBI (Linker 2) fusion protein was much more efficiently cleaved by BsMpr than any of the other linkers. Therefore, BBI and its variants were found to be effectively released from the BCE-DNNDPI-PDP-BBI fusion protein either by acid/heat treatment or proteolytic digestion with a glutamic acid specific protease such as BsMpr. Several other linkers designed for cleaved by Mpr (e.g., E, E3 linker, and fIe, provided above) were tested but none of them had any advantages over Linker 2 (the E3 linker was generated by faulty recombination in *E. coli* after transformation with the QuikChange® site-directed mutagensis reaction designed to construct the E linker). As shown above, there are two acid/heat labile cleavage sites in Linker 2 and three sites sensitive to cleavage by Mpr.

Linkers designed for cleavage by Furin or Blisterase (NEB) (BCEfurinBBI), or Enteropeptidase (Enterokinase, NEB) (BCEentBBI) were tested, but none of these sequences were cleaved efficiently by the appropriate protease. Four linkers were also designed (BCEgenen1BBI, BCEgenen2BBI, BCEgenen3BBI, and BCEgenen4BBI) and tested for cleavage by Genenase I (NEB). Efficient cleavage of the fusion protein was observed only with the Gen4 Linker (BCEgenen4BBI). BsMpr was also found to efficiently cleave the Gen4 linker.

After activation of the purified BCE-lnk2-2BBIck81 fusion protein, cleavage by BsMpr does not go to completion as judged by SDS-PAGE gels. However, it was discovered that complete cleavage after activation of BCE-BBI fusion proteins with Linker 2 (or the Gen4 linker) can be accomplished by using the Mpr protease isolated from *Bacillus licheniformis* (BlMpr). While it is not intended that the present invention be limited to any particular mechanism, cleavage after the third amino acid in mature BBI appeared to be more sensitive to BlMpr while cleavage after the sixth amino acid from the C-terminus of BBI is more sensitive to BsMpr cleavage.

In some embodiments, after cleavage, the BBI is purified away from the BCE103 catalytic domain by selective acid precipitation (pH 3 or lower) of the BCE103 catalytic domain as described above, ion exchange chromatography (See, Example 5), or by selective binding of BBI on an anhydrotrypsin-agarose (Sigma) column loaded in 50 mM Tris pH 8.0, washed with 50 mM Tris pH 8.0 with 150 mM NaCl, then eluting bound BBI with 50 mM glycine pH 2.2 with 300 mM NaCl).

EXAMPLE 5

Binding of BBIck81 to VegF

In this Example, experiments conducted to assess the binding of BBIck81 to VegF are described. The BCE103-Ink2-2BBIck81 fusion protein was produced in *B. subtilis* as described in Example 2. The fusion protein was purified, and the BBI trypsin inhibitory activity was increased by treatment with βME and oxidized glutathione as described in Example 3. The fusion protein was cleaved by BsMpr protease (See, Example 4) and the free 2BBIck81 was purified from the BCE103 catalytic domain by ion exchange chromatography using a Q-Sepharose column.

Briefly, after cleavage, the pH of the cleaved sample was adjusted to 5.5, the sample was then loaded onto the column (equilibrated with 25 mM MES pH 5.5). The free 2BBIck81 was washed through the column using 25 mM sodium acetate pH 5.0 while the BCE103 catalytic core remained bound to the resin. The 2BBIck81 fraction was concentrated by ultrafiltration and analyzed using an electrochemiluminescence (ECL) based binding assay (BioVeris). The Anti-VegF antibody (Santa Cruz) and VegF (PeproTech) were labeled with the electrochemiluminescent dye and biotin, respectively, as described by the manufacturer (BioVeris). All materials were in Dulbecco's PBS (Mediatech) supplemented with 0.1% TWEEN®-80. An initial dilution series of Anti-VegF antibody (125, 250 and 500 ng/ml) and VegF (100, 150, 200 and 250 ng/ml) were tested in the binding assay to determine the concentrations of each that would give a robust ECL signal.

For testing 2BBIck81 binding, 50 µL of 500 ng/ml ECL labeled Anti-VegF antibody, 50 µL of 250 ng/ml biotinylated VegF and 100 µL 2BBIck81 (series of 12.5, 15, 31.25, 62.5, 125, 250 or 500 ng/ml) were incubated at room temperature for 2 h with shaking. Then, 50 µL of 0.2 mg/ml streptavidin coated beads were added and the reaction was incubated at room temperature for 30 minutes. The ECL signal was measured using a BioVeris M8/384 Analyzer as described by the manufacturer (BioVeris). As shown in FIG. 6, the ECL signal decreased as increasing concentrations of 2BBIck81 displaced more of the labeled Anti-VegF antibody bound to VegF attached to the magnetic beads.

Thus, the CK37281 peptide when grafted onto the chymotrypsin inhibitory loop of BBI (2BBIck81) competed with the Anti-VegF antibody for binding to VegF at micromolar concentrations. In fact, 2BBIck81 competed for VegF binding better than the synthesized CK37281 peptide itself (See, FIG. 6). The CK37281 peptide inserted into the trypsin inhibitory loop, 1 BBIck81, also competed with the Anti-VegF antibody in the BioVeris assay. Thus, BBI was found to be useful as a scaffold to present active binding peptides selected by various screening methods.

EXAMPLE 6

Use of Alternative Fusion Partners for the Production of 2BBIck81

In this Example, experiments conducted to evaluate alternative fusion partners are described. The DNA sequence of the oligonucleotide primers used to amplify the dsbC gene (*E. coli*) from pET-40b(+) are provided below. These primers generate a BssHII site at the 5' end and a BamHI at the 3' end for cloning into p2JM103-Gen4-2BBIck81.

```
DsbCBBI-F
                                      (SEQ ID NO: 181)
AACATGAGCGCGCAGGCTGATGACGCGGCAATTCAACAAACGTTAG

DsbCBBI-R
                                      (SEQ ID NO: 182)
TCGTCTGGATCCGGTATGGGATCATTGTTGTCACCAGAACCACTAGTTGA
TCCTTTACCGCTGGTCATTTTTTGGTG
```

The DNA sequences of the oligonucleotides that were annealed together to make a cassette (Alw441-BamHI) for fusing the *P. mendocina* cutinase gene to BBI with Linker 2, are provided below.

```
CutinaseBBI+
                                      (SEQ ID NO: 183)
TGCACTTCTCTGCTTTGGTCTGTTGAACGCAGAGGTCTTGACAACAATGA
TCCTATTCCG CutinaseBBI-
                                      (SEQ ID NO: 184)
GATCCGGAATAGGATCATTGTTGTCAAGACCTCTGCGTTCAACAGACCAA
AGCAGAGAAG
```

Because the BBI moiety has seven disulfide bonds, it is contemplated that higher titers of active BBI will be obtained using fusion proteins other than the BCE103 cellulase catalytic domain. For example, in some embodiments, compositions such as thiol-disulfide oxidoreductases and/or protein disulfide isomerases find use as fusion proteins to help produce correctly folded BBI moieties. In this embodiment, no additional activation step is needed under most circumstances. In additional embodiments, other proteins produced at high titers in *B. subtilis* also find use as fusion partners. For example, the thermostable protein disulfide isomerase from the fungus *Humicola insolens* (hiPDI) has been used as a fusion partner to produce the light chain of immunoglobulin G (2 disulfides) in *Bacillus brevis* (See, Kajino et al., Appl. Env. Microbiol., 66:638-642 [2000]).

To determine whether hiPDI could be a better fusion partner than BCE103 for the production of BBI, this hiPDI gene was synthesized (DNA2.0) and cloned into the expression vector, p2JM103-Ink2-2BBIck81 (See, Example 4) as a BssHII-SacI fragment. In designing the synthetic gene, codons occurring with high frequency in highly expressed *B. subtilis* genes were selected except in cases where restriction sites were introduced or deleted. In the final construction, the N-terminus of the mature hiPDI gene was fused to the AprE signal sequence and the C-terminus was fused to a linker with an Enteropeptidase cleaveage site (Kajino et al., Appl. Env. Microbiol., 66:638-642 [2000]), which in turn was fused to 2BBIck81 (See, FIG. 7). This expression vector, p2JM-PDI-EK-2BBIck81, was used to transform *B. subtilis* BG6006 and the production of the fusion protein was determined in MBD medium (as described in Example 1) with or without 2 mM BME added 14 h after inoculation.

As determined by SDS-PAGE gels, the production of the PDI-2BBIck81 fusion protein was typically somewhat less than the BCE-2BBck81 grown under identical conditions. The BBI titers (trypsin inhibition) measured from the PDI-2BBIck81 cell free supernatants were also typically less than the BCE-2BBIck81 fusion. As with fusions to BCE103, the measured activities of BBI when fused to PDI were higher when grown in 2 mM BME and the BBI activity was increased by the addition of BME to the cell free supernatants after growth when grown in BME free medium (as described in Example 3). Thus, the thiol-disulfide oxidoreductase activity of PDI does not seem to significantly improve the titers of active 2BBIck81 in the fusion protein or obviate the need for activation of the BBI molecule.

In order to increase the reduction potential of the fusion protein, which was contemplated to improve the BBI titers during growth, DsbC from *Escherichia coli* was used as a fusion partner for 2BBIck81. The dsbC gene was amplified by PCR using Herculase Enhanced DNA polymerase as described by the manufacturer (Stratagene) using Dsb-CBBI-F and DsbCBBI-R as primers (sequences shown above) and pET-40b(+) (Novagen) as a template. The isolated PCR fragment was cloned into the vector p2JM103-Gen4-2BBIck81 (See, Example 4) as a BssHII-BamHI fragment. The correct sequence of the fusion gene was verified by DNA sequencing. In this case, the titers of the DsbC-2BBIck81 fusion protein were significantly lower than the BCE-2BBIck81 fusion protein as judged on SDS-PAGE gels and the titers of the active 2BBIck81 measured by trypsin inhibition were much lower as well.

Other proteins that are produced at high titers in *B. subtilis* find use as fusion partners for the production of BBI. One such protein is the cutinase from *Pseudomonas* mendocina, which has been expressed at high titers utilizing the aprE promoter from *B. subtilis* (See e.g., U.S. Pat. No. 5,429,950, herein incorporated by reference). The aprE-cutinase gene fusion as an EcoRI-Alw441 fragment (from pAK-15) was ligated with an Alw441-BamHI linker oligonucleotide cassette (See, sequence above) into the p2JM103-Ink2-2BBIck81 (See, Example 4) that had been cut with EcoRI and BamHI. This cutinase-linker2-2BBIck81 expression vector (See, FIG. 8 for the EcoRI-BamHI aprE-cutinase-linker2 sequence) was used to transform *B. subtilis* BG6006 cells and the fusion protein was produced in MBD medium as described previously for the other fusion proteins (See, Example 1). In this case, the cutinase-linker2-2BBIck81 fusion protein was not the major band observed on SDS-PAGE gels and the measured lipase titers (as measured using the methods provided in U.S. Pat. No. 5,429,950) and BBI titers were much less (ca. 20 fold) than found with the BCE-2BBIck81 fusion protein. Also, the BBI titers in the cutinase fusion protein were not improved significantly when 3 mM BME was added to the growth medium. Thus, the highest titers of active 2BBIck81 was consistently obtained by activation of the BCE-2BBIck81 fusion protein. Nonetheless, it is contemplated that various fusion partners will find use in the present invention.

EXAMPLE 7

Expression of Truncated BBI-AV (BBIt-AV; SEQ ID NO:187)

This Example describes experiments that were performed to improve the production of the 2BBIck81 BBI protein (BBI-AV; SEQ ID NO:186) DDESSKPCCDQCACTKSNP-PQCRCSDMRLNSCHSACKSCACYNLYG-WTCFCVDITDF CYEPCKPSEDDKEN (SEQ ID NO:18).

The Examples above and the journal article of Vogtentanz et al., 2007 (Protein Expr Purif 55:40-52 [2007]) describe a method for producing a fusion protein that comprises the soybean Bowman-Birk protease inhibitor (BBI) fused to the C-terminus of the BCE103 cellulase catalytic domain (BCE). As described above, this system has been used to produce BBI molecules with various variant peptides replacing the trypsin and/or chymotrypsin inhibitory loops. For example, a BBI molecule, BBI-AV (SEQ ID NO:186) containing the VEGF binding peptide, CK37281 (ACYNLYGWTC; SEQ ID NO:9), that replaces the native chymotrypsin inhibitory loop (ICALSYPAQC; SEQ ID NO:388) was produced, purified and shown to compete in an electrochemiluminescent (ECL) based binding assay (BioVeris) with a monclonal antibody for binding to VEGF. However, the recovered yield of the variant BBI-AV was less than that of the wild-type BBI most likely due to an initial higher percentage of molecules with incorrectly formed disulfide bonds.

A truncated form of the BBI-AV OF SEQ ID NO:186 (I.E. BBIT-AV OF SEQ ID NO:187) DDESSKPCCDQCACTK-SNPPQCRCSDMRLNSCHSACKSCACYN-LYGWTCFCVDITDF CYEPCKPSE (SEQ ID NO:187), which lacks the 5 C-terminal amino acids of SEQ ID NO:186 was shown to bind better than the full-length molecule (i.e. untruncated molecule) to VEGF in an ECL (BioVeris) assay using a labeled monoclonal antibody against VEGF as a competitor. The C-truncated version of BBI-AV, called BBIt-AV (SEQ ID NO:187), can be produced during the purification process by trimming the C-terminus with GluBL protease (glutamyl endopeptidase I from *Bacillus licheniformis*). Alternatively, the BBIt-AV can be obtained by introducing a stop codon using an engineered oligonucleotide cassette as follows.

The following BBI-trunc+ and BBI-trunc- oligonucleotides were annealed to generate an oligonucleotide cassette

```
BBI-trunc+
                                    (SEQ ID NO: 188)
5'-TCGACATCACGGACTTCTGCTATGAACCATGTAAACCAAGCGAGTAA
A
and BBI-trunc-
                                    (SEQ ID NO: 189)
5'-AGCTTTTACTCGCTTGGTTTACATGGTTCATAGCAGAAGTCCGTGAT
G
```

The oligonucleotide cassette was then ligated into the SalI and HindIII sites of the expression vector p2JM103-Ink2-2BBIck81, and the correct sequence was verified and the resulting expression vector was called p2JM103-Ink2-BBIt-AV.

To improve the expression, a polynucleotide sequence (SEQ ID NO:190 gctggtaaa) encoding the first three amino acids of the AprE pro-peptide, AGK (SEQ ID NO:191) (U.S. Pat. No. 5,429,950), was inserted between the end of the AprE signal sequence and the start of the mature BCE103 cellulase using a QuikChange® site-directed mutagenesis kit (Stratagene). The site directed mutagenesis was performed essentially as described by the manufacturer using p2JM103-Ink2-BBIt-AV as a template with the oligonucleotide primers:

```
BCE-AGK-F:
                                    (SEQ ID NO: 192)
5'-GCGCGCAGGCAGCTGGTAAAGATGATTATTCAGTTGTAGA
and BCE-AGK-R:
                                    (SEQ ID NO: 193)
5'-AATAATCATCTTTACCAGCTGCCTGCGCGCTCATGTTGCT
```

The correct insertion was verified by DNA sequencing and the resulting expression vector was called p2JMagk103-Ink2-BBIt-AV (SEQ ID NO:194).

```
                                    (SEQ ID NO: 194)
GAATTCTCCATTTTCTTCTGCTATCAAAATAACAGACTCGTGATTTTCCA

AACGAGCTTTCAAAAAAGCCTCTGCCCCTTGCAAATCGGATGCCTGTCTA

TAAAATTCCCGATATTGGTTAAACAGCGGCGCAATGGCGGCCGCATCTGA
```

-continued

```
TGTCTTTGCTTGGCGAATGTTCATCTTATTTCTTCCTCCCTCTCAATAAT
TTTTTCATTCTATCCCTTTTCTGTAAAGTTTATTTTTCAGAATACTTTTA
TCATCATGCTTTGAAAAAATATCACGATAATATCCATTGTTCTCACGGAA
GCACACGCAGGTCATTTGAACGAATTTTTTCGACAGGAATTTGCCGGGAC
TCAGGAGCATTTAACCTAAAAAAGCATGACATTTCAGCATAATGAACATT
TACTCATGTCTATTTTCGTTCTTTTCTGTATGAAAATAGTTATTTCGAGT
CTCTACGGAAATAGCGAGAGATGATATACCTAAATAGAGATAAAATCATC
TCAAAAAATGGGTCTACTAAAATATTATTCCATCTATTACAATAAATTC
ACAGAATAGTCTTTTAAGTAAGTCTACTCTGAATTTTTTTAAAAGGAGAG
GGTAAAGAGTGAGAAGCAAAAAATTGTGGATCAGCTTGTTGTTTGCGTTA
ACGTTAATCTTTACGATGGCGTTCAGCAACATGAGCGCGCAGGCAGCTGG
TAAAGATGATTATTCAGTTGTAGAGGAACATGGGCAACTAAGTATTAGTA
ACGGTGAATTAGTCAATGAACGAGGCGAACAAGTTCAGTTAAAAGGGATG
AGTTCCCATGGTTTGCAATGGTACGGTCAATTTGTAAACTATGAAAGCAT
GAAATGGCTAAGAGATGATTGGGGAATAACTGTATTCCGAGCAGCAATGT
ATACCTCTTCAGGAGGATATATTGACGATCCATCAGTAAAGGAAAAAGTA
AAAGAGACTGTTGAGGCTGCGATAGACCTTGGCATATATGTGATCATTGA
TTGGCATATCCTTTCAGACAATGACCCGAATATATATAAAGAAGAAGCGA
AGGATTTCTTTGATGAAATGTCAGAGTTGTATGGAGACTATCCGAATGTG
ATATACGAAATTGCAAATGAACCGAATGGTAGTGATGTTACGTGGGACAA
TCAAATAAAACCGTATGCAGAAGAAGTGATTCCGGTTATTCGTGACAATG
ACCCTAATAACATTGTTATTGTAGGTACAGGTACATGGAGTCAGGATGTC
CATCATGCAGCCGATAATCAGCTTGCAGATCCTAACGTCATGTATGCATT
TCATTTTTATGCAGGAACACATGGACAAAATTTACGAGACCAAGTAGATT
ATGCATTAGATCAAGGAGCAGCGATATTTGTTAGTGAATGGGGGACAAGT
GCAGCTACAGGTGATGGTGGTGTGTTTTTAGATGAAGCACAAGTGTGGAT
TGACTTTATGGATGAAAGAAATTTAAGCTGGGCCAACTGGTCTCTAACGC
ATAAGGATGAGTCATCTGCAGCGTTAATGCCAGGTGCAAATCCAACTGGT
GGTTGGACAGAGGCTGAACTATCTCCATCTGGTACATTTGTGAGGGAAAA
AATAAGAGAATCAGCATCTGACAACAATGATCCCATACCGGATCCAGACG
ATGAGAGCTCTAAACCCTGTTGCGATCAATGCGCATGTACGAAATCAAAT
CCTCCACAGTGTCGGTGTTCCGATATGCGTCTGAATTCCTGTCATAGTGC
CTGCAAAAGCTGCGCATGTTATAACCTGTACGGGTGGACCTGTTTTTGCG
TCGACATCACGGACTTCTGCTATGAACCATGTAAACCAAGCGAGTAAAAG
CTTAACTCGAGGTTAACAGAGGACGGATTTCCTGAAGGAAATCCGTTTTT
TTATTTTTAATTAAGAGCTTGGCGTAATCATGGTCATAGCTGTTTCCTGT
GTGAAATTGTTATCCGCTCACAATTCCACACAACATACGAGCCGGAAATA
AAGTGTAAAGCCTGGGGTGCCTAATGAGTGAGCTAACTCACATTAATTGC
GTTGCGCTCACTGCCCGCTTTCCAGTCGGGAAACCTGTCGTGCCAGCTGC
ATTAATGAATCGGCCAACGCGCGGGGAGAGGCGGTTTGCGTATTGGGCGC
```

-continued

```
TCTTCCGCTTCCTCGCTCACTGACTCGCTGCGCTCGGTCGTTCGGCTGCG
GCGAGCGGTATCAGCTCACTCAAAGGCGGTAATACGGTTATCCACAGAAT
CAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACC
CGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCA
GTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAA
CCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCT
GAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTC
TGACGCTCAGTGGAACGAAAACTCACGTTAAGGGATTTTGGTCATGAGAT
TATACAAAAAGGATCTTCACCTAGATCCTTTTAAATTAAAAATGAAGTTT
TAAATCAATCTAAAGTATATATGAGTAAACTTGGTCTGACAGTTACCAAT
GCTTAATCAGTGAGGCACCTATCTCAGCGATCTGTCTATTTCGTTCATCC
ATAGTTGCCTGACTCCCCGTCGTGTAGATAACTACGATACGGGAGGGCTT
ACCATCTGGCCCCAGTGCTGCAATGATACCGCGAGACCCACGCTCACCGG
CTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTCA
TTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCT
CTTACTGTCATGCCATCCGTAAGATGCTTTTCTGTGACTGGTGAGTACTC
AACCAAGTCATTCTGAGAATAGTGTATGCGGCGACCGAGTTGCTCTTGCC
CGGCGTCAATACGGGATAATACCGCGCCACATAGCAGAACTTTAAAGTG
CTCATCATTGGAAAACGTTCTTCGGGGCGAAAACTCTCAAGGATCTTACC
GCTGTTGAGATCCAGTTCGATGTAACCCACTCGTGCACCCAACTGATCTT
CAGCATCTTTTACTTTCACCAGCGTTTCTGGGTGAGCAAAAACAGGAAGG
CAAAATGCCGCAAAAAAGGGAATAAGGGCGACACGGAAATGTTGAATACT
CATACTCTTCCTTTTTCAATATTATTGAAGCATTTATCAGGGTTATTGTC
TCATGAGCGGATACATATTTGAATGTATTTAGAAAAATAAACAAATAGGG
GTTCCGCGCACATTTCCCCGAAAAGTGCCACCTGACGTCTAAGAAACCAT
TATTATCATGACATTAACCTATAAAAATAGGCGTATCACGAGGCCCTTTC
```

-continued
```
GTCTCGCGCGTTTCGGTGATGACGGTGAAAACCTCTGACACATGCAGCTC

CCGGAGACGGTCACAGCTTGTCTGTAAGCGGATGCCGGGAGCAGACAAGC

CCGTCAGGGCGCGTCAGCGGGTGTTGGCGGGTGTCGGGGCTGGCTTAACT

ATGCGGCATCAGAGCAGATTGTACTGAGAGTGCACCATAGATCTGGAGCT

GTAATATAAAAACCTTCTTCAACTAACGGGGCAGGTTAGTGACATTAGAA

AACCGACTGTAAAAAGTACAGTCGGCATTATCTCATATTATAAAAGCCAG

TCATTAGGCCTATCTGACAATTCCTGAATAGAGTTCATAAACAATCCTGC

ATGATAACCATCACAAACAGAATGATGTACCTGTAAAGATAGCGGTAAAT

ATATTGAATTACCTTTATTAATGAATTTTCCTGCTGTAATAATGGGTAGA

AGGTAATTACTATTATTATTGATATTTAAGTTAAACCCAGTAAATGAAGT

CCATGGAATAATAGAAAGAGAAAAAGCATTTTCAGGTATAGGTGTTTTGG

GAAACAATTTCCCCGAACCATTATATTTCTCTACATCAGAAAGGTATAAA

TCATAAAACTCTTTGAAGTCATTCTTTACAGGAGTCCAAATACCAGAGAA

TGTTTTAGATACACCATCAAAAATTGTATAAAGTGGCTCTAACTTATCCC

AATAACCTAACTCTCCGTCGCTATTGTAACCAGTTCTAAAAGCTGTATTT

GAGTTTATCACCCTTGTCACTAAGAAAATAAATGCAGGGTAAAATTTATA

TCCTTCTTGTTTTATGTTTCGGTATAAAACACTAATATCAATTTCTGTGG

TTATACTAAAAGTCGTTTGTTGGTTCAAATAATGATTAAATATCTCTTTT

CTCTTCCAATTGTCTAAATCAATTTTATTAAAGTTCATTTGATATGCCTC

CTAAATTTTTATCTAAAGTGAATTTAGGAGGCTTACTTGTCTGCTTTCTT

CATTAGAATCAATCCTTTTTTAAAAGTCAATATTACTGTAACATAAATAT

ATATTTTAAAAATATCCCACTTTATCCAATTTTCGTTTGTTGAACTAATG

GGTGCTTTAGTTGAAGAATAAAAGACCACATTAAAAAATGTGGTCTTTTG

TGTTTTTTTAAAGGATTTGAGCGTAGCGAAAAATCCTTTTCTTTCTTATC

TTGATAATAAGGGTAACTATTGCCGGATCGTCCTCAGGAGTAGGCGACAT

CGCTAAATAATGATCTATGCGGTGTGAAATACCGCACAGATGCGTAAGGA

GAAAATACCGCATCAGGCGCCATTCGCCATTCAGGCTGCGCAACTGTTGG

GAAGGGCGATCGGTGCGGGCCTCTTCGCTATTACGCCAGCTGGCGAAAGG

GGGATGTGCTGCAAGGCGATTAAGTTGGGTAACGCCAGGGTTTTCCCAGT

CACGACGTTGTAAAACGACGGCCAGT
```

The p2JMagk103-Ink2-BBIt-AV expression vector was used to transform bacterial cells to express BBIt-AV fused to the BCE protein (SEQ ID NO:195)

```
                                    (SEQ ID NO: 195)
AGKDDYSVVEEHGQLSISNGELVNERGEQVQLKGMSSHGLQWYGQFVNYE

SMKWLRDDWGITVFRAAMYTSSGGYIDDPSVKEKVKETVEAAIDLGIYVI

IDWHILSDNDPNIYKEEAKDFFDEMSELYGDYPNVIYEIANEPNGSDVTW

DNQIKPYAEEVIPVIRDNDPNNIVIVGTGTWSQDVHHAADNQLADPNVMY

AFHFYAGTHGQNLRDQVDYALDQGAAIFVSEWGTSAATGDGGVFLDEAQV
```

-continued

```
WIDFMDERNLSWANWSLTHKDESSAALMPGANPTGGWTEAELSPSGTFVR

EKIRESASDNNDPIPDPDDESSKPCCDQCACTKSNPPQCRCSDMRLNSCH

SACKSCACYNLYGWTCFCVDITDFCYEPCKPSE
```

EXAMPLE 8

BBIt-AV Site Saturation Libraries

This example describes experiments that were performed to generate modified variant BBPIs derived from the unmodified BBIt-AV by constructing site saturation libraries comprising substitutions at each of the 39 amino acid positions of the BBIt-AV molecule (SEQ ID NO:187) shown in FIG. 9.

BBIt-AV site-saturation libraries were created essentially as described by Amin et al. (Biotechniques 35: 1134-1140, [2003]) using a modified version of the QuikChange multi site-directed mutagenesis (QCMS) kit from Stratagene (La Jolla, Calif.) as follows. Overlapping forward and reverse primers with the NNS codon in the middle and 17-20 flanking bases were designed for each chosen site, and the sequences for each forward (F) and reverse (R) primer at each of the 66 amino acid positions in the BBI-AV molecule are shown in Table 1. Each mutagenesis reaction contained 50-100 ng template plasmid (p2JMagk103-Ink2-BBIt-AV; SEQ ID NO:194), 0.5 μl forward primer (25 μM), 0.5 μl reverse primer (25 μM), 1 μl dNTP's (QCMS kit), 2.5 μl 10× QCMS reaction buffer, 18.5 μl deionized water, and 1 μl of enzyme blend (QCMS kit), for a total volume of 25 μl. For BBI-AV libraries at residues 10, 11, 13 and 25, only 1 μL of the forward primer (25 μM) was used without the reverse primer. For libraries at residues 6, 37, 38, 50 and 53, the mutagenesis reaction was carried out with 0.5 μl of the forward mutagenic primer in combination with another primer (5'-ctatgcggcatcagagcagattgtac; SEQ ID NO:328 complementary to a sequence in the vector. For the mutagenesis reaction, the thermocycler program used was 1 cycle at 95° for 2 min., followed by 29 cycles of 95° C. for 30 sec, 55° C. for 1 min., and 68° C. for 10 minutes (MJ Research thermocycler). The template DNA was digested by the addition of 0.5-1 μl DpnI (from the QCMS kit) and incubation at 37° C. for 1-4 hours, followed by another addition of 0.5-1 μl DpnI and another incubation at 37° C. for 1-4 hours. The template DNA was obtained from *E. coli* $dam^+$ strains, such as TOP10 (Invitrogen, Carlsbad, Calif., USA), to ensure that it would be susceptible to Dpn I digestion.

For efficient transformation of *B. subtilis*, the DNA in each mutagensis reaction was amplified by rolling circle amplification (RCA) using the Templiphi kit from Amersham. Specifically, 1 μL of the undiluted QCMS reaction was mixed with 5 μL of sample buffer from the Templiphi kit. The mixture was heated for 3 minutes at 95° C. to denature the DNA. The reaction was placed on ice to cool for 2 minutes. Then, 5 μL of reaction buffer and 0.2 μL of phi29 polymerase were added to the reaction and incubated at 30° C. in a MJ Research thermocycler for 5 hours. Finally, the phi29 enzyme in the reaction was heat inactivated by incubation at 65° C. for 10 min in a MJ Research thermocycler. The amplified DNA was diluted 10-100 fold and 1 μL was used to transform 100 μL of competent *B. subtilis* BG6006 cells (Vogtentanz et al., 2007). Aliquots of 25 μL or 75 μL of the transformation mixture were plated on Luria Agar plates supplemented with 5 μg/ml chloramphenicol. After growth, individual transformants were picked to inoculate 200 μl of Luria broth supplemented with 5 μg/ml chloramphenicol in each well of a 96-well microtiter plate. The cultures were grown in a humidified and aerated box at 37° C. and 270 rpm (Innova 4230 incubator, New Brunswick Scientific). After growth, 80 μl of 50% glycerol were added to each well and mixed. A duplicate plate was made by removing 140 μl of the culture from each well and placing it in a new microtiter plate. Both plates were stored at −80° C. One plate was saved as a master and the other was submitted for DNA sequencing (Cogenics, Houston, Tex.) of the individual mutants. For DNA sequencing, an overnight culture of each colony grown in a microtiter plate was diluted 10-40 fold and 2 μL was used in a PCR reaction with Amersham Biosciences Ready-to-go PCR beads and the primers BBI-PCR-F and BBI-PCR-R. The thermo-cycling conditions were one cycle at 95° C. for 5 minutes, followed by 30 cycles of 95° C. for 1 minute, 55° C. for 1 minute and 72° C. for 1 minute, and a final cycle at 72° C. for 7 minutes. The PCR products were treated with Exonuclease I and shrimp alkaline phosphatase (EXOSAP-IT, Amersham Biosciences) or they were column purified before sequencing with the M13 reverse primer.

TABLE 1

NNS mutagenesis primers

| Primer name | Primer Sequence | SEQ ID NO: |
|---|---|---|
| Forward Primers | | |
| BBI1F | GATCCCATACCGGATCCANNSGATGAGAGCTCTAAACC | 196 |
| BBI2F | CCATACCGGATCCAGACNNSGAGAGCTCTAAACCCTG | 197 |
| BBI3F | CATACCGGATCCAGACGATNNSAGCTCTAAACCCTGTTG | 198 |
| BBI4F | CGGATCCAGACGATGAGNNSTCTAAACCCTGTTGCGATC | 199 |
| BBI5F | GATCCAGACGATGAGAGCNNSAAACCCTGTTGCGATCAATG | 200 |
| BBI6F | CAGACGATGAGAGCTCTNNSCCCTGTTGCGATCAATG | 201 |
| BBI7F | GACGATGAGAGCTCTAAANNSTGTTGCGATCAATGCGC | 202 |
| BBI8F | GATGAGAGCTCTAAACCCNNSTGCGATCAATGCGCATG | 203 |
| BBI9F | GAGAGCTCTAAACCCTGTNNSGATCAATGCGCATGTAC | 204 |
| BBI10F | GCTCTAAACCCTGTTGCNNSCAATGCGCATGTACGAAATC | 205 |
| BBI11F | CTAAACCCTGTTGCGATNNSTGCGCATGTACGAAATC | 206 |
| BBI12F | CTAAACCCTGTTGCGATCAANNSGCATGTACGAAATCAAATC | 207 |
| BBI13F | CCTGTTGCGATCAATGCNNSTGTACGAAATCAAATCC | 208 |
| BBI14F | GTTGCGATCAATGCGCANNSACGAAATCAAATCCTCC | 209 |
| BBI15F | GCGATCAATGCGCATGTNNSAAATCAAATCCTCCACAG | 210 |
| BBI16F | GATCAATGCGCATGTACGNNSTCAAATCCTCCACAGTG | 211 |
| BBI17F | CAATGCGCATGTACGAAANNSAATCCTCCACAGTGTCG | 212 |
| BBI18F | GCGCATGTACGAAATCANNSCCTCCACAGTGTCGGTG | 213 |
| BBI19F | CATGTACGAAATCAAATNNSCCACAGTGTCGGTGTTC | 214 |
| BBI20F | GTACGAAATCAAATCCTNNSCAGTGTCGGTGTTCCGATAT | 215 |
| BBI21F | CGAAATCAAATCCTCCANNSTGTCGGTGTTCCGATATG | 216 |
| BBI22F | GAAATCAAATCCTCCACAGNSCGGTGTTCCGATATGCG | 217 |
| BBI23F | CAAATCCTCCACAGTGTNNSTGTTCCGATATGCGTCTG | 218 |
| BBI24F | CAAATCCTCCACAGTGTCGGNNSTCCGATATGCGTCTGAATTC | 219 |
| BBI25F | CTCCACAGTGTCGGTGTNNSGATATGCGTCTGAATTC | 220 |
| BBI26F | CACAGTGTCGGTGTTCCNNSATGCGTCTGAATTCCTG | 221 |
| BBI27F | CAGTGTCGGTGTTCCGATNNSCGTCTGAATTCCTGTCATAG | 222 |
| BBI28F | GTCGGTGTTCCGATATGNNSCTGAATTCCTGTCATAG | 223 |
| BBI29F | GGTGTTCCGATATGCGTNNSAATTCCTGTCATAGTGC | 224 |
| BBI30F | GTTCCGATATGCGTCTGNNSTCCTGTCATAGTGCCTG | 225 |
| BBI31F | CCGATATGCGTCTGAATNNSTGTCATAGTGCCTGCAAAAG | 226 |
| BBI32F | GATATGCGTCTGAATTCCNNSCATAGTGCCTGCAAAAG | 227 |
| BBI33F | ATATGCGTCTGAATTCCTGTNNSAGTGCCTGCAAAAGCTG | 228 |
| BBI34F | GTCTGAATTCTGTCATNNSGCCTGCAAAAGCTGCGC | 229 |
| BBI35F | CTGAATTCCTGTCATAGTNNSTGCAAAAGCTGCGCATG | 230 |
| BBI36F | GAATTCCTGTCATAGTGCCNNSAAAAGCTGCGCATGTTATAA | 231 |
| BBI37F | CCTGTCATAGTGCCTGCNNSAGCTGCGCATGTTATAAC | 232 |
| BBI38F | GTCATAGTGCCTGCAAANNSTGCGCATGTTATAACCTG | 233 |
| BBI39F | CATAGTGCCTGCAAAAGCNNSGCATGTTATAACCTGTAC | 234 |
| BBI40F | GTGCCTGCAAAAGCTGCNNSTGTTATAACCTGTACGG | 235 |
| BBI41F | CCTGCAAAAGCTGCGCANNSTATAACCTGTACGGGTG | 236 |
| BBI42F | GCAAAAGCTGCGCATGTNNSAACCTGTACGGGTGGAC | 237 |
| BBI43F | CAAAAGCTGCGCATGTTATNNSCTGTACGGGTGGACCTG | 238 |
| BBI44F | GCTGCGCATGTTATAACNNSTACGGGTGGACCTGTTTTTG | 239 |
| BBI45F | GCGCATGTTATAACCTGNNSGGGTGGACCTGTTTTTG | 240 |
| BBI46F | CATGTTATAACCTGTACNNSTGGACCTGTTTTTGCGTC | 241 |

TABLE 1-continued

NNS mutagenesis primers

| Primer name | Primer Sequence | SEQ ID NO: |
|---|---|---|
| BBI47F | GTTATAACCTGTACGGGNNSACCTGTTTTTGCGTCGAC | 242 |
| BBI48F | GTTATAACCTGTACGGGTGGNNSTGTTTTTGCGTCGACATC | 243 |
| BBI49F | ATAACCTGTACGGGTGGACCNNSTTTTGCGTCGACATCAC | 244 |
| BBI50F | CTGTACGGGTGGACCTGTNNSTGCGTCGACATCACGGAC | 245 |
| BBI51F | GTACGGGTGGACCTGTTTTNNSGTCGACATCACGGACTTC | 246 |
| BBI52F | GGTGGACCTGTTTTTGCNNSGACATCACGGACTTCTG | 247 |
| BBI53F | GGACCTGTTTTTGCGTCNNSATCACGGACTTCTGCTATG | 248 |
| BBI54F | CCTGTTTTTGCGTCGACNNSACGGACTTCTGCTATGAAC | 249 |
| BBI55F | GTTTTTGCGTCGACATCNNSGACTTCTGCTATGAACC | 250 |
| BBI56F | GTTTTTGCGTCGACATCACGNNSTTCTGCTATGAACCATG | 251 |
| BBI57F | GCGTCGACATCACGGACNNSTGCTATGAACCATGTAAAC | 252 |
| BBI58F | GTCGACATCACGGACTTCNNSTATGAACCATGTAAACC | 253 |
| BBI59F | GACATCACGGACTTCTGCNNSGAACCATGTAAACCAAG | 254 |
| BBI60F | CATCACGGACTTCTGCTATNNSCCATGTAAACCAAGCGAG | 255 |
| BBI61F | CGGACTTCTGCTATGAANNSTGTAAACCAAGCGAGTAAAA | 256 |
| BBI62F | GACTTCTGCTATGAACCANNSAAACCAAGCGAGTAAAAG | 257 |
| BBI63F | CTTCTGCTATGAACCATGTNNSCCAAGCGAGTAAAAGCTTAA | 258 |
| BBI64F | GCTATGAACCATGTAAANNSAGCGAGTAAAAGCTTAAC | 259 |
| BBI65F | CTATGAACCATGTAAACCANNSGAGTAAAAGCTTAACTC | 260 |
| BBI66F | GAACCATGTAAACCAAGCNNSTAAAAGCTTAACTCGAG | 261 |

Reverse Primers

| Primer name | Primer Sequence | SEQ ID NO: |
|---|---|---|
| BBI1R | GGTTTAGAGCTCTCATCSNNTGGATCCGGTATGGGATC | 262 |
| BBI2R | CAGGGTTTAGAGCTCTCSNNGTCTGGATCCGGTATGG | 263 |
| BBI3R | CAACAGGGTTTAGAGCTSNNATCGTCTGGATCCGGTATG | 264 |
| BBI4R | GATCGCAACAGGGTTTAGASNNCTCATCGTCTGGATCCG | 265 |
| BBI5R | CATTGATCGCAACAGGGTTTSNNGCTCTCATCGTCTGGATC | 266 |
| BBI6R | CATTGATCGCAACAGGGSNNAGAGCTCTCATCGTCTG | 267 |
| BBI7R | GCGCATTGATCGCAACASNNTTTAGAGCTCTCATCGTC | 268 |
| BBI8R | CATGCGCATTGATCGCASNNGGGTTTAGAGCTCTCATC | 269 |
| BBI9R | GTACATGCGCATTGATCSNNACAGGGTTTAGAGCTCTC | 270 |
| BBI10R | GATTTCGTACATGCGCATTGSNNGCAACAGGGTTTAGAGC | 271 |
| BBI11R | GATTTCGTACATGCGCASNNATCGCAACAGGGTTTAG | 272 |
| BBI12R | GATTTGATTTCGTACATGCSNNTTGATCGCAACAGGGTTTAG | 273 |
| BBI13R | GGATTTGATTTCGTACASNNGCATTGATCGCAACAGG | 274 |
| BBI14R | GGAGGATTTGATTTCGTSNNTGCGCATTGATCGCAAC | 275 |
| BBI15R | CTGTGGAGGATTTGATTTSNNACATGCGCATTGATCGC | 276 |
| BBI16R | CACTGTGGAGGATTTGASNNCGTACATGCGCATTGATC | 277 |
| BBI17R | CGACACTGTGGAGGATTSNNTTTCGTACATGCGCATTG | 278 |
| BBI18R | CACCGACACTGTGGAGGSNNTGATTTCGTACATGCGC | 279 |
| BBI19R | GAACACCGACACTGTGGSNNATTTGATTTCGTACATG | 280 |
| BBI20R | ATATCGGAACACCGACACTGSNNAGGATTTGATTTCGTAC | 281 |
| BBI21R | CATATCGGAACACCGACASNNTGGAGGATTTGATTTCG | 282 |
| BBI22R | CGCATATCGGAACACCGSNNCTGTGGAGGATTTGATTC | 283 |
| BBI23R | CAGACGCATATCGGAACASNNACACTGTGGAGGATTTG | 284 |
| BBI24R | GAATTCAGACGCATATCGGASNNCCGACACTGTGGAGGATTTG | 285 |
| BBI25R | GAATTCAGACGCATATCSNNACACCGACACTGTGGAG | 286 |
| BBI26R | CAGGAATTCAGACGCATSNNGGAACACCGACACTGTG | 287 |
| BBI27R | CTATGACAGGAATTCAGACGSNNATCGGAACACCGACACTG | 288 |
| BBI28R | CTATGACAGGAATTCAGSNNCATATCGGAACACCGAC | 289 |
| BBI29R | GCACTATGACAGGAATTSNNACGCATATCGGAACACC | 290 |
| BBI30R | CAGGCACTATGACAGGASNNCAGACGCATATCGGAAC | 291 |
| BBI31R | CTTTTGCAGGCACTATGACASNNATTCAGACGCATATCGG | 292 |
| BBI32R | CTTTTGCAGGCACTATGSNNGGAATTCAGACGCATATC | 293 |
| BBI33R | CAGCTTTTGCAGGCACTSNNACAGGAATTCAGACGCATAT | 294 |
| BBI34R | GCGCAGCTTTTGCAGGCSNNATGACAGGAATTCAGAC | 295 |

TABLE 1-continued

NNS mutagenesis primers

| Primer name | Primer Sequence | SEQ ID NO: |
|---|---|---|
| BBI35R | CATGCGCAGCTTTTGCASNNACTATGACAGGAATTCAG | 296 |
| BBI36R | TTATAACATGCGCAGCTTTTSNNGGCACTATGACAGGAATTC | 297 |
| BBI37R | GTTATAACATGCGCAGCTSNNGCAGGCACTATGACAGG | 298 |
| BBI38R | CAGGTTATAACATGCGCASNNTTTGCAGGCACTATGAC | 299 |
| BBI39R | GTACAGGTTATAACATGCSNNGCTTTTGCAGGCACTATG | 300 |
| BBI40R | CCGTACAGGTTATAACASNNGCAGCTTTTGCAGGCAC | 301 |
| BBI41R | CACCCGTACAGGTTATASNNTGCGCAGCTTTTGCAGG | 302 |
| BBI42R | GTCCACCCGTACAGGTTSNNACATGCGCAGCTTTTGC | 303 |
| BBI43R | CAGGTCCACCCGTACAGSNNATAACATGCGCAGCTTTTG | 304 |
| BBI44R | CAAAAACAGGTCCACCCGTASNNGTTATAACATGCGCAGC | 305 |
| BBI45R | CAAAAACAGGTCCACCCSNNCAGGTTATAACATGCGC | 306 |
| BBI46R | GACGCAAAAACAGGTCCASNNGTACAGGTTATAACATG | 307 |
| BBI47R | GTCGACGCAAAAACAGGTSNNCCCGTACAGGTTATAAC | 308 |
| BBI48R | GATGTCGACGCAAAAACASNNCCACCCGTACAGGTTAAC | 309 |
| BBI49R | GTGATGTCGACGCAAAASNNGGTCCACCCGTACAGGTTAT | 310 |
| BBI50R | GTCCGTGATGTCGACGCASNNACAGGTCCACCCGTACAG | 311 |
| BBI51R | GAAGTCCGTGATGTCGACSNNAAAACAGGTCCACCCGTAC | 312 |
| BBI52R | CAGAAGTCCGTGATGTCSNNGCAAAAACAGGTCCACC | 313 |
| BBI53R | CATAGCAGAAGTCCGTGATSNNGACGCAAAAACAGGTCC | 314 |
| BBI54R | GTTCATAGCAGAAGTCCGTSNNGTCGACGCAAAAACAGG | 315 |
| BBI55R | GGTTCATAGCAGAAGTCSNNGATGTCGACGCAAAAAC | 316 |
| BBI56R | CATGGTTCATAGCAGAASNNCGTGATGTCGACGCAAAAAC | 317 |
| BBI57R | GTTTACATGGTTCATAGCASNNGTCCGTGATGTCGACGC | 318 |
| BBI58R | GGTTTACATGGTTCATASNNGAAGTCCGTGATGTCGAC | 319 |
| BBI59R | CTTGGTTTACATGGTTCSNNGCAGAAGTCCGTGATGTC | 320 |
| BBI60R | CTCGCTTGGTTTACATGGSNNATAGCAGAAGTCCGTGATG | 321 |
| BBI61R | TTTTACTCGCTTGGTTTACASNNTTCATAGCAGAAGTCCG | 322 |

TABLE 1-continued

NNS mutagenesis primers

| Primer name | Primer Sequence | SEQ ID NO: |
|---|---|---|
| BBI62R | CTTTTACTCGCTTGGTTTSNNTGGTTCATAGCAGAAGTC | 323 |
| BBI63R | TTAAGCTTTTACTCGCTTGGSNNACATGGTTCATAGCAGAAG | 324 |
| BBI64R | GTTAAGCTTTTACTCGCTSNNTTTACATGGTTCATAGC | 325 |
| BBI65R | GAGTTAAGCTTTTACTCSNNTGGTTTACATGGTTCATAG | 326 |
| BBI66R | CTCGAGTTAAGCTTTTASNNGCTTGGTTTACATGGTTC | 327 |

The cultures in each master plate were thawed and a pin replicator was used to inoculate a new sterile microtiter plate containing 150 µl of Luria broth with 5 µg/ml chloramphenicol in each well. The plates were grown for ~10 hrs in a humidified and aerated box as described above. For controls, the cultures in two wells were replaced with BBI and BBI-AV cultures that had been grown concurrently in 15 ml culture tubes (5 ml of Luria broth with 5 µg/ml chloramphenicol). After the cultures were grown, the plate was used to inoculate two duplicate 96-well filter plates (Millipore, MSGV2210) containing 150 µl of MBD medium (Vogtentanz et al., 2007) with 5 µg/ml chloramphenicol in each well by using a pin replicator. The duplicate plates were grown for ~14 hours (as above, with plastic spacers placed between the stacked plates to allow for efficient air flow around the plates) and then 2-mecaptoethanol was added to each well in one of the plates to a final concentration of 2 mM. The plates were then grown for an additional ~46 hours. The 96-well filter plates containing the culture broth (with or without added 2-mecaptoethanol) were then assayed for BBI and BCE activity.

EXAMPLE 9

Primary Screening of BBIt-AV Variants

BBI and BCE Activity Assays to Determine Variants Having the Highest BBIt-AV:BCE Activity Ratio In this Example, methods are provided for assessing the effect of the amino acid substitutions introduced into the modified variant BBIt-AVs generated according to the site-saturation methods. The trypsin inhibitory activity of the modified BBIt-AV generated by the site-saturation methods described above was measured and compared to the trypsin inhibitory activity of the control wild-type BBI (SEQ ID NO:13; BBI-wt or sBBI) and the control unmodified BBIt-AV (SEQ ID NO:187). It is not intended that the present invention be limited to these specific methods, as other suitable methods find use.

Trypsin Inhibitory Assay: BBI Activity Determination

The relative concentration of active control and modified BBIt-AV's was determined by a trypsin inhibitory assay using purified sBBI as a standard as described above. For some samples, the active BBI concentration was measured by residual trypsin activity according to the method described by Flecker (Flecker, P. FEBS Lett. 252:153-157 [1989]; Vogtentanz et al. supra).

Libraries were analyzed using dilutions of cultures grown in 96-well plates. Typically, the culture broth from each well was diluted (200 fold) in Assay Buffer (100 mM Tris pH 8.6, 0.005% Tween 80) and transferred to a second microtiter plate (CoStar 9017, Corning, Inc., Corning, N.Y.). Then, 20 µl of the diluted samples were transferred to a third microtiter plate. A standard curve was created by adding 20, 10, 5 or 2.5 µl of the diluted sBBI (SEQ ID NO:13) control culture to empty wells. Then, 80 µL of 50 ng/ml trypsin (bovine pancreatic trypsin, Worthington Biochemical Corp., Lakewood, N.J.) (prepared from a 1 mg/mL stock solution diluted into Assay Buffer) was added to each well of the plate. The reactions were mixed and incubated 15 min at room temperature. After the incubation, 100 µL of 0.5 mg/ml trypsin substrate (succinyl-Ala-Ala-Pro-Arg-para-nitroanilide, Bachem Bioscience, Inc., King of Prussia, Pa.), diluted in Assay Buffer from a 100 mg/ml solution in DMSO, was added to each well, mixed, and the absorbance at 405 nm was monitored for 15 min, with 1 time point recorded every 12 sec using a Spectra Max 250 (Molecular Devices). The data points were used to determine the rate for each reaction. The standard curve was generated by plotting the reaction rate versus the BBI volume and was fitted to a four-parameter equation. All data fitting was done using software supplied by the manufacturer (Molecular Devices Corp., Sunnyvale, Calif.). The activity of each BBIt-AV variant was calculated from the standard curve. Thus, the activities of all modified variant proteins were determined relative to the activity in the sBBI control (BBI-WT) culture. If the majority of the data did not fall near the $IC_{50}$ of the standard curve, a new dilution plate was made and assayed.

Cellulase Enzyme Activity Assay: BCE Assay

The concentration of BCE was determined by an activity assay using purified BCE as a standard as described above and by (Vogtentanz et al. 2007). For the analysis of libraries grown in 96-well microtiter plates, 20 µl of culture broth were transferred to each well of a new microtiter plate. A standard curve was created by adding 20, 10, 5 or 2.5 µl of the diluted BBI-WT control culture to these empty wells. Then, 180 µl of the BCE substrate (0.25 µg/ml in Assay Buffer), 4-nitrophenyl β-D-cellobioside (Sigma, St. Louis, Mo.), was added to the plate. The plate was mixed and the absorbance at 405 nm monitored for 15 min, with 1 time point recorded every 12 s using a Spectra Max 250 (Molecular Devices Corp., Sunnyvale, Calif.). The data points were used to determine the rate for each reaction. The standard curve was generated by plotting rate versus culture volume and was fit to a quadratic curve. The BCE concentration in each variant culture was determined relative to the standard control culture.

Enzyme Activity Ratio: BBIt-AV:BCE Ratios

From the microtiter plate assay results, the BBIt-AV:BCE activity ratio of each well was determined by dividing the relative BBIt-AV trypsin inhibitory activity values by the relative BCE activity values. The data were sorted based on the BBIt-AV:BCE activity ratio. Modified variants with the highest BBIt-AV:BCE activity ratios were selected and subjected to a secondary screening described below.

Analysis of Enzyme Activity Ratio BBIt-AV:BCE—Secondary Screening of Variants

In this example, modified BBIt-AVs having improved BBIt-AV:BCE activity relative to that of the control unmodified BBIt-AV when grown in the presence or absence of a reducing agent (2-mercaptoethanol), as determined in the primary screen, were arrayed and assayed in quadruplicate in a secondary screen. Initially, only the polynucleotides encoding each of the modified BBIt-AVs having the greatest BBIt-AV:BCE ratio as determined in the secondary screen were sequenced. Later, all BBIt-AV clones were sequenced.

Quadruplicate Testing in Microtiter Plates—Secondary Screen

For each plate, twenty-two samples of cultures containing modified BBIt-AVs selected from the initial screen, and two samples of control cultures containing sBBI and unmodified BBIt-AV, were grown for ~10 hrs in 5 ml of Luria broth with 5 ppm chloramphenicol (37° C., 250 rpm) in 15 ml culture tubes. Then, 150 µl of each of the 24 cultures were arrayed in quadruplicate in a 96-well microtiter plate. This arrayed plate was then used to inoculate duplicate filter plates (Millipore, MSGV2210) containing 150 µl of MBD medium with 5 µg/ml chloramphenicol per well by using a pin replicator. The plated cultures were grown (in the presence and absence of 2-β-mercaptoethanol (βME), and the BBI-AV:BCE ratios were determined and analyzed as described above.

FIG. 10 shows an example of the effect of all possible 19 amino acid substitutions at position 29 of SEQ ID NO:187 on the trypsin inhibitory activity of the modified variant BBIt. The data show the ratio of BBI and BCE activities determined from quadruplicate measurements of BCE and trypsin activities of the modified BBI-AVs having a single amino acid substitution at position 29 of SEQ ID NO:187.

EXAMPLE 10

Selection for Improved Modified BBIt-AVs with Known Amino Acid Substitutions

In this example, site saturation libraries were constructed to generate a complete set of amino acid substitutions at sites identified in the initial screen that resulted in BBIt-AVs having improved trypsin inhibitory activity when compared to the trypsin inhibitory activity of the unmodified parent BBI-AV. In addition, a complete set of amino acid substitutions at sites that had not been previously substituted with all possible 19 amino acids were generated by site-directed mutagenesis. A total of 39 site saturation libraries were generated and quadruplicate activity measurements of BBI trypsin inhibitory activity and BCE activity were analyzed to determine the single substitutions that resulted in modified BBIt-AV molecules having trypsin inhibitory activity that was greater than that of the control BBI molecules i.e. sBBI and unmodified BBIt-AV. The positions of the amino acids that were substituted in the unmodified BBIt-AV are shown in FIG. 9.

Construction of a Second Set of Site-Saturation Libraries at Sites 18, 38 and 61

First, to aid library construction, a synthetic gene was synthesized to replace the EcoRI site with a SphI site between the region coding for the trypsin inhibitory loop and the region encoding the chymotypsin inhibitory loop in the 2BBIck81 coding region (the location of the EcoRI site is shown in FIG. 3). The synthetic gene sequence is: 5'-GGATC-CAGACGATGAGAGCTCTAAACCTTGT-TGCGATCAATGCGCTTGTACAAAAT CAAACCCTC-CACAATGTCGTTGTTCTGATATGCGTTTAAATAGCT-GTCATTCTGCAT
GCAAATCATGTGCTTGCTATAACCTT-TACGGTTGGACATGTTTCTGCGTCGACATCA CTGACTTCTGCTATGAACCATGTAAAC-CTTCTGAATAAAAGCTT (SEQ ID NO:329). This synthetic gene was cloned into p2JMagk103-Ink2-BBIt-AV as a BamHI-HindIII fragment and the resulting vector was called p2JMagk103-Ink2-BBIt-AVsph.

Site-saturation libraries were constructed at positions 18, 37 and 61 using oligonucleotide cassettes as follows.

A site-saturation library at site 18 was constructed by annealing oligonucleotides 5'-GTACAAAATCANNSC-CTCCACAATGTCGTTGTTCTGATAT-GCGTTTAAATAGCTGTC ATTCTGCATG (SEQ ID NO:330) and 5'-CAGAATGACAGCTATTTAAACG-CATATCAGAACAACGACATTGTGGAGGSNNTGATT TT (SEQ ID NO:331) and ligating the resulting cassette into the BsrGI and SphI sites of p2JMagk103-Ink2-BBI-AVsph.

A site-saturation library at site 37 was constructed by annealing the oligonucleotides 5'-TCGACGCAGAAACAT-GTCCAACCGTAAAGGTTATAGCAAGCA-CATGASNNGCATG (SEQ ID NO:332) and 5'-CNNST-CATGTGCTTGCTATAACCTTTACGGTTGGACATGTT-TCTGCG (SEQ ID NO:333) and ligating the resulting cassette into the SalI and SphI sites of p2JMagk103-Ink2-BBI-AVsph.

The site-saturation library at position 61 was made by annealing oligonucleotide 5'-TCGACATCACTGACTTCT-GCTATGAANNSTGTAAACCTTCTGAATAAA (SEQ ID NO:334) with the two oligonucleotides 5'-TTCATAGCA-GAAGTCAGTGATG (SEQ ID NO:335) and 5'-AGCTTT-TATTCAGAAGGTTTACA (SEQ ID NO:336) and ligating this cassette into the SalI and HindIII sites of p2JMagk103-Ink2-BBIt-AVsph.

The ligation mixes were used to transform *E. coli* TOP10 cells (Invitrogen). Ninety six transformants were selected, and the amino acid substitution present in each clone was determined by DNA sequencing. Plasmids isolated from each single amino acid substitution were then used to transform *B. subtilis*.

Generation of Amino Acid Substitutions by Site Directed Mutagenesis

Amino acid substitutions at selected sites were constructed by ligating an oligonucleotide or an oligonucleotide cassette into the of p2JMagk103-Ink2-BBI-AVsph vector using the appropriate restriction sites. The substitutions, oligonucleotide sequences and restriction sites used are shown in Table 2.

TABLE 2

Oligonucleotides for site directed muatagenesis

| Amino Acid Substitution(s) | Oligonucleotide Pairs Sequence(s) | Restriction Sites |
|---|---|---|
| A13Y | 5'-Phos-GTACAGTAGCATTGATCGCAACAAGGTTTAGAGCT (SEQ ID NO: 337) | SacI & BsrGI |
| R23D, E | 5'-Phos-GTACAAAATCAAACCCTCCACAATGTGANTGTTCTGATATGCGTTTAAATAGCTGTCATTCTGCATG (SEQ ID NO: 338) 5'-CAGAATGACAGCTATTTAAACGCATATCAGAACANTCACATTGTGGAGGGTTTGATTTT (SEQ ID NO: 339) | BsrGI & SphI |
| S25M | 5'-Phos-GTACAAAATCAAACCCTCCACAATGTCGTTGTATGGATATGCGTTTAAATAGCTGTCATTCTGCATG (SEQ ID NO: 340) 5'-CAGAATGACAGCTATTTAAACGCATATCCATACAACGACATTGTGGAGGGTTTGATTTT (SEQ ID NO: 341) | BsrGI & SphI |
| S25W | 5'-Phos-CTACAAAATCAAACCCTCCACAATGTCGTTGTTGGGATATGCGTTTAAATAGCTGTCATTCTGCATG (SEQ ID NO: 342) 5'-CAGAATGACAGCTATTTAAACGCATATCCCAACAACGACATTGTGGAGGGTTTGATTTT (SEQ ID NO: 343) | BsrGI & SphI |
| S25A, V, G | 5'-Phos-GTACAAAATCAAACCCTCCACAATGTCGTTGTGBAGATATGCGTTTAAATAGCTGTCATTCTGCATG (SEQ ID NO: 344) 5'-CAGAATGACAGCTATTTAAACGCATATCTVCACAACGACATTGTGGAGGGTTTGATTTT (SEQ ID NO: 345) | BsrGI & SphI |
| S25N, Q, K, H | 5'-Phos-GTACAAAATCAAACCCTCCACAATGTCGTTGTMAWGATATGCGTTTAAATAGCTGTCATTCTGCATG (SEQ ID NO: 346) 5'-CAGAATGACAGCTATTTAAACGCATATCWTKACAACGACATTGTGGAGGGTTTGATTTT (SEQ ID NO: 347) | BsrGI & SphI |
| M27W | 5'-Phos-GTACAAAATCAAACCCTCCACAATGTCGTTGTTCTGATTGGCGTTTAAATAGCTGTCATTCTGCATG (SEQ ID NO: 348) 5'-CAGAATGACAGCTATTTAAACGCCAATCAGAACAACGACATTGTGGAGGGTTTGATTTT (SEQ ID NO: 349) | BsrGI & SphI |

TABLE 2-continued

Oligonucleotides for site directed muatagenesis

| Amino Acid Substitution(s) | Oligonucleotide Pairs Sequence(s) | Restriction Sites |
|---|---|---|
| M27H | 5'-Phos-GTACAAAATCAAACCCTCCACAATGTCGTTGT<br>TCTGATCACCGTTTAAATAGCTGTCATTCTGCATG<br>(SEQ ID NO: 350)<br>5'-CAGAATGACAGCTATTTAAACGGTGATCAGAACAACGA<br>CATTGTGGAGGGTTTGATTTT<br>(SEQ ID NO: 351) | BsrGI & SphI |
| M27G, A, V, D | 5'-Phos-GTACAAAATCAAACCCTCCACAATGTCGTTGT<br>TCTGATGNTCGTTTAAATAGCTGTCATTCTGCATG<br>(SEQ ID NO: 352)<br>5'-CAGAATGACAGCTATTTAAACGANCAT-<br>CAGAACAACGAC<br>ATTGTGGAGGGTTTGATTTT<br>(SEQ ID NO: 353) | BsrGI & SphI |
| M27F, I | 5'-Phos-GTACAAAATCAAACCCTCCACAATGTCGTTGT<br>TCTGATWTTCGTTTAAATAGCTGTCATTCTGCATG<br>(SEQ ID NO: 354)<br>5'-CAGAATGACAGCTATTTAAACGAAWATCAGAACAACGA<br>CATTGTGGAGGGTTTGATTTT<br>(SEQ ID NO: 355) | BsrGI & SphI |
| L29I | 5'-Phos-GTACAAAATCAAACCCTCCACAATGTCGTTGT<br>TCTGATATGCGTATTAATAGCTGTCATTCTGCATG<br>(SEQ ID NO: 356)<br>5'-CAGAATGACAGCTATTAATACGCATATCAGAACAACGA<br>CATTGTGGAGGGTTTGATTTT<br>(SEQ ID NO: 357) | BsrGI & SphI |
| L29D, E | 5'-Phos-GTACAAAATCAAACCCTCCACAATGTCGTTGT<br>TCTGATATGCGTGANAATAGCTGTCATTCTGCATG<br>(SEQ ID NO: 358)<br>5'-CAGAATGACAGCTATTNTCACGCATATCAGAACAACGA<br>CATTGTGGAGGGTTTGATTTT<br>(SEQ ID NO: 359) | BsrGI & SphI |
| S31M | 5'-Phos-GTACAAAATCAAACCCTCCACAATGTCGTTGT<br>TCTGATATGCGTTTAAATATGTGTCATTCTGCATG<br>(SEQ ID NO: 360)<br>5'-CAGAATGACACATATTTAAACGCATATCAGAACAACGA<br>CATTGTGGAGGGTTTGATTTT<br>(SEQ ID NO: 361) | BsrGI & SphI |
| S31D, E, Y | 5'-Phos-GTACAAAATCAAACCCTCCACAATGTCGTTGT<br>TCTGATATGCGTTTAAATKAWTGTCATTCTGCATG<br>(SEQ ID NO: 362)<br>5'-CAGAATGACAWTMATTTAAACGCATATCAGAACAACGA<br>CATTGTGGAGGGTTTGATTTT<br>(SEQ ID NO: 363) | BsrGI & SphI |
| S31Q, H | 5'-Phos-GTACAAAATCAAACCCTCCACAATGTCGTTGT<br>TCTGATATGCGTTTAAATCANTGTCATTCTGCATG<br>(SEQ ID NO: 364)<br>5'-CAGAATGACANTGATTTAAACGCATATCAGAACAACGA<br>CATTGTGGAGGGTTTGATTTT<br>(SEQ ID NO: 365) | BsrGI & SphI |
| S34I | 5'-Phos-GTACAAAATCAAACCCTCCACAATGTCGTTGT<br>TCTGATATGCGTTTAAATAGCTGTCATATCGCATG<br>(SEQ ID NO: 366)<br>5'-CGATATGACAGCTATTTAAACGCATATCAGAACAACGA<br>CATTGTGGAGGGTTTGATTTT<br>(SEQ ID NO: 367) | BsrGI & SphI |
| S34W | 5'-Phos-GTACAAAATCAAACCCTCCACAATGTCGTTGT<br>TCTGATATGCGTTTAAATAGCTGTCATTGGGCATG<br>(SEQ ID NO: 368)<br>5'-CCCAATGACAGCTATTTAAACGCATATCAGAACAACGA<br>CATTGTGGAGGGTTTGATTTT<br>(SEQ ID NO: 369) | BsrGI & SphI |

TABLE 2-continued

Oligonucleotides for site directed muatagenesis

| Amino Acid Substitution(s) | Oligonucleotide Pairs Sequence(s) | Restriction Sites |
|---|---|---|
| S34R, Q | 5'-Phos-GTACAAAATCAAACCCTCCACAATGTCGTTGT<br>TCTGATATGCGTTTAAATAGCTGTCATCRAGCATG<br>(SEQ ID NO: 370)<br>5'-CTYGATGACAGCTATTTAAACGCATATCAGAACAACGA<br>CATTGTGGAGGGTTTGATTTT<br>(SEQ ID NO: 371) | BsrGI & SphI |
| S34D, E | 5'-Phos-GTACAAAATCAAACCCTCCACAATGTCGTTGT<br>TCTGATATGCGTTTAAATAGCTGTCATGANGCATG<br>(SEQ ID NO: 372)<br>5'-CNTCATGACAGCTATTTAAACGCATATCAGAACAACGA<br>CATTGTGGAGGGTTTGATTTT<br>(SEQ ID NO: 373) | BsrGI & Sph |
| A40V, D | 5'-Phos-TCGACGCAGAAACATGTCCAACCGTAAAGGT<br>TATAGCAAWCACATGATTTGCATG<br>(SEQ ID NO: 374)<br>5'-CAAATCATGTGWTTGCTATAACCTTTACGGTTGGACAT<br>GTTTCTGCG<br>(SEQ ID NO: 375) | SphI & SalI |
| A40H, P | 5'-Phos-TCGACGCAGAAACATGTCCAACCGTAAAGGT<br>TATAGCAAKGACATGATTTGCATG<br>(SEQ ID NO: 376)<br>5'-CAAATCATGTCMTTGCTATAACCTTTACGGTTGGACAT<br>GTTTCTGCG<br>(SEQ ID NO: 377) | SphI & SalI |
| A40Y, W | 5'-Phos-TCGACGCAGAAACATGTCCAACCGTAAAGGT<br>TATAGCAMYAACATGATTTGCATG<br>(SEQ ID NO: 378)<br>5'-CAAATCATGTTRKTGCTATAACCTTTACGGTTGGACAT<br>GTTTCTGCG<br>(SEQ ID NO: 379) | SphI & SalI |
| F50D | 5'-Phos-TCGACGCAATCACATGTCCAACCGTAAAGGTT<br>ATAGCAAGCACATGATTTGCATG<br>(SEQ ID NO: 380)<br>5'-CAAATCATGTGCTTGCTATAACCTTTACGGTTGGACAT<br>GTGATTGCG<br>(SEQ ID NO: 381) | SphI & SalI |
| F50Q, P | 5'-Phos-TCGACGCATKGACATGTCCAACCGTAAAGGTT<br>ATAGCAAGCACATGATTTGCATG<br>(SEQ ID NO: 382)<br>5'-CAAATCATGTGCTTGCTATAACCTTTACGGTTGGACAT<br>GTCMATGCG<br>(SEQ ID NO: 383) | SphI & SalI |
| F50S, R | 5'-Phos-TCGACGCAKCTACATGTCCAACCGTAAAGGTT<br>ATAGCAAGCACATGATTTGCATG<br>(SEQ ID NO: 384)<br>5'-CAAATCATGTGCTTGCTATAACCTTTACGGTTGGACAT<br>GTAGMTGCG<br>(SEQ ID NO: 385) | SphI & SalI |
| V52D | 5'-Phos-CAAATCATGTGCTTGCTATAACCTTTACGGTT<br>GGACATGTTTCTGCGATGACATCACTGACTTCTGCTATGAA<br>CCATGTAAACCTTCTGAATAAA<br>(SEQ ID NO: 386)<br>5'-AGCTTTTATTCAGAAGGTTTACATGGTTCATAGCAGAA<br>GTCAGTGATGTCATCGCAGAAACATGTCCAACCGTAAAGGT<br>TATAGCAAGCACATGATTTGCATG<br>(SEQ ID NO: 387) | SphI & HindIII |

Secondary Screening of Individual Amino Acid Substitutions: Quadruplicate Testing in Microtiter Plates For each chosen site, clones were selected corresponding to individual amino acid substitutions. These clones were grown, along with cultures of BBI-WT, BBIt-AV and BBIt-AV-F50T as controls, in 5 ml of Luria broth with 5 ppm chloramphenicol (37° C., 250 rpm) in 15 ml culture tubes for ~10 hrs at 37° C. One hundred and fifty microliter aliquots of each the cultures were arrayed in the wells of a 96-well microtiter plate, 4 wells for each amino acid substitution and each control. Each culture grown in the arrayed plate was then used to inoculate duplicate filter plates (Millipore, MSGV2210) containing 150 µl of MBD medium with 5 µg/ml chloramphenicol per well by using a pin replicator. The cultures in the plates were grown in the presence and absence of 2-mercaptoethanol and analyzed as described above. BBIt-AV-F50T is a modified BBIt-AV that was identified as having an initial BBIt-AV:BCE activity ratio prior to activation that was comparable to that of the unmodified BBIt-AV parent, but which has a three-fold greater BBIt-AV:BCE activity ratio than that of the unmodified BBIt-AV after activation with a reducing agent such as 2-mercaptoethanol.

For each site, the BBI:BCE activity ratio was determined for each well and the average values for the quadruplicate measurements was calculated. The activity ratios for the individual amino acid substitutions were compared to the ratios calculated for unmodified parent BBIt-AV (SEQ ID NO:187), the wild-type BBI (SEQ ID NO:13) and the modified BBIt-AV named BBIt-AV-F50T.

FIGS. 11A and 11B show the average of the quadruplicate determinations of the BBI:BCE ratio determined in the presence of 2-mercaptoethanol (BME) relative to that determined for the sBBI for each of the substitutions at positions 50 and 37, respectively.

Overall, the data show single amino acid substitutions made at 16 of the 66 positions/sites in the parent BBIt-AV molecule resulted in BBIt-AV variants that had trypsin inhibitory activity equal or greater than that of the precursor BBIt-AV (data summarized in Table 3). Of all the single site substitutions, F50R resulted in the best BBIt-AV:BCE-activity ratio, while several substitutions at position 50 produced modified variant BBIt-AVs having a four-fold greater BBIt-AV:BCE activity ratios than that of the precursor unmodified BBIt-AV, and that were comparable to that of the wild-type inhibitor (FIG. 11A-B).

These data show that a single substitution in the BBI-AV molecule can have a significant effect on the activity of the BBI-AV.

TABLE 3

Substitutions that result in modified BBIt-AV molecules with greater BBI:BCE activity ratios than the unmodified BBIt-AV

| Position | Native Amino Acid | Improved Substitutions (with BME) |
|---|---|---|
| 1 | D | A, P, |
| 4 | S | V (4D13 insert)* |
| 5 | S | P, A |
| 11 | Q | G |
| 13 | A | Y, I, F, M, L V, K, R |
| 18 | N | I, V |
| 25 | S | K N, W, I, A, R |
| 27 | M | H, R, K, V, A, Q |
| 29 | L | R, K, P |
| 31 | S | Q, H, E, A, R, W, K, T |
| 38 | S | N, K, R |
| 40 | A | H, K, Q, R, Y |
| 50 | F | R, Q, K, T, V, M, S |

TABLE 3-continued

Substitutions that result in modified BBIt-AV molecules with greater BBI:BCE activity ratios than the unmodified BBIt-AV

| Position | Native Amino Acid | Improved Substitutions (with BME) |
|---|---|---|
| 52 | V | K, T, R, Q, L, H, A, M, S, E |
| 55 | T | M |
| 65 | S | E D |

*The 4D13 insert is a 13 amino acid sequence that was added to the N-terminus of the BBI protein as described below.

EXAMPLE 11

Selection of Modified Variants Having Improved Purification Yield

In this example, the methods described were used to identify modified BBIt-AVs containing single amino acid substitutions that retained trypsin inhibitory activity while being produced at yields greater than the corresponding unmodified precursor BBIt-AV.

Modified BBI-AVs that had been selected for having the greatest BBIt-AV:BCE activity ratio in the quadruplicate plate screens were further tested in a shake flask screen that was designed to mimic the acid/heat treatment that is used during the purification process to cleave the BBIt-AV from the BCE:BBIt-AV fusion protein. Thus, modified BBIt-AVs that retained a BBI:BCE activity ratio greater than that of the unmodified BBI-AV following acid/heat treatment were identified as modified BBIt-AVs that would be produced at yields greater than that of the unmodified precursor BBIt-AV.

After activation with reducing agent, e.g. 2-mercaptoethanol, a higher BBIt-AV:BCE activity ratio indicates that a given amino acid substitution has significantly increased the fraction of molecules with at least a correctly folded trypsin inhibitory loop. However, two different amino acid substitutions with similar BBIt-AV:BCE activity ratios could have somewhat different total yields after purification. For example, V52L and M27A activate to similar levels but M27A has about 40% better yield after acid/heat treatment. Thus, variants selected in the first screens as "good activators" were further evaluated by a second criterion that was developed to better predict purification yield.

Shake Flask Screen: Testing for the Purification Yield

To increase expression, the gene copy of the selected clones was amplified by sequentially streaking colonies on Luria agar plates with 25 µg/ml chloramphenicol until the growth rate was similar to growth on Luria agar plates without chloramphenicol. Cultures of the selected variants and controls were grown in 3 ml Luria broth with 25 µg/ml chloramphenicol in 15 ml tubes for ~10 h. These cultures (30 µl) were then used to inoculate 30 ml of MBD medium in 250 ml baffled shake flasks and grown at 37° C. and 225 rpm for ~60 h.

For selection of the variants with the best yields, the culture broths were processed as follows. The broth was first activated by mixing 20 ml of broth with 20 ml of 0.25 M glycine buffer (pH 9.3) and the pH was adjusted to 9.0 with 50% NaOH. Then, 2-mercaptoethanol was added to the diluted cultures to a final concentration of 2 mM and the cultures were incubated overnight at room temperature with gentle shaking. The BBIt-AV moiety was then cleaved from the fusion protein by acid/heat treatment, which was accomplished by first adjusting the pH of the activated broth to pH 1.9-2.0 with sulfuric acid, and followed by incubation at 60° C. for 16 hours, with shaking. The BBIt-AV-BCE fusion protein and the BCE catalytic domain are not soluble at pH 2, whereas the free BBI species is soluble. After the cleavage reaction, the insoluble material was removed by centrifugation (5 min. at 3,000 rpm) and the supernatant was analyzed for trypsin inhibitory activity as described above. The BBI activity was also determined for the starting material and for the samples taken after activation. The BCE activity of the starting material was also determined as described above. The BBIt-AV:BCE activity ratios were then calculated for each step in process. The modified BBIt-AVs produced at the highest yields following the acid/heat treatment were selected for further study.

Amino acid substitutions were found at sites 13, 25, 27, 29, 31, 40, 50 and 52 that significantly improved the BBIt-AV yield after acid/heat treatment. Other substitutions with improved yields after acid/heat treatment were D1C (when not activated), S4V, S5P, Q11G, S38N and S65E. An additional variant that was produced by an unexpected duplication of a primer (during the QuikChange reaction used to make the site-saturation library at position 4) also had a higher BBIt-AV:BCE activity ratio after acid/heat treatment. In this variant, the amino acid sequence, DDEPSKPCCDPDP (SEQ ID NO:389) (called the 4D13 insert), was inserted between the linker and the N-terminus of BBIt-AV (SEQ ID NO:187) to generate a modified BBIt-AV fused to the linker in SEQ ID NO:391.

(SEQ ID NO: 391)
DNNDPIPDPddepskpccdpdpDDESSKPCCDQCACTKSNPPQCRCSDMR

LNSCHSACKSCACYNLYGWTCFCVDITDFCYEPCKPSE.

The linker is shown in italicized letters, the insert is written in lower case letters and the BBIt-AV corresponding to SEQ ID NO:187 is in bold letters.

The sequence of the 4D13 modified BBtl-AV is:

(SEQ ID NO: 390)
DDEPSKPCCDPDPDDESSKPCCDQCACTKSNPPQCRCSDMRLNSCHSACK

SCACYNLYGWTCFCVDITDFCYEPCKPSE.

The synthetic gene encoding 4D13-BBIt-AV of
SEQ ID NO: 390 is:
(SEQ ID NO: 394)
GGATCCAGATGACGAACCGAGCAAACCTTGCTGTGATCCAGACCCTGACG

ATGAGAGCTCTAAACCCTGTTGCGATCAATGCATTTGTACGAAATCAAAT

CCTCCACAGTGTCGGTGTTCCGATATGCGTCCGAATTCCTGTCATAGTGC

CTGCAAAAGCTGCAAGTGTTATAACCTGTACGGGTGGACCTGTACATGCG

CCGACATCACGGACTTCTGCTATGAACCATGTAAACCAAGCGAGTAAAAG

CTT.

EXAMPLE 12

Combinations of Mutations

In this example, the single amino acid substitutions that resulted in BBIt-AVs having improved BBI:BCE activity ratios in either the plate screens or in the shake flask screen were combined to generate modified BBIt-AVs that have greater BBIt-AV:BCE activity ratios and/or production yields than those of modified BBIt-AVs carrying single amino acid substitutions.

Following the primary and secondary screens described in Examples 9 and 10 above, three modified BBIt-AVs each containing a single amino acid substitution A13I, F50T and V52A, respectively, were identified as having an improved BBI:BCE activity ratio relative to the respective control. A library was constructed to select for the best combination of these three substitutions. The library was made by the QuikChange® mutagenesis protocol described above using equimolar concentrations of the following primers in the reaction mixture: primer 5'-ctgttgcgatcaatgcatttgtacgaaatc (SEQ ID NO:395) was used to generate the A13I substitution, primer 5'-ctgtacgggtggacctgtacatgcgycgacatcacggacttc (SEQ ID NO:396) was used to generate the F50T and F50T-V52A substitutions, and primer 5'-gacctgttttgcgycgacat-cacggac (SEQ ID NO:397) was used to generate the V52A substitution in the reaction mixture. Clones were selected and screened in microtiter plates and screened as described above.

The modified double variant BBIt-AV containing the F50T and the V52A substitutions (BBIt-AV-F50T-V52A; SEQ ID NO:595) was obtained, and determined to have the polynucleotide sequence of SEQ ID NO:398.

BBIt-AV-F50T-V52A
(SEQ ID NO: 398)
GGATCCAGACGATGAGAGCTCTAAACCCTGTTGCGATCAATGCGCATGTA
CGAAATCAAATCCTCCACAGTGTCGGTGTTCCGATATGCGTCTGAATTCC
TGTCATAGTGCCTGCAAAAGCTGCGCATGTTATAACCTGTACGGGTGGAC
CTGTACATGCGCCGACATCACGGACTTCTGCTATGAACCATGTAAACCAA
GCGAGTAAAAGCTT (SEQ ID NO: 595)
DPDDESSKPCCDQCACTKSNPPQCRCSDMRLNSCHSACKSCACYNLYGWT
CTCADITDFCYEPCKPSE.

Generation of Modified BBIt-AVs Containing Three, Four and Five Amino Acid Substitutions Combinations of four productive substitutions, A13I, S25L, L29P and A40K, identified in the screens described in Examples 9 and 10 above were made in the BBIt-AV-F50T-V52A double variant. These substitutions were combined by using synthetic genes that were cloned into the BamHI and HindIII sites of the p2JMagk103Ink2BBIt-AV vector. The polynucleotide sequences encoding the corresponding amino acid sequences for the modified BBIt-AVs comprising combinations of substitutions are given below.

BBIt-AV-A13I-S25L-F50T-V52A
(SEQ ID NO: 399)
GGATCCAGACGATGAGAGCTCTAAACCCTGTTGCGATCAATGCATTTGTA
CGAAATCAAATCCTCCACAGTGTCGGTCTCTTGATATGCGTCTGAATTCC
TGTCATAGTGCCTGCAAAAGCTGCGCATGTTATAACCTGTACGGGTGGAC
CTGTACATGCGCCGACATCACGGACTTCTGCTATGAACCATGTAAACCAA
GCGAGTAAAAGCTT (SEQ ID NO: 596)
DPDDESSKPCCDQCICTKSNPPQCRCLDMRLNSCHSACKSCACYNLYGWT
CTCADITDFCYEPCKPSE

BBIt-AV-A13I-S25L-L29P-F50T-V52A
(SEQ ID NO: 400)
GGATCCAGACGATGAGAGCTCTAAACCCTGTTGCGATCAATGCATTTGTA
CGAAATCAAATCCTCCACAGTGTCGGTGTCTTGATATGCGTCCGAATTCC
TGTCATAGTGCCTGCAAAAGCTGCGCATGTTATAACCTGTACGGGTGGAC
CTGTACATGCGCCGACATCACGGACTTCTGCTATGAACCATGTAAACCAA
GCGAGTAAAAGCTT (SEQ ID NO: 597)
DPDDESSKPCCDQCICTKSNPPQCRCLDMRPNSCHSACKSCACYNLYGWT
CTCADITDFCYEPCKPSE.

BBIt-AV-A13I-S25L-L29P-A40K-F50T-V52A
(SEQ ID NO: 401)
GGATCCAGACGATAGAGACTCTAAACCCTGTTGCGATCAATGCATTTGTA
CGAAATCAAATCCTCCACAGTGTCGGTGTCTTGATATGCGTCCGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 598)
DPDDESSKPCCDQCICTKSNPPQCRCLDMRPNSCHSACKSCKCYNLYGWT
CTCADITDFCYEPCKPSE

BBIt-AV-A13I-S25L-A40K-F50T-V52A
(SEQ ID NO: 402)
GGATCCAGACGATGAGAGCTCTAAACCCTGTTGCGATCAATGCATTTGTA
CGAAATCAAATCCTCCACAGTGTCGGTGTCTTGATATGCGTCTGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 599)
DPDDESSKPCCDQCICTKSNPPQCRCLDMRLNSCHSACKSCKCYNLYGWT
CTCADITDFCYEPCKPSE

BBIt-AV-A13I-L29P-F50T-V52A
(SEQ ID NO: 403)
GGATCCAGACGATGAGAGCTCTAAACCCTGTTGCGATCAATGCATTTGTA
CGAAATCAAATCCTCCACAGTGTCGGTGTTCCGATATGCGTCCGAATTCC
TGTCATAGTGCCTGCAAAAGCTGCGCATGTTATAACCTGTACGGGTGGAC
CTGTACATGCGCCGACATCACGGACTTCTGCTATGAACCATGTAAACCAA
GCGAGTAAAAGCTT (SEQ ID NO: 600)
DPDDESSKPCCDQCICTKSNPPQCRCSDMRPNSCHSACASCACYNLYGWT
CTCADITDFCYEPCKPSE

BBIt-AV-A13I-L29P-A40K-F50T-V52A (TA5)
(SEQ ID NO: 404)
GGATCCAGACGATGAGAGCTCTAAACCCTGTTGCGATCAATGCATTTGTA
CGAAATCAAATCCTCCACAGTGTCGGTGTTCCGATATGCGTCCGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 601)
DPDDESSKPCCDQCICTKSNPPQCRCSDMRPNSCHSACKSCKCYNLYGWT
CTCADITDFCYEPCKPSE

BBIt-AV-A13I-A40K-F50T-V52A
(SEQ ID NO: 405)
GGATCCAGACGATGAGAGCTCTAAACCCTGTTGCGATCAATGCATTTGTA
CGAAATCAAATCCTCCACAGTGTCGGTGTTCCGATATGCGTCTGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 602)
DPDDESSKPCCDQCICTKSNPPQCRCSDMRLNSCHSACKSCKCYNLYGWT
CTCADITDFCYEPCKPSE

BBIt-AV-S25L-F50T-V52A
(SEQ ID NO: 406)
GGATCCAGACGATGAGAGCTCTAAACCCTGTTGCGATCAATGCGCATGTA
CGAAATCAAATCCTCCACAGTGTCGGTGTCTTGATATGCGTCTGAATTCC
TGTCATAGTGCCTGCAAAAGCTGCGCATGTTATAACCTGTACGGGTGGAC
CTGTACATGCGCCGACATCACGGACTTCTGCTATGAACCATGTAAACCAA
GCGAGTAAAAGCTT (SEQ ID NO: 603)
DPDDESSKPCCDQCACTKSNPPQCRCLDMRLNSCHSACKSCACYNLYGWT
CTCADITDFCYEPCKPSE

BBIt-AV-S25L-L29P-F50T-V52A
(SEQ ID NO: 407)
GGATCCAGACGATGAGAGCTCTAAACCCTGTTGCGATCAATGCGCATGTA
CGAAATCAAATCCTCCACAGTGTCGGTGTCTTGATATGCGTCCGAATTCC
TGTCATAGTGCCTGCAAAAGCTGCCATGTTATAACCTGTACGGGTGGAC
CTGTACATGCGCCGACATCACGGACTTCTGCTATGAACCATGTAAACCAA
GCGAGTAAAAGCTT (SEQ ID NO: 604)
DPDDESSKPCCDQCACTKSNPPQCRCLDMRPNSCHSACKSCACYNLYGWT
CTCADITDFCYEPCKPSE

BBIt-AV-S25L-L29P-A40K-F50T-V52A
(SEQ ID NO: 408)
GGATCCAGACGATGAGAGCTCTAAACCCTGTTGCGATCAATGCGCATGTA
CGAAATCAAATCCTCCACAGTGTCGGTGTCTTGATATGCGTCCGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 605)
DPDDESSKPCCDQCACTKSNPPQCRCLDMRPNSCHSACKSCKCYNLYGWT
CTCADITDFCYEPCKPSE

BBIt-AV-S25L-A40K-F50T-V52A
(SEQ ID NO: 409)
GGATCCAGACGATGAGAGCTCTAAACCCTGTTGCGATCAATGCGCATGTA
CGAAATCAAATCCTCCACAGTGTCGGTGTCTTGATATGCGTCTGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 606)
DPDDESSKPCCDQCACTKSNPPQCRCLDMRLNSCHSACKSCKCYNLYGWT
CTCADITDFCYEPCKPSE

BBIt-AV-L29P-F50T-V52A
(SEQ ID NO: 410)
GGATCCAGACGATGAGAGCTCTAAACCCTGTTGCGATCAATGCGCATGTA
CGAAATCAAATCCTCCACAGTGTCGGTGTTCCGATATGCGTCCGAATTCC
TGTCATAGTGCCTGCAAAAGCTGCGCATGTTATAACCTGTACGGGTGGAC
CTGTACATGCGCCGACATCACGGACTTCTGCTATGAACCATGTAAACCAA
GCGAGTAAAAGCTT (SEQ ID NO: 607)
DPDDESSKPCCDQCACTKSNPPQCRCSDMRPNSCHSACKSCACYNLYGWT
CTCADITDFCYEPCKPSE

BBIt-AV-L29P-A40K-F50T-V52A
(SEQ ID NO: 411)
GGATCCAGACGATGAGAGCTCTAAACCCTGTTGCGATCAATGCGCATGTA
CGAAATCAAATCCTCCACAGTGTCGGTGTTCCGATATGCGTCCGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 608)
DPDDESSKPCCDQCACTKSNPPQCRCSDMRPNSCHSACKSCKCYNLYGWT
CTCADITDFCYEPCKPSE

BBIt-AV-A40K-F50T-V52A
(SEQ ID NO: 412)
GGATCCAGACGATGAGAGCTCTAAACCCTGTTGCGATCAATGCGCATGTA
CGAAATCAAATCCTCCACAGTGTCGGTGTTCCGATATGCGTCTGAATTCC
TGTCATAGTGCCTGCAAAAGCTGCAAGTGTTATAACCTGTACGGGTGGAC
CTGTACATGCGCCGACATCACGGACTTCTGCTATGAACCATGTAAACCAA
GCGAGTAAAAGCTT (SEQ ID NO: 609)
DPDDESSKPCCDQCACTKSNPPQCRCSDMRLNSCHSACKSCKCYNLYGWT
CTCADITDFCYEPCKPSE

Generation of Modified BBIt-AVs Containing Six and Seven Amino Acid Substitutions Additional modified BBIt-AV were generated to comprise variations including the 4D13 insertion, single amino acid substitutions D1C, S4V, S5P, Q11G, I13L, S25R, M27R, P29K, S31A, S31R, S38N, T50K, A52T, S65E, and double amino acid substitutions including S25R-S31R and S25R-S31 with substitutions present in a quintuple variant (BBIt-AV-A13I-L29P-A40K-F50T-V52A) encoded by the polynucleotide of SEQ ID NO:404.

The 4D13 peptide was inserted into the p2JM103 based vector constructed for the expression of BBIt-AV-A13I-L29P-A40K-F50T-V52A (SEQ ID NO:404) with an oligonucleotide cassette having BamHI and SacI restriction sites on the ends using the oligonucleotides:

(SEQ ID NO: 392)
5'-GATCCAGATGACGAACCGAGCAAACCTTGCTGTGATCCAGACCCTGACGATGAGAGCT
and
(SEQ ID NO: 393).
5'-CTCATCGTCAGGGTCTGGATCACAGCAAGGTTTGCTCGGTTCGTCATCTG Amino acid sequence of BBIt-AV-4D13 insert-A13I-L29P-A40K-F50T-V52A:
(SEQ ID NO: 413)
DPDDEPSKPCCDPDPDDESSKPCCDQCICTKSNPPQCRCSDMRPNSCHSACKSCKCYNYLGWTCTCADITDFCYEPCKPSE The other variants were made by cloning synthetic genes into the BamHI and HindIII sites of p2JM103-Ink2. The polynucleotide sequences of each of the synthetic genes and resulting modified amino acid sequences of the modified variant BBIt-AVs are given in Table 4.

TABLE 4

BBIt-AVs comprising substitutions/modifications based on the BBIt-AV-A13I-L29P-A40K-F50T-V52A variant (SEQ ID NO: 601)

| Amino Acid in BBIt-AV | Synthetic Gene Sequence Encoding the BBIt-AV Variant | Amino Acid Sequence of the BBIt-AV Variant |
|---|---|---|
| BBIt-AV-D1C-A13I-L29P-A40K-F50T-V52A | GGATCCATGCGATGAGAGCTCTAAACCTTGT TGCGATCAATGCATTTGTACTAAATCAAACCC TCCACAATGTCGTTGTTCTGATATGCGTCCTA ATTCATGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 414) | DPCDESSKPCCDQ CICTKSNPPQCRCS DMRPNSCHSACKS CKCYNLYGWTCTCA DITDFCYEPCKPSE (SEQ ID NO: 611) |
| BBIt-AV-S4V-A13I-L29P-A40K-F50T-V52A | GGATCCAGACGATGAGGTTTCTAAACCTTGT TGCGATCAATGCATTTGTACTAAATCAAACCC TCCACAATGTCGTTGTTCTGATATGCGTCCTA ATTCATGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 415) | DPDDEVSKPCCDQ CICTKSNPPQCRCS DMRPNSCHSACKS CKCYNLYGWTCTCA DITDFCYEPCKPSE (SEQ ID NO: 612) |
| BBIt-AV-S5P-A13I-L29P-A40K-F50T-V52A | GGATCCAGACGATGAGAGCCCTAAACCTTGT TGCGATCAATGCATTTGTACTAAATCAAACCC TCCACAATGTCGTTGTTCTGATATGCGTCCTA ATAGCTGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 416) | DPDDESPKPCCDQ CICTKSNPPQCRCS DMRPNSCHSACKS CKCYNLYGWTCTCA DITDFCYEPCKPSE (SEQ ID NO: 613) |
| BBIt-AV-Q11G-A13I-L29P-A40K-F50T-V52A | GGATCCAGACGATGAGAGCTCTAAACCTTGT TGCGATGGCTGCATTTGTACTAAATCAAACC CTCCACAATGTCGTTGTTCTGATATGCGTCCT AATTCATGTCATTCTGCATGCAAATCATGTAA ATGCTATAACCTTTACGGTTGGACATGTACAT GCGCAGATATCACTGACTTCTGCTATGAACC ATGTAAACCTTCTGAATAAAAGCTT (SEQ ID NO: 417) | DPDDESSKPCCDG CICTKSNPPQCRCS DMRPNSCHSACKS CKCYNLYGWTCTCA DITDFCYEPCKPSE (SEQ ID NO: 614) |
| BBIt-AV-A13L-L29P-A40K-F50T-V52A | GGATCCAGACGATGAGAGCTCTAAACCTTGT TGCGATCAATGCCTTTGTACTAAATCAAACCC TCCACAATGTCGTTGTTCTGATATGCGTCCTA ATTCATGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 418) | DPDDESSKPCCDQ CLCTKSNPPQCRCS DMRPNSCHSACKS CKCYNLYGWTCTCA DITDFCYEPCKPSE (SEQ ID NO: 615) |
| BBIt-AV-A13I-S25R-L29P-A40K-F50T-V52A | GGATCCAGACGATGAGAGCTCTAAACCTTGT TGCGATCAATGCATTTGTACTAAATCAAACCC TCCACAATGTCGTTGTAGAGATATGCGTCCT AATAGCTGTCATTCTGCATGCAAATCATGTAA ATGCTATAACCTTTACGGTTGGACATGTACAT GCGCAGATATCACTGACTTCTGCTATGAACC ATGTAAACCTTCTGAATAAAAGCTT (SEQ ID NO: 419) | DPDDESSKPCCDQ CICTKSNPPQCRCR DMRPNSCHSACKS CKCYNLYGWTCTCA DITDFCYEPCKPSE (SEQ ID NO: 616) |

TABLE 4-continued

BBIt-AVs comprising substitutions/modifications based on the
BBIt-AV-A13I-L29P-A40K-F50T-V52A variant (SEQ ID NO: 601)

| Amino Acid in BBIt-AV | Synthetic Gene Sequence Encoding the BBIt-AV Variant | Amino Acid Sequence of the BBIt-AV Variant |
|---|---|---|
| BBIt-AV-A13I-S25R-L29P-S31A-A40K-F50T-V52A | GGATCCAGACGATGAGAGCTCTAAACCTTGT TGCGATCAATGCATTTGTACTAAATCAAACCC TCCACAATGTCGTTGTAGAGATATGCGTCCT AATGCTTGTCATTCTGCATGCAAATCATGTAA ATGCTATAACCTTTACGGTTGGACATGTACAT GCGCAGATATCACTGACTTCTGCTATGAACC ATGTAAACCTTCTGAATAAAAGCTT (SEQ ID NO: 420) | DPDDESSKPCCDQ CICTKSNPPQCRCR DMRPNACHSACKS CKCYNLYGWTCTCA DITDFCYEPCKPSE (SEQ ID NO: 617) |
| BBIt-AV-A13I-S25R-L29P-S31R-A40K-F50T-V52A | GGATCCAGACGATGAGAGCTCTAAACCTTGT TGCGATCAATGCATTTGTACTAAATCAAACCC TCCACAATGTCGTTGTAGAGATATGCGTCCT AATCGCTGTCATTCTGCATGCAAATCATGTAA ATGCTATAACCTTTACGGTTGGACATGTACAT GCGCAGATATCACTGACTTCTGCTATGAACC ATGTAAACCTTCTGAATAAAAGCTT (SEQ ID NO: 421) | DPDDESSKPCCDQ CICTKSNPPQCRCR DMRPNRCHSACKS CKCYNLYGWTCTCA DITDFCYEPCKPSE (SEQ ID NO: 618) |
| BBIt-AV-A13I-M27R-L29P-A40K-F50T-V52A | GGATCCAGACGATGAGAGCTCTAAACCTTGT TGCGATCAATGCATTTGTACTAAATCAAACCC TCCACAATGTCGTTGTTCTGATAGACGTCCTA ATTCATGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 422) | DPDDESSKPCCDQ CICTKSNPPQCRCS DRRPNSCHSACKSC KCYNLYGWTCTCAD ITDFCYEPCKPSE (SEQ ID NO: 619) |
| BBIt-AV-A13I-L29K-A40K-F50T-V52A | GGATCCAGACGATGAGAGCTCTAAACCTTGT TGCGATCAATGCATTTGTACTAAATCAAACCC TCCACAATGTCGTTGTTCTGATATGCGTAAAA ATTCATGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 423) | DPDDESSKPCCDQ CICTKSNPPQCRCS DMRKNSCHSACKS CKCYNLYGWTCTCA DITDFCYEPCKPSE (SEQ ID NO: 620) |
| BBIt-AV-A13I-L29P-S31A-A40K-F50T-V52A | GGATCCAGACGATGAGAGCTCTAAACCTTGT TGCGATCAATGCATTTGTACTAAATCAAACCC TCCACAATGTCGTTGTTCTGATATGCGTCCTA ATGCTTGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 424) | DPDDESSKPCCDQ CICTKSNPPQCRCS DMRPNACHSACKS CKCYNLYGWTCTCA DITDFCYEPCKPSE (SEQ ID NO: 621) |
| BBIt-AV-A13I-L29P-S31R-A40K-F50T-V52A | GGATCCAGACGATGAGAGCTCTAAACCTTGT TGCGATCAATGCATTTGTACTAAATCAAACCC TCCACAATGTCGTTGTTCTGATATGCGTCCTA ATAGATGTCATTCTGCATGCAAATCATGTAAA TGCTATAACCTTTACGGTTGGACATGTACATG CGCAGATATCACTGACTTCTGCTATGAACCAT GTAAACCTTCTGAATAAAAGCTT (SEQ ID NO: 425) | DPDDESSKPCCDQ CICTKSNPPQCRCS DMRPNRCHSACKS CKCYNLYGWTCTCA DITDFCYEPCKPSE (SEQ ID NO: 622) |
| BBIt-AV-A13I-L29P-S38N-A40K-F50T-V52A | GGATCCAGACGATGAGAGCTCTAAACCTTGT TGCGATCAATGCATTTGTACTAAATCAAACCC TCCACAATGTCGTTGTTCTGATATGCGTCCTA ATAGCTGTCATTCTGCATGCAAAAACTGTAAA TGCTATAACCTTTACGGTTGGACATGTACATG CGCAGATATCACTGACTTCTGCTATGAACCAT GTAAACCTTCTGAATAAAAGCTT (SEQ ID NO: 426) | DPDDESSKPCCDQ CICTKSNPPQCRCS DMRPNSCHSACKN CKCYNLYGWTCTCA DITDFCYEPCKPSE (SEQ ID NO: 623) |
| BBIt-AV-A13I-L29P-A40K-F50K-V52A | GGATCCAGACGATGAGAGCTCTAAACCTTGT TGCGATCAATGCATTTGTACTAAATCAAACCC TCCACAATGTCGTTGTTCTGATATGCGTCCTA ATTCATGTCATTCTGCATGCAAATCATGTAAA TGCTATAACCTTTACGGTTGGACATGTAAATG CGCAGATATCACTGACTTCTGCTATGAACCAT GTAAACCTTCTGAATAAAAGCTT (SEQ ID NO: 427) | DPDDESSKPCCDQ CICTKSNPPQCRCS DMRPNSCHSACKS CKCYNLYGWTCKC ADITDFCYEPCKPSE (SEQ ID NO: 624) |

TABLE 4-continued

BBIt-AVs comprising substitutions/modifications based on the BBIt-AV-A13I-L29P-A40K-F50T-V52A variant (SEQ ID NO: 601)

| Amino Acid in BBIt-AV | Synthetic Gene Sequence Encoding the BBIt-AV Variant | Amino Acid Sequence of the BBIt-AV Variant |
|---|---|---|
| BBIt-AV-A13I-L29P-A40K-F50T-V52T | GGATCCAGACGATGAGAGCTCTAAACCTTGT TGCGATCAATGCATTTGTACTAAATCAAACCC TCCACAATGTCGTTGTTCTGATATGCGTCCTA ATTCATGTCATTCTGCATGCAAATCATGTAAA TGCTATAACCTTTACGGTTGGACATGTACATG CACAGATATCACTGACTTCTGCTATGAACCAT GTAAACCTTCTGAATAAAAGCTT (SEQ ID NO: 428) | DPDDESSKPCCDQ CICTKSNPPQCRCS DMRPNSCHSACKS CKCYNLYGWTCTCT DITDFCYEPCKPSE (SEQ ID NO: 625) |
| BBIt-AV-A13I-L29P-A40K-F50T-V52A-S65E | GGATCCAGACGATGAGAGCTCTAAACCTTGT TGCGATCAATGCATTTGTACTAAATCAAACCC TCCACAATGTCGTTGTTCTGATATGCGTCCTA ATAGCTGTCATTCTGCATGCAAATCATGTAAA TGCTATAACCTTTACGGTTGGACATGTACATG CGCAGATATCACTGACTTCTGCTATGAACCAT GTAAACCTGAAGAATAAAAGCTT (SEQ ID NO: 429) | DPDDESSKPCCDQ CICTKSNPPQCRCS DMRPNSCHSACKS CKCYNLYGWTCTCA DITDFCYEPCKPEE (SEQ ID NO: 626) |

The BBI:BCE ratio of the modified variant BBIt-AVs was determined as described above, and the yield for each of the modified variant BBIt-AVs was calculated. The modified BBIt-AVs BBIt-AV-A13I-S25R-L29P-S31R-A40K-F50T-V52A (SEQ ID NO:618), BBIt-AV-A13I-S25R-L29P-S31A-A40K-F50T-V52A (SEQ ID NO:617), BBIt-AV-A13I-S25R-L29P-A40K-F50T-V52A (SEQ ID NO:616), BBIt-AV-A13I-L29P-S31R-A40K-F50T-V52A (SEQ ID NO:622) had significantly better yields after acid/heat treatment than quintuple BBIt-AV-A13I-L29P-A40K-F50T-V52A (SEQ ID NO:601), while BBIt-AV-A13I-L29P-A40K-F50K-V52A (SEQ ID NO:624), BBIt-AV-A13L-L29P-A40K-F50T-V52A (SEQ ID NO:615) and BBIt-AV-4D13 insert -A13I-L29P-A40K-F50T-V52A (SEQ ID NO:413) had slightly better yields than BBIt-AV-A13I-L29P-A40K-F50T-V52A (SEQ ID NO:601). The modified BBIt-AV-A13I-L29P-A40K-F50T-V52A-S65E (SEQ ID NO:626) and BBIt-AV-A13I-L29P-S38N-A40K-F50T-V52A (SEQ ID NO:623) had similar yields as BBIt-AV-A13I-L29P-A40K-F50T-V52 (SEQ ID NO:624), BBIt-AV-A13I-M27R-L29P-A40K-F50T-V52A (SEQ ID NO:619), BBIt-AV-A13I-L29P-S31A-A40K-F50T-V52A (SEQ ID NO:621) and BBIt-AV-A13I-L29P-A40K-F50T-V52T (SEQ ID NO:625) somewhat less, while BBIt-AV-S4V-A13I-L29P-A40K-F50T-V52A (SEQ ID NO:612), BBIt-AV-Q11G-A13I-L29P-A40K-F50T-V52A (SEQ ID NO:614), BBIt-AV-A13I-L29K-A40K-F50T-V52A (SEQ ID NO:620) and BBIt-AV-S5P-A13I-L29P-A40K-F50T-V52A (SEQ ID NO:611) all had significantly lower yields than BBIt-AV-A13I-L29P-A40K-F50T-V52A (SEQ ID NO:601), after acid-heat treatment. The yield of BBIt-AV-D1C-A13I-L29P-A40K-F50T-V52A (SEQ ID NO:611) in the absence of activation was also much lower than BBIt-AV-A13I-L29P-A40K-F50T-V52A (SEQ ID NO:601). However, the yield after acid/heat treatment of BBIt-AV-D1C-A13I-L29P-A40K-F50T-V52A (SEQ ID NO:611) when not activated was about two fold higher than BBIt-AV-A13I-L29P-A40K-F50T-V52A (SEQ ID NO:601) when activated but similar to BBIt-AV-A13I-L29P-A40K-F50T-V52A (SEQ ID NO:601) when it was not activated. Thus, no substitutions were found that could produce high yields without activation.

Generation of Modified BBI-AVs Containing Eight Amino Acid Substitutions: Octuple Variants Following the testing of the quintuple-based modified BBI-AVs, additional modified variant BBIs (octuple variants) were generated to contain eight amino acid substitutions. The activity and purification yield of the octuple variants were determined as described above. Construction of the octuple modified BBIt-AVs was achieved as described above using the synthetic genes shown in Table 5.

TABLE 5

Octuple Modified Variant BBIt-AVs

| Amino Acid Substitutions | Synthetic Gene Sequence Encoding the Octuple Variant | Amino Acid Sequence of the BBIt-AV Variant |
|---|---|---|
| BBIt-AV-A13I-S25R-M27A-L29P-S31A-A40H-F50K-V52T (KT8) | GGATCCAGACGATGAGAGCTCTAAACCTT GTTGCGATCAATGCATCTGTACAAAATCA AACCCTCCACAATGTCGTTGTAGAGATGC TCGTCCTAATGCATGTCATTCTGCATGCA AATCATGTCACTGCTATAACCTTTACGGTT GGACATGTAAATGCACAGACATCACTGAC TTCTGCTATGAACCATGTAAACCTTCTGAA TAAAAGCTT (SEQ ID NO: 486) | DPDDESSKPCCDQCICTKSNP PQCRCRDARPNACHSACKSC HCYNLYGWTCKCTDITDFCYE PCKPSE (SEQ ID NO: 627) |

TABLE 5-continued

Octuple Modified Variant BBIt-AVs

| Amino Acid Substitutions | Synthetic Gene Sequence Encoding the Octuple Variant | Amino Acid Sequence of the BBIt-AV Variant |
|---|---|---|
| BBIt-AV-A13I-<br>S25K-M27A-<br>L29R-S31E-<br>A40K-F50Q-<br>V52Q (QQ8) | GGATCCAGACGATGAGAGCTCTAAACCTT<br>GTTGCGATCAATGCATCTGTACAAAATCA<br>AACCCTCCACAATGTCGTTGTAAAGATGC<br>TCGTAGAAATGAATGTCATTCTGCATGCA<br>AATCATGTAAATGCTATAACCTTTACGGTT<br>GGACATGTCAATGCCAAGACATCACTGAC<br>TTCTGCTATGAACCATGTAAACCTTCTGAA<br>TAAAAGCTT<br>(SEQ ID NO: 487) | DPDDESSKPCCDQCICTKSNP<br>PQCRCKDARRNE CHSACKSC<br>KCYNLYGWTCQCQDITDFCYE<br>PCKPSE<br>(SEQ ID NO: 628) |
| BBIt-AV-A13I-<br>S25K-M27R-<br>L29E-S31A-<br>A40H-F50R-<br>V52K (RK8) | GGATCCAGACGATGAGAGCTCTAAACCTT<br>GTTGCGATCAATGCATCTGTACAAAATCA<br>AACCCTCCACAATGTCGTTGTAAAGATAG<br>ACGTGAAAATGCTTGTCATTCTGCATGCA<br>AATCATGTCACTGCTATAACCTTTACGGTT<br>GGACATGTAGATGCAAAGACATCACTGAC<br>TTCTGCTATGAACCATGTAAACCTTCTGAA<br>TAAAAGCTT<br>(SEQ ID NO: 488) | DPDDESSKPCCDQCICTKSNP<br>PQCR CKDRRENACHSACKSC<br>HCYNLYGWTCRCKDITDFCYE<br>PCKPSE<br>(SEQ ID NO: 629) |
| BBIt-AV-A13I-<br>S25K-M27A-<br>L29R-S31A-<br>A40H-F50R-<br>V52L (RL8) | GGATCCAGACGATGAGAGCTCTAAACCTT<br>GTTGCGATCAATGCATCTGTACAAAATCA<br>AACCCTCCACAATGTCGTTGTAAAGATGC<br>TCGTAGAAATGCTTGTCATTCTGCATGCA<br>AATCATGTCACTGCTATAACCTTTACGGTT<br>GGACATGTAGATGCTTAGACATCACTGAC<br>TTCTGCTATGAACCATGTAAACCTTCTGAA<br>TAAAAGCTT<br>(SEQ ID NO: 489) | DPDDESSKPCCDQCICTKSNP<br>PQCRCKDARRNACHSACKSC<br>HCYNLYGWTCRCLDITDFCYE<br>PCKPSE<br>(SEQ ID NO: 630) |
| BBIt-AV-A13I-<br>S25K-M27Q-<br>L29P-S31E-<br>A40H-F50R-<br>V52Q (RQ8) | GGATCCAGACGATGAGAGCTCTAAACCTT<br>GTTGCGATCAATGCATCTGTACAAAATCA<br>AACCCTCCACAATGTCGTTGTAAAGATCA<br>ACGTCCTAATGAATGTCATTCTGCATGCA<br>AATCATGTCACTGCTATAACCTTTACGGTT<br>GGACATGTAGATGCCAAGACATCACTGAC<br>TTCTGCTATGAACCATGTAAACCTTCTGAA<br>TAAAAGCTT<br>(SEQ ID NO: 490) | DPDDESSKPCCDQCICTKSNP<br>PQCRCKDQRPNECHSACKSC<br>HCYNLYGWTCRCQDITDFCYE<br>PCKPSE<br>(SEQ ID NO: 631) |

The best octuple variants selected in the shake flask screen were tested in the purification process essentially as described above, and including the following changes: 1) after growth, the culture was two fold diluted in glycine buffer (125 mM final concentration and pH adjusted to 9.0) instead of CHES buffer; 2) samples were activated with 2 mM 2-mercaptoethanol only (no sodium sulfite was added; 3) the acid precipitated fusion protein was resuspended in 100 ml of 125 mM glycine (rather than 350 ml of 40 mM glycine); and 4) the pellet collected after the acid/heat treatment was washed with 10 ml water, filtered, and this "washed pellet" filtrate was combined with the original filtrate. The final filtrates were concentrated and trimmed with Glu-BL as described above The results show that octuple variant BBIt-AV molecules QQ8 (SEQ ID NO:628) and KT8 (SEQ ID NO:627) resulted in purification yields that were greater than that of the quintuple modified variant BBIt-AV-A13I-L29P-A40K-F50T-V52A variant (SEQ ID NO:601). The modified octuple variants BBIt-AV-A13I-S25K-M27A-L29R-S31A-A40H-F50R-V52L (RL8; SEQ ID NO:630), BBIt-AV-A13I-S25K-M27A-L29R-S31 E-A40K-F50Q-V52Q (QQ8; SEQ ID NO:628) and BBIt-AV-A13I-S25R-M27A-L29P-S31A-A40H-F50K-V52T (KT8; SEQ ID NO:627) resulted in yields that were better than the wild-type sBBI molecule/protein (FIG. 13).

EXAMPLE 13

Improved Production of BBI Scaffolds Carrying FGF5 or TGFβ1 Binding Peptides

In this example, the same amino acid substitutions that resulted in modified variant BBIt-AVs having improved trypsin inhibitory activity and/or purification yields (see Examples 7-13) were tested for improving the trypsin inhibitory activity and/or the purification yield of variant BBI scaffolds in which the chymotrypsin loop was replaced with either an FGF-5 or a TGFβ1 binding peptide.

Generation of Variant and Modified Variant BBI-FGF-5 Proteins:

Modified variant BBIt-FGF-5 protease inhibitors comprising the combination of substitutions A13I-L29P-F50T-V52A (all with alanine at position 40) and either the FGF-5 binding peptide MM007: RTQPYPL (SEQ ID NO:670), or FGF-5 binding peptide FGFps2: TWIDSTP (SEQ ID NO:671) in place of the chymotrypsin loop, were constructed by ligating a synthetic gene into the BamHI and HindIII sites of the vector p2JMagk103-Ink2-BBIt-AV. The amino acid sequences and DNA sequences of the synthetic genes encoding the resulting modified variant MM007-Q-BBIt-FGF-5 (SEQ ID NO:432; SEQ ID NO:433) and the modified variant FGFps2-Q-BBIt-FGF-5, respectively (SEQ ID NO:434 SEQ ID NO:435) are as follows.

MM007-Q-BBIt-FGF-5 synthetic gene (SEQ ID NO: 433)
GGATCCAGACGATGAGAGCTCTAAACCTTGTTGCGATCAATGCATTTGTA
CTAAATCAAATCCTCCACAATGTCGTTGTTCTGATATGCGTCCTAATAGC
TGTCATTCTGCATGCAAATCATGTGCTTGCCGTACTCAACCATACCCTCT
TTGTACATGCGCAGACATCACTGACTTCTGCTATGAACCATGTAAACCAT
CTGAATAAAAGCTT MM007-Q-BBIt-FGF-5 protein (SEQ ID NO: 432)
DPDDESSKPCCDQCICTKSNPPQCRCSDMRPNSCHSACKSCACRTQPYPL
CTCADITDFCYEPCKPSE FGFps2-Q-BBIt-FGF-5

(SEQ ID NO: 435)
GGATCCAGACGATGAGAGCTCTAAACCTTGTTGCGATCAATGCATTTGTA
CTAAATCAAATCCTCCACAATGTCGTTGTTCTGATATGCGTCCTAATAGC
TGTCATTCTGCATGCAAATCATGTGCTTGCACTTGGATTGATTCAACACC
ATGTACATGCGCAGACATCACTGACTTCTGCTATGAACCATGTAAACCAT
CTGAATAAAAGCTT (SEQ ID NO: 434)
DPDDESSKPCCDQCICTKSNPPQCRCSDMRPNSCHSACKSCACTWIDST
PCTCADITDFCYEPCKPSE

Generation of Variant and Modified Variant BBI-TGFβ Proteins:

The chymotrypsin inhibitory loop of the BBIt-AV of SEQ ID NO:187 was replaced with the TGFβ1 binding peptide PEN3: CLCPENINVLPCN (SEQ ID NO:436), the TGFβ1 binding peptide MM021 W: CICKHNVDWLCF (SEQ ID NO:437) or the TGFβ1 binding peptide WTQ: CICWTQHIHNCF (SEQ ID NO:438) to generate variant BBPIs according to the method described in Example 2, as follows.

Oligonucleotide pairs were used to make cassettes to replace the FGFhl binding peptide in the chymotrypsin reactive site loop encoded by the p2JM103-Ink2-2BBI-FGFhl expression vector with the TGFβ1 binding peptides, PEN3, MM021W or WTQ. The p2JM103-Ink2-2BBI-FGFhl was constructed using the primers (SEQ ID NO:91 and SEQ ID NO:92) and QuikChange® method as described in Example 2. The TGFβ binding cassettes were ligated into the SphI and SalI restriction sites in the vector p2JM103Ink2-2BBI-FGFhl to construct the variant BBI molecules PEN3-BBlt-TGFβ1, MMO21W-BBIt-TGFβ and WTQ-BBlt-TGFβ1, respectively. The DNA sequences of the oligonucleotides used to make the cassettes are shown below.

PEN3 (2$^{nd}$ loop)

(SEQ ID NO: 439)
CAAAAGCTGTCTTTGTCCTGAAAATATTAACGTTCTTCCTTGTAACTGCG
And (SEQ ID NO: 440)
TCGACGCAGTTACAAGGAAGAACGTTAATATTTTCAGGACAAAGACAGCT
TTTGCATG

MM021W (2$^{nd}$ loop)

(SEQ ID NO: 129)
CAAATCATGCATTTGTAAACACAACGTAGATTGGTTATGTTTTTGCG
And (SEQ ID NO: 130)
TCGACGCAAAAACATAACCAATCTACGTTGTGTTTACAAATGCATGATTT
GCATG

WTQ (2$^{nd}$ loop)

(SEQ ID NO: 441)
CAAATCATGCATTTGTTGGACACAACATATCCACAACTGTTTTTGCG
And (SEQ ID NO: 442)
TCGACGCAAAAACAGTTGTGGATATGTTGTGTCCAACAAATGCATGATTT
GCATG

In addition, modified variant BBPI-TGFβ1 variants comprising the combination of substitutions A13I-L29P-V52A (all also have alanine at position 40 and threonine at position 50) and the TGFβ1 binding peptide PEN3-Q: CPENINVLPC (SEQ ID NO:672), MM021W-Q: CKHNVDWLC (SEQ ID NO:673) or WTQ-Q: CWTQHIHNC (SEQ ID NO:674) in place of the chymotrypsin loop, were constructed by ligating a synthetic gene into the BamHI and HindIII sites of the vector p2JMagk103-Ink2-BBIt-AV. The amino acid sequences and DNA sequences of the synthetic genes encoding the resulting modified variant PEN3-Q-BBlt-TGFβ1 (SEQ ID NO:443; SEQ ID NO:444), the modified variant MM021W-BBI-TGFβ1 (SEQ ID NO:445; SEQ ID NO:446), and the modified variant WTQ-BBI-TGFβ1 (SEQ ID NO:447; SEQ ID NO:448) are as follows.

PEN3-Q-BBIt-TGFβ1

(SEQ ID NO: 443)
DPDDESSKPCCDQCICTKSNPPQCRCSDMRPNSCHSACKSCACPENINVL
PCTCADITDFCYEPCKPSE

PEN3-Q-BBIt-TGFβ1

(SEQ ID NO: 444)
GGATCCAGACGATGAGAGCTCTAAACCTTGTTGCGATCAATGCATTTGTA
CTAAATCAAATCCTCCACAATGTCGTTGTTCTGATATGCGTCCTAATAGC
TGTCATTCTGCATGCAAATCATGTGCTTGCCCAGAAAACATCAACGTTCT
TCCTTGTACATGCGCAGACATCACTGACTTCTGCTATGAACCATGTAAAC
CATCTGAATAAAAGCTT

MM021W-Q-BBIt-TGFβ1

(SEQ ID NO: 445)
DPDDESSKPCCDQCICTKSNPPQCRCSDMRPNSCHSACKSCACKHNVDWL
CTCADITDFCYEPCKPSE

MM021W-Q-BBIt-TGFβ1

(SEQ ID NO: 446)
GGATCCAGACGATGAGAGCTCTAAACCTTGTTGCGATCAATGCATTTGTA
CTAAATCAAATCCTCCACAATGTCGTTGTTCTGATATGCGTCCTAATAGC
TGTCATTCTGCATGCAAATCATGTGCTTGCAAACATAACGTTGATTGGCT
TTGTACATGCGCAGACATCACTGACTTCTGCTATGAACCATGTAAACCAT
CTGAATAAAAGCTT

WTQ-Q-BBIt-TGFβ1

(SEQ ID NO: 447)
DPDDESSKPCCDQCICTKSNPPQCRCSDMRPNSCHSACKSCACWTQHIHNC
TCADITDFCYEPCKPSE

WTQ-Q-BBIt-TGFβ1

(SEQ ID NO: 448)
GGATCCAGACGATGAGAGCTCTAAACCTTGTTGCGATCAATGCATTTGTA
CTAAATCAAATCCTCCACAATGTCGTTGTTCTGATATGCGTCCTAATAGC
TGTCATTCTGCATGCAAATCATGTGCTTGCTGGACACAACATATCCACAA
CTGTACATGCGCAGACATCACTGACTTCTGCTATGAACCATGTAAACCAT
CTGAATAAAAGCTT

The ten vectors comprising the variant and modified variant BBIs containing an FGF-5 or a TGFβ binding peptide were used to transform B. subtilis BG6006 host cells. The transformants were grown and the engineered BBIs produced by the host cells were tested for trypsin inhibitory activities and production yields as described above.

FIG. 14 shows the trypsin inhibitory activity of the unmodified variant parent MM007-PT-BBIt-FGF-5 (SEQ ID NO:678): (DDESSKPCCDQCACTKSNPPQCRCSDM-RLNSCHSACKSCAC RTQPYPL CFCVDITDF-CYEPCKPSE; SEQ ID NO:678), the unmodified variant parent FGFps2-PT-BBIt-FGF5 (SEQ ID NO:679): (DDESSKPCCDQCACTKSNPPQCRCSDM-RLNSCHSACKSCAC TWIDSTP CFCVDITDF- CYEPCKPSE; SEQ ID NO:679), the unmodified variant parent PEN3-PT-BBIt-TGFβ1 (SEQ ID NO:680): (DDESSKPCCDQCACTKSNPPQCRCSDM-RLNSCHSACKSCAC PENINVLP CFCVDITDF-CYEPCKPSE; SEQ ID NO:680), the unmodified variant parent WTQ-PT-TGFβ1 (SEQ ID NO:681): (DDESSKPCCDQCACTKSNPPQCRCSDM-RLNSCHSACKSCAC WTQHIHNCF CFCVDITDF-CYEPCKPSE; SEQ ID NO:681), and the unmodified variant parent MM0021W-PT-TGFβ1 (SEQ ID NO:682): (DDESSKPCCDQCACTKSNPPQCRCSDM-RLNSCHSACKSCAC KHNVDWL CFCVDITDF-CYEPCKPSE; SEQ ID NO:682), (designated PT in FIG. 14) and the corresponding modified variant MM007-Q-BBIt-FGF-5 (SEQ ID NO:432), the modified variant FGFps2-Q-BBIt-FGF5 (SEQ ID NO:434), the modified variant PEN3-Q-BBIt-TGFβ1 (SEQ ID NO:443), the modified variant WTQ-Q-BBIt-TGFβ1 (SEQ ID NO:445), and the modified variant MM0021W-Q-BBIt-TGFβ1 (SEQ ID NO:447) proteins (designated Q in FIG. 14) measured after growth, after activation with 2-mercaptoethanol and after acid/heat treatment. The data show that the combination of the amino acids 13I-29P-40A-50T-52A when present in the BBIt scaffold carrying FGF-5 or TGFβ1 binding peptides improve the trypsin inhibitory activity after growth and activation, and the production yield after acid/heat treatment when compared to the corresponding parent BBI scaffold carrying the binding peptides.

The data also evidences that substitutions that were shown to improve the trypsin inhibitory activity and/or purification yield of a modified variant BBI in which the chymotrypsin loop had been replaced with a VEGF binding peptide are not specific to BBI-AVs as the same substitutions improve the trypsin inhibitory activity and/or the production yield of BBIs in which the chymotrypsin loop was replaced by other binding peptides e.g. FGF-5 binding peptides and TGFβ1 binding peptides.

Therefore, the amino acid substitutions made in the BBI scaffold that increase the production yield and/or the trypsin activity of BBIt-AV are expected to be generally applicable to BBI scaffolds carrying other binding peptides.

EXAMPLE 14

Performance of Bowman Birk Inhibitor Scaffolds

In this example, the ability to predict the effect of amino acid substitutions on the trypsin activity and/or production yield of a variant Bowman Birk Inhibitor e.g. BBIt-AV (SEQ ID NO:187) was tested by substituting amino acids that are not conserved across Bowman Birk Inhibitor sequences from *Dolichos biflorus* (BBdb, Acc. No. AAK97765; SEQ ID NO:449) PSESSKPCCDQCACTKSIPPQCRCTD-VRLNSCHSACSSCVCTFSIPAQCVCVDMKDFC YEPCK (SEQ ID NO:449), from *Glycine max* (soybean) protease inhibitor IV or D-II (BBsb3, Acc. No. P01064; SEQ ID NO: 450) DDEYSKPCCDLCMCTRSMPPQC-SCEDIRLNSCHSDCKSCMCTRSQPGQCRCLDT NDF-CYKPCKSRDD (SEQ ID NO:450), and from *Torresea (Amburana) cearensis* (BBtc, Acc. No. P83283; SEQ ID NO:451) SSKWEACCDRCACTKSIPPQCHCA-DIRLNSCHSACESCACTHSIPAQCRCFDITDFCYK PCSG (SEQ ID NO:451), into the BBIt-AV scaffold.

Variant Bowman Birk Inhibitors were generated by replacing the second protease inhibitory loop of the Bowman Birk Inhibitor from *Dolichos biflorus* (BBdb, Acc. No. AAK97765; SEQ ID NO:449), the second protease inhibitory loop of the Bowman Birk Inhibitor from *Glycine max* (soybean) protease inhibitor IV or D-II (BBsb3, Acc. No. P01064; SEQ ID NO: 450) and the second protease inhibitory loop of the Bowman Birk Inhibitor from *Torresea (Amburana) cearensis* (BBtc, Acc. No. P83283; SEQ ID NO:451) with the VEGF binding peptide CK37281 (ACYNLYGWTC; SEQ ID NO:9) to generate the corresponding variant BBdb-AV (SEQ ID NO:452), BBsb3-AV (SEQ ID NO:453), and BBtc-AV (SEQ ID NO:454).

The sequences were aligned, as shown in FIG. 15, and amino acids at positions equivalent to positions 11, 13, 18, 23, 25, 27, 35, 37, 52, 54 and 55 of the BBPI of SEQ ID NO:187 (BBIt-AV) were identified as not being conserved across the four inhibitors, and were chosen to modify the BBIt-AV scaffold.

The synthetic genes encoding BBdb-AV (SEQ ID NO:455) and BBsb3-AV (SEQ ID NO:456) were ligated into the p2JMagk103-Ink2-BBIt-AV as BamHI-HindIII fragments. For cloning the BBtc-AV gene, the gene was first digested with BfrI, the overhang filled in with T4 DNA polymerase and dNTP's, the DNA purified, and then digested with BamHI. This fragment was ligated into the p2JMagk103-Ink2-BBIt-AV vector that had been digested with HindIII, the overhang filled in with T4 DNA polymerase and dNTP's, the DNA purified, and then digested with BamHI. The DNA sequences and the corresponding amino acid sequences of the variant PIs are as follows.

BBdb-AV
(SEQ ID NO: 455)
GGATCCTTCTGAGAGCTCTAAACCATGCTGTGATCAATGCGCTTGTACAA
AATCTATCCCTCCACAATGCCGTTGCACTGATGTTCGTCTTAACTCATGT
CACTCTGCATGCAGCTCATGCGCTTGTTACAACCTTTACGGTTGGACATG
CGTTTGCGTCGACATGAAAGATTTCTGCTACGAACCTTGTAAATAAAAGC
TT

BBdb-AV
(SEQ ID NO: 452)
DPSESSKPCCDQCACTKSIPPQCRCTDVRLNSCHSACSSCACYNLYGWTC
VCVDMKDFCYEPCK

BBsb3-AV
(SEQ ID NO: 456)
GGATCCAGATGACGAATACTCTAAACCTTGCTGTGATCTTTGCATGTGTA
CACGTTCTATGCCACCTCAATGCTCATGTGAAGACATCCGCCTTAACTCT
TGCCACTCAGATTGCAAAAGCTGCGCTTGTTACAACCTTTACGGTTGGAC
ATGCCGTTGTTTAGATACTAACGATTTCTGCTACAAACCTTGCAAATCTC
GTGATGATTAAAAGCTT

BBsb3-AV AA
(SEQ ID NO: 453)
DPDDEYSKPCCDLCMCTRSMPPQCSCEDIRLNSCHSDCKSCACYNLYGWT
CRCLDTNDFCYKPCKSRDD

BBtc-AV
(SEQ ID NO: 457)
GGATCCTTCTTCAAAATGGGAAGCTTGCTGTGATCGTTGCGCATGCACAA
AATCTATCCCTCCACAATGCCACTGCGCTGATATCCGTCTTAACTCATGC
CATTCTGCATGCGAAAGCTGCGCTTGTTACAACCTTTACGGTTGGACATG
CCGTTGCTTCGATATCACTGATTTCTGTTACAAACCTTGCTCTGGCTAAA
AGCTTAAAAGGAGACCGTTAATCTAAAATCATTATTTGAGGCCCGAGCTT
AAAGCTTAAG

BBtc-AV AA
(SEQ ID NO: 454)
DPSSKWEACCDRCACTKSIPPQCHCADIRLNSCHSACESCACYNLYGWTC
RCFDITDFCYKPCSG

The three expression vectors comprising the variant inhibitor sequences were used to transform *B. subtilis* host cells BG6006.

Typically, substitutions at the N-terminal and C-terminal ends, which are outside of the first disulfide bond ($C_8$-$C_{62}$), have small effects on the trypsin inhibitory activity and/or purification yield. Thus, only substitutions of amino acids at positions between C8 and C62 were studied. The substitutions targeted in this study are shown in FIG. 15 (bold and underlined).

The individual amino acid substitutions at positions 11, 13, 18, 23, 25, 27, 35, 37, 50, 52, 54, 55, and 60 in BBIt-AV (SEQ ID NO:187) were constructed as described in Examples 8 and 10. These substitutions were analyzed by screening in microtiter plates (with and without reducing agent) as described in Examples 9 and 10. The results are summarized in Table 6 below.

TABLE 6

Effect of single amino acid substitutions present in the BBItc-AV, BBdb-AV and BBsb3-AV scaffolds on the trypsin activity of the modified variant BBIt-AV Amino acid present in the alternative scaffold and relative activity of the amino acid substitution

| Position and amino acid present in the BBIt-AV scaffold | BBItc-AV (SEQ ID NO: 454) | BBIdb-AV (SEQ ID NO: 452) | BBIsb3-AV (SEQ ID NO: 453) |
| --- | --- | --- | --- |
| Q11 | R (+/−) | wt* | L (+/−)** |
| A13 | wt | wt | M (+)*** |
| N18 | I (+++) | I (+++) | M (+/−) |
| R23 | H (−) | wt | S (−−−) |
| S25 | A (+) | T (+/−) | E (−−−) |
| M27 | I (+/−) | V (+/−) | I (+/−) |
| A35 | wt | wt | D (+/−) |
| K37 | E (+/−) | S (+/−) | wt |
| F50 | R (++) | V (+) | R (++) |
| V52 | F (+/−) | wt | L (+) |
| I54 | wt | M (−) | T (−)**** |
| T55 | wt | K (−) | N (+/−) |
| E60 | K (+/−) | wt | K (+/−) |

*wt indicates that the amino acid at this position is the same as in the BBIt-AV scaffold (SEQ ID NO: 187)
**(+/−) indicates that the relative BBI:BCE activity ratio in the presence of reducing agent is not significantly different than that of BBIt-AV.
***(+) indicates that the the relative BBI:BCE activity ratio in the presence of reducing agent is greater than that of BBIt-AV; the greater the number of "+", the greater the difference.
****(−) indicates that the the relative BBI:BCE activity ratio in the presence of reducing agent is less than that of BBIt-AV; the greater the number of "−", the greater the difference.

Assuming the effects of the amino acid substitutions are additive, the data provided in Table 6 predicts that the variant BBItc-AV would perform significantly better than BBIt-AV, while BBIsb3-AV, should perform significantly worse than BBIt-AV. In addition, one would predict that BBIdb-AV would perform somewhat better than BBIt-AV in terms of activation with reducing agent.

To test these predictions, the trypsin activity and production yield of BBIdb-AV, BBIsb3-AV and BBItc-AV were tested using the Shake Flask Screen described in Example 11 and their activity compared to that of the unmodified variant BBIt-AV.

The data shown in FIG. 16 show that, as predicted, BBItc-AV had the highest trypsin inhibitory activity after activation, and BBIdb-AV inhibitory activity was also greater than that of the BBIt-AV inhibitor but less than that of the BBItc-AV inhibitor. In addition, and as predicted, BBIsb3-AV had very low trypsin inhibitory activity and did not activate with reducing agent (inhibitory activity was too small to be shown in FIG. 16). Furthermore, not only did BBItc-AV and BBIdb-AV have higher inhibitory activities after activation than BBIt-AV, they also had higher inhibitory activities after acid/heat treatment indicating improved production yields.

Therefore, the results indicate that activity data obtained when testing single amino acid substitutions in BBIt-AV can be used to predict the performance of other Bowman Birk Inhibitors when used as scaffolds with binding peptides replacing the second protease inhibitory loop.

EXAMPLE 15

Binding of Modified Variant BBIs to Target Proteins

In this example, the capacity of variant peptides to retain their ability to bind the corresponding target proteins was tested when the variant peptides were grafted into a modified Bowman Birk Inhibitor scaffold to replace the chymotrypsin loop.

The construction of the expression vector for BBI is described in Example 1 and the constructions of vectors for variant BBIs containing the VEGF-binding peptide CK37281 (SEQ ID NO:9), the FGF-5-binding peptide MM007 (SEQ ID NO:430) or the FGF-5-binding peptide FGF5ps2 (SEQ ID NO:431) in place of the chymotrypsin inhibitory sequence are described in Example 13 above. The method for the construction of expression vectors encoding for the modified variant BBIt-AVs having various combinations of amino acid substitution is described in Example 12 and the method for constructing the FGF5 and TGFβ-binding BBIs is described in Example 13.

VEGF-binding peptides named VegK (KYYLYWW; SEQ ID NO:458), VegT (TLWKSYW; SEQ ID NO:459) and VegKD (KYDLYWW; SEQ ID NO: 460) were introduced into the chymotrypsin inhibitory loop by ligating oligonucleotide cassettes into the SphI and SalI sites of p2JM103-Ink2-2BBIck81. The sequences of the oligonucleotides used to generate the modified variant VEGK and VEGT BBPIs are shown below VegK:
(SEQ ID NO: 461)
CAAATCTTGCGCATGTAAATATTACCTTTACTGGTGGTGTTTTGCG And (SEQ ID NO: 462)
TCGACGCAAAAACACCACCAGTAAAGGTAATATTTACATGCGCAAGATTT
GCATG BBIT-VEGK
(SEQ ID NO: 640)
DPDDESSKPCCDQCICTKSNPPQCRCRDARPNACHSACKSCACKYYLYWW
CKCTDITDFCYEPCKPSE VegT:
(SEQ ID NO: 463)
CAAATCTTGCGCGTGCACACTTTGGAAATCTTACTGGTGTTTTTGCG And (SEQ ID NO: 464)
TCGACGCAAAAACACCAGTAAGATTTCCAAAGTGTGCACGCGCAAGATTT
GCATG BBIt-VEGT
(SEQ ID NO: 641)
DPDDESSKPCCDQCICTKSNPPQCRCRDARPNACHSACKSCAC TLWKSY
WCKCTDITDFCYEPCKPSE VegKD:
(SEQ ID NO: 465)
CAAATCTTGCATCTGTAAATATGATCTTTACTGGTGGTGTTTTGCG And (SEQ ID NO: 466)
TCGACGCAAAAACACCACCAGTAAAGATCATATTTACAGATGCAAGATTT
GCATG The VEGF-binding peptide named VegKD was introduced into the variant BBI-A13I-S25K-L29P-V52K by ligating a synthetic gene (VegKD-Q) into the BamHI and HindIII sites of p2JMagk103-Ink2-2BBIck81. The sequence of the synthetic gene is shown and encoded BBPI are shown below.

VegKD-Q:
(SEQ ID NO: 467)
GGATCCAGACGATGAGAGCTCTAAACCTTGTTGCGATCAATGCATCTGTA
CAAAATCAAACCCTCCACAATGTCGTTGTAAAGATATGCGTCCTAATAGC
TGTCATTCTGCATGCAAATCATGTATCTGCAAATATGACCTTTACTGGTG
GTGTTTCTGCAAAGACATCACTGACTTCTGCTATGAACCATGTAAACCTT
CTGAATAAAAGCTT (SEQ ID NO: 642)
DPDDESSKPCCDQCICTKSNPPQCRCRDARPNACHSACKSCACKYDLYW
WCKCTDITDFCYEPCKPSE

The VEGF-binding peptides V1 (SKHSQIT; SEQ ID NO:468), V2 (KTNPSGS; SEQ ID NO:469), V3 (RPTGHSL; SEQ ID NO:470), V4 (KHSAKAE; SEQ ID NO:471),V5 (KPSSASS; SEQ ID NO:472) and V6 (PVTKRVH; SEQ ID NO:473), and the TNFα-binding peptides T1 (RYWQDIP; SEQ ID NO:474), T2 (APEPILA; SEQ ID NO:475) and T3 (DMIMVSI; SEQ ID NO:476), were introduced into the chymotrypsin inhibitory loop of a modified BBIt containing amino acid substitutions A13I-S25R-M27A-L29P-S31A-I40A-F50K-V52T by ligating synthetic genes into the BamHI and HindIII sites of p2JMagk103-Ink2-2BBIck81. The DNA sequences of the synthetic genes encoding the resulting modified BBIs are shown below.

BBIt-AV-V1:
(SEQ ID NO: 477)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCAGCAAACACTCTCAAATTAC
TTGTAAATGCACAGACATCACTGACTTCTGCTATGAACCATGTAAACCTT
CTGAATAAAAGCTT (SEQ ID NO: 491)
DPDDESSKPCCDQCICTKSNPPQCRCRDARPNACHSACKSCACSKHSQIT
CKCTDITDFCYEPCKPSE

BBIt-AV-V2:
(SEQ ID NO: 478)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCAAAACAAACCCAAGCGGTTC
TTGTAAATGCACAGACATCACTGACTTCTGCTATGAACCATGTAAACCTT
CTGAATAAAAGCTT (SEQ ID NO: 632)
DPDDESSKPCCDQCICTKSNPPQCRCRDARPNACHSACKSCACKTNPSGS
CKCTDITDFCYEPCKPSE

BBIt-AV-V3:
(SEQ ID NO: 479)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCAGACCAACTGGTCACAGCCT
TTGTAAATGCACAGACATCACTGACTTCTGCTATGAACCATGTAAACCTT
CTGAATAAAAGCTT (SEQ ID NO: 633)
DPDDESSKPCCDQCICTKSNPPQCRCRDARPNACHSACKSCACRPTGHSL
CKCTDITDFCYEPCKPSE

BBIt-AV-V4:
(SEQ ID NO: 480)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCAAACACAGCGCTAAAGCAGA
ATGTAAATGCACAGACATCACTGACTTCTGCTATGAACCATGTAAACCTT
CTGAATAAAAGCTT (SEQ ID NO: 634)
DPDDESSKPCCDQCICTKSNPPQCRCRDARPNACHSACKSCACKHSAKAE
CKDTDITDFCYEPCKPSE

BBIt-AV-V5:
(SEQ ID NO: 481)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCAAACCAAGCTCTGCTTCATC
TTGTAAATGCACAGACATCACTGACTTCTGCTATGAACCATGTAAACCTT
CTGAATAAAAGCTT (SEQ ID NO: 635)
DPDDESSKPCCDQCICTKSNPPQCRCRDARPNACHSACKSCACKPSSASS
CKCTDITDFCYEPCKPSE

BBIt-AV-V6:
(SEQ ID NO: 482)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCCCAGTTACTAAAAGAGTACA
CTGTAAATGCACAGACATCACTGACTTCTGCTATGAACCATGTAAACCTT
CTGAATAAAAGCTT (SEQ ID NO: 636)
DPDDESSKPCCDQCICTKSNPPQCRCRDARPNACHSACKSCACPVTKRVH
CKCTDITDFCYEPCKPSE

BBIt-TNF-T1:
(SEQ ID NO: 483)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCAGATACTGGCAAGATATTCC
ATGTAAATGCACAGACATCACTGACTTCTGCTATGAACCATGTAAACCTT
CTGAATAAAAGCTT (SEQ ID NO: 637)
DPDDESSKPCCDQCICTKSNPPQCRCRDARPNACHSACKSCACRYWQDIP
CKCTDITDFCYEPCKPSE

BBIt-TNF-T2:
(SEQ ID NO: 484)
GGATCCAGACGATGAGAGCTCTAAACCTTGTTGCGATCAATGCATCTGTA
CAAAATCAAACCCTCCACAATGTCGTTGTAGAGATGCTCGTCCTAATGCA
TGTCATTCTGCATGCAAATCATGTGCTTGCGCACCAGAACCTATTCTTGC
TTGTAAATGCACAGACATCACTGACTTCTGCTATGAACCATGTAAACCTT
CTGAATAAAAGCTT (SEQ ID NO: 638)
DPDDESSKPCCDQCICTKSNPPQCRCRDARPNACHSACKSCACAPEPILA
CKCTDITDFCYEPCKPSE

BBIt-TNF-T3:
(SEQ ID NO: 485)
GGATCCAGACGATGAGAGCTCTAAACCTTGTTGCGATCAATGCATCTGT
ACAAAATCAAACCCTCCACAATGTCGTTGTAGAGATGCTCGTCCTAATGC
ATGTCATTCTGCATGCAAATCATGTGCTTGCGATATGATTATGGTTAGCA
TCTGTAAATGCACAGACATCACTGACTTCTGCTATGAACCATGTAAACCT
TCTGAATAAAAGCTT (SEQ ID NO: 639)
DPDDESSKPCCDQCICTKSNPPQCRCRDARPNACHSACKSCACDMIMVSI
CKCTDITDFCYEPCKPSE

The resulting vectors were used to transform B. subtilis BG6006 host cells. Cultures were grown in 500 ml of MBD medium and the BBI species were purified essentially as described above and by Vogtentanz et al., 2007 (Protein Expr Purif 55:40-52 [2007]). BioVeris binding assays were performed essentially as outlined in Example 5 and by the manufacturer. Binding of the modified variant BBIs to their respective target proteins was measured using a BioVeris® binding assay, which is a competition assay that determines the binding of the modified variant BBIs to its target protein (e.g. VEGF, FGF5, TGFβ and TNFα) in the presence or absence of a labeled competitor. The competitor can be a labeled monoclonal antibody raised against the target protein or a labeled native receptor of the target protein. The electrochemiluminescent binding assays were performed essentially as described in Example 5. The apparent IC50s were determined from binding data by determining the concentration of the BBI species needed to reduce the BioVeris signal by one half. BBI scaffolds without the target binding peptide in the chymotrypsin inhibitory loop were used as negative controls.

The results are summarized in Table 7 below.

TABLE 7

Binding activity of modified variant Bowman Birk Inhibitors in which the chymotrypsin loop was replaced by a VEGF-, FGF-5-, TGFβ- or TNFα-binding variant peptide

| Target Protein | Variant Peptide Name· | Variant Peptide Sequence▲ | Bowman Birk Inhibitor Scaffold | Resulting Modified Variant Bowman Birk Inhibitor | BioVeris Binding* |
|---|---|---|---|---|---|
| VEGF | CK37281 | YNLYGWT (SEQ ID NO: 676) | BBIt | BBIt-AV of SEQ ID NO: 187 | +++ |
| VEGF | CK37281 | YNLYGWT (SEQ ID NO: 676) | BBIt-A13I-A40K-F50T-V52A | BBIt-AV of SEQ ID NO: 602 | +++ |
| VEGF | CK37281 | YNLYGWT (SEQ ID NO: 676) | BBIt-A13I-L29P-A40K-F50T-V52A | BBIt-AV of SEQ ID NO: 601 | +++ |
| VEGF | CK37281 | YNLYGWT (SEQ ID NO: 676) | BBIt-A13I-S25R-M27A-L29P-S31A-A40H-F50K-V52T (KT8) | BBIt-AV of SEQ ID NO: 627 | +++ |
| VEGF | CK37281 | YNLYGWT (SEQ ID NO: 676) | BBIt-A13I-S25K-M27A-L29R-S31E-A40K-F50Q-V52Q (QQ8) | BBIt-AV of SEQ ID NO: 628 | +++ |
| VEGF | CK37281 | YNLYGWT (SEQ ID NO: 676) | BBIt-A13I-S25K-M27A-L29R-S31A-A40H-F50R-V52L (RL8) | BBIt-AV of SEQ ID NO: 630 | +++ |
| VEGF | CK37281 | YNLYGWT (SEQ ID NO: 676) | BBdb | BBdb-AV SEQ ID NO: 452 | +++ |
| VEGF | CK37281 | YNLYGWT (SEQ ID NO: 676) | BBtc | BBtc-AV SEQ ID NO: 454 | +++ |
| VEGF | Veg K | KYYLYWW (SEQ ID NO: 458) | BBIt | BBIt-AV of SEQ ID NO: 640 | +++ |
| VEGF | Veg T | TLWKSYW (SEQ ID NO: 459) | BBIt | BBIt-AV of SEQ ID NO: 641 | +++ |
| VEGF | Veg KD | KYDLYWW (SEQ ID NO: 460) | BBIt | BBIt-AV of SEQ ID NO: 642 | +++ |
| VEGF | Veg KD | KYDLYWW (SEQ ID NO: 460) | BBIt-A13I-S25K-L29P-V52K | BBIt-AV of SEQ ID NO: 643 | +++ |
| VEGF | V1 | SKHSQIT (SEQ ID NO: 468) | BBIt-A13I-S25R-M27A-L29P-S31A-F50K-V52T | BBIt-AV-V1 of SEQ ID NO: 491 | ++ |
| VEGF | V2 | KTNPSGS (SEQ ID NO: 469) | BBIt-A13I-S25R-M27A-L29P-S31A-F50K-V52T | BBIt-AV-V2 of SEQ ID NO: 632 | +++ |
| VEGF | V3 | RPTGHSL (SEQ ID NO: 470) | BBIt-A13I-S25R-M27A-L29P-S31A-F50K-V52T | BBIt-AV-V3 of SEQ ID NO: 633 | ++ |
| VEGF | V4 | KHSAKAE (SEQ ID NO: 471) | BBIt-A13I-S25R-M27A-L29P-S31A-F50K-V52T | BBIt-AV-V4 of SEQ ID NO: 634 | +++ |
| VEGF | V5 | KPSSASS (SEQ ID NO: 472) | BBIt-A13I-S25R-M27A-L29P-S31A-I40A-F50K-V52T | BBIt-AV-V5 of SEQ ID NO: 635 | ++ |
| VEGF | V6 | PVTKRVH (SEQ ID NO: 473) | BBIt-A13I-S25R-M27A-L29P-S31A-F50K-V52T | BBIt-AV-V6 of SEQ ID NO: 636 | ++ |

TABLE 7-continued

Binding activity of modified variant Bowman Birk Inhibitors in which the chymotrypsin loop was replaced by a VEGF-, FGF-5-, TGFβ- or TNFα-binding variant peptide

| Target Protein | Variant Peptide Name* | Variant Peptide Sequence▲ | Bowman Birk Inhibitor Scaffold | Resulting Modified Variant Bowman Birk Inhibitor | BioVeris Binding* |
|---|---|---|---|---|---|
| VEGF | Wild-type negative control for VEGF binding | ALSYPAQ (SEQ ID NO: 675) | BBI | sBBI SEQ ID NO: 13 | − |
| FGF-5 | MM007 | RTQPYPL (SEQ ID NO: 670) | BBIt-A13I-L29P-F50T-V52A | MM007-Q-BBIt-FGF-5 of SEQ ID NO: 432 | ++ |
| FGF-5 | FGFps2 | TWIDSTP (SEQ ID NO: 671) | BBIt-A13I-L29P-F50T-V52A | FGFps2-Q-BBIt-FGF-5 of SEQ ID NO: 434 | ++ |
| FGF-5 | Wild-type negative control for FGF-5 binding | ALSYPAQ (SEQ ID NO: 675) | BBI | sBBI SEQ ID NO: 13 | − |
| TGFβ1 | PEN3 | PENINVLP (SEQ ID NO: 672) | BBIt-A40L-F50N | PEN3-Q-BBIt-TGF-A40L-F50N (SEQ ID NO: 677) | ++ |
| TGFβ1 | PEN3 | PENINVLP (SEQ ID NO: 672) | BBIt-A13I-L29P-F50T-V52A | PEN3-Q-BBIt-TGF (SEQ ID NO: 443) | ++ |
| TGFβ1 | MM021W | KHNVDWL (SEQ ID NO: 673) | BBIt-A13I-L29P-F50T-V52A | MM021W-Q-BBIt-TGF (SEQ ID NO: 445) | ++ |
| TGFβ1 | WTQ | WTQHIHN (SEQ ID NO: 674) | BBIt-A13I-L29P-F50T-V52A | WTQ-BBIt-Q-TGF (SEQ ID NO: 447) | ++ |
| TGFβ1 | FGFps2 Negative control for TGFβ binding | TWIDSTP (SEQ ID NO: 671) | BBIt-A13I-L29P-F50T-V52A | FGFps2-Q-BBIt-FGF-5 of SEQ ID NO: 434 | − |
| TNFα | T1 | RWYQDIP (SEQ ID NO: 474) | BBIt-A13I-S25R-M27A-L29P-S31A-F50K-V52T | BBIt-TNF-T1 SEQ ID NO: 637 | ++ |
| TNFα | T2 | APEPILA (SEQ ID NO: 475) | BBIt-A13I-S25R-M27A-L29P-S31A-F50K-V52T | BBIt-TNF-T2 SEQ ID NO: 638 | + |
| TNFα | T3 | DMINVSI (SEQ ID NO: 476) | BBIt-A13I-S25R-M27A-L29P-S31A-F50K-V52T | BBIt-TNF-T3 SEQ ID NO: 639 | + |
| TNFα | V1 Negative control for TNFα binding | SKHSQIT (SEQ ID NO: 468) | BBIt-A13I-S25R-M27A-L29P-S31A-F50K-V52T | BBIt-AV of SEQ ID NO: 491 | − |

*Binding peptide used to replace the chymotrypsin loop of BBIt scaffold.
▲Amino acid sequence of the binding peptide that replaces amino acids 42-48 of the BBIt of SEQ ID NO: 187.
*(+++) indicates and IC50 value of about 2-10 μM; (++) indicates an IC50 value of about 10-50 μM; (+) indicates an IC50 value of about 50-250 μM; and (−) indicates an IC50 value greater than about 250 μM These data show that modified variant BBPIs in which the chymotrypsin loop is replaced by different VEGF binding peptides, and which further comprise at least one amino acid substitution in the backbone of the scaffold, specifically bind their target protein i.e. VEGF. Similarly, the modified variant BBPIs in which the chymotrypsin loop is replaced by other variant peptides e.g. FGF-5, TGFβ and TNFα, also specifically bind their corresponding target proteins i.e. FGF, TGF and TNF. In addition, other BBPI scaffolds i.e. BBtc, BBsb3 and BBdb in which the chymotrypsin loop has been replaced by a variant peptide e.g. VEGF variant peptide, are also capable of specifically binding to the VEGF target protein.

In conclusion, these data show that modified variant BBPI scaffolds comprising at least one amino acid substitution and carrying different variant peptides in place of the chymotrypsin loop retain the ability to bind the target protein that is bound by the free (ungrafted) binding peptide. Thus, the data indicate that different binding peptide sequences that were previously shown to bind their corresponding target protein can be used to replace the chymotrypsin inhibitory loop of a modified BBI protein and be expected to bind the cognate target protein.

EXAMPLE 16

Identification of Peptide T-cell Epitopes in wt BBI

The i-mune® assay was performed for the identification of peptide T-cell epitopes in wild type BBI using naïve human T-cells, as described in WO9953038A2 and Stickler et al, 2000 (J. Immunotherapy, 23(6), 654-660, [2000]). Peptides for use in the assay were prepared based on the wild-type BBI amino acid sequence DDESSKPCCDQCACTKSNPPQCRCSDMRLNSCHSACKSCICALSYPAQCFCVDITDF CYEPCKPSEDDKEN (SEQ ID NO:13). From the full length amino acid sequence of BBI, 15mer peptides were synthetically prepared by Mimotopes US West (San Diego, Calif.). Each 15mer peptide sequence was designed to overlap with the previous and subsequent 15mer, except for three residues. The 20 peptides used to screen for T-cell epitopes, corresponding to wild type BBI sequence, were:

```
P1    DDESSKPCCDQCACT    (P1; SEQ ID NO: 649)
P2    SSKPCCDQCACTKSN    (P2; SEQ ID NO: 650)
P3    PCCDQCACTKSNPPQ    (P3; SEQ ID NO: 651)
P4    DQCACTKSNPPQCRC    (P4; SEQ ID NO: 652)
P5    ACTKSNPPQCRCSDM    (P5; SEQ ID NO: 653)
P6    KSNPPQCRCSDMRLN    (P6; SEQ ID NO: 654)
P7    PPQCRCSDMRLNSCH    (P7; SEQ ID NO: 655)
P8    CRCSDMRLNSCHSAC    (P8; SEQ ID NO: 656)
P9    SDMRLNSCHSACKSC    (P9; SEQ ID NO: 657)
P10   RLNSCHSACKSCICA    (P10; SEQ ID NO: 658)
P11   SCHSACKSCICALSY    (P11; SEQ ID NO: 659)
P12   SACKSCICALSYPAQ    (P12; SEQ ID NO: 660)
P13   KSCICALSYPAQCFC    (P13; SEQ ID NO: 661)
P14   ICALSYPAQCFCVDI    (P14; SEQ ID NO: 662)
P15   LSYPAQCFCVDITDF    (P15; SEQ ID NO: 663)
P16   PAQCFCVDITDFCYE    (P16; SEQ ID NO: 664)
P17   CFCVDITDFCYEPCK    (P17; SEQ ID NO: 665)
P18   VDITDFCYEPCKPSE    (P18; SEQ ID NO: 666)
P19   TDFCYEPCKPSEDDK    (P19; SEQ ID NO: 667)
P20   FCYEPCKPSEDDKEN    (20; SEQ ID NO: 668)
```

Figure 18A:
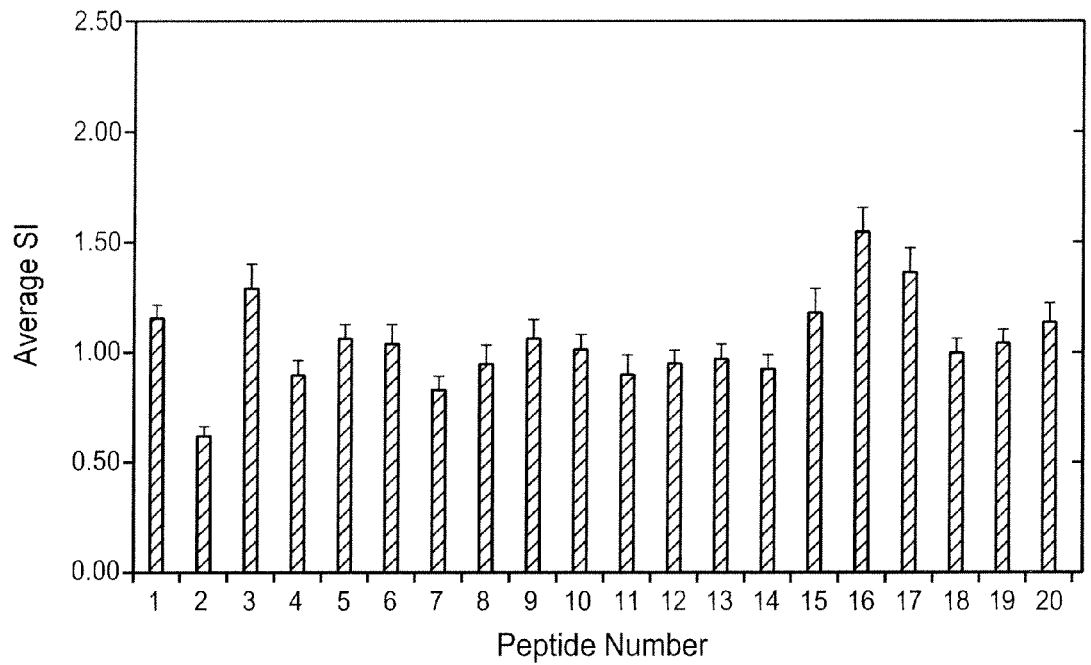
Figure 18B:
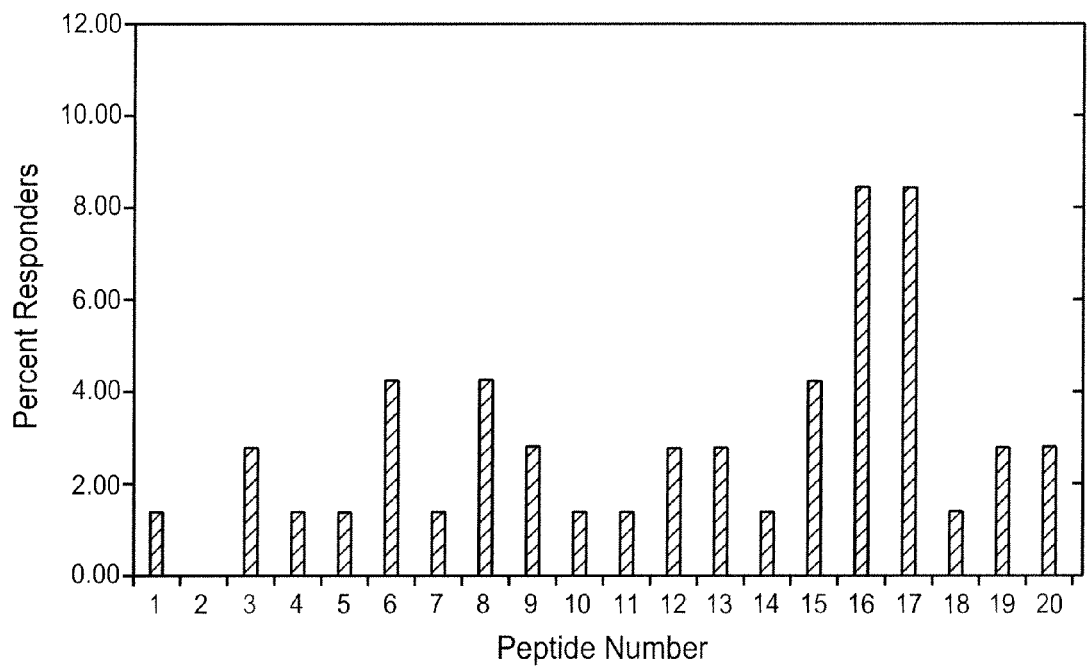

Briefly, human CD4+ T cells were co-cultured with dendritic cells and peptide for the intact peptide set, using the peptides shown in Figure Y. Cytokine responses were averaged within each experiment as described in Strickler et al, 2000 and a response to a peptide was tabulated as positive if the stimulation index (SI) was greater than 2.95 (FIG. 18A). SI values for each donor were compiled for each peptide set and the percent of donors responsive to each peptide is shown in FIG. 18B. The percent background response, 2.89%, was determined as the average percent responders over all the peptides in the set. The standard deviation for this dataset was 2.21%. Major epitopes are defined as having a percentage response that is 3-fold or more than the background. Based on the data shown in FIGS. 18A and 18B, none of the peptide responses were significant based on the statistical method for an unexposed donor population with a low background response rate.

Therefore, these data indicate that the wild type BBI molecule may be considered to have low immunogenicity potential in humans.

EXAMPLE 17

Personal Care Compositions

In this EXAMPLE, various personal care compositions comprising any of the modified variant BBPI compounds of the present invention are provided as follows. In these formulations, the amounts are given as percentages of the total composition, unless otherwise indicated. Also, unless otherwise indicated in the following formulations, the concentration of BBI-AV (referred to as "Compound" below) ranges from about 0.01% to about 1.0%. In some formulations, the preferred concentration is in the range of about 0.1% to about 0.2%, while in other formulations, the preferred concentration is in the range of about 0.05% to about 0.1% (e.g., for some hair growth inhibition embodiments); from about 0.02 to 0.1% (e.g., for some skin lightening embodiments); from about 0.5% to about 1.0% (e.g., for some skin lightening embodiments); or at concentrations greater than about 0.1% (e.g., for some rosacea treating embodiments). Those of skill in the art know how to determine the suitable (i.e., optimum) concentration of BBI-AV for each product. In some of the compositions provided below, the "Compound" amount is indicated as "SA." This indicates that the formulator should use the appropriate concentration of BBI-AV as indicated above herein, or as appropriate for the specific formulation.

| MOISTURIZING BODYWASH (pH 7) | |
|---|---|
| RAW MATERIAL (INCI Designation) | Amount |
| Deionized Water | QS |
| Glycerin | 4.0 |
| PEG-6 Caprylic/Capric Glycerides | 4.0 |
| Palm Kernel Fatty acids | 3.0 |
| Sodium Laureth-3 Sulphate | 45.0 |
| Cocamide MEA | 3.0 |
| Sodium Lauroamphoacetate | 25.0 |
| Soybean Oil | 10.0 |
| Polyquaternium-10 | 0.70 |
| Preservative, fragrance, color | QS |
| Compound | 1000 ppm |

BODY WASH

| RAW MATERIAL (INCI Designation) | pH 8 Amount | pH 6.5 Amount | pH 7 Amount |
|---|---|---|---|
| Deionized water | QS | QS | QS |
| Sodium Laureth Sulphate | 12 | 15 | 8 |
| Cocamidopropyl Betaine | 8 | 10 | 15 |
| Decyl Glucoside | 0 | 2 | 1 |
| Polyquaternium-10 | 0.25 | 0 | 0 |
| Polyquaternium-7 | 0 | 0 | 0.7 |
| Preservative, fragrance, color | QS | QS | QS |
| Compound | 250 ppm | 500 ppm | 1000 ppm |

BODY LOTION

| RAW MATERIAL (INCI Designation) | pH 7 Amount | pH 7 Amount | pH 7.5 Amount | pH 7 Amount |
|---|---|---|---|---|
| Deionized Water | QS | QS | QS | QS |
| Glycerine | 8 | 8 | 0 | 12 |
| Isohexadecane | 3 | 3 | 3 | 6 |
| Niacinamide | 0 | 3 | 5 | 6 |
| Isopropyl Isostearate | 3 | 3 | 3 | 3 |
| Polyacrylamide (and) Isoparaffin (and) Laureth-7 | 3 | 3 | 3 | 3 |
| Petrolatum | 4 | 4 | 4 | 2 |
| Nylon 12 | 2 | 2 | 2.5 | 2.5 |
| Dimethicone | 2 | 2 | 2.5 | 2.5 |
| Sucrose Polycottonseed Oil | 1.5 | 1.5 | 1.5 | 1.5 |
| Stearyl Alcohol 97% | 1 | 1 | 1 | 1 |
| D Panthenol | 1 | 1 | 1 | 1 |
| DL-alphaTocopherol Acetate | 1 | 1 | 1 | 1 |
| Cetyl Alcohol 95% | 0.5 | 0.5 | 0.5 | 1 |
| Behenyl Alcohol | 1 | 1 | 1 | 0.5 |
| Cetearyl Alcohol (and) Cetearyl Glucoside | 0.4 | 0.4 | 0.5 | 0.5 |
| Stearic Acid | 0.15 | 0.15 | 0.15 | 0.15 |
| PEG-100-Stearate | 0.15 | 0.15 | 0.15 | 0.15 |
| Preservative, fragrance, color | QS | QS | QS | QS |
| Compounds | 250 ppm | 500 ppm | 750 ppm | 1000 ppm |

ULTRA-HIGH MOISTURIZING EMULSION

| RAW MATERIAL (INCI Designation) | pH 7 Amount | pH 7 Amount |
|---|---|---|
| Deionized water | QS | QS |
| Glycerin | 12 | 5 |
| PEG 400 | 0 | 10 |
| Niacinamide | 5 | 7 |
| Isohexadecane | 5 | 5 |
| Dimethicone | 3 | 2 |
| Polyacrylamide (and) Isoparaffin (and) Laureth-7 | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Tocopherol Acetate | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate | 0.15 | 0.15 |
| Preservative, fragrance, color | QS | QS |
| Compound | 250 ppm | 100 ppm |

MOISTURIZING CREAM

| RAW MATERIAL (INCI Designation) | pH 7 Amount | pH 7 Amount | pH 7.5 Amount |
|---|---|---|---|
| Deionized water | QS | QS | QS |
| Glycerine | 3 | 5 | 10 |
| Petrolatum | 3 | 3 | 0 |
| Cetyl Alcohol 95% | 1.5 | 1.5 | 1 |
| Dimethicone Copolyol | 2 | 2 | 2 |
| Isopropyl Palmitate | 1 | 1 | 0.5 |
| Carbopol 954 (Noveon) | 0.7 | 0.7 | 0.7 |
| Dimethicone (350cs) | 1 | 1 | 1 |
| Stearyl Alcohol 97% | 0.5 | 0.5 | 1 |
| Stearic acid | 0.1 | 0.1 | 0.1 |
| Peg-100-stearate | 0.1 | 0.1 | 0.1 |
| Titanium Dioxide | 0.3 | 0.3 | 0.3 |
| Preservative, color, fragrance | QS | QS | QS |
| Compound | 50 ppm | 250 ppm | 1000 ppm |

FACIAL CLEANSING EMULSION

| RAW MATERIAL (INCI Designation) | Amount |
|---|---|
| Water | 69.05 |
| Disodium EDTA | 0.1 |
| Glyceryl polymethacrylate (and) Propylene glycol | 1.0 |
| Glycerin | 2.0 |
| Xanthan gum | 0.5 |
| Hydroxyethyl cellulose | 0.5 |
| Tridecyl neopentanoate | 4.0 |
| Isocetyl stearate | 6.0 |
| Octyl palmitate | 8.0 |
| Glyceryl dilaurate | 4.0 |
| PEG-20 stearate | 2.0 |
| Glyceryl stearate (and) Laureth-23 | 2.0 |
| Lauryl pyrrolidone | 0.5 |
| Chamomile extract | 0.2 |
| *Aloe vera* (200x) | 0.05 |
| Fragrance, preservative | QS |
| Compound | SA |

SURFACTANT-BASED FACIAL CLEANSER

| RAW MATERIAL (INCI Designation) | Amount |
|---|---|
| Water | 62.55 |
| Acrylates/Steareth-20 methacrylate copolymer | 3.3 |
| Disodium EDTA | 0.05 |
| Glycerin | 2.0 |
| Glyceryl polymethacrylate (and) Propylene glycol (and) PVM/MA copolymer | 0.5 |
| Sodium laureth sulfate (30%) | 17.5 |
| Cetearyl alcohol | 1.0 |
| Shea butter | 1.0 |

SURFACTANT-BASED FACIAL CLEANSER

| RAW MATERIAL (INCI Designation) | Amount |
|---|---|
| Disodium oleamido PEG-2 sulfosuccinate | 5.0 |
| Cocoamidopropyl Betaine | 3.0 |
| Sodium lauroyl sarcosinate | 1.0 |
| PEG-7 glyceryl cocoate | 1.0 |
| Isodecyl oleate | 1.5 |
| Peppermint extract | 0.25 |
| *Eucalyptus* extract | 0.25 |
| Fragrance, preservative, color, pH adjust | QS |
| Compound | SA |

FACIAL EXFOLIATING GEL

| RAW MATERIAL (INCI Designation) | Amount |
|---|---|
| Water | 64.39 |
| Disodium EDTA | 0.05 |
| *Aloe vera* (200x) | 0.01 |
| Benzophenone-4 | 0.25 |
| Propylene glycol | 1.0 |
| Acrylates/C10-30 alkyl acrylate crosspolymer (2%) | 20.0 |
| Glyceryl polymethacrylate (and) Propylene glycol | 10.0 |
| Glyceryl polymethacrylate (and) Propylene glycol (and) PVM/MA copolymer | 1.0 |
| Hydrogenated jojoba oil | 1.5 |
| Fragrance, preservative, color, pH adjust | QS |
| Compound | SA |

FACIAL TONER

| RAW MATERIAL (INCI Designation) | Amount |
|---|---|
| Water | 93.99 |
| Disodium EDTA | 0.1 |
| Butylene glycol | 2.0 |
| *Aloe vera* (200x) | 0.1 |
| Allantoin | 0.1 |
| Benzophenone-4 | 0.5 |
| Witch hazel extract | 0.3 |
| Propylene glycol (and) *Euphrasia* extract (and) Golden seal root extract (and) Green tea extract | 0.01 |
| PEG-40 hydrogenated castor oil | 0.5 |
| Quaternium-22 | 0.5 |
| Sandlewood oil | 0.02 |
| Fragrance, preservative, color, pH adjust | QS |
| Compound | SA |

EXFOLIATING CREAM

| RAW MATERIAL (INCI Designation) | Amount |
|---|---|
| Water | 68.80 |
| Disodium EDTA | 0.1 |
| PVM/MA decadiene crosspolymer | 1.0 |
| Butylene glycol | 3.0 |
| PEG-20 stearate | 1.0 |
| Glyceryl stearate (and) Laureth-23 | 2.0 |
| Diisopropyl adipate | 2.0 |
| Isodecyl oleate | 2.0 |

EXFOLIATING CREAM

| RAW MATERIAL (INCI Designation) | Amount |
|---|---|
| Isocetyl stearoyl stearate | 5.0 |
| Myristyl myristate | 1.0 |
| Glyceryl dilaurate | 2.0 |
| Sodium hydroxide, 10% | 2.6 |
| Glyceryl polymethacrylate (and) Propylene glycol | 5.0 |
| Glyceryl polymethacrylate (and) Propylene glycol (and) PVM/MA copolymer | 0.5 |
| Hydrogenated jojoba oil | 3.0 |
| Fragrance, preservative, color, pH adjust | QS |
| Compound | SA |

FACIAL MASK

| RAW MATERIAL (INCI Designation) | Amount |
|---|---|
| Water | 76.4 |
| Disodium EDTA | 0.1 |
| Bentonite | 12.5 |
| Potassium C12-13 Alkyl Phosphate | 5.0 |
| Propylene glycol | 4.0 |
| Sodium Coco PG-Dimonium Chloride Phosphate | 1.0 |
| Fragrance, preservative, color, pH adjust | QS |
| Compound | SA |

AFTER-SHAVE BALM

| RAW MATERIAL (INCI Designation) | Amount |
|---|---|
| Water | 82.12 |
| Disodium EDTA | 0.1 |
| Acrylate copolymer | 2.0 |
| Acrylate/Stareth-20 methacrylate copolymer | 1.0 |
| Propylene glycol | 3.0 |
| Sodium hydroxide (10%) | 1.28 |
| Glyceryl stearate (and) Cetyl alcohol (and) Stearyl alcohol (and) Behenyl alcohol (and) Palmitic acid (and) Stearic acid (and) Hydroxyethyl cetearamidopropyldimonium chloride | 3.5 |
| Isocetyl stearate | 1.0 |
| C12-15 alkyl lactate | 1.5 |
| Octyldodecyl stearate | 3.0 |
| Glyceryl polymethacrylate (and) Propylene glycol (and) PVM/MA copolymer | 1.0 |
| Polyquaternium-11 | 0.5 |
| Fragrance, preservative, color, pH adjust | QS |
| Compound | SA |

EYE GEL

| RAW MATERIAL (INCI Designation) | Amount |
|---|---|
| Water | 89.14 |
| VP/Acrylates/Lauryl methacrylate copolymer | 0.5 |
| Glycerin | 5.0 |
| Aminomethyl propanol | 0.3 |
| *Aloe vera* (200x) | 0.05 |
| Benzophenone-4 | 0.1 |
| Glyceryl polymethacrylate (and) Propylene glycol (and) PVM/MA copolymer | 0.2 |

EYE GEL

| RAW MATERIAL (INCI Designation) | Amount |
|---|---|
| Butylene glycol (and) Water (and) Witch hazel extract | 0.5 |
| Butylene glycol (and) Water (and) Cucumber extract | 0.3 |
| PEG-40 hydrogenated castor oil | 0.01 |
| Acrylates/Beheneth-25 methacrylate copolymer | 2.4 |
| Fragrance, preservative, color, pH adjust | QS |
| Compound | SA |

HIGH MELTING POINT LIPSTICK

| RAW MATERIAL (INCI Designation) | Amount |
|---|---|
| Ozokerite wax | 5.0 |
| Candelilla wax | 11.0 |
| Octyl dodecanol | 26.0 |
| C30-45 alkyl methicone | 5.0 |
| Cyclomethicone | 4.8 |
| Petrolatum | 3.0 |
| Lanolin oil | 9.0 |
| Avocado oil | 2.0 |
| Oleyl alcohol | 8.0 |
| Pigment/cyclomethicone | 25.0 |
| Fragrance, preservative | QS |
| Compound | SA |

LIPSTICK

| RAW MATERIAL (INCI Designation) | Amount |
|---|---|
| Candelilla wax | 9.1 |
| Isopropyl myristate | 9.6 |
| Lanolin | 5.0 |
| Beeswax | 4.0 |
| Paraffin (130/135) | 2.0 |
| Ozokerite wax | 2.5 |
| Castor oil | 53.7 |
| Carnauba wax | 1.5 |
| Pigments | 7.5 |
| Mineral oil | 4.0 |
| Fragrance, preservative | QS |
| Compound | SA |

LIP GLOSS

| RAW MATERIAL (INCI Designation) | Amount |
|---|---|
| Bis-diglyceryl polyacyladipate-1 | 43.5 |
| Bis-diglyceryl polyacyladipate-2 | 10 |
| Glycerol ricinoleate | 10 |
| Polyisobutene 1000 | 13 |
| Lanolin wax | 10 |
| Candelilla wax | 2.5 |
| Mica (and) titanium dioxide | 3 |
| d-Panthenol | 5 |
| Fragrance, preservative, color | QS |
| Compound | SA |

LIP GLOSS WITH SUNSCREEN

| RAW MATERIAL (INCI Designation) | Amount |
|---|---|
| Triisostearyl Citrate | 58.4 |
| Candelilla wax | 8.0 |
| Myristyl lactate | 7.5 |
| Microcrystalline wax | 5.0 |
| Carnauba wax | 2.0 |
| Diisopropyl dimmer dilinoleate | 10.0 |
| Mica (and) Bismuth oxychloride (and) Carmine | 6.0 |
| Zinc oxide (microfine) | 2.0 |
| Fragrance, preservative | QS |
| Compound | SA |

LIP BALM

| RAW MATERIAL (INCI Designation) | Amount |
|---|---|
| Petrolatum | 47.3 |
| Isopropyl lanolate | 6.0 |
| Ozokerite wax | 16.5 |
| Candelilla wax | 4.5 |
| Diisopropyl dilinoleate | 25.0 |
| Retinyl palmitate | 0.5 |
| Tocopherol acetate | 0.2 |
| Fragrance, preservative | QS |
| Compound | SA |

WATERPROOF MASCARA

| RAW MATERIAL (INCI Designation) | Amount |
|---|---|
| Water | 49.45 |
| Propylene glycol | 3.0 |
| Triethanolamine (99%) | 3.1 |
| Acrylates/Octylacrylamine Copolymer | 5.0 |
| Diisostearoyl trimethylolpropane siloxy silicate | 5.0 |
| Candelilla wax | 4.5 |
| Beeswax | 5.5 |
| Ozokerite wax | 2.0 |
| Carnauba wax | 1.0 |
| Cetyl alcohol | 3.0 |
| Stearic acid | 5.0 |
| Iron oxides | 11.0 |
| Fragrance, preservative | QS |
| Compound | SA |

ANHYDROUS WATERPROOF MASCARA

| RAW MATERIAL (INCI Designation) | Amount |
|---|---|
| C9-11 Isoparaffin | 30.95 |
| Polyethylene | 11.0 |
| Candelilla wax | 4.5 |
| Hydroxylated lanolin | 0.25 |
| Pentaerythrityl rosinate | 2.0 |
| Zinc stearate | 1.0 |
| Silica silylate | 1.0 |

-continued

ANHYDROUS WATERPROOF MASCARA

| RAW MATERIAL (INCI Designation) | Amount |
|---|---|
| Petroleum distillates (and) Quaternium-18 hectorite (and) Propylene Carbonate | 35.0 |
| Iron oxides | 12.0 |
| Fragrance, preservative | QS |
| Compound | SA |

WATER-BASED MASCARA

| RAW MATERIAL (INCI Designation) | Amount |
|---|---|
| Water | 43.32 |
| Polyvinyl pyrrolidone (K30) | 2.0 |
| Hydroxyethyl cellulose | 1.0 |
| Triethanolamine (99%) | 2.0 |
| Disodium EDTA | 0.1 |
| Iron Oxides | 10.0 |
| Stearic acid | 4.5 |
| Glyceryl monostearate | 2.0 |
| Beeswax | 7.0 |
| Carnauba wax | 4.5 |
| Hydroxylated lanolin | 1.0 |
| Acrylates copolymer | 20.0 |
| Fragrance, preservative | QS |
| Compound | SA |

LIQUID EYELINER

| RAW MATERIAL (INCI Designation) | Amount |
|---|---|
| Water | 50-70 |
| Gellant | 0.5-1.5 |
| Wetting agent(s) | 1-3 |
| Polyol | 4-8 |
| Colorants | 10-20 |
| Alcohol | 5-10 |
| Film former | 3-8 |
| Fragrance, preservative | QS |
| Compound | SA |

NAIL ENAMEL

| RAW MATERIAL (INCI Designation) | Amount |
|---|---|
| Solvent(s) | 40-70 |
| Resin(s) | 10-20 |
| Plasticizer | 3-12 |
| Gellant | 0-2 |
| Colorants | 0-3 |
| Fragrance, preservative | QS |
| Compound | SA |

CUTICLE TREATMENT

| RAW MATERIAL (INCI Designation) | Amount |
|---|---|
| Petrolatum | 34.8 |
| Beeswax | 7.2 |
| Ozokerite wax | 4.3 |
| Candelilla wax | 4.0 |
| Cocoa butter | 1.0 |
| Shea butter | 1.0 |
| Glyceryl dilaurate | 8.0 |
| Ethylhexyl palmitate | 20.0 |
| C12-15 alkyl lactate | 6.0 |
| PVP/Eicosene copolymer | 3.5 |
| Diisopropyl adipate | 2.0 |
| Octinoxate | 7.5 |
| Retinyl palmitate | 0.1 |
| Tocopherol acetate | 0.1 |
| Fragrance, preservative, color, pH adjust | QS |
| Compound | SA |

PRESSED POWDER FORMULATIONS

| | Loose Powder | Pressed Powder | Foundation | Blush | Eye Shadow |
|---|---|---|---|---|---|
| Fillers (e.g., talc, mica, seracite) | 70-95 | 40-90 | 40-80 | 40-80 | 40-80 |
| Compression aids (e.g., metallic soaps, waxes) | 0-2.5 | 3-5 | 2-5 | 2-7 | 2-10 |
| Texture enhancers | 10-40 | 5-40 | 10-40 | 10-40 | 0-30 |
| Colorants (e.g., iron oxides, organic colors) | 2-10 | 2-10 | 5-20 | 2-10 | 1-40 |
| Pearls (e.g. titanated mica, bismuth oxychloride) | 0-20 | 0-10 | 0-5 | 0-20 | 0-60 |
| Wet binder (e.g., Octyldodecyl stearoyl stearate, di-PPG3 myristyl ether adipate, isocetyl stearate, cetyl dimethicone) | 0-3 | 2-5 | 2-5 | 3-10 | 3-15 |
| Dry binder (e.g., calcium silicate, kaolin) | 0-2 | 2-5 | 2-5 | 3-8 | 3-8 |
| Fragrance, preservative | QS | QS | QS | QS | QS |
| Compound | SA | SA | SA | SA | SA |

WATER-IN-OIL FOUNDATION

| RAW MATERIAL (INCI Designation) | Amount |
|---|---|
| Cyclomethicone | 12.0 |
| Dimethicone | 5.0 |
| Cyclomethicone (and) Dimethicone copolyol | 20.0 |
| Laureth-7 | 0.5 |
| Colorants (hydrophobically treated) | 2.2 |
| Titanium dioxide (and) methicone | 8.5 |
| Talc (and) methicone | 3.3 |
| Water | 37.2 |
| Sodium chloride | 2.0 |
| Propylene glycol | 8.0 |
| Fragrance, preservative | QS |
| Compound | SA |

ANHYDROUS MAKEUP STICK

| RAW MATERIAL (INCI Designation) | Amount |
| --- | --- |
| Ozokerite wax | 5.6 |
| Polyethylene | 5.3 |
| Glyceryl dilaurate | 5.5 |
| Isostearyl neopentanoate | 13.0 |
| Octyldodecyl stearoyl stearate | 12.0 |
| Myristyl myristate | 11.0 |
| Ethylhexyl methoxycinnamate | 7.5 |
| PVP/Eicosene copolymer | 0.5 |
| Tocopherol acetate | 0.1 |
| Dimethicone (and) Trimethylsiloxysilicate | 8.0 |
| Cyclopentasiloxane | 9.0 |
| Mica | 10.0 |
| Talc | 1.7 |
| Titanium dioxide (and) Isopropyl titanium triisostearate | 8.86 |
| Iron oxides (and) Isopropyl titanium triisostearate | 1.94 |
| Fragrance, preservative | QS |
| Compound | SA |

WATER-IN-SILICONE FOUNDATION

| RAW MATERIAL (INCI Designation) | Amount |
| --- | --- |
| Cetyl dimethicone copolyol | 0.45 |
| Polyglycerol-4 isostearate (and) Cetyl dimethicone copolyol (and) Hexyl laurate | 1.75 |
| Polyalkylene polysiloxane copolymer | 0.9 |
| Cetyl dimethicone | 0.9 |
| Beeswax | 0.7 |
| Castor wax (and) hydrogenated castor oil | 0.35 |
| Octyl palmitate | 7.0 |
| Cyclomethicone | 7.95 |
| Phenyl trimethicone | 2.2 |
| Titanium dioxide (and) Caprylyl silane | 7.5 |
| Iron oxides (and) Caprylyl silane | 1.1 |
| Talc (and) Caprylyl silane | 3.8 |
| Cyclomethicone | 7.95 |
| Dimethicone | 1.3 |
| Water | 49.55 |
| Sodium chloride | 0.5 |
| Propylene glycol | 5.3 |
| Fragrance, preservative | QS |
| Compound | SA |

OIL-IN-WATER FOUNDATION

| RAW MATERIAL (INCI Designation) | [724] Amount |
| --- | --- |
| Water | 59.85 |
| Polyvinylpyrrolidone | 5.0 |
| Magnesium aluminum silicate | 2.0 |
| Xanthan gum | 0.4 |
| Trisodium EDTA | 0.05 |
| Glyceryl polymethacrylate (and) Propylene glycol (and) PVM/MA copolymer | 1.0 |
| Polysorbate 20 | 1.0 |
| Kaolin | 0.8 |
| Butylene glycol | 4.0 |
| Titanium dioxide | 6.05 |
| Iron oxides | 1.15 |
| Dimethicone | 6.0 |
| Ethylhexyl palmitate | 2.0 |
| PEG/PPG-25/25 Dimethicone | 1.0 |

OIL-IN-WATER FOUNDATION (continued)

| RAW MATERIAL (INCI Designation) | [724] Amount |
| --- | --- |
| Tocopherol acetate | 0.1 |
| Retinyl palmitate | 0.1 |
| Silica | 3.0 |
| Cyclopentasiloxane | 5.0 |
| Fragrance, preservative | QS |
| Compound | SA |

SUNSCREEN FORMULAE

| RAW MATERIAL (INCI Designation) | Amount SPF~25 | SPF~15 |
| --- | --- | --- |
| Water | 52.65 | 71.10 |
| PVM/MA decadiene crosspolymer | 0.5 | 0.5 |
| Butylene glycol | 3.0 | 3.0 |
| Disodium EDTA | 0.1 | 0.1 |
| PEG-20 stearate | 1.5 | 1.5 |
| Glyceryl stearate (and) Laureth-23 | 2.0 | 2.0 |
| Isostearyl neopentanoate | 1.0 | 1.0 |
| Ethylhexyl palmitate | 2.0 | 2.0 |
| Glyceryl dilaurate | 0.5 | 0.5 |
| Octinoxate | 7.5 | 7.5 |
| Oxybenzone | 2.0 | 2.0 |
| Ethylhexyl salicylate | 3.0 | 3.0 |
| Sodium hydroxide (10%) | 1.3 | 1.3 |
| Glyceryl polymethacrylate (and) Propylene glycol | 3.0 | 3.0 |
| Glyceryl polymethacrylate (and) Propylene glycol (and) PVM/MA copolymer | 0.5 | 0.5 |
| Styrene/Acrylates copolymer (27% solids) | 18.45 | — |
| Fragrance, preservative | QS | QS |
| Compound | SA | SA |

VERY WATER-RESISTANT SUNSCREEN FORMULAE

| RAW MATERIAL (INCI Designation) | Amount SPF~12 | SPF~22 |
| --- | --- | --- |
| Water | 65.16 | 46.53 |
| Acrylates copolymer | 3.0 | 3.0 |
| Disodium EDTA | 0.1 | 0.1 |
| Butylene glycol | 2.0 | 2.0 |
| Gylceryl polymethacrylate (and) Propylene glycol (and) PVM/MA copolymer | 1.0 | 1.0 |
| Butylated PVP | 0.05 | 0.05 |
| Glyceryl stearate (and) Behenyl alcohol (and) Palmitic acid (and) Stearic acid (and) Lecithin (and) Lauryl alcohol | 4.5 | 4.5 |
| Tricontanyl PVP | 1.0 | 1.0 |
| Octyl palmitate | 2.0 | 2.0 |
| Octinoxate | 7.5 | 7.5 |
| Oxybenzone | 2.0 | 2.0 |
| Ethylhexyl salicylate | 3.0 | 3.0 |
| Tridecyl neopentanoate | 3.0 | 3.0 |
| Glyceryl dilaurate | 0.5 | 0.5 |
| Sodium hydroxide (10%) | 1.89 | 1.89 |
| Cyclopentasiloxane | 2.0 | 2.0 |
| Butylene glycol | 1.0 | 1.0 |
| Styrene/Acrylates copolymer (27% solids) | 18.45 | — |
| Fragrance, preservative | QS | QS |
| Compound | SA | SA |

WATER-IN-SILICONE SUNSCREEN

| RAW MATERIAL (INCI Designation) | Amount |
|---|---|
| Cetyl PEG/PPG-15/15 butyl ether dimethicone | 2.0 |
| Mineral oil | 3.0 |
| Ethylhexyl palmitate | 1.0 |
| Ethylhexyl salicylate | 5.0 |
| Hydrogenated castor oil | 0.5 |
| Beeswax | 0.5 |
| Octinoxate | 7.5 |
| Polyethylene | 1.0 |
| PEG-30 dipolyhydroxystearate | 2.0 |
| Cyclopentasiloxane | 5.0 |
| Dimethicone | 5.0 |
| Sodium chloride | 0.6 |
| Acrylates/C12-22 alkylmethacrylate copolymer | 0.5 |
| Water | 66.4 |
| Fragrance, preservative | QS |
| Compound | SA |

LEAVE-ON HAIR CONDITIONER

| RAW MATERIAL (INCI Designation) | Amount |
|---|---|
| Deionized Water | QS |
| Isostearamidopropyl Morpholine Lactate | 6.0 |
| Hydroxyethylcellulose | 1.0 |
| Preservative, fragrance, color | QS |
| Compound | 1000 ppm |

CREAM RINSE (pH 4)

| RAW MATERIAL (INCI Designation) | Amount |
|---|---|
| Deionized Water | QS |
| Behentrimonium Chloride | 2.0 |
| Trilaureth-4 Phosphate | 1.5 |
| Cetyl alcohol | 2.0 |
| Citric acid | QS |
| Preservative, fragrance, color | QS |
| Compound | 1000 ppm |

NOURISHING HAIR CONDITIONER/TREATMENT (pH 6)

| RAW MATERIAL (INCI Designation) | Amount |
|---|---|
| Deionized Water | QS |
| Behentrimonium Methosulfate (and) Cetyl Alcohol | 4.0 |
| Wheat germ oil | 1.0 |
| Cetyl alcohol | 0.5 |
| Propylene glycol | 5.0 |
| PEG-60 Lanolin | 1.0 |
| Panthenol | 2.0 |
| Lupin amino acids | 1.0 |
| Cocodimonium Hydroxypropyl Hydrolyzed Wheat Protein | 1.0 |
| Fragrance, preservative, color | QS |
| Compound | 1000 ppm |

CONDITIONING SHAMPOO

| RAW MATERIAL (INCI Designation) | Amount |
|---|---|
| Deionized Water | QS |
| Sodium Laureth Sulfate 30% | 27.0 |
| Cocamidopropyl Betaine | 3.7 |
| Coco-Glucoside (and) Glyceryl Oleate | 5.0 |
| Coco-Glucoside (and) Glycol Distearate (and) Glycerine | 3.0 |
| Guar Hydroxypropyl Trimonium Chloride | 0.1 |
| Laureth-2 | 1.55 |
| Fragrance, preservative, color | QS |
| Compound | 1000 ppm |

ANTI-DANDRUFF SHAMPOO

| RAW MATERIAL (INCI Designation) | Amount |
|---|---|
| Deionized Water | QS |
| Magnesium Aluminum Silicate | 1.0 |
| Hydroxypropyl Methylcellulose | 0.8 |
| Sodium Olefin Sulfate 40% | 35.0 |
| Lauramide DEA | 4.0 |
| Soyamide DEA | 1.0 |
| Quaternium-70 Hydrolyzed Collagen | 2.0 |
| Zinc Pyrithione 40% | 4.0 |
| Fragrance, preservative, color | QS |
| Compound | 1000 ppm |

CLEAR SHAMPOO

| RAW MATERIAL (INCI Designation) | Formulations (Amounts) | | | | |
|---|---|---|---|---|---|
| | 1 | 2 | 3 | 4 | 5 |
| Texapon N 70 | 13.00 | 15.00 | 10.50 | 12.50 | 10.00 |
| Dehyton PK 45 | 7.50 | 7.00 | 5.00 | 5.50 | 10.00 |
| Cetiol HE | 2.00 | 2.50 | 3.50 | 5.00 | 2.30 |
| Fragrance | 0.10 | 0.10 | 0.10 | 0.10 | 0.10 |
| Compound | SA | SA | SA | SA | SA |
| D-Panthenol USP | 1.00 | 1.50 | 1.80 | 1.70 | 1.40 |
| Preservative | 0.10 | 0.10 | 0.10 | 0.10 | 0.10 |
| Citric Acid | 0.10 | 0.10 | 0.10 | 0.10 | 0.10 |
| Luviquat Ultra Care | 1.50 | 1.00 | 1.50 | 1.20 | 1.10 |
| Sodium Chloride | 1.50 | 1.40 | 1.40 | 1.30 | 1.50 |
| Water | QS (100) | QS (100) | QS (100) | QS (100) | QS (100) |

SHAMPOO

| RAW MATERIAL (INCI Designation) | Formulations (Amounts) | | | | |
|---|---|---|---|---|---|
| | 1 | 2 | 3 | 4 | 5 |
| Texapon NSO | 35.00 | 40.00 | 30.00 | 45.00 | 27.00 |
| Plantacare 2000 | 5.00 | 5.50 | 4.90 | 3.50 | 7.00 |
| Tego Betain L7 | 10.00 | 5.00 | 12.50 | 7.50 | 15.00 |
| Fragrance | 0.10 | 0.10 | 0.10 | 0.10 | 0.10 |
| Compound | SA | SA | SA | SA | SA |
| D-Panthenol USP | 0.50 | 1.00 | 0.80 | 1.50 | 0.50 |
| Preservative | 0.10 | 0.10 | 0.10 | 0.10 | 0.10 |
| Citric Acid | 0.10 | 0.10 | 0.10 | 0.10 | 0.10 |

SHAMPOO

| RAW MATERIAL (INCI Designation) | Formulations (Amounts) | | | | |
|---|---|---|---|---|---|
| | 1 | 2 | 3 | 4 | 5 |
| Rewopal LA 3 | 0.50 | 2.00 | 0.50 | 0.50 | 2.00 |
| Sodium Chloride | 1.50 | 1.50 | 1.50 | 1.50 | 1.50 |
| Water | QS (100) | QS (100) | QS (100) | QS (100) | QS (100) |

CLEAR CONDITIONING SHAMPOO

| RAW MATERIAL (INCI Designation) | Formulations (Amounts) | | | | |
|---|---|---|---|---|---|
| | 1 | 2 | 3 | 4 | 5 |
| Amphotensid GB 2009 | 10.00 | 15.00 | 20.00 | 12.00 | 17.00 |
| Plantacare 2000 | 5.00 | 6.00 | 7.00 | 8.00 | 4.00 |
| Tego Betain L7 | 15.00 | 12.00 | 10.00 | 18.00 | 20.00 |
| Luviquat FC 550 | 0.30 | 0.20 | 0.20 | 0.20 | 0.30 |
| Fragrance | 0.10 | 0.10 | 0.10 | 0.10 | 0.10 |
| Compound | SA | SA | SA | SA | SA |
| Cremophor PS 20 | 5.00 | 1.00 | 1.00 | 7.00 | 5.00 |
| Preservative | 0.10 | 0.10 | 0.10 | 0.10 | 0.10 |
| Rewopal LA 3 | 2.00 | 1.00 | 0.50 | 2.00 | 2.00 |
| Citric Acid | 0.20 | 0.20 | 0.20 | 0.20 | 0.20 |
| Stepan PEG 600 DS | 3.00 | 2.00 | 2.00 | 3.00 | 2.50 |
| Water | QS (100) | QS (100) | QS (100) | QS (100) | QS (100) |

FOAM O/W-EMULSION

| RAW MATERIAL (INCI Designation) | Formulations (Amounts) | |
|---|---|---|
| | 1 | 2 |
| Stearic acid | 5.00 | 1.00 |
| Cetyl alcohol | 5.50 | |
| Cetylstearyl alcohol | | 2.00 |
| PEG-40 Stearate | 8.50 | |
| PEG-20 Stearate | | 1.00 |
| Caprylsäure/Caprinsäure triglyceride | 4.00 | 2.00 |
| C12-15 Alkylbenzoate | 10.00 | 15.00 |
| Cyclomethicone | 4.00 | |
| Dimethicone | | 0.50 |
| Compound | SA | SA |
| Octylisostearate | | 5.00 |
| Myristyl Myristate | | 2.00 |
| Ceresin | 1.50 | |
| Glycerine | | 3.00 |
| Filter | | |
| Hydroxypropyl distärke phosphate | 1.00 | 3.50 |
| BHT | | 0.02 |
| Disodium EDTA | 0.50 | 0.10 |
| Parfüm, Konservierungsmittel | QS | QS |
| Colorant | QS | QS |
| Potassium hydroxide | QS | QS |
| Water dem. | QS (100) | QS (100) |
| | pH adjusted to 6.5-7.5 | pH adjusted to 5.0-6.0 |
| Emulsion 1 | | |
| Emulsion 2 | | |
| Gas (Stickstoff) | | |
| Gas (Helium) | | |

CONDITIONER SHAMPOO WITH PEARLESCENT

| RAW MATERIAL (INCI Designation) | Formulations (Amounts) | | |
|---|---|---|---|
| | 1 | 2 | 3 |
| Polyquarternium-10 | 0.50 | 0.50 | 0.40 |
| Sodiumlaurethsulfat | 9.00 | 8.50 | 8.90 |
| Cocoamidopropylbetain | 2.50 | 2.60 | 3.00 |
| Benzophenon-4 | 1.50 | 0.50 | 1.00 |
| Compound | SA | SA | SA |
| Pearlescent compound | 2.00 | 2.50 | |
| Disodium EDTA | 0.10 | 0.15 | 0.05 |
| Preservative, Perfume, thickener | QS | QS | QS |
| Water dem. | QS (100) | QS (100) | QS (100) | pH adjusted to 6.0

CLEAR CONDITIONING SHAMPOO

| RAW MATERIAL (INCI Designation) | Formulations (Amounts) | | |
|---|---|---|---|
| | 1 | 2 | 3 |
| Polyquarternium-10 | 0.50 | 0.50 | 0.50 |
| Sodiumlaurethsulfat | 9.00 | 8.50 | 9.50 |
| Compound | SA | SA | SA |
| Benzophenon-3 | 1.00 | 1.50 | 0.50 |
| Imidosuccinicacid, Na | 0.20 | 0.20 | 0.80 |
| Preservative, Perfume, thickener | QS | QS | QS |
| Water dem. | QS (100) | QS (100) | QS (100) | pH adjusted to 6.0

CLEAR CONDITIONING SHAMPOO WITH VOLUME EFFECT

| RAW MATERIAL (INCI Designation) | Formulations (Amounts) | | |
|---|---|---|---|
| | 1 | 2 | 3 |
| Natriumlaurethsulfat | 10.00 | 10.50 | 11.00 |
| Ethylhexyl Methoxycinnamat | 2.00 | 1.50 | 2.30 |
| Compound | SA | SA | SA |

CONDITIONER SHAMPOO WITH PEARLESCENT

| RAW MATERIAL | Formulations (Amounts) | | |
|---|---|---|---|
| Cocoamidopropylbetain | 2.50 | 2.60 | 2.20 |
| Disodium EDTA | 0.01 | 0.10 | 0.01 |
| Preservative, Perfume, thickener | QS | QS | QS |
| Water dem. | QS (100) | QS (100) | QS (100) | pH adjusted to 6.0

CONDITIONING SHAMPOO WITH PEARLESCENT

| RAW MATERIAL | Formulations (Amounts) | | |
|---|---|---|---|
| (INCI Designation) | 1 | 2 | 3 |
| Polyquarternium-10 | 0.50 | 0.50 | 0.40 |
| Sodiumlaurethsulfat | 9.00 | 8.50 | 8.90 |
| Cocoamidopropylbetain | 2.50 | 2.60 | 3.00 |
| Benzophenon-4 | 1.50 | 0.50 | 1.00 |
| Compound | SA | SA | SA |
| Pearlescent compound | 2.00 | 2.50 | |
| Disodium EDTA | 0.10 | 0.15 | 0.05 |
| Preservative, Perfume, thickener | QS | QS | QS |
| Water dem. | QS (100) | QS (100) | QS (100) | pH adjusted to 6.0

CLEAR CONDITIONING SHAMPOO

| RAW MATERIAL | Formulations (Amounts) | | |
|---|---|---|---|
| (INCI Designation) | 1 | 2 | 3 |
| Polyquarternium-10 | 0.50 | 0.50 | 0.50 |
| Sodiumlaurethsulfat | 9.00 | 8.50 | 9.50 |
| Compound | SA | SA | SA |
| Benzophenon-3 | 1.00 | 1.50 | 0.50 |

CONDITIONER SHAMPOO WITH PEARLESCENT

| | Formulations (Amounts) | | |
|---|---|---|---|
| Imidosuccinicacid, Na | 0.20 | 0.20 | 0.80 |
| Preservative, Perfume, thickener | QS | QS | QS |
| Water dem. | QS (100) | QS (100) | QS (100) | pH adjusted to 6.0

CLEAR CONDITIONING SHAMPOO WITH VOLUME EFFECT

| RAW MATERIAL | Formulations (Amounts) | | |
|---|---|---|---|
| (INCI Designation) | 1 | 2 | 3 |
| Natriumlaurethsulfate | 10.00 | 10.50 | 11.00 |
| Ethylhexyl Methoxycinnamat | 2.00 | 1.50 | 2.30 |
| Compound | SA | SA | SA |
| Cocoamidopropylbetain | 2.50 | 2.60 | 2.20 |
| Disodium EDTA | 0.01 | 0.10 | 0.01 |
| Preservative, Perfume, thickener | QS | QS | QS |
| Water dem. | QS (100) | QS (100) | QS (100) | pH adjusted to 6.0

GEL CREME

| RAW MATERIAL | Formulations (Amounts) | | | |
|---|---|---|---|---|
| (INCI Designation) | 1 | 2 | 3 | 4 |
| Acrylat/C10-30 Alkylacrylat Crosspolymer | 0.40 | 0.35 | 0.40 | 0.35 |
| Polyacrylicacid | 0.20 | 0.22 | 0.20 | 0.22 |
| Xanthan Gummi | 0.10 | 0.13 | 0.10 | 0.13 |
| Cetearylalkohol | 3.00 | 2.50 | 3.00 | 2.50 |
| C12-15 Alkylbenzoat | 4.00 | 4.50 | 4.00 | 4.50 |
| Caprylic/Capric Triglycerid | 3.00 | 3.50 | 3.00 | 3.50 |
| Aminobenzophenon (e.g., UVINUL A PLUS ™) | 2.00 | 1.50 | 0.75 | 1.00 |
| UVASorb K2A | | 3.00 | | |
| Ethylhexyl Methoxycinnamat | 3.00 | | 1.00 | |
| Bis-Ethylhexyloxyphenol methoxyphenyl Triazin | | 1.50 | | 2.00 |
| Butyl Methoxy-dibenzoylmethan | | | 2.00 | |
| Disodium Phenyl Dibenzimidazol Tetrasulfonat | 2.50 | | 0.50 | 2.00 |
| Ethyhexyl Triazon | 4.00 | | 3.00 | 4.00 |
| Octocrylen | | 4.00 | | |
| Diethylhexyl Butamido Triazon | 1.00 | | | 2.00 |
| Phenylbenzimidazol Sulfonsäure | 0.50 | | 3.00 | |
| Methylen Bis-Benzotriazolyl Tetramethylbutylphenol | 2.00 | | 0.50 | 1.50 |
| Ethylhexysalicylate | | | 3.00 | |
| Drometrizol Trisiloxan | | | 0.50 | |
| Terephthaliden Dicamphor Sulfonsäure | | 1.50 | | 1.00 |
| Diethylhexyl-2, 6-naphtalate | 3.50 | 4.00 | 7.00 | 9.00 |
| Titanium dioxide-microfine | 1.00 | | 3.00 | |
| Zincoxide-microfine | | | | 0.25 |
| Compound | SA | SA | SA | SA |
| Cyclisches Dimethylpolysiloxane | 5.00 | 5.50 | 5.00 | 5.50 |
| Dimethicon Polydimethylsiloxane | 1.00 | 0.60 | 1.00 | 0.60 |
| Glycerine | 1.00 | 1.20 | 1.00 | 1.20 |
| Sodium hydoxide | QS. | QS | QS | QS |
| Preservative | 0.30 | 0.23 | 0.30 | 0.23 |
| Perfume | 0.20 | | 0.20 | |
| Water | QS (100) | QS (100) | QS (100) | QS (100) | pH adjusted to 6.0

O/W SUNSCREEN FORMULATION

| RAW MATERIAL (INCI Designations) | Formulation (Amounts) | | | | | | |
|---|---|---|---|---|---|---|---|
| | 1 | 2 | 3 | 4 | 5 | 6 | 7 |
| Glycerin monostearate SE | 0.50 | 1.00 | 3.00 | | | 1.50 | |
| Glycerl Stearate Citrate | 2.00 | | 1.00 | 2.00 | 4.00 | | |
| Stearic acid | | 3.00 | | 2.00 | | | |
| PEG-40 Stearate | 0.50 | | | | | 2.00 | |
| Cetyl Phosphate | | | | | | 1.00 | |
| Cetearyl Sulfate | | | | | | | 0.75 |
| Stearyl Alcohol | | | 3.00 | | | 2.00 | 0.60 |
| Cetyl Alcohol | 2.50 | 1.10 | | 1.50 | 0.60 | | 2.00 |
| Compound | SA | SA | SA | SA | SA | SA | SA |
| Aminobenzophenon (e.g., UVINUL A PLUS ™) | 2.00 | 1.50 | 0.75 | 1.00 | 2.10 | 4.50 | 5.00 |
| UVASorb K2A | | | | | | | |
| Ethylhexyl Methoxycinnamate | | | | | 5.00 | 6.00 | 8.00 |
| Bis-Ethylhexyloxyphenol methoxyphenyl Triazin | | 1.50 | | 2.00 | 2.50 | | 2.50 |
| Butyl Methoxydibenzoylmethane | | | 2.00 | | 2.00 | 1.50 | |
| Dinatrium Phenyl Dibenzimidazol Tetrasulfonate | 2.50 | | 0.50 | 2.00 | | 0.30 | |
| Ethyhexyl Triazone | 4.00 | | 3.00 | 4.00 | | 2.00 | |
| Octocrylen | | 4.00 | | | | | 7.50 |
| Diethylhexyl Butamido Triazon | 1.00 | | | 2.00 | 1.00 | | 1.00 |
| Phenylbenzimidazol Sulfonsäure | 0.50 | 3.00 | | | | | |
| Methylen Bis-Benzotriazolyl Tetramethylbutylphenol | 2.00 | | 0.50 | 1.50 | 2.50 | | |
| Ethylhexysalicylat | | | 3.00 | | | | 5.00 |
| Drometrizol Trisiloxan | | | 0.50 | | | 1.00 | |
| Terephthaliden Dicamphor Sulfonic Acid | | 1.50 | | 1.00 | 1.00 | | 0.50 |
| Diethylhexyl-2,6-naphthalat | 3.50 | | 7.00 | | 6.00 | 9.00 | |
| Titandioxid-microfine | 1.00 | | 3.00 | | 3.50 | | 1.50 |
| Zinkoxid-microfine | | | | 0.25 | | 2.00 | |
| C12-15 Alkyl Benzoate | | 0.25 | | | 4.00 | 7.00 | |
| Dicapryl Ether | | | 3.50 | 2.00 | | | |
| Butylenglycol Dicaprylat/Dicaprat | 5.00 | | 6.00 | | | | |
| Cocoglyceride | | | 6.00 | | 2.00 | | |
| Dimethicon | 0.50 | | 1.00 | | 2.00 | | |
| Cyclomethicone | 2.00 | | 0.50 | | 0.50 | | |
| Shea Butter | | 2.00 | | | | | |
| PVP Hexadecen Copolymer | 0.20 | | | 0.50 | | 1.00 | |
| Glycerin | 3.00 | 7.50 | | 7.50 | 5.00 | | 2.50 |
| Xanthan Gum | 0.15 | | 0.05 | | | 0.30 | |
| Sodium Carbomer | | 0.20 | | 0.15 | 0.25 | | |
| Vitamin E Acetat | 0.60 | | 0.23 | | 0.70 | 1.00 | |
| Fucogel 1000 | | 3.00 | 10.00 | | | | |
| Glycin Soja | | | | 0.50 | | 1.50 | 1.00 |
| Ethylhexyloxyglycin | 0.30 | | | | | | |
| DMDM Hydantoin | | 0.60 | 0.40 | 0.20 | | | |
| Glyacil-L | | | | 0.18 | 0.20 | | |
| Methylparaben | 0.15 | | 0.25 | | 0.50 | | |
| Phenoxyethanol | 1.00 | 0.40 | | | 0.40 | 0.50 | 0.40 |
| Trinatrium EDTA | 0.02 | | 0.05 | | | | |
| Iminosuccinicacid | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | QS (100) | QS (100) | QS (100) | QS (100) | QS (100) | QS (100) | QS (100) |

HYDRODISPERSION

| RAW MATERIAL (INCI Designation) | Formulations (Amounts) | | | | |
|---|---|---|---|---|---|
| | 1 | 2 | 3 | 4 | 5 |
| Ceteareth-20 | 1.00 | | | 0.50 | |
| Cetyl Alkohol | | | 1.00 | | |
| Sodium Carbomer | | 0.20 | | 0.30 | |
| Acrylat/C10-30 Alkyl Acrylat Crosspolymer | 0.50 | | 0.40 | 0.10 | 0.50 |
| Xanthan Gummi | | 0.30 | 0.15 | | |
| Compound | SA | SA | SA | SA | SA |
| Aminobenzophenon (e.g., UVINUL A PLUS ™) | 2.00 | 1.50 | 0.75 | 1.00 | 2.10 |
| UVASorb K2A | | | | 3.50 | |

HYDRODISPERSION

| RAW MATERIAL (INCI Designation) | Formulations (Amounts) | | | | |
|---|---|---|---|---|---|
| | 1 | 2 | 3 | 4 | 5 |
| Ethylhexyl Methoxycinnamat | | | | | 5.00 |
| Bis-Ethylhexyloxyphenol methoxyphenyl Triazin | | 1.50 | | 2.00 | 2.50 |
| Butyl Methoxydibenzoylmethan | | | 2.00 | | 2.00 |
| Dinatrium Phenyl Dibenzimidazol Tetrasulfonat | 2.50 | | 0.50 | 2.00 | |
| Ethyhexyl Triazon | 4.00 | | 3.00 | 4.00 | |
| Octocrylen | | 4.00 | | | |
| Diethylhexyl Butamido Triazon | 1.00 | | | 2.00 | 1.00 |
| Phenylbenzimidazol Sulfonsäure | 0.50 | | 3.00 | | |
| Methylen Bis-Benzotriazolyl Tetramethylbutylphenol | 2.00 | | 0.50 | 1.50 | 2.50 |
| Ethylhexysalicylat | | | 3.00 | | |
| Drometrizol Trisiloxan | | | 0.50 | | |
| Terephthaliden Dicamphor Sulfonsäure | | 1.50 | | 1.00 | 1.00 |
| Diethylhexyl-2,6-naphthalat | | | 7.00 | | 9.00 |
| Titaniumdioxide-microfine | 1.00 | | 3.00 | | 3.50 |
| Zincoxide-microfine | | | | 0.25 | |
| C12-15 Alkyl Benzoat | 2.00 | 2.50 | | | |
| Dicapryl Ether | | 4.00 | | | |
| Butylenglycol Dicaprylat/Dicaprat | 4.00 | | 2.00 | 6.00 | |
| Dicapryl Carbonat | | 2.00 | 6.00 | | |
| Dimethicon | | 0.50 | 1.00 | | |
| Phenyltrimethicon | 2.00 | | 0.50 | | |
| Shea Butter | | 2.00 | | 5.00 | |
| PVP Hexadecen Copolymer | 0.50 | | | 0.50 | 1.00 |
| Tricontanyl PVP | 0.50 | | 1.00 | | |
| Ethylhexylglycerin | | | 1.00 | | 0.80 |
| Glycerin | 3.00 | 7.50 | | 7.50 | 8.50 |
| Gylcin Soja | | | 1.50 | | 1.00 |
| Vitamin E Acetat | 0.50 | | 0.25 | | 1.00 |
| Alpha-Glucosilrutin | 0.60 | | | 0.25 | |
| Fucogel 1000 | | 2.50 | 0.50 | | 2.00 |
| DMDM Hydantoin | | 0.60 | 0.45 | 0.25 | |
| Glyacil-S | 0.20 | | | | |
| Methylparaben | 0.50 | | 0.25 | 0.15 | |
| Phenoxyethanol | 0.50 | 0.40 | | 1.00 | |
| Trinatrium EDTA | | 0.01 | 0.05 | | 0.10 |
| Ethanol | 3.00 | 2.00 | 1.50 | | 7.00 |
| Perfume | 0.20 | | 0.05 | 0.40 | |
| Water | QS (100) | QS (100) | QS (100) | QS (100) | QS (100) |

W/O SUNSCREEN EMULSION

| RAW MATERIAL (INCI Designation) | Formulations (Amounts) | | | | |
|---|---|---|---|---|---|
| | 1 | 2 | 3 | 4 | 5 |
| Cetyldimethicon Copolyol | | 2.50 | | 4.00 | |
| Polyglyceryl-2-dipolyhydroxystearat | 5.00 | | | | 4.50 |
| PEG-30-dipolyhydroxystearat Compound | SA | SA | 5.00 SA | SA | SA |
| Aminobenzophenon (e.g., UVINUL A PLUS ™) | 2.00 | 1.50 | 0.75 | 1.00 | 2.10 |
| UVASorb K2A | | 2.00 | | | |
| Ethylhexyl Methoxycinnamat | | | | | 5.00 |
| Bis-Ethylhexyloxyphenol methoxyphenyl Triazin | | 1.50 | | 2.00 | 2.50 |
| Butyl Methoxydibenzoylmethan | | | 2.00 | | 2.00 |
| Dinatrium Phenyl Dibenzimidazol Tetrasulfonat | 2.50 | | 0.50 | 2.00 | |
| Ethyhexyl Triazon | 4.00 | | 3.00 | 4.00 | |
| Octocrylen | | 4.00 | | | |
| Diethylhexyl Butamido Triazon | 1.00 | | | 2.00 | 1.00 |
| Phenylbenzimidazol Sulfonsäure | 0.50 | | 3.00 | | |
| Methylen Bis-Benzotriazolyl Tetramethylbutylphenol | 2.00 | | 0.50 | 1.50 | 2.50 |
| Ethylhexysalicylat | | | 3.00 | | |
| Drometrizol Trisiloxan | | | 0.50 | | |
| Terephthaliden Dicamphor Sulfonsäure | | 1.50 | | 1.00 | 1.00 |
| Diethylhexyl-2,6-naphthalat | | | 7.00 | | 4.00 |
| Titaniumdioxide-microfine | 1.00 | | 3.00 | | 3.50 |
| Zincoxide-microfine | | | | 0.25 | |
| Mineraloil | | 12.00 | 10.00 | | 8.00 |
| C12-15 Alkyl Benzoat | | | | 9.00 | |
| Dicaprylyl Ether | 10.00 | | | | 7.00 |
| Butylenglycol Dicaprylat/Dicaprat | | | 2.00 | 8.00 | 4.00 |
| Dicaprylyl Carbonat | 5.00 | | 6.00 | | |
| Dimethicon | | 4.00 | 1.00 | 5.00 | |
| Cyclomethicon | 2.00 | 2.50 | | | 2.00 |
| Shea Butter | | | 3.00 | | |
| Vaseline | | 4.50 | | | |
| PVP Hexadecen Copolymer | 0.50 | | | 0.50 | 1.00 |
| Ethylhexylglycerin | | 0.30 | 1.00 | | 0.50 |
| Glycerin | 3.00 | 7.50 | | 7.50 | 8.50 |
| Glycin Soja | | 1.00 | 1.50 | | 1.00 |
| MgSO4 | 1.00 | 0.50 | | 0.50 | |
| MgCl2 | | | 1.00 | | 0.70 |
| Vitamin E Acetat | 0.50 | | 0.25 | | 1.00 |
| Ascorbyl Palmitat | 0.50 | | | 2.00 | |
| Fucogel 1000 | | | | 3.50 | 1.00 |
| DMDM Hydantoin | | 0.60 | 0.40 | 0.20 | |
| Methylparaben | 0.50 | | 0.25 | 0.15 | |
| Phenoxyethanol | 0.50 | 0.40 | | 1.00 | |
| Trisodium EDTA | 0.12 | 0.05 | | 0.30 | |
| Ethanol | 3.00 | | 1.50 | | 5.00 |
| Perfume | 0.20 | | 0.40 | 0.35 | |
| Water | QS (100) | QS (100) | QS (100) | QS (100) | QS (100) |

STICKS

| RAW MATERIAL (INCI Designation) | Formulations (Amounts) | | | |
|---|---|---|---|---|
| | 1 | 2 | 3 | 4 |
| Caprylic/Capric Triglycerid | 12.00 | 10.00 | 6.00 | |
| Octyldodecanol | 7.00 | 14.00 | 8.00 | 3.00 |
| Butylene Glycol Dicaprylat/Dicaprat | | | | 12.00 |
| Pentaerythrityl Tetraisostearat | 10.00 | 6.00 | 8.00 | 7.00 |
| Polyglyceryl-3 Diisostearat | 2.50 | | | |
| Bis-Diglyceryl Polyacyladipate-2 | 9.00 | 8.00 | 10.00 | 8.00 |
| Cetearyl Alcohol | 8.00 | 11.00 | 9.00 | 7.00 |
| Myristyl Myristate | 3.50 | 3.00 | 4.00 | 3.00 |
| Beeswax | 5.00 | 5.00 | 6.00 | 6.00 |
| Cera Carnauba | 1.50 | 2.00 | 2.00 | 1.50 |
| Cera Alba | 0.50 | 0.50 | 0.50 | 0.40 |
| C16-40 Alkyl Stearat | | 1.50 | 1.50 | 1.50 |
| Compound | SA | SA | SA | SA |

STICKS

| RAW MATERIAL (INCI Designation) | Formulations (Amounts) | | | |
|---|---|---|---|---|
| | 1 | 2 | 3 | 4 |
| Aminobenzophenon (e.g., UVINUL A PLUS ™) | 2.00 | 1.50 | 0.75 | 9.00 |
| UVASorb K2A | | 2.00 | | 4.00 |
| Ethylhexyl Methoxycinnamat | | 3.00 | | |
| Bis-Ethylhexyloxyphenol methoxyphenyl Triazin | | 1.50 | | 2.00 |
| Butyl Methoxy-dibenzoylmethan | | | 2.00 | |
| Dinatrium Phenyl Dibenzimidazol Tetrasulfonat | 2.50 | | 0.50 | 2.00 |
| Ethyhexyl Triazon | 4.00 | | 3.00 | 4.00 |
| Octocrylen | | 4.00 | | |
| Diethylhexyl Butamido Triazon | 1.00 | | | 2.00 |
| Phenylbenzimidazol Sulfonsäure | 0.50 | | 3.00 | |
| Methylen Bis-Benzotriazolyl Tetramethylbutylphenol | 2.00 | | 0.50 | 1.50 |
| Ethylhexysalicylat | | | 3.00 | |
| Drometrizol Trisiloxan | | | 0.50 | |
| Terephthaliden Dicamphor Sulfonsäure | | 1.50 | | 1.00 |
| Diethylhexyl-2,6-naphthalat | | | 7.00 | |
| Titaniumdioxide-microfine | 1.00 | | 3.00 | |
| Zincoxide-microfine | | | | 0.25 |
| Vitamin E Acetat | 0.50 | 1.00 | | |
| Ascorbyl Palmitat | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | QS (100) | QS (100) | QS (100) | QS (100) |

PIT-EMULSION

| RAW MATERIAL (INCI Designation) | Formulations (Amounts) | | | | | | | |
|---|---|---|---|---|---|---|---|---|
| | 1 | 2 | 3 | 4 | 5 | 6 | 7 | 8 |
| Glycerinmonostearat SE | 0.50 | 2.00 | 3.00 | 5.00 | | 0.50 | 4.00 | |
| Glyceryl Isostearat | | | | | 3.50 | 4.00 | 2.00 | |
| Isoceteth-20 | | 0.50 | | | 2.00 | | | |
| Ceteareth-12 | | 5.00 | | 1.00 | | | 3.50 | 5.00 |
| Ceteareth-20 | | 5.00 | | 1.00 | | | | 3.50 |
| PEG-100 Stearat | | | | 2.80 | | 2.30 | 3.30 | |
| Cetyl Alkohol | 5.20 | | 1.20 | 1.00 | 1.30 | | 0.50 | 0.30 |
| Cetyl Palmitat | 2.50 | 1.20 | | 1.50 | | 0.50 | | 1.50 |
| Cetyl Dimethicon Copolyol | | | | 0.50 | | 1.00 | | |
| Polyglyceryl-2 | | | | 0.75 | 0.30 | | | |
| Compound | SA | SA | SA | SA | SA | SA | SA | SA |
| Aminobenzophenon (e.g., UVINUL A PLUS ™) | 2.00 | 1.50 | 0.75 | 1.00 | 2.10 | 4.50 | 5.00 | 2.10 |
| UVASorb K2A | | | | 4.00 | | | 1.50 | |
| Ethylhexyl Methoxycinnamat | | | | | 5.00 | 6.00 | 8.00 | 5.00 |
| Bis-Ethylhexyloxyphenol methoxyphenyl Triazin | | 1.50 | | 2.00 | 2.50 | | 2.50 | 2.50 |
| Butyl Methoxydibenzoylmethan | | | 2.00 | | 2.00 | 1.50 | | 2.00 |
| Dinatrium Phenyl Dibenzimidazol Tetrasulfonat | 2.50 | | 0.50 | 2.00 | | 0.30 | | |
| Ethyhexyl Triazon | 4.00 | | 3.00 | 4.00 | | 2.00 | | |
| Octocrylen | | 4.00 | | | | | 7.50 | |
| Diethylhexyl Butamido Triazon | 1.00 | | | 2.00 | 1.00 | | 1.00 | 1.00 |
| Phenylbenzimidazol Sulfonsaure | 0.50 | | 3.00 | | | | | |
| Methylen Bis-Benzotriazolyl Tetramethylbutylphenol | 2.00 | | 0.50 | 1.50 | 2.50 | | | 2.50 |
| Ethylhexysalicylat | | | 3.00 | | | | 5.00 | |
| Drometrizol Trisiloxan | | | 0.50 | | | 1.00 | | |
| Terephthaliden Dicamphor Sulfonsäure | | 1.50 | | 1.00 | 1.00 | | 0.50 | 1.00 |
| Diethylhexyl-2,6-naphthalat | | | 7.00 | | 10.00 | 7.50 | | 8.00 |
| Titandioxid-microfine | 1.00 | | 3.00 | | 3.50 | | 1.50 | 3.50 |
| Zinkoxid-microfine | | | | 0.25 | | 2.00 | | |
| C12-15 Alkyl Benzoat | 3.50 | | | 6.35 | | | | 0.10 |
| Cocoglyceride | | | 3.00 | | 3.00 | | | 1.00 |
| Dicapryl Ether | 4.50 | | | | | | | |
| Dicaprylyl Carbonat | | | 4.30 | | 3.00 | | | 7.00 |
| Dibutyl Adipate | | | | | 0.50 | | | 0.30 |
| Phenyltrimethicone | 2.00 | | | 3.50 | | 2.00 | | |
| Cyclomethicon | | | 3.00 | | | | | |

| PIT-EMULSION | | | | | | | | |
|---|---|---|---|---|---|---|---|---|
| RAW MATERIAL | Formulations (Amounts) | | | | | | | |
| (INCI Designation) | 1 | 2 | 3 | 4 | 5 | 6 | 7 | 8 |
| Ethyl Galaktomannan | | 0.50 | | | 2.00 | | | |
| Hydrierte Coco-Glyceride | | | | | 3.00 | 4.00 | | |
| Abil Wax 2440 | | | | | | 1.50 | 2.00 | |
| PVP Hexadecen Copolymer | | | | 1.00 | 1.20 | | | |
| Glycerin | 4.00 | 6.00 | 5.00 | | 8.00 | 10.00 | | |
| Vitamin E Acetat | 0.20 | 0.30 | 0.40 | | 0.30 | | | |
| Shea Butter | | 2.00 | | 3.60 | | 2.00 | | |
| Iodopropyl Butylcarbamat | 0.12 | | | | 0.20 | | | |
| Fucogel 1000 | | | | 0.10 | | | | |
| DMDM Hydantoin | 0.10 | | | | 0.12 | | 0.13 | |
| Methylparaben | | 0.50 | 0.30 | | 0.35 | | | |
| Phenoxyethanol | 0.50 | 0.40 | | 1.00 | | | | |
| Octoxyglycerin | | 0.30 | | | 1.00 | | 0.35 | |
| Ethanol | 2.00 | | 2.00 | | | 5.00 | | |
| Trinatrium EDTA | 0.40 | | 0.15 | | 0.20 | | | |
| Perfume | 0.20 | | 0.20 | 0.24 | 0.16 | 0.10 | 0.10 | |
| Water | QS (100) | QS (100) | QS (100) | QS (100) | QS (100) | QS (100) | QS (100) | QS (100) |

| GEL CREME | | | | |
|---|---|---|---|---|
| RAW MATERIAL | Formulations (Amounts) | | | |
| (INCI Designation) | 1 | 2 | 3 | 4 |
| Acrylat/C10-30 alkylacrylat crosspolymer | 0.40 | 0.35 | 0.40 | 0.35 |
| Polyacrylic acid | 0.20 | 0.22 | 0.20 | 0.22 |
| Luvigel EM | 1.50 | 2.50 | 2.80 | 3.50 |
| Xanthan gum | 0.10 | 0.13 | 0.10 | 0.13 |
| Cetearylalkohol | 3.00 | 2.50 | 3.00 | 2.50 |
| C12-15 Alkylbenzoate | 4.00 | 4.50 | 4.00 | 4.50 |
| Caprylic/Capric Triglyceride | 3.00 | 3.50 | 3.00 | 3.50 |
| Titan dioxide-microfine | 1.00 | | 1.50 | |
| Zinc oxide-microfine | | 2.00 | | 0.25 |
| Compound | SA | SA | SA | SA |

| GEL CREME | | | | |
|---|---|---|---|---|
| RAW MATERIAL | Formulations (Amounts) | | | |
| (INCI Designation) | 1 | 2 | 3 | 4 |
| Dihydroxyacetone | | | 3.00 | 5.00 |
| Cyclisches Dimethylpolysiloxan | 5.00 | 5.50 | 5.00 | 5.50 |
| Dimethicon Polydimethylsiloxan | 1.00 | 0.60 | 1.00 | 0.60 |
| Glycerine | 1.00 | 1.20 | 1.00 | 1.20 |
| Natrium hydroxide | QS | QS | QS | QS |
| Preservatives | 0.30 | 0.23 | 0.30 | 0.23 |
| Perfume | 0.20 | | 0.20 | |
| Water | QS (100) | QS (100) | QS (100) | QS (100) | pH adjusted to 6.0

| O/W SELF TANNER FORMULATIONS | | | | | | | |
|---|---|---|---|---|---|---|---|
| RAW MATERIAL | Formulations (Amounts) | | | | | | |
| (INCI Designation) | 1 | 2 | 3 | 4 | 5 | 6 | 7 |
| Glycerin monostearate SE | 0.50 | 1.00 | 3.00 | | | 1.50 | |
| Glycerlstearate citrate | 2.00 | | 1.00 | 2.00 | 4.00 | | |
| Stearic acid | | 3.00 | | 2.00 | | | |
| PEG-40 stearate | 0.50 | | | | | 2.00 | |
| Cetyl phosphate | | | | | | 1.00 | |
| Cetearyl sulfate | | | | | | | 0.75 |
| Stearyl alcohol | | | 3.00 | | | 2.00 | 0.60 |
| Cetyl alcohol | 2.50 | 1.10 | | 1.50 | 0.60 | | 2.00 |
| Compound | SA | SA | SA | SA | SA | SA | SA |
| Dihydroxy acetone | | | 3.00 | 5.00 | | 4 | |
| Titanium dioxide-microfine | 1.00 | | | | 1.50 | | 1.50 |
| Zinc oxide-microfine | | | | 0.25 | | 2.00 | |
| C12-15 Alkyl benzoate | | 0.25 | | | 4.00 | 7.00 | |
| Dicapryl ether | | | 3.50 | | | 2.00 | |

O/W SELF TANNER FORMULATIONS

| RAW MATERIAL (INCI Designation) | Formulations (Amounts) | | | | | | |
|---|---|---|---|---|---|---|---|
| | 1 | 2 | 3 | 4 | 5 | 6 | 7 |
| Butylenglycol Dicaprylaet/Dicaprat | 5.00 | | 6.00 | | | | |
| Cocoglyceride | | | 6.00 | | 2.00 | | |
| Dimethicon | 0.50 | | 1.00 | | 2.00 | | |
| Cyclomethicon | 2.00 | | 0.50 | | 0.50 | | |
| Shea butter | | 2.00 | | | | | |
| PVP hexadecen copolymer | 0.20 | | | 0.50 | | 1.00 | |
| Glycerin | 3.00 | 7.50 | | 7.50 | 5.00 | | 2.50 |
| Xanthan gum | 0.15 | | 0.05 | | | 0.30 | |
| Sodium carbomer | | 0.20 | | 0.15 | 0.25 | | |
| Vitamin E acetate | 0.60 | | 0.23 | | 0.70 | 1.00 | |
| Fucogel 1000 | | 3.00 | 10.00 | | | | |
| *Glycin Soja* | | | | 0.50 | | 1.50 | 1.00 |
| Ethylhexyloxy glycin | 0.30 | | | | | | |
| DMDM hydantoin | | 0.60 | 0.40 | 0.20 | | | |
| Glyacil-L | | | | 0.18 | 0.20 | | |
| Methylparaben | 0.15 | | 0.25 | | 0.50 | | |
| Phenoxyethanol | 1.00 | 0.40 | | | 0.40 | 0.50 | 0.40 |
| Trinatrium EDTA | 0.02 | | 0.05 | | | | |
| Iminobernsteinsaure | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | QS (100) | QS (100) | QS (100) | QS (100) | QS (100) | QS (100) | QS (100) |

O/W MAKE UP

| RAW MATERIAL (INCI Desigation) | Formulations (Amounts) | | | | | | |
|---|---|---|---|---|---|---|---|
| | 1 | 2 | 3 | 4 | 5 | 6 | 7 |
| Glycerinmonostearat SE | 0.50 | 1.00 | 3.00 | | | 1.50 | |
| Glycerl Stearat Citrat | 2.00 | | 1.00 | 2.00 | 4.00 | | |
| Stearicacid | | 3.00 | | 2.00 | | | |
| PEG-40 Stearat | 0.50 | | | | | 2.00 | |
| Cetyl Phosphat | | | | | | 1.00 | |
| Cetearyl Sulfat | | | | | | | 0.75 |
| Stearyl Alkohol | | | 3.00 | | | 2.00 | 0.60 |
| Cetyl Alkohol | 2.50 | 1.10 | | 1.50 | 0.60 | | 2.00 |
| Compound | SA | SA | SA | SA | SA | SA | SA |
| Titaniumoxide | 10.00 | 12.00 | 9.00 | 8.50 | 11.00 | 9.50 | 10.00 |
| Ironoxide | 2.00 | 4.00 | 3.00 | 5.00 | 3.40 | 6.00 | 4.40 |
| Zincoxide | | 4.00 | | 2.00 | | 3.00 | |
| C12-15 Alkyl Benzoat | | 0.25 | | | 4.00 | 7.00 | |
| Dicapryl Ether | | | 3.50 | | 2.00 | | |
| Butylenglycol Dicaprylat/Dicaprat | 5.00 | | 6.00 | | | | |
| Cocoglyceride | | | 6.00 | | 2.00 | | |
| Dimethicon | 0.50 | | 1.00 | | 2.00 | | |
| Cyclomethicon | 2.00 | | 0.50 | | 0.50 | | |
| Shea Butter | | 2.00 | | | | | |
| PVP Hexadecen Copolymer | 0.20 | | | 0.50 | | 1.00 | |
| Glycerin | 3.00 | 7.50 | | 7.50 | 5.00 | | 2.50 |
| Xanthan Gummi | 0.15 | | 0.05 | | | 0.30 | |
| Sodium Carbomer | | 0.20 | | 0.15 | 0.25 | | |
| Vitamin E Acetat | 0.60 | | 0.23 | | 0.70 | 1.00 | |
| *Glycin Soja* | | | | 0.50 | | 1.50 | 1.00 |
| Ethylhexyloxyglycin | 0.30 | | | | | | |
| DMDM Hydantoin | | 0.60 | 0.40 | 0.20 | | | |
| Glyacil-L | | | | 0.18 | 0.20 | | |
| Methylparaben | 0.15 | | 0.25 | | 0.50 | | |
| Phenoxyethanol | 1.00 | 0.40 | | | 0.40 | 0.50 | 0.40 |
| Trinatrium EDTA | 0.02 | | 0.05 | | | | |
| Iminosuccinicacid | | | | 0.25 | 1.00 | | |
| Ethanol | 2.00 | 1.50 | | 3.00 | | 1.20 | 5.00 |

O/W MAKE UP

| RAW MATERIAL (INCI Desigation) | Formulations (Amounts) | | | | | | |
|---|---|---|---|---|---|---|---|
| | 1 | 2 | 3 | 4 | 5 | 6 | 7 |
| Perfume | 0.10 | 0.25 | 0.30 | | 0.40 | 0.20 | |
| Water | QS (100) | QS (100) | QS (100) | QS (100) | QS (100) | QS (100) | QS (100) |

SELF TANNER HYDRODISPERSION

| RAW MATERIAL (INCI Designation) | Formulations (Amounts) | | | | |
|---|---|---|---|---|---|
| | 1 | 2 | 3 | 4 | 5 |
| Ceteaereth-20 | 1.00 | | | 0.50 | |
| Cetyl Alkohol | | | 1.00 | | |
| Luvigel EM | | 2.00 | | 2.50 | 2.00 |
| Acrylat/C10-30 Alkyl Acrylat Crosspolymer | 0.50 | | 0.40 | 0.10 | 0.50 |
| Xanthan Gummi | | 0.30 | 0.15 | | |
| Compound | SA | SA | SA | SA | SA |
| Dihydroxyaceton | | | 3.00 | 5.00 | |
| Aminobenzophenon (e.g., UVINUL A PLUS ™) | 2.00 | 1.50 | 0.75 | 1.00 | 2.10 |
| Titandioxid-microfine | 1.00 | | 1.00 | | 1.00 |
| Zinkoxid-microfine | | 1.90 | | 0.25 | |
| C12-15 Alkyl Benzoat | 2.00 | 2.50 | | | |
| Dicapryl Ether | | 4.00 | | | |
| Butylenglycol Dicaprylat/Dicaprat | 4.00 | | 2.00 | 6.00 | |
| Dicapryl Carbonat | | 2.00 | 6.00 | | |
| Dimethicon | | 0.50 | 1.00 | | |
| Phenyltrimethicon | 2.00 | | 0.50 | | |
| Shea Butter | | 2.00 | | 5.00 | |
| PVP Hexadecen Copolymer | 0.50 | | | 0.50 | 1.00 |
| Tricontanyl PVP | 0.50 | | 1.00 | | |
| Ethylhexylglycerin | | | 1.00 | | 0.80 |
| Glycerin | 3.00 | 7.50 | | 7.50 | 8.50 |
| *Gylcin Soja* | | | 1.50 | | 1.00 |
| Vitamin E Acetat | 0.50 | | 0.25 | | 1.00 |
| Alpha-Glucosilrutin | 0.60 | | | 0.25 | |
| DMDM Hydantoin | | 0.60 | 0.45 | 0.25 | |
| Glyacil-S | 0.20 | | | | |
| Methylparaben | 0.50 | | 0.25 | 0.15 | |
| Phenoxyethanol | 0.50 | 0.40 | | 1.00 | |
| Trinatrium EDTA | | 0.01 | 0.05 | | 0.10 |
| Ethanol | 3.00 | 2.00 | 1.50 | | 7.00 |
| Parfüm | 0.20 | | 0.05 | 0.40 | |
| Water | QS (100) | QS (100) | QS (100) | QS (100) | QS (100) |

AFTER SUN HYDRODISPERSION

| | Formulations (Amounts) | | | | |
|---|---|---|---|---|---|
| | 1 | 2 | 3 | 4 | 5 |
| Ceteaereth-20 | 1.00 | | | 0.50 | |
| Cetyl Alkohol | | | 1.00 | | |
| Luvigel EM | | 2.00 | | 2.50 | 2.00 |
| Acrylat/C10-30 Alkyl Acrylat Crosspolymer | 0.50 | 0.30 | 0.40 | 0.10 | 0.50 |
| Xanthan Gummi | | 0.30 | 0.15 | | |
| Compound | SA | SA | SA | SA | SA |
| C12-15 Alkyl Benzoat | 2.00 | 2.50 | | | |
| Dicapryl Ether | | 4.00 | | | |

-continued

AFTER SUN HYDRODISPERSION

| | Formulations (Amounts) | | | | |
|---|---|---|---|---|---|
| | 1 | 2 | 3 | 4 | 5 |
| Butylenglycol Dicaprylat/Dicaprat | 4.00 | | 2.00 | 6.00 | |
| Dicapryl Carbonat | | 2.00 | 6.00 | | |
| Dimethicon | | 0.50 | 1.00 | | |
| Phenyltrimethicon | 2.00 | | 0.50 | | |
| Tricontanyl PVP | 0.50 | | 1.00 | | |
| Ethylhexylglycerin | | | 1.00 | | 0.80 |
| Glycerin | 3.00 | 7.50 | | 7.50 | 8.50 |
| *Gylcin Soja* | | | 1.50 | | 1.00 |
| Vitamin E Acetat | 0.50 | | 0.25 | | 1.00 |
| Alpha-Glucosilrutin | 0.60 | | | 0.25 | |
| Trinatrium EDTA | | 0.01 | 0.05 | | 0.10 |
| Ethanol | 1.00 | 10.00 | 8.00 | 12.00 | 9.00 |
| Perfume | 0.20 | | 0.05 | 0.40 | |
| Water | QS (100) | QS (100) | QS (100) | QS (100) | QS (100) |

WO-EMULSIONS

| RAW MATERIAL (INCI Designation) | Formulations (Amounts) | | | | |
|---|---|---|---|---|---|
| | 1 | 2 | 3 | 4 | 5 |
| Cetyldimethicon Copolyol | | 2.50 | | 4.00 | |
| Polyglyceryl-2-dipolyhydroxystearat | 5.00 | | | | 4.50 |
| PEG-30-dipolyhydroxystearat | | | 5.00 | | |
| Compound | SA | SA | SA | SA | SA |
| Aminobenzophenon (e.g., UVINUL A PLUS ™) | 2.00 | 1.50 | 0.75 | 1.00 | 2.10 |
| Titaniumdioxide-microfine | 1.00 | | 3.00 | | 3.50 |
| Zincoxide-microfine | | 0.90 | | 0.25 | |
| Mineralöl | | 12.00 | 10.00 | | 8.00 |
| C12-15 Alkyl Benzoat | | | | 9.00 | |
| Dicaprylyl Ether | 10.00 | | | | 7.00 |
| Butylenglycol Dicaprylat/Dicaprat | | | 2.00 | 8.00 | 4.00 |
| Dicaprylyl Carbonat | 5.00 | | 6.00 | | |
| Dimethicon | | 4.00 | 1.00 | 5.00 | |
| Cyclomethicon | 2.00 | 25.00 | | | 2.00 |
| Shea Butter | | | 3.00 | | |
| Vaseline | | 4.50 | | | |
| PVP Hexadecen Copolymer | 0.50 | | | 0.50 | 1.00 |
| Ethylhexylglycerin | | 0.30 | 1.00 | | 0.50 |
| Glycerin | 3.00 | 7.50 | | 7.50 | 8.50 |
| *Glycin Soja* | | 1.00 | 1.50 | | 1.00 |
| MgSO4 | 1.00 | 0.50 | | 0.50 | |
| MgCl2 | | | 1.00 | | 0.70 |
| Vitamin E Acetat | 0.50 | | 0.25 | | 1.00 |
| Ascorbyl Palmitat | 0.50 | | | 2.00 | |
| Fucogel 1000 | | | | 3.50 | 7.00 |
| DMDM Hydantoin | | 0.60 | 0.40 | 0.20 | |
| Methylparaben | 0.50 | | 0.25 | 0.15 | |
| Phenoxyethanol | 0.50 | 0.40 | | 1.00 | |
| Trinatrium EDTA | 0.12 | 0.05 | | 0.30 | |
| Ethanol | 3.00 | | 1.50 | | 5.00 |
| Perfume | 0.20 | | 0.40 | 0.35 | |
| Water | QS (100) | QS (100) | QS (100) | QS (100) | QS (100) |

SOLID STABILIZED EMULSIONS (PICKERING EMULSIONS)

| RAW MATERIAL (INCI Designation) | Formulations (Amounts) | | | | |
|---|---|---|---|---|---|
| | 1 | 2 | 3 | 4 | 5 |
| Mineral oil | | | 16.00 | 16.00 | |
| Octyldodecanol | 9.00 | 9.00 | 5.00 | | |
| Caprylic/Capric Triglycerid | 9.00 | 9.00 | 6.00 | | |
| C12-15 Alkyl Benzoat | | | | 5.00 | 8.00 |
| Butylen Glycol Dicaprylat/Dicaprat | | | | | 8.00 |
| Dicaprylyl Ether | 9.00 | | | 4.00 | |
| Dicaprylyl Carbonat | | 9.00 | | | |
| Hydroxyoctacosanyl Hydroxystearat | 2.00 | 2.00 | 2.20 | 2.50 | 1.50 |
| Disteardimonium Hectorit | 1.00 | 0.75 | | 0.50 | 0.25 |
| Cera Microcristallina + Paraffinum Liquidum | | 0.35 | | | 5.00 |
| Hydroxypropyl Methylcellulose | | | 0.10 | | 0.05 |
| Dimethicon | | | | | 3.00 |
| Compound | SA | SA | SA | SA | SA |
| Titaniumdioxide + Alumina + Simethicon + Aqua | | 3.00 | | | |
| Titaniumdioxide + Trimethoxycaprylylsilan | | 2.00 | 4.00 | 2.00 | 4.00 |
| Silica Dimethyl Silylat | 2.50 | | | 6.00 | 2.50 |
| Bornitrid | | | 1.00 | | |
| Stärke/-Natriummetaphosphat-Polymer | 2.00 | | | | |
| Tapioca Stärke | | 0.50 | | | |
| Sodium Chlorid | 5.00 | 7.00 | 8.50 | 3.00 | 4.50 |
| Glycerin | | | | 1.00 | |
| Trinatrium EDTA | 1.00 | 1.00 | 1.00 | 1.00 | 1.00 |
| Vitamin E Acetat | 5.00 | 10.00 | 3.00 | 6.00 | 10.00 |
| Ascorbyl Palmitat | 1.00 | 1.00 | | 1.00 | |
| Methylparaben | | 0.60 | | | 0.20 |
| Propylparaben | | | | | 0.20 |
| Phenoxyethanol | | | 0.20 | | |
| Hexamidin Diisethionat | | | 0.40 | 0.50 | 0.40 |
| Diazolidinyl Harnstoff | | | | | 0.08 |
| Ethanol | | | 0.23 | 0.20 | |
| Perfume | 5.00 | | 3.00 | 4.00 | |
| Water | 0.20 | 0.30 | 0.10 | | |
| | QS (100) | QS (100) | QS (100) | QS (100) | QS (100) |

STICKS

| RAW MATERIAL (INCI Designation) | Formulations (Amounts) | | | |
|---|---|---|---|---|
| | 1 | 2 | 3 | 4 |
| Caprylic/Capric Triglycerid | 12.00 | 10.00 | 6.00 | |
| Octyldodecanol | 7.00 | 14.00 | 8.00 | 3.00 |
| Butylene Glycol Dicaprylat/Dicaprat | | | | 12.00 |
| Pentaerythrityl Tetraisostearat | 10.00 | 6.00 | 8.00 | 7.00 |
| Polyglyceryl-3 Diisostearat | 2.50 | | | |
| Bis-Diglyceryl Polyacyladipate-2 | 9.00 | 8.00 | 10.00 | 8.00 |
| Cetearyl Alcohol | 8.00 | 11.00 | 9.00 | 7.00 |
| Myristyl Myristate | 3.50 | 3.00 | 4.00 | 3.00 |
| Beeswax | 5.00 | 5.00 | 6.00 | 6.00 |
| Cera Carnauba | 1.50 | 2.00 | 2.00 | 1.50 |
| Cera Alba | 0.50 | 0.50 | 0.50 | 0.40 |
| C16-40 Alkyl Stearat | | 1.50 | 1.50 | 1.50 |
| Compound | SA | SA | SA | SA |
| Aminobenzophenon (e.g., UVINUL A PLUS ™) | 2.00 | 1.50 | 0.75 | 9.00 |
| Titaniumdioxide-microfine | 1.00 | | 3.00 | |
| Zincoxide-microfine | | 1.00 | | 0.25 |
| Vitamin E Acetat | 0.50 | 1.00 | | |
| Ascorbyl Palmitat | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | QS (100) | QS (100) | QS (100) | QS (100) |

SELF TANNER PIT-EMULSION

| | Formulations (Amounts) | | | | | | | |
|---|---|---|---|---|---|---|---|---|
| | 1 | 2 | 3 | 4 | 5 | 6 | 7 | 8 |
| Glycerinmonostearat SE | 0.50 | 2.00 | 3.00 | 5.00 | | 0.50 | 4.00 | |
| Glyceryl Isostearat | | | | | 3.50 | 4.00 | 2.00 | |
| Isoceteth-20 | | 0.50 | | | 2.00 | | | |
| Ceteareth-12 | | 5.00 | | 1.00 | | | 3.50 | 5.00 |
| Ceteareth-20 | | 5.00 | | 1.00 | | | | 3.50 |
| PEG-100 Stearat | | | | 2.80 | | 2.30 | 3.30 | |
| Cetyl Alkohol | 5.20 | | 1.20 | 1.00 | 1.30 | | 0.50 | 0.30 |
| Cetyl Palmitat | 2.50 | 1.20 | | 1.50 | | 0.50 | | 1.50 |
| Cetyl Dimethicon Copolyol | | | | 0.50 | | 1.00 | | |
| Polyglyceryl-2 Compound | SA | SA | SA | 0.75 SA | 0.30 SA | SA | SA | SA |
| Dihydroxyaceton | | | 3.00 | 5.00 | | | 4.00 | |
| Aminobenzophenon (e.g., UVINUL A PLUS ™) | 2.00 | 1.50 | 0.75 | 1.00 | 2.10 | 4.50 | 5.00 | 2.10 |
| Titandioxide-microfine | 1.00 | | 1.50 | | 3.50 | | 1.50 | 1.00 |
| Zinkoxide-microfine | | 1.00 | | 0.25 | | 2.00 | | 1.50 |
| C12-15 Alkyl Benzoat | 3.50 | | | 6.35 | | | | 0.10 |
| Cocoglyceride | | 3.00 | | 3.00 | | | | 1.00 |
| Dicapryl Ether | 4.50 | | | | | | | |
| Dicaprylyl Carbonat | | 4.30 | | 3.00 | | | | 7.00 |
| Dibutyl Adipate | | | | 0.50 | | | | 0.30 |
| Phenyltrimethicone | 2.00 | | | 3.50 | | 2.00 | | |
| Cyclomethicon | | 3.00 | | | | | | |
| Ethyl Galaktomannan | | 0.50 | | | 2.00 | | | |
| Hydrogenated Coco-Glyceride | | | | | 3.00 | 4.00 | | |
| Abil Wax 2440 | | | | | | | 1.50 | 2.00 |
| PVP Hexadecen Copolymer | | | | 1.00 | 1.20 | | | |
| Glycerin | 4.00 | 6.00 | 5.00 | | 8.00 | 10.00 | | |
| Vitamin E Acetat | 0.20 | 0.30 | 0.40 | | 0.30 | | | |
| Shea Butter | | 2.00 | | 3.60 | | 2.00 | | |
| Iodopropyl Butylcarbamat | 0.12 | | | 0.20 | | | | |
| DMDM Hydantoin | 0.10 | | | 0.12 | | | 0.13 | |
| Methylparaben | | 0.50 | 0.30 | 0.35 | | | | |
| Phenoxyethanol | 0.50 | 0.40 | | 1.00 | | | | |
| Octoxyglycerin | | 0.30 | | 1.00 | | | 0.35 | |
| Ethanol | 2.00 | | 2.00 | | 5.00 | | | |
| Trinatrium EDTA | 0.40 | 0.15 | | | | 0.20 | | |
| Perfume | 0.20 | | 0.20 | 0.24 | 0.16 | | 0.10 | 0.10 |
| Water | QS (100) | QS (100) | QS (100) | QS (100) | QS (100) | QS (100) | QS (100) | QS (100) |

OILGELS

| RAW MATERIAL (INCI Designation) | Formulations (Amounts) | | | |
|---|---|---|---|---|
| | 1 | 2 | 3 | 4 |
| Caprylic/Capric Triglycerid | 12.00 | 10.00 | 6.00 | |
| Octyldodecanol | 7.00 | 14.00 | 8.00 | 3.00 |
| Butylene Glycol Dicaprylat/Dicaprat | | | | 12.00 |
| Pentaerythrityl Tetraisostearat | 10.00 | 6.00 | 8.00 | 7.00 |
| Polyglyceryl-3 Diisostearat | 2.50 | | | |
| Bis-Diglyceryl Polyacyladipate-2 | 9.00 | 8.00 | 10.00 | 8.00 |
| Myristyl Myristate | 3.50 | 3.00 | 4.00 | 3.00 |
| Bentone-34 | 5.00 | 5.00 | 6.00 | 6.00 |
| Propylencarbonat | 15.00 | 20.00 | 18.00 | 19.50 |
| Compound | SA | SA | SA | SA |
| Vitamin E Acetat | 0.50 | 1.00 | | |
| Ascorbyl Palmitat | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | QS (100) | QS (100) | QS (100) | QS (100) |

In still further embodiments, the present invention comprises at least one inorganic pigment. In some preferred embodiments, these inorganic pigments are based on metaloxides and/or other water slightly soluble or insoluble metal compounds, including but not limited to compounds such as zinc oxides (ZnO), titanium ($TiO_2$), iron (e.g., $Fe_2O_3$), zirconium ($ZrO_2$), silica ($SiO_2$), manganese (e.g., MnO), aluminium ($Al_2O_3$), cer (e.g., $Ce_2O_3$), and mixed oxides of these oxides, as well as blends thereof. In some embodiments, the metaloxides are microfine grade, while in other embodiments, the metaloxides are pigment grade. In further embodiments, the metaloxides are a mixture of microfine and pigment grades.

In additional embodiments, the inorganic pigments are coated (i.e., they are treated on the surface). In some particularly preferred embodiments, the surface is coated with a thin, hydrophobic film. In some other particularly preferred embodiments, the surface is coated with a thin, hydrophilic film. In yet additional embodiments, the present invention provides compositions comprising various make ups and make up constituents. For example, in some embodiments, the present invention provides various dyes and/or pigments. In some embodiments, useful pigments include, but are not limited to titanium dioxide, mica, iron oxides (e.g. $Fe_2O_3$, $Fe_3O_4$, FeO(OH), etc.) and/or stannous oxide. The present invention further provides colorants, including but not limited to carmine, blue, chromooxide, ultramarine and/or purple manganese. The colorants and pigments of some most preferred embodiments are known to those in the art and provided previously (See e.g., Colour Index Nummern (CIN), *Rowe Colour Index*, $3^{rd}$ ed., Society of Dyers and Colourists, Bradford, England [1971]).

In additional embodiments, pearlescent pigments based on mica/metaloxide find use, as described above. However, it is not intended that the present invention be limited to these particular pigments, as additional pearlescent pigments find use in various embodiments of the present invention.

The following formulations provide additional examples of the use of the present invention.

| RAW MATERIAL (INCI Designation | Formulation (Amounts) | | | | |
|---|---|---|---|---|---|
| | 1 | 2 | 3 | 4 | 5 |
| Sodium Carbomer | | 0.2 | | | |
| Acrylates/$C_{10}$-$C_{30}$ Alkyl Acrylate Crosspolymer | 0.3 | 0.2 | 0.6 | | |
| Hydroxypropyl Cellulose | | | | 1.0 | 1.50 |
| Xanthan Gummi | | 0.6 | 0.2 | 1.0 | 1.0 |
| Compound | 0.5 | 0.1 | 0.01 | 0.01 | 1.0 |
| Dioctyl Butamidotriazon | 2.0 | 2.0 | 1.0 | | |
| Ethylhexyl Triazon | 4.0 | 4.0 | 5.0 | | |
| Aniso Triazin | 1.0 | 0.5 | | 2.0 | 2.5 |
| Bisoctyltriazol | | | | 6.0 | |
| Drometrizole Trisiloxane | | | | | |
| PhenylbenzmidazSulfonicacid | 2.0 | | | 1.0 | |
| Bisimidazylate | | | | 1.0 | |
| Terephthalylidene Dicamphor Sulfonic Acid | | | | 0.2 | |
| Ethylhexyl Methoxycinnamat | 7.5 | 10.0 | | 5.0 | |
| Octocrylen | | | | | 5.0 |
| Dimethicone-diethylbenzalmalonate | | | | 4.0 | |
| Ethylhexyl Salicylate | | | | | |
| Homosalate | | | | | |
| Butyl Methoxydibenzoylmethan | 1.0 | 1.0 | 4.0 | | |
| Titan dioxide | 1.0 | 4.0 | | | |
| Zinc oxide | | | | 4.0 | |
| Caprylic/Capric Triglycerid | | | 2.0 | | |
| Hydrogenated Coco-Glyceride | | | 3.0 | | |
| C12-15 Alkyl Benzoat | 2.0 | 2.5 | 3.0 | | |
| Dicaprylyl Ether | | 4.0 | | | |
| Butylenglycol Dicaprylat/Dicaprat | 4.0 | | 2.0 | 6.0 | |
| Dicaprylyl Carbonat | | 2.0 | | | |
| Cetyl Dimethicon | 2.0 | 0.5 | 1.0 | | |
| Shea Butter | | 2.0 | | | |
| PVP Hexadecen Copolymer | 0.5 | | 0.05 | 0.5 | |
| Glycerin | 3.0 | 7.5 | | 7.5 | 2.5 |
| Tocopherol | | 0.5 | 0.75 | | 0.2 |
| Trisodium EDTA | 1.0 | 0.5 | 0.5 | 1.0 | 1.5 |
| Natriumcitrat | | 0.2 | | | |
| Zitronensäure | | 0.1 | | 0.1 | 0.1 |
| DMDM Hydantoin | | 0.6 | | 0.2 | |
| Methylparaben | 0.5 | | 0.3 | 0.15 | |
| Phenoxyethanol | 0.5 | 0.4 | 0.4 | 1.0 | 0.60 |
| Ethanol | 3.0 | 2.0 | 3.0 | | 1.0 |
| Perfume | 0.2 | | | 0.2 | 0.2 |
| Water | QS (100) | QS (100) | QS (100) | QS (100) | QS (100) |

| RAW MATERIAL (INCI Designation) | Formulations (Amounts) | | | | |
|---|---|---|---|---|---|
| | 1 | 2 | 3 | 4 | 5 |
| Sodium Carbomer | 0.5 | | | 1.5 | |
| Acrylates/C$_{10}$-C$_{30}$ Alkyl Acrylate Crosspolymer | | 0.4 | 0.1 | | 0.75 |
| Hydroxypropyl Cellulose | | | 0.5 | | 0.25 |
| Xanthan Gummi | 0.2 | 0.4 | | | |
| Compound | 0.5 | 0.1 | 0.01 | 0.01 | 1.0 |
| Dioctyl Butamidotriazon | 1.0 | | 2.0 | | |
| Ethylhexyl Triazon | | 2.0 | | 2.0 | |
| Aniso Triazin | 1.0 | 0.2 | 3.0 | 1.0 | |
| Bisoctyltriazol | | | | | 8.0 |
| Drometrizole Trisiloxane | | | | | 4.0 |
| Phenylbenzmidazole Sulfonicacid | | 1.5 | | | |
| Bisimidazylate | | | 1.5 | | |
| Terephthalylidene Dicamphor Sulfonic Acid | | | | | 0.5 |
| Ethylhexyl Methoxycinnamat | | 7.5 | 5.0 | 10.0 | |
| Octocrylen | 10.0 | | 5.0 | | 5.0 |
| Dimethicone-diethylbenzalmalonate | | | | | 2.5 |
| Ethylhexyl Salicylate | | | 3.5 | 5.0 | |
| Homosalate | | | 4.0 | | |
| Butyl Methoxydibenzoylmethan | 0.5 | | | | |
| Titandioxide | 1.5 | 2.0 | 1.0 | | 2.5 |
| Zincoxide | | | 1.0 | | 0.5 |
| Caprylic/Capric Triglycerid | | | | | |
| Hydrogenierte Coco-Glyceride | | | | | |
| C12-15 Alkyl Benzoat | | | | | 5.0 |
| Dicaprylyl Ether | | | | | 7.5 |
| Butylenglycol Dicaprylat/Dicaprat | | | | | |
| Dicaprylyl Carbonat | | 7.5 | | | |
| Cetyl Dimethicon | | | | | |
| Shea Butter | | | | | 3.0 |
| PVP Hexadecen Copolymer | 0.5 | | 0.75 | | 1.0 |
| Glycerin | 5.0 | | 10.0 | | |
| Tocopherol | 0.3 | | 1.5 | | 1.0 |
| Trisodium EDTA | 0.5 | | 0.1 | 0.5 | |
| Natriumcitrat | | | 0.3 | | |
| Zitronensäure | | | 0.15 | | |
| DMDM Hydantoin | | | | 0.3 | 0.15 |
| Methylparaben | | 0.4 | | | |
| Phenoxyethanol | | 1.0 | | | |
| Ethanol | 7.5 | | 5.0 | | 7.0 |
| Perfume | | 0.25 | | 0.2 | |
| Water | QS (100) | QS (100) | QS (100) | QS (100) | QS (100) |

| RAW MATERIAL (INCI Designation) | Formulations (Amounts) | | | | | |
|---|---|---|---|---|---|---|
| | 1 | 2 | 3 | 4 | 5 | 6 |
| Sodium Carbomer | 0.5 | 1.5 | 1.0 | | | 0.5 |
| Acrylates/C$_{10}$-C$_{30}$ Alkyl Acrylate Crosspolymer | 1.0 | | | 0.75 | 1.0 | |
| Hydroxypropyl Cellulose | | | 0.4 | 1.0 | | 1.0 |
| Xanthan Gummi | | 0.6 | 0.2 | 1.0 | 1.0 | |
| BBI | 4.0 | 0.5 | 3.0 | 2.0 | 4.0 | 1.5 |
| Dioctyl Butamidotriazon | 2.0 | 2.0 | | 2.0 | | 1.0 |
| Ethylhexyl Triazon | | 4.0 | 5.0 | 4.0 | | |
| Aniso Triazin | 1.0 | | | 1.0 | 2.5 | 1.0 |
| Bisoctyltriazol | | | 4.0 | | | |
| Drometrizole Trisiloxane | | 3.0 | | | | |
| Phenylbenzmidazole Sulfonicacid | 2.0 | | | 1.0 | | |
| Bisimidazylate | | | 1.5 | | | 3.5 |
| Terephthalylidene Dicamphor Sulfonic Acid | | | | 0.2 | | 1.0 |

-continued

| RAW MATERIAL (INCI Designation) | 1 | 2 | 3 | 4 | 5 | 6 |
|---|---|---|---|---|---|---|
| Ethylhexyl Methoxycinnamat | | 10.0 | | 5.0 | | |
| Octocrylen | 10.0 | | | | 5.0 | |
| Dimethicone-diethylbenzalmalonate | | | | 4.0 | | |
| Ethylhexyl Salicylate | | | | | | 5.0 |
| Homosalate | | | | 5.0 | | |
| Butyl Methoxy-dibenzoylmethan | 1.0 | 1.0 | 4.0 | | | 0.5 |
| Titandioxide | 1.0 | 4.0 | | | | 1.5 |
| Zincoxide | | | | 4.0 | | |
| Caprylic/Capric Triglycerid | | | 2.0 | | | |
| Paraffinöl | | | | 1.0 | | |
| $C_{12}$-$C_{15}$ Alkyl Benzoat | 2.0 | 2.5 | 3.0 | | | |
| Dicaprylyl Ether | | 4.0 | | | | |
| Isohexadecen | 4.0 | | 2.0 | 6.0 | | |
| Dicaprylyl Carbonat | | 2.0 | | | | |
| Dibutyl Adipat | 2.0 | 0.5 | 1.0 | | | |
| Cylomethicon | | | | 3.0 | | |
| Jojobaöl | | 2.0 | | | | |
| PVP Hexadecen Copolymer | 0.5 | | 0.05 | 0.5 | | 0.5 |
| Butylen Glycol | 3.0 | 7.5 | | 7.5 | 2.5 | 5.0 |
| Ascorbyl-Palmitate | | 0.5 | 0.75 | | 0.2 | 0.3 |
| Octoxyglycerin | | 1.0 | | 0.5 | | 1.0 |
| *Glycin Soja* | | | 2.0 | | | 1.5 |
| Trisodium EDTA | 1.0 | 0.5 | 0.5 | | 1.5 | 0.5 |
| Caustic acid | 1.0 | 0.2 | 0.25 | | | |
| Iodopropyl Butylcarbamat | | 0.6 | | 0.2 | | |
| Phenoxyethanol | | 0.4 | | 1.0 | | |
| Ethanol | 5.0 | 2.0 | 7.0 | | | |
| Perfume | 0.2 | | | 0.2 | 0.2 | |
| Water | QS (100) | QS (100) | QS (100) | QS (100) | QS (100) | QS (100) |

The following formula provides an example of an after-shave product comprising the BBI-AV of the present invention.

AFTER SHAVE LOTION

| | % | Ingredient | INCI |
|---|---|---|---|
| A | 10.0 | Luvitol EHO | Cetearyl Ethylhexanoate |
| | 5.0 | Vitamin E Acetate | Tocopheryl Acetate |
| | 1.0 | Bisabolol rac. | Bisabolol |
| | 0.1 | Perfume | |
| | 0.3 | Carbopol Ultrez 21 | Acrylates/C10-30 Alkyl Acrylate Crosspolymer |
| B | 15.0 | Ethanol | Alcohol |
| | 1.0 | D-Panthenol USP | Panthenol |
| | 3.0 | Glyerin 87% | Glycerin |
| | 0.1 | Triethanolamine Care | Triethanolamine |
| | SA | Compound | |
| | QS | Water dem. | Aqua dem. |

Production: Weigh out the components of Phase A and mix them. Dissolve Phase B, stir it into Phase A and homogenize well.

Measure Values:
Viscosity: 18 500 mPa s Brookfield RVD II+
pH value: 5.8

The following formula provides an example of an after-shave product comprising the BBI-AV of the present invention.

PRE SHAVE

| | % | Ingredient | INCI |
|---|---|---|---|
| A | 80 | Ethanol | Alcohol |
| | 3.0 | Vitamin E Acetate | Tocopheryl Acetate |
| | 1.0 | Bisabolol rac. | Bisabolol |
| | 0.2 | Perfume | |
| | 0.1 | Menthol | Menthol |
| | 4.0 | Luvitol EHO | Cetearyl Ethylhexanoate |
| | 2.0 | Eutanol G | Octyldodecanol |
| | 2.0 | Miglyol 812 | Caprylic/Capric Triglyceride |
| | 2.0 | D-Panthenol USP | Panthenol |
| | 2.0 | Whitch Hazel Distillate | *Hamamelis Virginiana* (Whitch Hazel) Distillate |
| | 2.0 | Jojoba Oil | *Simmondsia Chinensis* (Jojoba) Seed Oil |
| | SA | Compound | |

Production: Weigh out the components of Phase A and dissolve them clearly.

The after-shave and pre-shave formula provided above contain sufficient BBI-AV (Compound) to provide the desired effect(s). In some embodiments, the concentration of BBI-AV is in the range of about 1,000 ppm to about 10,000 ppm. In the following formulations, typical concentrations of BBI-AV used range from about 100 ppm to about 1,000 ppm or from about 1,000 ppm to about 10,000 ppm. However, it is not intended that the present invention be limited to this specific concentration range, as other concentrations find use in other embodiments of the present invention.

The following formula provides an example of an after-sun product comprising the BBI-AV of the present invention.

AFTER SUN LOTION

| | % | Ingredient | INCI |
|---|---|---|---|
| A | 0.4 | Carbopol 1342 | Acrylates/C10-30 Alkyl Acrylate Crosspolymer |
| | 15.0 | Luvitol EHO | Cetearyl Ethylhexanoate |
| | 0.2 | Bisabolol rac. | Bisabolol |
| | 1.0 | Vitamin E Acetate | Tocopheryl Acetate |
| | q.s. | Perfume | |
| B | 1.0 | D-Panthenol USP | Panthenol |
| | 15.0 | Ethanol 96% | Alcohol |
| | 3.0 | Glycerin 87% | Glycerin |
| | SA | Compound | |
| | 64.2 | Water dem. | Aqua dem. |
| C | 0.2 | Triethanolamine Care | Triethanolamine |

Production: Mix the components of Phase A. Dissolve Phase B and stir it into Phase A whilst homogenizing. Neutralize with Phase C and homogenize again.

Measure Values:
Viscosity: 7 500 mPa s Haake Viscotester VT-02
pH value: 6.0

The following formula provides an example of a facial cleanser product comprising the BBI-AV of the present invention.

FACIAL CLEANSER

| | % | Ingredient | INCI |
|---|---|---|---|
| A | 10.0 | Luvitol EHO | Cetearyl Ethylhexanoate |
| | 10.0 | Miglyol 812 | Caprylic/Capric Triglyceride |
| | 1.5 | Dow Corning 345 Fluid | Cyclopentasiloxane, Cyclohexasilosane |
| | 2.0 | Cremophor CO 40 | PEG-40 Hydrogenated Castor Oil |
| B | 3.5 | Luvigel EM | Caprylic/Capric Triglyceride, Sodium Acrylates Copolymer |
| C | 1.0 | Vitamin E Acetate | Tocopheryl Acetate |
| | 0.2 | Bisabolol rac. | Bisabolol |
| | QS | Preservative | |
| | QS | Perfume | |
| D | 3.0 | Luviquat Care | Polyquaternium-44 |
| | 0.5 | Luviquat Mono LS | Cocotrimonium Methosulfate |
| | 0.5 | Cremophor A 25 | Ceteareth-25 |
| | 0.2 | D-Panthenol 50 P | Panthenol, Propylene Glycol |
| | 4.0 | 1,2 Propylene Glycol Care | Propylene Glycol |
| | 0.1 | Edeta BD | Disodium EDTA |
| | SA | Compound | |
| | QS | Water dem. | Aqua dem. |

Production: Dissolve Phase A, then stir in Phase B. Fold in Phase C. Dissolve Phase D, stir it into the combined Phases A+B+C, homogenize and stir again for 15 min.

Measure Values:
Viscosity: 7 200 mPa s Brookfield RVT
pH value: 5.8

The following formula provides an example of a daily care body spray product with SPF 8 comprising the BBI-AV of the present invention.

DAILY CARE BODY SPRAY - SPF 8

| | % | Ingredient | INCI |
|---|---|---|---|
| A | 3.0 | Uvinul MC 80 | Ethylhexyl Methoxycinnamate |
| | 2.0 | Uvinul A Plus ™ | Diethylamino Hydroxybenzoyl Hexyl Benzoate |
| | 1.0 | Luviquat UltraCare | Polyquaternium-44 |
| | 3.0 | 1,2 Propylenglycol Care | Propylene Glycol |
| | 2.0 | D-Panthenol 50 P | Panthenol, Propylene Glycol |
| | 1.0 | Dow Corning 345 Fluid | Cyclopentasiloxane, Cyclohexasiloxane |
| | 10.0 | Eutanol G | Octyldodecanol |
| | 0.5 | Luviskol K 30 | PVP |
| | 10.0 | Miglyol 812 | Caprylic/Capric Triglyceride |
| | 3.0 | Finsolv TN | C12-15 Alkyl Benzoate |
| | 3.0 | Glycerin 87% | Glycerin |
| | 1.0 | Vitamin E Acetate | Tocopheryl Acetate |
| | 0.3 | Bisabolol rac. Compound | Bisabolol |
| | QS | Ethanol | Alcohol |

Production: Weigh out the components of Phase A and dissolve them clearly.

Measure Values:
SPF: 8 Colipa Task Force "Sun Protection Measurement"

The following formula provides an example of a daily care sun care lotion product with SPF 27 comprising the BBI-AV of the present invention.

SUN CARE LOTION - SPF 27

| | % | Ingredient | INCI |
|---|---|---|---|
| A | 4.5 | Uvinul MC 80 | Ethylhexyl Methoxycinnamate |
| | 2.0 | Uvinul A Plus ™ | Diethylamino Hydroxybenzoyl Hexyl Benzoate |
| | 3.0 | Uvinul N 539 T | Octocrylene |
| | 2.5 | Cosmacol EMI | Di-C12-13 Alkyl Malate |
| | 0.5 | Vitamin E Acetate | Tocopheryl Acetate |
| | 4.0 | Tego Care 450 | Polyglyceryl-3 Methyl Glucose Distearate |
| B | 3.5 | Cetiol SN Deo | Cetearyl Isononanoate |
| | 1.0 | Ganex V-220 | VP/Eicosene Copolymer |
| | 5.0 | Isohexadecane | Isohexadecane |
| | 2.5 | Cosmacol EMI | Di-C12-13 Alkyl Malate |
| | 3.0 | Uvinul TiO2 | Titanium Dioxide, Trimethoxycaprylylsilane |
| C | 5.0 | Glycerin 87% | Glycerin |
| | 1.0 | Lanette E | Sodium Cetearyl Sulfate |
| | 0.5 | Keltrol | Xanthan Gum |
| | 60.7 | Water dem. | Aqua dem. |
| D | SA | Compound | |
| | 1.0 | Phenonip | Phenoxyethanol, Methylparaben, Ethylparaben, |
| | 0.3 | Bisabolol rac. | Bisabolol |

Production: Heat Phases A and B separately to about 80° C. Stir Phase B into Phase A whilst homogenizing. Heat Phase C to about 80° C. and stir it into the combined Phases A+B whilst homogenizing. Cool to about 40° C. add Phase D and homogenize again.

Measure Values:
Viscosity: 3 200 mPa s Brookfield RVD II+
pH value: 6.0
SPF: 27 Colipa Task Force "Sun Protection Measurement"

SUN CARE LOTION - SPF 24

| | % | Ingredient | INCI |
|---|---|---|---|
| A | 2.0 | Cremophor A 6 | Ceteareth-6, Stearyl Alcohol |
| | 2.0 | Cremophor A 25 | Ceteareth-25 |
| | 3.0 | Syncrowax HRC | Tribehenin |
| | 2.0 | Lanette O | Cetearyl Alcohol |
| | 2.0 | Luvitol EHO | Cetearyl Ethylhexanoate |
| | 5.0 | Uvinul MC 80 | Ethylhexyl Methoxycinnamate |
| | 1.0 | Uvinul T 150 | Ethylhexyl Triazone |
| | 1.0 | Ganex V-220 | VP/Eicosene Copolymer |
| | 7.0 | Isopropyl Myristate | Isopropyl Myristate |
| B | 5.0 | Z-Cote HP-1 | Zinc Oxide, Triethoxycaprylylsilane |
| C | 0.2 | Keltrol | Hydroxyethyl Acrylate/Sodium Acryloyldimethyl Taurate Copolymer, Squalane, Polysorbate 60 |
| | 0.2 | Edeta BD | Disodium EDTA |
| | 5.0 | 1,2 Propylene Glycol Care | Propylene Glycol |
| | 0.5 | D-Panthenol USP | Panthenol |
| | 61.9 | Water dem. | Aqua dem. |
| D | SA | Compound | |
| | 0.5 | Euxyl K 300 | Phenoxyethanol, Methylparaben, Butylparaben, Ethylparaben, Propylparaben, Isobutylparaben |
| | 1.0 | Vitamin E Acetate | Tocopheryl Acetate |
| | 0.2 | Bisabolol rac. | Bisabolol |

Production: Heat Phase A to 80° C., add Phase B and homogenize for 3 min. Heat Phase C to about 80° C., and stir it into the combined Phases A+B whilst homogenizing. Cool to about 40° C., add Phase D, and homogenize.

Measure Values:
Viscosity: 5 000 mPa s Brookfield RVD II+
pH value: 7.5
SPF: 24 Colipa Task Force "Sun Protection Measurement"

The following formula provides an example of a sun screen emulsion product with SPF 28 comprising the BBI-AV of the present invention.

SUN SCREEN EMULSION - SPF 28

| | % | Ingredient | INCI |
|---|---|---|---|
| A | 3.5 | Cremophor A 6 | Ceteareth-6, Stearyl Alcohol |
| | 1.5 | Cremophor A 25 | Ceteareth-25 |
| | 7.5 | Uvinul MC 80 | Ethylhexyl Methoxycinnamate |
| | 2.0 | Uvinul A Plus ™ | Diethylamino Hydroxybenzoyl Hexyl Benzoate |
| | 2.0 | Dow Corning 345 Fluid | Cyclopentasiloxane, Cyclohexasiloxane |
| | 0.5 | Bees Wax 3044 PH | Bees Wax |
| | 3.0 | Lanette O | Cetearyl Alcohol |
| | 10.0 | Miglyol 812 | Caprylic/Capric Triglyceride |
| B | 5.0 | T-Lite SF-S | Titanium Dioxide, Silica, Methicone, Alumina |
| C | 3.0 | Glycerin 87% | Glycerin |
| | 0.2 | Edeta BD | Disodium EDTA |
| | 0.3 | Keltrol T | Xanthan Gum |
| | 1.0 | Plantacare 2000 | Decyl Glucoside |
| | 2.0 | D-Panthenol 50 P | Panthenol, Propylene Glycol |
| | 57.3 | Water dem. | Aqua dem. |

SUN SCREEN EMULSION - SPF 28 -continued

| | % | Ingredient | INCI |
|---|---|---|---|
| D | SA | Compound | |
| | 1.0 | Vitamin E Acetate | Tocopheryl Acetate |
| | 0.2 | Bisabolol rac. | Bisabolol |
| | QS | Perfume | |
| | QS | Preservative | |

Production: Heat Phase A to 80° C., add Phase B and homogenize for 3 min. Heat Phase C to about 80° C., and stir it into the combined Phases A+B whilst homogenizing. Cool to about 40° C., add Phase D and homogenize.

Measure Values:
Viscosity: 7 500 mPa s Brookfield RVD II+
pH value: 6.6
SPF: 28 Colipa Task Force "Sun Protection Measurement"

The following formula provides an example of a foot balm product comprising the BBI-AV of the present invention.

FOOT BALM

| | % | Ingredient | INCI |
|---|---|---|---|
| A | 2.0 | Cremophor A 6 | Ceteareth-6, Stearyl Alcohol |
| | 2.0 | Cremophor A 25 | Ceteareth-25 |
| | 5.0 | Luvitol EHO | Cetearyl Ethylhexanoate |
| | 4.0 | Lanette 16 | Cetyl Alcohol |
| | 4.0 | Cutina Gms | Glyceryl Stearate |
| | 5.0 | Paraffin Oil | Mineral Oil |
| | 0.2 | Menthol | Menthol |
| | 0.5 | Camphor | Camphor |
| B | 70.3 | Water dem. | Aqua dem. |
| | QS | Preservative | |
| C | SA | Compound | |
| | 1.0 | Bisabolol rac. | Bisabolol |
| | 1.0 | Vitamin E Acetate | Tocopheryl Acetate |
| D | 5.0 | Witch Hazel Extract | Witch Hazel Extract |

Production: Heat Phases A and B to about 80° C. separately. Stir Phase B into Phase A whilst homogenizing. Cool to about 40° C., add Phases C and D and homogenize again. Cool to room temperature.

Measure Values:
Viscosity: 20 500 mPa s Brookfield RVD II+
pH value: 6.0

The following formula provides an example of a refreshing foot gel product comprising the BBI-AV of the present invention.

REFRESHING FOOT GEL

| | % | Ingredient | INCI |
|---|---|---|---|
| A | 0.6 | Carbopol Ultrez 21 | Acrylates/C10-30 Alkyl Acrylate Crosspolymer |
| | 45.9 | Water dem. | Aqua dem. |
| B | 1.0 | Bisabolol rac. | Bisabolol |
| | 0.5 | Farnesol | Farnesol |
| | q.s. | Perfume | |
| | 4.5 | Cremophor CO 40 | PEG-40 Hydrogenated Castor Oil |
| | 1.0 | Neutrol TE | Tetrahydroxypropyl Ethylenediamine |
| | 1.5 | Menthol | Menthol |

REFRESHING FOOT GEL (continued)

| % | Ingredient | INCI |
|---|---|---|
| SA | Compound | |
| 45.0 | Ethanol 96% | Alcohol |
| QS | FD&C Blue No. 1 | C.I. 42 090, FD&C Blue No. 1 |

Production: Phase A: Intersperse the Carbopol and let it settle on the bottom of the beaker. Dissolve Phase B and stir it into Phase A.

Measure Values:
Viscosity: 14 500 mPa s Brookfield RVD II+
pH value: 7.5

The following formula provides an example of a skin conditioning gel product comprising the BBI-AV of the present invention.

Skin Conditioning Gel

| | % | Ingredient | INCI |
|---|---|---|---|
| A | 3.6 | Cremophor CO 40 | PEG-40 Hydrogenated Castor Oil |
| | 15.0 | Ethanol | Alcohol |
| | 0.1 | Bisabolol rac. | Bisabolol |
| | 0.5 | Vitamin E Acetate | Tocopheryl Acetate |
| | QS | Perfume | |
| B | 3.0 | D-Panthenol USP | Panthenol |
| | 0.6 | Carbopol 940 | Carbomer |
| | SA | Compound | |
| | 76.4 | Water dem. | Aqua dem. |
| C | 0.8 | Triethanolamine Care | Triethanolamine |

Production: Dissolve Phase A clearly. Allow Phase B to swell and neutralize with Phase C. Stir Phase A into the neutralized Phase B and homogenize.

Measure Values:
Viscosity: 57 600 mPa s Brookfield RVD II+
pH value: 7.7

The following formula provides an example of a W/O emulsion comprising the BBI-AV of the present invention.

W/O EMULSION

| | % | Ingredient | INCI |
|---|---|---|---|
| A | 6.0 | Cremophor WO 7 | PEG-7 Hydrogenated Castor Oil |
| | 8.0 | Luvitol EHO | Cetearyl Ethylhexanoate |
| | 5.0 | Isopropyl Myristate | Isopropyl Myristate |
| | 15.0 | Paraffin Oil | Mineral Oil |
| | 0.3 | Magnesium Stearate | Magnesium Stearate |
| | 0.3 | Aluminum Stearate | Aluminum Stearate |
| | 2.0 | Elfacos ST9 | PEG-45/Dodecyl Glycol Copolymer |
| B | 5.0 | Glycerin 87% | Glycerin |
| | 0.7 | Magnesium Sulfate-7-hydrate | Magnesium Sulfate |
| | 56.6 | Water dem. | Aqua dem. |
| C | SA | Compound | |
| | 0.5 | Vitamin E Acetate | Tocopheryl Acetate |
| | 0.6 | Bisabolol rac. | Bisabolol |

Production: Heat Phases A and B separately to about 85° C. Stir Phase B into Phase A and homogenize. Cool to about 40° C. whilst stirring, add Phase C and homogenize again. Cool to room temperature.

Measure Values:
Viscosity: 37 500 mPa s Brookfield RVD II+

The following formula provides an example of a O/W emulsion product comprising the BBI-AV of the present invention.

O/W EMULSION

| | % | Ingredient | INCI |
|---|---|---|---|
| A | 1.7 | Cremophor A 6 | Ceteareth-6, Stearyl Alcohol |
| | 0.7 | Cremophor A 25 | Ceteareth-25 |
| | 2.0 | Uvinul A Plus ™ | Diethylamino Hydroxybenzoyl Hexyl Benzoate |
| | 2.0 | Abil B 8843 | PEG-14 Dimethicone |
| | 3.6 | Lanette O | Cetearyl Alcohol |
| | 6.0 | Uvinul MC 80 | Ethylhexyl Methoxycinnamate |
| | 2.0 | Cetiol B | Dibutyl Adipate |
| B | 5.0 | Glycerin 87% | Glycerin |
| | 0.2 | Edeta BD | Disodium EDTA |
| | 1.0 | D-Panthenol 75 W | Panthenol |
| | q.s. | Preservative | |
| | 68.8 | Water dem. | Aqua dem. |
| C | 4.0 | Luvigel EM | Caprylic/Capric Triglyceride, Sodium Acrylates Copolymer |
| D | 0.2 | Sodium Ascorbyl Phosphate | Sodium Ascorbyl Phosphate |
| | 1.0 | Vitamin E Acetate | Tocopheryl Acetate |
| | 0.2 | Bisabolol rac. | Bisabolol |
| E | q.s. | Sodium Hydroxide 10% aq. w/w | Sodium Hydroxide |
| F | 1.0 | RetiSTAR | Caprylic/Capric Triglyceride, Sodium Ascorbate, Tocopherol, Retinol |
| | SA | Compound | |

Production: Heat Phase A and B separately to about 80° C. Stir Phase B into Phase A and homogenize. Stir Phase C into the combined Phases A+B and homogenize. Cool to about 40° C., add Phase D, then adjust the pH value with Phase E to 6.5. Add Phase F and homogenize. Cool to room temperature.

Measure Values:
Viscosity: 37 500 mPa s Brookfield RVD II+
pH value: 6.3

The following formula provides an example of a protective day cream product comprising the BBI-AV of the present invention.

PROTECTIVE DAY CREAM

| | % | Ingredient | INCI |
|---|---|---|---|
| A | 1.7 | Cremophor A 6 | Ceteareth-6, Stearyl Alcohol |
| | 0.7 | Cremophor A 25 | Ceteareth-25 |
| | 2.0 | Uvinul A Plus ™ | Diethylamino Hydroxybenzoyl Hexyl Benzoate |
| | 2.0 | Abil B 8843 | PEG-14 Dimethicone |
| | 3.6 | Lanette O | Cetearyl Alcohol |
| | 6.0 | Uvinul MC 80 | Ethylhexyl Methoxycinnamate |
| | 2.0 | Cetiol B | Dibutyl Adipate |
| B | 5.0 | Glycerin 87% | Glycerin |
| | 0.2 | Edeta BD | Disodium EDTA |
| | 1.0 | D-Panthenol 75 W | Panthenol |
| | QS | Preservative | |
| | 69.6 | Water dem. | Aqua dem. |
| C | 4.0 | Luvigel EM | Caprylic/Capric Triglyceride, Sodium Acrylates Copolymer |
| D | 1.0 | Sodium Ascorbyl Phosphate | Sodium Ascorbyl Phosphate |
| | 1.0 | Vitamin E Acetate | Tocopheryl Acetate |
| | SA | Compound | |
| | 0.2 | Bisabolol rac. | Bisabolol |

| | PROTECTIVE DAY CREAM | |
|---|---|---|
| % | Ingredient | INCI |
| E | QS | Sodium Hydroxide 10% aq. w/w | Sodium Hydroxide |

Production: Heat Phase A and B separately to about 80° C. Stir Phase B into Phase A and homogenize. Stir Phase C into the combined Phases A+B and homogenize. Cool to about 40° C., add Phase D, then adjust the pH value with Phase E to 6.5 and homogenize. Cool to room temperature.

Measure Values:
Viscosity: 24 000 mPa s Brookfield RVD II+
pH value: 6.4

The following formulae provide examples of hair care products comprising the BBI-AV of the present invention.

| | HAIR CONDITIONERS | |
|---|---|---|
| | % | Ingredients (INCI) |
| A | 10.0 | PVP/VA Copolymer |
| | 0.2 | Hydroxyethyl Cetyldimonium Phosphate |
| | 0.2 | Ceteareth-25 |
| | 0.5 | Dimethicone Copolyol |
| | QS | Perfume |
| | 10.0 | Alcohol |
| | SA | Compound |
| | 68.1 | Aqua dem. |
| B | 10.0 | Propane/Butane |
| A | 10.0 | PVP/VA Copolymer |
| | 0.2 | Hydroxyethyl Cetyldimonium Phosphate |
| | 0.2 | Ceteareth-25 |
| | 0.5 | Dimethicone Copolyol |
| | QS | Perfume |
| | 10.0 | Alcohol |
| | SA | Compound |
| | 64.1 | Aqua dem. |
| B | 10.0 | Propane/Butane |

Production: Add all compounds to Phase A and stir to homogenize. Fill into appropriate container and charge with Phase B.

| | FOAM CONDITIONERS | |
|---|---|---|
| | % | Ingredients (INCI) |
| A | 1.0 | Polyquaternium-4 |
| | 0.5 | Hydroxyethyl Cetyldimonium Phosphate Compound |
| | QS | Perfume |
| | QS | Preservative |
| | 91.5 | Aqua dem. |
| B | 6.0 | Propane/Butane |
| A | 1.0 | Polyquaternium-4 |
| | 0.5 | Hydroxyethyl Cetyldimonium Phosphate Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

| | FOAM CONDITIONERS | |
|---|---|---|
| | % | Ingredients (INCI) |
| A | 1.0 | Polyquaternium-11 |
| | 0.5 | Hydroxyethyl Cetyldimonium Phosphate Compound |
| | QS | Perfume |
| | QS | Preservative |
| | 91.5 | Aqua dem. |
| B | 6.0 | Propane/Butane |
| A | 1.0 | Polyquaternium-11 |
| | 0.5 | Hydroxyethyl Cetyldimonium Phosphate Compound |
| | SA | Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

| | STYLING FOAMS | |
|---|---|---|
| | % | Ingredients (INCI) |
| A | 0.5 | Laureth-4 |
| | QS | Perfume |
| B | 77.3 | Aqua dem. |
| | 10.0 | Polyquaternium-28 Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 0.5 | Laureth-4 |
| | QS | Perfume |
| B | 73.3 | Aqua dem. |
| | 10.0 | Polyquaternium-28 |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

| | % | Ingredients (INCI) |
|---|---|---|
| A | 2.0 | Cocotrimonium Methosulfate |
| | QS | Perfume |
| B | 78.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |

| | % | Ingredients (INCI) |
|---|---|---|
| C | 10.0 | HFC 152 A |
| A | 2.0 | Cocotrimonium Methosulfate |
| | QS | Perfume |
| B | 74.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

STYLING FOAM

| | % | Ingredients (INCI) |
|---|---|---|
| A | 2.0 | Cocotrimonium Methosulfate |
| | QS | Perfume |
| B | 7.70 | Polyquaternium-44 |
| | SA | Compound |
| | QS | Preservative |
| | 79.3 | Aqua dem. |
| C | 10.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAM

| | % | Ingredients (INCI) |
|---|---|---|
| A | 2.00 | Cocotrimonium Methosulfate |
| | QS | Perfume |
| B | 72.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cocotrimonium Methosulfate |
| | QS | Perfume |
| B | 68.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | 2.00 | Cetrimonium Chloride |
| | QS | Perfume |
| B | 67.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cetrimonium Chloride |
| | QS | Perfume |
| B | 63.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | QS | PEG-40 Hydrogenated Castor Oil |
| | QS | Perfume |
| | 85.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 81.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | QS | PEG-40 Hydrogenated Castor Oil |
| | QS | Perfume |
| | 92.0 | Aqua dem. |
| B | 0.5 | Polyquaternium-10 |
| | 1.0 | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 88.0 | Aqua dem. |
| B | 0.5 | Polyquaternium-10 |
| | 5.0 | Compound |
| | 0.5 | Cetrimonium Bromide |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

| | % | Ingredients (INCI) |
|---|---|---|
| A | QS | PEG-40 Hydrogenated Castor Oil |
| | QS | Perfume |
| | 82.5 | Aqua dem. |
| B | 10.0 | Polyquaternium-16 |
| | SA | Compound |
| | 0.5 | Hydroxyethyl Cetyldimonium Phosphate |
| | QS | Preservative |
| C | 6.0 | Propane/Butane |
| A | QS | PEG-40 Hydrogenated Castor Oil |
| | QS | Perfume |
| | 78.5 | Aqua dem. |
| B | 100 | Polyquaternium-16 |
| | SA | Compound |
| | 0.5 | Hydroxyethyl Cetyldimonium Phosphate |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 84.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |
| A | 2.0 | Cocotrimonium Methosulfate |
| | QS | Perfume |
| B | 80.0 | Aqua dem. |
| | 2.0 | Chitosan |
| | SA | Compound |

STYLING FOAMS (-continued)

| | % | Ingredients (INCI) |
|---|---|---|
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |

Production: Weight out the compounds of Phase A and mix them. Dissolve Phase B, stir into Phase A and homogenize. Adjust pH to 6-7. Fill into appropriate container and charge with Phase C.

SHAMPOOS

| | % | Ingredients (INCI) |
|---|---|---|
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 |
| | SA | Compound |
| | 7.7 | Polyquaternium-44 |
| | 2.0 | Amodimethicone |
| | QS | Perfume |
| | QS | Preservative |
| | 1.0 | Sodium Chloride |
| | 43.3 | Aqua dem. |
| B | QS | Citric Acid |
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 Compound |
| | 7.7 | Polyquaternium-44 |
| | 2.0 | Amodimethicone |
| | QS | Perfume |
| | QS | Preservative |
| | 1.0 | Sodium Chloride |
| | 39.3 | Aqua dem. |
| B | QS | Citric Acid |

Production: Weight out the compounds of Phase A and mix them. Adjust pH to 6-7 with citric acid.

SHOWER GELS

| | % | Ingredients (INCI) |
|---|---|---|
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 46.0 | Aqua dem. |
| B | QS | Citric Acid |
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |

-continued

SHOWER GELS

| | % | Ingredients (INCI) |
|---|---|---|
| | QS | Preservative |
| | 2.0 | Sodium Chloride |
| | 42.0 | Aqua dem. |
| B | QS | Citric Acid |

Production: Weight out the compounds of Phase A and mix them. Adjust pH to 6-7 with citric acid.

SHAMPOOS

| | % | Ingredients (INCI) |
|---|---|---|
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 44.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 40.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |

Production: Weight out the compounds of Phase A and mix them. Adjust pH to 6-7 with citric acid.

SHAMPOOS

| | % | Ingredients (INCI) |
|---|---|---|
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | SA | Compound |
| | 0.15 | Guar Hydroxypropyltrimonium Chloride |
| | 2.00 | Laureth-3 |
| | 58.00 | Aqua dem. |
| | QS | Citric Acid |
| B | 3.00 | PEG-150 Distearate |
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | | Compound |

-continued

SHAMPOOS

| | % | Ingredients (INCI) |
|---|---|---|
| | 0.15 | Guar Hydroxypropyltrimonium Chloride |
| | 2.00 | Laureth-3 |
| | 54.00 | Aqua dem. |
| | QS | Citric Acid |
| B | 3.00 | PEG-150 Distearate |

Production: Weight out the compounds of Phase A and mix them. Adjust pH to 6-7. Add Phase B and heat to max. 40° C.

BODY LOTIONS

| | % | Ingredients (INCI) |
|---|---|---|
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 65.5 | Aqua dem. |
| C | QS | Perfume |
| D | QS | Citric Acid |
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 61.5 | Aqua dem. |
| C | QS | Perfume |
| D | QS | Citric Acid |

Production: Heat Phases A and B separately to approx. 40° C. Add Phase B to Phase A and homogenize by stirring. Add Phase C to the combined Phase A and B and homogenize again. Adjust pH with Phase D to 6-7. Homogenize by stirring and cool to room temperature.

BODY LOTIONS

| | % | Ingredients (INCI) |
|---|---|---|
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |

-continued

BODY LOTIONS

| | % | Ingredients (INCI) |
|---|---|---|
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 62.9 | Aqua dem. |
| C | QS | Perfume |
| | SA | Compound |
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 58.9 | Aqua dem. |
| C | QS | Perfume |
| | SA | Compound |

Production: Heat Phases A and B separately to approx. 80° C. Add Phase B to Phase A and homogenize by stirring. Cool to 40° C. and add Phase C. Homogenize again and cool to room temperature.

HAIR CONDITIONERS

| | % | Ingredients (INCI) |
|---|---|---|
| A | 10.0 | PVP/VA Copolymer |
| | 0.2 | Hydroxyethyl Cetyldimonium Phosphate |
| | 0.2 | Ceteareth-25 |
| | 0.5 | Dimethicone Copolyol |
| | QS | Perfume |
| | 10.0 | Alcohol |
| | SA | Compound |
| | 68.1 | Aqua dem. |
| B | 10.0 | Propane/Butane |
| A | 10.0 | PVP/VA Copolymer |
| | 0.2 | Hydroxyethyl Cetyldimonium Phosphate |
| | 0.2 | Ceteareth-25 |
| | 0.5 | Dimethicone Copolyol |
| | QS | Perfume |
| | 10.0 | Alcohol |
| | SA | Compound |
| | 64.1 | Aqua dem. |
| B | 10.0 | Propane/Butane |

Production: Add all compounds to Phase A and stir to homogenize. Fill into appropriate container and charge with Phase B.

FOAM CONDITIONERS

| | % | Ingredients (INCI) |
|---|---|---|
| A | 1.0 | Polyquaternium-4 |
| | 0.5 | Hydroxyethyl Cetyldimonium Phosphate |
| | SA | Compound |
| | QS | Perfume |
| | QS | Preservative |
| | 91.5 | Aqua dem. |
| B | 6.0 | Propane/Butane |

FOAM CONDITIONERS

| | % | Ingredients (INCI) |
|---|---|---|
| A | 1.0 | Polyquaternium-4 |
| | 0.5 | Hydroxyethyl Cetyldimonium Phosphate |
| | SA | Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

FOAM CONDITIONERS

| | % | Ingredients (INCI) |
|---|---|---|
| A | 1.0 | Polyquaternium-11 |
| | 0.5 | Hydroxyethyl Cetyldimonium Phosphate |
| | | Compound |
| | QS | Perfume |
| | QS | Preservative |
| | 91.5 | Aqua dem. |
| B | 6.0 | Propane/Butane |
| A | 1.0 | Polyquaternium-11 |
| | 0.5 | Hydroxyethyl Cetyldimonium Phosphate |
| | SA | Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

STYLING FOAMS

| | % | Ingredients (INCI) |
|---|---|---|
| A | 0.5 | Laureth-4 |
| | QS | Perfume |
| B | 77.3 | Aqua dem. |
| | 10.0 | Polyquaternium-28 |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 0.5 | Laureth-4 |
| | QS | Perfume |
| B | 73.3 | Aqua dem. |
| | 10.0 | Polyquaternium-28 |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 78.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 2.0 | Cocotrimonium Methosulfate |
| | QS | Perfume |
| B | 74.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 7.70 | Polyquaternium-44 |
| | SA | Compound |
| | QS | Preservative |
| | 79.3 | Aqua dem. |
| C | 10.0 | Propane/Butane |
| A | 2.0 | Cocotrimonium Methosulfate |
| | QS | Perfume |
| B | 7.70 | Polyquaternium-44 |
| | SA | Compound |
| | QS | Preservative |
| | 75.3 | Aqua dem. |
| C | 10.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | 2.00 | Cocotrimonium Methosulfate |
| | QS | Perfume |
| B | 72.32 | Aqua dem. |
| | 2.00 | VP/Acrylates/Lauryl Methacrylate Copolymer |

-continued

STYLING FOAMS

| | % | Ingredients (INCI) |
|---|---|---|
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cocotrimonium Methosulfate |
| | QS | Perfume |
| B | 68.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | 2.00 | Cetrimonium Chloride |
| | QS | Perfume |
| B | 67.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cetrimonium Chloride |
| | QS | Perfume |
| B | 63.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | QS | PEG-40 Hydrogenated Castor Oil |
| | QS | Perfume |
| | 85.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 81.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | QS | PEG-40 Hydrogenated Castor Oil |
| | QS | Perfume |
| | 92.0 | Aqua dem. |
| B | 0.5 | Polyquaternium-10 |
| | 1.0 | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 88.0 | Aqua dem. |
| B | 0.5 | Polyquaternium-10 |
| | 5.0 | Compound |
| | 0.5 | Cetrimonium Bromide |
| | QS | Preservative |
| C | 6.0 | Propane/Butane |

Production: Weigh out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | QS | PEG-40 Hydrogenated Castor Oil |
| | QS | Perfume |
| | 82.5 | Aqua dem. |
| B | 10.0 | Polyquaternium-16 |
| | SA | Compound |
| | 0.5 | Hydroxyethyl Cetyldimonium Phosphate |
| | QS. | Preservative |
| C | 6.0 | Propane/Butane |
| A | QS | PEG-40 Hydrogenated Castor Oil |
| | QS | Perfume |
| | 78.5 | Aqua dem. |
| B | 10.0 | Polyquaternium-16 |
| | SA | Compound |

-continued

STYLING FOAMS

| | % | Ingredients (INCI) |
|---|---|---|
| | 0.5 | Hydroxyethyl Cetyldimonium Phosphate |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 84.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |
| A | 2.0 | Cocotrimonium Methosulfate |
| | QS | Perfume |
| B | 80.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |

Production: Weight out the compounds of Phase A and mix them. Dissolve Phase B, stir into Phase A and homogenize. Adjust pH to 6-7. Fill into appropriate container and charge with Phase C.

SHAMPOOS

| | % | Ingredients (INCI) |
|---|---|---|
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 |
| | SA | Compound |
| | 7.7 | Polyquaternium-44 |
| | 2.0 | Amodimethicone |
| | QS | Perfume |
| | QS | Preservative |
| | 1.0 | Sodium Chloride |
| | 43.3 | Aqua dem. |
| B | QS | Citric Acid |
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 |
| | SA | Compound |
| | 7.7 | Polyquaternium-44 |
| | 2.0 | Amodimethicone |
| | SA | Perfume |

SHAMPOOS

| | % | Ingredients (INCI) |
|---|---|---|
| | SA. | Preservative |
| | 1.0 | Sodium Chloride |
| | 39.3 | Aqua dem. |
| B | QS | Citric Acid |

Production: Weight out the compounds of Phase A and mix them. Adjust pH to 6-7 with citric acid.

SHOWER GELS

| | % | Ingredients (INCI) |
|---|---|---|
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 46.0 | Aqua dem. |
| B | QS | Citric Acid |
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 42.0 | Aqua dem. |
| B | QS | Citric Acid |

Production: Weight out the compounds of Phase A and mix them. Adjust pH to 6-7 with citric acid.

SHAMPOOS

| | % | Ingredients (INCI) |
|---|---|---|
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 44.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 40.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |

Production: Weight out the compounds of Phase A and mix them. Adjust pH to 6-7 with citric acid.

SHAMPOOS

| | % | Ingredients (INCI) |
|---|---|---|
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | SA | Compound |
| | 0.15 | Guar Hydroxypropyltrimonium Chloride |
| | 2.00 | Laureth-3 |
| | 58.00 | Aqua dem. |
| | QS | Citric Acid |
| B | 3.00 | PEG-150 Distearate |
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | SA | Compound |
| | 0.15 | Guar Hydroxypropyltrimonium Chloride |
| | 2.00 | Laureth-3 |
| | 54.00 | Aqua dem. |
| | QS | Citric Acid |
| B | 3.00 | PEG-150 Distearate |

Production: Weight out the compounds of Phase A and mix them. Adjust pH to 6-7. Add Phase B and heat to max. 40° C.

BODY LOTIONS

| | % | Ingredients (INCI) |
|---|---|---|
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 65.5 | Aqua dem. |
| C | QS | Perfume |
| D | QS | Citric Acid |
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 61.5 | Aqua dem. |
| C | QS | Perfume |
| D | QS | Citric Acid |

Production: Heat Phases A and B separately to approx. 40° C. Add Phase B to Phase A and homogenize by stirring. Add Phase C to the combined Phase A and B and homogenize again. Adjust pH with Phase D to 6-7. Homogenize by stirring and cool to room temperature.

| | BODY LOTIONS | |
|---|---|---|
| | % | Ingredients (INCI) |
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 62.9 | Aqua dem. |
| C | QS. | Perfume |
| | SA | Compound |
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 58.9 | Aqua dem. |
| C | QS | Perfume |
| | SA | Compound |

Production: Heat Phases A and B separately to approx. 80° C. Add Phase B to Phase A and homogenize by stirring. Cool to 40° C. and add Phase C. Homogenize again and cool to room temperature.

| | DAILY SKIN CARE O/W | |
|---|---|---|
| | % | Ingredients (INCI) |
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 67.8 | Aqua dem. |
| C | 4.0 | Caprylic/Capric Triglyceride, Sodium Acrylates Copolymer |
| D | 0.2 | Sodium Ascorbyl Phosphate |
| | 1.0 | Tocopheryl Acetate |
| | 0.2 | Bisabolol |
| | 1.0 | Caprylic/Capric Triglyceride, Sodium Ascorbate, Tocopherol, Retinol |
| | SA | Compound |
| E | QS | Sodium Hydroxide |
| A | 1.7 | Ceteareth-6, Stearyl Alcohol |
| | 0.7 | Ceteareth-25 |
| | 2.0 | Diethylamino Hydroxybenzoyl Hexyl Benzoate |

-continued

| | DAILY SKIN CARE O/W | |
|---|---|---|
| | % | Ingredients (INCI) |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 63.8 | Aqua dem. |
| C | 4.0 | Caprylic/Capric Triglyceride, Sodium Acrylates Copolymer |
| D | 0.2 | Sodium Ascorbyl Phosphate |
| | 1.0 | Tocopheryl Acetate |
| | 0.2 | Bisabolol |
| | 1.0 | Caprylic/Capric Triglyceride, Sodium Ascorbate, Tocopherol, Retinol |
| | SA | Compound |
| E | QS | Sodium Hydroxide |

Production: Heat Phase A and B separately to approx. 80° C. Add Phase B to Phase A and homogenize by stirring. Add Phase C to the combined Phase A and B and homogenize again. Cool to approx. 40° C. and add Phase D. Adjust pH with Phase E to approx. 6.5. Homogenize by stirring and cool to room temperature.

| | PROTECTIVE DAY SKIN CREME O/W | |
|---|---|---|
| | % | Ingredients (INCI) |
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 68.6 | Aqua dem. |
| C | 4.0 | Caprylic/Capric Triglyceride, Sodium Acrylates Copolymer |
| D | 1.0 | Sodium Ascorbyl Phosphate |
| | 1.0 | Tocopheryl Acetate |
| | 0.2 | Bisabolol |
| | SA | Compound |
| E | QS | Sodium Hydroxide |
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 64.6 | Aqua dem. |
| C | 4.0 | Caprylic/Capric Triglyceride, Sodium Acrylates Copolymer |
| D | 1.0 | Sodium Ascorbyl Phosphate |
| | 1.0 | Tocopheryl Acetate |
| | 0.2 | Bisabolol |
| | | Compound |
| E | QS | Sodium Hydroxide |

Production: Heat Phase A and B separately to approx. 80° C. Add Phase B to Phase A and homogenize by stirring. Add Phase C to the combined Phase A and B and homogenize again. Cool to approx. 40° C. and add Phase D. Adjust pH with Phase E to approx. 6.5. Homogenize by stirring and cool to room temperature.

FACIAL CLEANSER O/W

| | % | Ingredients (INCI) |
|---|---|---|
| A | 10.0 | Cetearyl Ethylhexanoate |
| | 10.0 | Caprylic/Capric Triglyceride |
| | 1.5 | Cyclopentasiloxane, Cyclohexasilosane |
| | 2.0 | PEG-40 Hydrogenated Castor Oil |
| B | 3.5 | Caprylic/Capric Triglyceride, Sodium Acrylates Copolymer |
| C | 1.0 | Tocopheryl Acetate |
| | 0.2 | Bisabolol |
| | QS | Preservative |
| | QS | Perfume |
| D | 3.0 | Polyquaternium-44 |
| | 0.5 | Cocotrimonium Methosulfate |
| | 0.5 | Ceteareth-25 |
| | 2.0 | Panthenol, Propylene Glycol |
| | 4.0 | Propylene Glycol |
| | 0.1 | Disodium EDTA |
| | SA | Compound |
| | 60.7 | Aqua dem. |
| A | 10.0 | Cetearyl Ethylhexanoate |
| | 10.0 | Caprylic/Capric Triglyceride |
| | 1.5 | Cyclopentasiloxane, Cyclohexasilosane |
| | 2.0 | PEG-40 Hydrogenated Castor Oil |
| B | 3.5 | Caprylic/Capric Triglyceride, Sodium Acrylates Copolymer |
| C | 1.0 | Tocopheryl Acetate |
| | 0.2 | Bisabolol |
| | QS | Preservative |
| | QS | Perfume |
| D | 3.0 | Polyquaternium-44 |
| | 0.5 | Cocotrimonium Methosulfate |
| | 0.5 | Ceteareth-25 |
| | 2.0 | Panthenol, Propylene Glycol |
| | 4.0 | Propylene Glycol |
| | 0.1 | Disodium EDTA |
| | SA | Compound |
| | 56.7 | Aqua dem. |

Production: Dissolve Phase A and add Phase B to Phase A and homogenize by stirring. Add. Phase C to the combined Phase A and B and homogenize again. Add. Phase D to the combined Phase A, B and C and homogenize again. Dissolve Phase D and add to Phase A, B, and C and homogenize again. Stir for 15 minutes.

DAILY CARE BODY SPRAY

| | % | Ingredients (INCI) |
|---|---|---|
| A | 3.0 | Ethylhexyl Methoxycinnamate |
| | 2.0 | Diethylamino Hydroxybenzoyl Hexyl Benzoate |
| | 1.0 | Polyquaternium-44 |
| | 3.0 | Propylene Glycol |
| | 2.0 | Panthenol, Propylene Glycol |
| | 1.0 | Cyclopentasiloxane, Cyclohexasiloxane |
| | 10.0 | Octyldodecanol |
| | 0.5 | PVP |
| | 10.0 | Caprylic/Capric Triglyceride |
| | 3.0 | C12-15 Alkyl Benzoate |
| | 3.0 | Glycerin |
| | 1.0 | Tocopheryl Acetate |
| | 0.3 | Bisabolol |
| | SA | Compound |
| | 59.2 | Alcohol |
| A | 3.0 | Ethylhexyl Methoxycinnamate |
| | 2.0 | Diethylamino Hydroxybenzoyl Hexyl Benzoate |
| | 1.0 | Polyquaternium-44 |
| | 3.0 | Propylene Glycol |

-continued

DAILY CARE BODY SPRAY

| | % | Ingredients (INCI) |
|---|---|---|
| | 2.0 | Panthenol, Propylene Glycol |
| | 1.0 | Cyclopentasiloxane, Cyclohexasiloxane |
| | 10.0 | Octyldodecanol |
| | 0.5 | PVP |
| | 10.0 | Caprylic/Capric Triglyceride |
| | 3.0 | C12-15 Alkyl Benzoate |
| | 3.0 | Glycerin |
| | 1.0 | Tocopheryl Acetate |
| | 0.3 | Bisabolol |
| | SA | Compound |
| | 55.2 | Alcohol |

Production: Weight all ingredients of Phase A and dissolve completely by stirring.

SKIN CARE GEL

| | % | Ingredients (INCI) |
|---|---|---|
| A | 3.6 | PEG-40 Hydrogenated Castor Oil |
| | 15.0 | Alcohol |
| | 0.1 | Bisabolol |
| | 0.5 | Tocopheryl Acetate |
| | QS | Perfume |
| B | 3.0 | Panthenol |
| | 0.6 | Carbomer |
| | SA | Compound |
| | 75.4 | Aqua dem, |
| C | 0.8 | Triethanolamine |
| A | 3.6 | PEG-40 Hydrogenated Castor Oil |
| | 15.0 | Alcohol |
| | 0.1 | Bisabolol |
| | 0.5 | Tocopheryl Acetate |
| | QS | Perfume |
| B | 3.0 | Panthenol |
| | 0.6 | Carbomer |
| | SA | Compound |
| | 71.4 | Aqua dem, |
| C | 0.8 | Triethanolamine |

Production: Dissolve Phase A. Swell Phase B and neutralize with Phase C. Add Phase A to Phase B and C and homogenize by stirring.

AFTER SHAVE LOTIONS

| | % | Ingredients (INCI) |
|---|---|---|
| A | 10.0 | Cetearyl Ethylhexanoate |
| | 5.0 | Tocopheryl Acetate |
| | 1.0 | Bisabolol |
| | 0.1 | Perfume |
| | 0.3 | Acrylates/C10-30 Alkyl Acrylate Crosspolymer |
| B | 15.0 | Alcohol |
| | 1.0 | Panthenol |
| | 3.0 | Glycerin |
| | SA | Compound |
| | 1.0 | Triethanolamine |
| | 63.5 | Aqua dem. |
| A | 10.0 | Cetearyl Ethylhexanoate |
| | 5.0 | Tocopheryl Acetate |
| | 1.0 | Bisabolol |
| | 0.1 | Perfume |
| | 0.3 | Acrylates/C10-30 Alkyl Acrylate Crosspolymer |
| B | 15.0 | Alcohol |
| | 1.0 | Panthenol |

AFTER SHAVE LOTIONS

| % | Ingredients (INCI) |
|---|---|
| 3.0 | Glycerin |
| SA | Compound |
| 0.1 | Triethanolamine |
| 59.5 | Aqua dem. |

Production: Dissolve Phase A. Dissolve Phase B and add to Phase A. Homogenize by stirring.

AFTER SUN LOTIONS

| | % | Ingredients (INCI) |
|---|---|---|
| A | 0.4 | Acrylates/C10-30 Alkyl Acrylate Crosspolymer |
|  | 15.0 | Cetearyl Ethylhexanoate |
|  | 0.2 | Bisabolol |
|  | 1.0 | Tocopheryl Acetate |
|  | QS. | Perfume |
| B | 1.0 | Panthenol |
|  | 15.0 | Alcohol |
|  | 3.0 | Glycerin |
|  | SA | Compound |
|  | 63.2 | Aqua dem, |
| C | 0.2 | Triethanolamine |
| A | 0.4 | Acrylates/C10-30 Alkyl Acrylate Crosspolymer |
|  | 15.0 | Cetearyl Ethylhexanoate |
|  | 0.2 | Bisabolol |
|  | 1.0 | Tocopheryl Acetate |
|  | QS | Perfume |
| B | 1.0 | Panthenol |
|  | 15.0 | Alcohol |
|  | 3.0 | Glycerin |
|  | SA | Compound |
|  | 59.2 | Aqua dem, |
| C | 0.2 | Triethanolamine |

Production: Dissolve Phase A. Dissolve Phase B and add to Phase A. Homogenize by stirring. Neutralize Phase A and B by adding Phase C and homogenize again.

SUNSCREEN LOTIONS

| | % | Ingredients (INCI) |
|---|---|---|
| A | 4.5 | Ethylhexyl Methoxycinnamate |
|  | 2.0 | Diethylamino Hydroxybenzoyl Hexyl Benzoate |
|  | 3.0 | Octocrylene |
|  | 2.5 | Di-C12-13 Alkyl Malate |
|  | 0.5 | Tocopheryl Acetate |
|  | 4.0 | Polyglyceryl-3 Methyl Glucose Distearate |
| B | 3.5 | Cetearyl Isononanoate |
|  | 1.0 | VP/Eicosene Copolymer |
|  | 5.0 | Isohexadecane |
|  | 2.5 | Di-C12-13 Alkyl Malate |
|  | 3.0 | Titanium Dioxide, Trimethoxycaprylylsilane |
| C | 5.0 | Glycerin |
|  | 1.0 | Sodium Cetearyl Sulfate |
|  | 0.5 | Xanthan Gum |
|  | 59.7 | Aqua dem. |
| D | SA | Compound |
|  | 1.0 | Phenoxyethanol, Methylparaben, Ethylparaben, Butylparaben, Propylparaben, Isobutylparaben |
|  | 0.3 | Bisabolol |
| A | 4.5 | Ethylhexyl Methoxycinnamate |
|  | 2.0 | Diethylamino Hydroxybenzoyl Hexyl Benzoate |
|  | 3.0 | Octocrylene |

SUNSCREEN LOTIONS

| | % | Ingredients (INCI) |
|---|---|---|
|  | 2.5 | Di-C12-13 Alkyl Malate |
|  | 0.5 | Tocopheryl Acetate |
|  | 4.0 | Polyglyceryl-3 Methyl Glucose Distearate |
| B | 3.5 | Cetearyl Isononanoate |
|  | 1.0 | VP/Eicosene Copolymer |
|  | 5.0 | Isohexadecane |
|  | 2.5 | Di-C12-13 Alkyl Malate |
|  | 3.0 | Titanium Dioxide, Trimethoxycaprylylsilane |
| C | 5.0 | Glycerin |
|  | 1.0 | Sodium Cetearyl Sulfate |
|  | 0.5 | Xanthan Gum |
|  | 55.7 | Aqua dem. |
| D | SA | Compound |
|  | 1.0 | Phenoxyethanol, Methylparaben, Ethylparaben, Butylparaben, Propylparaben, Isobutylparaben |
|  | 0.3 | Bisabolol |

Production: Heat Phase A and B separately to approx. 80° C. Add Phase B to Phase A and homogenize by stirring. Heat Phase C to 80° C. and add to the combined Phase A and B and homogenize again. Cool to approx. 40° C. and add Phase D. Homogenize again.

SUNSCREEN LOTIONS O/W

| | % | Ingredients (INCI) |
|---|---|---|
| A | 2.0 | Ceteareth-6, Stearyl Alcohol |
|  | 2.0 | Ceteareth-25 |
|  | 3.0 | Tribehenin |
|  | 2.0 | Cetearyl Alcohol |
|  | 2.0 | Cetearyl Ethylhexanoate |
|  | 5.0 | Ethylhexyl Methoxycinnamate |
|  | 1.0 | Ethylhexyl Triazone |
|  | 1.0 | VP/Eicosene Copolymer |
|  | 7.0 | Isopropyl Myristate |
| B | 5.0 | Zinc Oxide, Triethoxycaprylylsilane |
| C | 0.2 | Xanthan Gum |
|  | 0.5 | Hydroxyethyl Acrylate/Sodium Acryloyldimethyl Taurate Copolymer, Squalane, Polysorbate 60 |
|  | 0.2 | Disodium EDTA |
|  | 5.0 | Propylene Glycol |
|  | 0.5 | Panthenol |
|  | 60.9 | Aqua dem. |
| D | SA | Compound |
|  | 0.5 | Phenoxyethanol, Methylparaben, Butylparaben, Ethylparaben, Propylparaben, Isopropylparaben |
|  | 1.0 | Tocopheryl Acetate |
|  | 0.2 | Bisabolol |
| A | 2.0 | Ceteareth-6, Stearyl Alcohol |
|  | 2.0 | Ceteareth-25 |
|  | 3.0 | Tribehenin |
|  | 2.0 | Cetearyl Alcohol |
|  | 2.0 | Cetearyl Ethylhexanoate |
|  | 5.0 | Ethylhexyl Methoxycinnamate |
|  | 1.0 | Ethylhexyl Triazone |
|  | 1.0 | VP/Eicosene Copolymer |
|  | 7.0 | Isopropyl Myristate |
| B | 5.0 | Zinc Oxide, Triethoxycaprylylsilane |
| C | 0.2 | Xanthan Gum |
|  | 0.5 | Hydroxyethyl Acrylate/Sodium Acryloyldimethyl Taurate Copolymer, Squalane, Polysorbate 60 |

-continued

SUNSCREEN LOTIONS O/W

| | % | Ingredients (INCI) |
|---|---|---|
| | 0.2 | Disodium EDTA |
| | 5.0 | Propylene Glycol |
| | 0.5 | Panthenol |
| | 56.9 | Aqua dem. |
| D | SA | Compound |
| | 0.5 | Phenoxyethanol, Methylparaben, Butylparaben, Ethylparaben, Propylparaben, Isopropylparaben |
| | 1.0 | Tocopheryl Acetate |
| | 0.2 | Bisabolol |

Production: Heat Phase A and B separately to approx. 80° C. Add Phase B to Phase A and homogenize by stirring. Heat Phase C to 80° C. and add to the combined Phase A and B and homogenize again. Cool to approx. 40° C. and add Phase D. Homogenize again.

SUNSCREEN LOTIONS O/W

| | % | Ingredients (INCI) |
|---|---|---|
| A | 3.5 | Ceteareth-6, Stearyl Alcohol |
| | 1.5 | Ceteareth-25 |
| | 7.5 | Ethylhexyl Methoxycinnamate |
| | 2.0 | Diethylamino Hydroxybenzoyl Hexyl Benzoate |
| | 2.0 | Cyclopentasiloxane, Cyclohexasiloxane |
| | 0.5 | Bees Wax |
| | 3.0 | Cetearyl Alcohol |
| | 10.0 | Caprylic/Capric Triglyceride |
| B | 5.0 | Titanium Dioxide, Silica, Methicone, Alumina |
| C | 3.0 | Glycerin |
| | 0.2 | Disodium EDTA |
| | 0.3 | Xanthan Gum |
| | 1.0 | Decyl Glucoside |
| | 2.0 | Panthenol, Propylene Glycol |
| | 56.3 | Aqua dem. |
| D | SA | Compound |
| | 1.0 | Tocopheryl Acetate |
| | 0.2 | Bisabolol |
| | QS | Parfumol |
| | QS | Preservative |
| A | 3.5 | Ceteareth-6, Stearyl Alcohol |
| | 1.5 | Ceteareth-25 |
| | 7.5 | Ethylhexyl Methoxycinnamate |
| | 2.0 | Diethylamino Hydroxybenzoyl Hexyl Benzoate |
| | 2.0 | Cyclopentasiloxane, Cyclohexasiloxane |
| | 0.5 | Bees Wax |
| | 3.0 | Cetearyl Alcohol |
| | 10.0 | Caprylic/Capric Triglyceride |
| B | 5.0 | Titanium Dioxide, Silica, Methicone, Alumina |
| C | 3.0 | Glycerin |
| | 0.2 | Disodium EDTA |
| | 0.3 | Xanthan Gum |
| | 1.0 | Decyl Glucoside |
| | 2.0 | Panthenol, Propylene Glycol |
| | 52.3 | Aqua dem. |
| D | SA | Compound |
| | 1.0 | Tocopheryl Acetate |
| | 0.2 | Bisabolol |
| | QS | Perfume |
| | QS | Preservative |

Production: Heat Phase A and B separately to approx. 80° C. Add Phase B to Phase A and homogenize by stirring. Heat Phase C to 80° C. and add to the combined Phase A and B and homogenize again. Cool to approx. 40° C. and add Phase D. Homogenize again.

FOOT BALM

| | % | Ingredients (INCI) |
|---|---|---|
| A | 2.0 | Ceteareth-6, Stearyl Alcohol |
| | 2.0 | Ceteareth-25 |
| | 5.0 | Cetearyl Ethylhexanoate |
| | 4.0 | Cetyl Alcohol |
| | 4.0 | Glyceryl Stearate |
| | 5.0 | Mineral Oil |
| | 0.2 | Menthol |
| | 0.5 | Camphor |
| B | 69.3 | Aqua dem. |
| | QS | Preservative |
| C | 1.0 | Bisabolol |
| | 1.0 | Tocopheryl Acetate |
| D | SA | Compound |
| | 5.0 | Witch Hazel Extract |
| A | 2.0 | Ceteareth-6, Stearyl Alcohol |
| | 2.0 | Ceteareth-25 |
| | 5.0 | Cetearyl Ethylhexanoate |
| | 4.0 | Cetyl Alcohol |
| | 4.0 | Glyceryl Stearate |
| | 5.0 | Mineral Oil |
| | 0.2 | Menthol |
| | 0.5 | Camphor |
| B | 65.3 | Aqua dem. |
| | QS | Preservative |
| C | 1.0 | Bisabolol |
| | 1.0 | Tocopheryl Acetate |
| D | SA | Compound |
| | 5.0 | Witch Hazel Extract |

Production: Heat Phase A and B separately to approx. 80° C. Add Phase B to Phase A and homogenize by stirring. Cool to approx. 40° C. and add Phase C and D. Homogenize by stirring and cool to room temperature

W/O

| | % | Ingredients (INCI) |
|---|---|---|
| A | 6.0 | PEG-7 Hydrogenated Castor Oil |
| | 8.0 | Cetearyl Ethylhexanoate |
| | 5.0 | Isopropyl Myristate |
| | 15.0 | Mineral Oil |
| | 0.3 | Magnesium Stearate |
| | 0.3 | Aluminum Stearate |
| | 2.0 | PEG-45/Dodecyl Glycol Copolymer |
| B | 5.0 | Glycerin |
| | 0.7 | Magnesium Sulfate |
| | 55.6 | Aqua dem. |
| C | 1.0 | Compound |
| | 0.5 | Tocopheryl Acetate |
| | 0.6 | Bisabolol |
| A | 6.0 | PEG-7 Hydrogenated Castor Oil |
| | 8.0 | Cetearyl Ethylhexanoate |
| | 5.0 | Isopropyl Myristate |
| | 15.0 | Mineral Oil |
| | 0.3 | Magnesium Stearate |
| | 0.3 | Aluminum Stearate |
| | 2.0 | PEG-45/Dodecyl Glycol Copolymer |
| B | 5.0 | Glycerin |
| | 0.7 | Magnesium Sulfate |
| | 51.6 | Aqua dem. |
| C | 5.0 | Compound |
| | 0.5 | Tocopheryl Acetate |

Production: Heat Phase A and B separately to approx. 85° C. Add Phase B to Phase A and homogenize by stirring. Cool to approx. 40° C. and add Phase C. Homogenize by stirring and cool to room temperature.

LIQUID MAKE-UP - TYPE O/W

|   | % | Ingredients (INCI) |
|---|---|---|
| A | 2.0 | Ceteareth-6, Stearyl Alcohol |
|   | 2.0 | Ceteareth-25 |
|   | 6.0 | Glyceryl Stearate |
|   | 1.0 | Cetyl Alcohol |
|   | 8.0 | Mineral Oil |
|   | 7.0 | Cetearyl Ethylhexanoate |
|   | 0.2 | Dimethicone |
| B | 3.0 | Propylene Glycol |
|   | 1.0 | Panthenol |
|   | QS | Preservative |
|   | 61.9 | Aqua dem. |
| C | 0.1 | Bisabolol |
|   | SA | Compound |
|   | QS | Perfume |
| D | 5.7 | C.I. 77 891, Titanium Dioxide |
|   | 1.1 | Iron Oxides |
| A | 2.0 | Ceteareth-6, Stearyl Alcohol |
|   | 2.0 | Ceteareth-25 |
|   | 6.0 | Glyceryl Stearate |
|   | 1.0 | Cetyl Alcohol |
|   | 8.0 | Mineral Oil |
|   | 7.0 | Cetearyl Ethylhexanoate |
|   | 0.2 | Dimethicone |
| B | 3.0 | Propylene Glycol |
|   | 1.0 | Panthenol |
|   | QS | Preservative |
|   | 57.9 | Aqua dem. |
| C | 0.1 | Bisabolol |
|   | SA | Compound |
|   | QS | Perfume |
| D | 5.7 | C.I. 77 891, Titanium Dioxide |
|   | 1.1 | Iron Oxides |

Production: Heat Phase A and B separately to approx. 80° C. Add Phase B to Phase A and homogenize by stirring. Cool to 40° C. and add Phase C and D. Homogenize again and cool to room temperature.

FOUNDATION

| Ingredient | INCI Name | % |
|---|---|---|
| Water Phase | | |
| Dow Corning 9011 Elastomer Blend | Cyclopentasiloxane, PEG-12 Dimethicone Copolymer | 15.00 |
| Dow Corning 245 Fluid | Cyclopentasiloxane | 5.00 |
| Silcare 31 M50 SV | Caprylyl Trimethicone | 6.35 |
| Propylparaben | | 0.05 |
| AS 5811 | Titanium Dioxide, Triethoxycaprylylsilane | 7.50 |
| AS 5131 | Iron Oxides, Triethoxycaprylylsilane | 0.70 |
| AS 5146 | Iron Oxides, Triethoxycaprylylsilane | 0.05 |
| AS 5126 | Iron Oxides, Triethoxycaprylylsilane | 0.35 |
| AS 50230 | Talc, Triethoxycaprylylsilane | 3.50 |
| Oil Phase | | |
| Deionized Water | | 53.30 |
| 1.80 Butylene Glycol | | 6.00 |
| Methylparaben | | 0.20 |
| Benzoic Acid | | 0.20 |
| Compound | | SA |

The pigments (AS 5811, 5131, 5146, 5126, and 50230; Color Techniques) and propylparaben are dispersed in Silcare 31 M50 SV (Clariant), stirring until wet. The mixture is then passed over a three roll mill at tight setting until particle size is <10 μm. Then, DC 9011 Elastomer Blend (Dow Corning) and DC 245 Fluid are combined in finishing vessel, stirring until homogenous. The color grind is added with slow homogenizer agitation. The water is weighed into a separate vessel and Compound is gradually added with propeller agitation. stirring until dissolved. Methylparaben and benzoic acid are added to butylene glycol. The mixture is warmed slightly, and stirred until dissolved. The mixture is cooled to 30° C. and added to the Compound-containing solution. The water phase is added slowly to the oil phase with rapid agitation. When addition is complete, the preparation is homogenized for five minutes. This preparation is useful as a makeup foundation for application to skin.

Mascara Formulation

The ingredients of both a control preparation and a mascara containing 2% are as follows:

| Trade Name | INCI Name | % Control 1 | % Compound 2 |
|---|---|---|---|
| Phase # Water Phase | | | |
| 1 Deionized Water | | 42.96 | 42.96 |
| 2 Butylene Glycol | | 5.00 | 5.00 |
| 2 Methylparaben | | 0.30 | 0.30 |
| 3 33-5198 | (Black) Iron Oxides (Sun) | 10.00 | 10.00 |
| 4 Natrosol 250 MR | Hydroxyethylcellulose (Aqualon) | 0.20 | 0.20 |
| 5 10% KOH | Potassium Hydroxide | 0.01 | 0.01 |
| 6 Arlacel 165 | Glyceryl Stearate, PEG-100 Stearate (Uniqema) | 3.00 | 3.00 |
| 7 10% Citric Acid | | 0.27 | 0.27 |
| Phase # Wax Phase | | | |
| 8 Arlacel 165 | | 1.00 | 1.00 |
| 8 Cerasynt SD | Glyceryl Stearate (ISP) | 3.50 | 3.50 |
| 8 Beeswax, White SP 424 | Beeswax (S&P) | 7.50 | 7.50 |
| 8 Carnauba #1 | *Copernica Cerifera* (Carnauba) Wax (S&P) | 4.80 | 4.80 |
| 8 Propylparaben | | 0.10 | 0.10 |
| 9 Deionized Water | | 20.00 | — |
| 9 10% Compound/Water | | — | 20.00 |
| 10 Deionized Water | | 1.00 | 1.00 |
| 10 Glydant | DMDM Hydantoin (Lonza) | 0.36 | 0.36 |
| | | 100.00 | 100.00 |

To produce the mascara formulation, the wax phase 8 is combined and heated to 85-90° C. with propeller mixing. The 10% Compound solution is prepared by adding Compound to water while propeller mixing. Phase 1 water is added to a tared stainless steel beaker (approximately 50 g excess is added to compensate for loss). Phase 2 methylparaben is added to butylene glycol and stirred while warming on top of a steam bath until dissolved, then added to the water with slow homomixer agitation. Then, the phase 4 black iron oxide is added, while maintaining agitation. Then, Natrosol is sprinkled in, while maintaining agitation. The 10% KOH is added, and heating is begun to 85° C., with the beaker covered as tightly as possible. When the Natrosol is dissolved, the 10% citric acid is added dropwise, maintaining temperature and agitation. Then, the Arlacel 165 is added slowly and mixed for at least 5 minutes to insure dissolution. At 85-90° C., the wax phase is slowly added to the water phase while homomixing. The temperature and agitation are maintained for 10 minutes. The batch is removed from the steam bath and allowed to cool while homomixing with occasional hand scraping of the beaker walls. At 55° C., the batch is weighed to check for water loss. Mixing is resumed and water is added back, if necessary. At 45° C., phases 9 and 10 are added. Cooling is continued using cold water to 30° C. At this point, continuous hand scraping of beaker walls is necessary.

In this preparation, the small amount of KOH (in Phase 5) is used to raise the pH to disperse the Natrosol which is coated with glyoxal to retard wetting, and prevent agglomeration. In phase 7, the citric acid is added slowly to adjust pH to 5.5, below the isoelectric point of the iron oxides. In phases 7 and 8, the Arlacel 165 is split between the oil and water phases, as the emulsification is easier to accomplish with surfactant in both phases. In phase 9, the deionized water is added in the control batch instead of Compound. The Compound solution is prepared while the emulsion is being processed, so it is absolutely fresh. This preparation provides a formulation suitable for use as a mascara.

EXAMPLE 18

Hair Growth Inhibition

In this Example, experiments to determine the ability of the compositions of the present invention to inhibit the growth of hair are described. In particular, these experiments are conducted in order to assess the ability of the compositions of the present invention to decrease hair growth after depilation by shaving or use of depilatory creams or waxing.

A lotion for inhibiting hair growth and containing a modified variant BBPI in which the chymotrypsin loop of the parent BBPI is replaced with a VEGF-binding peptide is prepared according to the following formulation (A):

| Ingredient (INCI name) | % in weight |
|---|---|
| Water | 85.97 |
| Cetearyl alcohol | 8.50 |
| Ceteareth-20 | 2.70 |
| PPG-15 Stearyl Ether | 0.60 |
| *Prunus Amygdalus Dulcis* Oil (1) | 0.10 |
| Paraffinum Liquidum | 0.10 |
| Allantoin | 0.20 |
| Propylene glycol | 0.13 |
| CI77891 Titanium dioxide | 0.17 |
| Tetra sodium EDTA | 0.10, |
| VEGF-BBPI | 0.10 |
| Sodium Chloride | 0.091 |
| Citric acid | 0.11 |
| Sodium Hydroxyde | 0.034 |
| Phenoxyethanol | 1.0 |
| Robertet Artlande G10029876 (2) | 0.10 |

The composition includes at least one type of modified variant BBPI in which the chymotrypsin loop is a VEGF-binding peptide as described herein (see section 5.3). In some embodiments, the VEGF-BBPI chosen from SEQ ID NOS: 601, 602, 627-631, 643, 491, 632-636. In some embodiments, the composition comprises at least two, at least three, at least four or at least five different types of VEGF-BBPIs chosen from SEQ ID NOS:601, 602, 627-631, 643, 491, 632-636.

The formulation comprising the VEGF-BBPI is manufactured as follows:

1) Blending the fatty alcohol emulsifier and oil gelling agent together into a molten phase at a temperature of 60, preferably 70° C. or more,
2) emulsifying the molten phase into an aqueous phase, the temperature of the aqueous phase prior to emulsification being 50° C., preferably 60° C., more preferably 70° C. or more, whereby an emulsion is formed,
3) cooling the emulsion to a temperature of 35° C. or less,
4) dispersing the perfume, preservative, citric acid solution buffer solution in the emulsion.
5) adding in the same manner the solution of VEGF-BBPI, finishing with the buffer solution over a period of approximately 5 min.
6) Agitating the mixture for a further 10 minutes A control formulation (B) is prepared according to the method described for the preparation of formulation A but excluding the VEGF-BBPI.

Facial Hair Experiments

In these experiments, a group (e.g., 5) male subjects with Fitzpatrick Skin Classification II are tested. Individuals are requested to use no topical facial treatment prior to beginning the experiments. On day 1, facial hair growth is visually evaluated and photographed. Following this evaluation and photography, the composition(s) to be tested, as well as a vehicle control are applied at the desired concentration(s). Beginning on day 2, the individuals apply the composition(s) immediately after shaving. No other pre- or post-shave treatment is used for the duration of the experiments. In most cases, the experiment continues for a time period of 30 to 45 days. Facial hair growth is visually evaluated and photographed every third day during the experiments. The number of hairs, as well as the hair shaft length and width are measured using computerized image analysis. In preferred embodiments, there is a decrease in the number of hairs, hair thickness and/or hair length due to the application of the test compound(s).

Leg Hair Experiments

In these experiments, a group (e.g., 5) female subjects with Fitzpatrick Skin Classification II are tested. Individuals are requested to use no topical leg treatment prior to beginning the experiments. On day 1, areas on both legs of each individual are marked and the hair growth is visually evaluated and photographed. Following this evaluation and photography, the composition(s) to be tested are applied at the desired concentration(s). Following this evaluation and photography, the composition(s) to be tested (i.e., test compounds containing a desired concentration of VEGF-BBP), as well as a vehicle control, are applied at the desired concentration(s). In some methods, each individual is provided with two tubes, one of which contains the VEGF-BBPI and the other containing the vehicle control. These tubes are marked "left" and "right." Each day during the experiments, the subject applies the compositions in the two tubes the respective legs. After 7 days of application, the individuals are visually evaluated and photographs are taken. Both legs are then shaved or exposed to a depilatory and the test individuals continue to apply the compositions as before. Hair growth is then evaluated visually and by photographing appropriate areas on the legs every 2 days. After 10 days, the legs are again shaved and the test subjects continue to apply the compositions as before. In some methods, the experiments are conducted for 3 cycles and the hair growth is visually evaluated and photographs were taken. The experiments are then continued for an additional 8 days. In preferred embodiments, there is a decrease in the number of hairs, hair thickness and/or hair length due to the application of the test compound(s) in the marked area(s).

Beginning on day 2, the individuals apply the composition(s) immediately after shaving. No other pre- or post-shave treatment is used for the duration of the experiments. In most cases, the experiment continues for a time period of 30 to 45 days. Facial hair growth is visually evaluated and photographed every third day during the experiments. The number of hairs, as well as the hair shaft length and width are measured using computerized image analysis. In preferred embodiments, there is a decrease in the number of hairs, hair thickness and/or hair length due to the application of the test compound(s).

We claim:

1. A personal care composition comprising a modified variant Bowman Birk Protease Inhibitor (BBPI),
   wherein said modified variant BBPI comprises
   a BBPI scaffold selected from the group consisting of: BBI (SEQ ID NO: 13), BBIt (SEQ ID NO:185), BBI-AV (SEQ ID NO:186), BBIt-AV (SEQ ID NO:187), BBIt-VEGK (SEQ ID NO:640), BBIt-VEGT (SEQ ID NO:641), BBIt-VEGKD (SEQ ID NO:642), BBdb (SEQ ID NO:449), BBsb3 (SEQ ID NO:450), BBtc (SEQ ID NO:451), BBdb-AV (SEQ ID NO:452), BBsb3-AV (SEQ ID NO:453) and BBtc-AV (SEQ ID NO:454),
      wherein the second protease inhibitory loop of the BBPI scaffold is replaced with a binding peptide selected from the group consisting of a vascular endothelial growth factor (VEGF) binding peptide, a fibroblast growth factor-5 (FGF) binding peptide, a transforming growth factor β (TGF) binding peptide and a tumor necrosis factor α (TNF) binding peptide; and
      wherein the backbone of the BBPI scaffold is substituted at one or more amino acid positions selected from the group consisting of positions equivalent to positions 1, 4, 5, 11, 13, 18, 25, 27, 29, 31,38, 40, 50, 52, 55 and 65 of SEQ ID NO:187;

wherein the substitution at position 1 is to A or C, the substitution at position 4 is to V, the substitution at position 5 is to P or A, the substitution at position 11 is to G, the substitution at position 13 is to Y, I, F, M, L, V, K or R, the substitution at position 18 is to I, V or L, the substitution at position 25 is to K, N, W, I, A, R or L, the substitution at position 27 is to R, K, V, A or Q, the substitution at position 29 is to R, K, P or E, the substitution at position 31 is to Q, H, E, A, R, W, K or T, the substitution at position 38 is to N, K or R, the substitution at position 40 is to H, K, Q, R or Y, the substitution at position 50 is to R, Q, K, T, V, M or S, the substitution at position 52 is to K, T, R, Q, L, H, A, M, S or E, the substitution at position 55 is to M and the substitution at position 65 is to E, Q or D.

2. The personal care composition of claim 1, wherein the substitutions in the backbone of the BBPI scaffold are a combination of substitutions chosen from 50T-52A, 25L-50T-52A, 29P-50T-52A, 40K-50T-52A, 13I-25L-50T-52A, 13I-29P-50T-52A, 13I-40K-50T-52A, 25L-29P-50T-52A, 25L-40K-50T-52A, 29P-40K-50T-52A, 13I-25K-29P-52K, 13I-25L-29P-50T-52A, 13I-29P-40K-50T-52A, 13I-25L-40K-50T-52A, 25L-29P-40K-50T-52A, 13L-29P-40K-50T-52A, 13I-29K-40K-50T-52A, 13I-29P-40K-50K-52A, 13I-29P-40K-50T-52A, 13I-25L-29P-40K-50T-52A, D1C-13I-29P-40K-50T-52A, S4V-13I-29P-40K-50T-52A, S5P-13I-29P-40K-50T-52A, 11G-13I-29P-40K-50T-52A, 13I-25R-29P-40K-50T-52A, 13I-27R-29P-40K-50T-52A, 13I-29P-31A-40K-50T-52A, 13I-29P-31R-40K-50T-52A, 13I-29P-38N-40K-50T-52A, 13I-29P-40K-50T-52A-65E, 13L-25R-29P-31A-40K-50T-52A, 13L-25R-29P-31R-40K-50T-52A, 13I-25R-27A-29P-31A-50K-52T, 13I-25R-27A-29P-31A-40H-50K-52T, 13I-25K-27A-29R-31E-40K-50Q-52Q, 13I-25K-27R-29E-31A-40H-50R-52K, 13I-25K-27A-29R-31A-40H-50R-52L, and 13I-25K-27Q-29P-31E-40H-50R-52Q.

3. The personal care composition of claim 1, wherein said modified variant BBPI binds a target protein chosen from VEGF, FGF5, TGFβ and TNFα.

4. The personal care composition of claim 1, wherein said VEGF binding peptide is chosen from YNLYGWT (SEQ ID NO:676), ACYNLYGWTC (SEQ ID NO:9), KYYLYWW (SEQ ID NO:458), TLWKSYW (SEQ ID NO:459), DLYWW (SEQ ID NO:460),SKHSQIT (SEQ ID NO:468) KTNPSGS (SEQ ID NO:469) RPTGHSL (SEQ ID NO:470), KHSAKAE (SEQ ID NO:471) KPSSASS (SEQ ID NO:472), PVTKRVH (SEQ ID NO:473), TLHWWVT (SEQ ID NO:492), PYKASFY (SEQ ID NO:493), PLRTSHT (SEQ ID NO:494), EATPROT (SEQ ID NO:495), NPLHTLS (SEQ ID NO:496), KHERIWS (SEQ ID NO:497), ATNPPPM (SEQ ID NO:498), STTSPNM (SEQ ID NO:499), ADRSFRY (SEQ ID NO:500), PKADSKQ (SEQ ID NO:501), PNQSHLH (SEQ ID NO:502), SGSETWM (SEQ ID NO:503), ALSAPYS (SEQ ID NO:504), KMPTSKV (SEQ ID NO:505), ITPKRPY (SEQ ID NO:506), KWIVSET (SEQ ID NO:507), PNANAPS (SEQ ID NO:508), NVQSLPL (SEQ ID NO:509), TLWPTFW (SEQ ID NO:510), NLWPHFW (SEQ ID NO:511), SLWPAFW (SEQ ID NO:512), SLWPHFW (SEQ ID NO:513), APWNSHI (SEQ ID NO:514), APWNLHI (SEQ ID NO:515), LPSWHLR (SEQ ID NO:516), PTILEWY (SEQ ID NO:517), TLYPQFW (SEQ ID NO:518), HLAPSAV (SEQ ID NO:519), KYYLSWW (SEQ ID NO:520), WYTLYKW (SEQ ID NO:521), TYRLYWW (SEQ ID NO:522), RYSLYYW (SEQ ID NO:523), YYLYYWK (SEQ ID NO:524), NYQLYGW (SEQ ID NO:525), TKWPSYW (SEQ ID NO:226), TLWKSYW (SEQ ID NO:527), PLWPSYW (SEQ ID NO:528), RLWPSYW (SEQ ID NO:529), TLWPKYW (SEQ ID NO:530), KYDLYWW (SEQ ID NO:531), RYDLYWW (SEQ ID NO:532), DYRLYWW (SEQ ID NO:533), DYKLYWW (SEQ ID NO:534), EYKLYWW (SEQ ID NO:535), and RYPLYWW (SEQ ID NO:536).

5. The personal care composition of claim 1, wherein said FGF binding peptide is chosen from CACRTQPYPLCF (MM007; SEQ ID NO:430), CICTWIDSTPC (PS2; SEQ ID NO:431), CYGLPFTRC (SEQ ID NO:537), CEEIWTMLC (SEQ ID NO:538), CWALTVKTC (SEQ ID NO:539), CLTVLWTTC (SEQ ID NO:540), CTLWNRSPC (SEQ ID NO:541), CHYLLTNYC (SEQ ID NO:542), CRIHLAHKC (SEQ ID NO:543), TNIDSTP (SEQ ID NO:544), HLQTTET (SEQ ID NO:545), SLNNLTV (SEQ ID NO:546), TNIDSTP (SEQ ID NO:547), TNIDSTP (SEQ ID NO:548), LRILANK (SEQ ID NO:549), LLTPTLN (SEQ ID NO:550), ALPTHSN (SEQ ID NO:551), TNIDSTP (SEQ ID NO:552), LCRRFEN (SEQ ID NO:553), TNIDSTP (SEQ ID NO:554), TNIDSTP (SEQ ID NO:555), HLQTTET (SEQ ID NO:556), PLGLCPP (SEQ ID NO:557), GYFIPSI (SEQ ID NO:558), TKIDSTP (SEQ ID NO:559), HLQTTET (SEQ ID NO:560), WNIDSTP (SEQ ID NO:561), TWIDWTP (SEQ ID NO:562), RTQPYPL (SEQ ID NO:670) and TWIDSTP (SEQ ID NO:671).

6. The personal care composition of claim 1, wherein said TGF binding peptide is chosen from CLCPENINVLPCN (PEN3; SEQ ID NO:436), CICKHNVDWLCF (MMO21W; SEQ ID NO:437), CICWTQHIHNCF (WTQ; SEQ ID NO:438), CVTTDWIEC (SEQ ID NO:563), CYYSQFHQC (SEQ ID NO:564), CPTLWTHMC (SEQ ID NO:565), QSACIVYYVGRKPKVECASSD (SEQ ID NO:566), QSACILYYIGKTPKIECASSD (SEQ ID NO:567), QSACILYYVGRTPKVECASSD (SEQ ID NO:568), KHNVRLL (SEQ ID NO:570), NDTPSYF (SEQ ID NO:571), AKLYAGS (SEQ ID NO:572), RGPAHSL (SEQ ID NO:573), NSLAERR (SEQ ID NO:574), HPLASPH (SEQ ID NO:575), QPWNKLK (SEQ ID NO:576), PTKPAQQ (SEQ ID NO:578), PSLNRPQ (SEQ ID NO:579), HHARQEW (SEQ ID NO:580), RHHTPGP (SEQ ID NO:581), ASAINPH (SEQ ID NO:582), CHGYDRAPC (SEQ ID NO:644), CFAPADQAC (SEQ ID NO:645), CIPSRFITC (SEQ ID NO:646), CHGHTKLAC (SEQ ID NO:647), CNGKSKLAC (SEQ ID NO:648), PENINVLP (SEQ ID NO:672), KHNVDWL (SEQ ID NO:673) and WTQHIHNC (SEQ ID NO:674).

7. The personal care composition of claim 1, wherein said TNF binding peptide is chosen from RYWQDIP (T1; SEQ ID NO:474), APEPILA (T2; SEQ ID NO:475), DMIMVSI (T3; SEQ ID NO:476), WTPKPTQ (SEQ ID NO:583), ATFPNQS (SEQ ID NO:584), ASTVGGL (SEQ ID NO:585), TMLPYRP (SEQ ID NO:586), AWHSPSV (SEQ ID NO:587), TQSFSS (SEQ ID NO:588), THKNTLR (SEQ ID NO:589), GQTHFHV (SEQ ID NO:590), LPILTQT (SEQ ID NO:591), SILPVSH (SEQ ID NO:592), SQPIPI (SEQ ID NO:593), and QPLRKLP (SEQ ID NO:594).

8. The personal care composition of claim 1, wherein said modified variant BBPI comprises from about 0.0001 weight percent to about 5 weight percent of said personal care composition.

9. The personal care composition of claim 1, wherein the substitutions in the backbone of the BBPI scaffold increase the trypsin inhibitory activity and production yield of the modified variant BBPI.

10. The personal care composition of claim 1, wherein said binding peptide is a VEGF-binding peptide chosen from SEQ ID NOS: 9, 458, 459, 460, 468, 469, 470, 471, 472, 676 and 473.

11. The personal care composition of claim 10, wherein said scaffold is BBIt-AV (SEQ ID NO:187).

12. The personal care composition of claim 10, wherein the substitutions in the backbone of the BBPI scaffold are a combination of substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, and 13I-25K-27A-29R-31A-40H-50R-52L.

13. The personal care composition of claim 1, wherein said modified variant BBPI is a VEGF-binding BBPI (VEGF-BBPI) chosen from SEQ ID NOs: 601, 602, 627, 628, 630, 631, 643, 491, 632, 633, 634, 635, and 636.

14. The personal care composition of claim 10, wherein said personal care composition is a skin care composition selected from the group consisting of skin creams, lotions, sprays, emulsions, colloidal suspensions, foams, aerosols, liquids, gels, sera, and solids.

15. The personal care composition of claim 10, wherein said personal care composition is a skin care composition selected from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, sunscreens, dipilatories, hair growth inhibitors and radioprotectives.

16. The personal care composition of claim 15, wherein said skin care composition further comprises topically applied over-the-counter compositions, anti-fungal treatments, anti-acne treatments, skin protectants, sunscreens, deodorants, and antiperspirants.

17. The personal care composition of claim 15, wherein said radioprotective is a sunscreen selected from non-water-resistant sunscreens, very water-resistant sunscreens, and water-in-silicone sunscreens.

18. The personal care composition of claim 14, wherein said personal care composition is a cosmetic composition chosen from pressed powder formulations, and foundations.

19. The personal care composition of claim 18, wherein said cosmetic composition comprises at least one pigment.

20. The personal care composition of claim 18, wherein said cosmetic composition is a pressed powder formulation selected from loose powders, blushes, and bronzing powders.

21. The personal care composition of claim 18, wherein said cosmetic composition is a foundation selected from water-in-oil foundations, water-in-silicone foundations, oil-in-water foundations, anhydrous makeup sticks, and cream-to-powder foundations.

22. The personal care composition of claim 10, wherein said personal care composition is a skin care composition for improving the appearance and/or condition of skin in a subject suffering from an angiogenic skin disorder chosen from psoriasis, scleroderma, venous ulcers, acne, rosacea, warts, eczema, hemangiomas and lymphangiogenesis.

23. The personal care composition of claim 10, wherein said personal care composition is a hair care composition.

24. The personal care composition of claim 23, wherein said hair care composition is selected from the group consisting of shampoos, conditioners, hair styling compositions, hair colorants, permanent wave formulations, creams, gels, mousses, sprays, emulsions, colloidal suspensions, liquids, foams, and solids.

25. The personal care composition of claim 24, wherein said hair care composition further comprises a radioprotective.

26. The personal care composition of claim 25, wherein said radioprotective is a sunscreen selected from non-water-resistant sunscreens, very water-resistant sunscreens, and water-in-silicone sunscreens.

27. The personal care composition of claim 10, wherein said personal care composition is capable of inhibiting hair growth.

28. A method for inhibiting hair growth of a subject, comprising the steps of:
    a) providing the personal care composition of claim 10;
    b) providing a subject to be treated; and
    c) applying said composition to said subject in an area in which inhibition of hair growth is desired.

29. The method of claim 28, wherein the area is chosen from face, underarm, leg, torso, arm and head.

30. The method of claim 28, wherein said modified variant BBPI is a VEGF-BBPI chosen from SEQ ID NOS: 601, 602, 627, 628, 630, 631, 643, 491, 632, 633, 634, 635, and 636.

31. A method for improving the appearance and/or condition of the skin of a subject suffering from an angiogenic skin disorder chosen from psoriasis, scleroderma, venous ulcers, acne, rosacea, warts, eczema, hemangiomas and lymphangiogenesis, comprising the steps of:
    a) providing the personal care composition of claim 10;
    b) providing said subject; and
    c) applying said composition to the skin of said subject.

32. The method of claim 31, wherein said modified variant BBPI is a VEGF-BBI chosen from SEQ ID NOs: 601, 602, 627, 628, 630, 631, 643, 491, 632, 633, 634, 635, and 636.

33. The personal care composition of claim 1, wherein said binding peptide is an FGF binding peptide chosen from SEQ ID NOS: 670 and 671.

34. The personal care composition of claim 33, wherein said BBPI scaffold is BBIt-AV (SEQ ID NO:187).

35. The personal care composition of claim 33, wherein the substitutions in the backbone of the BBPI scaffold are a combination of substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, and 13I-25K-27A-29R-31A-40H-50R-52L.

36. The personal care composition of claim 33, wherein said modified variant BBPI is an FGF-binding BBPI (FGF-BBPI) chosen from SEQ ID NOs:432 and 434.

37. The personal care composition of claim 33, wherein said personal care composition is a hair care composition.

38. The personal care composition of claim 37, wherein said hair care composition is selected from the group consisting of shampoos, conditioners, hair styling compositions, hair colorants, permanent wave formulations, creams, gels, mousses, sprays, emulsions, colloidal suspensions, liquids, foams, and solids.

39. The personal care composition of claim 38, wherein said hair care composition further comprises a radioprotective.

40. The personal care composition of claim 39, wherein said radioprotective is a sunscreen selected from non-water-resistant sunscreens, very water-resistant sunscreens, and water-in-silicone sunscreens.

41. The personal care composition of claim 37, wherein said personal care composition is capable of promoting hair growth.

42. A method for promoting hair growth of a subject, comprising the steps of:
    a) providing the personal care composition of claim 33;
    b) providing a subject to be treated; and
    c) applying said composition to said subject in an area in which promotion of hair growth is desired.

43. The method of claim 42, wherein the area is chosen from face, underarm, leg, torso, arm and head.

44. The method of claim 42, wherein said subject is suffering from a condition that involves hair loss.

45. The method of claim 44, wherein said condition is chosen from inflammatory alopecias, pseudopelade, scleroderma, tick bites, lichen planus, psoriasis, lupus, seborrheic dermatitis, loose hair syndrome, hemochromatosis, androgenic alopecia, and alopecia areata.

46. The method of claim 42, wherein said modified variant BBPI is an FGF-binding BBPI (FGF-BBPI) chosen from SEQ ID NOS:432 and 434.

47. The personal care composition of claim 1, wherein said binding peptide is a TGF binding peptide chosen from SEQ ID NOS:436, 437, 438, 672, 673, and 674.

48. The personal care composition of claim 47, wherein said scaffold is BBIt-AV (SEQ ID NO:187).

49. The personal care composition of claim 47, wherein the substitutions in the backbone of the BBPI scaffold are a combination of substitutions chosen from 13I-40K-50T-52A, 13I-25K -29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, and 13I-25K-27A-29R-31A-40H-50R-52L.

50. The personal care composition of claim 47, wherein said modified variant BBPI is TGF-binding BBPI (TGF-BBPI) chosen from SEQ ID NOs: 443, 445 and 447.

51. The personal care composition of claim 47, wherein said personal care composition is a hair care or a skin care composition.

52. The personal care composition of claim 51, wherein said hair care or skin care composition is selected from the group consisting of shampoos, conditioners, hair styling compositions, hair colorants, permanent wave formulations, creams, gels, mousses, sprays, emulsions, colloidal suspensions, liquids, foams, and solids.

53. The personal care composition of claim 52, wherein said personal care composition is a skin care composition selected from moisturizing body washes, body washes, anti-microbial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, sunscreens, and radioprotectives.

54. The personal care composition of claim 53, wherein said skin care composition further comprises topically applied over-the-counter compositions, anti-fungal treatments, anti-acne treatments, skin protectants, sunscreens, deodorants, and antiperspirants.

55. The personal care composition of claim 53, wherein said radioprotective is a sunscreen selected from non-water-resistant sunscreens, very water-resistant sunscreens, and water-in-silicone sunscreens.

56. The personal care composition of claim 51, wherein said personal care composition is a cosmetic composition.

57. The personal care composition of claim 56, wherein said cosmetic composition is elected from mascaras, eyeliners, pressed powder formulations, and foundations.

58. The personal care composition of claim 52, wherein said hair care composition further comprises a radioprotective.

59. The personal care composition of claim 58, wherein said radioprotective is a sunscreen selected from non-water-resistant sunscreens, very water-resistant sunscreens, and water-in-silicone sunscreens.

60. The personal care composition of claim 47, wherein said personal care composition is capable of promoting hair growth.

61. A method for promoting hair growth of a subject, comprising the steps of:
a) providing the personal care composition of claim 47;
b) providing a subject to be treated; and
c) applying said composition to said subject in an area in which promotion of hair growth is desired.

62. The method of claim 61, wherein the area is chosen from face, underarm, leg, torso, arm and head.

63. The method of claim 61, wherein said subject is suffering from a condition that involves hair loss.

64. The method of claim 63, wherein said condition is chosen from inflammatory alopecias, pseudopelade, scleroderma, tick bites, lichen planus, psoriasis, lupus, seborrheic dermatitis, loose hair syndrome, hemochromatosis, androgenic alopecia, and alopecia areata.

65. The method of claim 61, wherein said modified variant BBPI is a TGF-BBPI chosen from SEQ ID NOS: 443, 445 and 447.

66. A method for improving the appearance and/or condition of the skin of a subject suffering from a skin disorder chosen from psoriasis, scleroderma, and skin cancer comprising the steps of;
a) providing the personal care composition of claim 47;
b) providing said subject; and
c) applying said composition to the skin of said subject.

67. The method of claim 66, wherein said modified variant BBPI is a TGF-BBPI chosen from SEQ ID NOS: 443, 445 and 447.

68. The personal care composition of claim 1, wherein said binding peptide is a TNF binding peptide chosen from SEQ ID NOS: 474, 475 and 476.

69. The personal care composition of claim 68, wherein said scaffold is BBIt-AV (SEQ ID NO:187).

70. The personal care composition of claim 68, wherein the substitutions in the backbone of the BBPI scaffold are a combination of substitutions chosen from 13I-40K-50T-52A, 13I-25K-29P-52K, 13I-29P-40K-50T-52A, 13I-25R-27A-29P-31A-50K-52T, 13I-25R-27A-29P-31A-40H-50K-52T, 13I-25K-27A-29R-31E-40K-50Q-52Q, and 13I-25K-27A-29R-31A-40H-50R-52L.

71. The personal care composition of claim 68, wherein said modified variant BBPI is TNF-BBPI chosen from SEQ ID NOS:637, 638 and 639.

72. The personal care composition of claim 68, wherein said personal care composition is a hair care composition.

73. The personal care composition of claim 72, wherein said hair care composition is capable of promoting hair growth in a subject suffering from psoriasis.

74. The personal care composition of claim 72, wherein said hair care composition is selected from the group consisting of shampoos, conditioners, hair styling compositions, hair colorants, permanent wave formulations, creams, gels, mousses, sprays, emulsions, colloidal suspensions, liquids, foams, and solids.

75. The personal care composition of claim 74, wherein said hair care composition further comprises a radioprotective.

76. The personal care composition of claim 75, wherein said radioprotective is a sunscreen selected from non-water-resistant sunscreens, very water-resistant sunscreens, and water-in-silicone sunscreens.

77. The personal care composition of claim 68, wherein said personal care composition is capable of promoting hair growth.

78. The personal care composition of claim 68, wherein said personal care composition is a skin care composition.

79. The personal care composition of claim 68, wherein said skin care composition is capable of improving the appearance and/or condition of the skin of a subject suffering from an psoriasis or scleroderma.

80. The personal care composition of claim 78, wherein said personal care composition is a skin care composition selected from the group consisting of skin creams, lotions, sprays, emulsions, colloidal suspensions, foams, aerosols, liquids, gels, sera, and solids.

81. The personal care composition of claim 78, wherein said personal care composition is a skin care composition selected from moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, and radioprotectives.

82. The personal care composition of claim 80, wherein said skin care composition further comprises topically applied over-the-counter compositions, anti-fungal treatments, anti-acne treatments, skin protectants, sunscreens, deodorants, and antiperspirants.

83. The personal care composition of claim 68, wherein said personal care composition is a cosmetic composition.

84. The personal care composition of claim 83, wherein said cosmetic composition is elected from mascaras, eyeliners, pressed powder formulations, and foundations.

85. The personal care composition of claim 84, wherein said cosmetic composition comprises at least one pigment.

86. The personal care composition of claim 85, wherein said cosmetic composition comprising at least one pigment is a mascara selected from non-waterproof mascaras, waterproof mascaras, volumizing mascaras, lengthening mascaras, curling mascaras, anhydrous waterproof mascaras, water-based mascaras, and eyelash or eyebrow treatments.

87. The personal care composition of claim 85, wherein said cosmetic composition is a pressed powder formulation selected from loose powders, blushes, eye shadows, and bronzing powders.

88. The personal care composition of claim 85, wherein said cosmetic composition is a foundation selected from water-in-oil foundations, water-in-silicone foundations, oil-in-water foundations, anhydrous makeup sticks, and cream-to-powder foundations.

89. A method for promoting hair growth of a subject suffering from psoriasis, comprising the steps of:
 a) providing the personal care composition of claim 68;
 b) providing a subject to be treated; and
 c) applying said composition to said subject in an area in which promotion of hair growth is desired.

90. The method of claim 89, wherein the area is chosen from face, underarm, leg, torso, arm and head.

91. The method of claim 89, wherein said modified variant BBPI is a TNF-BBPI chosen from SEQ ID NOS: 637, 638 and 639.

92. A method for improving the appearance and/or condition of the skin of a subject suffering from psoriasis comprising the steps of;
 a) providing the personal care composition of claim 68;
 b) providing said subject; and
 c) applying said composition to the skin of said subject.

93. The method of claim 92, wherein said modified variant BBPI is a TNF-BBPI chosen from SEQ ID NOS: 637, 638 and 639.

* * * * *